(12) United States Patent
Wang et al.

(10) Patent No.: US 7,501,420 B2
(45) Date of Patent: *Mar. 10, 2009

(54) COMPOSITION AND ANTIVIRAL OF SUBSTITUTED AZAINDOLEOXOACETIC PIPERAZINE DERIVATIVES

(75) Inventors: Tao Wang, Farmington, CT (US); Zhongxing Zhang, Madison, CT (US); Nicholas A. Meanwell, East Hampton, CT (US); John F. Kadow, Wallingford, CT (US); Zhiwei Yin, Glastonbury, CT (US); Qiufen May Xue, Newbury Park, CA (US); Alicia Regueiro-Ren, Middletown, CT (US); John D. Matiskella, Wallingford, CT (US); Yasutsugu Ueda, Clinton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/015,776

(22) Filed: Jan. 17, 2008

(65) Prior Publication Data

US 2008/0119480 A1    May 22, 2008

Related U.S. Application Data

(63) Continuation of application No. 10/969,675, filed on Oct. 20, 2004, now Pat. No. 7,354,924, which is a continuation of application No. 10/630,278, filed on Jul. 30, 2003, now abandoned, which is a continuation-in-part of application No. 10/214,982, filed on Aug. 7, 2002, now abandoned, which is a continuation-in-part of application No. 10/038,306, filed on Jan. 2, 2002, now abandoned.

(60) Provisional application No. 60/314,406, filed on Aug. 23, 2001, provisional application No. 60/266,183, filed on Feb. 2, 2001.

(51) Int. Cl.
*A61K 31/437*    (2006.01)
(52) U.S. Cl. .................. 514/253.04; 544/362
(58) Field of Classification Search .................. None
See application file for complete search history.

(56) References Cited

U.S. PATENT DOCUMENTS

| 5,023,265 | A | 6/1991 | Scherlock et al. |
| 5,124,327 | A | 6/1992 | Greenlee et al. |
| 5,424,329 | A | 6/1995 | Boschelli et al. |
| 7,354,924 | B2 * | 4/2008 | Wang et al. ............ 514/253.04 |
| 2002/0061892 | A1 | 5/2002 | Wang et al. |
| 2005/0209246 | A1 | 9/2005 | Ueda et al. |
| 2007/0155702 | A1 | 7/2007 | Chen et al. |
| 2007/0249579 | A1 | 10/2007 | Wang et al. |

FOREIGN PATENT DOCUMENTS

| EP | 0530907 A1 | 3/1993 |
| WO | WO 93/01181 | 1/1993 |
| WO | WO 95/04742 | 2/1995 |
| WO | WO 96/11929 | 4/1996 |
| WO | WO 00/71535 | 11/2000 |
| WO | WO 0076521 A1 | 12/2000 |
| WO | WO 01/62255 | 8/2001 |

OTHER PUBLICATIONS

M. Font, et al., "Indoles and Pyridazino[4,5[b]indoles as Non-nucleoside Analog Inhibitors of HIV-1 Reverse Transcriptase," Eur. J. Med. Chem., 30, pp. 963-971, 1995.
D. L. Romero, et al., J. Med. Chem., 36, pp. 1505-1508, 1993.
S.D. Young, et al., "2-Heterocyclic Indole-3-Sulfones as Inhibitors of HIV-1 Reverse Transcriptase," Bioorganic & Medicinal Chemistry Letters, 5(5), pp. 491-496, 1995.
M.J. Genin, et al., "Synthesis and Bioactivity of Novel Bis(Heteroaryl) Piperazine (BHAP) Reverse Transcriptase Inhibitors: Structure-Activity Relationships and Increased Metabolic Stability of Novel Substituted Pyridine Analogs," J. Med. Chem., 39, pp. 5267-5275, 1996.
R. Silvestri, et al., Antiviral Chemistry & Chemotherapy, 9, pp. 139-148, 1998.
A. Fredenhagen, et al., "Semicochiliodinol A and B: Inhibitors of HIV-1 Protease and EGF-R Protein Tyrosine Kinase Related to Asterriquinones Produced by the Fungus *Chrysosporium merdarium*," Journal of Antibiotics, 50(5), pp. 395-401, 1997.
M. Kato, et al., "New 5HT$_3$ (Serotonin-3) Receptor Antagonists. IV. Synthesis and Structure-Activity Redlationships of Azabicycloalkaneacetamide Derivatives." Chem. Pharm. Bull., 43(8), pp. 1351-1357, 1995.
V. Levacher, et al., "Broadening in the Scope of NADH Models by Using Chiral and Non-chiral Pyrrolo[2,3[b]Pyridine Derivatives," Tetrahedron, 47(3), pp. 429-440, 1991.

* cited by examiner

*Primary Examiner*—Emily Bernhardt
(74) *Attorney, Agent, or Firm*—John F. Levis; Jennifer C. Chapman; Samuel J. DuBoff

(57) ABSTRACT

This invention provides compounds having drug and bio-affecting properties, their pharmaceutical compositions and method of use. In particular, the invention is concerned with azaindoleoxoacetyl piperazine derivatives. These compounds possess unique antiviral activity, whether used alone or in combination with other antivirals, antiinfectives, immunomodulators or HIV entry inhibitors. More particularly, the present invention relates to the treatment of HIV and AIDS.

10 Claims, No Drawings

COMPOSITION AND ANTIVIRAL OF SUBSTITUTED AZAINDOLEOXOACETIC PIPERAZINE DERIVATIVES

CROSS REFERENCE TO RELATED APPLICATIONS

This Continuation application claims the benefit of U.S. Ser. No. 10/969,675 filed Oct. 20, 2004, now U.S. Pat. No. 7,354,924, which in turn is a Continuation application which claims the benefit of U.S. Ser. No. 10/630,278 filed Jul. 30, 2003, now abandoned, which in turn is a Continuation in Part application which claims the benefit of U.S. Ser. No. 10/214,982 filed Aug. 7, 2002, now abandoned, which in turn is a Continuation in Part application which claims the benefit of U.S. Ser. No. 10/038,306 filed Jan. 2, 2002, now abandoned, which in turn claims the benefit of U.S. Provisional Application Ser. Nos. 60/314,406 filed Aug. 23, 2001 and 60/266,183 filed Feb. 2, 2001, now expired.

BACKGROUND OF THE INVENTION

1. Field of the Invention

This invention provides compounds having drug and bio-affecting properties, their pharmaceutical compositions and method of use. In particular, the invention is concerned with azaindole piperazine diamide derivatives that possess unique antiviral activity. More particularly, the present invention relates to compounds useful for the treatment of HIV and AIDS.

2. Background Art

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include nine nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains –3TC plus AZT), Trizivir® (contains abacavir, lamivudine, and zidovudine); three non-nucleoside reverse transcriptase inhibitors: nevirapine (or Viramune®), delavirdine (or Rescriptor®) and efavirenz (or Sustiva®), and eight peptidomimetic protease inhibitors or approved formulations: saquinavir, indinavir, ritonavir, nelfinavir, amprenavir, lopinavir, Kaletra®(lopinavir and Ritonavir), and Atazanavir (Reyataz®). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present (Larder and Kemp; Gulick; Kuritzkes; Morris-Jones et al; Schinazi et al; Vacca and Condra; Flexner; Berkhout and Ren et al; (Ref. 6-14)). Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections (Pedersen & Pedersen, Ref 15). At least 30 different classes of NNRTI have been described in the literature (De Clercq, Ref 16) and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance (Pedersen & Pedersen, Ref 15).

Several indole derivatives including indole-3-sulfones, piperazino indoles, pyrazino indoles, and 5H-indolo[3,2-b][1,5]benzothiazepine derivatives have been reported as HIV-1 reverse transciptase inhibitors (Greenlee et al, Ref. 1; Williams et al, Ref. 2; Romero et al, Ref. 3; Font et al, Ref. 17; Romero et al, Ref. 18; Young et al, Ref. 19; Genin et al, Ref. 20; Silvestri et al, Ref. 21). Indole 2-carboxamides have also been described as inhibitors of cell adhesion and HIV infection (Boschelli et al, U.S. Pat. No. 5,424,329, Ref 4). Finally, 3-substituted indole natural products (Semicochliodinol A and B, didemethylasterriquinone and isocochliodinol) were disclosed as inhibitors of HIV-1 protease (Fredenhagen et al, Ref. 22). Other indole derivatives exhibiting antiviral activity useful for treating HIV are disclosed in PCT WO 00/76521 (Ref. 93). Also, indole derivatives are disclosed in PCT WO 00/71535 (Ref. 94).

Structurally related aza-indole amide derivatives have been disclosed previously (Kato et al, Ref. 23; Levacher et al, Ref. 24; Dompe Spa, WO-09504742, Ref 5(a); SmithKline Beecham PLC, WO-09611929, Ref. 5(b); Schering Corp., U.S. Pat. No. 0,502,3265, Ref. 5(c)). However, these structures differ from those claimed herein in that they are aza-indole mono-amide rather than unsymmetrical aza-indole piperazine diamide derivatives, and there is no mention of the use of these compounds for treating viral infections, particularly HIV. Other azaindoles have been also disclosed by Wang et al, Ref. 95. Indole and azaindole piperazine containing derivatives have been disclosed in four different PCT and issued U.S. patent applications (Reference 93-95, 106). Nothing in these references can be construed to disclose or suggest the novel compounds of this invention and their use to inhibit HIV infection.

REFERENCES CITED

Patent Documents

1. Greenlee, W. J.; Srinivasan, P. C. Indole reverse transcriptase inhibitors. U.S. Pat. No. 5,124,327.
2. Williams, T. M.; Ciccarone, T. M.; Saari, W. S.; Wai, J. S.; Greenlee, W. J.; Balani, S. K.; Goldman, M. E.; Theohrides, A. D. Indoles as inhibitors of HIV reverse transcriptase. European Patent 530907.

3. Romero, D. L.; Thomas, R. C.; Preparation of substituted indoles as anti-AIDS pharmaceuticals. PCT WO 93/01181.
4. Boschelli, D. H.; Connor, D. T.; Unangst, P. C. Indole-2-carboxamides as inhibitors of cell adhesion. U.S. Pat. No. 5,424,329.
5. (a) Mantovanini, M.; Melillo, G.; Daffonchio, L. Tropyl 7-azaindol-3-ylcarboxyamides as antitussive agents. PCT WO 95/04742 (Dompe Spa). (b) Cassidy, F.; Hughes, I.; Rahman, S.; Hunter, D. J. Bisheteroaryl-carbonyl and carboxamide derivatives with 5HT 2C/2B antagonists activity. PCT WO 96/11929. (c) Scherlock, M. H.; Tom, W. C. Substituted 1H-pyrrolopyridine-3-carboxamides. U.S. Pat. No. 5,023,265.

Other Publications

6. Larder, B. A.; Kemp, S. D. Multiple mutations in the HIV-1 reverse transcriptase confer high-level resistance to zidovudine (AZT). *Science,* 1989, 246, 1155-1158.
7. Gulick, R. M. Current antiretroviral therapy: An overview. *Quality of Life Research,* 1997, 6, 471-474.
8. Kuritzkes, D. R. HIV resistance to current therapies. *Antiviral Therapy,* 1997, 2 (Supplement 3), 61-67.
9. Morris-Jones, S.; Moyle, G.; Easterbrook, P. J. Antiretroviral therapies in HIV-1 infection. *Expert Opinion on Investigational Drugs,* 1997, 6(8), 1049-1061.
10. Schinazi, R. F.; Larder, B. A.; Mellors, J. W. Mutations in retroviral genes associated with drug resistance. *International Antiviral News,* 1997, 5, 129-142.
11. Vacca, J. P.; Condra, J. H. Clinically effective HIV-1 protease inhibitors. *Drug Discovery Today,* 1997, 2, 261-272.
12. Flexner, D. HIV-protease inhibitors. *Drug Therapy,* 1998, 338, 1281-1292.
13. Berkhout, B. HIV-1 evolution under pressure of protease inhibitors: Climbing the stairs of viral fitness. *J. Biomed. Sci.,* 1999, 6, 298-305.
14. Ren, S.; Lien, E. J. Development of HIV protease inhibitors: A survey. *Prog. Drug Res.,* 1998, 51, 1-31.
15. Pedersen, O. S.; Pedersen, E. B. Non-nucleoside reverse transcriptase inhibitors: the NNRTI boom. *Antiviral Chem. Chemother.* 1999, 10, 285-314.
16. (a) De Clercq, E. The role of non-nucleoside reverse transcriptase inhibitors (NNRTIs) in the therapy of HIV-1 infection. *Antiviral Research,* 1998, 38, 153-179. (b) De Clercq, E. Perspectives of non-nucleoside reverse transcriptase inhibitors (NNRTIs) in the therapy of HIV infection. IL. *Farmaco,* 1999, 54, 26-45.
17. Font, M.; Monge, A.; Cuartero, A.; Elorriaga, A.; Martinez-Irujo, J. J.; Alberdi, E.; Santiago, E.; Prieto, I.; Lasarte, J. J.; Sarobe, P. and Borras, F. Indoles and pyrazino [4,5-b]indoles as nonnucleoside analog inhibitors of HIV-1 reverse transcriptase. *Eur. J. Med. Chem.,* 1995, 30, 963-971.
18. Romero, D. L.; Morge, R. A.; Genin, M. J.; Biles, C.; Busso, M; Resnick, L.; Althaus, I. W.; Reusser, F.; Thomas, R. C and Tarpley, W. G. Bis(heteroaryl)piperazine (BHAP) reverse transcriptase inhibitors: structure-activity relationships of novel substituted indole analogues and the identification of 1-[(5-methanesulfonamido-1H-indol-2-yl)-carbonyl]-4-[3-[1-methylethyl)amino]-pyridinyl]piperazine momomethansulfonate (U-90152S), a second generation clinical candidate. *J. Med. Chem.,* 1993, 36, 1505-1508.
19. Young, S. D.; Amblard, M. C.; Britcher, S. F.; Grey, V. E.; Tran, L. O.; Lumma, W. C.; Huff, J. R.; Schleif, W. A.; Emini, E. E.; O'Brien, J. A.; Pettibone, D. J. 2-Heterocyclic indole-3-sulfones as inhibitors of HIV-reverse transcriptase. *Bioorg. Med. Chem. Lett.,* 1995, 5, 491-496.
20. Genin, M. J.; Poel, T. J.; Yagi, Y.; Biles, C.; Althaus, I.; Keiser, B. J.; Kopta, L. A.; Friis, J. M.; Reusser, F.; Adams, W. J.; Olmsted, R. A.; Voorman, R. L.; Thomas, R. C. and Romero, D. L. Synthesis and bioactivity of novel bis(heteroaryl)piperazine (BHAP) reverse transcriptase inhibitors: structure-activity relationships and increased metabolic stability of novel substituted pyridine analogs. *J. Med. Chem.,* 1996, 39, 5267-5275.
21. Silvestri, R.; Artico, M.; Bruno, B.; Massa, S.; Novellino, E.; Greco, G.; Marongiu, M. E.; Pani, A.; De Montis, A and La Colla, P. Synthesis and biological evaluation of 5H-indolo[3,2-b][1,5]benzothiazepine derivatives, designed as conformationally constrained analogues of the human immunodeficiency virus type 1 reverse transcriptase inhibitor L-737,126. *Antiviral Chem. Chemother.* 1998, 9, 139-148.
22. Fredenhagen, A.; Petersen, F.; Tintelnot-Blomley, M.; Rosel, J.; Mett, H. and Hug, P. J. Semicochliodinol A and B: Inhibitors of HIV-1 protease and EGF-R protein Tyrosine Kinase related to Asterriquinones produced by the fungus *Chrysosporium nerdarium. Antibiotics,* 1997, 50, 395-401.
23. Kato, M.; Ito, K.; Nishino, S.; Yamakuni, H.; Takasugi, H. New 5-HT$_3$ (Serotonin-3) receptor antagonists. IV. Synthesis and structure-activity relationships of azabicycloalkaneacetamide derivatives. *Chem. Pharm. Bull.,* 1995, 43, 1351-1357.
24. Levacher, V.; Benoit, R.; Duflos, J; Dupas, G.; Bourguignon, J.; Queguiner, G. Broadening the scope of NADH models by using chiral and non chiral pyrrolo[2,3-b]pyridine derivatives. *Tetrahedron,* 1991, 47, 429-440.
25. Shadrina, L. P.; Dormidontov, Yu. P.; Ponomarev, V. G.; Lapkin, I. I. Reactions of organomagnesium derivatives of 7-aza- and benzoindoles with diethyl oxalate and the reactivity of ethoxalylindoles. *Khim. Geterotsikl. Soedin.,* 1987, 1206-1209.
26. Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.,* 1987, 100-106.
27. (a) Desai, M.; Watthey, J. W. H.; Zuckerman, M. A convenient preparation of 1-aroylpiperazines. *Org. Prep. Proced. Int.,* 1976, 8, 85-86. (b) Adamczyk, M.; Fino, J. R. Synthesis of procainamide metabolites. N-acetyl desethylprocainamide and desethylprocainamide. *Org. Prep. Proced. Int.* 1996, 28, 470-474. (c) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.,* 1995, 36, 6419-6422. (d) Wang, T.; Zhang, Z.; Meanwell, N. A. Benzoylation of Dianions: Preparation of mono-Benzoylated Symmetric Secondary Diamines. *J. Org. Chem.,* 1999, 64, 7661-7662.
28. Li, H.; Jiang, X.; Ye, Y.-H.; Fan, C.; Romoff, T.; Goodman, M. 3-(Diethoxyphosphoryloxy)-1,2,3-benzotriazin-4(3H)-one (DEPBT): A new coupling reagent with remarkable resistance to racemization. *Organic Lett.,* 1999, 1, 91-93.
29. Harada, N.; Kawaguchi, T.; Inoue, I.; Ohashi, M.; Oda, K.; Hashiyama, T.; Tsujihara, K. Synthesis and antitumor activity of quaternary salts of 2-(2'-oxoalkoxy)-9-hydroxyellipticines. *Chem. Pharm. Bull.,* 1997, 45, 134-137.

30. Schneller, S. W.; Luo, J.-K. Synthesis of 4-amino-1H-pyrrolo[2,3-b]pyridine (1,7-Dideazaadenine) and 1H-pyrrolo[2,3-b]pyridin-4-ol (1,7-Dideazahypoxanthine). *J. Org. Chem.*, 1980, 45, 4045-4048.
31. Shiotani, S.; Tanigochi, K. Furopyridines. XXII [1]. Elaboration of the C-substitutents alpha to the heteronitrogen atom of furo[2,3-b]-, -[3.2-b]-, -[2.3-c]- and -[3,2-c] pyridine. *J. Het. Chem.*, 1997, 34, 901-907.
32. Minakata, S.; Komatsu, M.; Ohshiro, Y. Regioselective functionalization of 1H-pyrrolo[2,3-b]pyridine via its N-oxide. *Synthesis*, 1992, 661-663.
33. Klemm, L. H.; Hartling, R. Chemistry of thienopyridines. XXIV. Two transformations of thieno[2,3-b]pyridine 7-oxide (1). *J. Het. Chem.*, 1976, 13, 1197-1200.
34. Antonini, I.; Claudi, F.; Cristalli, G.; Franchetti, P.; Crifantini, M.; Martelli, S. Synthesis of 4-amino-1-□-D-ribofuranosyl-1H-pyrrolo[2,3-b]pyridine (1-Deazatubercidin) as a potential antitumor agent. *J. Med. Chem.*, 1982, 25, 1258-1261.
35. (a) Regnouf De Vains, J. B.; Papet, A. L.; Marsura, A. New symmetric and unsymmetric polyfunctionalized 2,2'-bipyridines. *J. Het. Chem.*, 1994, 31, 1069-1077. (b) Miura, Y.; Yoshida, M.; Hamana, M. Synthesis of 2,3-fused quinolines from 3-substituted quinoline 1-oxides. Part II, *Heterocycles*, 1993, 36, 1005-1016. (c) Profft, V. E.; Rolle, W. Uber 4-merkaptoverbindungedes 2-methylpyridins. *J. Prakt. Chem.*, 1960, 283 (11), 22-34.
36. Nesi, R.; Giomi, D.; Turchi, S.; Tedeschi, P., Ponticelli, F. A new one step synthetic approach to the isoxazolo[4,5-b]pyridine system. *Synth. Comm.*, 1992, 22, 2349-2355.
37. (a) Walser, A.; Zenchoff, G.; Fryer, R. I. Quinazolines and 1,4-benzodiazepines. 75. 7-Hydroxyaminobenzodiazepines and derivatives. *J. Med. Chem.*, 1976, 19, 1378-1381. (b) Barker, G.; Ellis, G. P. Benzopyrone. Part I. 6-Amino- and 6-hydroxy-2-substituted chromones. *J. Chem. Soc.*, 1970, 2230-2233.
38. Ayyangar, N. R.; Lahoti, R J.; Daniel, T. An alternate synthesis of 3,4-diaminobenzophenone and mebendazole. *Org. Prep. Proced. Int.*, 1991, 23, 627-631.
39. Mahadevan, I.; Rasmussen, M. Ambident heterocyclic reactivity: The alkylation of pyrrolopyridines (azaindoles, diazaindenes). *Tetrahedron*, 1993, 49, 7337-7352.
40. Chen, B. K.; Saksela, K.; Andino, R.; Baltimore, D. Distinct modes of human immunodeficiency type 1 proviral latency revealed by superinfection of nonproductively infected cell lines with recombinant luciferase-encoding viruses. *J. Virol.*, 1994, 68, 654-660.
41. Bodanszky, M.; Bodanszky, A. "*The Practice of Peptide Synthesis*" $2^{nd}$ Ed., Springer-Verlag: Berlin Heidelberg, Germany, 1994.
42. Albericio, F. et al. *J. Org. Chem.* 1998, 63, 9678.
43. Knorr, R. et al. *Tetrahedron Lett.* 1989, 30, 1927.
44. (a) Jaszay Z. M. et al. *Synth. Commun.*, 1998 28, 2761 and references cited therein; (b) Bernasconi, S. et al. *Synthesis*, 1980, 385.
45. (a) Jaszay Z. M. et al. *Synthesis*, 1989, 745 and references cited therein; (b) Nicolaou, K. C. et al. *Angew. Chem. Int. Ed.* 1999, 38, 1669.
46. Ooi, T. et al. *Synlett.* 1999, 729.
47. Ford, R. E. et al. *J. Med. Chem.* 1986, 29, 538.
48. (a) Yeung, K.-S. et al. Bristol-Myers Squibb Unpublished Results. (b) Wang, W. et al. *Tetrahedron Lett.* 1999, 40, 2501.
49. Brook, M. A. et al. *Synthesis*, 1983, 201.
50. Yamazaki, N. et al. *Tetrahedron Lett.* 1972, 5047.
51. Barry A. Bunin "The Combinatorial Index" 1998 Academic Press, San Diego/London pages 78-82.
52. Richard C. Larock Comprehensive Organic Transformations 2nd Ed. 1999, John Wiley and Sons New York.
53. M. D. Mullican et. al. *J. Med. Chem.* 1991, 34, 2186-2194.
54. Protective groups in organic synthesis 3rd ed./Theodora W. Greene and Peter G. M. Wuts. New York: Wiley, 1999.
55. Katritzky, Alan R. Lagowski, Jeanne M. The principles of heterocyclic Chemistry New York: Academic Press, 1968.
56. Paquette, Leo A. Principles of modern heterocyclic chemistry New York: Benjamin.
57. Katritzky, Alan R.; Rees, Charles W.; Comprehensive heterocyclic chemistry: the structure, reactions, synthesis, and uses of heterocyclic compounds 1st ed. Oxford (Oxfordshire); New York: Pergamon Press, 1984. 8 v.
58. Katritzky, Alan R H and book of heterocyclic 1st ed Oxford (Oxfordshire); New York: Pergamon Press, 1985.
59. Davies, David I Aromatic Heterocyclic Oxford; New York: Oxford University Press, 1991.
60. Ellis, G. P. Synthesis of fused Chichester [Sussex]; New York: Wiley, c1987-c1992. Chemistry of heterocyclic compounds; v. 47.
61. Joule, J. A Mills, K., Smith, G. F. Heterocyclic Chemistry, 3rd ed London; New York Chapman & Hall, 1995.
62. Katritzky, Alan R., Rees, Charles W., Scriven, Eric F. V. Comprehensive heterocyclic chemistry II: a review of the literature 1982-1995.
63. The structure, reactions, synthesis, and uses of heterocyclic compounds 1st ed. Oxford; New York: Pergamon, 1996. 11 v. in 12: ill.; 28 cm.
64. Eicher, Theophil, Hauptmann, Siegfried. The chemistry of heterocycles structure, reactions, syntheses, and applications Stuttgart; New York: G. Thieme, 1995.
65. Grimmett, M. R. Imidazole and benzimidazole Synthesis London; San Diego Academic Press, 1997.
66. Advances in heterocyclic chemistry. Published in New York by Academic Press, starting in 1963-present.
67. Gilchrist, T. L. (Thomas Lonsdale) Heterocyclic chemistry 3rd ed. Harlow, Essex: Longman, 1997. 414 p.: ill.; 24 cm.
68. Farina, Vittorio; Roth, Gregory P. Recent advances in the Stille reaction; *Adv. Met.-Org. Chem.* 1996, 5, 1-53.
69. Farina, Vittorio; Krishnamurthy, Venkat; Scott, William J. The Stille reaction; Org. React. (N.Y.) (1997), 50, 1-652.
70. Stille, J. K. Angew. *Chem. Int. Ed. Engl* 1986, 25, 508-524.
71. Norio Miyaura and Akiro Suzuki *Chem. Rev.* 1995, 95, 2457.
72. Home, D. A. *Heterocycles* 1994, 39, 139.
73. Kamitori, Y. et. al. *Heterocycles*, 1994, 37(1), 153.
74. Shawali, J. *Heterocyclic Chem.* 1976, 13, 989.
75. a) Kende, A. S. et al. *Org. Photochem. Synth.* 1972, 1, 92. b) Hankes, L. V.; *Biochem. Prep.* 1966, 11, 63. c) *Synth. Meth.* 22, 837.
76. Hulton et. al. *Synth. Comm.* 1979, 9, 789.
77. Pattanayak, B. K. et. al. *Indian J. Chem.* 1978, 16, 1030.
78. *Chemische Berichte* 1902, 35, 1545.
79. *Chemische Berichte* Ibid 1911, 44, 493.
80. Moubarak, I., Vessiere, R. *Synthesis* 1980, Vol. 1, 52-53.
81. *Ind J. Chem.* 1973, 11, 1260.
82. Roomi et. al. *Can J. Chem.* 1970, 48, 1689.
83. Sorrel, T. N. *J. Org. Chem.* 1994, 59, 1589.
84. Nitz, T. J. et. al. *J. Org. Chem.* 1994, 59, 5828-5832.
85. Bowden, K. et. al. *J. Chem. Soc.* 1946, 953.
86. Nitz, T. J. et. al. *J. Org. Chem.* 1994, 59, 5828-5832.
87. Scholkopf et. al. *Angew. Int. Ed. Engl.* 1971, 10(5), 333.
88. (a) Behun, J. D.; Levine, R. *J. Org. Chem.* 1961, 26, 3379. (b) Rossen, K.; Weissman, S. A.; Sager, J.; Reamer, R. A.; Askin, D.; Volante, R. P.; Reider, P. J. Asymmetric Hydrogenation of tetrahydropyrazines: Synthesis of (S)-piperazine 2-tert-butylcarboxamide, an intermediate in the preparation of the HIV protease inhibitor Indinavir. *Tetrahedron Lett.*, 1995, 36, 6419-6422. (c) Jenneskens, L. W.; Mahy, J.; den Berg, E. M. M. de B.-v.; Van der Hoef, I.; Lugtenburg, J. *Recl. Trav. Chim. Pays-Bas* 1995, 114, 97.
89. Wang, T.; Zhang, Z.; Meanwell, N. A. Benzoylation of Dianions: Preparation of mono-Benzoylated Symmetric Secondary Diamines. *J. Org. Chem.*, 1999, 64, 7661-7662.
90. (a) Adamczyk, M.; Fino, J. R. Synthesis of procainamide metabolites. N-acetyl desethylprocainamide and desethylprocainamide. *Org. Prep. Proced. Int.* 1996, 28, 470-474. (b) Wang, T.; Zhang, Z.; Meanwell, N. A. Regioselective mono-Benzoylation of Unsymmetrical piperazines. *J. Org. Chem.* 2000, 65, 4740.
91. Masuzawa, K.; Kitagawa, M.; Uchida, H. *Bull Chem. Soc. Jpn.* 1967, 40, 244-245.
92. Furber, M.; Cooper, M. E.; Donald, D. K. *Tetrahedron Lett.* 1993, 34, 1351-1354.
93. Blair, Wade S.; Deshpande, Milind; Fang, Haiquan; Lin, Pin-fang; Spicer, Timothy P.; Wallace, Owen B.; Wang, Hui; Wang, Tao; Zhang, Zhongxing; Yeung, Kap-sun. Preparation of antiviral indoleoxoacetyl piperazine derivatives U.S. Pat. No. 6,469,006. Preparation of antiviral indoleoxoacetyl piperazine derivatives. PCT Int. Appl. (PCT/US00/14359), WO 0076521 A1, filed May 24, 2000, published Dec. 21, 2000.
94. Wang, Tao; Wallace, Owen B.; Zhang, Zhongxing; Meanwell, Nicholas A.; Bender, John A. Antiviral azaindole derivatives. U.S. Pat. No. 6,476,034 and Wang, Tao; Wallace, Owen B.; Zhang, Zhongxing; Meanwell, Nicholas A.; Bender, John A. Preparation of antiviral azaindole derivatives. PCT Int. Appl. (PCT/US01/02009), WO 0162255 A1, filed Jan. 19, 2001, published Aug. 30, 2001.
95. Wallace, Owen B.; Wang, Tao; Yeung, Kap-Sun; Pearce, Bradley C.; Meanwell, Nicholas A.; Qiu, Zhilei; Fang, Haiquan; Xue, Qiufen May; Yin, Zhiwei. Composition and antiviral activity of substituted indoleoxoacetic piperazine derivatives. U.S. patent application Ser. No. 10/027,612 filed Dec. 19, 2001, which is a continuation-in-part application of U.S. Ser. No. 09/888,686 filed Jun. 25, 2001 (corresponding to PCT Int. Appl. (PCT/US01/20300), WO 0204440 A1, filed Jun. 26, 2001, published Jan. 17, 2002.
96. J. L. Marco, S. T. Ingate, and P. M. Chinchon Tetrahedron 1999, 55, 7625-7644.
97. C. Thomas, F. Orecher, and P. Gmeiner Synthesis 1998, 1491.
98. M. P. Pavia, S. J. Lobbestael, C. P. Taylor, F. M. Hershenson, and D. W. Miskell
99. Buckheit, Robert W., Jr. Expert Opinion on Investigational Drugs 2001, 10(8), 1423-1442.
100. Balzarini, J.; De Clercq, E. Antiretroviral Therapy 2001, 31-62.
101. E. De clercq Journal of Clinical Virology, 2001, 22, 73-89.
102. Merour, Jean-Yves; Joseph, Benoit. Curr. Org. Chem. (2001), 5(5), 471-506.
103. T. W. von Geldern et al. J. Med. Chem 1996, 39, 968.
104. M. Abdaoui et al. Tetrahedron 2000, 56, 2427.
105. W. J. Spillane et al. J. Chem. Soc., Perkin Trans. 1, 1982, 3, 677
106. Wang, Tao; Wallace, Owen B.; Zhang, Zhongxing; Meanwell, Nicholas A.; Kadow, John F. Yin, Zhiwei. Composition and Antiviral Activity of Substituted Azaindoleoxoacetic piperazine Derivatives. U.S. patent application Ser. No. 10/214,982 filed Aug. 7, 2002, which is a continuation-in-part application of U.S. Ser. No. 10/038,306 filed Jan. 2, 2002 (corresponding to PCT Int. Appl. (PCT/US02/00455), WO 02/062423 A1, filed Jan. 2, 2002, published Aug. 15, 2002.

SUMMARY DESCRIPTION OF THE INVENTION

The present invention comprises compounds of Formula I, or pharmaceutically acceptable salts thereof, which are effective antiviral agents, particularly as inhibitors of HIV.

A first embodiment of a first aspect of the invention are compounds of Formula I, including pharmaceutically acceptable salts thereof,

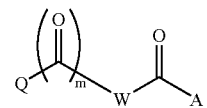

wherein:

Q is selected from the group consisting of:

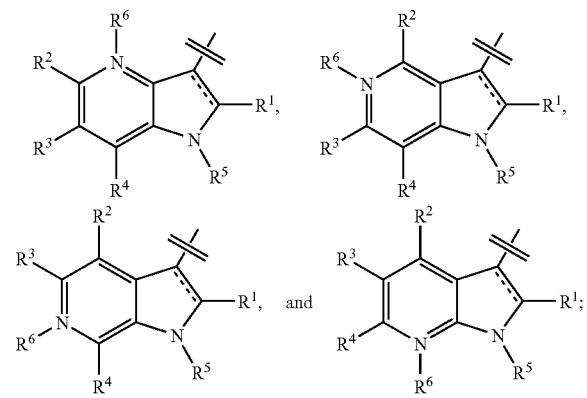

$R^1$, $R^2$, $R^3$, and $R^4$, are independently selected from the group consisting of hydrogen, halogen, cyano, nitro, $COOR^{56}$, $XR^{57}$, $C(O)R^7$, $C(O)NR^{55}R^{56}$, B, D, and F with the proviso that at least one of $R^1$-$R^4$ is selected from B or E;

wherein —represents a carbon-carbon bond or does not exist;

m is 1 or 2;

$R^5$ is hydrogen or $(CH_2)_nCH_3$, $-C(O)(CH_2)_nCH_3$, $-C(O)O(CH_2)_nCH_3$, $-C(O)(CH_2)_nN(CH_3)_2$ wherein n is 0-5;

$R^6$ is O or does not exist;

A is selected from the group consisting of $C_{1-6}$alkoxy, aryl and heteroaryl; in which said aryl is phenyl or napthyl; said heteroaryl is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and said aryl or heteroaryl is optionally substituted with one or two of the same or different members selected from the group consisting of amino, nitro, cyano, hydroxy, $C_{1-6}$alkoxy, $-C(O)NH_2$, $C_{1-6}$alkyl, $-NHC(O)CH_3$, halogen and trifluoromethyl;

—W— is

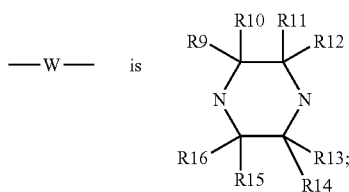

B is selected from the group consisting of —C(=NR$^{46}$)(R$^{47}$), C(O)NR$^{40}$R$^{41}$, aryl, heteroaryl, heteroalicyclic, S(O)$_2$R$^8$, C(O)R$^7$, XR$^{8a}$, (C$_{1-6}$)alkylNR$^{40}$R$^{41}$, (C$_{1-6}$)alkylCOOR$^{8b}$; wherein said aryl, heteroaryl, and heteroalicyclic are optionally substituted with one to three same or different halogens or from one to three same or different substituents selected from the group F; wherein aryl is napthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;

q is 0, 1, or 2;

D is selected from the group consisting of (C$_{1-6}$)alkyl and (C$_{2-6}$)alkenyl; wherein said (C$_{1-6}$)alkyl and (C$_{2-6}$)alkenyl are optionally substituted with one to three same or different halogens or from one to three same or different substituents selected from the group consisting of C(O)NR$^{55}$R$^{56}$, hydroxy, cyano and XR$^{57}$;

E is selected from the group consisting of (C$_{1-6}$)alkyl and (C$_{2-6}$)alkenyl; wherein said (C$_{1-6}$)alkyl and (C$_{2-6}$)alkenyl are independently optionally substituted with a member selected from the group consisting of phenyl, heteroaryl, SMe, SPh, —C(O)NR$_{56}$R$_{57}$, C(O)R$_{57}$, SO$_2$(C$_{1-6}$)alkyl and SO$_2$Ph; wherein heteroaryl is a monocyclic system which contains from 3 to 7 ring atoms, including from 1 to 4 heteroatoms;

F is selected from the group consisting of (C$_{1-6}$)alkyl, (C$_{3-7}$)cycloalkyl, aryl, heteroaryl, heteroalicyclic, hydroxy, (C$_{1-6}$)alkoxy, aryloxy, (C$_{1-6}$)thioalkoxy, cyano, halogen, nitro, —C(O)R$^{57}$, benzyl, —NR$^{42}$C(O)—(C$_{1-6}$)alkyl, —NR$^{42}$C(O)—(C$_{3-6}$)cycloalkyl, —NR$^{42}$C(O)-aryl, —NR$^{42}$C(O)-heteroaryl, —NR$^{42}$C(O)-heteroalicyclic, a 4, 5, or 6 membered ring cyclic N-lactam, —NR$^{42}$S(O)$_2$—(C$_{1-6}$)alkyl, —NR$^{42}$S(O)$_2$—(C$_{3-6}$)cycloalkyl, —NR$^{42}$S(O)$_2$-aryl, —NR$^{42}$S(O)$_2$-heteroaryl, —NR$^{42}$S(O)2-heteroalicyclic, S(O)$_2$(C$_{1-6}$)alkyl, S(O)$_2$aryl, —S(O)$_2$NR$^{42}$R$^{43}$, NR$^{42}$R$^{43}$, (C$_{1-6}$)alkylC(O)NR$^{42}$R$^{43}$, C(O)NR$^{42}$R$^{43}$, NHC(O)NR$^{42}$R$^{43}$, OC(O)NR$^{42}$R$^{43}$, NHC(O)OR$^{54}$, (C$_{1-6}$)alkylNR$^{42}$R$^{43}$, COOR$^{54}$, and (C$_{1-6}$)alkylCOOR$^{54}$; wherein said (C$_{1-6}$)alkyl, (C$_{3-7}$)cycloalkyl, aryl, heteroaryl, heteroalicyclic, (C$_{1-6}$)alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

G is selected from the group consisting of (C$_{1-6}$)alkyl, (C$_{3-7}$)cycloalkyl, aryl, heteroaryl, heteroalicyclic, hydroxy, (C$_{1-6}$)alkoxy, aryloxy, cyano, halogen, nitro, —C(O)R$^{57}$, benzyl, —NR$^{48}$C(O)—(C$_{1-6}$)alkyl, —NR$^{48}$C(O)—(C$_{3-6}$)cycloalkyl, —NR$^{48}$C(O)-aryl, —NR$^{48}$C(O)-heteroaryl, —NR$^{48}$C(O)-heteroalicyclic, a 4, 5, or 6 membered ring cyclic N-lactam, —NR$^{48}$S(O)$_2$—(C$_{1-6}$)alkyl, —NR$^{48}$S(O)$_2$—(C$_{3-6}$)cycloalkyl, —NR$^{48}$S(O)2-aryl, —NR$^{48}$S(O)$_2$-heteroaryl, —NR$^{48}$S(O)2-heteroalicyclic, sulfinyl, sulfonyl, sulfonamide, NR$^{48}$R$^{49}$, (C$_{1-6}$)alkylC(O)NR$^{48}$R$^{49}$, C(O)NR$^{48}$R$^{49}$, NHC(O)NR$^{48}$R$^{49}$, OC(O)NR$^{48}$R$^{49}$, NHC(O)OR$^{54'}$, (C$_{1-6}$)alkylNR$^{48}$R$^{49}$, COOR$^{54}$, and (C$_{1-6}$)alkylCOOR$^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

R$^7$ is selected from the group consisting of aryl, heteroaryl, and heteroalicyclic; wherein said aryl, heteroaryl, and heteroalicyclic are optionally substituted with one to three same or different halogens or with from one to three same or different substituents selected from the group F;

wherein for R$^7$, R$^8$, R$^{8a}$, R$^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

R$^8$ is selected from the group consisting of hydrogen, (C$_{1-6}$)alkyl, (C$_{3-7}$)cycloalkyl, (C$_{2-6}$)alkenyl, (C$_{3-7}$)cycloalkenyl, (C$_{2-6}$)alkynyl, aryl, heteroaryl, and heteroalicyclic; wherein said (C$_{1-6}$)alkyl, (C$_{3-7}$)cycloalkyl, (C$_{2-6}$)alkenyl, (C$_{3-7}$)cycloalkenyl, (C$_{2-6}$)alkynyl, aryl, heteroaryl, and heteroalicyclic are optionally substituted with one to six same or different halogens or from one to five same or different substituents selected from the group F;

R$^{8a}$ is a member selected from the group consisting of aryl, heteroaryl, and heteroalicyclic; wherein each member is independently optionally substituted with one to six same or different halogens or from one to five same or different substituents selected from the group F;

R$^{8b}$ is selected from the group consisting of hydrogen, (C$_{1-6}$)alkyl and phenyl; R$^9$, R$^{10}$, R$^{11}$, R$^{12}$, R$^{13}$, R$^{14}$, R$^{15}$, R$^{16}$, are each independently selected from the group consisting of hydrogen and (C$_{1-6}$)alkyl; wherein said (C$_{1-6}$)alkyl is optionally substituted with one to three same or different halogens;

X is selected from the group consisting of NH or NCH$_3$, O, and S;

R$^{40}$ and R$^{41}$ are independently selected from the group consisting of (a) hydrogen; (b) (C$_{1-6}$)alkyl or (C$_{3-7}$)cycloalkyl substituted with one to three same or different halogens or from one to two same or different substituents selected from the group F; and (c) (C$_{1-6}$)alkoxy, aryl, heteroaryl or heteroalicyclic; or R$^{40}$ and R$^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for R$^{40}$ and R$^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is C(O)NR$^{40}$R$^{41}$, at least one of R$^{40}$ and R$^{41}$ is not selected from groups (a) or (b);

R$^{42}$ and R$^{43}$ are independently selected from the group consisting of hydrogen, (C$_{1-6}$)alkyl, allyl, (C$_{1-6}$)alkoxy, (C$_{3-7}$) cycloalkyl, aryl, heteroaryl and heteroalicyclic; or R$^{42}$ and R$^{43}$ taken together with the nitrogen to which they are attached form a member selected from the group consisting of aziridine, azetidine, pyrrolidine, piperazine, 4-NMe piperazine, piperidine, azepine, and morpholine; and wherein said (C$_{1-6}$)alkyl, (C$_{1-6}$)alkoxy, (C$_{3-7}$)cycloalkyl, aryl, heteroaryl, and heteroalicyclic are optionally substituted with one to three same or different halogens or from one to two same or different substituents selected from the group G; wherein for R$^{42}$ and R$^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

R$_a$ and R$_b$ are each independently H, (C$_{1-6}$)alkyl or phenyl;

R$^{46}$ is selected from the group consisting of H, OR$^{57}$, and NR$^{55}$R$^{56}$;

R$^{47}$ is selected from the group consisting of H, amino, halogen, phenyl, and (C$_{1-6}$)alkyl;

R$^{48}$ and R$^{49}$ are independently selected from the group consisting of hydrogen, (C$_{1-6}$)alkyl and phenyl;

R$^{50}$ is selected from the group consisting of H, (C$_{1-6}$)alkyl, (C$_{3-6}$)cycloalkyl, and benzyl; wherein each of said (C$_{1-6}$) alkyl, (C$_{3-7}$)cycloalkyl and benzyl are optionally substituted with one to three same or different halogen, amino, OH, CN or NO$_2$;

R$^{54}$ is selected from the group consisting of hydrogen and (C$_{1-6}$)alkyl;

R$^{54'}$ is (C$_{1-6}$)alkyl;

R$^{55}$ and R$^{56}$ are independently selected from the group consisting of hydrogen and (C$_{1-6}$)alkyl; and R$^{57}$ is selected from the group consisting of hydrogen, (C$_{1-6}$) alkyl and phenyl.

A preferred embodiment are compounds of Formula I, including pharmaceutically acceptable salts thereof, wherein:

R$^1$ is hydrogen;

Q is either:

(a)

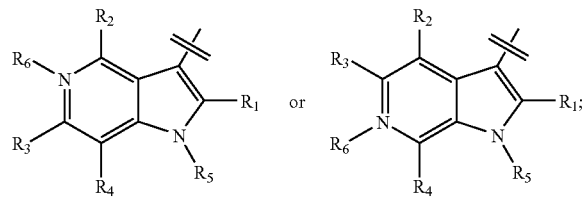

wherein R$^2$ is selected from the group consisting of hydrogen, halogen, hydroxy, —O(C$_{1-6}$)alkyl, cyano, nitro and XR$^{57}$;

wherein R$^3$ is selected from the group consisting of hydrogen, halogen, hydroxy, —O(C$_{1-6}$)alkyl, cyano, —COOR$^{56}$, nitro, XR$^{57}$; phenyl optionally substituted with one to three same or different halogens or one of methoxy, hydroxy or XR$^{57}$; furyl, oxazolyl, or pyrazolyl, independently optionally substituted with halogen, methoxy, (C$_{1-3}$)alkyl or XR$^{57}$; or (b) Q is:

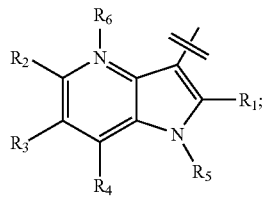

wherein R$^2$ and R$^3$ are independently selected from the group consisting of hydrogen, halogen, hydroxy, —O(C$_{1-6}$)alkyl, cyano, nitro, —COOR$^{56}$, XR$^{57}$, —C(O) NR$^{55}$R$^{56}$; phenyl optionally substituted with one to three same or different halogens or one of methoxy, hydroxy or XR$^{57}$; furyl, oxalzolyl or pyrazolyl, independently optionally substituted with (C$_{1-3}$)alkyl, halogen, methoxy or XR$^{57}$;

and for both (a) and (b):

m is 2;

R$^5$ is hydrogen;

R$^6$ does not exist;

A is selected from the group consisting of C$_{1-6}$alkoxy, aryl and heteroaryl; wherein said aryl is phenyl; heteroaryl is selected from the group consisting of pyridinyl, pyrimidinyl, pyrazinyl, triazinyl, furanyl, thienyl, pyrrolyl, imidazolyl, thiazolyl, oxazolyl and isoxazolyl; and said aryl or heteroaryl is optionally substituted with one or two of the same or different members selected from the group consisting of amino, cyano, hydroxy C$_{1-6}$alkoxy, C$_{1-6}$alkyl, —NHC(O)CH$_3$, halogen and trifluoromethyl;

═ represents a carbon-carbon bond;

X is NH or NCH$_3$;

R$^{57}$ is H or (C$_{1-3}$)alkyl; and

R$^{55}$ and R$^{56}$ are independently H or (C$_{1-6}$)alkyl.

Another preferred embodiment of the invention are compounds of Formula I, including pharmaceutically acceptable salts thereof, wherein:

A is selected from the group consisting of phenyl and heteroaryl; wherein heteroaryl is pyridinyl, furanyl or thienyl; and said phenyl or said heteroaryl is optionally substituted with one to two of the same or different amino, C$_{1-6}$alkyl, hydroxy, or halogen;

R$^9$, R$^{10}$, R$^{11}$, R$^{12}$, R$^{13}$, R$^{14}$, R$^{15}$, and R$^{16}$ are each independently hydrogen or methyl with the proviso that only one is methyl;

Q is either:

(a)

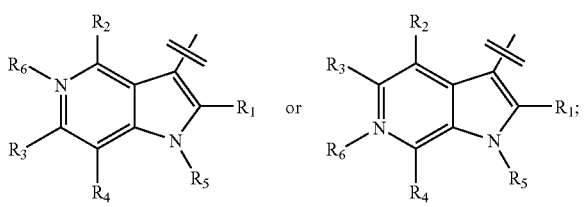

and then R$^2$ is selected from the group consisting of hydrogen, halogen and methoxy; and $R_3$ is hydrogen; or (b) Q is:

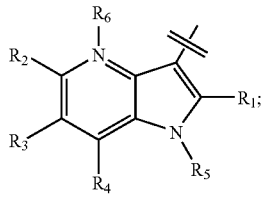

and $R^2$ is halogen or hydrogen and $R^3$ is hydrogen;

and for both (a) and (b):

$R^4$ is selected from the group consisting of B;

B is selected from the group consisting of —C(O)NR$^{40}$R$^{41}$, substituted phenyl, heteroaryl, oxazoline, pyrazinone and methylene dioxy or ethylene dioxy fused to a benzene or pyridine; wherein said heteroaryl or phenyl is optionally substituted with one to three same or different halogens or from one to two same or different substituents selected from the group F.

Another preferred embodiment of the invention are compounds of Formula I, including pharmaceutically acceptable salts thereof, wherein:

B is selected from the group consisting of —C(O)NR$^{40}$R$^{41}$, substituted phenyl and heteroaryl; wherein said phenyl is substituted and heteroaryl is optionally substituted with one to three same or different halogens or from one to two same or different substituents selected from the group F;

F is selected from the group consisting of $(C_{1-6})$alkyl, $(C_{3-6})$ cycloalkyl, aryl, heteroaryl, heteroalicyclic, hydroxy, $(C_{1-6})$alkoxy, $(C_{1-6})$thioalkoxy, cyano, halogen, —C(O)R$^{57}$, benzyl, —NR$^{42}$C(O)—$(C_{1-6})$alkyl, —NR$^{42}$C(O)—$(C_{3-6})$ cycloalkyl, —NR$^{42}$C(O)-aryl, —NR$^{42}$C(O)-heteroaryl, —NR$^{42}$C(O)-heteroalicyclic, 4, 5, or 6 membered ring cyclic N-lactam, —NR$^{42}$S(O)$_2$—$(C_{1-6})$alkyl, —NR$^{42}$R$^{43}$, C(O)NR$^{42}$R$^{43}$ and COOR$^{54}$; wherein said $(C_{1-6})$alkyl, $(C_{3-6})$cycloalkyl, aryl, heteroaryl, heteroalicyclic, $(C_{1-6})$ alkoxy, are optionally substituted with one to three same or different halogens or from one to two same or different substituents selected from the group G;

G is selected from the group consisting of $(C_{1-6})$alkyl, hydroxy, $(C_{1-6})$alkoxy, halogen, —NR$^{48}$C(O)—$(C_{1-6})$ alkyl, —NR$^{48}$C(O)—$(C_3)$cycloalkyl, 4, 5, or 6 membered ring cyclic N-lactam, —NR$^{48}$S(O)$_2$—$(C_{1-6})$alkyl, NR$^{48}$R$^{49}$, $(C_{1-6})$alkyl C(O)NR$^{48}$R$^{49}$, C(O)NR$^{48}$R$^{49}$ and $(C_{1-6})$alkylNR$^{48}$R$^{49}$;

$R^{40}$ is hydrogen; and $R^{41}$ is selected from the group consisting of $(C_{1-6})$alkyl, $(C_{3-7})$cycloalkyl, phenyl and heteroaryl; wherein said $(C_{1-6})$ alkyl, $(C_{3-7})$cycloalkyl, phenyl, or heteroaryl are substituted with one to three same or different halogens or one to two same or different substituents selected from the group consisting of methyl, $(C_{1-3})$alkoxy, heteroaryl and aryl; wherein said aryl or heteroaryl are optionally substituted with one to three same or different halogens or from one to two same or different substituents selected from the group consisting of $(C_{1-6})$alkyl, hydroxy, $(C_{1-6})$alkoxy, —NR$^{42}$C (O)—$(C_{1-6})$alkyl, NR$^{42}$R$^{43}$ and C(O)NR$^{42}$R$^{43}$.

Another preferred embodiment of the invention are compounds of Formula I, including pharmaceutically acceptable salts thereof, wherein:

Q is

A is Phenyl, 2-pyridyl, or 3-pyridyl;

B is selected from the group consisting of —C(O)NR$^{40}$R$^{41}$ or heteroaryl; wherein said heteroaryl is optionally substituted with one to three same or different halogens or from one to two same or different substituents selected from the group F.

Another preferred embodiment of the invention are compounds of Formula I, including pharmaceutically acceptable salts thereof, wherein:

B is heteroaryl, wherein said heteroaryl is optionally substituted with one to three same or different halogens or from one to two same or different substituents selected from the group F.

Another preferred embodiment of the invention are compounds of Formula I, including pharmaceutically acceptable salts thereof, wherein:

Q is

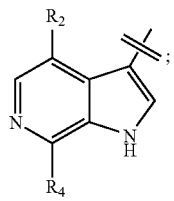

$R^2$ is selected from the group consisting of hydrogen, halogen, and methoxy;

$R^4$ is B;

B is selected from the group consisting of —C(O)NR$^{40}$R$^{41}$ or heteroaryl; wherein said heteroaryl is optionally substituted with one to three same or different halogens or from one to two same or different substituents selected from the group F.

Another preferred embodiment of the invention are compounds of Formula I, including pharmaceutically acceptable salts thereof, wherein:

A is phenyl, 2-pyridyl, or 3-pyridyl.

Another preferred embodiment of the invention are compounds of Formula I, including pharmaceutically acceptable salts thereof, wherein:

B is —C(O)NR$^{40}$R$^{41}$.

Another preferred embodiment of the invention are compounds of Formula I, including pharmaceutically acceptable salts thereof, wherein:
B is heteroaryl, wherein said heteroaryl is optionally substituted with one to three same or different halogens or from one to two same or different substituents selected from the group F.

Another preferred embodiment of the invention are compounds of Formula I, including pharmaceutically acceptable salts thereof,
wherein:
F is selected from the group consisting of $(C_{1-6})$alkyl, $(C_{3-6})$cycloalkyl $(C_{1-6})$alkoxy, hydroxy, heteroaryl, heteroalicyclic, methoxy, —S$(C_{1-3})$alkyl, halogen, —C(O)R$^{57}$, C(O)NR$^{42}$R$^{43}$, —NR$^{42}$C(O)—$(C_{1-6})$alkyl, —NR$^{42}$C(O)—$(C_{3-6})$cycloalkyl, —NR$^{42}$C(O)-aryl, —NR$^{42}$C(O)-heteroaryl, —NR$^{42}$C(O)-heteroalicyclic, 4, 5, or 6 membered ring cyclic N-lactam, —NR$^{42}$S(O)$_2$—$(C_{1-6})$alkyl, —NR$^{42}$S(O)$_2$—$(C_{3-6})$cycloalkyl, —NR$^{42}$S(O)2-aryl, —NR$^{42}$S(O)$_2$-heteroaryl, —NR$^{42}$S(O)2-heteroalicyclic, NR$^{42}$R$^{43}$, NR$^{55}$$(C_{1-3})$alkylNR$^{55}$R$^{56}$ and COOR$^{54}$.

Another preferred embodiment of the invention are compounds of Formula I, including pharmaceutically acceptable salts thereof,
wherein:
A is phenyl, 2-pyridyl, or 3-pyridyl.

Another preferred embodiment of the invention are compounds of Formula I, including pharmaceutically acceptable salts thereof,
wherein:
Q is

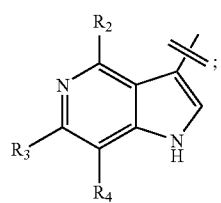

$R^2$ is selected from the group consisting of hydrogen and methoxy;
$R^3$ is hydrogen; and
B is selected from the group consisting of —C(O)NR$^{40}$R$^{41}$ and heteroaryl; wherein said heteroaryl is optionally substituted with one to three same or different halogens or from one to two same or different substituents selected from the group F.

Another preferred embodiment of the invention are compounds of Formula I, including pharmaceutically acceptable salts thereof,
wherein:
$R^2$ is fluoro.

Another preferred embodiment of the invention are compounds of Formula I, including pharmaceutically acceptable salts thereof,
wherein:
$R^2$ is methoxy.

Another preferred embodiment of the invention are compounds of Formula I, including pharmaceutically acceptable salts thereof,
wherein:
B is heteroaryl selected from the group consisting of thiazole, pyridazine, pyrazine, pyrazole, isoxazole, isothiazole, imidazole, furyl, thienyl, oxazole, oxadiazole, thiadiazole, pyrimidine, pyrazole, triazine, triazole, tetrazole, pyridyl, indole, azaindole, and diaza-indole; wherein said heteroaryl is optionally substituted with one to three same or different halogens or from one to two same or different substituents selected from the group F.

Another preferred embodiment of the invention are compounds of Formula I, including pharmaceutically acceptable salts thereof,
wherein:
B is heteroaryl selected from the group consisting of thiazole, pyridazine, pyrazine, pyrazole, isoxazole, isothiazole, imidazole, furyl, thienyl, oxazole, oxadiazole, thiadiazole, pyrimidine, pyrazole, triazine, triazole, tetrazole, pyridyl, indole, azaindole, and diaza-indole; wherein said heteroaryl is optionally substituted with one to three same or different halogens or from one to two same or different substituents selected from the group F.

Another preferred embodiment of the invention are compounds of Formula I, including pharmaceutically acceptable salts thereof,
wherein:
B is heteroaryl selected from the group consisting of thiazole, pyridazine, pyrazine, pyrazole, isoxazole, isothiazole, imidazole, furyl, thienyl, oxazole, oxadiazole, thiadiazole, pyrimidine, pyrazole, triazine, triazole, tetrazole, pyridyl, indole, azaindole, and diaza-indole; wherein said heteroaryl is optionally substituted with one to three same or different halogens or from one to two same or different substituents selected from the group F.

Another preferred embodiment of the invention are compounds of Formula I, including pharmaceutically acceptable salts thereof,
wherein:
B is heteroaryl selected from the group consisting of thiazole, pyridazine, pyrazine, pyrazole, isoxazole, isothiazole, imidazole, furyl, thienyl, oxazole, oxadiazole, thiadiazole, pyrimidine, pyrazole, triazine, triazole, tetrazole, pyridyl, indole, azaindole, and diaza-indole; wherein said heteroaryl is optionally substituted with one to three same or different halogens or from one to two same or different substituents selected from the group F.

Another preferred embodiment of the invention are compounds of Formula I, including pharmaceutically acceptable salts thereof,
wherein:
B is heteroaryl optionally substituted with one to three same or different halogens or a substituent selected from the group consisting of hydroxy, $C_1$-$C_6$ alkyl, $C_1$-$C_6$ alkoxy, $C_1$-$C_3$ thioalkoxy, amino, —C(O)H, —COOH, —COOC$_1$-C$_6$ alkyl, —NHC(O)—($C_1$-$C_6$ alkyl), —NHS(O)$_2$—($C_1$-$C_6$ alkyl), —C(O)—NH$_2$, C(O)NHMe, C(O)NMe2, trifluoromethyl, —NR$^{55}$R$^{56}$, NR$^{55}$R$^{56}$—($C_1$-$C_6$ alkyl)-NR$^{55}$R$^{56}$, -thiazole, pyrrole, piperazine, pyrrolidine and N-pyrrolidone.

Another preferred embodiment of the invention are compounds of Formula I, including pharmaceutically acceptable salts thereof,
wherein:
B is —C(O)NH-heteroaryl wherein said heteroaryl is optionally substituted with one to three same or different halogens or a substituent selected from the group consisting of ($C_1$-$C_6$ alkyl), amino, —NHC(O)—($C_1$-$C_6$ alkyl), -methoxy, —NHC($C_1$-$C_6$ alkyl) and —N($C_1$-$C_6$ alkyl)$_2$.

Another preferred embodiment of the invention are compounds of Formula I, including pharmaceutically acceptable salts thereof,
wherein:
B is heteroaryl optionally substituted with one to three same or different halogens or a substituent selected from the group consisting of ($C_1$-$C_6$ alkyl), amino, —NHC(O)—($C_1$-$C_6$ alkyl), —NHS(O)$_2$—($C_1$-$C_6$ alkyl), methoxy, —C(O)—NH$_2$, C(O)NHMe, C(O)NMe2, trifluoromethyl, —NHC($C_1$-$C_6$ alkyl), —N($C_1$-$C_6$ alkyl)$_2$, -heteroaryl and a 4, 5, or 6 membered cyclic N-lactam.

Another preferred embodiment of the invention are compounds of Formula I, including pharmaceutically acceptable salts thereof, wherein:

B is —C(O)NH-heteroaryl wherein said heteroaryl is optionally substituted with one to three same or different halogens or a substituent selected from the group consisting of ($C_1$-$C_6$ alkyl), amino, —NHC(O)—($C_1$-$C_6$ alkyl), -methoxy, —NHC($C_1$-$C_6$ alkyl) and —N($C_1$-$C_6$ alkyl)$_2$.

Another preferred embodiment of the invention are compounds of Formula I, including pharmaceutically acceptable salts thereof, wherein:

B is heteroaryl optionally substituted with one to three same or different halogens or a substituent selected from the group consisting of hydroxy, $C_1$-$C_6$ alkyl, $C_1$-$C_6$ alkoxy, $C_1$-$C_3$ thioalkoxy, amino, —C(O)H, —COOH, —COOC$_1$-$C_6$ alkyl, —NHC(O)—($C_{1-6}$alkyl), —NHS(O)$_2$—($C_1$-$C_6$ alkyl), methoxy, —C(O)—NH$_2$, C(O)NHMe, C(O)NMe2, trifluoromethyl, —NR$^{55}$R$^{56}$, NR$^{55}$R$^{56}$—($C_1$-$C_6$ alkyl)-NR$^{55}$R$^{56}$, -thiazole, pyrrole, piperazine, pyrrolidine and N-pyrrolidone.

Another preferred embodiment of the invention are compounds of Formula I, including pharmaceutically acceptable salts thereof, wherein:

B is —C(O)NH-heteroaryl wherein said heteroaryl is optionally substituted with one to three same or different halogens or a substituent selected from the group consisting of ($C_1$-$C_6$ alkyl), amino, —NHC(O)—($C_1$-$C_6$ alkyl), -methoxy, —NHC($C_1$-$C_6$ alkyl) and —N($C_1$-$C_6$ alkyl)$_2$.

Another preferred embodiment of the invention are compounds of Formula I, including pharmaceutically acceptable salts thereof, wherein:

B is thienyl.

Another preferred embodiment of the invention are compounds of Formula I, including pharmaceutically acceptable salts thereof, wherein:

B is thienyl optionally substituted with one to three same or different halogens or a substituent selected from the group consisting of hydroxy, $C_1$-$C_6$ alkyl, $C_1$-$C_6$ alkoxy, $C_1$-$C_3$ thioalkoxy, amino, —C(O)H, —COOH, —COOC$_1$-$C_6$ alkyl, —NHC(O)—($C_1$-$C_6$ alkyl), —NHS(O)$_2$—($C_1$-$C_6$ alkyl), —C(O)—NH$_2$, C(O)NHMe, C(O)NMe2, trifluoromethyl, —NR$^{55}$R$^{56}$, NR$^{55}$R$^{56}$—($C_1$-$C_6$ alkyl)-NR$^{55}$R$^{56}$, heteroaryl, piperazine, pyrrolidine, N-pyrrolidone and trifluoromethyl.

Another preferred embodiment of the invention are compounds of Formula I, including pharmaceutically acceptable salts thereof, wherein:

B is thienyl.

Another preferred embodiment of the invention are compounds of Formula I, including pharmaceutically acceptable salts thereof, wherein:

B is thienyl optionally substituted with one to three same or different halogens or a substituent selected from the group consisting of hydroxy, $C_1$-$C_6$ alkyl, amino, —NHC(O)—($C_1$-$C_6$ alkyl), —C(O)—NH$_2$, C(O)NHMe, C(O)NMe$_2$ and —NR$^{55}$R$^{56}$.

Another preferred embodiment of the invention are compounds of Formula I, including pharmaceutically acceptable salts thereof, wherein:

B is thienyl optionally substituted with one to three same or different halogens or a substituent selected from the group consisting of hydroxy, $C_1$-$C_6$ alkyl, $C_1$-$C_6$ alkoxy, $C_1$-$C_3$ thioalkoxy, amino, —C(O)H, —COOH, —COOC$_1$-$C_6$ alkyl, —NHC(O)—($C_1$-$C_6$ alkyl), —NHS(O)$_2$—($C_1$-$C_6$ alkyl), methoxy, —C(O)—NH$_2$, C(O)NHMe, C(O)NMe2, trifluoromethyl, —NR$^{55}$R$^{56}$, NR$^{55}$R$^{56}$—($C_1$-$C_6$ alkyl)-NR$^{55}$R$^{56}$, heteroaryl, piperazine, pyrrolidine, N-pyrrolidone and trifluoromethyl.

Another preferred embodiment of the invention are compounds of Formula I, including pharmaceutically acceptable salts thereof, wherein:

B is heteroaryl selected from the group consisting of thiazole, pyridazine, pyrazine, pyrazole, isoxazole, isothiazole, imidazole, furyl, thienyl, oxazole, oxadiazole, thiadiazole, pyrimidine, pyrazole, triazine, triazole, tetrazole and pyridyl; wherein said heteroaryl is optionally substituted with one to three same or different halogens or a substituent selected from the group F consisting of hydroxy, $C_1$-$C_6$ alkyl, $C_1$-$C_6$ alkoxy, $C_1$-$C_3$ thioalkoxy, amino, —C(O)H, —COOH, —COOC$_1$-$C_6$ alkyl, —NHC(O)—($C_1$-$C_6$ alkyl), —NHS(O)$_2$—($C_1$-$C_6$ alkyl), methoxy, —C(O)—NH$_2$, C(O)NHMe, C(O)NMe2, trifluoromethyl, —NR$^{55}$R$^{56}$, NR$^{55}$R$^{56}$—($C_1$-$C_6$ alkyl)-NR$^{55}$R$^{56}$, heteroaryl, piperazine, pyrrolidine, N-pyrrolidone and trifluoromethyl.

Another preferred embodiment of the invention are compounds of Formula I, including pharmaceutically acceptable salts thereof, wherein:

B is heteroaryl selected from the group consisting of thiazole, pyridazine, pyrazine, pyrazole, isoxazole, isothiazole, imidazole, furyl, thienyl, oxazole, oxadiazole, thiadiazole, pyrimidine, pyrazole, triazine, triazole, tetrazole and pyridyl; wherein said heteroaryl is optionally substituted with one to three same or different halogens or a substituent selected from the group F consisting of hydroxy, $C_1$-$C_6$ alkyl, $C_1$-$C_6$ alkoxy, $C_1$-$C_3$ thioalkoxy, amino, —C(O)H, —COOH, —COOC$_1$-$C_6$ alkyl, —NHC(O)—($C_1$-$C_6$ alkyl), —NHS(O)$_2$—($C_1$-$C_6$ alkyl), methoxy, —C(O)—NH$_2$, C(O)NHMe, C(O)NMe2, trifluoromethyl, —NR$^{55}$R$^{56}$, NR$^{55}$R$^{56}$—($C_1$-$C_6$ alkyl)-NR$^{55}$R$^{56}$, heteroaryl, piperazine, pyrrolidine, N-pyrrolidone and trifluoromethyl.

Another preferred embodiment of the invention are compounds of Formula I, including pharmaceutically acceptable salts thereof, wherein:

B is heteroaryl selected from the group consisting of thiazole, pyridazine, pyrazine, pyrazole, isoxazole, isothiazole, imidazole, furyl, thienyl, oxazole, oxadiazole, thiadiazole, pyrimidine, pyrazole, triazine, triazole, tetrazole and pyridyl; wherein said heteroaryl is optionally substituted with one to three same or different halogens or a substituent selected from the group F consisting of hydroxy, $C_1$-$C_6$ alkyl, $C_1$-$C_6$ alkoxy, $C_1$-$C_3$ thioalkoxy, amino, —C(O)H, —COOH, —COOC$_1$-C$_6$ alkyl, —NHC(O)—(C$_1$-C$_6$ alkyl), —NHS(O)$_2$—(C$_1$-C$_6$ alkyl), methoxy, —C(O)—NH$_2$, C(O)NHMe, C(O)NMe2, trifluoromethyl, —NR$^{55}$R$^{56}$, NR$^{55}$R$^{56}$—(C$_1$-C$_6$ alkyl)-NR$^{55}$R$^{56}$, heteroaryl, piperazine, pyrrolidine, N-pyrrolidone and trifluoromethyl.

Another preferred embodiment of the invention are compounds of Formula I, including pharmaceutically acceptable salts thereof,
wherein:
A compound of claim 3 is depicted in Table 2.

Another preferred embodiment of the invention are compounds of Formula I, including pharmaceutically acceptable salts thereof,
wherein:
A compound of claim 3 is depicted in Table 2-1.

Another preferred embodiment of the invention are compounds of Formula I, including pharmaceutically acceptable salts thereof,
wherein:
A compound of claim 3 is depicted in Table 3.

Another preferred embodiment of the invention are compounds of Formula I, including pharmaceutically acceptable salts thereof,
wherein:
A compound of claim 3 is depicted in Table 4.

Another preferred embodiment of the invention are compounds of Formula I, including pharmaceutically acceptable salts thereof,
wherein:
A compound of claim 3 is depicted in Table 5.

Another preferred embodiment of the invention are compounds of Formula I, including pharmaceutically acceptable salts thereof,
wherein:
A is selected from the group consisting of phenyl and heteroaryl; wherein heteroaryl is pyridinyl, furanyl or thienyl; wherein said phenyl or heteroaryl is independently optionally substituted with one to two of the same or different amino, C$_{1-6}$alkyl, or halogen;
—represents a carbon-carbon bond;
R$^9$, R$^{10}$, R$^{11}$, R$^{12}$, R$^{13}$, R$^{14}$, R$^{15}$, and R$^{16}$ are each independently hydrogen or methyl, with the proviso that only zero, one, or two is methyl;
Q is either:
(a)

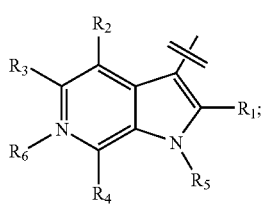

R$^2$ is selected from the group consisting of hydrogen, halogen, and methoxy; and
R$_3$ is hydrogen; or (b) Q is:

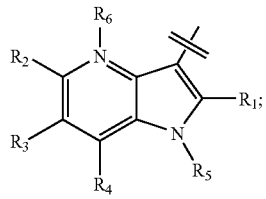

R$^2$ and R$^3$ are hydrogen;
and for both (a) and (b):
R$^4$ is selected from the group consisting of B;
B is heteroaryl selected from the group consisting of triazole, pyrazole, oxazole, pyrazine, pyrimidine and oxadiazole; wherein said heteroaryl is optionally substituted with one to three same or different halogens or from one to two same or different substituents selected from the group F;
F is selected from the group consisting of (C$_{1-6}$)alkyl, heteroaryl, —NR$^{42}$C(O)—(C$_{1-6}$)alkyl, —NR$^{42}$R$^{43}$ and C(O)NR$^{42}$R$^{43}$;
R$^5$ is hydrogen;
R$^6$ does not exist; and
R$^{42}$ and R$^{43}$ are independently selected from the group consisting of hydrogen and (C$_{1-6}$)alkyl; or R$^{42}$ and R$^{43}$ taken together with the nitrogen to which they are attached form a heteroalicyclic selected from the group consisting of aziridine, azetidine, pyrrolidine, piperazine, tetrahydrofuran, tetrahydropyran, azepine and morpholine.

Another preferred embodiment of the invention are compounds of Formula I, including pharmaceutically acceptable salts thereof,
wherein:
R$^2$ is H, Cl, F, or methoxy; and
R$^4$ is selected from the group consisting of

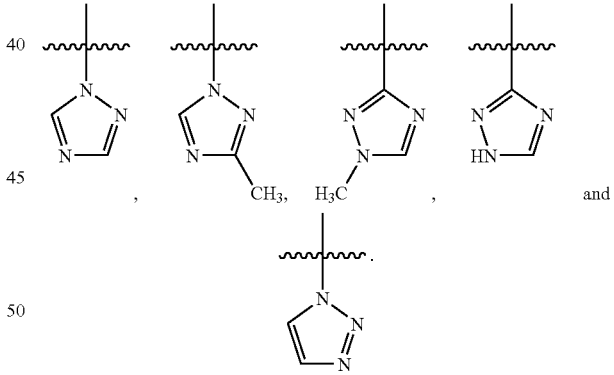

Another preferred embodiment of the invention are compounds of Formula I, including pharmaceutically acceptable salts thereof,
wherein:
R$^2$ is methoxy or fluoro; and
one of R$^9$, R$^{10}$, R$^{11}$ R$^{12}$, R$^{13}$, R$^{14}$, R$^{15}$, or R$^{16}$ is methyl and the others are hydrogen.

Another preferred embodiment of the invention are compounds of Formula I, including pharmaceutically acceptable salts thereof,
wherein:
R$^2$ is methoxy; and
R$^9$, R$^{10}$, R$^{11}$, R$^{12}$, R$^{13}$, R$^{14}$, R$^{15}$, and R$^{16}$ are each hydrogen.

Another preferred embodiment of the invention are compounds of Formula I, including pharmaceutically acceptable salts thereof,
wherein:
one of $R^9$, $R^{10}$, $R^{11}$, $R^{12}$, $R^{13}$, $R^{14}$, $R^{15}$, or $R^{16}$ is (R)-methyl and the others are hydrogen.

Another preferred embodiment of the invention are compounds of Formula I, including pharmaceutically acceptable salts thereof,
wherein:
one of $R^9$, $R^{10}$, $R^{11}$, $R^{12}$, $R^{13}$, $R^{14}$, $R^{15}$, or $R^{16}$ is (S)-methyl and the others are hydrogen.

Another preferred embodiment of the invention are compounds of Formula I, including pharmaceutically acceptable salts thereof,
wherein:
$R^2$ is methoxy, hydrogen, chloro, or fluoro; and
$R^4$ is oxadiazole.

Another preferred embodiment of the invention are compounds of Formula I, including pharmaceutically acceptable salts thereof,
wherein:
$R^2$ is methoxy, hydrogen, chloro or fluoro; and
$R^4$ is oxadiazole substituted with a single fluoro, chloro, amino or methyl group.

Another preferred embodiment of the invention are compounds of Formula I, including pharmaceutically acceptable salts thereof,
wherein:
A is selected from the group consisting of phenyl and heteroaryl; wherein said heteroaryl is pyridinyl, furanyl or thienyl; and said phenyl or said heteroaryl is optionally substituted with one to two of the same or different amino, $C_{1-6}$alkyl, hydroxy, or halogen;
$R^9$, $R^{10}$, $R^{11}$, $R^{12}$, $R^{15}$, and $R^{16}$ are each hydrogen;
$R^{13}$ and $R^{14}$ are each independently hydrogen or methyl with the proviso that only one is methyl;
Q is either:

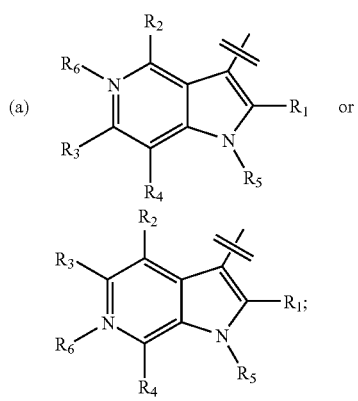

$R^2$ is selected from the group consisting of hydrogen, halogen and methoxy; and
$R_3$ is hydrogen; or (b) Q is:

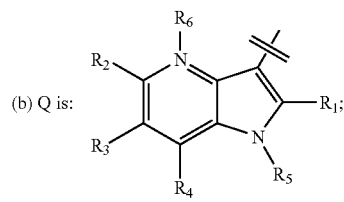

and $R^2$ is halogen or hydrogen and $R^3$ is hydrogen;
and for both (a) and (b):
$R^4$ is selected from the group consisting of B; and
B is selected from the group consisting of —C(O)NR$^{40}$R$^{41}$, substituted phenyl, heteroaryl, oxazoline, pyrazinone, methylene dioxy or ethylene dioxy fused to a benzene or pyridine; wherein said heteroaryl or phenyl is optionally substituted with one to three same or different halogens or from one to two same or different substituents selected from the group F.

Another preferred embodiment of the invention are compounds of Formula I, including pharmaceutically acceptable salts thereof,
wherein:
B is selected from the group consisting of —C(O)NR$^{40}$R$^{41}$, substituted phenyl and heteroaryl; wherein said phenyl is substituted and heteroaryl is optionally substituted with one to three same or different halogens or from one to two same or different substituents selected from the group F;
F is selected from the group consisting of $(C_{1-6})$alkyl, $(C_{3-6})$cycloalkyl, aryl, heteroaryl, heteroalicyclic, hydroxy, $(C_{1-6})$alkoxy, $(C_{1-6})$thioalkoxy, cyano, halogen, —C(O)R$^{57}$, benzyl, —NR$^{42}$C(O)—$(C_{1-6})$alkyl, —NR$^{42}$C(O)—$(C_{3-6})$cycloalkyl, —NR$^{42}$C(O)-aryl, —NR$^{42}$C(O)-heteroaryl, —NR$^{42}$C(O)-heteroalicyclic, 4, 5, or 6 membered ring cyclic N-lactam, —NR$^{42}$S(O)$_2$—$(C_{1-6})$alkyl, —NR$^{42}$R$^{43}$, C(O)NR$^{42}$R$^{43}$ and COOR$^{54}$; wherein said $(C_{1-6})$alkyl, $(C_{3-6})$cycloalkyl, aryl, heteroaryl, heteroalicyclic, $(C_{1-6})$alkoxy, are optionally substituted with one to three same or different halogens or from one to two same or different substituents selected from the group G;
G is selected from the group consisting of $(C_{1-6})$alkyl, hydroxy, $(C_{1-6})$alkoxy, halogen, —NR$^{48}$C(O)—$(C_{1-6})$alkyl, —NR$^{48}$C(O)—$(C_3)$cycloalkyl, 4, 5, or 6 membered ring cyclic N-lactam, —NR$^{48}$S(O)$_2$—$(C_{1-6})$alkyl, NR$^{48}$R$^{49}$, $(C_{1-6})$alkyl C(O)NR$^{48}$R$^{49}$, C(O)NR$^{48}$R$^{49}$ and $(C_{1-6})$alkylNR$^{48}$R$^{49}$;
$R^{40}$ is hydrogen;
$R^{41}$ is $(C_{1-6})$alkyl, $(C_{3-7})$cycloalkyl, phenyl, or heteroaryl; wherein said $(C_{1-6})$alkyl, $(C_{3-7})$cycloalkyl, phenyl, or heteroaryl are substituted with one to three same or different halogens or one to two same or different methyl, $(C_{1-3})$alkoxy, heteroaryl or aryl; wherein said aryl or heteroaryl are optionally substituted with one to three same or different halogens or from one to two same or different substituents selected from the group consisting of $(C_{1-6})$alkyl, hydroxy, $(C_{1-6})$alkoxy, —NR$^{42}$C(O)—$(C_{1-6})$alkyl, NR$^{42}$R$^{43}$ and C(O)NR$^{42}$R$^{43}$.

Another preferred embodiment of the invention are compounds of Formula I, including pharmaceutically acceptable salts thereof,
wherein:
A is selected from the group consisting of phenyl and heteroaryl; wherein heteroaryl is pyridinyl, furanyl or thienyl;

and said phenyl or said heteroaryl is optionally substituted with one to two of the same or different amino, $C_{1-6}$alkyl, hydroxy, or halogen;

$R^9$, $R^{10}$, $R^{11}$, $R^{12}$, $R^{13}$, $R^{14}$, $R^{15}$ and $R^{16}$ are each independently hydrogen or methyl with the proviso that only one is methyl;

Q is either:

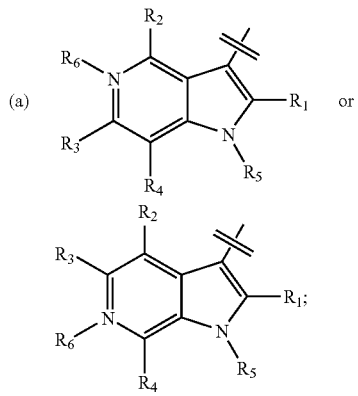

wherein $R^2$ is selected from the group consisting of hydrogen, halogen and methoxy; and
$R_3$ is hydrogen; or (b) Q is:

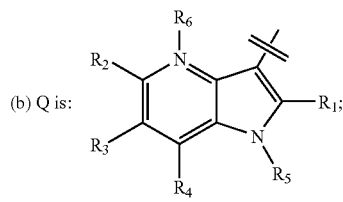

wherein $R^2$ is halogen or hydrogen; and $R^3$ is hydrogen;
and for both (a) and (b):
$R^4$ is selected from the group consisting of B;
B is selected from the group consisting of —C(O)NR$^{40}$R$^{41}$, substituted phenyl, heteroaryl, oxazoline, pyrazinone, methylene dioxy or ethylene dioxy fused to a benzene or pyridine; wherein said heteroaryl or phenyl is optionally substituted with one to three same or different halogens or from one to two same or different substituents selected from the group F.

Another preferred embodiment of the invention are compounds of Formula I, including pharmaceutically acceptable salts thereof,
wherein:
B is selected from the group consisting of pyrazinone and methylene dioxy or ethylene dioxy fused to a benzene ring; wherein said group is optionally substituted with one to three same or different halogens or a substituent selected from the group —F consisting of ($C_1$-$C_6$ alkyl), amino, —NHC(O)—($C_1$-$C_6$ alkyl), —NHS(O)$_2$—($C_1$-$C_6$ alkyl), methoxy, —C(O)—NH$_2$, C(O)NHMe, C(O)NMe2, trifluoromethyl, —NHC($C_1$-$C_6$ alkyl), —N($C_1$-$C_6$ alkyl)$_2$, -heteroaryl and a 4, 5, or 6 membered cyclic N-lactam.

Another preferred embodiment of the invention are compounds of Formula I, including pharmaceutically acceptable salts thereof,
wherein:
B is selected from the group consisting of oxadiazole, triazole, pyrazole, pyrazine and pyrimidine; wherein said group is optionally substituted with one to three same or different halogens or a substituent selected from the group F consisting of ($C_1$-$C_6$ alkyl), amino, —NHC(O)—($C_1$-$C_6$ alkyl), —NHS(O)$_2$—($C_1$-$C_6$ alkyl), methoxy, —C(O)—NH$_2$, C(O)NHMe, C(O)NMe2, trifluoromethyl, —NHC($C_1$-$C_6$ alkyl), —N($C_1$-$C_6$ alkyl)$_2$, -heteroaryl, a 4, 5, or 6 membered cyclic N-lactam and ($C_{1-6}$)alkylNR$^{48}$R$^{49}$.

Another preferred embodiment of the invention are compounds of Formula I, including pharmaceutically acceptable salts thereof,
wherein:
heteroaryl in B is selected from the group consisting of pyrazine and pyrimidine.

Another preferred embodiment of the invention are compounds of Formula I, including pharmaceutically acceptable salts thereof,
wherein:
heteroaryl in B is selected from the group consisting of pyrazine and pyrimidine.

Another preferred embodiment of the invention are compounds of Formula I, including pharmaceutically acceptable salts thereof,
wherein:
wherein $R^9$, $R^{10}$, $R^{15}$ and $R^{16}$ are each hydrogen; and $R^{11}$, $R^{12}$, $R^{13}$, and $R^{14}$ are each independently hydrogen or methyl with the proviso that up to one can be methyl.

Another preferred embodiment of the invention are compounds of Formula I, including pharmaceutically acceptable salts thereof,
wherein:
one of $R^{11}$, $R^{12}$, $R^{13}$, and $R^{14}$ is methyl.

Another preferred embodiment of the invention are compounds of Formula I, including pharmaceutically acceptable salts thereof,
wherein:
the carbon atom of the piperazine ring to which the methyl group of $R^{11}$, $R^{12}$, $R^{13}$, and $R^{14}$ is attached has an (R) configuration.

Another preferred embodiment of the invention are compounds of Formula I, including pharmaceutically acceptable salts thereof,
wherein:
$R^{11}$, $R^{12}$, $R^{13}$, and $R^{14}$ are each hydrogen; and $R^9$, $R^{10}$, $R^{15}$ and $R^{16}$ are each independently hydrogen or methyl with the proviso that up to one can be methyl.

Another preferred embodiment of the invention are compounds of Formula I, including pharmaceutically acceptable salts thereof,
wherein:
one of $R^9$, $R^{10}$, $R^{15}$ and $R^{16}$ is methyl.

Another preferred embodiment of the invention are compounds of Formula I, including pharmaceutically acceptable salts thereof,
wherein:
the carbon atom of the piperazine ring to which the methyl group of $R^9$, $R^{10}$, $R^{15}$ and $R^{16}$ is attached has an (R) configuration.

Another preferred embodiment of the invention are compounds of Formula I, including pharmaceutically acceptable salts thereof,
wherein:
$R^1$ is hydrogen;
m is 2;
$R^5$ is hydrogen;

$R^6$ does not exist;

A is selected from the group consisting of $C_{1-6}$alkoxy, aryl and heteroaryl; wherein aryl is phenyl; heteroaryl is selected from the group consisting of pyridinyl, pyrimidinyl, pyrazinyl, triazinyl, furanyl, thienyl, pyrrolyl, imidazolyl, thiazolyl, oxazolyl and isoxazolyl; and said aryl or heteroaryl is optionally substituted with one or two of the same or different amino, cyano, hydroxy $C_{1-6}$alkoxy, $C_{1-6}$alkyl, —NHC(O)CH$_3$, halogen and trifluoromethyl; and — represents a carbon-carbon bond.

A most preferred embodiment is a compound of Formula Ia, including pharmaceutically acceptable salts thereof,

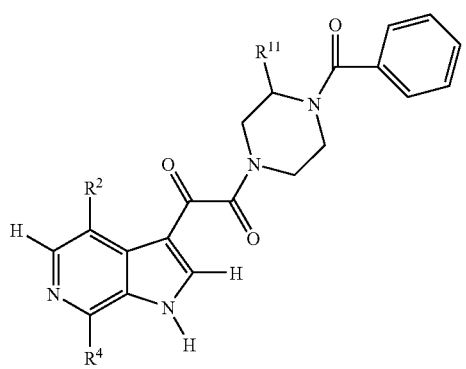

Ia wherein:
$R^2$ is methoxy, fluoro or chloro.
$R^4$ is selected from the group consisting of either:

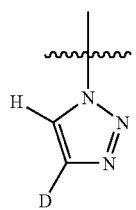

which is a 1,2,3 triazole directly attached via the nitrogen atom of position 1 of the triazole wherein said 1,2,3 triazole is substituted with D at position 4 or $R^4$ is:

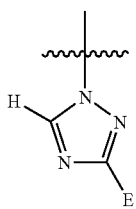

which is a 1,2,4 triazole attached via the nitrogen atom of position 1 of the triazole wherein said 1,2,4 triazole is substituted with E at position 3.
D is selected from hydrogen or $C_1$-$C_3$ alkyl.
E is selected from the group consisting hydrogen, ($C_1$-$C_3$) alkyl, O($C_1$-$C_3$)alkyl or CH$_2$OCH$_3$.

$R^{11}$ is either hydrogen or methyl in which the configuration to which the methyl is attached is (R) with the proviso that when $R^4$ is 1,2,3 triazole, then $R^{11}$ is hydrogen.

Another embodiment of the invention is a pharmaceutical formulation comprising an antiviral effective amount of a compound of Formula I, including pharmaceutically acceptable salts thereof and a pharmaceutically acceptable carrier. When used for treating HIV infection, said formulation can optionally additionally contain an antiviral effective amount of an AIDS treatment agent selected from the group consisting of: an AIDS antiviral agent; an antiinfective agent; an immunomodulator; and HIV entry inhibitors.

A third embodiment of the invention is a method for treating mammals infected with a virus, such as HIV, comprising administering to said mammal an antiviral effective amount of a compound of Formula I, including pharmaceutically acceptable salts thereof, a pharmaceutically acceptable carrier, optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

Definitions

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —NR$^x$R$^y$ with R$^x$ and R$^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a Z$_3$CC (=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z and R$^X$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—

A "S-sulfonamido" group refers to a —S(=O)$_2$NR$^X$R$^Y$, with R$^X$ and R$^Y$ as defined herein.

A "N-Sulfonamido" group refers to a R"S(=O)$_2$NR$_X$— group with R$_x$ as defined herein.

A "O-carbamyl" group refers to a —OC(=O)NR$^x$R$^y$ as defined herein.

A "N-carbamyl" group refers to a R$^x$OC(=O)NR$^y$ group, with R$^x$ and R$^y$ as defined herein.

A "O-thiocarbamyl" group refers to a —OC(=S)NR$^x$R$^y$ group with R$^x$ and R$^y$ as defined herein.

A "N-thiocarbamyl" group refers to a R$^x$OC(=S)NR$^y$— group with R$^x$ and R$^y$ as defined herein.

An "amino" group refers to an —NH$_2$ group.

A "C-amido" group refers to a —C(=O)NR$^x$R$^y$ group with R$^x$ and R$^y$ as defined herein.

A "C-thioamido" group refers to a —C(=S)NR$^x$R$^y$ group, with R$^x$ and R$^y$ as defined herein.

A "N-amido" group refers to a R$^x$C(=O)NR$^y$— group, with R$^x$ and R$^y$ as defined herein.

A cyclic 4, 5, or six membered ring N-lactam refers to rings of 4, 5 or 6 atoms containing a single amide group as two of the ring atoms which is linked to the parent molecule at the amide nitrogen.

An "ureido" group refers to a —NR$^x$C(=O)NR$^y$R$^{y2}$ group with R$^x$ and R$^y$ as defined herein and R$^{y2}$ defined the same as R$^x$ and R$^y$.

A "guanidino" group refers to a —R$^x$NC(=N)NR$^y$R$^{y2}$ group, with R$^x$, R$^y$ and R$^{y2}$ as defined herein.

A "guanyl" group refers to a R$^x$R$^y$NC(=N)— group, with R$^x$ and R$^Y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with R$^x$ as defined herein.

A "hydrazino" group refers to a —NR$^x$NR$^y$R$^{y2}$ group with R$^x$, R$^y$ and R$^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

| ANTIVIRALS | | |
|---|---|---|
| Drug Name | Manufacturer | Indication |
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus | MedImmune | CMV retinitis |

-continued

ANTIVIRALS

| Drug Name | Manufacturer | Indication |
|---|---|---|
| Immune globin | | |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON (or T-20) | Roche/Trimeris | HIV infection AIDs, viral Fusion inhibitor |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony | Schering-Plough | AIDS, combination |

-continued

IMMUNOMODULATORS

| Drug Name | Manufacturer | Indication |
|---|---|---|
| Stimulating Factor HIV Core Particle Immunostimulant | Rorer | w/AZT Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |

-continued

ANTI-INFECTIVES

| Drug Name | Manufacturer | Indication |
|---|---|---|
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butyl-carboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The preparative procedures and anti-HIV-1 activity of the novel azaindole piperazine diamide analogs of Formula I are summarized below in Schemes 1-64.

ABBREVIATIONS

The following abbreviations, most of which are conventional abbreviations well known to those skilled in the art, are used throughout the description of the invention and the examples. Some of the abbreviations used are as follows:
h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydrofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
mCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
PMB=4-Methoxybenzyl
DDQ=2,3-Dichloro-5,6-dicyano-1,4-benzoquinone
OTf=Trifluoromethanesulfonoxy
NMM=4-Methylmorpholine
PIP—COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahydrofuran
EtOAc=Ethyl Acetate
LDA=Lithium diisopropylamide
TMP-Li=2,2,6,6-tetramethylpiperidinyl lithium
DME=Dimethoxyethane
DIBALH=Diisobutylaluminum hydride
HOBT=1-hydroxybenzotriazole
CBZ=Benzyloxycarbonyl
PCC=Pyridinium chlorochromate
Me=Methyl
Ph=Phenyl Chemistry The present invention comprises compounds of Formula I, their pharmaceutical formulations, and their use in patients suffering from or susceptible to HIV infection. The compounds of Formula I include pharmaceutically acceptable salts thereof.

General procedures to construct substituted azaindole piperazine diamides of Formula I and intermediates useful for their synthesis are described in the following Schemes, 1-81.

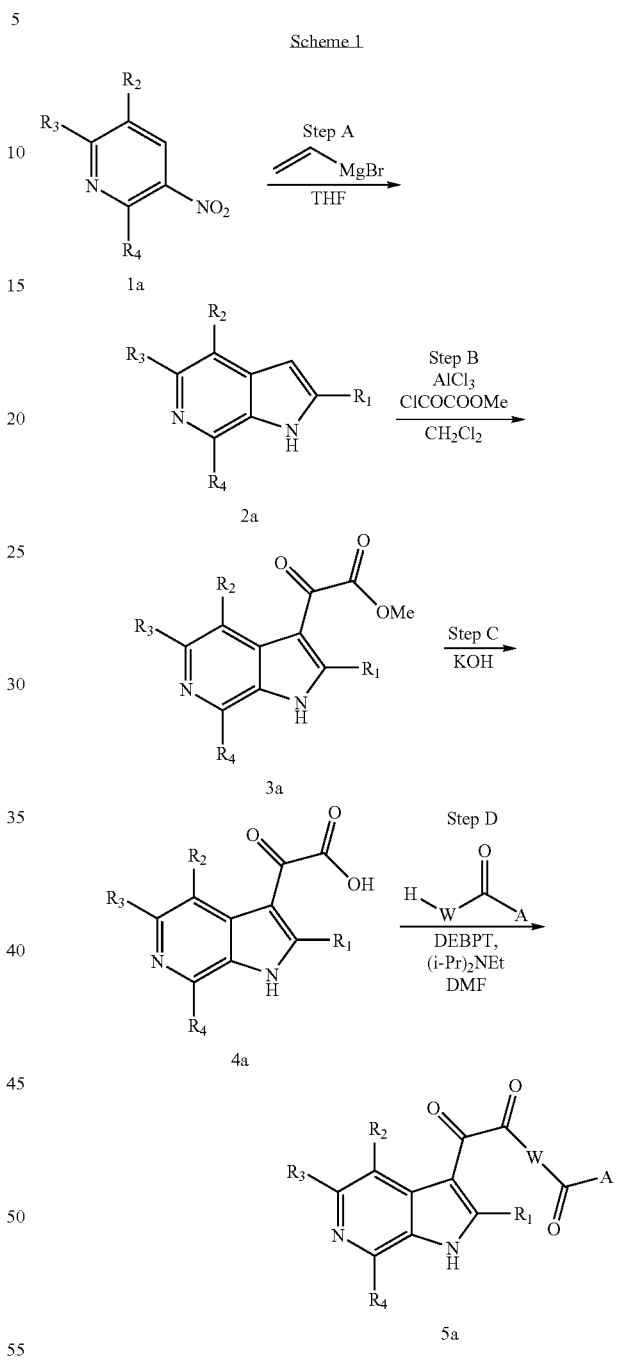

Step A in Scheme 1 depicts the synthesis of an aza indole intermediate, 2a, via the well known Bartoli reaction in which vinyl magnesium bromide reacts with an aryl or heteroaryl nitro group, such as in 1, to form a five-membered nitrogen containing ring as shown. Some references for the above transformation include: Bartoli et al. a) *Tetrahedron Lett.* 1989, 30, 2129. b) *J. Chem. Soc. Perkin Trans.* 1 1991, 2757. c) *J. Chem. Soc. Perkin Trans. II* 1991, 657. d) SynLett (1999), 1594. In the preferred procedure, a solution of vinyl Magnesium bromide in THF (typically 1.0M but from 0.25 to 3.0M) is added dropwise to a solution of the nitro pyridine in THF at −78° under an inert atmosphere of either nitrogen or Argon. After addition is completed, the reaction temperature is allowed to warm to −20° and then is stirred for approximately 12 h before quenching with 20% aq ammonium chloride solution. The reaction is extracted with ethyl acetate and then worked up in a typical manner using a drying agent such as anhydrous magnesium sulfate or sodium sulfate. Products are generally purified using chromatography over Silica gel. Best results are generally achieved using freshly prepared vinyl Magnesium bromide. In some cases, vinyl Magnesium chloride may be substituted for vinyl Magnesium bromide.

Substituted azaindoles may be prepared by methods described in the literature or may be available from commercial sources. Thus there are many methods for carrying out step A in the literature and the specific examples are too numerous to even list. Alternative syntheses of aza indoles and general methods for carrying out step A include, but are not limited to, those described in the following references (a-k below): a) Prokopov, A. A.; Yakhontov, L. N. *Khim.-Farm. Zh.* 1994, 28(7), 30-51; b) Lablache-Combier, A. Heteroaromatics. Photoinduced Electron Transfer 1988, Pt. C, 134-312; c) Saify, Zafar Said. *Pak. J. Pharmacol.* 1986, 2(2), 43-6; d) Bisagni, E. *Jerusalem Symp. Quantum Chem. Biochem.* 1972, 4, 439-45; e) Yakhontov, L. N. *Usp. Khim.* 1968, 37(7), 1258-87; f) Willette, R. E. *Advan. Heterocycl. Chem.* 1968, 9, 27-105; g) Mahadevan, I.; Rasmussen, M. *Tetrahedron* 1993, 49(33), 7337-52; h) Mahadevan, I.; Rasmussen, M. *J. Heterocycl. Chem.* 1992, 29(2), 359-67; i) Spivey, A. C.; Fekner, T.; Spey, S. E.; Adams, H. *J. Org. Chem.* 1999, 64(26), 9430-9443; j) Spivey, A. C.; Fekner, T.; Adams, H. *Tetrahedron Lett.* 1998, 39(48), 8919-8922; k) Advances in Heterocyclic Chemistry (Academic press) 1991, Vol. 52, pg 235-236 and references therein.

Step B. Intermediate 3a can be prepared by reaction of aza-indole, intermediate 2a, with an excess of ClCOCOOMe in the presence of AlCl$_3$ (aluminum chloride) (Sycheva et al, Ref. 26, Sycheva, T. V.; Rubtsov, N. M.; Sheinker, Yu. N.; Yakhontov, L. N. Some reactions of 5-cyano-6-chloro-7-azaindoles and lactam-lactim tautomerism in 5-cyano-6-hydroxy-7-azaindolines. *Khim. Geterotsikl. Soedin.*, 1987, 100-106). Typically an inert solvent such as CH$_2$Cl$_2$ is used but others such as THF, Et$_2$O, DCE, dioxane, benzene, or toluene may find applicability either alone or in mixtures. Other oxalate esters such as ethyl or benzyl mono esters of oxalic acid could also suffice for either method shown above. More lipophilic esters ease isolation during aqueous extractions. Phenolic or substituted phenolic (such as pentafluorophenol) esters enable direct coupling of the HW(C=O)A group, such as a piperazine, in Step D without activation. Lewis acid catalysts, such as tin tetrachloride, titanium IV chloride, and aluminum chloride are employed in Step B with aluminum chloride being most preferred. Alternatively, the azaindole is treated with a Grignard reagent such as MeMgI (methyl magnesium iodide), methyl magnesium bromide or ethyl magnesium bromide and a zinc halide, such as ZnCl$_2$ (zinc chloride) or zinc bromide, followed by the addition of an oxalyl chloride mono ester, such as ClCOCOOMe (methyl chlorooxoacetate) or another ester as above, to afford the aza-indole glyoxyl ester (Shadrina et al, Ref. 25). Oxalic acid esters such as methyl oxalate, ethyl oxalate or as above are used. Aprotic solvents such as CH$_2$Cl$_2$, Et$_2$O, benzene, toluene, DCE, or the like may be used alone or in combination for this sequence. In addition to the oxalyl chloride mono esters, oxalyl chloride itself may be reacted with the azaindole and then further reacted with an appropriate amine, such as a piperazine derivative (See Scheme 52, for example).

Step C. Hydrolysis of the methyl ester, (intermediate 3a, Scheme 1) affords a potassium salt of intermediate 4a, which is coupled with mono-benzoylated piperazine derivatives as shown in Step D of Scheme 1. Some typical conditions employ methanolic or ethanolic sodium hydroxide followed by careful acidification with aqueous hydrochloric acid of varying molarity but 1M HCl is preferred. The acidification is not utilized in many cases as described above for the preferred conditions. Lithium hydroxide or potassium hydroxide could also be employed and varying amounts of water could be added to the alcohols. Propanols or butanols could also be used as solvents. Elevated temperatures up to the boiling points of the solvents may be utilized if ambient temperatures do not suffice. Alternatively, the hydrolysis may be carried out in a non polar solvent such as CH$_2$Cl$_2$ or THF in the presence of Triton B. Temperatures of −78° C. to the boiling point of the solvent may be employed but −10° C. is preferred. Other conditions for ester hydrolysis are listed in reference 41 and both this reference and many of the conditions for ester hydrolysis are well known to chemists of average skill in the art.

Alternative Procedures for Step B and C:

Imidazolium Chloroaluminate:

We found that ionic liquid 1-alkyl-3-alkylimidazolium chloroaluminate is generally useful in promoting the Friedel-Crafts type acylation of indoles and azaindoles. The ionic liquid is generated by mixing 1-alkyl-3-alkylimidazolium chloride with aluminium chloride at room temperature with vigorous stirring. 1:2 or 1:3 molar ratio of 1-alkyl-3-alkylimidazolium chloride to aluminium chloride is preferred. One particular useful imidazolium chloroaluminate for the acylation of azaindole with methyl or ethyl chlorooxoacetate is the 1-ethyl-3-methylimidazolium chloroaluminate. The reaction is typically performed at ambient temperature and the azaindoleglyoxyl ester can be isolated. More conveniently, we found that the glyoxyl ester can be hydrolyzed in situ at ambient temperature on prolonged reaction time (typically overnight) to give the corresponding glyoxyl acid for amide formation (Scheme 1).

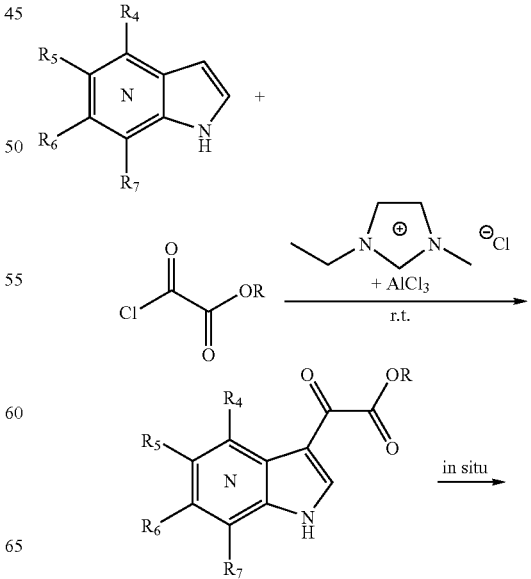

Scheme 1

-continued

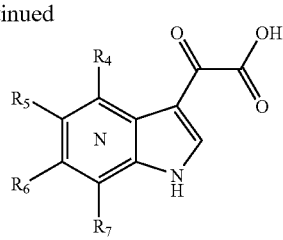

R = Me or Et

A representative experimental procedure is as follows: 1-ethyl-3-methylimidazolium chloride (2 equiv.; purchased from TCI; weighted under a stream of nitrogen) was stirred in an oven-dried round bottom flask at r.t. under a nitrogen atmosphere, and added aluminium chloride (6 equiv.; anhydrous powder packaged under argon in ampules purchased from Aldrich preferred; weighted under a stream of nitrogen). The mixture was vigorously stirred to form a liquid, which was then added azaindole (1 equiv.) and stirred until a homogenous mixture resulted. The reaction mixture was added dropwise ethyl or methyl chlorooxoacetate (2 equiv.) and then stirred at r.t. for 16 h. After which time, the mixture was cooled in an ice-water bath and the reaction quenched by carefully adding excess water. The precipitates were filtered, washed with water and dried under high vacuum to give the azaindoleglyoxyl acid. For some examples, 3 equivalents of 1-ethyl-3-methylimidazolium chloride and chlorooxoacetate may be required.

Related references: (1) Welton, T. *Chem. Rev.* 1999, 99, 2071; (2) Surette, J. K. D.; Green, L.; Singer, R. D. *Chem. Commun.* 1996, 2753; (3) Saleh, R. Y. WO 0015594.

Step D. The acid intermediate, 4a, from step C of Scheme 1 is coupled with an amine A(C=O)WH preferably in the presence of DEPBT (3-(diethoxyphosphoryloxy)-1,2,3-benzotriazin-4(3H)-one) and N,N-diisopropylethylamine, commonly known as Hunig's base, to provide azaindole piperazine diamides. DEPBT was prepared according to the procedure of Ref. 28, Li, H.; Jiang, X.; Ye, Y.-H.; Fan, C.; Romoff, T.; Goodman, M. *Organic Lett.*, 1999, 1, 91-93. Typically an inert solvent such as DMF or THF is used but other aprotic solvents could be used. The group W as referred to herein is

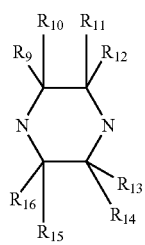

The amide bond construction reaction could be carried out using the preferred conditions described above, the EDC conditions described below, other coupling conditions described in this application, or alternatively by applying the conditions or coupling reagents for amide bond construction described later in this application for construction of substituents $R_1$-$R_4$. Some specific nonlimiting examples are given in this application.

The mono-substituted piperazine derivatives can be prepared according to well established procedures such as those described by Desai et al, Ref. 27(a), Adamczyk et al, Ref. 27(b), Rossen et al, Ref. 27(c), and Wang et al, 27(d).

Additional procedures for synthesizing, modifying and attaching groups: $(C=O)_m$—WC(O)-A are contained in PCT WO 00/71535.

Scheme 2

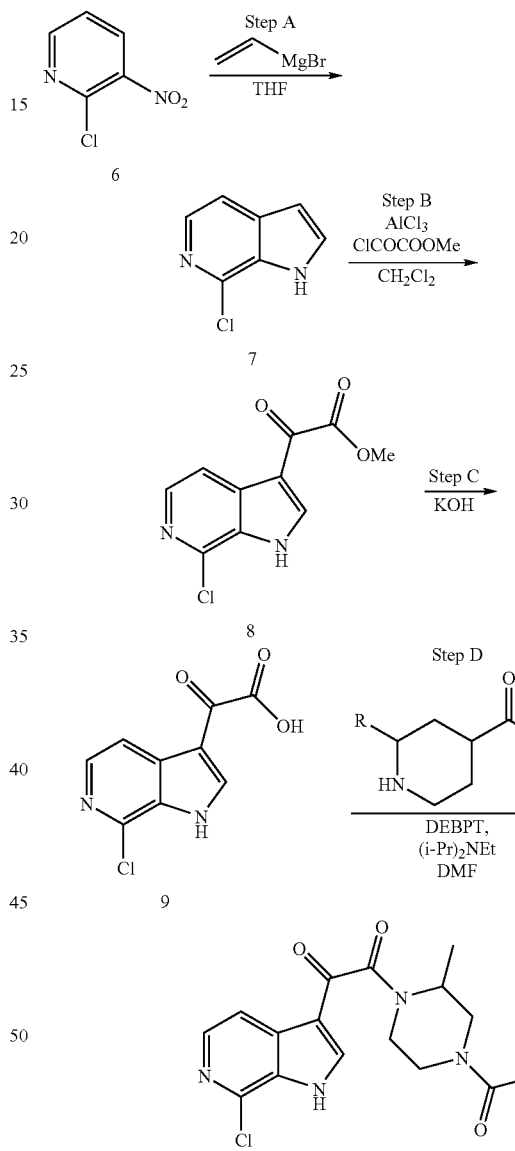

Scheme 2 provides a more specific example of the transformations previously described in Scheme 1. Intermediates 6-10 are prepared by the methodologies as described for intermediates 1a-5a in Scheme 1. Scheme 2A is another embodiment of the transformations described in Schemes 1 and 2. Conversion of the phenol to the chloride (Step S, Scheme 2A) may be accomplished according to the procedures described in Reimann, E.; Wichmann, P.; Hoefner, G.; *Sci. Pharm.* 1996, 64(3), 637-646; and Katritzky, A. R.; Rachwal, S.; Smith, T. P.; Steel, P. J.; *J. Heterocycl. Chem.* 1995, 32(3), 979-984. Step T of Scheme 2A can be carried out as described for Step A of Scheme 1. The bromo intermediate can then be converted into alkoxy, chloro, or fluoro intermediates as shown in Step U of Scheme 2A, Scheme 2A describes the preferred method for preparing intermediate 6c or other closely related compounds containing a 4 methoxy group in the 6-azaindole system. When step U is the conversion of the bromide into alkoxy derivatives, the conversion may be carried out by reacting the bromide with an excess of sodium methoxide in methanol with cuprous salts, such as copper I bromide, copper I iodide, and copper I cyanide. The temperature may be carried out at temperatures of between ambient and 175° but most likely will be around 115° C. or 100° C. The reaction may be run in a pressure vessel or sealed tube to prevent escape of volatiles such as methanol. The preferred conditions utilize 3 eq of sodium methoxide in methanol, CuBr as the reaction catalyst (0.2 to 3 equivalents with the preferred being 1 eq or less), and a reaction temperature of 115° C. The reaction is carried out in a sealed tube or sealed reaction vessel. The conversion of the bromide into alkoxy derivatives may also be carried out according to procedures described in Palucki, M.; Wolfe, J. P.; Buchwald, S. L.; *J. Am. Chem. Soc.* 1997, 119(14), 3395-3396; Yamato, T.; Komine, M.; Nagano, Y.; *Org. Prep. Proc. Int.* 1997, 29(3), 300-303; Rychnovsky, S. D.; Hwang, K.; *J. Org. Chem.* 1994, 59(18), 5414-5418. Conversion of the bromide to the fluoro derivative (Step U, Scheme 2A) may be accomplished according to Antipin, I. S.; Vigalok, A. I.; Konovalov, A. I.; *Zh. Org. Khim.* 1991, 27(7), 1577-1577; and Uchibori, Y.; Umeno, M.; Seto, H.; Qian, Z.; Yoshioka, H.; *Synlett.* 1992, 4, 345-346. Conversion of the bromide to the chloro derivative (Step U, Scheme 2A) may be accomplished according to procedures described in Gilbert, E. J.; Van Vranken, D. L.; *J. Am. Chem. Soc.* 1996, 118(23), 5500-5501; Mongin, F.; Mongin, O.; Trecourt, F.; Godard, A.; Queguiner, G.; *Tetrahedron Lett.* 1996, 37(37), 6695-6698; and O'Connor, K. J.; Burrows, C. J.; *J. Org. Chem.* 1991, 56(3), 1344-1346. Steps V, W and X of Scheme 2A are carried out according to the procedures previously described for Steps B, C, and D of Scheme 1, respectively. The steps of Scheme 2A may be carried out in a different order as shown in Scheme 2B and Scheme 2C.

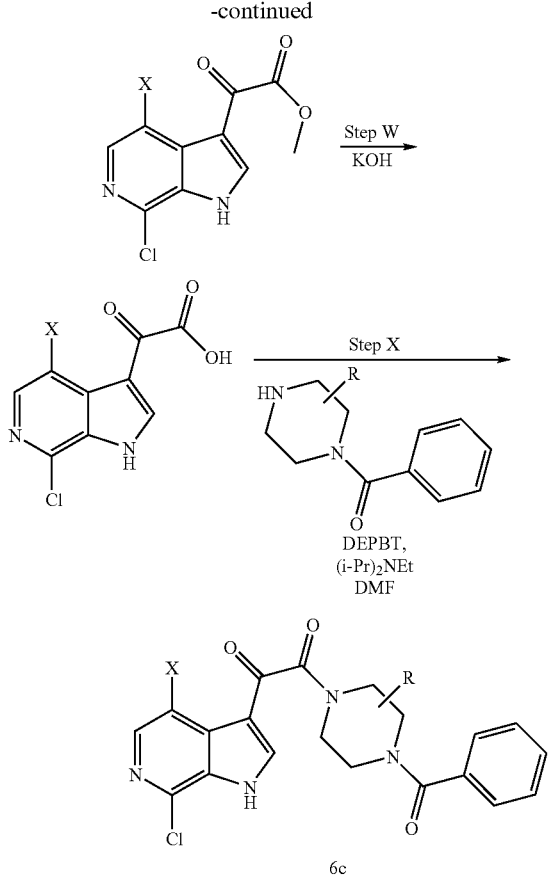

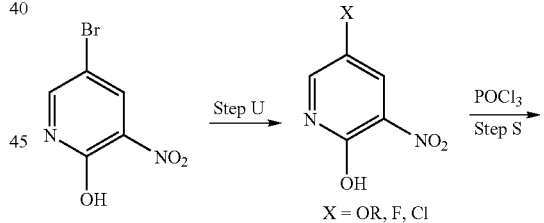

Scheme 2B

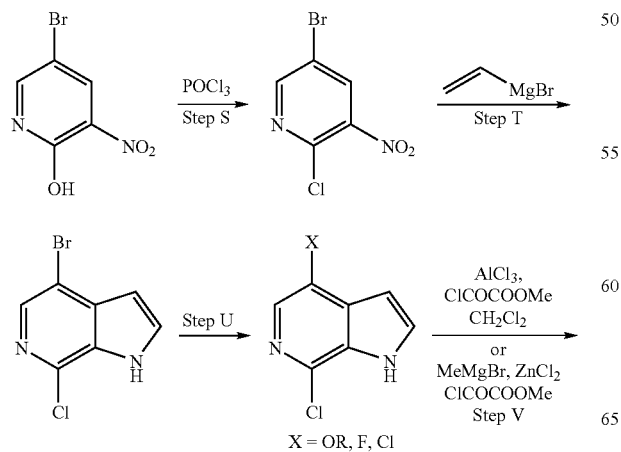

Scheme 2A

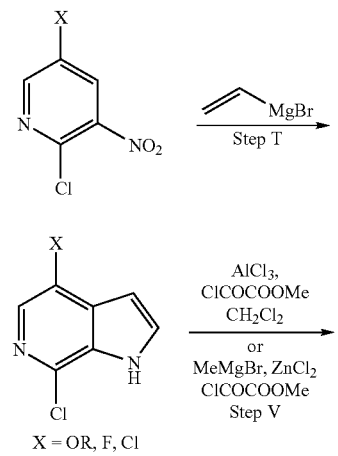

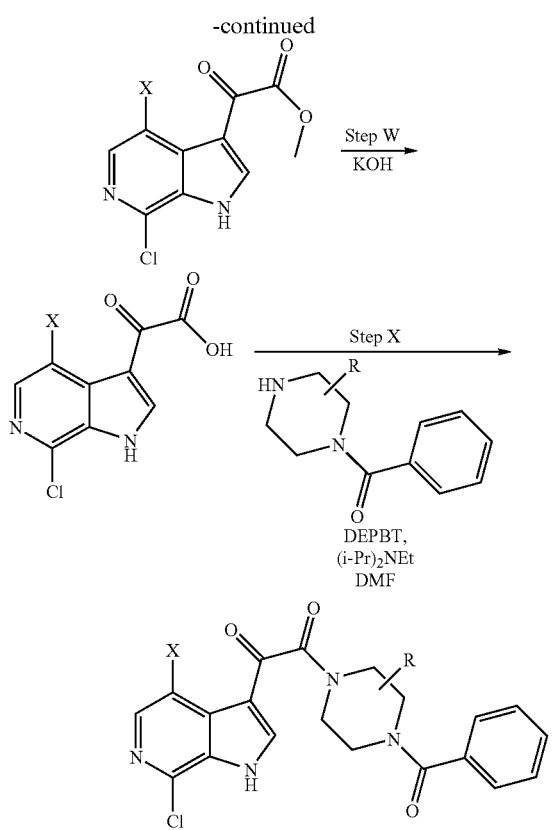
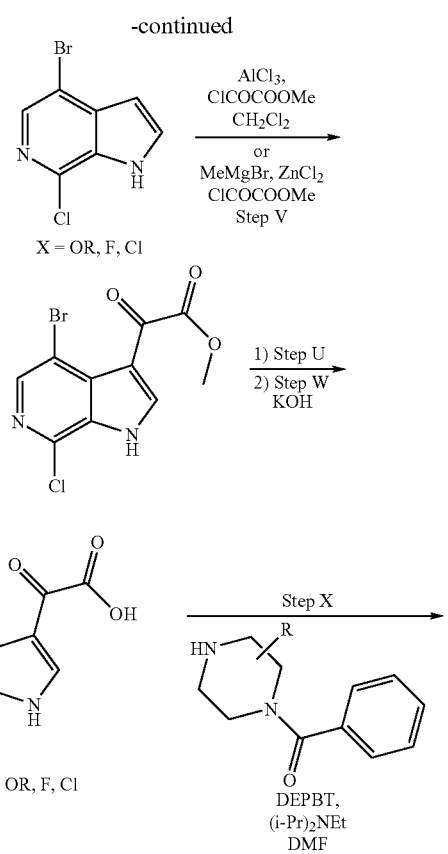
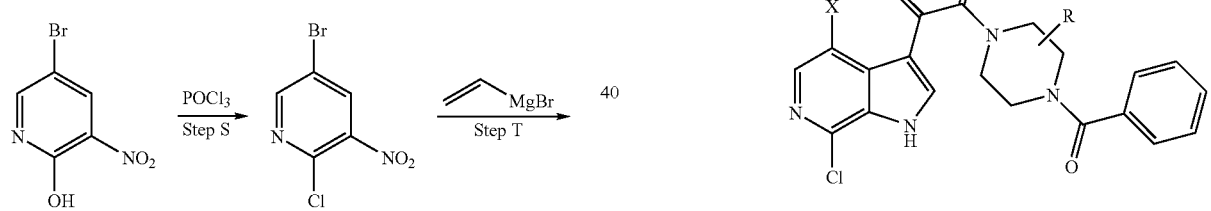
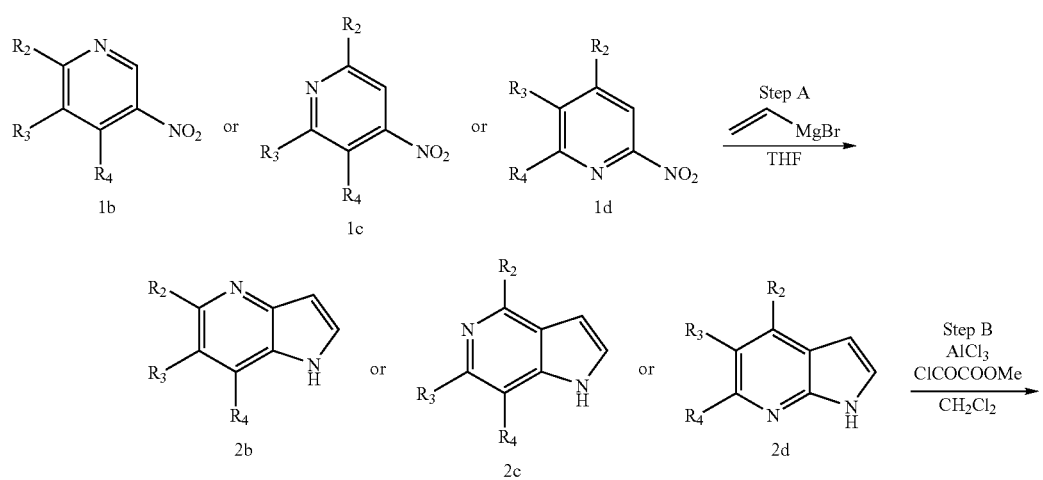

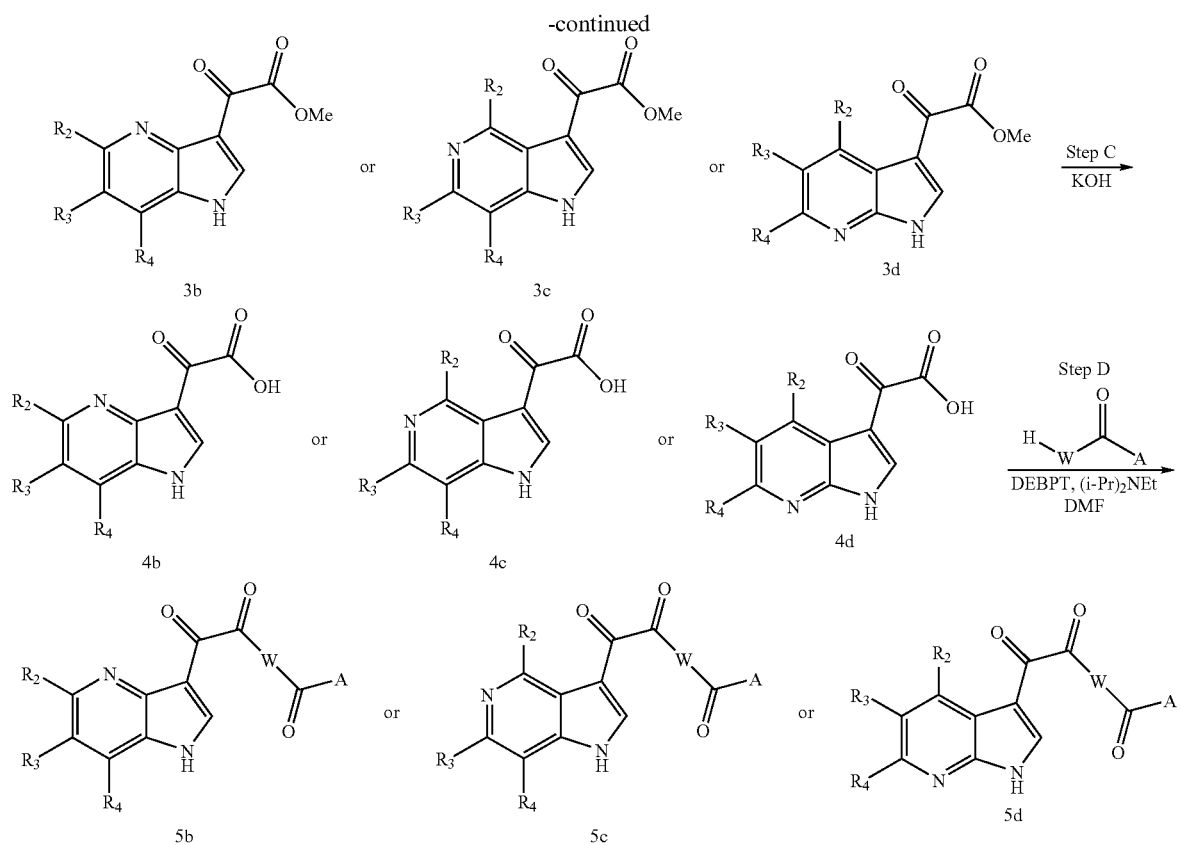

Scheme 3 shows the synthesis of 4-azaindole derivatives 1b-5b, 5-azaindole derivatives 1c-5c, and 7-azaindole derivatives 1d-5d. The methods used to synthesize 1b-5b, 1c-5c, and 1d-5d are the same methods described for the synthesis of 1a-5a as described in Scheme 1. It is understood, for the purposes of Scheme 3, that 1b is used to synthesize 2b-5b, 1c provides 2c-5c and 1d provides 2d-5d.

The compounds where there is a single carbonyl between the azaindole and group W can be prepared by the method of Kelarev, V. I.; Gasanov, S. Sh.; Karakhanov, R. A.; Polivin, Yu. N.; Kuatbekova, K. P.; Panina, M. E.; *Zh. Org. Khim* 1992, 28(12), 2561-2568. In this method azaindoles are reacted with trichloroacetyl chloride in pyridine and then subsequently with KOH in methanol to provide the 3-carbomethoxy azaindoles shown in Scheme 4 which can then be hydrolyzed to the acid and carried through the coupling sequence with HW(C=O)A to provide the compounds of Formula I wherein a single carbonyl links the azaindole moiety and group W.

Scheme 4

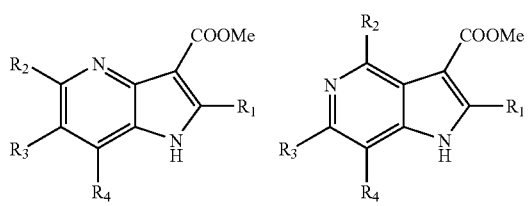

-continued

An alternative method for carrying out the sequence outlined in steps B-D (shown in Scheme 5) involves treating an azaindole, such as 11, obtained by procedures described in the literature or from commercial sources, with MeMgI and $ZnCl_2$, followed by the addition of ClCOCOCl (oxalyl chloride) in either THF or $Et_2O$ to afford a mixture of a glyoxyl chloride azaindole, 12a, and an acyl chloride azaindole, 12b. The resulting mixture of glyoxyl chloride azaindole and acyl chloride azaindole is then coupled with mono-benzoylated piperazine derivatives under basic conditions to afford the products of step D as a mixture of compounds, 13a and 13b, where either one or two carbonyl groups link the azaindole and group W. Separation via chromatographic methods which are well known in the art provides the pure 13a and 13b. This sequence is summarized in Scheme 5, below.

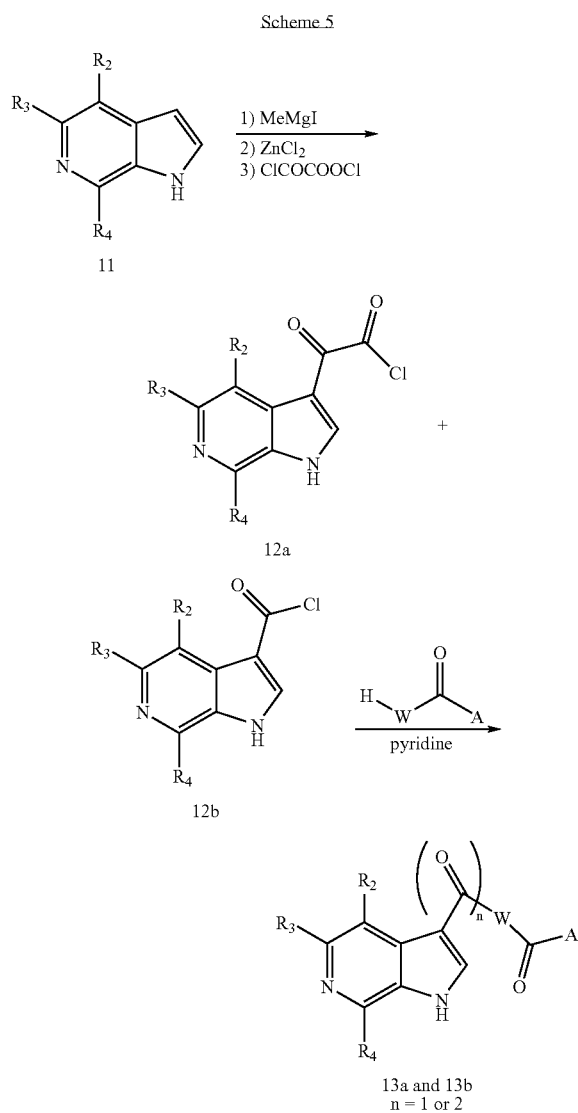

Scheme 5

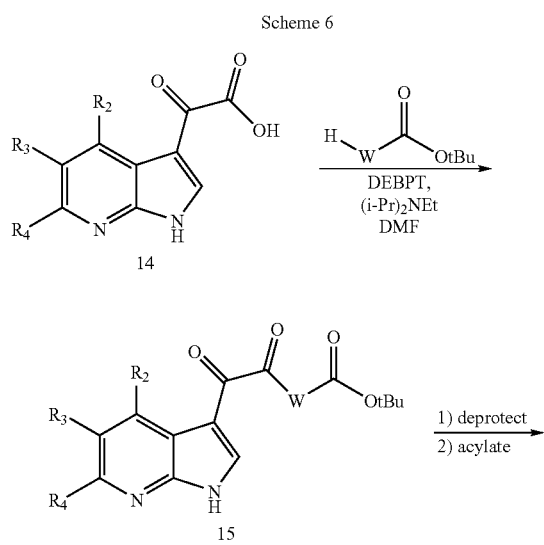

Scheme 6

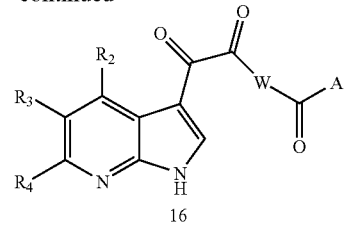

16

Scheme 6 depicts a general method for modifying the substituent A. Coupling of H—W—C(O)OtBu using the conditions described previously for W in Scheme 1, Step D provides Boc protected intermediate, 15. Intermediate 15 is then deprotected by treatment with an acid such as TFA, hydrochloric acid or formic acid using standard solvents or additives such as $CH_2Cl_2$, dioxane, or anisole and temperatures between −78° C. and 100° C. Other acids such as aq hydrochloric or perchloric may also be used for deprotection. Alternatively other nitrogen protecting groups on W such as Cbz or TROC, may be utilized and could be removed via hydrogenation or treatment with zinc respectively. A stable silyl protecting group such as phenyl dimethylsilyl could also be employed as a nitrogen protecting group on W and can be removed with fluoride sources such as tetrabutylammonium fluoride. Finally, the free amine is coupled to acid A-C(O)OH using standard amine-acid coupling conditions such as those used to attach group W or as shown below for amide formation on positions $R_1$-$R_4$ to provide compound 16.

Some specific examples of general methods for preparing functionalized azaindoles or for interconverting functionality on aza indoles which will be useful for preparing the compounds of this invention are shown in the following sections for illustrative purposes. It should be understood that this invention covers substituted 4, 5, 6, and 7 azaindoles and that the methodology shown below may be applicable to all of the above series while other shown below will be specific to one or more. A typical practitioner of the art can make this distinction when not specifically delineated. Many methods are intended to be applicable to all the series, particularly functional group installations or interconversions. For example, a general strategy for providing further functionality of this invention is to position or install a halide such as bromo, chloro, or iodo, aldehyde, cyano, or a carboxy group on the azaindole and then to convert that functionality to the desired compounds. In particular, conversion to substituted heteroaryl, aryl, and amide groups on the ring are of particular interest.

General routes for functionalizing azaindole rings are shown in Schemes 7, 8 and 9. As depicted in Scheme 7, the azaindole, 17, can be oxidized to the corresponding N-oxide derivative, 18, by using mCPBA (meta-Chloroperbenzoic Acid) in acetone or DMF (eq. 1, Harada et al, Ref. 29 and Antonini et al, Ref. 34). The N-oxide, 18, can be converted to a variety of substituted azaindole derivatives by using well documented reagents such as phosphorus oxychloride ($POCl_3$) (eq. 2, Schneller et al, Ref. 30), tetramethylammonium fluoride ($Me_4NF$) (eq. 3), Grignard reagents RMgX (R=alkyl or aryl, X=Cl, Br or I) (eq. 4, Shiotani et al, Ref. 31), trimethylsilyl cyanide (TMSCN) (eq. 5, Minakata et al, Ref. 32) or $Ac_2O$ (eq. 6, Klemm et al, Ref. 33). Under such conditions, a chlorine (in 19), fluorine (in 20), nitrile (in 22), alkyl (in 21), aromatic (in 21) or hydroxyl group (in 24) can be introduced to the pyridine ring. Nitration of azaindole N-oxides results in introduction of a nitro group to azaindole ring, as shown in Scheme 8 (eq. 7, Antonini et al, Ref. 34). The nitro group can subsequently be displaced by a variety of nucleophilic agents, such as OR, NR$^1$R$^2$ or SR, in a well established chemical fashion (eq. 8, Regnouf De Vains et al, Ref. 35(a), Miura et al, Ref. 35(b), Profft et al, Ref. 35(c)). The resulting N-oxides, 26, are readily reduced to the corresponding azaindole, 27, using phosphorus trichloride (PCl$_3$) (eq. 9, Antonini et al, Ref. 34 and Nesi et al, Ref. 36). Similarly, nitro-substituted N-oxide, 25, can be reduced to the azaindole, 28, using phosphorus trichloride (eq. 10). The nitro group of compound 28 can be reduced to either a hydroxylamine (NHOH), as in 29, (eq. 11, Walser et al, Ref 37(a) and Barker et al, Ref. 37(b)) or an amino (NH$_2$) group, as in 30, (eq. 12, Nesi et al, Ref 36 and Ayyangar et al, Ref. 38) by carefully selecting different reducing conditions.

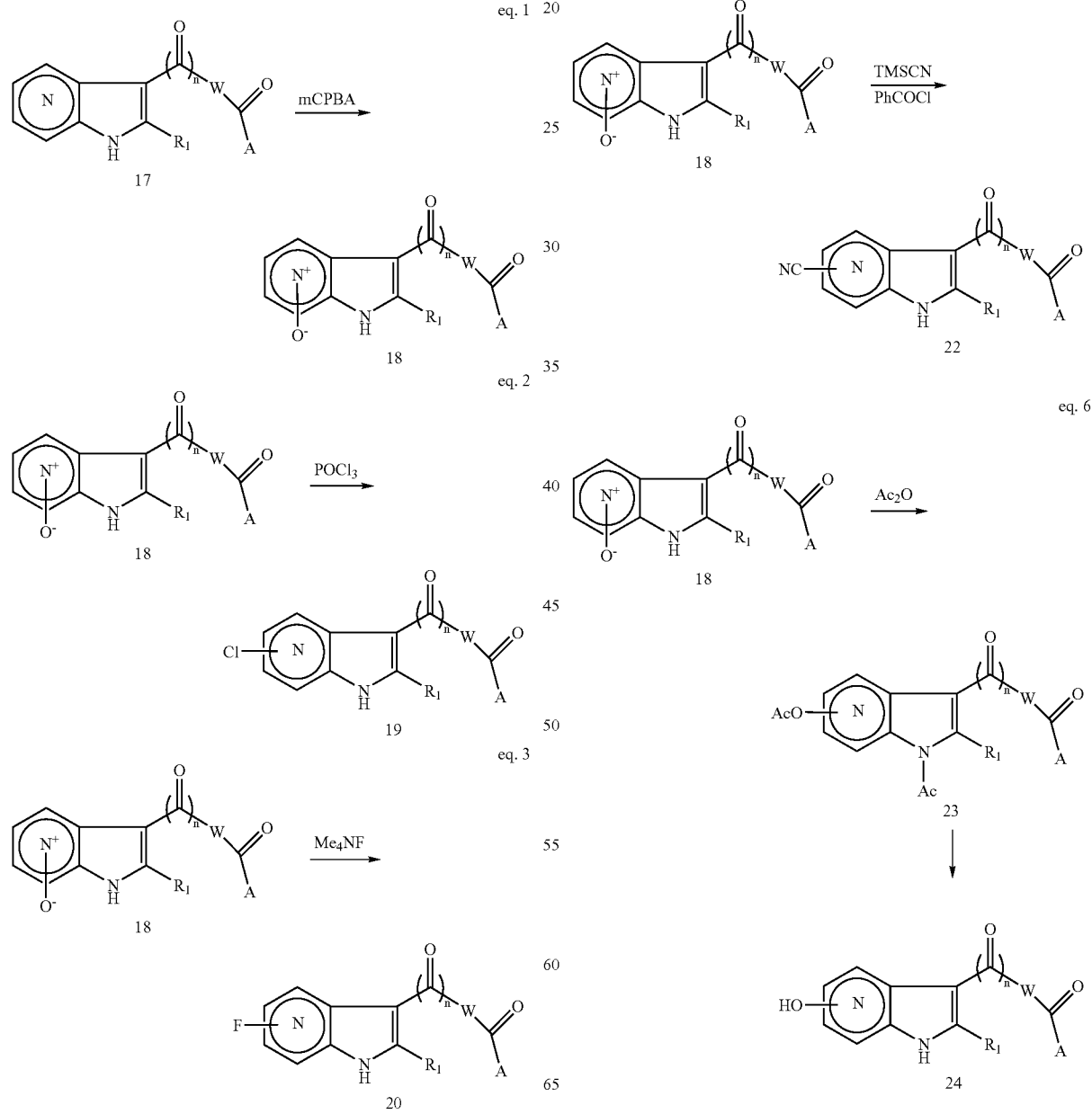

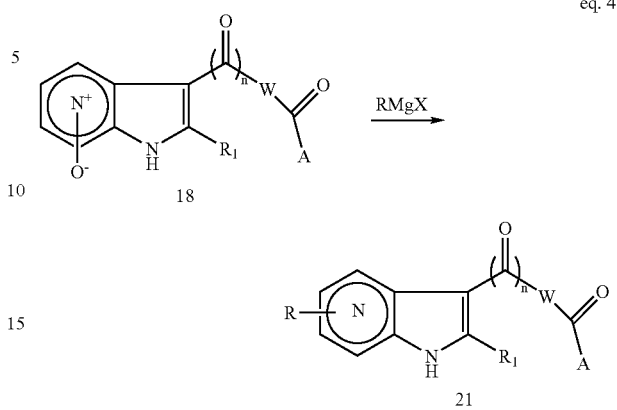

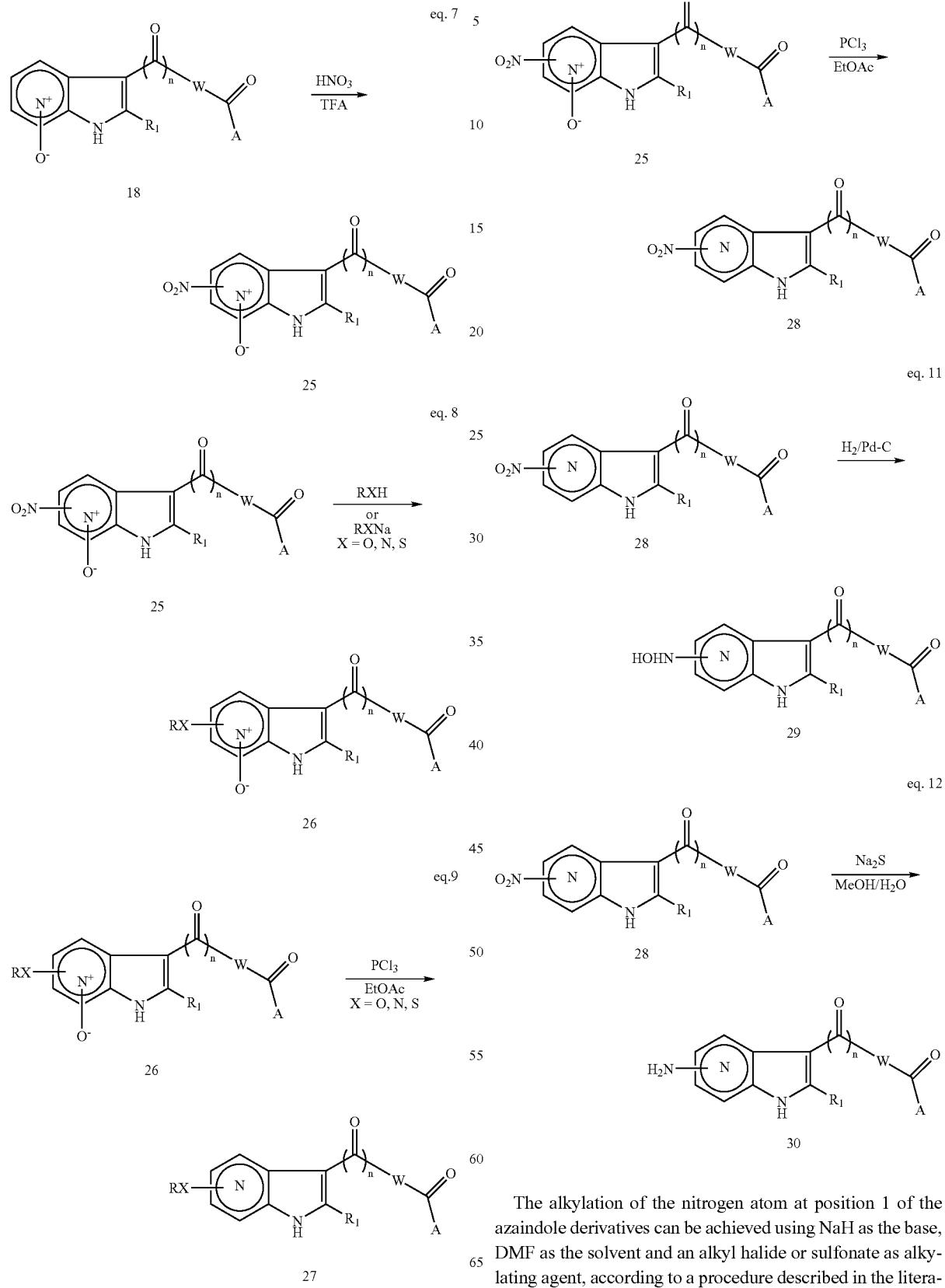
The alkylation of the nitrogen atom at position 1 of the azaindole derivatives can be achieved using NaH as the base, DMF as the solvent and an alkyl halide or sulfonate as alkylating agent, according to a procedure described in the literature (Mahadevan et al, Ref. 39) (Scheme 9).

Scheme 9

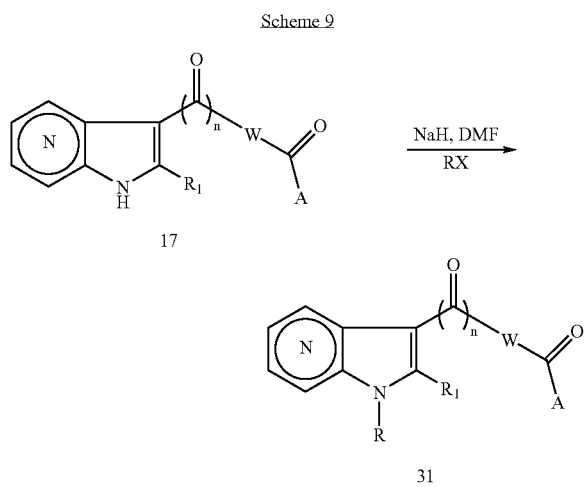

In the general routes for substituting the azaindole ring described above, each process can be applied repeatedly and combinations of these processes is permissible in order to provide azaindoles incorporating multiple substituents. The application of such processes provides additional compounds of Formula I.

Scheme 10

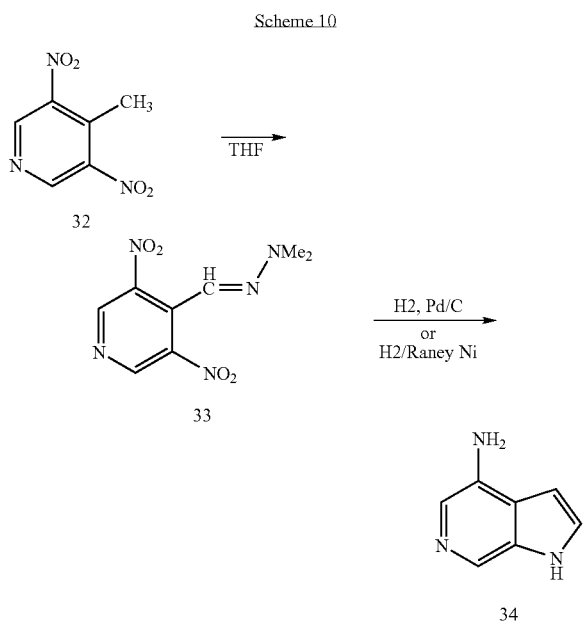

The synthesis of 4-aminoazaindoles which are useful precursors for 4, 5, and/or 7-substituted azaindoles is shown in Scheme 10 above.

The synthesis of 3,5-dinitro-4-methylpyridine, 32, is described in the following two references by Achremowicz et. al.: Achremowicz, Lucjan. Pr. Nauk. Inst. Chem. Org. Fiz. Politech. Wroclaw. 1982, 23, 3-128; Achremowicz, Lucjan. Synthesis 1975, 10, 653-4. In the first step of Scheme 10, the reaction with dimethylformamide dimethyl acetal in an inert solvent or neat under conditions for forming Batcho-Leimgruber precursors provides the cyclization precursor, 33, as shown. Although the step is anticipated to work as shown, the pyridine may be oxidized to the N-oxide prior to the reaction using a peracid such as MCPBA or a more potent oxidant like meta-trifluoromethyl or meta nitro peroxy benzoic acids. In the second step of Scheme 10, reduction of the nitro group using for example hydrogenation over Pd/C catalyst in a solvent such as MeOH, EtOH, or EtOAc provides the cyclized product, 34. Alternatively the reduction may be carried out using tin dichloride and HCl, hydrogenation over Raney nickel or other catalysts, or by using other methods for nitro reduction such as described elsewhere in this application.

The amino indole, 34, can now be converted to compounds of Formula I via, for example, diazotization of the amino group, and then conversion of the diazonium salt to the fluoride, chloride or alkoxy group. See the discussion of such conversions in the descriptions for Schemes 17 and 18. The conversion of the amino moiety into desired functionality could then be followed by installation of the oxoacetopiperazine moiety by the standard methodology described above. 5 or 7-substitution of the azaindole can arise from N-oxide formation at position 6 and subsequent conversion to the chloro via conditions such as $POCl_3$ in chloroform, acetic anhydride followed by $POCl_3$ in DMF, or alternatively TsCl in DMF. Literature references for these and other conditions are provided in some of the later Schemes in this application. The synthesis of 4-bromo-7-hydroxy or protected hydroxy-4-azaindole is described below as this is a useful precursor for 4 and/or 7 substituted 6-aza indoles.

The synthesis of 5-bromo-2-hydroxy-4-methyl-3-nitro pyridine, 35, may be carried out as described in the following reference: Betageri, R.; Beaulieu, P. L.; Llinas-Brunet, M; Ferland, J. M.; Cardozo, M.; Moss, N.; Patel, U.; Proudfoot, J. R. PCT Int. Appl. WO 9931066, 1999. Intermediate 36 is prepared from 35 according to the method as described for Step 1 of Scheme 10. PG is an optional hydroxy protecting group such as triallylsilyl or the like. Intermediate 37 is then prepared from 36 by the selective reduction of the nitro group in the presence of bromide and subsequent cyclization as described in the second step of Scheme 10. $Fe(OH)_2$ in DMF with catalytic tetrabutylammonium bromide can also be utilized for the reduction of the nitro group. The bromide may then be converted to fluoride via displacement with fluoride anions or to other substituents. The compounds are then converted to compounds of Formula I as above.

Scheme 11

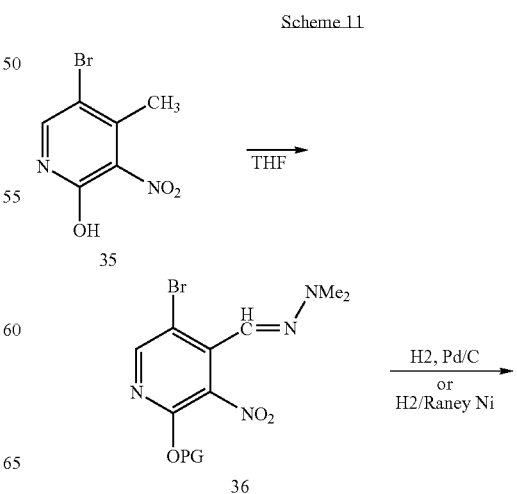

-continued

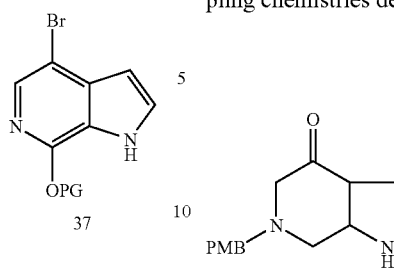

37

An alternate method for preparing substituted 6-azaindoles is shown below in Schemes 12 and 13. It should be recognized that slight modifications of the route depicted below are possible. For example, acylation reactions of the 3 position of what will become the azaindole five membered ring, prior to aromatization of the azaindole, may be carried out in order to obtain higher yields. In addition to a para-methoxybenzyl group (PMB), a benzyl group can be carried through the sequence and removed during azaindole formation by using TsOH, p-Chloranil, in benzene as the oxidant if DDQ is not optimal. The benzyl intermediate, 38, has been described by Ziegler et al. in *J. Am. Chem. Soc.* 1973, 95(22), 7458. The transformation of 38 to 40 is analogous to the transformation described in *Heterocycles* 1984, 22, 2313.

Scheme 12

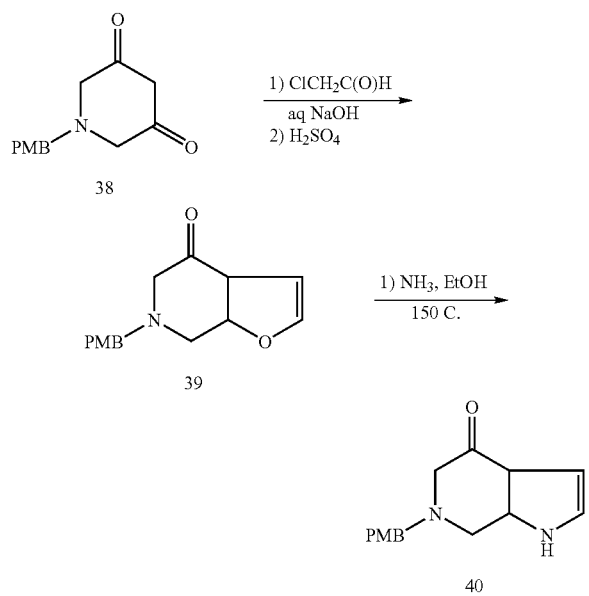

Scheme 13 describes various transformations of intermediate 40 which ultimately provide compounds of Formula I. The conversions of the phenol moiety to other functionality at position 4 ($R_2$ position in Scheme 13) may be carried out by the following methods: 1) conversion of a phenol to methoxy group with silver oxide and MeI or diazomethane; 2) conversion of a phenolic hydroxy group to chloro using cat $ZnCl_2$, and N,N dimethylaniline in $CH_2Cl_2$ or $PCl_5$ and $POCl_3$ together; 3) conversion of a phenolic hydroxy group to fluoro using diethylamine-$SF_3$ as in *Org. Prep. Proc. Int.* 1992, 24(1), 55-57. The method described in EP 427603, 1991, using the chloroformate and HF will also be useful. Other transformations are possible. For example the phenol can be converted to a triflate by standard methods and used in coupling chemistries described later in this application.

Scheme 13

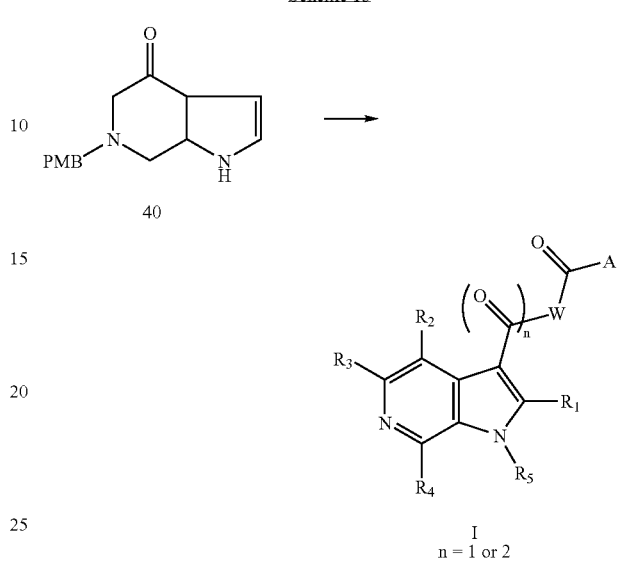

I
n = 1 or 2

1) Ketone alkylation to install $R_3$
2) DDQ oxidation to form azaindole
3) Tramsformation of-phenol ($R_2$ = OH) into methyl ether, or Fluoro, chloro, etc
4) Use of C-7 directing group to functionalize at $R_4$ or formation of N-oxide and $POCl_3$ to make $R_4$ = chloro
5) Conversion to compounds of Formula I as above Step E. Scheme 14 depicts the nitration of an azaindole, 41, ($R_2$=H). Numerous conditions for nitration of the azaindole may be effective and have been described in the literature. $N_2O_5$ in nitromethane followed by aqueous sodium bisulfite according to the method of Bakke, J. M.; Ranes, E.; *Synthesis* 1997, 3, 281-283 could be utilized. Nitric acid in acetic may also be employed as described in Kimura, H.; Yotsuya, S.; Yuki, S.; Sugi, H.; Shigehara, I.; Haga, T.; *Chem. Pharm. Bull* 1995, 43(10), 1696-1700. Sulfuric acid followed by nitric acid may be employed as in Ruefenacht, K.; Kristinsson, H.; Mattem, G.; *Helv Chim Acta* 1976, 59, 1593. Coombes, R. G.; Russell, L. W.; *J. Chem. Soc., Perkin Trans.* 1 1974, 1751 describes the use of a Titatanium based reagent system for nitration. Other conditions for the nitration of the azaindole can be found in the following references: Lever, O. W. J.; Werblood, H. M.; Russell, R. K.; *Synth. Comm.* 1993, 23(9), 1315-1320; Wozniak, M.; Van Der Plas, H. C.; *J. Heterocycl Chem.* 1978, 15, 731.

Scheme 14

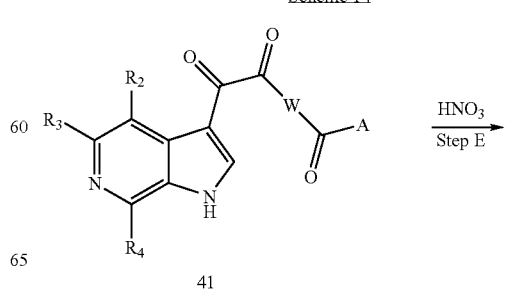

41

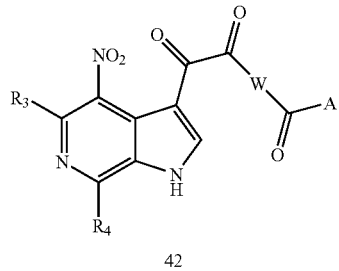

42

Scheme 15

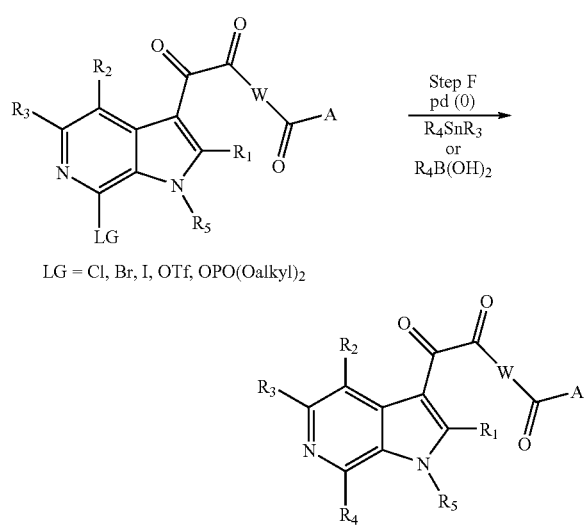

LG = Cl, Br, I, OTf, OPO(Oalkyl)₂

Step F

As shown above in Scheme 15, Step F, substituted azaindoles containing a chloride, bromide, iodide, triflate, or phosphonate undergo coupling reactions with a boronate (Suzuki type reactions) or a stannane to provide substituted azaindoles. Stannanes and boronates are prepared via standard literature procedures or as described in the experimental section of this application. The substituted indoles may undergo metal mediated coupling to provide compounds of Formula I wherein $R_4$ is aryl, heteroaryl, or heteroalicyclic for example. The bromoazaindole intermediates, (or azaindole triflates or iodides) may undergo Stille-type coupling with heteroarylstannanes as shown in Scheme 15. Conditions for this reaction are well known in the art and the following are three example references a) Farina, V.; Roth, G. P. Recent advances in the Stille reaction; *Adv. Met.-Org. Chem.* 1996, 5, 1-53. b) Farina, V.; Krishnamurthy, V.; Scott, W. J. The Stille reaction; *Org. React.* (N.Y.) 1997, 50, 1-652. and c) Stille, J. K. *Angew. Chem. Int. Ed. Engl* 1986, 25, 508-524. Other references for general coupling conditions are also in the reference by Richard C. Larock Comprehensive Organic Transformations 2nd Ed. 1999, John Wiley and Sons New York. All of these references provide numerous conditions at the disposal of those skilled in the art in addition to the specific examples provided in Scheme 15 and in the specific embodiments. It can be well recognized that an indole stannane could also couple to a heterocyclic or aryl halide or triflate to construct compounds of Formula I. Suzuki coupling (Norio Miyaura and Akiro Suzuki *Chem. Rev.* 1995, 95, 2457.) between a triflate, bromo, or chloro azaindole intermediate and a suitable boronate could also be employed and some specific examples are contained in this application, Palladium catalyzed couplings of stannanes and boronates between chloro azaindole intermediates are also feasible and have been utilized extensively for this invention. Preferred procedures for coupling of a chloro azaindole and a stannane employ dioxane, stoichiometric or an excess of the tin reagent (up to 5 equivalents), 0.1 to 1 eq of Palladium (0) tetrakis triphenyl phosphine in dioxane heated for 5 to 15 h at 110 to 120°. Other solvents such as DMF, THF, toluene, or benzene could be employed. Preferred procedures for Suzuki coupling of a chloro azaindole and a boronate employ 1:1 DMF water as solvent, 2 equivalents of potassium carbonate as base stoichiometric or an excess of the boron reagent (up to 5 equivalents), 0.1 to 1 eq of Palladium (0) tetrakis triphenyl phosphine heated for 5 to 15 h at 110 to 120°. If standard conditions fail new specialized catalysts and conditions can be employed. Some references (and the references therein) describing catalysts which are useful for coupling with aryl and heteroaryl chlorides are:

Littke, A. F.; Dai, C.; Fu, G. C. *J. Am. Chem. Soc.* 2000, 122(17), 4020-4028;

Varma, R. S.; Nicker, K. P. *Tetrahedron Lett.* 1999, 40(3), 439-442; Wallow, T. I.;

Novak, B. M. *J. Org. Chem.* 1994, 59(17), 5034-7; Buchwald, S.; Old, D. W.;

Wolfe, J. P.; Palucki, M.; Kamikawa, K.; Chieffi, A.; Sadighi, J. P.; Singer, R. A.;

Ahman, J PCT Int. Appl. WO 0002887 2000; Wolfe, J. P.; Buchwald, S. L. *Angew. Chem., Int. Ed.* 1999, 38(23), 3415; Wolfe, J. P.; Singer, R. A.; Yang, B. H.;

Buchwald, S. L. *J. Am. Chem. Soc.* 1999, 121(41), 9550-9561; Wolfe, J. P.;

Buchwald, S. L. *Angew. Chem., Int. Ed.* 1999, 38(16), 2413-2416; Bracher, F.;

Hildebrand, D.; *Liebigs Ann. Chem.* 1992, 12, 1315-1319; and Bracher, F.;

Hildebrand, D.; *Liebigs Ann. Chem.* 1993, 8, 837-839.

Alternatively, the boronate or stannane may be formed on the azaindole via methods known in the art and the coupling performed in the reverse manner with aryl or heteroaryl based halogens or triflates.

Known boronate or stannane agents could be either purchased from commercial resources or prepared following disclosed documents. Additional examples for the preparation of tin reagents or boronate reagents are contained in the experimental section.

Novel stannane agents could be prepared from one of the following routes.

Scheme Tin-01

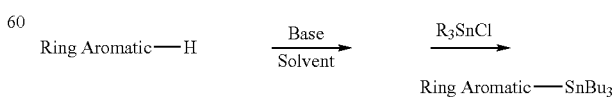

Base = LDA, TMP-Li, n-BuLi, S-BuLi, t-BuLi
Solvent = THF, ether, DME
R = Me, Bu

Scheme Tin-02

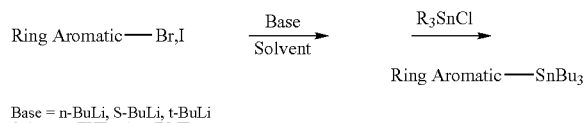

Base = n-BuLi, S-BuLi, t-BuLi
Solvent = THF, ether, DME
R = Me, Bu

SCHEME 15aa

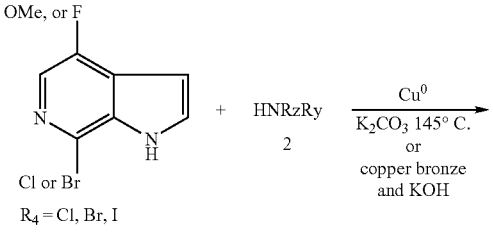

Scheme Tin-03

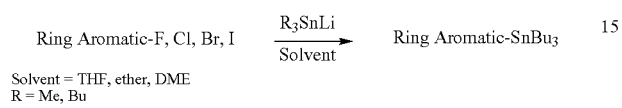

Solvent = THF, ether, DME
R = Me, Bu

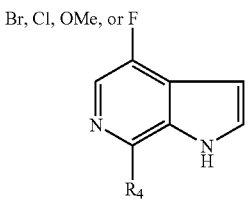

$R_4$ = NRzRy where
$R_4$ is heteroaryl or
amino as defined by
the invention

3

Scheme Tin-04

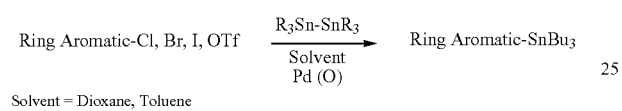

Solvent = Dioxane, Toluene
R = Me, Bu

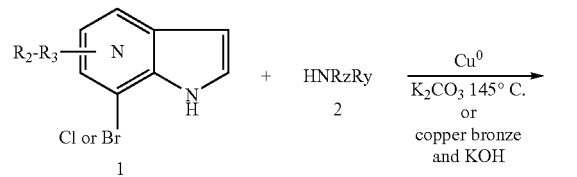

1

Scheme Tin-05

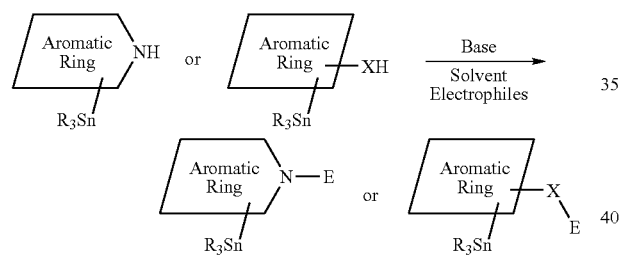

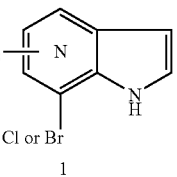

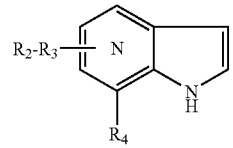

$R_4$ = NRzRy where
$R_4$ is heteroaryl or
amino as defined by
the invention

E = Electrophile = R'-halide, R'COCl, R'OCOCl,
R'R"NCOCl, RSO₂Cl, R'NCO, R'NSO, R'NCNR"

Solvent = CH₂Cl₂, THF, Ether, DMF

R = Me, Bu

Base = NaH, BuLi, LDA, K₂CO₃, Et₃N, DBU, DMAP, NaHMDS

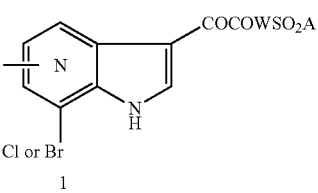

1

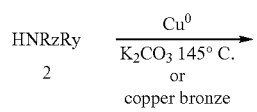

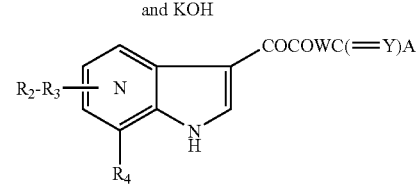

$R_4$ = NRzRy where
$R_4$ is heteroaryl or
amino as defined by
the invention

Boronate reagents are prepared as described in reference 71. Reaction of lithium or Grignard reagents with trialkyl borates generates boronates. Alternatively, Palladium catalyzed couplings of alkoxy diboron or alkyl diboron reagents with aryl or heteroaryl halides can provide boron reagents for use in Suzuki type couplings. Some example conditions for coupling a halide with (MeO)BB(OMe)2 utilize PdCl2 (dppf), KOAc, DMSO, at 80° C. until reaction is complete when followed by TLC or HPLC analysis.

Related examples are provided in the following experimental section.

Methods for direct addition of aryl or heteroaryl organometallic reagents to alpha chloro nitrogen containing heterocyles or the N-oxides of nitrogen containing heterocycles are known and applicable to the azaindoles. Some examples are Shiotani et. Al. *J. Heterocyclic Chem.* 1997, 34(3), 901-907; Fourmigue et. al. *J. Org. Chem.* 1991, 56(16), 4858-4864.

SCHEME 15bb

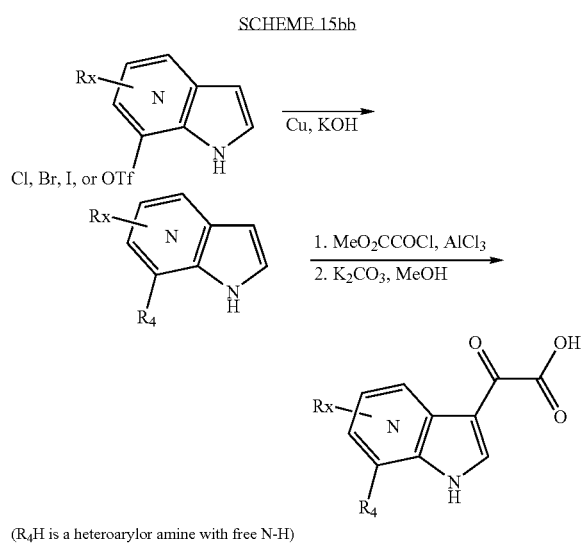

(R₄H is a heteroaryl or amine with free N-H)
Rₓ = R₂-R₄ for azaindoles or R₂-R₅ for indoles

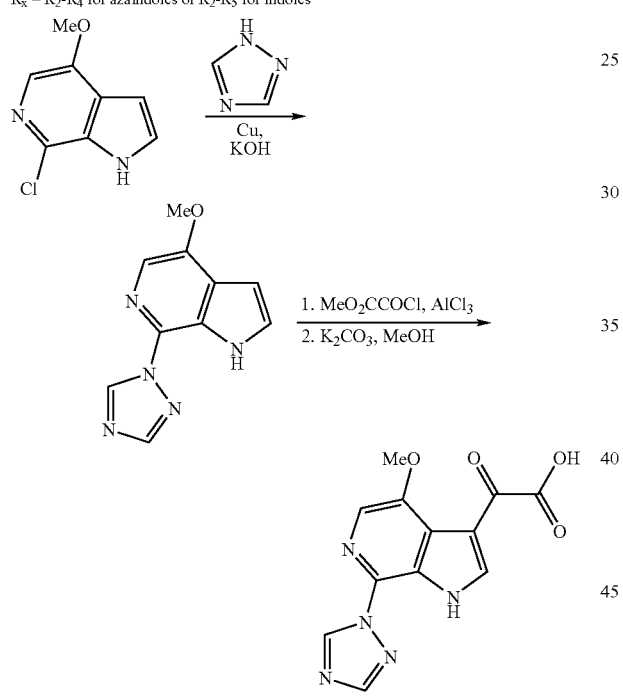

Direct displacements to install amine or N linked heteroaryl substituents can also be used to prepare compounds of Formula I. As shown in Schemes 15aa and 15bb, a mixture of halo-indole or halo-azaindole intermediate, 1-2 equivalents of copper powder, with 1 equivalent preferred for the 4-F,6-azaindole series and 2 equivalents for the 4-methoxy, 6-azaindole series; 1-2 equivalents of potassium carbonate, with 1 equivalent preferred for the 4-F,6-azaindole series and 2 equivalents for the 4-methoxy,6-azaindole series; and a 2-30 equivalents of the corresponding heterocyclic reagent, with 10 equivalents preferred; was heated at 135-160° C. for 4 to 9 hours, with 5 hours at 160° C. preferred for the 4-F,6-azaindole series and 7 hours at 135° C. preferred for the 4-methoxy, 6-azaindole series. The reaction mixture was cooled to room temperature and filtered through filter paper. The filtrate was diluted with methanol and purified either by preparative HPLC or silica gel. In many cases no chromatography is necessary, the product can be obtained by crystallization with methanol.

Alternatively, the installation of amines or N linked heteroaryls may be carried out by heating 1 to 40 equivalents of the appropriate amine and an equivalent of the appropriate aza indole chloride, bromide or iodide with copper bronze (from 0.1 to 10 equivalents (preferably about 2 equivalents) and from 1 to 10 equivalents of finely pulverized potassium hydroxide (preferably about 2 equivalents). Temperatures of 120° to 200° may be employed with 140-160° generally preferred. For volatile starting materials a sealed reactor may be employed. The reaction is most commonly used when the halogen being displaced is at the 7-position of a 6-aza (or 4-azaindole, not shown) but the method can work in the 5-azaseries or when the halogen is at a different position (4-7 position possible). As shown above the reaction can be employed on azaindoles unsubstituted at position 3 or intermediates which contain the dicarbonyl or the intact dicarbonyl piperazine urea or thioureas contained in compounds of formula I.

Scheme 16

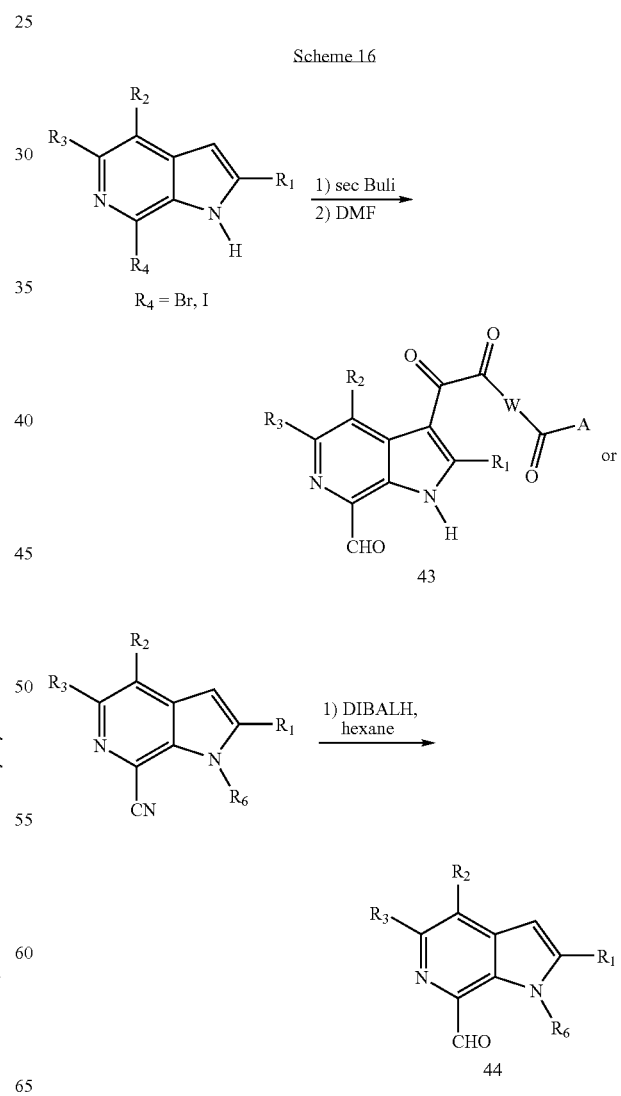

The preparation of a key aldehyde intermediate, 43, using a procedure adapted from the method of Gilmore et. Al. *Synlett* 1992, 79-80. Is shown in Scheme 16 above. The aldehyde substituent is shown only at the $R_4$ position for the sake of clarity, and should not be considered as a limitation of the methodology. The bromide or iodide intermediate is converted into an aldehyde intermediate, 43, by metal-halogen exchange and subsequent reaction with dimethylformamide in an appropriate aprotic solvent. Typical bases used include, but are not limited to, alkyl lithium bases such as n-butyl lithium, sec butyl lithium or tert butyl lithium or a metal such as lithium metal. A preferred aprotic solvent is THF. Typically the transmetallation is initiated at −78° C. The reaction may be allowed to warm to allow the transmetalation to go to completion depending on the reactivity of the bromide intermediate. The reaction is then recooled to −78° C. and allowed to react with dimethylformamide. (allowing the reaction to warm may be required to enable complete reaction) to provide an aldehyde which is elaborated to compounds of Formula I. Other methods for introduction of an aldehyde group to form intermediates of formula 43 include transition metal catalyzed carbonylation reactions of suitable bromo, trifluoromethane sulfonyl, or stannyl azaindoles. Alternative the aldehydes can be introduced by reacting indolyl anions or indolyl Grignard reagents with formaldehyde and then oxidizing with $MnO_2$ or TPAP/NMO or other suitable oxidants to provide intermediate 43.

The methodology described in T. Fukuda et. al. *Tetrahedron* 1999, 55, 9151 and M. Iwao et. Al. *Heterocycles* 1992, 34(5), 1031 provide methods for preparing indoles with substituents at the 7-position. The Fukuda references provide methods for functionalizing the C-7 position of indoles by either protecting the indole nitrogen with 2,2-diethyl propanoyl group and then deprotonating the 7-position with sec/Buli in TMEDA to give an anion. This anion may be quenched with DMF, formaldehyde, or carbon dioxide to give the aldehyde, benzyl alcohol, or carboxylic acid respectively and the protecting group removed with aqueous t butoxide. Similar transformations can be achieved by converting indoles to indoline, lithiation at C-7 and then reoxidation to the indole such as described in the Iwao reference above. The oxidation level of any of these products may be adjusted by methods well known in the art as the interconversion of alcohol, aldehyde, and acid groups has been well studied. It is also well understood that a cyano group can be readily converted to an aldehyde. A reducing agent such as DIBALH in hexane such as used in Weyerstahl, P.; Schlicht, V.; *Liebigs Ann/Recl.* 1997, 1, 175-177 or alternatively catecholalane in THF such as used in Cha, J. S.; Chang, S. W.; Kwon, O. O.; Kim, J. M.; *Synlett.* 1996, 2, 165-166 will readily achieve this conversion to provide intermediates such as 44 (Scheme 16). Methods for synthesizing the nitriles are shown later in this application. It is also well understood that a protected alcohol, aldehyde, or acid group could be present in the starting azaindole and carried through the synthetic steps to a compound of Formula I in a protected form until they can be converted into the desired substituent at $R_1$ through $R_4$. For example, a benzyl alcohol can be protected as a benzyl ether or silyl ether or other alcohol protecting group; an aldehyde may be carried as an acetal, and an acid may be protected as an ester or ortho ester until deprotection is desired and carried out by literature methods.

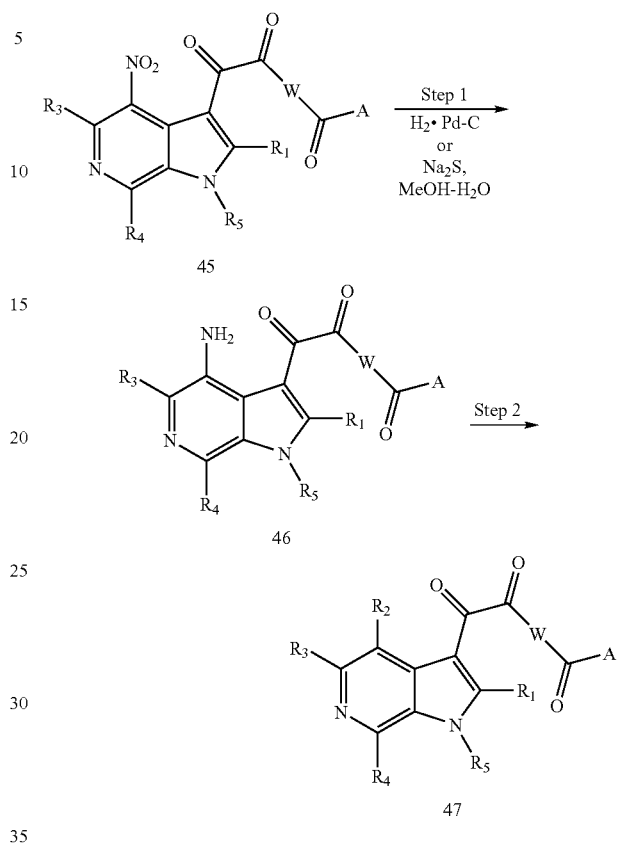

Scheme 17

Step G. Step 1 of Scheme 17 shows the reduction of a nitro group on 45 to the amino group of 46. Although shown on position 4 of the azaindole, the chemistry is applicable to other nitro isomers. The procedure described in Ciurla, H.; Puszko, A.; *Khim Geterotsikl Soedin* 1996, 10, 1366-1371 uses hydrazine Raney-Nickel for the reduction of the nitro group to the amine. Robinson, R. P.; DonahueO, K. M.; Son, P. S.; Wagy, S. D.; *J. Heterocycl. Chem.* 1996, 33(2), 287-293 describes the use of hydrogenation and Raney Nickel for the reduction of the nitro group to the amine. Similar conditions are described by Nicolai, E.; Claude, S.; Teulon, J. M.; *J. Heterocycl. Chem.* 1994, 31(1), 73-75 for the same transformation. The following two references describe some trimethylsilyl sulfur or chloride based reagents which may be used for the reduction of a nitro group to an amine. Hwu, J. R.; Wong, F. F.; Shiao, M. J.; *J. Org. Chem.* 1992, 57(19), 5254-5255; Shiao, M. J.; Lai, L. L.; Ku, W. S.; Lin, P. Y.; Hwu, J. R.; *J. Org. Chem.* 1993, 58(17), 4742-4744.

Step 2 of Scheme 17 describes general methods for conversion of amino groups on azaindoles into other functionality. Scheme 18 also depicts transformations of an amino azaindole into various intermediates and compounds of Formula I.

The amino group at any position of the azaindole, such as 46 (Scheme 17), may be converted to a hydroxy group using sodium nitrite, sulfuric acid, and water via the method of Klemm, L. H.; Zell, R.; *J. Heterocycl. Chem.* 1968, 5, 773. Bradsher, C. K.; Brown, F. C.; Porter, H. K.; *J. Am. Chem. Soc.* 1954, 76, 2357 describes how the hydroxy group may be alkylated under standard or Mitsonobu conditions to form ethers. The amino group may be converted directly into a methoxy group by diazotization (sodium nitrite and acid) and trapping with methanol.

The amino group of an azaindole, such as 46, can be converted to fluoro via the method of Sanchez using $HPF_6$, $NaNO_2$, and water by the method described in Sanchez, J. P.; Gogliotti, R. D.; *J. Heterocycl. Chem.* 1993, 30(4), 855-859. Other methods useful for the conversion of the amino group to fluoro are described in Rocca, P.; Marsais, F.; Godard, A.; Queguiner, G.; *Tetrahedron Lett.* 1993, 34(18), 2937-2940 and Sanchez, J. P.; Rogowski, J. W.; *J. Heterocycl. Chem.* 1987, 24, 215.

The amino group of the azaindole, 46, can also be converted to a chloride via diazotization and chloride displacement as described in Ciurla, H.; Puszko, A.; *Khim Geterotsikl Soedin* 1996, 10, 1366-1371 or the methods in Raveglia, L. F.; Giardina, G. A.; Grugni, M.; Rigolio, R.; Farina, C.; *J. Heterocycl. Chem.* 1997, 34(2), 557-559 or the methods in Matsumoto, J. I.; Miyamoto, T.; Minamida, A.; Mishimura, Y.; Egawa, H.; Mishimura, H.; *J. Med. Chem.* 1984, 27(3), 292; or as in Lee, T. C.; Salemnick, G.; *J. Org. Chem.* 1975, 24, 3608.

The amino group of the azaindole, 46, can also be converted to a bromide via diazotization and displacement by bromide as described in Raveglia, L. F.; Giardina, G. A.; Grugni, M.; Rigolio, R.; Farina, C.; *J. Heterocycl. Chem.* 1997, 34(2), 557-559; Talik, T.; Talik, Z.; Ban-Oganowska, H.; *Synthesis* 1974, 293; and Abramovitch, R. A.; Saha, M.; *Can. J. Chem.* 1966, 44, 1765.

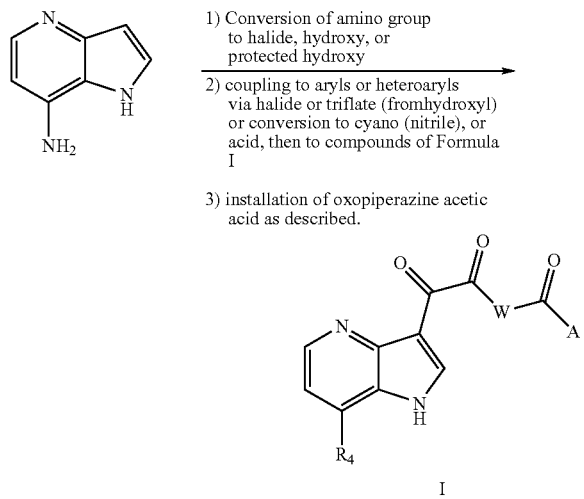

Scheme 18

1) Conversion of amino group to halide, hydroxy, or protected hydroxy
2) coupling to aryls or heteroaryls via halide or triflate (from hydroxyl) or conversion to cyano (nitrile), or acid, then to compounds of Formula I
3) installation of oxopiperazine acetic acid as described.

Steps 2 and 3 may be reversed as appropriate

The preparation of 4-amino 4-azaindole and 7-methyl-4-azaindole is described by Mahadevan, I.; Rasmussen, M. *J. Heterocycl. Chem.* 1992, 29(2), 359-67. The amino group of the 4-amino 4-azaindole can be converted to halogens, hydroxy, protected hydroxy, triflate, as described above in Schemes 17-18 for the 4-amino compounds or by other methods known in the art. Protection of the indole nitrogen of the 7-methyl-4-azaindole via acetylation or other strategy followed by oxidation of the 7-methyl group with potassium permanganate or chromic acid provides the 7-acid/4-N-oxide. Reduction of the N-oxide, as described below, provides an intermediate from which to install various substituents at position $R_4$. Alternatively the parent 4-azaindole which was prepared as described in Mahadevan, I.; Rasmussen, M. *J. Heterocycl. Chem.* 1992, 29(2), 359-67 could be derivatized at nitrogen to provide the 1-(2,2-diethylbutanoyl)azaindole which could then be lithiated using TMEDA/sec BuLi as described in T. Fukuda et. Al. *Tetrahedron* 1999, 55, 9151-9162; followed by conversion of the lithio species to the 7-carboxylic acid or 7-halogen as described. Hydrolysis of the N-amide using aqueous tert-butoxide in THF regenerates the free NH indole which can now be converted to compounds of Formula I. The chemistry used to functionalize position 7 can also be applied to the 5 and 6 indole series.

Scheme 19 shows the preparation of a 7-chloro-4-azaindole, 50, which can be converted to compounds of Formula I by the chemistry previously described, especially the palladium catalyzed tin and boron based coupling methodology described above. The chloro nitro indole, 49, is commercially available or can be prepared from 48 according to the method of Delarge, J.; Lapiere, C. L. *Pharm. Acta Helv.* 1975, 50(6), 188-91.

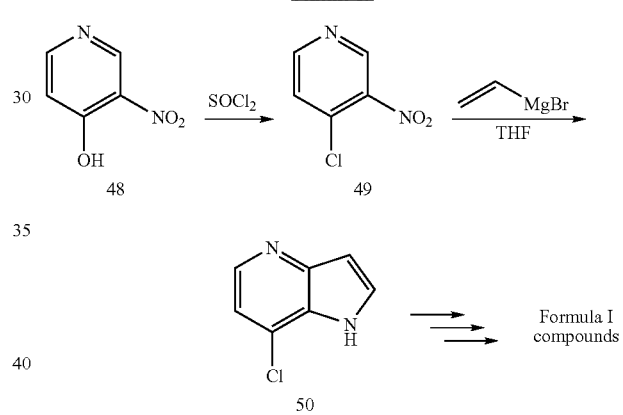

Scheme 19

Scheme 20, below, shows another synthetic route to substituted 4-aza indoles. The 3-aminopyrrole, 51, was reacted to provide the pyrrolopyridinone, 52, which was then reduced to give the hydroxy azaindole, 53. The pyrrolo[2,3-b]pyridines described were prepared according to the method of Britten, A. Z.; Griffiths, G. W. G. *Chem. Ind.* (London) 1973, 6, 278. The hydroxy azaindole, 53, can then be converted to the triflate then further reacted to provide compounds of Formula I.

Scheme 20

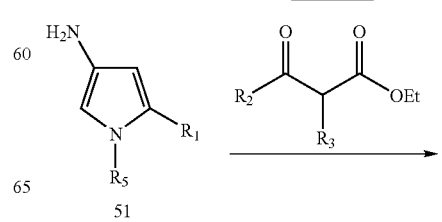

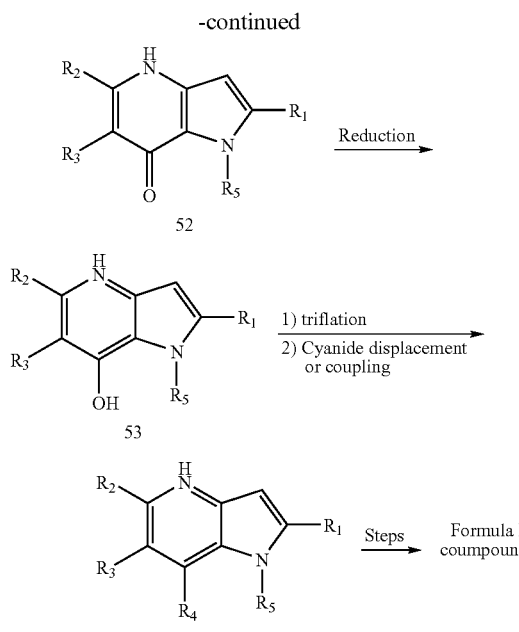

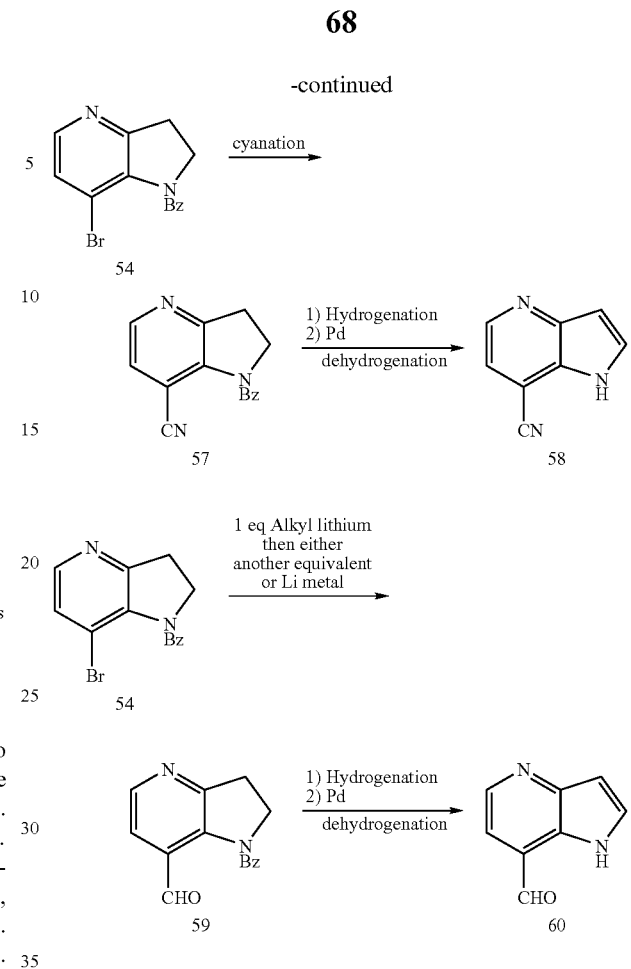

The following references describe the synthesis of 7-halo or 7 carboxylic acid, or 7-amido derivatives of 5-azaindoline which can be used to construct compounds of Formula I. Bychikhina, N. N.; Azimov, V. A.; Yakhontov, L. N. *Khim. Geterotsikl. Soedin.* 1983, 1, 58-62; Bychikhina, N. N.; Azimov, V. A.; Yakhontov, L. N. *Khim. Geterotsikl. Soedin.* 1982, 3, 356-60; Azimov, V. A.; Bychikhina, N. N.; Yakhontov, L. N. *Khim. Geterotsikl. Soedin.* 1981, 12, 1648-53; Spivey, A. C.; Fekner, T.; Spey, S. E.; Adams, H. *J. Org. Chem.* 1999, 64(26), 9430-9443; Spivey, A. C.; Fekner, T.; Adams, H. *Tetrahedron Lett.* 1998, 39(48), 8919-8922. The methods described in Spivey et al. (preceding two references) for the preparation of 1-methyl-7-bromo-4-azaindoline can be used to prepare the 1-benzyl-7-bromo-4-azaindoline, 54, shown below in Scheme 21. This can be utilized in Stille or Suzuki couplings to provide 55, which is deprotected and dehydrogenated to provide 56. Other useful azaindole intermediates, such as the cyano derivatives, 57 and 58, and the aldehyde derivatives, 59 and 60, can then be further elaborated to compounds of Formula I.

Alternatively the 7-functionalized 5-azaindole derivatives may be obtained by functionalization using the methodologies of T. Fukuda et. al. *Tetrahedron* 1999, 55, 9151 and M. Iwao et. Al. *Heterocycles* 1992, 34(5), 1031 described above for the 4 or 6 azaindoles. The 4 or 6 positions of the 5 aza indoles can be functionalized by using the azaindole N-oxide.

The conversion of indoles to indolines is well known in the art and can be carried out as shown or by the methods described in Somei, M.; Saida, Y.; Funamoto, T.; Ohta, T. *Chem. Pharm. Bull.* 1987, 35(8), 3146-54; M. Iwao et. Al. *Heterocycles* 1992, 34(5), 1031; and Akagi, M.; Ozaki, K. *Heterocycles* 1987, 26(1), 61-4.

Scheme 21

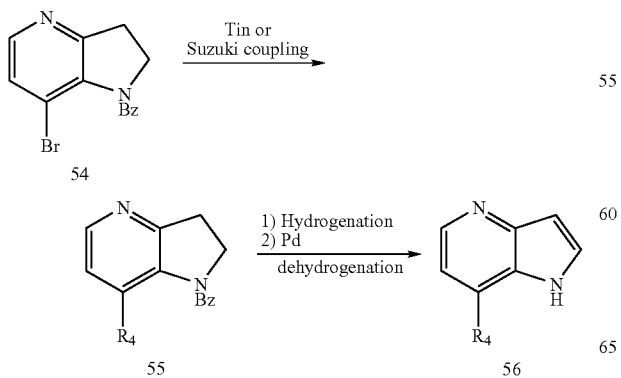

Scheme 22

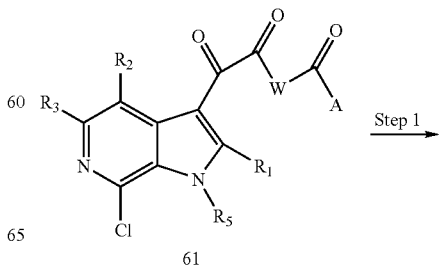

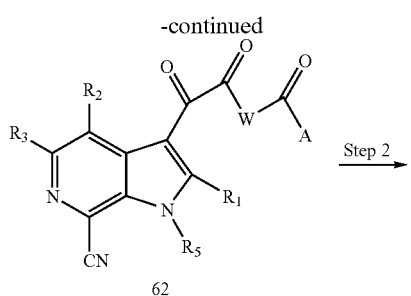

62

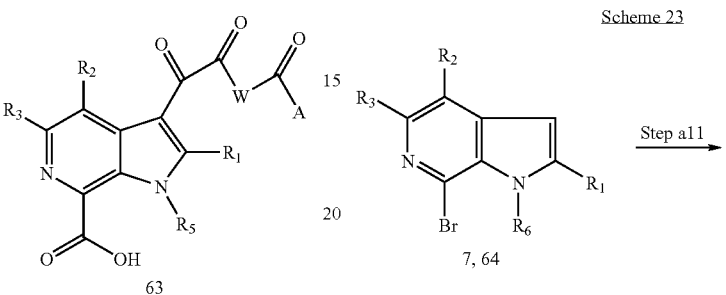

63

The preparation of azaindole oxoacetyl or oxo piperidines with carboxylic acids can be carried out from nitrile, aldehyde, or anion precursors via hydrolysis, oxidation, or trapping with $CO_2$ respectively. As shown in the Scheme 22, Step 1, or the scheme below step a12 one method for forming the nitrile intermediate, 62, is by cyanide displacement of a halide in the aza-indole ring. The cyanide reagent used can be sodium cyanide, or more preferably copper or zinc cyanide. The reactions may be carried out in numerous solvents which are well known in the art. For example DMF is used in the case of copper cyanide. Additional procedures useful for carrying out step 1 of Scheme 24 are Yamaguchi, S.; Yoshida, M.; Miyajima, I.; Araki, T.; Hirai, Y.; *J. Heterocycl. Chem.* 1995, 32(5), 1517-1519 which describes methods for copper cyanide; Yutilov, Y. M.; Svertilova, I. A.; *Khim Geterotsikl Soedin* 1994, 8, 1071-1075 which utilizes potassium cyanide; and Prager, R. H.; Tsopelas, C.; Heisler, T.; *Aust. J. Chem.* 1991, 44 (2), 277-285 which utilizes copper cyanide in the presence of $MeOS(O)_2F$. The chloride or more preferably a bromide on the azaindole may be displaced by sodium cyanide in dioxane via the method described in *Synlett.* 1998, 3, 243-244. Alternatively, Nickel dibromide, Zinc, and triphenyl phosphine in can be used to activate aromatic and heteroaryl chlorides to displacement via potassium cyanide in THF or other suitable solvent by the methods described in Eur. Pat. Appl., 831083, 1998.

The conversion of the cyano intermediate, 62, to the carboxylic acid intermediate, 63, is depicted in step 2, Scheme 22 or in step a12, Scheme 23. Many methods for the conversion of nitrites to acids are well known in the art and may be employed. Suitable conditions for step 2 of Scheme 22 or the conversion of intermediate 65 to intermediate 66 below employ potassium hydroxide, water, and an aqueous alcohol such as ethanol. Typically the reaction must be heated at refluxing temperatures for one to 100 h. Other procedures for hydrolysis include those described in:

Shiotani, S.; Taniguchi, K.; *J. Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; Macor, J. E.; Post, R.; Ryan, K.; *J. Heterocycl. Chem.* 1992, 29(6), 1465-1467.

The acid intermediate, 66 (Scheme 23), may then be esterified using conditions well known in the art. For example, reaction of the acid with diazomethane in an inert solvent such as ether, dioxane, or THF would give the methyl ester. Intermediate 67 may then be converted to intermediate 68 according to the procedure described in Scheme 2. Intermediate 68 may then be hydrolyzed to provide intermediate 69.

Scheme 23

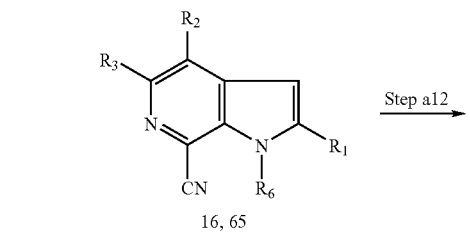

7, 64

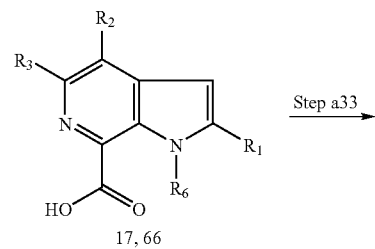

16, 65

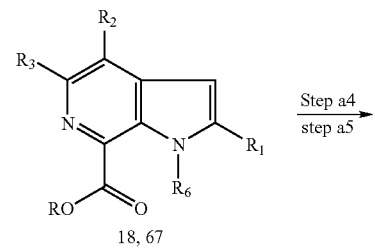

17, 66

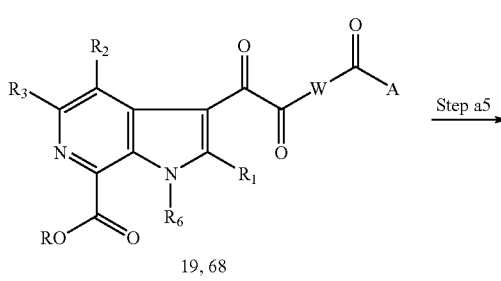

18, 67

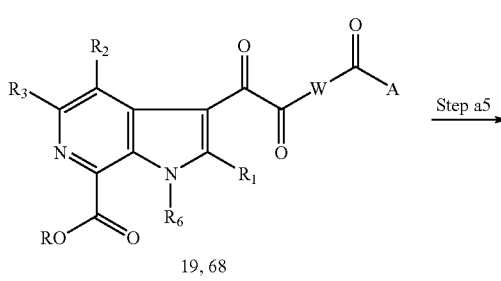

19, 68

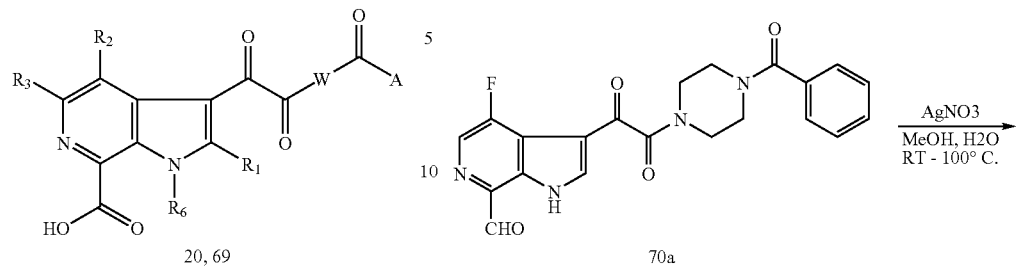

20, 69

As shown in Scheme 24, step a13 another preparation of the indoleoxoacetylpiperazine 7-carboxylic acids, 69, is carried out by oxidation of the corresponding 7-carboxaldehyde, 70. Numerous oxidants are suitable for the conversion of aldehyde to acid and many of these are described in standard organic chemistry texts such as: Larock, Richard C., Comprehensive organic transformations: a guide to functional group preparations $2^{nd}$ ed. New York: Wiley-VCH, 1999. One preferred method is the use of silver nitrate or silver oxide in a solvent such as aqueous or anhydrous methanol at a temperature of ~25° C. or as high as reflux. The reaction is typically carried out for one to 48 h and is typically monitored by TLC or LC/MS until complete conversion of product to starting material has occurred. Alternatively, $KmnO_4$ or $CrO_3/H_2SO_4$ could be utilized.

Scheme 25

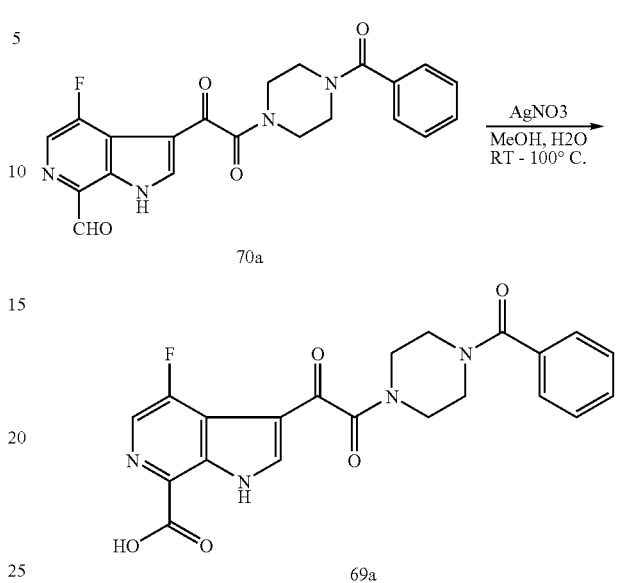

70a

69a

Alternatively, intermediate 69 can be prepared by the nitrile method of synthesis carried out in an alternative order as shown in Scheme 26. The nitrile hydrolyis step can be delayed and the nitrile carried through the synthesis to provide a nitrile which can be hydrolyzed to provide the free acid, 69, as above.

Scheme 24

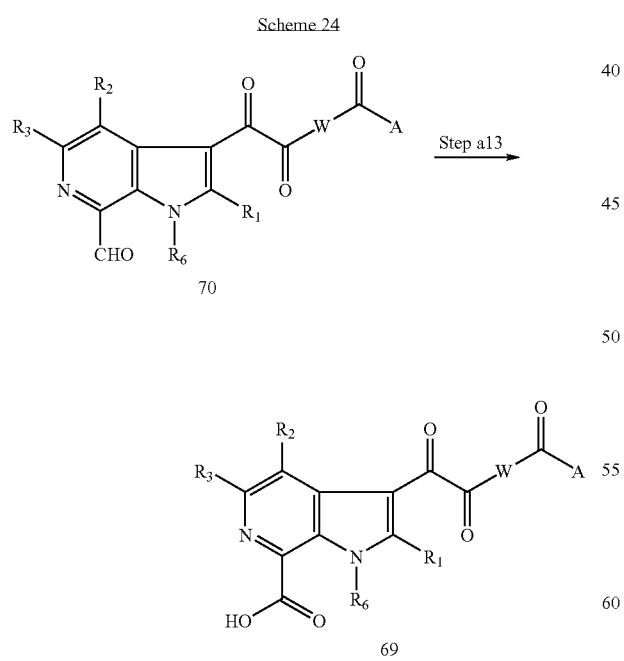

Scheme 25 gives a specific example of the oxidation of an aldehyde intermediate, 70a, to provide the carboxylic acid intermediate, 69a.

Scheme 26

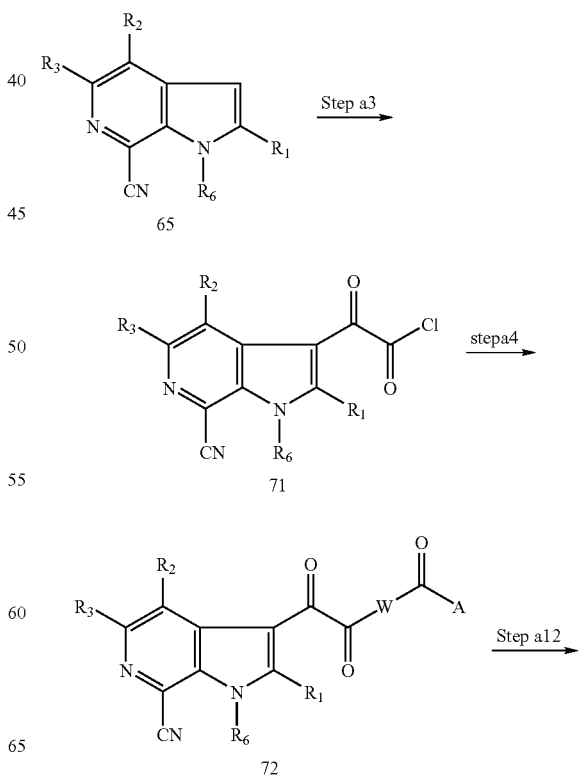

Waernmark, K.; Moberg, C.; *J. Org. Chem.* 1994, 59(8), 2004-2009; and El Hadri, A.; Leclerc, G.; *J. Heterocycl Chem.* 1993, 30(3), 631-635.

Step I. For NH2

Shiotani, S.; Taniguchi, K.; *J. Heterocycl. Chem.* 1997, 34(2), 493-499; Boogaard, A. T.; Pandit, U. K.; Koomen, G.-J.; *Tetrahedron* 1994, 50(8), 2551-2560; Rivalle, C.; Bisagni, E.; *Heterocycles* 1994, 38(2), 391-397; Macor, J. E.; Post, R.; Ryan, K.; *J. Heterocycl. Chem.* 1992, 29(6), 1465-1467.

Step J.

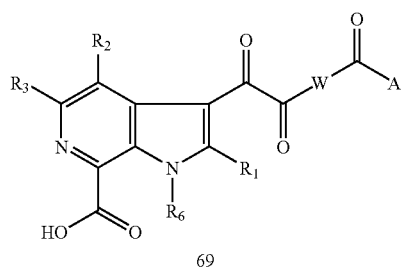

Scheme 27

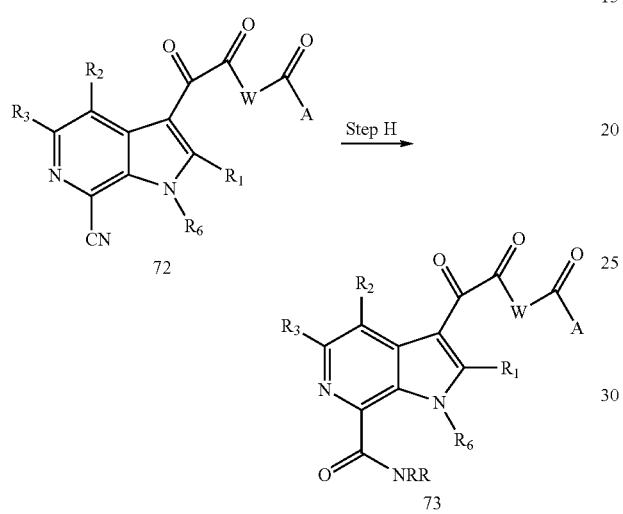

Step H. The direct conversion of nitriles, such as 72, to amides, such as 73, shown in Scheme 27, Step H, can be carried out using the conditions as described in Shiotani, S.; Taniguchi, K.; *J. Heterocycl Chem.* 1996, 33(4), 1051-1056 (describes the use of aqueous sulfuric acid); Memoli, K. A.; *Tetrahedron Lett.* 1996, 37(21), 3617-3618; Adolfsson, H.;

Scheme 28

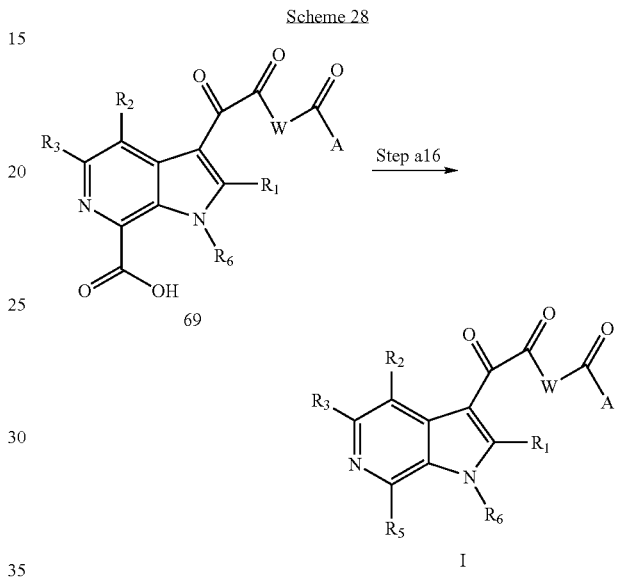

The following scheme (28A) shows an example for the preparation of 4-fluoro-7substituted azaindoles from a known starting materials. References for the Bartoli indole synthesis were mentioned earlier. The conditions for transformation to the nitrites, acids, aldeheydes, heterocycles and amides have also been described in this application.

Scheme 28A

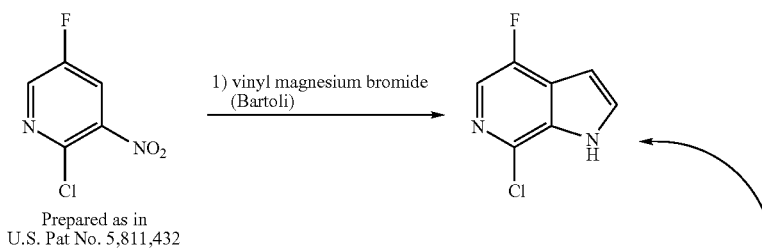

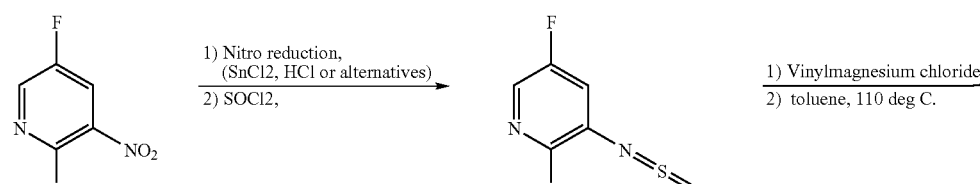

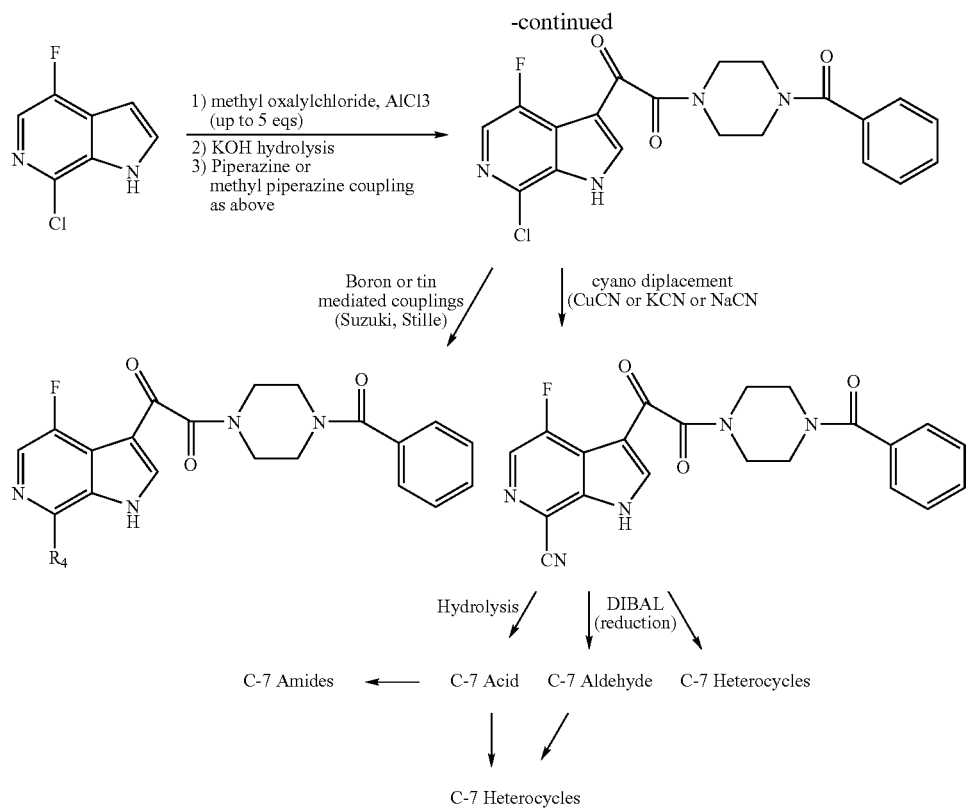
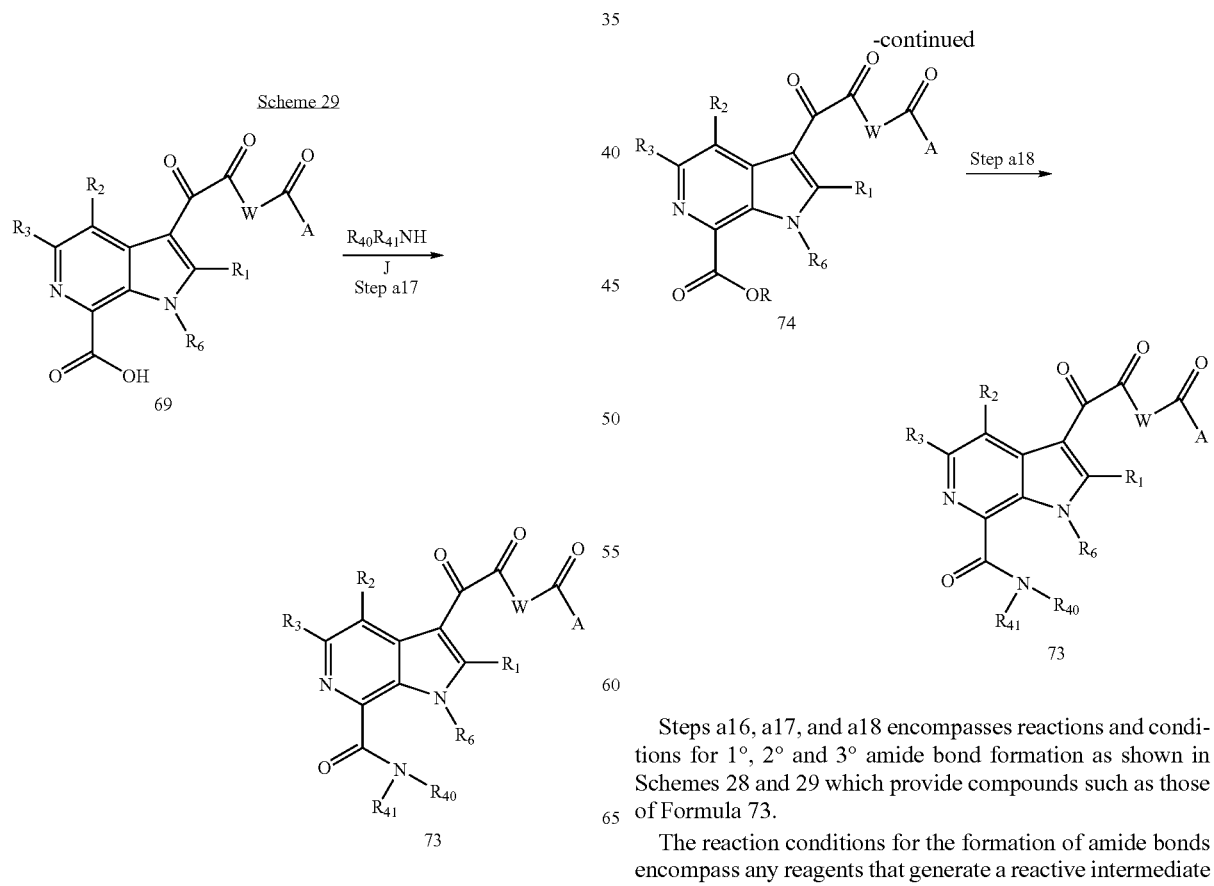
Steps a16, a17, and a18 encompasses reactions and conditions for 1°, 2° and 3° amide bond formation as shown in Schemes 28 and 29 which provide compounds such as those of Formula 73.
The reaction conditions for the formation of amide bonds encompass any reagents that generate a reactive intermediate for activation of the carboxylic acid to amide formation, for example (but not limited to), acyl halide, from carbodiimide, acyl iminium salt, symmetrical anhydrides, mixed anhydrides (including phosphonic/phosphinic mixed anhydrides), active esters (including silyl ester, methyl ester and thioester), acyl carbonate, acyl azide, acyl sulfonate and acyloxy N-phosphonium salt. The reaction of the indole carboxylic acids with amines to form amides may be mediated by standard amide bond forming conditions described in the art. Some examples for amide bond formation are listed in references 41-53 but this list is not limiting. Some carboxylic acid to amine coupling reagents which are applicable are EDC, Diisopropylcarbodiimide or other carbodiimides, PyBop (benzotriazolyloxytris(dimethylamino) phosphonium hexafluorophosphate), 2-(1H-benzotriazole-1-yl)-1,1,3,3-tetramethyl uronium hexafluorophosphate (HBTU). A particularly useful method for azaindole 7-carboxylic acid to amide reactions is the use of carbonyl imidazole as the coupling reagent as described in reference 53. The temperature of this reaction may be lower than in the cited reference, from 80° C. (or possibly lower) to 150° C. or higher. A more specific application is depicted in Scheme 30.

Method 2:
To a mixture of an appropriate amine (4 equiv.) and HOBT (16 mg, 0.12 mmol) in THF (0.5 mL) was added an acid intermediate, such as 69, (25 mg, 0.06 mmol) and NMM (50 μl, 0.45 mmol), followed by EDC (23 mg, 0.12 mmol). The reaction mixture was shaken at rt for 12 h. The volatiles were evaporated in vacuo; and the residue dissolved in MeOH and subjected to preparative reverse phase HPLC purification.

Method 3:
To a mixture of an acid intermediate, such as 69, (0.047 mmol), amine (4 equiv.) and DEPBT (prepared according to Li, H.; Jiang, X. Ye, Y.; Fan, C.; Todd, R.; Goodman, M. *Organic Letters* 1999, 1, 91; 21 mg, 0.071 mmol) in DMF (0.5 mL) was added TEA (0.03 mL, 0.22 mmol). The resulting mixture was shaken at rt for 12 h; and then diluted with MeOH (2 mL) and purified by preparative reverse phase HPLC.

Method 4:
A mixture of an acid intermediate, such as 69, (0.047 mmol) and 8.5 mg (0.052 mmol) of 1,1-carbonyldiimidazole in anhydrous THF (2 mL) was heated to reflux under nitrogen. After 2.5 h, 0.052 mmol of amine was added and heating

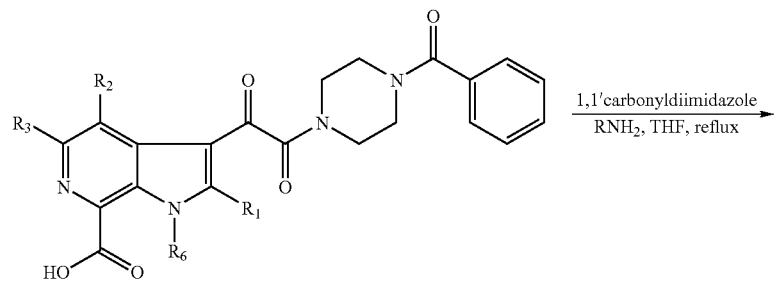

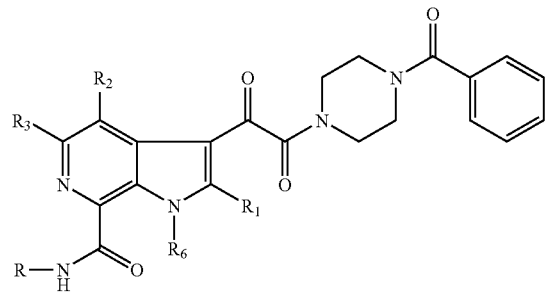

The following four general methods provide a more detailed description for the preparation of indolecarboamides and these methods were employed for the synthesis of compounds of Formula I.

Method 1:
To a mixture of an acid intermediate, such as 69, (1 equiv., 0.48 mmol), an appropriate amine (4 equiv.) and DMAP (58 mg, 0.47 mmol) dissolved CH$_2$Cl$_2$ (1 mL) was added EDC (90 mg, 0.47 mmol). The resulting mixture was shaken at rt for 12 h, and then evaporated in vacuo. The residue was dissolved in MeOH, and subjected to preparative reverse phase HPLC purification.

continued. After an additional period of 3~20 h at reflux, the reaction mixture was cooled and concentrated in vacuo. The residue was purified by chromatography on silica gel to provide a compound of Formula I.

In addition, the carboxylic acid may be converted to an acid chloride using reagents such as thionyl chloride (neat or in an inert solvent) or oxalyl chloride in a solvent such as benzene, toluene, THF, or CH$_2$Cl$_2$. The amides may alternatively, be formed by reaction of the acid chloride with an excess of ammonia, primary, or secondary amine in an inert solvent such as benzene, toluene, THF, or CH$_2$Cl$_2$ or with stoichiometric amounts of amines in the presence of a tertiary amine such as triethylamine or a base such as pyridine or 2,6-lutidine. Alternatively, the acid chloride may be reacted with an amine under basic conditions (Usually sodium or potassium hydroxide) in solvent mixtures containing water and possibly a miscible co solvent such as dioxane or THF. Scheme 25B depicts a typical preparation of an acid chloride and derivatization to an amide of Formula I. Additionally, the carboxylic acid may be converted to an ester preferably a methyl or ethyl ester and then reacted with an amine. The ester may be formed by reaction with diazomethane or alternatively trimethylsilyl diazomethane using standard conditions which are well known in the art. References and procedures for using these or other ester forming reactions can be found in reference 52 or 54.

Additional references for the formation of amides from acids are: Norman, M. H.; Navas, F. III; Thompson, J. B.; Rigdon, G. C.; *J. Med. Chem.* 1996, 39(24), 4692-4703; Hong, F.; Pang, Y.-P.; Cusack, B.; Richelson, E.; *J. Chem. Soc., Perkin Trans* 1 1997, 14, 2083-2088; Langry, K. C.; *Org. Prep. Proc. Int.* 1994, 26(4), 429-438; Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; et al.; *J. Med. Chem.* 1994, 37(7), 999-1014; Bhattacharjee, A.; Mukhopadhyay, R.; Bhattacharjya, A.; *Indian J. Chem., Sect B* 1994, 33(7), 679-682.

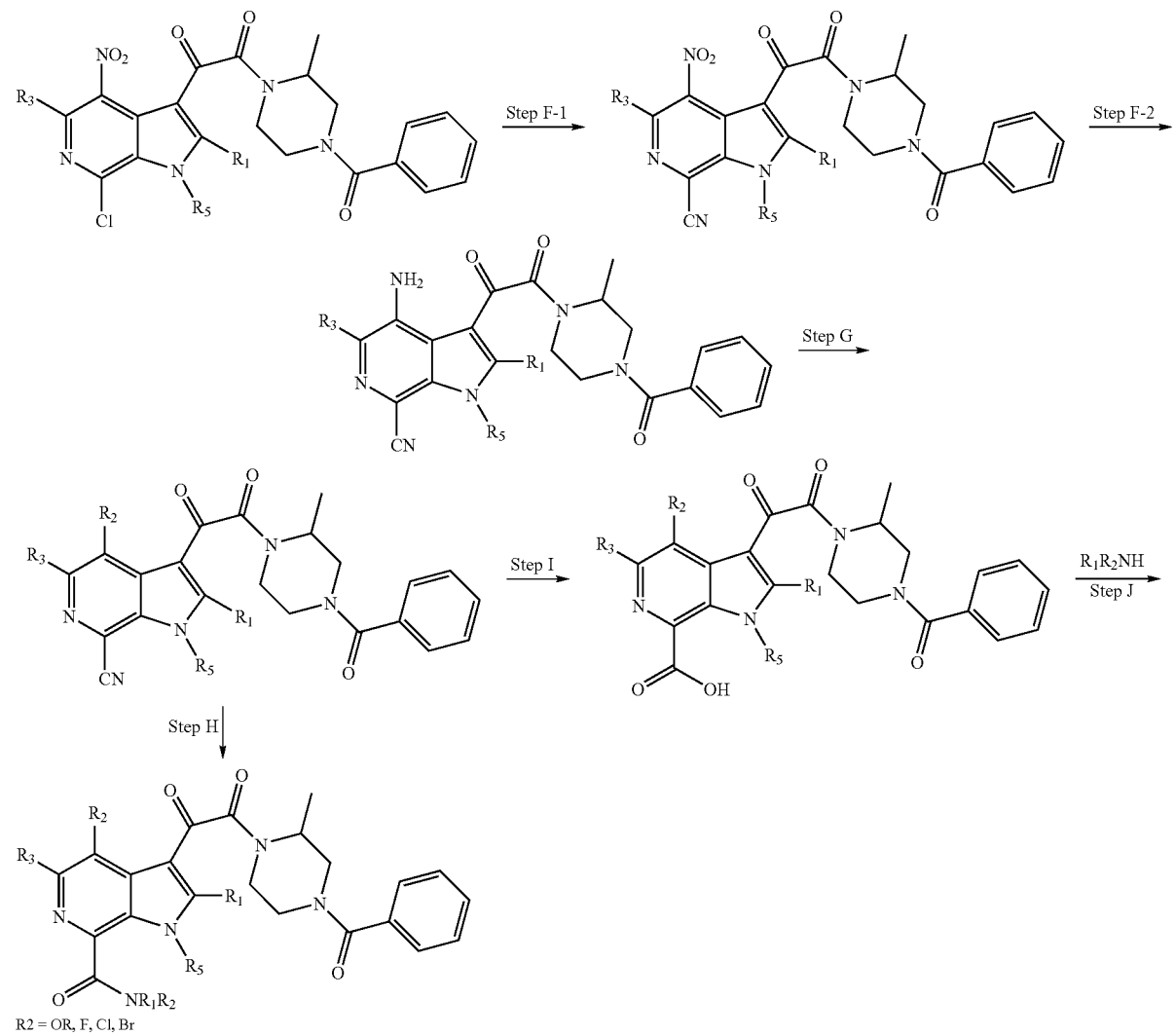

Scheme 31 shows synthetic transformations on a chloro nitro azaindole. Step F-1 of Scheme 31 can be carried may be carried out according to the following procedures: Yamaguchi, S.; Yoshida, M.; Miyajima, I.; Araki, T.; Hirai, Y.; *J. Heterocycl Chem.* 1995, 32(5), 1517-1519;

Yutilov, Y. M.; Svertilova, I. A.; *Khim Geterotsikl Soedin* 1994, 8, 1071-1075; and Prager, R. H.; Tsopelas, C.; Heisler, T.; *Aust. J. Chem.* 1991, 44(2), 277-285. Step F-2 of Scheme 31 may be accomplished according to the procedures set forth in: Ciurla, H.; Puszko, A.; *Khim Geterotsikl Soedin* 1996, 10, 1366-1371; Robinson, R. P.; Donahue, K. M.; Son, P. S.; Wagy, S. D.; *J. Heterocycl. Chem.* 1996, 33(2), 287-293; Nicolai, E.; Claude, S.; Teulon, J. M.; *J. Heterocycl. Chem.* 1994, 31(1), 73-75; Hwu, J. R.; Wong, F. F.; Shiao, M.-J.; *J.*

Org. Chem. 1992, 57(19), 5254-5255; Shiao, M.-J.; Lai, L.-L.; Ku, W.-S.; Lin, P.-Y.; Hwu, J. R.; J. Org. Chem. 1993, 58(17), 4742-4744.

The introduction of an alkoxy or aryloxy substituent onto the azaindole (Step G, Scheme 31, $R_2$ is alkoxy or aryloxy) may be accomplished by the f procedures described in Klemm, L. H.; Zell, R.; J. Heterocycl. Chem. 1968, 5, 773; Bradsher, C. K.; Brown, F. C.; Porter, H. K.; J. Am. Chem. Soc. 1954, 76, 2357; and Hodgson, H. H.; Foster, C. K.; J. Chem. Soc. 1942, 581.

The introduction of a fluorine substituent onto the azaindole (Step G, Scheme 31) may be accomplished according to the procedures as described in Sanchez, J. P.; Gogliotti, R. D.; J. Heterocycl. Chem. 1993, 30(4), 855-859; Rocca, P.; Marsais, F.; Godard, A.; Queguiner, G.; Tetrahedron Lett. 1993, 34(18), 2937-2940; and Sanchez, J. P.; Rogowski, J. W.; J. Heterocycl. Chem. 1987, 24, 215.

The introduction of a chlorine substituent onto the azaindole (Step G, Scheme 31) may be accomplished according to the procedures as described in Ciurla, H.; Puszko, A.; Khim Geterotsikl Soedin 1996, 10, 1366-1371; Raveglia, L. F.; Giardinal, G. A. M.; Grugni, M.; Rigolio, R.; Farina, C.; J. Heterocycl Chem. 1997, 34(2), 557-559; Matsumoto, J. I.; Miyamoto, T.; Minamida, A.; Mishimura, Y.; Egawa, H.; Mishimura, H.; J. Med. Chem. 1984, 27(3), 292; Lee, T.-C.; Salemnick, G.; J. Org. Chem. 1975, 24, 3608.

The introduction of a bromine substituent onto the azaindole (Step G, Scheme 31) may be accomplished according to the procedures as described in Raveglia, L. F.; Giardina, G. A. M.; Grugni, M.; Rigolio, R.; Farina, C.; J. Heterocycl. Chem. 1997, 34(2), 557-559; Talik, T.; Talik, Z.; Ban-Oganowska, H.; Synthesis 1974, 293; Abramovitch, R. A.; Saha, M.; Can. J. Chem. 1966, 44, 1765.

It is well known in the art that heterocycles may be prepared from an aldehyde, carboxylic acid, carboxylic acid ester, carboxylic acid amide, carboxylic acid halide, or cyano moiety or attached to another carbon substituted by a bromide or other leaving group such as a triflate, mesylate, chloride, iodide, or phosphonate. The methods for preparing such intermediates from intermediates typified by the carboxylic acid intermediate, 69, bromo intermediate, 76, or aldehyde intermediate, 70 described above are known by a typical chemist practitioner. The methods or types of heterocycles which may be constructed are described in the chemical literature. Some representative references for finding such heterocycles and their construction are included in reference 55 through 67 but should in no way be construed as limiting. However, examination of these references shows that many versatile methods are available for synthesizing diversely substituted heterocycles and it is apparent to one skilled in the art that these can be applied to prepare compounds of Formula I. Chemists well versed in the art can now easily, quickly, and routinely find numerous reactions for preparing heterocycles, amides, oximes or other substituents from the above mentioned starting materials by searching for reactions or preparations using a conventional electronic database such as Scifinder (American Chemical Society), Crossfire (Beilstein), Theilheimer, or Reaccs (MDS). The reaction conditions identified by such a search can then be employed using the substrates described in this application to produce all of the compounds envisioned and covered by this invention. In the case of amides, commercially available amines can be used in the synthesis. Alternatively, the above mentioned search programs can be used to locate literature preparations of known amines or procedures to synthesize new amines. These procedures are then carried out by one with typical skill in the art to provide the compounds of Formula I for use as antiviral agents.

As shown below in Scheme 32, step a13, suitable substituted azaindoles, such as the bromoazaindole intermediate, 76, may undergo metal mediated couplings with aryl groups, heterocycles, or vinyl stannanes to provide compounds of Formula I wherein $R_5$ is aryl, heteroaryl, or heteroalicyclic for example. The bromoazaindole intermediates, 76, (or azaindole triflates or iodides) may undergo Stille-type coupling with heteroarylstannanes as shown in Scheme 32, step a13. Conditions for this reaction are well known in the art and references 68-70 as well as reference 52 provide numerous conditions in addition to the specific examples provided in Scheme 14 and in the specific embodiments. It can be well recognized that an indole stannane could also couple to a heterocyclic or aryl halide or triflate to construct compounds of Formula I. Suzuki coupling (reference 71) between the bromo intermediate, 76, and a suitable boronate could also be employed and some specific examples are contained in this application.

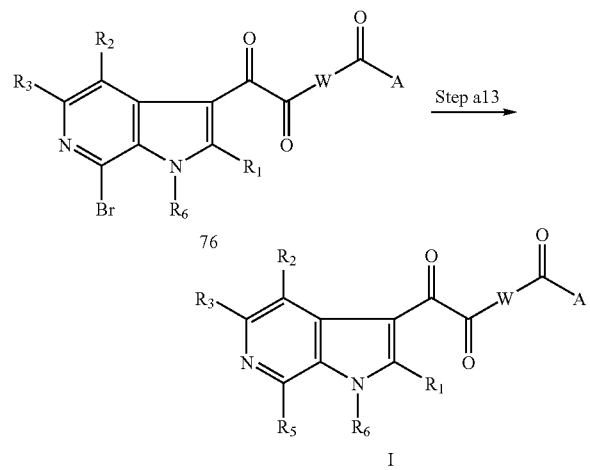

Scheme 32

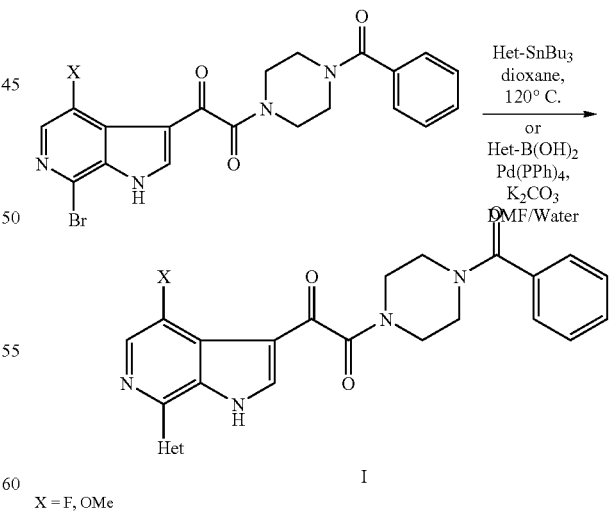

Scheme 33

X = F, OMe

As shown in Scheme 34, step a14, aldehyde intermediates, 70, may be used to generate numerous compounds of Formula I. The aldehyde group may be a precursor for any of the substituents $R_1$ through $R_5$ but the transformation for $R_5$ is depicted above for simplicity. The aldehyde intermediate 70, may be reacted to become incorporated into a ring as Scheme 34

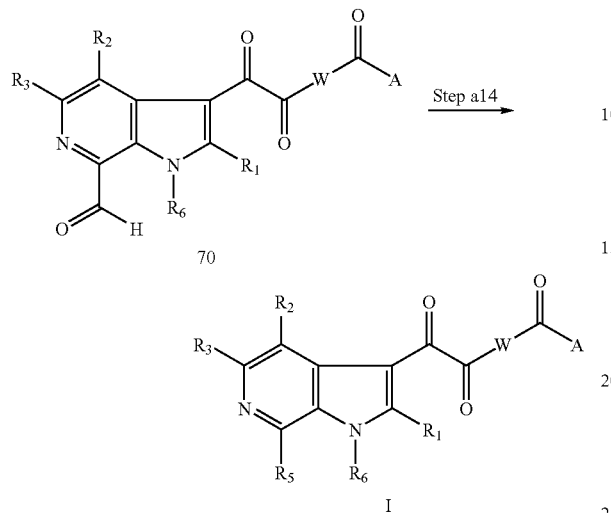

hyde could be converted to benzyl amines via reductive amination. An example of oxazole formation via a Tosmic reagent is shown below in Scheme 35. The same reaction would work with aldehydes at other positions and also in the 5 and 6 aza indole series.

Scheme 35

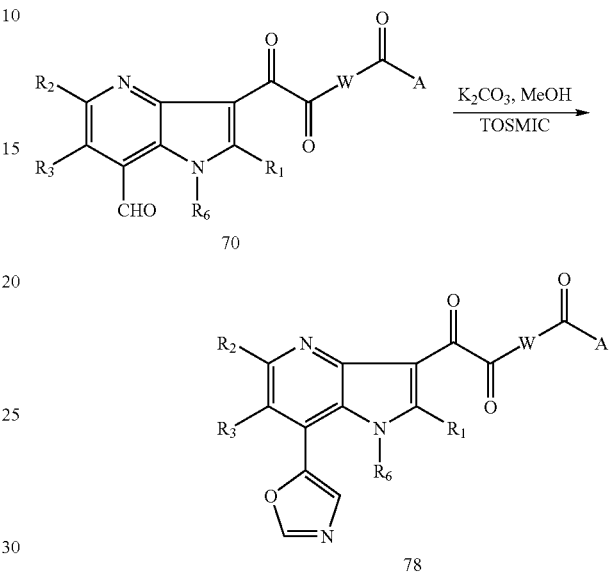

$R_2 = Cl$ described in the claims or be converted into an acyclic group. The aldehyde, 70, may be reacted with a Tosmic based reagent to generate oxazoles (references 42 and 43 for example). The aldehyde, 70, may be reacted with a Tosmic reagent and than an amine to give imidazoles as in reference 72 or the aldehyde intermediate, 70, may be reacted with hydroxylamine to give an oxime which is a compound of Formula I as described below. Oxidation of the oxime with NBS, t-butyl hypochlorite, or the other known reagents would provide the N-oxide which react with alkynes or 3 alkoxy vinyl esters to give isoxazoles of varying substitution. Reaction of the aldehyde intermediate 70, with the known reagent, 77 (reference 70) shown below under basic conditions would provide 4-aminotrityl oxazoles.

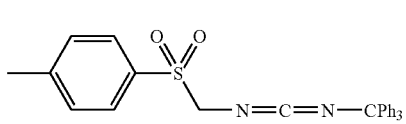

Removal of the trityl group would provide 4-amino oxazoles which could be substituted by acylation, reductive alkylation or alkylation reactions or heterocycle forming reactions. The trityl could be replaced with an alternate protecting group such as a monomethoxy trityl, CBZ, benzyl, or appropriate silyl group if desired. Reference 73 demonstrates the preparation of oxazoles containing a triflouoromethyl moiety and the conditions described therein demonstrates the synthesis of oxazoles with fluorinated methyl groups appended to them.

The aldehyde could also be reacted with a metal or Grignard (alkyl, aryl, or heteroaryl) to generate secondary alcohols. These would be efficacious or could be oxidized to the ketone with TPAP or $MnO_2$ or PCC for example to provide ketones of Formula I which could be utilized for treatment or reacted with metal reagents to give tertiary alcohols or alternatively converted to oximes by reaction with hydroxylamine hydrochlorides in ethanolic solvents. Alternatively the alde- Scheme 36 shows in step a15, a cyano intermediate, such as 62, which could be directly converted to compounds of Formula I via heterocycle formation or reaction with organometallic reagents.

Scheme 36

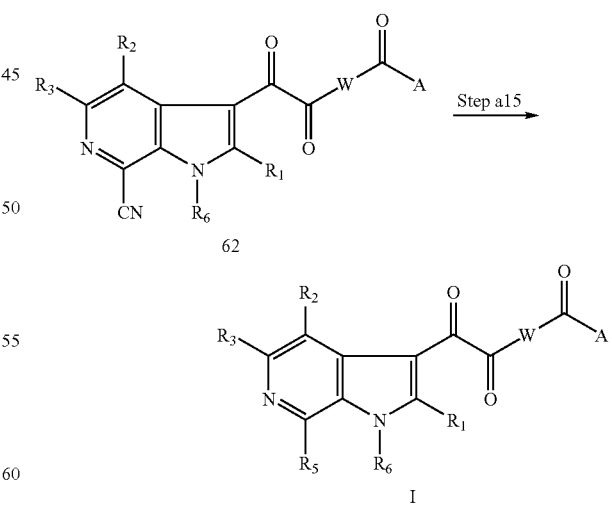

Scheme 37 shows a method for acylation of a cyanoindole intermediate of formula 65 with oxalyl chloride which would give acid chloride, 79, which could then be coupled with the appropriate amine in the presence of base to provide 80.

Scheme 37
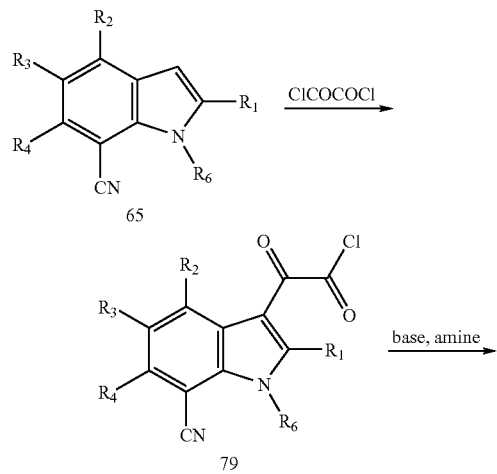
The nitrile intermediate, 80, could be converted to the tetrazole of formula 81, which could then be alkylated with trimethylsilyldiazomethane to give the compound of formula 82 (Scheme 38).
Scheme 38
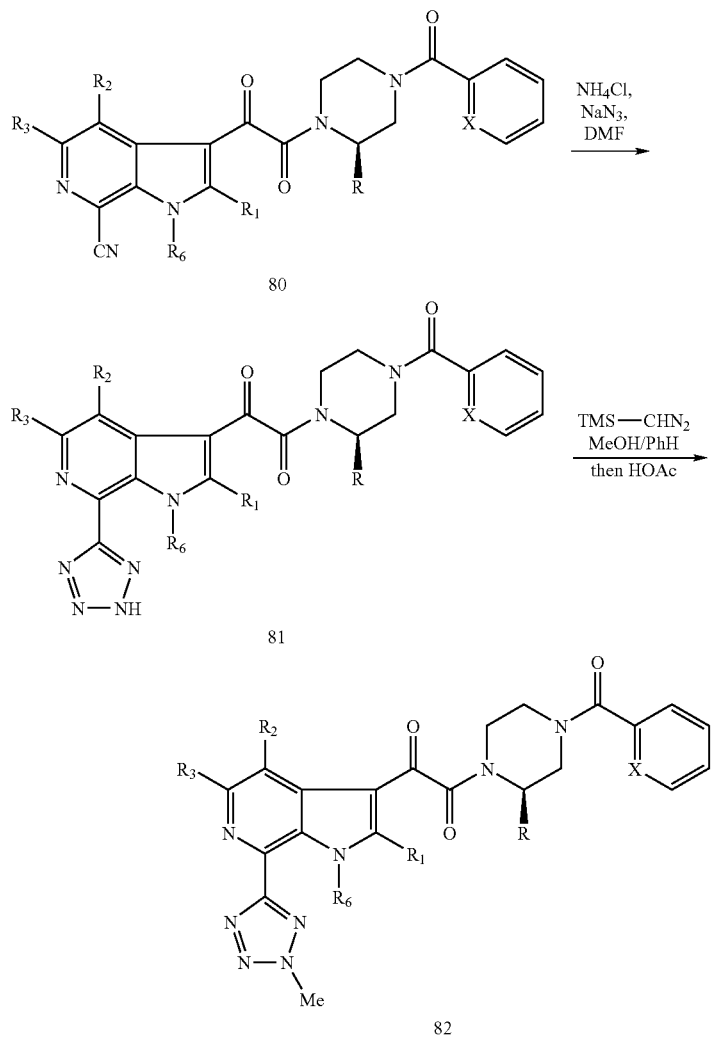

Tetrazole alkylation with alkyl halides would be carried out prior to azaindole acylation as shown in Scheme 39. Intermediate 65 could be converted to tetrazole, 83, which could be alkylated to provide 84. Intermediate 84 could then be acylated and hydrolyzed to provide 85 which could be subjected to amide formation conditions to provide 86. The group appended to the tetrazole may be quite diverse and still exhibit impressive potency.

Scheme 39

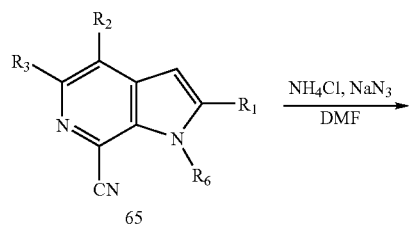

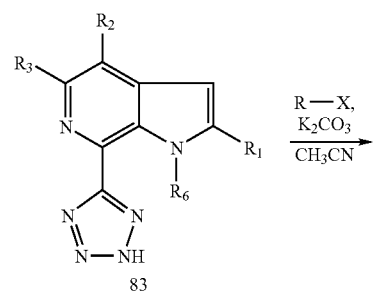

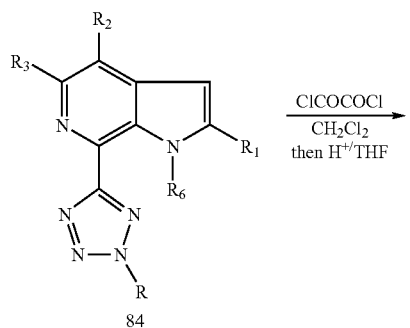

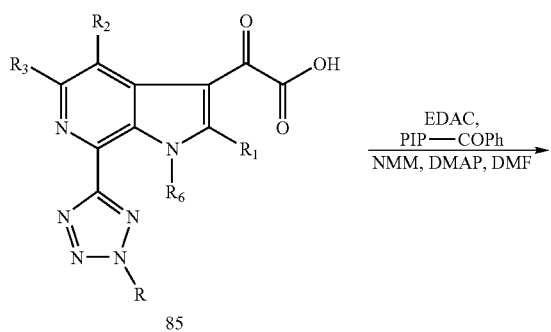

-continued

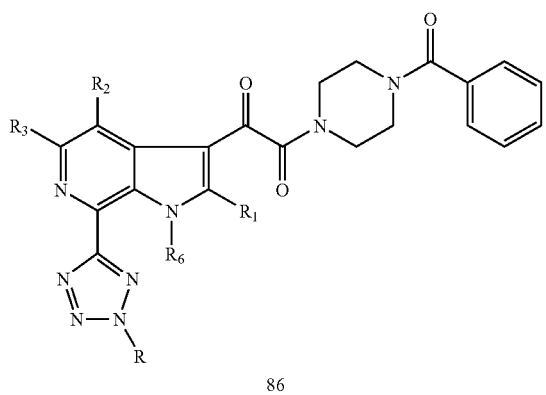

Scheme 40 shows that an oxadiazole such as, 88, may be prepared by the addition of hydroxylamine to the nitrile, 80, followed by ring closure of intermediate 87 with phosgene. Alkylation of oxadiazole, 88, with trimethylsilyldiazomethane would give the compound of formula 89.

Scheme 40

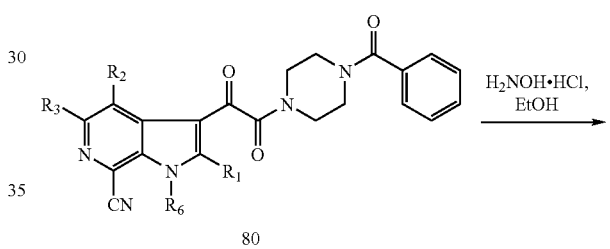

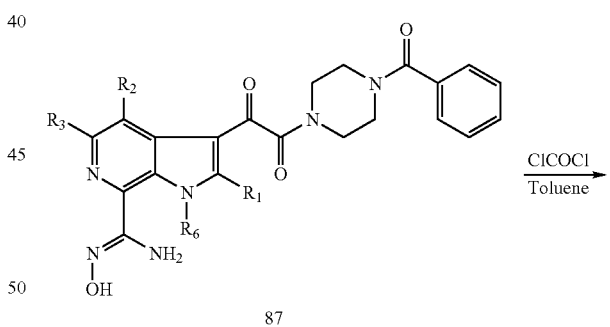

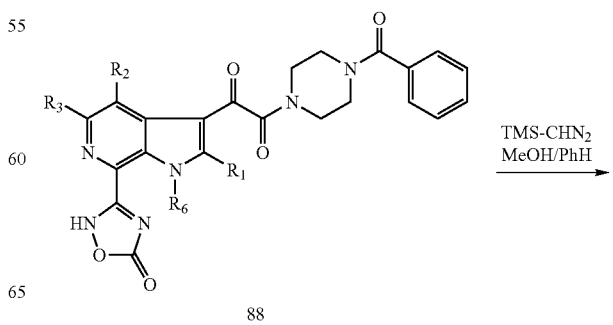

-continued

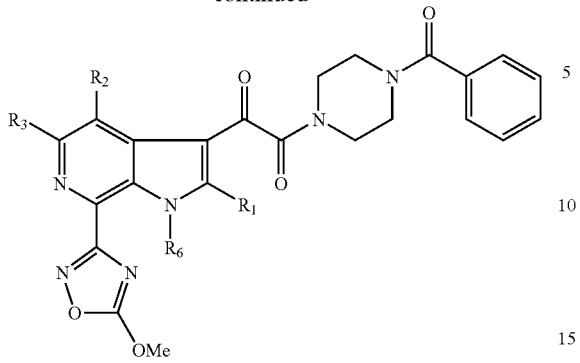

89

A 7-cyanoindole, such as 80, could be efficiently converted to the imidate ester under conventional Pinner conditions using 1,4-dioxane as the solvent. The imidate ester can be reacted with nitrogen, oxygen and sulfur nucleophiles to provide C7-substituted indoles, for example: imidazolines, benzimidazoles, azabenzimidazoles, oxazolines, oxadiazoles, thiazolines, triazoles, pyrimidines and amidines etc. For example the imidate may be reacted with acetyl hydrazide with heating in a nonparticipating solvent such as dioxane, THF, or benzene for example. (aqueous base or aqueous base in an alcoholic solvent may need to be added to effect final dehydrative cyclization in some cases) to form a methyl triazine. Other hydrazines can be used. Triazines can also be installed via coupling of stannyl triazines with 4,5,6, or 7-bromo or chloro azaindoles. The examples give an example of the formation of many of these heterocycles.

REFERENCES (1) Das, B. P.; Boykin, D. W. *J. Med. Chem.* 1977, 20, 531.
(2) Czarny, A.; Wilson, W. D.; Boykin, D. W. *J. Heterocyclic Chem.* 1996, 33, 1393.
(3) Francesconi, I.; Wilson, W. D.; Tanious, F. A.; Hall, J. E.; Bender, B. C.; Tidwell, R. R.; McCurdy, D.; Boykin, D. W. *J. Med. Chem.* 1999, 42, 2260.

Scheme 41 shows addition of either hydroxylamine or hydroxylamine acetic acid to aldehyde intermediate 90 may give oximes of Formula 91.

Scheme 41

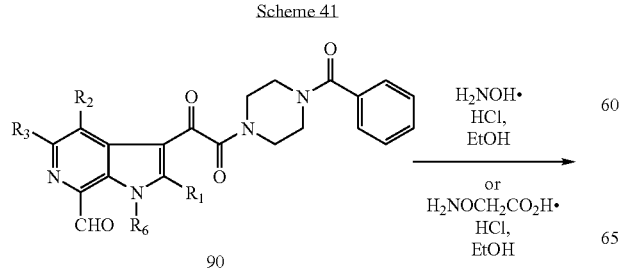

90

-continued

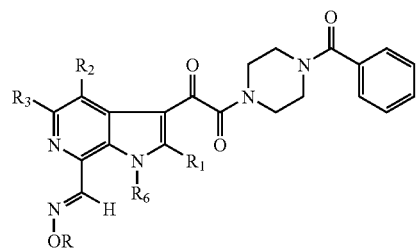

91

An acid may be a precursor for substituents $R_1$ through $R_5$ when it occupies the corresponding position such as $R_5$ as shown in Scheme 42.

Scheme 41a

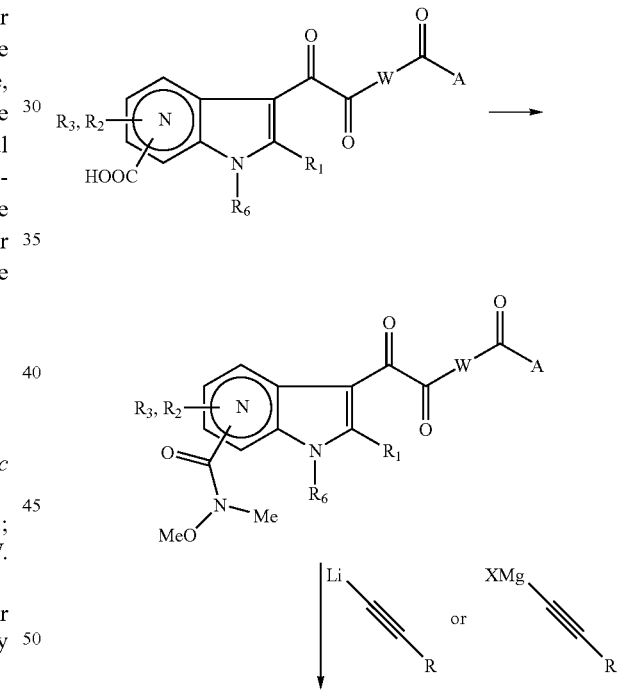

-continued

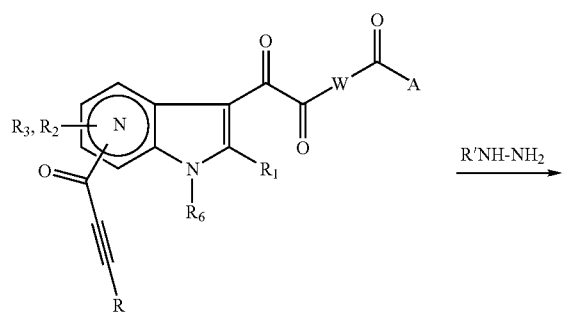

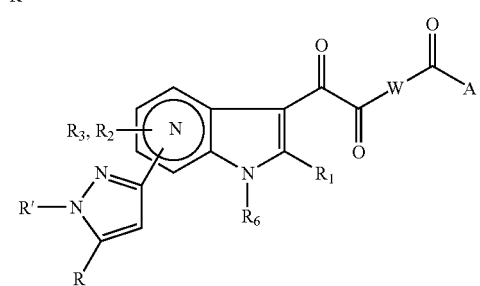

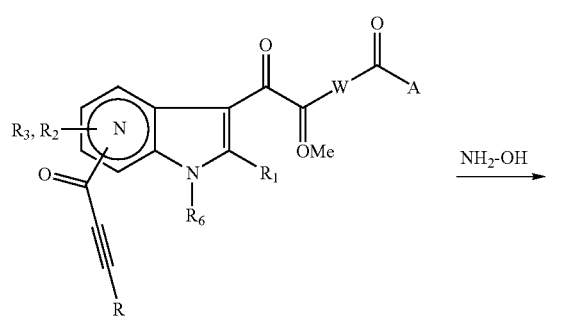

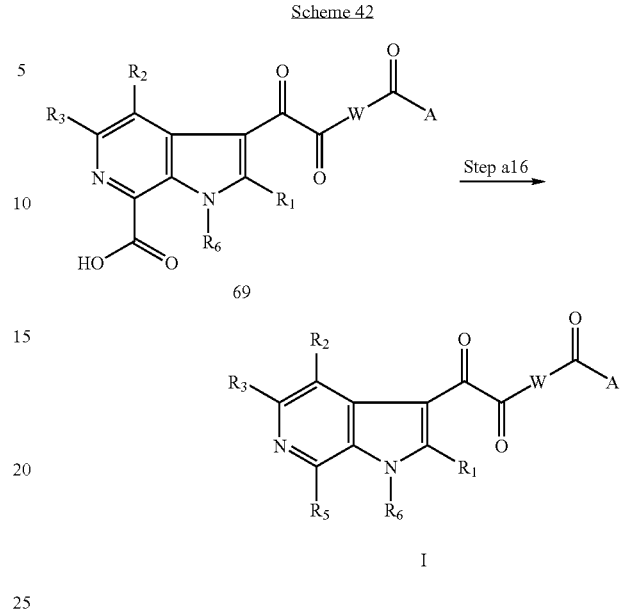

Scheme 42

An acid intermediate, such as 69, may be used as a versatile precursor to generate numerous substituted compounds. The acid could be converted to hydrazonyl bromide and then a pyrazole via reference 74. One method for general heterocycle synthesis would be to convert the acid to an alpha bromo ketone (ref 75) by conversion to the acid chloride using standard methods, reaction with diazomethane, and finally reaction with HBr. The alpha bromo ketone could be used to prepare many different compounds of Formula I as it can be converted to many heterocycles or other compounds of Formula I. Alpha amino ketones can be prepared by displacement of the bromide with amines. Alternatively, the alpha bromo ketone could be used to prepare heterocycles not available directly from the aldeheyde or acid. For example, using the conditions of Hulton in reference 76 to react with the alpha bromo ketone would provide oxazoles. Reaction of the alpha bromoketone with urea via the methods of reference 77 would provide 2-amino oxazoles. The alpha bromoketone could also be used to generate furans using beta keto esters (ref 78-80) or other methods, pyrroles (from beta dicarbonyls as in ref 81 or by Hantsch methods (ref 82) thiazoles, isoxazoles and imidazoles (ref 83) example using literature procedures. Coupling of the aforementioned acid chloride with N-methyl-O-methyl hydroxylamine would provide a "Weinreb Amide" which could be used to react with alkyl lithiums or Grignard reagents to generate ketones. Reaction of the Weinreb anion with a dianion of a hydroxylamine would generate isoxazoles (ref 84). Reaction with an acetylenic lithium or other carbanion would generate alkynyl indole ketones. Reaction of this alkynyl intermediate with diazomethane or other diazo compounds would give pyrazoles (ref 85). Reaction with azide or hydroxylamine would give heterocycles after elimination of water. Nitrile oxides would react with the alkynyl ketone to give isoxazoles (ref 86). Reaction of the initial acid to provide an acid chloride using for example oxalyl chloride or thionyl chloride or triphenyl phosphine/carbon tetrachloride provides a useful intermediate as noted above. Reaction of the acid chloride with an alpha ester substituted isocyanide and base would give 2-substituted oxazoles (ref 87). These could be converted to amines, alcohols, or halides using standard reductions or Hoffman/Curtius type rearrangements.

Scheme 43 describes alternate chemistry for installing the oxoacetyl piperazine moiety onto the 3 position of the azaindoles. Step A''' in Scheme 43 depicts reaction with formaldehyde and dimethylamine using the conditions in Frydman, B.; Despuy, M. E.; Rapoport, H.; *J. Am. Chem. Soc.* 1965, 87, 3530 will provide the dimethylamino compound shown.

Step B''' shows displacement with potassium cyanide would provide the cyano derivative according to the method described in Miyashita, K.; Kondoh, K.; Tsuchiya, K.; Miyabe, H.; Imanishi, T.; *Chem. Pharm. Bull* 1997, 45(5), 932-935 or in Kawase, M.; Sinhababu, A. K.; Borchardt, R. T.; *Chem. Pharm. Bull.* 1990, 38(11), 2939-2946. The same transformation could also be carried out using TMSCN and a tetrabutylammonium fluoride source as in Iwao, M.; Motoi, O.; *Tetrahedron Lett.* 1995, 36(33), 5929-5932. Sodium cyanide could also be utilized.

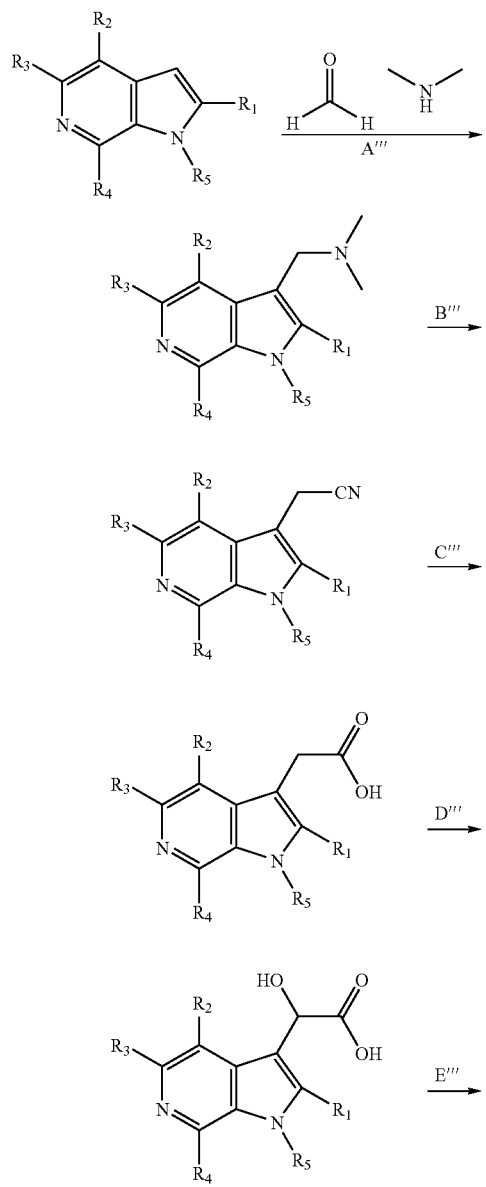

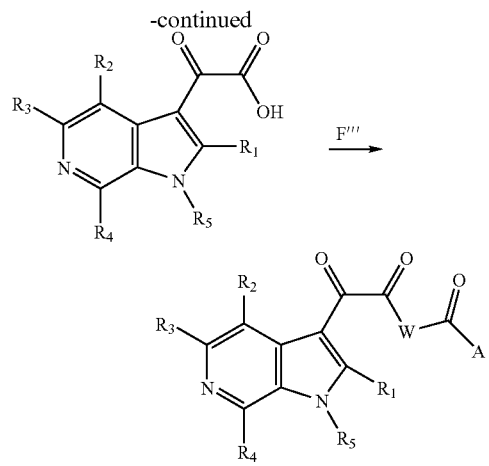

Step C''' of Scheme 43 depicts hydrolysis of the nitrile with sodium hydroxide and methanol would provide the acid via the methods described in Iwao, M.; Motoi, O.; *Tetrahedron Lett.* 1995, 36(33), 5929-5932 for example. Other basic hydrolysis conditions using either NaOH or KOH as described in Thesing, J.; et al.; *Chem. Ber.* 1955, 88, 1295 and Geissman, T. A.; Armen, A.; *J. Am. Chem. Soc.* 1952, 74, 3916. The use of a nitrilase enzyme to achieve the same transformation is described by Klempier N, de Raadt A, Griengl H, Heinisch G, *J. Heterocycl. Chem.*, 1992 29, 93, and may be applicable.

Step D''' of Scheme 43 depicts an alpha hydroxylation which may be accomplished by methods as described in Hanessian, S.; Wang, W.; Gai, Y.; *Tetrahedron Lett.* 1996, 37(42), 7477-7480; Robinson, R. A.; Clark, J. S.; Holmes, A. B.; *J. Am. Chem. Soc.* 1993, 115(22), 10400-10401 (KN(TMS)$_2$ and then camphorsulfonyloxaziridine or another oxaziridine; and Davis, F. A.; Reddy, R. T.; Reddy, R. E.; *J. Org. Chem.* 1992, 57(24), 6387-6389.

Step E''' of Scheme 43 shows methods for the oxidation of the alpha hydroxy ester to the ketone which may be accomplished according to the methods described in Mohand, S. A.; Levina, A.; Muzart, J.; *Synth. Comm.* 1995, 25 (14), 2051-2059.

A preferred method for step E''' is that of Ma, Z.; Bobbitt, J. M.; *J. Org. Chem.* 1991, 56(21), 6110-6114 which utilizes 4-(NH—Ac)-TEMPO in a solvent such as $CH_2Cl_2$ in the presence of para toluenesulfonic acid. The method described in Corson, B. B.; Dodge, R. A.; Harris, S. A.; Hazen, R. K.; *Org. Synth.* 1941, I, 241 for the oxidation of the alpha hydroxy ester to the ketone uses $KmnO_4$ as oxidant. Other methods for the oxidation of the alpha hydroxy ester to the ketone include those described in Hunaeus; Zincke; *Ber. Dtsch Chem. Ges.* 1877, 10, 1489; Acree; *Am. Chem.* 1913, 50, 391; and Claisen; *Ber. Dtsch. Chem. Ges.* 1877, 10, 846.

Step F''' of Scheme 43 depicts the coupling reactions which may be carried out as described previously in the application and by a preferred method which is described in Li, H.; Jiang, X.; Ye, Y.-H.; Fan, C.; Romoff, T.; Goodman, M. *Organic Lett.*, 1999, 1, 91-93 and employs 3-(Diethoxyphosphoryloxy)-1,2,3-benzotriazin-4(3H)-one (DEPBT); a new coupling reagent with remarkable resistance to racemization.

Scheme 44
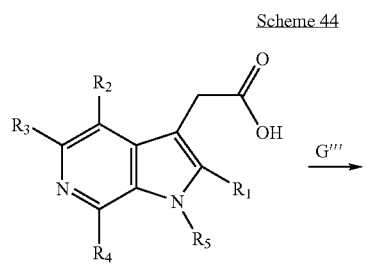
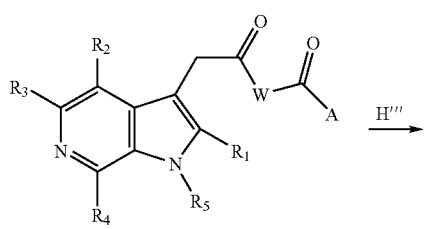
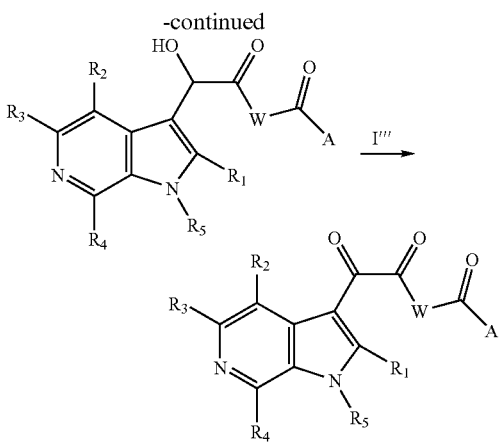
Scheme 44 depicts the preparation of Formula I compounds by coupling HWC(O)A to the acid as described in Step F''' of Scheme 43, followed by hydroxylation as in Step D''' of Scheme 43 and oxidation as described in Step E''' of Scheme 43.
Scheme 45
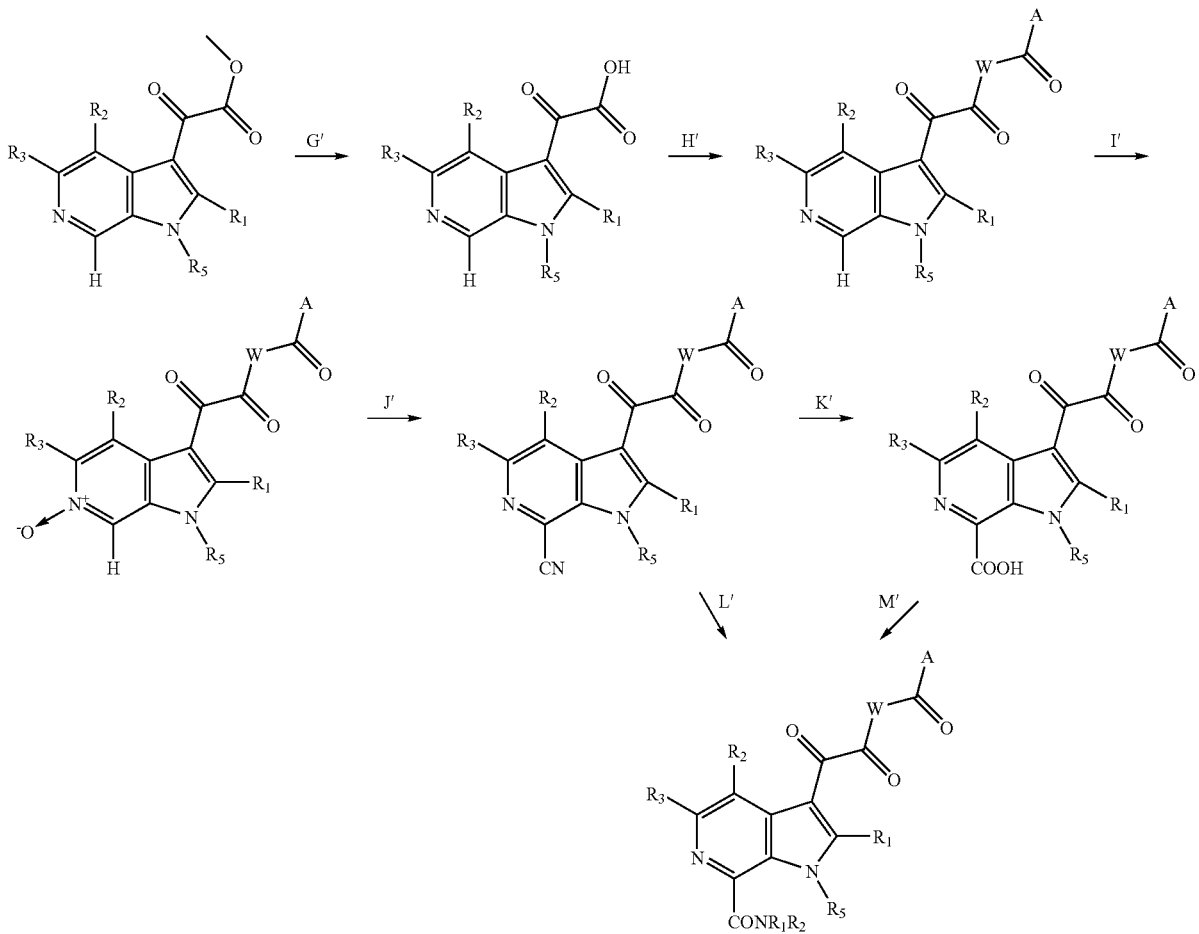

Scheme 45 depicts a method for the preparation which could be used to obtain amido compounds of Formula I. Step G' represents ester hydrolysis followed by amide formation (Step H' as described in Step F'" of Scheme 43). Step I' of Scheme 45 depicts the preparation of the N-oxide which could be accomplished according to the procedures in Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606; Suzuki, H.; Yokoyama, Y.; Miyagi, C.; Murakami, Y.; Chem. Pharm. Bull. 1991, 39(8), 2170-2172; and Ohmato, T.; Koike, K.; Sakamoto, Y.; Chem. Pharm. Bull. 1981, 29, 390. Cyanation of the N-oxide is shown in Step J' of Scheme 45 which may be accomplished according to Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606 and Suzuki, H.; Yokoyama, Y.; Miyagi, C.; Murakami, Y.; Chem. Pharm. Bull. 1991, 39(8), 2170-2172. Hydrolysis of the nitrile to the acid is depicted in Step K' of Scheme 45 according to procedures such as Shiotani, S.; Taniguchi, K.; *J. Heterocycl. Chem.* 1996, 33(4), 1051-1056; Memoli, K. A.; *Tetrahedron Lett.* 1996, 37(21), 3617-3618; Adolfsson, H.; Waernmark, K.; Moberg, C.; *J. Org. Chem.* 1994, 59(8), 2004-2009; and El Hadri, A.; Leclerc, G.; *J. Heterocycl. Chem.* 1993, 30(3), 631-635. Step L' of Scheme 45 depicts a method which could be utilized for the preparation of amido compounds of Formula I from the cyano derivative which may be accomplished according to procedures described in Shiotani, S.; Taniguchi, K.; *J. Heterocycl. Chem.* 1997, 34(2), 493-499; Boogaard, A. T.; Pandit, U.K.; Koomen, G.-*J.; Tetrahedron* 1994, 50(8), 2551-2560; Rivalle, C.; Bisagni, E.; *Heterocycles* 1994, 38(2), 391-397; and Macor, J. E.; Post, R.; Ryan, K.; *J. Heterocycl. Chem.* 1992, 29(6), 1465-1467. Step M' of Scheme 45 shows a method which could be used for the preparation of amido compounds of Formula I from the acid derivative which may be accomplished according to procedures described in Norman, M. H.; Navas, F. III; Thompson, J. B.; Rigdon, G. C.; *J. Med. Chem.* 1996, 39(24), 4692-4703; Hong, F.; Pang, Y.-P.; Cusack, B.; Richelson, E.; *J. Chem. Soc., Perkin Trans 1* 1997, 14, 2083-2088; Langry, K. C.; *Org. Prep. Proced. Int.* 1994, 26(4), 429-438; Romero, D. L.; Morge, R. A.; Biles, C.; Berrios-Pena, N.; May, P. D.; Palmer, J. R.; Johnson, P. D.; Smith, H. W.; Busso, M.; Tan, C.-K.; Voorman, R. L.; Reusser, F.; Althaus, I. W.; Downey, K. M.; et al.; *J. Med. Chem.* 1994, 37(7), 999-1014 and Bhattacharjee, A.; Mukhopadhyay, R.; Bhattacharjya, A.; *Indian J. Chem.*, Sect B 1994, 33(7), 679-682.

Scheme 46 shows a method which could be used for the synthesis of an azaindole acetic acid derivative. Protection of the amine group could be effected by treatment with di-tert-butyldicarbonate to introduce the t-Butoxycarbonyl (BOC) group. Introduction of the oxalate moiety may then be accomplished as shown in Step A of Scheme 46 according to the procedures described in Hewawasam, P.; Meanwell, N. A.; *Tetrahedron Lett.* 1994, 35(40), 7303-7306 (using t-Buli, or s-buli, THF); or Stanetty, P.; Koller, H.; Mihovilovic, M.; *J. Org. Chem.* 1992, 57(25), 6833-6837 (using t-Buli). The intermediate thus formed could then be cyclized to form the azaindole as shown in Step B of Scheme 46 according to the procedures described in Fuerstner, A.; Ernst, A.; Krause, H.; Ptock, A.; *Tetrahedron* 1996, 52(21), 7329-7344 (using. TiCl3, Zn, DME); or Fuerstner, A.; Hupperts, A.; *J. Am. Chem. Soc.* 1995, 117(16), 4468-4475 (using Zn, excess Tms-Cl, TiCl3 (cat.), MeCN).

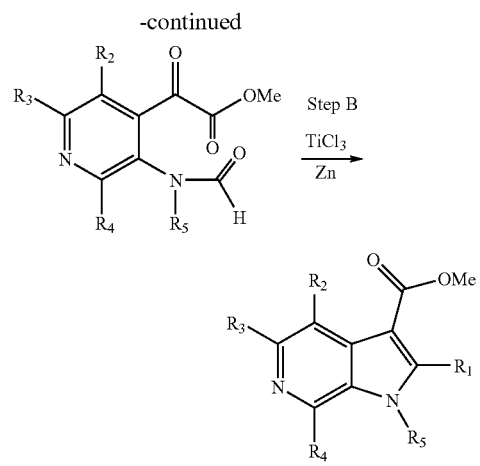

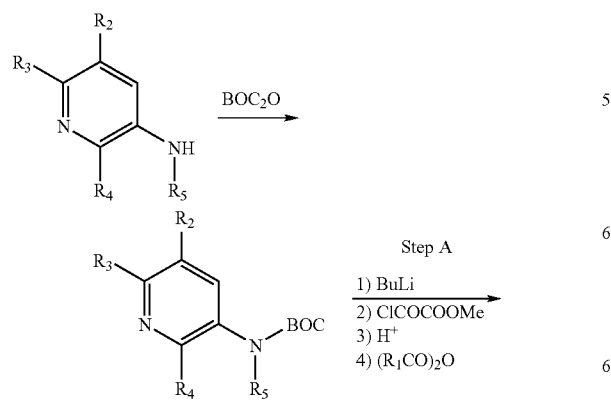

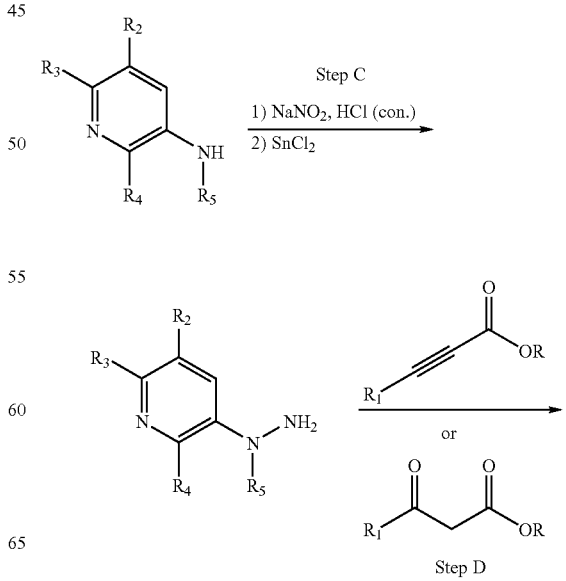

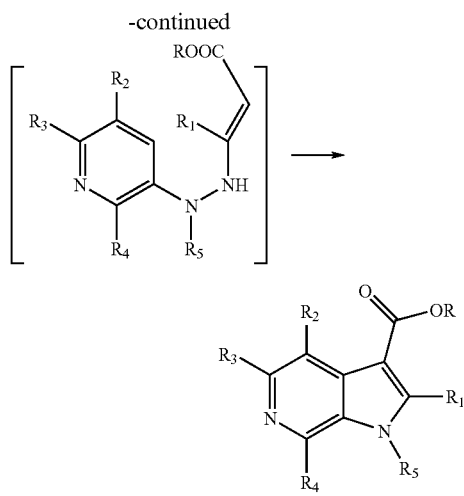

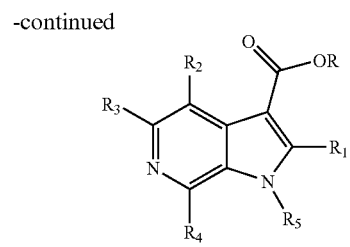

Scheme 47 describes an alternate synthesis which could be used to prepare azaindole acetic acid derivatives. Step C of Scheme 47 could be accomplished by using the procedures described in Harden, F. A.; Quinn, R. J.; Scammells, P. J.; *J. Med. Chem.* 1991, 34(9), 2892-2898 [use of 1. NaNO$_2$, conc. HCl 2. SnCl$_2$, conc. HCl (cat.)]. Typically, 10 equivalents of NaNO$_2$ and 1.0 equivalents of substrate reacted at 0° C. for 0.25 to 1 h and to this reaction mixture was added 3.5 equivalents of SnCl$_2$. Alternatively, the procedure described in De Roos, K. B.; Salemink, C. A.; *Recl. Trav. Chim. Pays-Bas* 1971, 90, 1181 (use of NaNO$_2$, AcOH, H$_2$O) could be used. The intermediate thus formed could be further reacted and cyclized to provide azaindole acetic acid derivatives as shown in Step D of Scheme 47 and according to the procedures described in Atkinson, C. M.; Mattocks, A. R.; *J. Chem. Soc.* 1957, 3722; Ain Khan, M.; Ferreira Da Rocha, J.; *Heterocycles* 1978, 9, 1617; Fusco, R.; Sannicolo, F.; *Tetrahedron* 1980, 36, 161 [use of HCl (conc)]; Abramovitch, R. A.; Spenser, I. D.; *Adv. Heterocycl Chem.* 1964, 3, 79 (use of ZnCl$_2$, p-Cymene); and Clemo, G. R.; Holt, R. J. W.; *J. Chem. Soc.* 1953, 1313; (use of ZnCl$_2$, EtOH, Sealed tube).

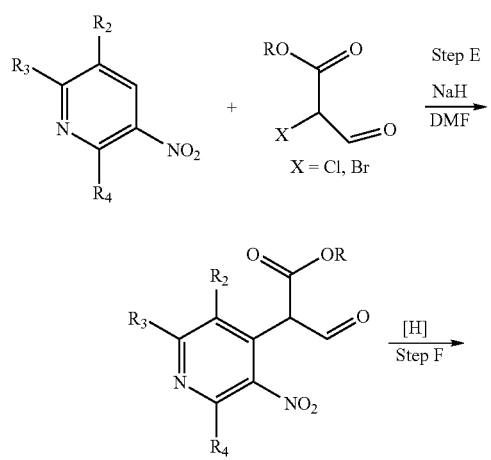

Scheme 48 depicts another possible route to azaindole acetic acid derivatives. Step E of Scheme 48 could be carried out as shown or according to procedures such as those described in Yurovskaya, M. A.; Khamlova, I. G.; Nesterov, V. N.; Shishkin, O. V.; Struchkov, T.; Khim Geterotsikl Soedin 1995, 11, 1543-1550; Grzegozek, M.; Wozniak, M.; Baranski, A.; Van Der Plas, H. C.; *J. Heterocycl Chem.* 1991, 28(4), 1075-1077 (use of NaOH, DMSO); Lawrence, N. J.; Liddle, J.; Jackson, D. A.; *Tetrahedron Lett.* 1995, 36(46), 8477-8480 (use of. NaH, DMSO); Haglund, O.; Nilsson, M.; *Synthesis* 1994, 3, 242-244; (use of 2.5 equiv. CuCl, 3.5 equiv. TBu-OK, DME, Py); Makosza, M.; Sienkiewicz, K.; Wojciechowski, K.; *Synthesis* 1990, 9, 850-852; (use of KO-tBu, DMF); Makosza, M.; Nizamov, S.; *Org. Prep. Proceed. Int.* 1997, 29(6), 707-710; (use of tBu-OK, THF). Step F of Scheme 48 shows the cyclization reaction which could provide the azaindole acetic acid derivatives. This reaction could be accomplished according to procedures such as those described in Frydman, B.; Baldain, G.; Repetto, J. C.; *J. Org. Chem.* 1973, 38, 1824 (use of H$_2$, Pd—C, EtOH); Bistryakova, I. D.; Smirnova, N. M.; Safonova, T. S.; Khim Geterotsikl Soedin 1993, 6, 800-803 (use of H$_2$, Pd—C (cat.), MeOH); Taga, M.; Ohtsuka, H.; Inoue, I.; Kawaguchi, T.; Nomura, S.; Yamada, K.; Date, T.; Hiramatsu, H.; Sato, Y.; *Heterocycles* 1996, 42(1), 251-263 (use of SnCl$_2$, HCl, Et$_2$O); Arcari, M.; Aveta, R.; Brandt, A.; Cecchetelli, L.; Corsi, G. B.; Dirella, M.; *Gazz. Chim. Ital.* 1991, 121(11), 499-504 [use of Na$_2$S$_2$O$_6$, THF/EtOH/H$_2$O (2:2:1)]; Moody, C. J.; Rahimtoola, K. F.; *J. Chem. Soc., Perkin Trans* 1 1990, 673 (use of TiCl$_3$, NH$_4$Oac, acetone, H$_2$O).

Scheme 49 provides another route to azaindole intermediates which could then be further elaborated to provide compounds of Formula I, such as the amido derivatives shown. Steps G" and H" of Scheme 49 may be carried out according to the procedures described in Takahashi, K.; Shibasaki, K.; Ogura, K.; Iida, H.; *Chem. Lett.* 1983, 859; and Itoh, N.; *Chem. Pharm. Bull.* 1962, 10, 55. Elaboration of the intermediate to the amido compound of Formula I could be accomplished as previously described for Steps I'-M' of Scheme 45.

Scheme 49

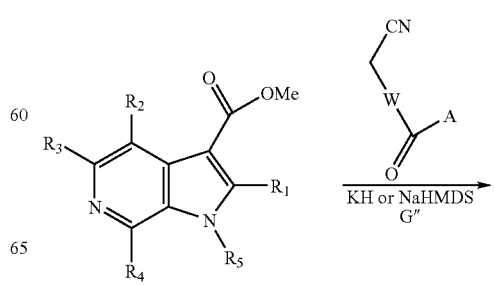

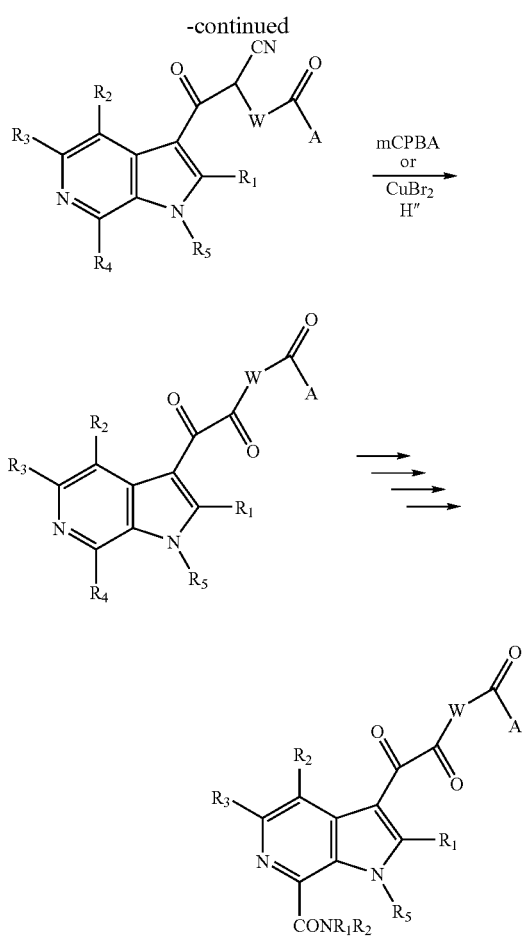

Scheme 50 shows the preparation of azaindole oxalic acid derivatives. The starting materials in Scheme 50 may be prepared according to *Tetrahedron Lett.* 1995, 36, 2389-2392. Steps A', B', C', and D' of Scheme 50 may be carried out according to procedures described in Jones, R. A.; Pastor, J.; Siro, J.; Voro, T. N.; *Tetrahedron* 1997, 53(2), 479-486; and Singh, S. K.; Dekhane, M.; Le Hyaric, M.; Potier, P.; Dodd, R. H.; *Heterocycles* 1997, 44(1), 379-391. Step E' of Scheme 50 could be carried out according to the procedures described in Suzuki, H.; Iwata, C.; Sakurai, K.; Tokumoto, K.; Takahashi, H.; Hanada, M.; Yokoyama, Y.; Murakami, Y.; *Tetrahedron* 1997, 53(5), 1593-1606; Suzuki, H.; Yokoyama, Y.; Miyagi, C.; Murakami, Y.; *Chem. Pharm. Bull.* 1991, 39(8), 2170-2172; Hagen, T. J.; Narayanan, K.; Names, J.; Cook, J. M.; *J. Org. Chem.* 1989, 54, 2170; Murakami, Y.; Yokoyama, Y.; Watanabe, T.; Aoki, C.; et al.; *Heterocycles* 1987, 26, 875; and Hagen, T. J.; Cook, J. M.; *Tetrahedron Lett.* 1988, 29(20), 2421. Step F' of Scheme 50 shows the conversion of the phenol to a fluoro, chloro or bromo derivative. Conversion of the phenol to the fluoro derivative could be carried out according to procedures described in Christe, K. O.; Pavlath, A. E.; *J. Org. Chem.* 1965, 30, 3170; Murakami, Y.; Aoyama, Y.; Nakanishi, S.; *Chem. Lett.* 1976, 857; Christe, K. O.; Pavlath, A. E.; *J. Org. Chem.* 1965, 30, 4104; and Christe, K. O.; Pavlath, A. E.; *J. Org. Chem.* 1966, 31, 559. Conversion of the phenol to the chloro derivative could be carried out according to procedures described in Wright, S. W.; *Org. Prep. Proc. Int.* 1997, 29(1), 128-131; Hartmann, H.; Schulze, M.; Guenther, R.; *Dyes Pigm* 1991, 16(2), 119-136; Bay, E.; Bak, D. A.; Timony, P. E.; Leone-Bay, A.; *J. Org. Chem.* 1990, 55, 3415; Hoffmann, H.; et al.; *Chem. Ber.* 1962, 95, 523; and Vanallan, J. A.; Reynolds, G. A.; *J. Org. Chem.* 1963, 28, 1022. Conversion of the phenol to the bromo derivative may be carried out according to procedures described in Katritzky, A. R.; Li, J.; Stevens, C. V.; Ager, D. J.; *Org. Prep. Proc. Int.* 1994, 26(4), 439-444; Judice, J. K.; Keipert, S. J.; Cram, D. J.; *J. Chem. Soc., Chem. Commun.* 1993, 17, 1323-1325; Schaeffer, J. P.; Higgins, J.; *J. Org. Chem.* 1967, 32, 1607; Wiley, G. A.; Hershkowitz, R. L.; Rein, R. M.; Chung, B. C.; *J. Am. Chem. Soc.* 1964, 86, 964; and Tayaka, H.; Akutagawa, S.; Noyori, R.; *Org. Syn.* 1988, 67, 20.

Scheme 50

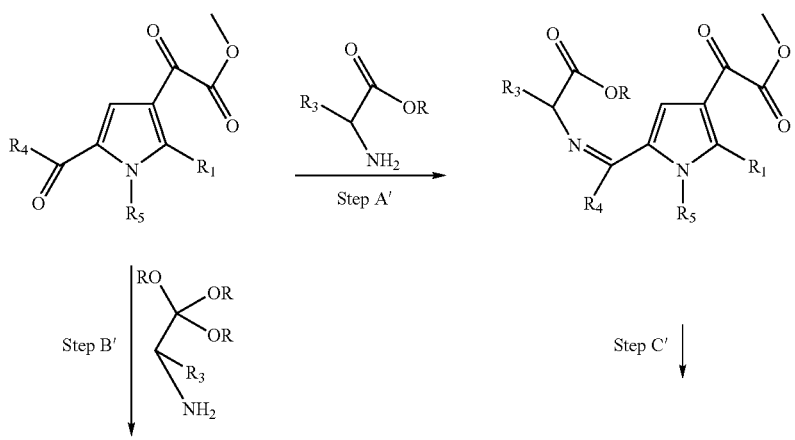

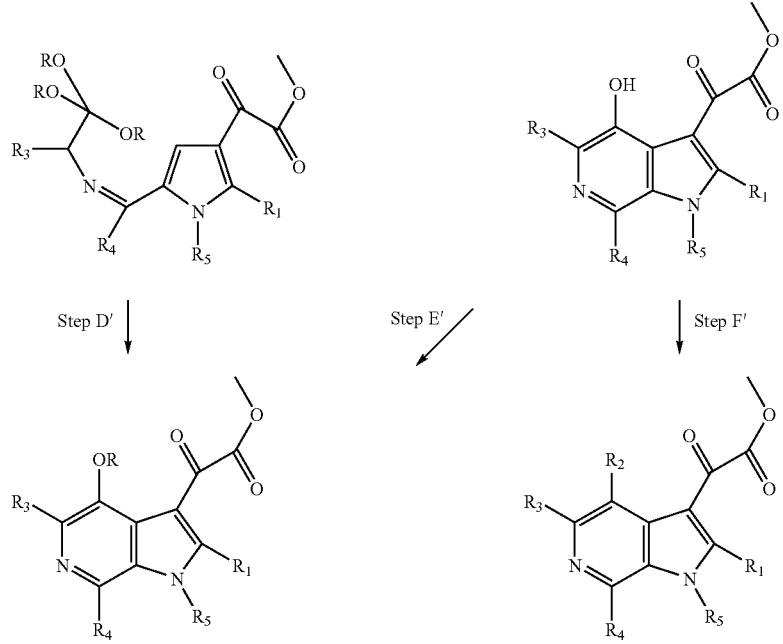

Scheme 51 describes methods for the preparation of azaindole acetic acid derivatives by the same methods employed for the preparation of azaindole oxalic acid derivatives as shown and described in Scheme 50 above. The starting material employed in Scheme 51 could be prepared according to *J. Org. Chem.* 1999, 64, 7788-7801. Steps A", B", C", D", and E" of Scheme 51 could be carried out in the same fashion as previously described for Steps A', B', C', D', and E' of Scheme 50.

Scheme 51

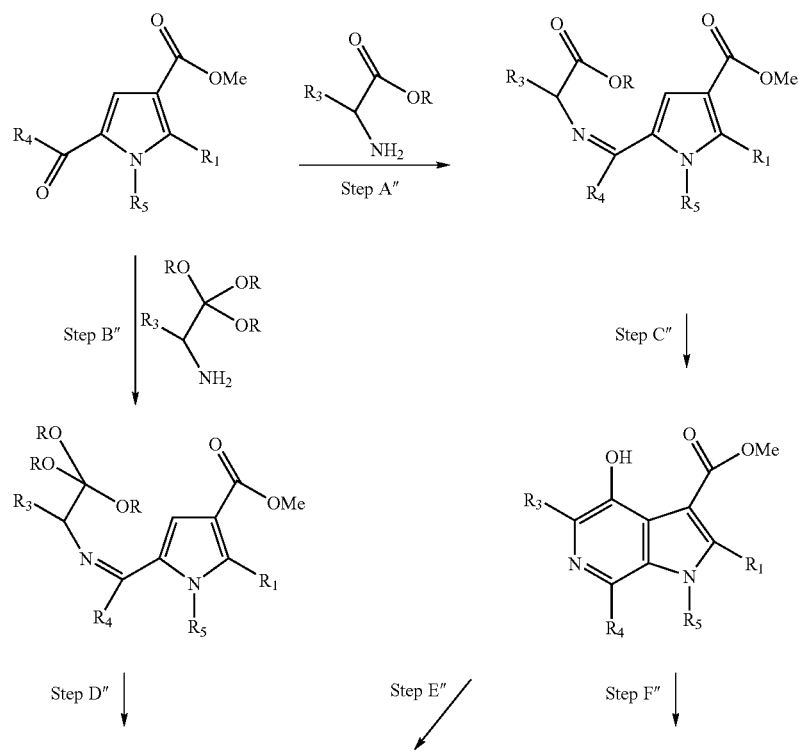

-continued

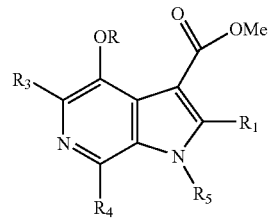
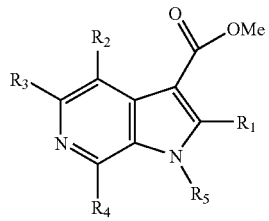

The remaining schemes provide additional background, examples, and conditions for carrying out this invention. Specific methods for preparing W and modifying A are presented. As shown in Scheme 52, the azaindoles may be treated with oxalyl chloride in either THF or ether to afford the desired glyoxyl chlorides according to literature procedures (Lingens, F.; Lange, J. *Justus Liebigs Ann. Chem.* 1970, 738, 46-53). The intermediate glyoxyl chlorides may be coupled with benzoyl piperazines (Desai, M.; Watthey, J. W. *Org. Prep. Proc. Int.* 1976, 8, 85-86) under basic conditions to afford compounds of Formula I directly.

-continued

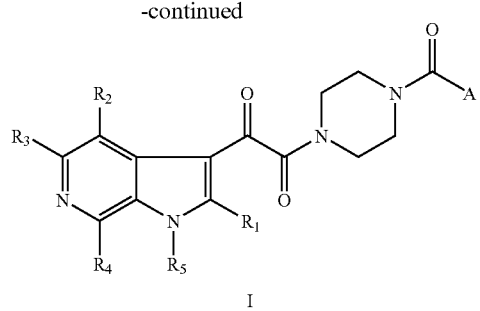

Alternatively, Scheme 52 treatment of the azaindole-3-glyoxyl chloride, (Scheme 52) with tert-butyl 1-piperazinecarboxylate affords the piperazine coupled product. It is apparent to one skilled in the art that use of an alternative Boc protected piperazine which are synthesized as shown below would provide compounds of formula I with alternative groups of formula W. As discussed earlier, other amine protecting groups which do not require acidic deprotection conditions could be utilized if desired. Deprotection of the Boc group is effected with 20% TFA/CH$_2$Cl$_2$ to yield the free piperazine. This product is then coupled with carboxylic acid in the presence of polymer supported 1-(3-Dimethylaminopropyl)-3-ethylcarbodiimide (P-EDC) to afford products of Formula I. This sequence provides a general method for synthesizing compounds of varied A in formula I.

Scheme 52

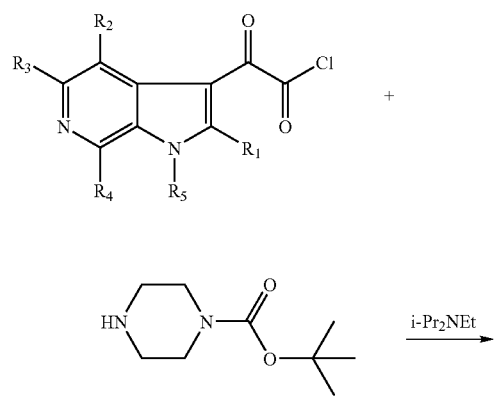

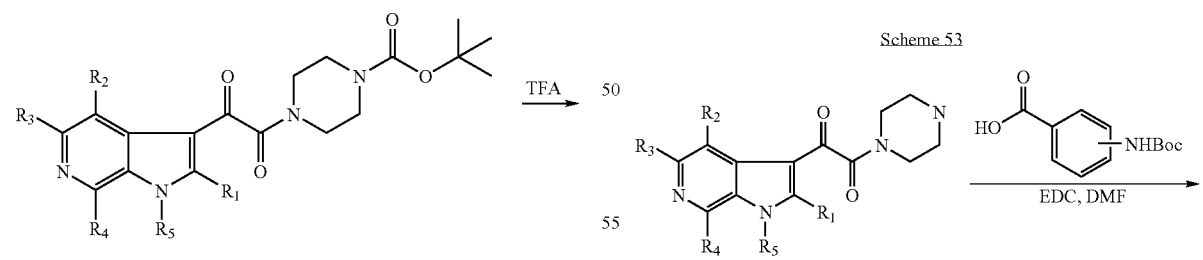

Scheme 53

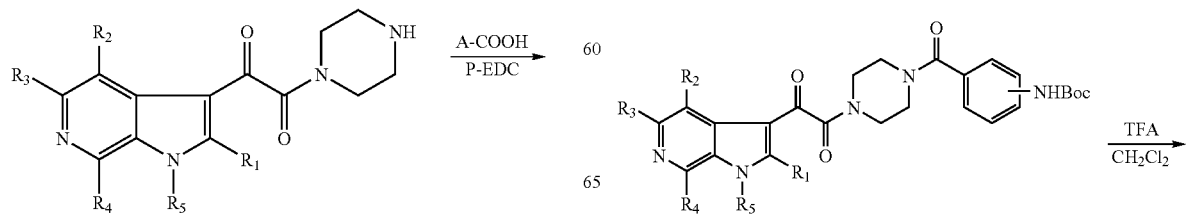

-continued

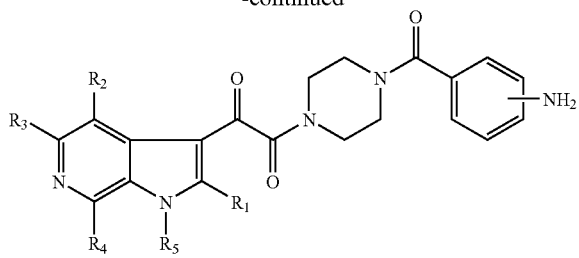

An example for preparing compounds of Formula I which possess substituents in A (or other parts of the molecule) which might interfere with the standard reaction schemes reactions is shown in Scheme 53. The piperazine derivative (Scheme 53) was treated with Boc-protected aminobenzoic acid in the presence of EDC to afford the piperazine diamide. A portion of the resulting product was separated and subjected to TFA in order to remove the Boc group, thus yielding amino derivatives.

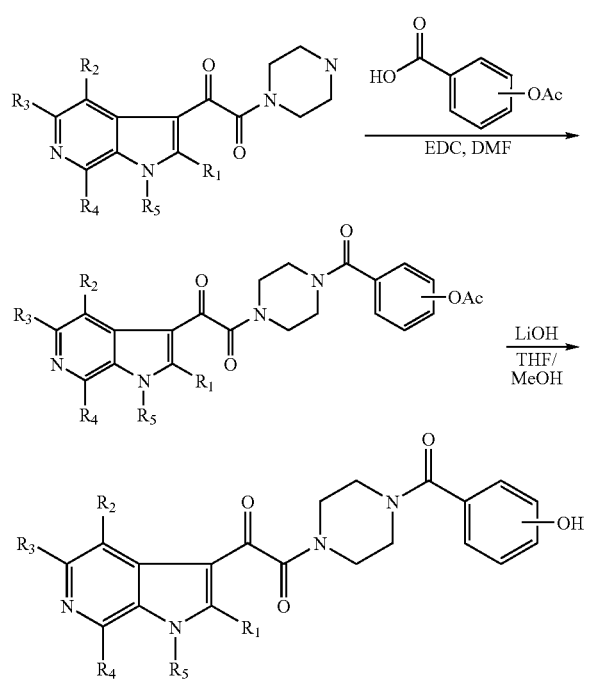

Scheme 54

Similarly, substituents which possess a reactive alcohol can be incorporated as below. The piperazine derivative (Scheme 54) was treated with acetoxybenzoic acid in the presence of EDC to afford the piperazine diamide derivative. A portion of the resulting product was separated and subjected to LiOH hydrolysis in order to remove the acetate group, thus yielding hydroxy derivatives.

Examples containing substituted piperazines are prepared using the general procedures outlined in Schemes 55-38. Substituted piperazines are either commercially available from Aldrich, Co. or prepared according to literature procedures (Behun et al, Ref. 88(a), Scheme 31, eq. 01). Hydrogenation of alkyl substituted pyrazines under 40 to 50 psi pressure in EtOH afforded substituted piperazines. When the substituent was an ester or amide, the pyrazine systems could be partially reduced to the tetrahydropyrazine (Rossen et al, Ref. 88(b), Scheme 55, eq. 02). The carbonyl substituted piperazines could be obtained under the same conditions described above by using commercially available dibenzyl piperazines (Scheme 55, eq. 03).

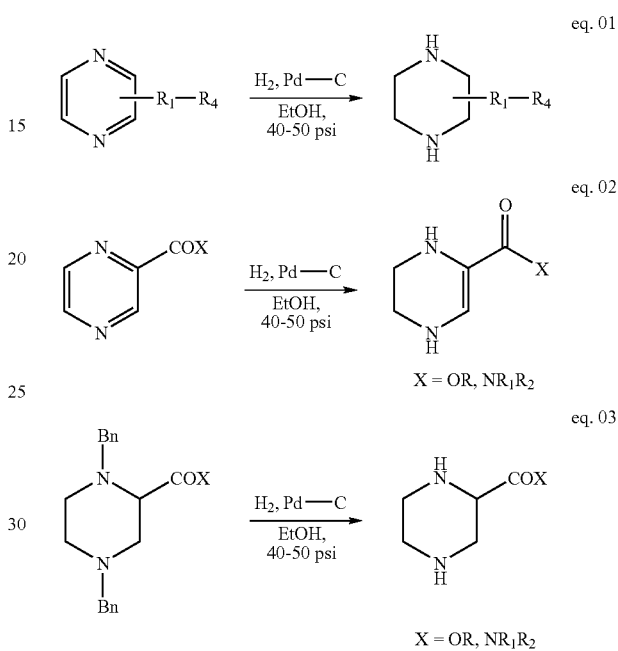

Scheme 55

2-Trifluoromethylpiperazine (Jenneskens et al., Ref 88c) was prepared through a four step route (Scheme 56). Using Lewis acid $TiCl_4$, N,N'-dibenzylethylenediamine reacted with trifluoropyruvates to afford the hemiacetal, which was reduced at room temperature by $Et_3SiH$ in TFA to afford the lactam. $LiAlH_4$ treatment then reduced the lactam to 1,4-dibenzyl-2-trifluoromethylpiperazine. Finally, hydrogenation of the dibenzyl-2-trifluoromethylpiperazine in HOAc gave the desired product, 2-trifluoromethylpiperazine.

Scheme 56

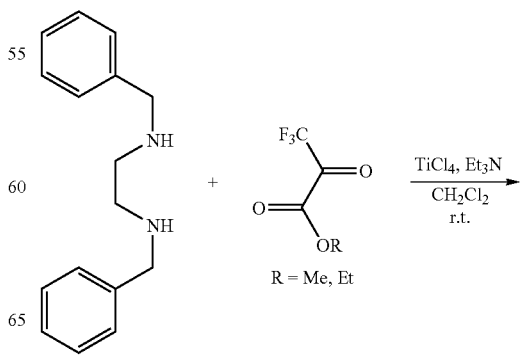

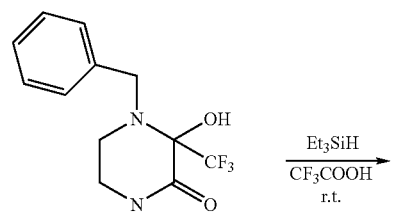

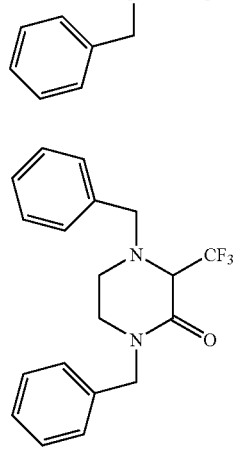

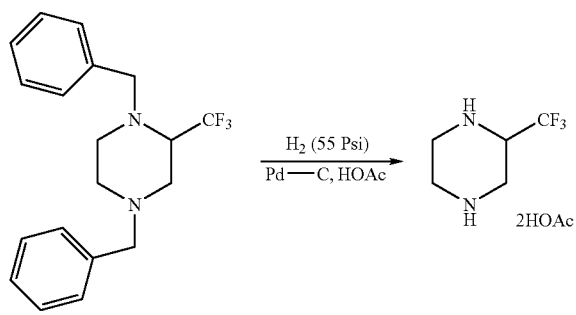

Mono-benzoylation of symmetric substituted piperazines could be achieved by using one of the following procedures (Scheme 57). (a) Treatment of a solution of piperazine in acetic acid with acetyl chloride afforded the desired mon-benzoylated piperazine (Desai et al. Ref 27, Scheme 57, eq. 04). (b) Symmetric piperazines were treated with 2 equivalents of n-butyllithium, followed by the addition of benzoyl chloride at room temperature (Wang et al, Ref. 89, Scheme 57, eq. 05).

Scheme 57

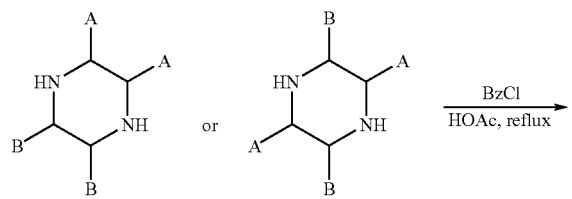

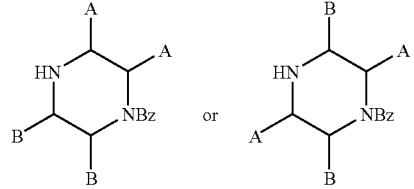

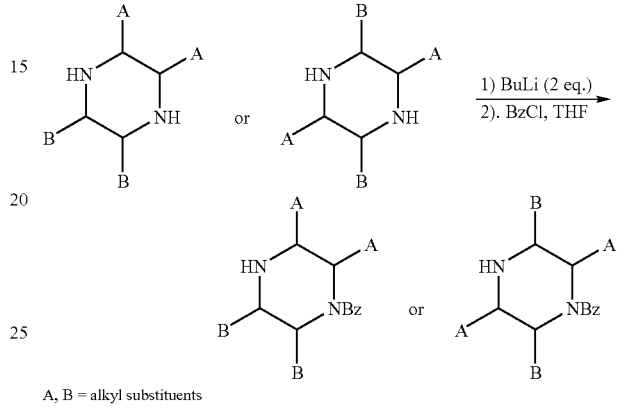

A, B = alkyl substituents

Mono-benzoylation of unsymmetric substituted piperazines could be achieved by using one of the following procedures (Scheme 57), in which all the methods were exemplified by mono-alkyl substituted piperazines. (a) Unsymmetric piperazines were treated with 2 equivalents of n-butyllithium, followed by the addition of benzoyl chloride at room temperature to afford a mixture of two regioisomers, which could be separated by chromatography (Wang et al, Ref. 89 and 90(b), Scheme 58 eq. 06); (b) Benzoic acid was converted to its pentafluorophenyl ester, and then further reaction with 2-alkylpiperazine to provide the mono-benzoylpiperazines with the benzoyl group at the less hindered nitrogen (Adamczyk et al, Ref. 90(a), Scheme 58, eq. 07); (c) A mixture of piperazine and methyl benzoate was treated with dialkylaluminum chloride in methylene chloride for 2-4 days to yield the mono-benzoylpiperazine with the benzoyl group at the less hindered nitrogen (Scheme 58 eq. 08); (d) Unsymmetric piperazines were treated with 2 equivalents of n-butyllithium, followed by subsequent addition of triethylsilyl chloride and benzoyl chloride in THF at room temperature to afford mono-benzoylpiperazines with the benzoyl group at the more hindered nitrogen (Wang et al, Ref. 90(b), Scheme 58, eq. 09). When the substituent at position 2 was a ester or amide, the mono-benzoylation with benzoyl chloride occurred at the less hindered nitrogen of the piperazine with triethylamine as base in THF (Scheme 58, eq. 10).

Scheme 58

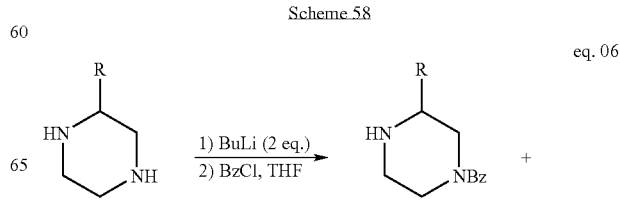

-continued

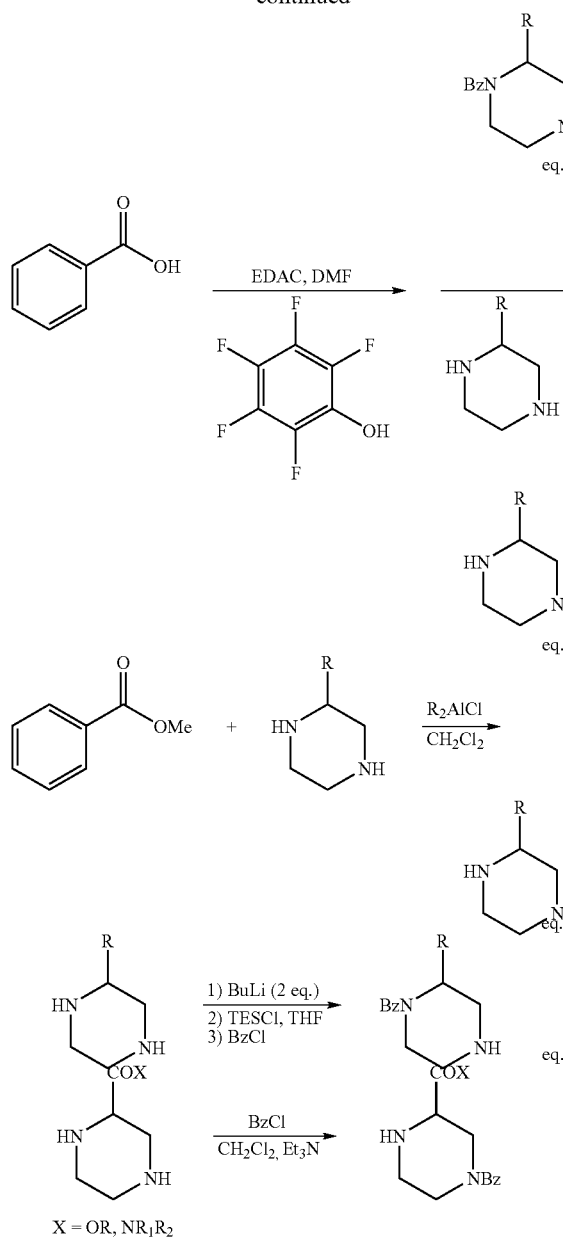

In the case of tetrahydropyrazines (Scheme 59, eq. 11), mono-benzoylation occurred at the more hindered nitrogen under the same conditions as those in equation 10 of Scheme 58, in the well precedented manner. (Rossen et al, Ref. 88(b)).

Scheme 59

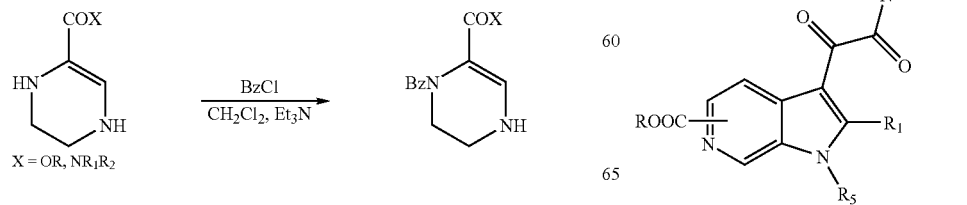

Furthermore, the ester group can be selectively reduced by $NaBH_4$ in the presence of the benzamide (Masuzawa et al, Ref. 91), which is shown in Scheme 60.

Scheme 60

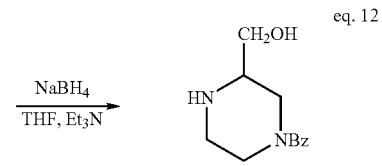

The ester groups on either the piperazine linkers or on the azaindole nucleus could be hydrolyzed to the corresponding acid under basic conditions such as $K_2CO_3$ (Scheme 61, eq. 13) or NaOMe (Scheme 61, eq. 14) as bases in MeOH and water.

Scheme 61

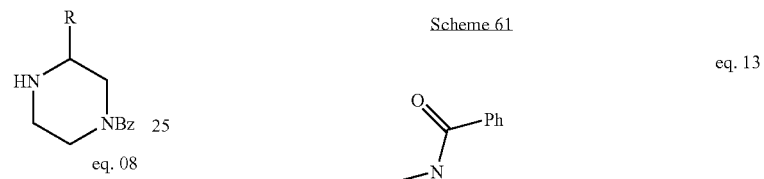

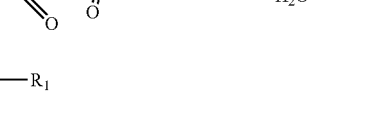

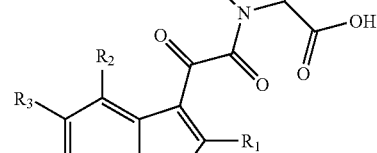

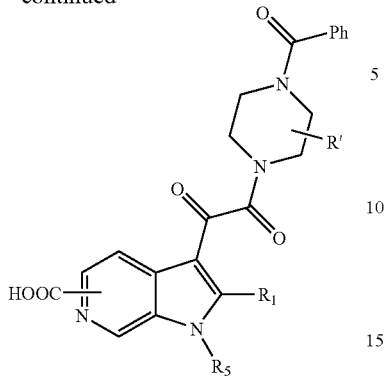

Reaction of an azaindole glyoxyl chloride with substituted benzoyl piperazines or tetrahydropyrazines in CH$_2$Cl$_2$ using I—Pr$_2$Net as base afforded the coupled products as shown in Scheme 62.

Scheme 62

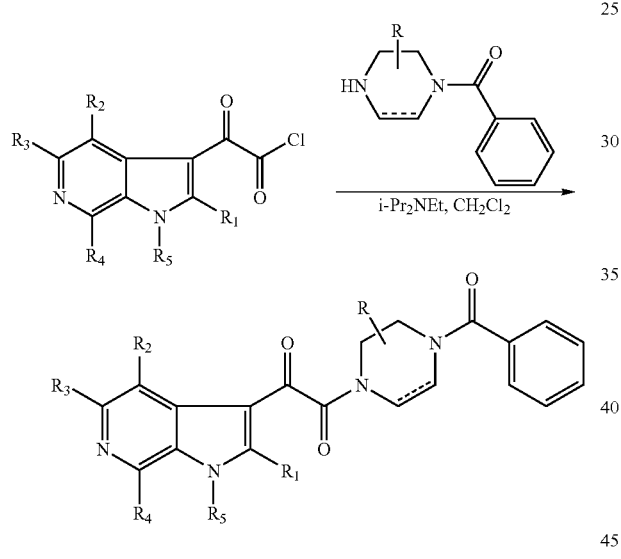

In the case of coupling reactions using 3-hydroxylmethyl-benzoylpiperazine, the hydroxyl group was temporarily protected as its TMS ether with BSTFA (N,O-bistrimethylsilyl) trifluoroacetamide) (Furber et al, Ref. 92). The unprotected nitrogen atom can then be reacted with glyoxyl chlorides to form the desired diamides. During workup, the TMS masking group was removed to give free hydroxylmethylpiperazine diamides as shown in Scheme 63.

Scheme 63

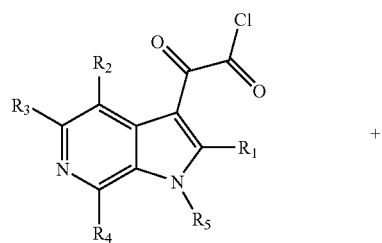

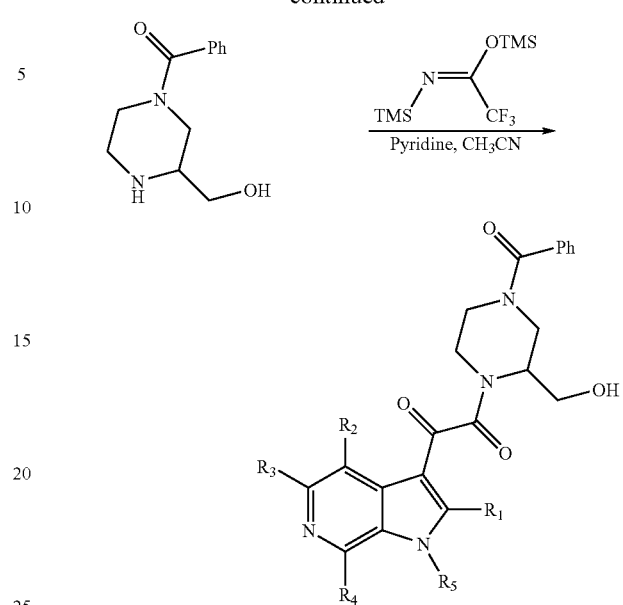

Piperazine intermediates were prepared using standard chemistry as shown in Scheme 64.

Scheme 64

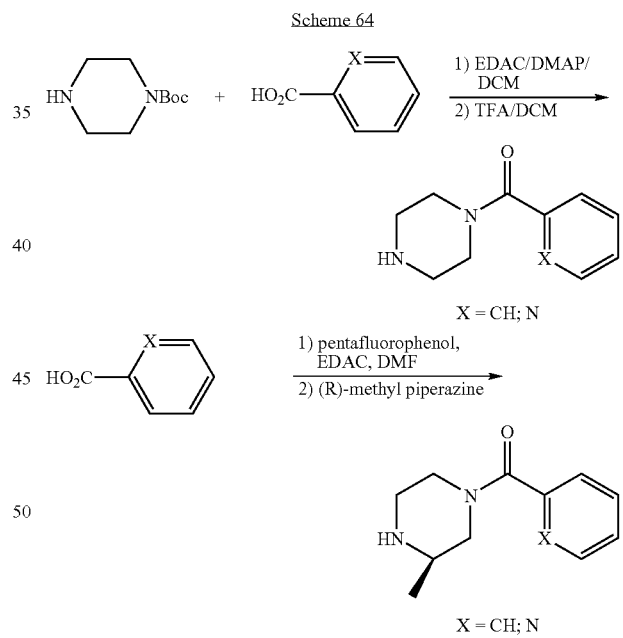

Scheme 65

Scheme 65 depicts some more specific methodology for preparing 5-azindoles for use in preparation of the claimed compounds. Some reductive cyclizations conditions include Fe in acetic acid, Tin II chloride in aq HCl, or Zinc powder in acetic acid. Hydrogenation conditions or other conditions used in LeimGruber-Batch indole synthesis sequences can also be employed.

More specific route to 5-azaindoles:

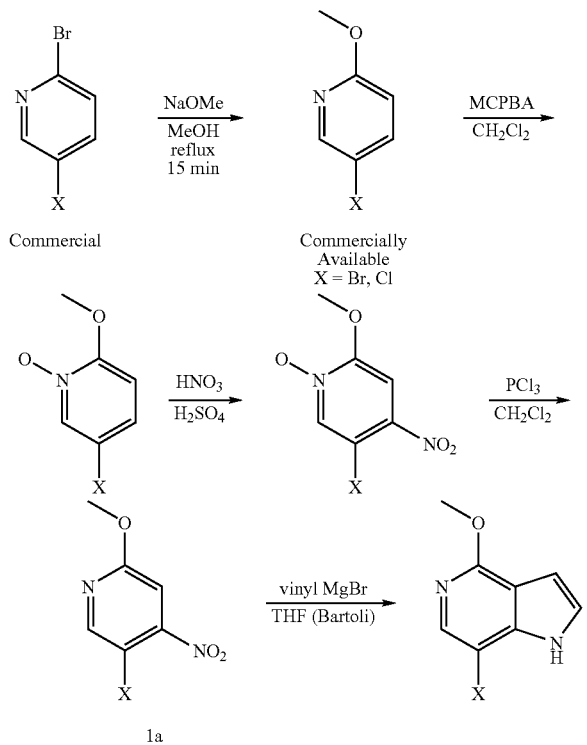

X = chloro or bromo or may be converted to a substituent and then carried through the sequence Tautomers of nitrogen containing heterocycles are covered by this patent application. For example, a hydroxy pyrazine is also known to represent its corresponding tautomer as well as shown in Scheme 66.

Scheme 66

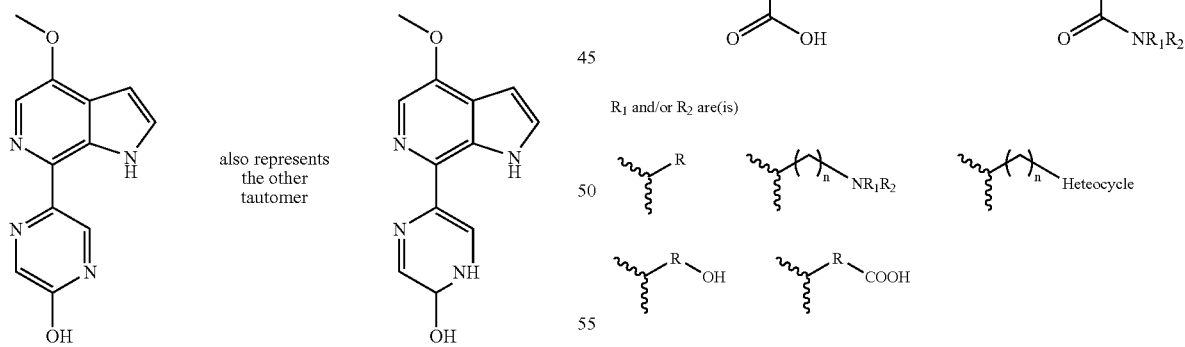

Scheme 67-74 provides some nonlimiting methodology for the preparation of substituted pyrazines which can be incorporated into substituents of compounds of claim 1, particularly as part of $R^4$. It should be noted that the nomenclature in these schemes does not coincide with that of the claims but rather shows examples of methods which can be used to prepare pieces which make up the compounds of the claims. Thus $R_1$ and $R_2$ in these schemes does not refer to the $R_1$ and $R_2$ in the claims but for example refers to chemically compatible groups which might be envisioned by chemists skilled in the art and which can be utilized to prepare compounds of the claims.

Scheme 67

Pyrazines

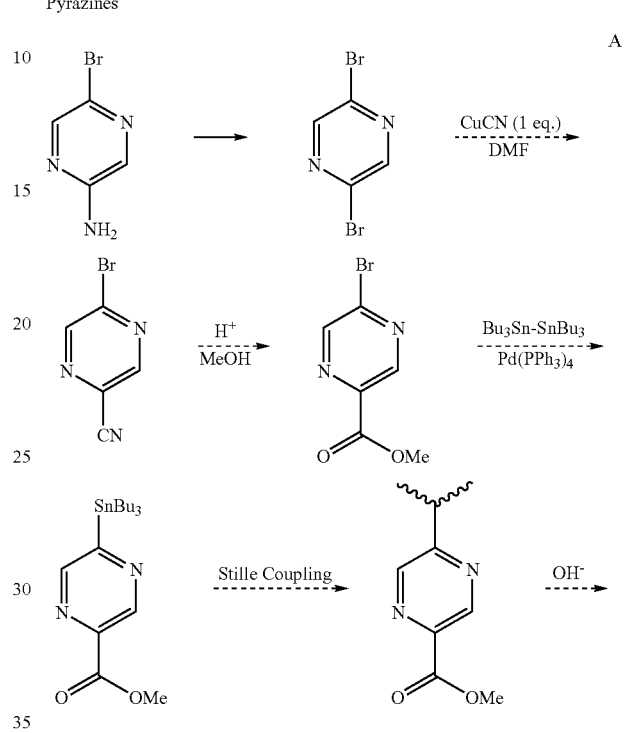

$R_1$ and/or $R_2$ are(is)

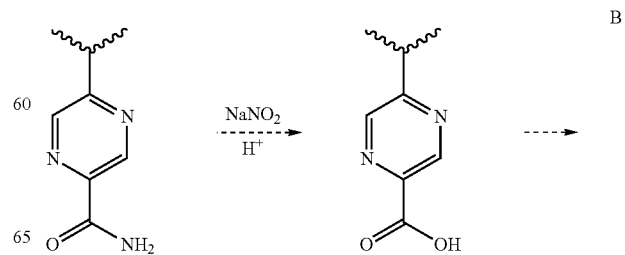

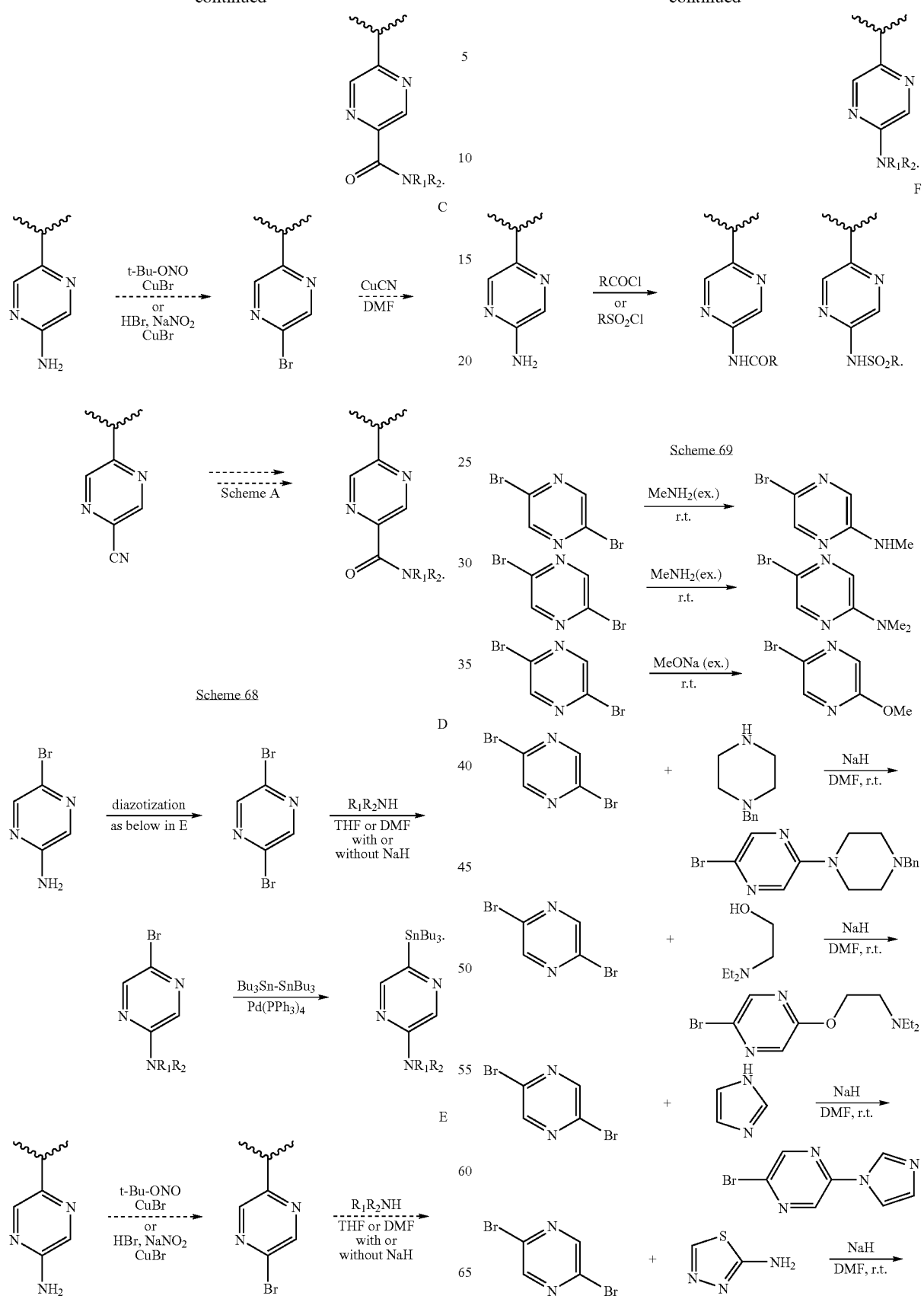

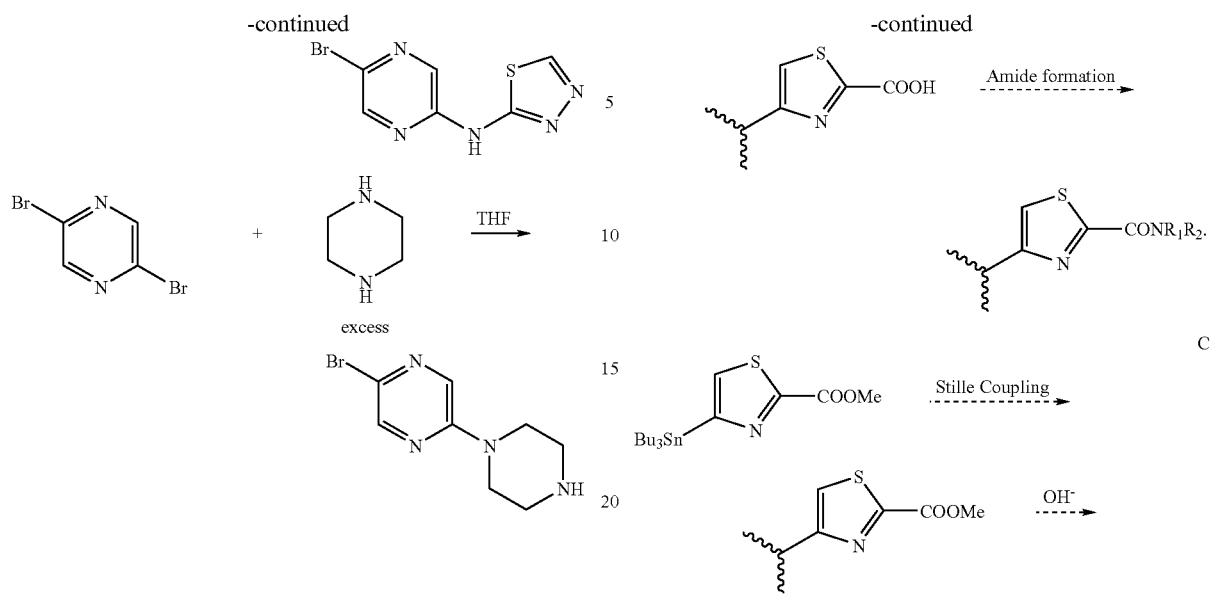
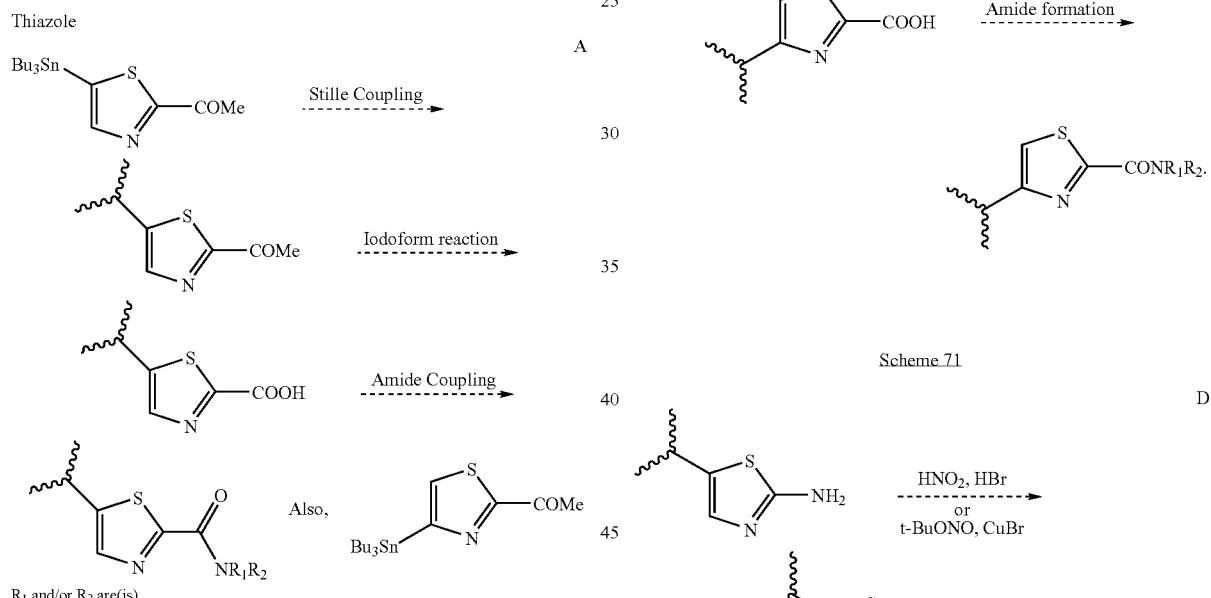
Scheme 70
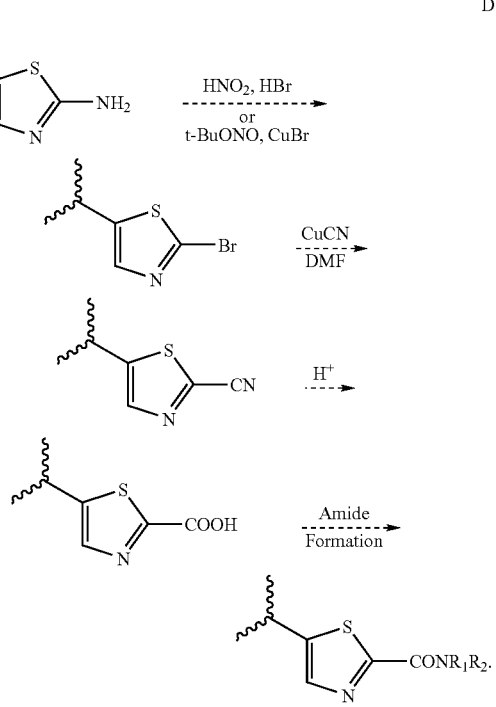
Scheme 71
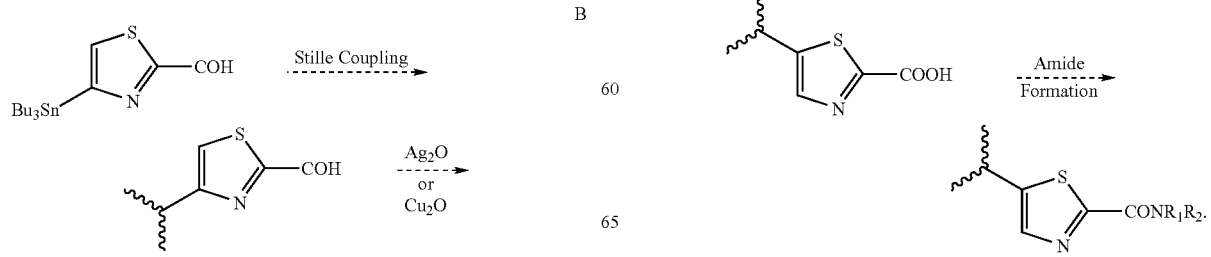

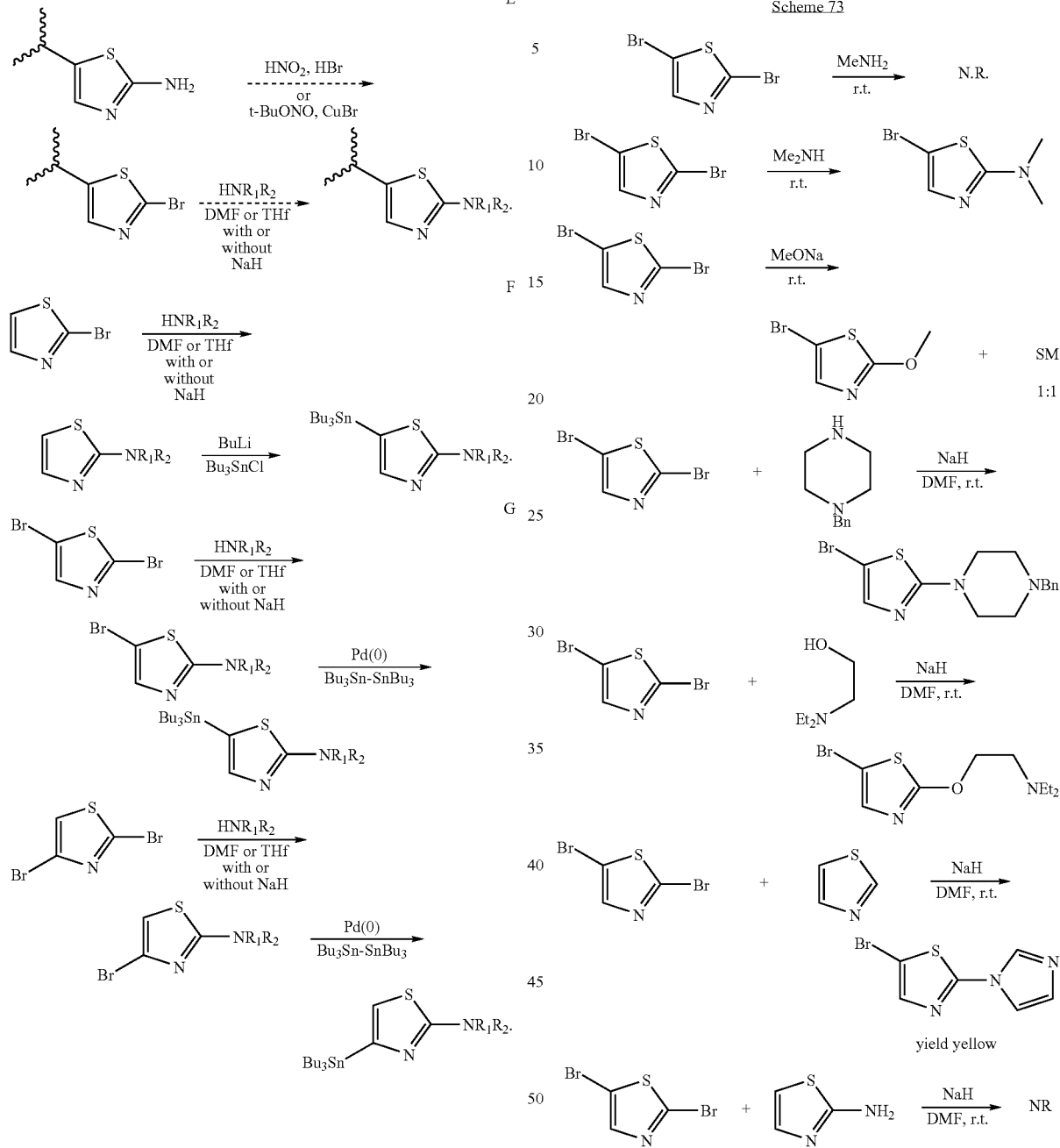
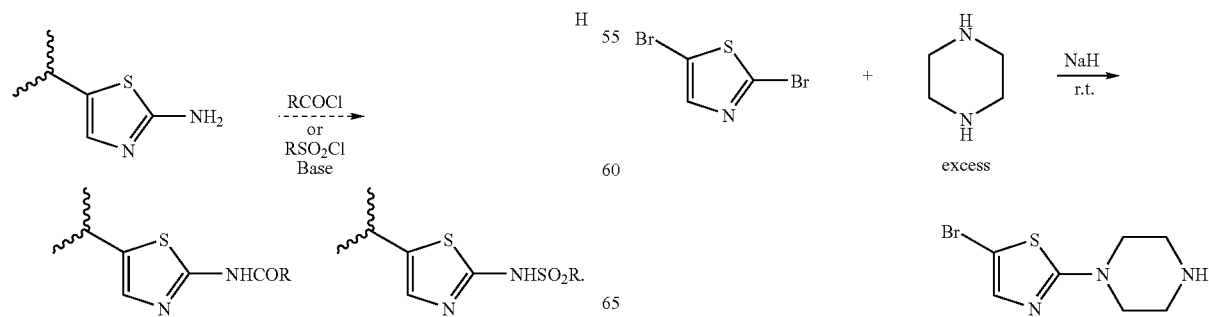

123

Scheme 74

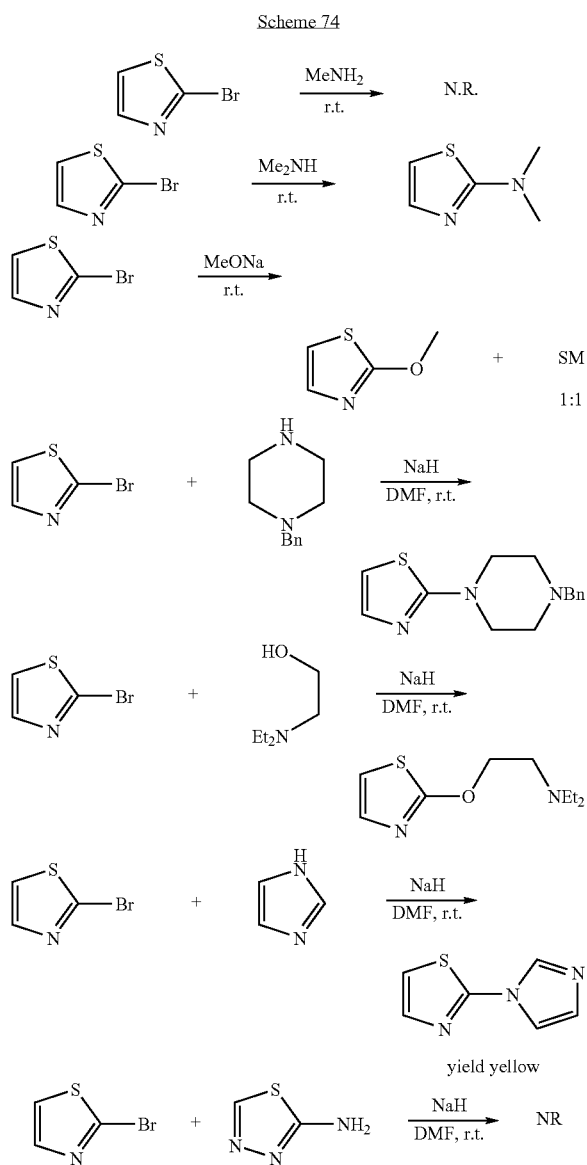

124

Throughout the chemistry discussion, chemical transformations which are well known in the art have been discussed. The average practitioner in the art knows these transformations well and a comprehensive list of useful conditions for nearly all the transformations is available to organic chemists and this list is contained in reference 52 authored by Larock and is incorporated in its entirety for the synthesis of compounds of Formula I.

Schemes 75-78 provide more specific examples of the general synthesis described in Scheme 1. The examples describe the synthesis of compounds of the invention in which the piperazine of group W contains a substituent on the ring at a position next to the nitrogen which comprises part of the amide attached to group A. While other substitution patterns are important aspects of the invention, we have found that compounds with a single group adjacent to the amide attached to group A may have metabolic stability advantages in humans and yet retain exceptional antiviral properties. The specific substituted piperazines described in Schemes 75-78 may be prepared as described in reference 90(b) or as described for intermediates 17a-d in the experimental section. In schemes 75 and 76 the most preferred groups for $R_9$ and $R_{11}$ are C1-C6 alkyl groups. As shown in schemes 77 and 78 the most preferred groups are methyl. As shown in schemes 75-78, the compounds may be single isomers or enantiomers or may be used as a racemic mixture or mixture of isomers. Preferred groups A as shown in the schemes 75-78 are the same as those described for the invention. Most preferred groups A are 2-pyridyl or phenyl. In Schemes 75 and 77, the most preferred groups for $R_2$ are methoxy, halogen, or hydrogen. In schemes 75-76 the most preferred group for R1 and R3 is hydrogen. In scheme 76 the most preferred group for R2 is hydrogen. In schemes 75-78, the most preferred groups for R4 are phenyl, substituted phenyl, heteroaryl, substituted heteroaryl, —C(O)NH2, —C(O)NHMe, or C(O)heteroaryl. Most preferred substituents on the substituted aryl or heteroaryl are methyl, amino, halogen, C(O)NHMe, COOH, COOMe, COOEt, or benzyl but this list should not be construed to be rate limiting as the R4 position is extremely tolerant of broad substitution. Particular groups at R4 of definite importance are triazole, oxadiazole, oxazole, pyrazole, pyrazine, pyrimidine, tetrazole, and phenyl but should not be construed as limiting.

Scheme 75

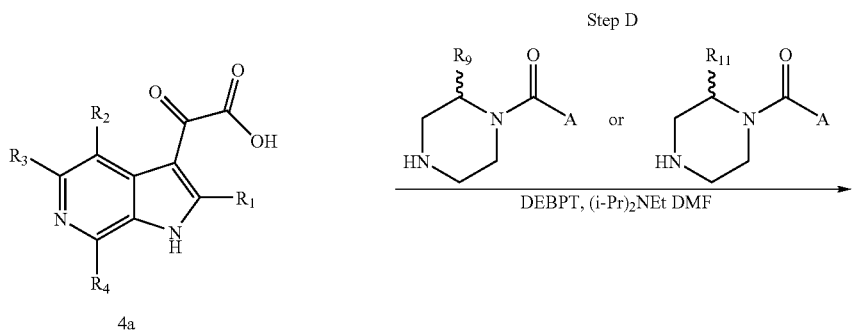

-continued
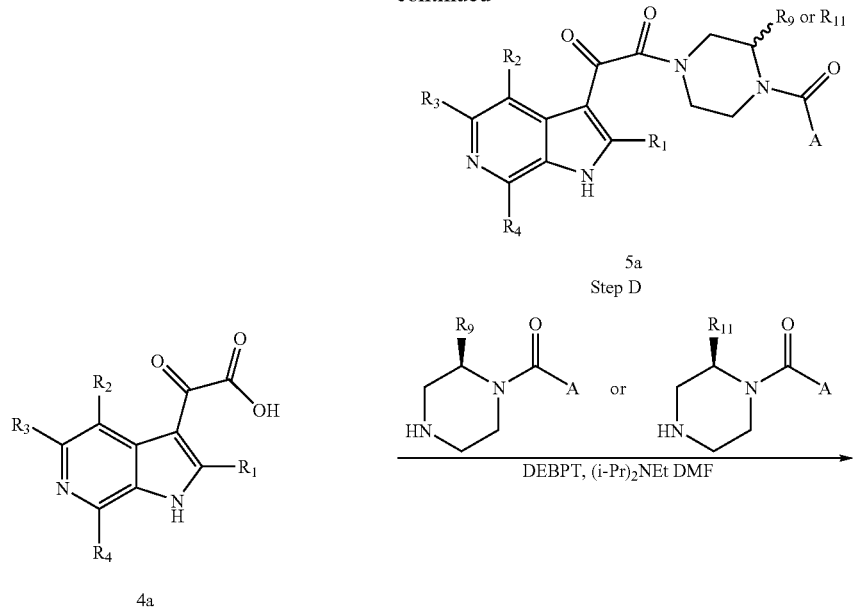
5a
Step D
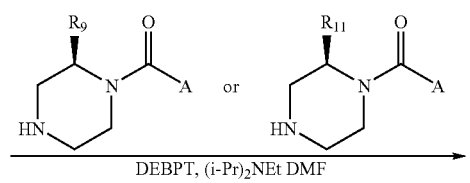
4a
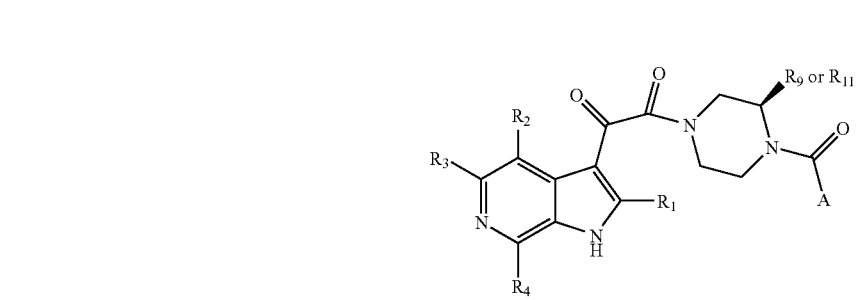
5a
Step D
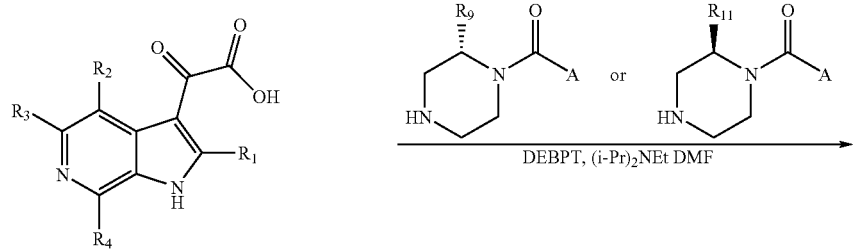
4a
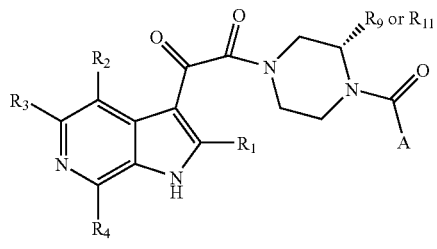
5a

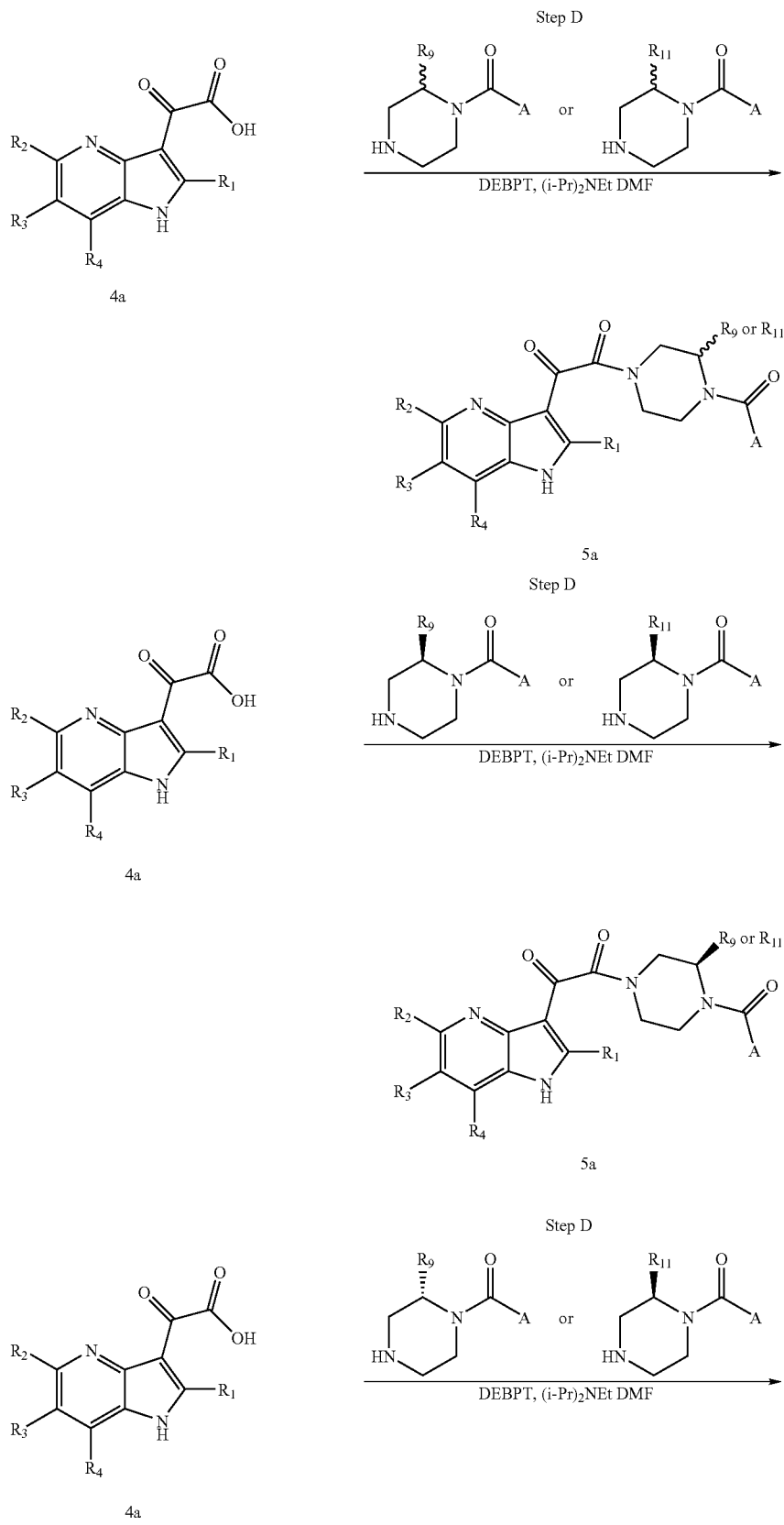

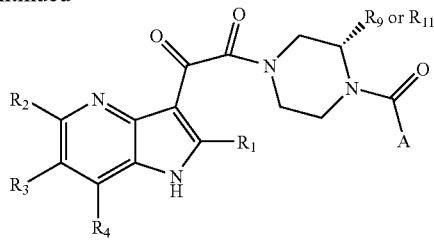
5a
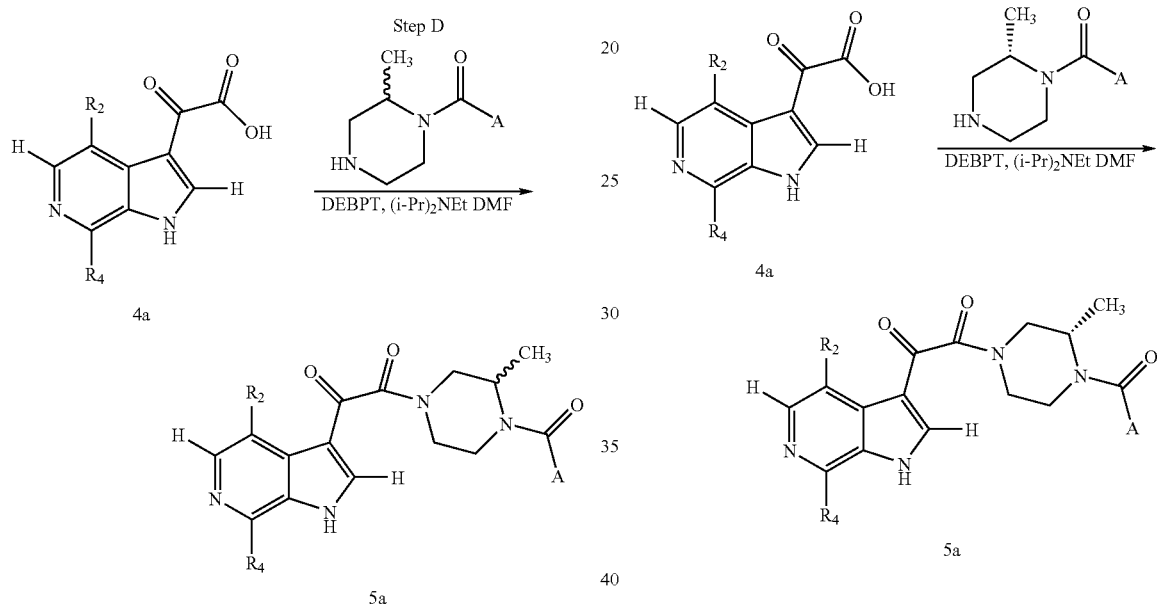
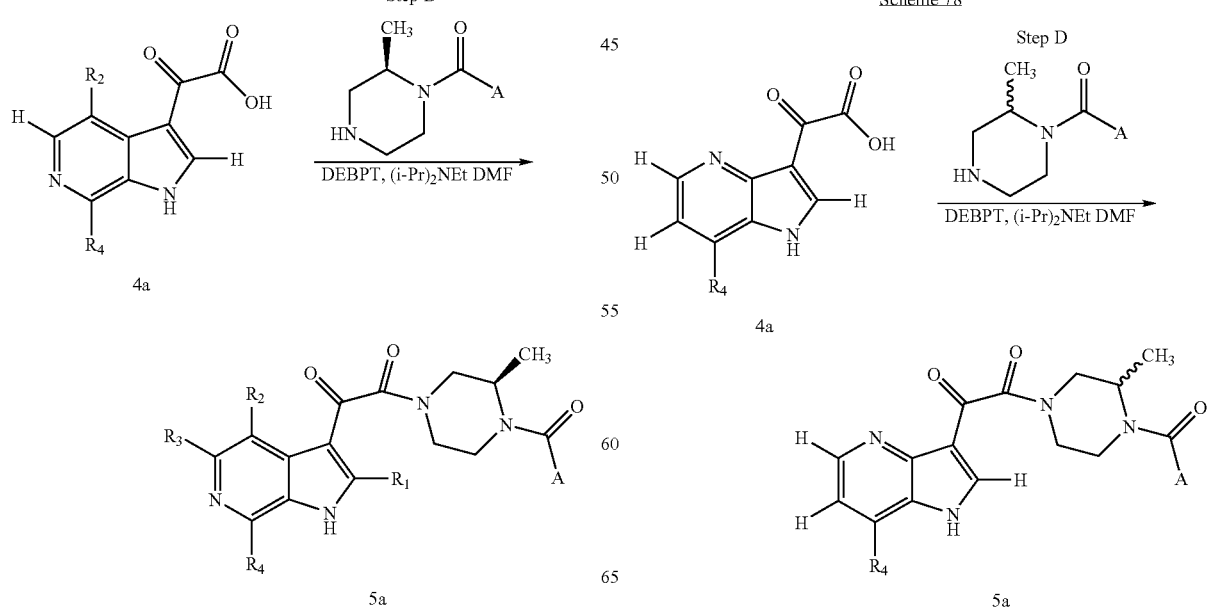

-continued

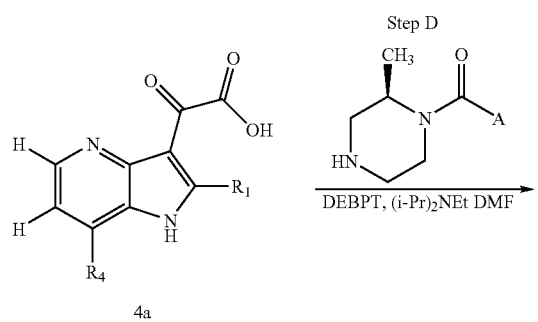

4a

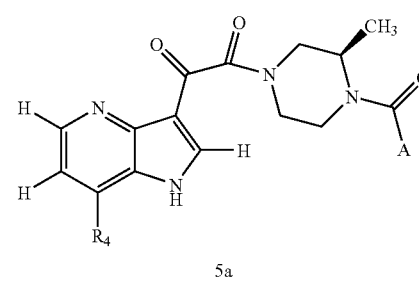

5a

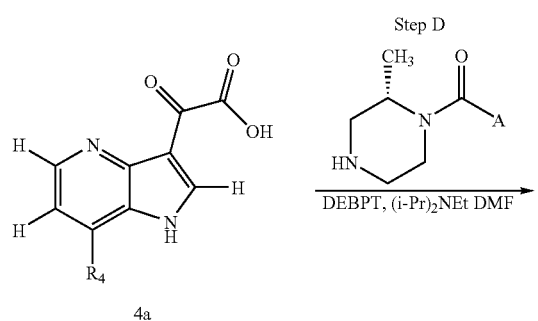

4a

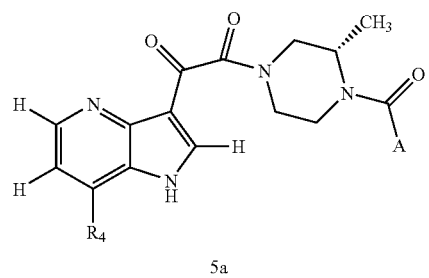

5a

Schemes 79 provides examples and typical conditions for forming intermediates 2 which contain an oxadiazole or substituted oxadiazole. These intermediates can be converted to compounds of claim 1 via the standard methodology described in Scheme 1 and the rest of the application. An alternate sequence is shown in Scheme 79a which utilizes cyano substituted intermediates 5 to generate the oxadiazoles of claim 1. Specific examples are given in the experimental section. Other oxadiazole isomers may be prepared via standard literature methodology.

Scheme 79

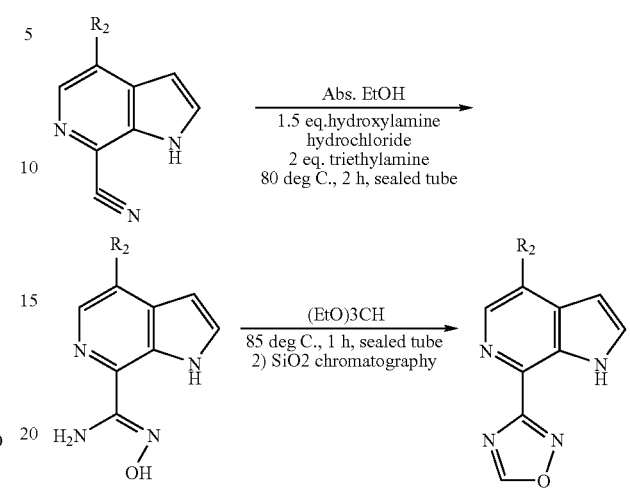

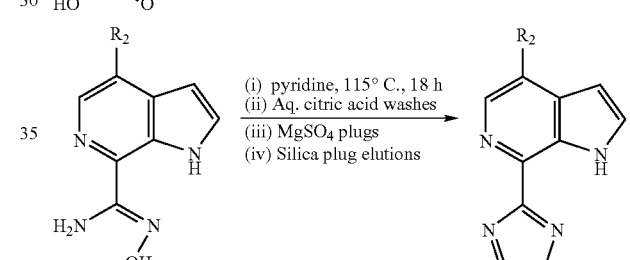

Scheme 79a

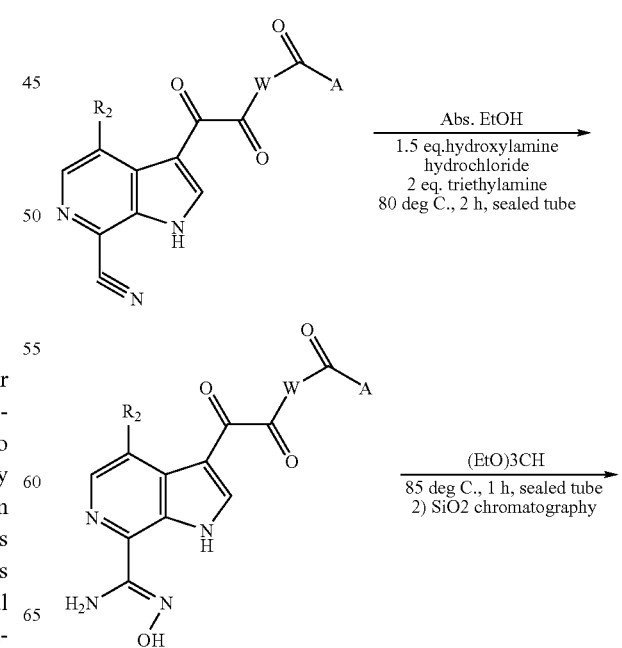

-continued

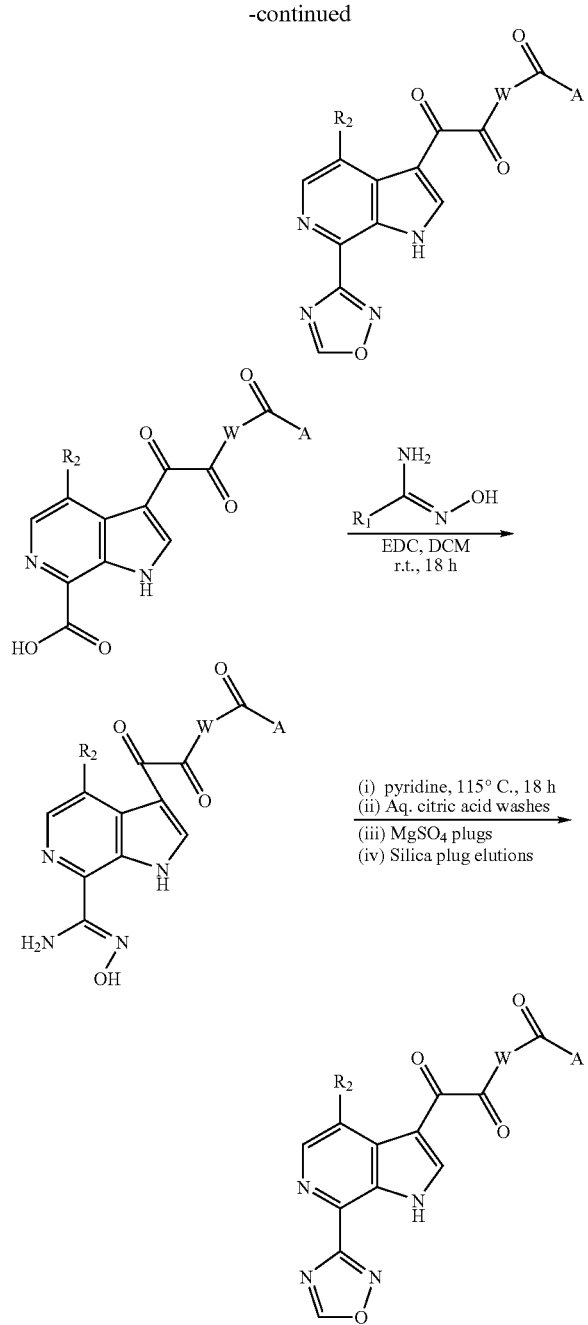

Scheme 80 is a preferred method for making compounds of Formula I and Ia where $R^2$ is fluoro. This is exemplified specifically in the preparation of compound Example 216. The synthesis of 2-hydroxy-3-nitro-5-fluoropyridine 5-80 as shown was carried out generally via the methods of A. Marfat and R. P. Robinson U.S. Pat. No. 5,811,432 (column 25, example 5) and Nesnow and Heidleberger (*J. Heterocyclic Chem.* 1973, 10, pg 779) except that a number of procedural enhancements were incorporated as noted in the description of each step. 2-Hydroxy 5-fluoropyridine 4-80 is also commercially available. The formation of diazonium tetrafluoroborate salt 2-80 from 5-amino-2-methoxy pyridine 1-80 proceeded in essentially quantitative yield and was isolated via filtration. The Schiemann reaction provided poor yields of the desired 2-methoxy-fluoropyridine using the literature conditions due mainly to significant contamination with 3-fluoro 1-(N)-methyl pyridone and other byproducts. However, adoption of a procedure similar to that described in Sanchez, J. P.; Rogowski, J. W.; *J Heterocycl Chem* 1987, 24, 215 for a related compound provided very high yields of essentially clean but volatile 2-methoxy-5-fluoro pyridine 3-80 as a solution in toluene. In the interest of expediency, demethylation was achieved on large scale using aqueous HCl in pressure bottles at 140° C. for 1 hr. Prior to heating, the toluene solution was stirred with the aq HCl and then the toluene was removed by decantation. The literature method for carrying out this step using HBr at 100° C. was also successful on small scale and had the advantage of avoiding the use of pressure bottles. Nitration of 4-80 as described by Marfat provided lower than expected yields so the procedure was modified slightly, using guidance from A. G. Burton, P. J. Hallis, and A. R. Katritzky (*Tetrahedron Letters* 1971, 24, 2211-2212) on the control of the regiochemistry of nitration of pyridones via modulation of the acidity of the medium. The chemical yields of 2-hydroxy-3-nitro-5-fluoro pyridine 5-80 were significantly improved using the procedure described in the experimental section. Occasionally the product failed to precipitate during workup and then considerable efforts were necessary to isolate this highly water soluble compound from the aqueous layer. Using neat excess $POBr_3$, compound 5-80 was converted to 2-bromo-3-nitro-5-fluoro pyridine 6 which could be used without further purification in the subsequent azaindole forming reaction. Addition of the pyridine 6 to excess vinyl magnesium bromide in THF at low temperature afforded the desired 4-fluoro-7-bromo-6-azaindol (precursor 5j) in yields of up to 35% following acidic work up and isolation via crystallization. A disadvantage of this method is the workup is difficult due to the large amounts of salts formed as co-products in the reaction and the low conversion to albeit clean product. The reaction is also exothermic and thus would require care on larger scales. Despite the moderate yields, as mentioned above the reaction proceeds cleanly and provides pure product precursor 5j without chromatography so it is anticipated that more detailed studies of this chemistry could result in yield enhancements. A selective copper/potassium carbonate mediated displacement of the 7-bromo group by commercially available 1,2,3-triazole provided an approximately 1:1 mixture of triazoles from which the desired 7-80 was isolated via chromatography in 25-35% yields. Copper-bronze rather than copper powder can also be used to carry out similar transformations. This reaction must not be allowed to overheat since concomitant displacement of the fluorine is possible and has been observed. Acylation occurred most efficiently under conditions that utilized excess acidic imidazolium chloro aluminate ionic liquid to provide highly activated glyoxylating reagent (K. S. Yeung et al. *Tetrahedron Lett.* 2002, 43, 5793). The acylation of 7-80 usually does not proceed to completion and typically results in about 75% conversion as measured by LC/MS. An advantage to these conditions is that the typical next step, ester hydrolysis, proceeded in situ to provide the desired acid 8-80 which was isolated directly by precipitation during workup. Coupling of the piperazine benzamide was found to be cleaner and produced higher yields of the compound of Example 216 using the depicted HATU based coupling than with other standard coupling reagents such as EDC or DEPBT.

Scheme 80

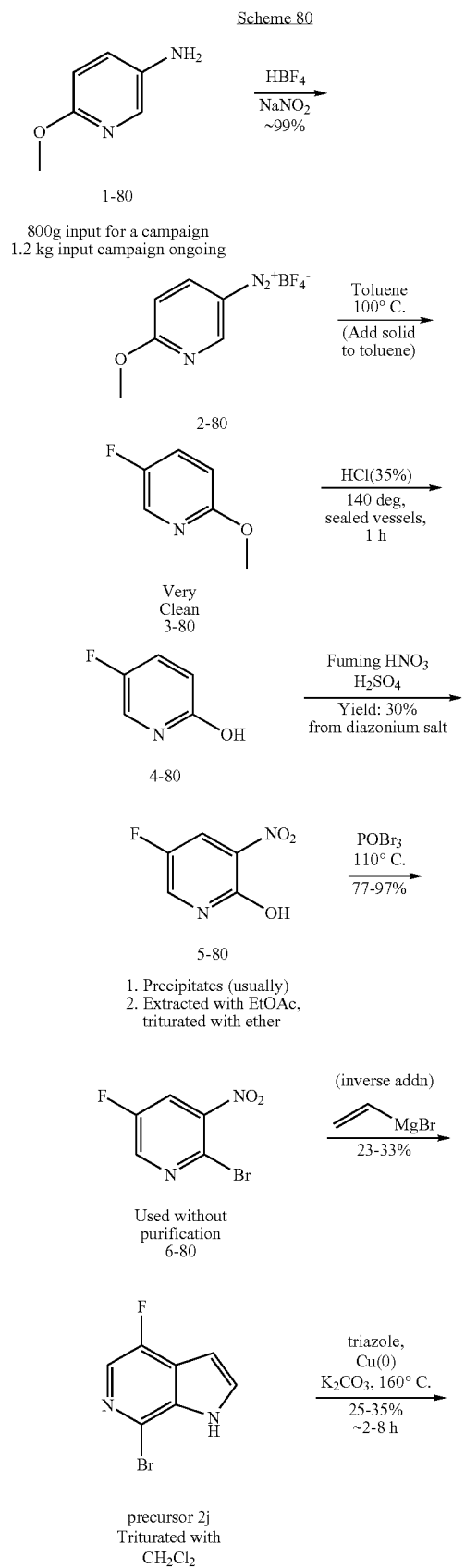

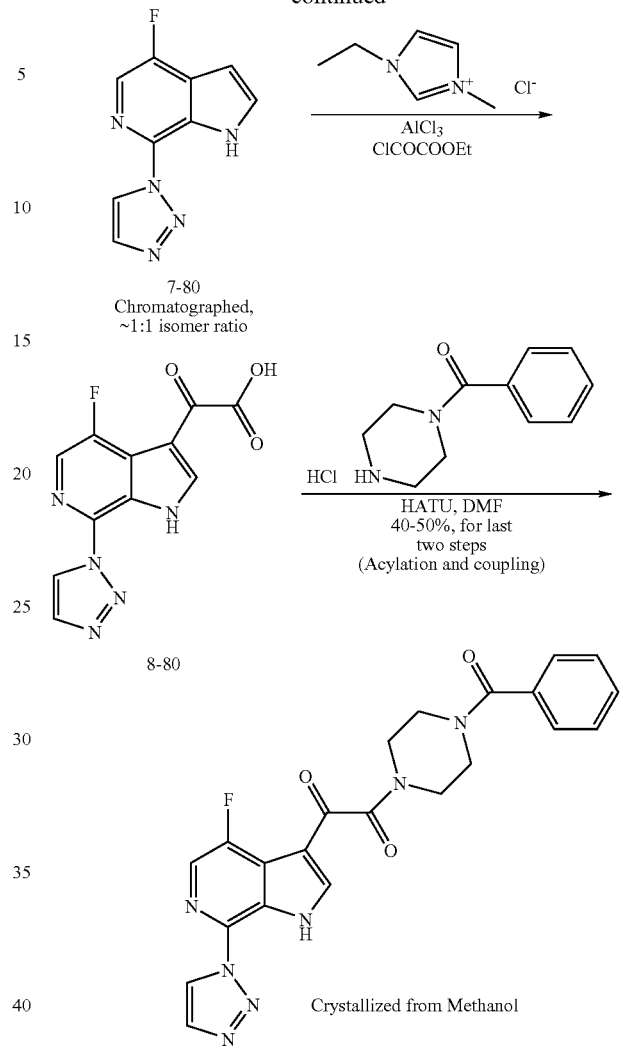

Example 216

Chemistry

General:

Additional preparations of starting materials and precursors are contained in Wang et. al. U.S. Ser. No. 09/912,710 filed Jul. 25, 2001 (which is a continuation-in-part of U.S. Ser. No. 09/765,189 filed Jan. 18, 2001, abandoned, corresponding to PCT WO 01/62255) which is incorporated by reference.

Chemistry

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

| LC/MS Method (i.e., compound identification) | |
|---|---|
| Column A: | YMC ODS-A S7 3.0 × 50 mm column |
| Column B: | PHX-LUNA C18 4.6 × 30 mm column |
| Column C: | XTERRA ms C18 4.6 × 30 mm column |

-continued

| | LC/MS Method (i.e., compound identification) |
|---|---|
| Column D: | YMC ODS-A C18 4.6 × 30 mm column |
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Column H: | YMC C18 S5 4.6 × 33 mm column |
| Column I: | YMC ODS-A C18 S7 3.0 × 50 mm column |
| Column J: | XTERRA C-18 S5 4.6 × 50 mm column |
| Column K: | YMC ODS-A C18 4.6 × 33 mm column |
| Column L: | Xterra MS C18 5 uM 4.6 × 30 mm column |
| Column M: | YMC ODS-A C18 S3 4.6 × 33 mm column |

Standard LC Run Conditions (used Unless Otherwise Note):

| | |
|---|---|
| Gradient: | 100% Solvent A/0% Solvent B to 0% Solvent A/ 100% Solvent B Solvent A = 10% MeOH - 90% $H_2O$ - 0.1% TFA, Solvent B = 90% MeOH - 10% $H_2O$ - 0.1% TFA; and $R_t$ in min. |
| Gradient time: | 2 minutes |
| Hold time | 1 minute |
| Flow rate: | 5 mL/min |
| Detector Wavelength: | 220 nm |
| Solvent A: | 10% MeOH/90% $H_2O$/0.1% Trifluoroacetic Acid |
| Solvent B: | 10% $H_2O$/90% MeOH/0.1% Trifluoroacetic Acid |

Alternate LC Run Conditions B:

| | |
|---|---|
| Gradient: | 100% Solvent A/0% Solvent B to 0% Solvent A/ 100% Solvent B Solvent A = 10% MeOH - 90% $H_2O$ - 0.1% TFA, Solvent B = 90% MeOH - 10% $H_2O$ - 0.1% TFA; and $R_t$ in min. |
| Gradient time: | 4 minutes |
| Hold time | 1 minute |
| Flow rate: | 4 mL/min |
| Detector Wavelength: | 220 nm |
| Solvent A: | 10% MeOH/90% $H_2O$/0.1% Trifluoroacetic Acid |
| Solvent B: | 10% $H_2O$/90% MeOH/0.1% Trifluoroacetic Acid |

Compounds purified by preparative HPLC were diluted in MeOH (1.2 mL) and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.

Preparative HPLC Method (i.e. Compound Purification)

Purification Method Initial gradient (40% B, 60% A) ramp to final gradient (100% B, 0% A) over 20 minutes, hold for 3 minutes (100% B, 0% A)

| | |
|---|---|
| Solvent A: | 10% MeOH/90% $H_2O$/0.1% Trifluoroacetic Acid |
| Solvent B: | 10% $H_2O$/90% MeOH/0.1% Trifluoroacetic Acid |
| Column: | YMC C18 S5 20 × 100 mm column |
| Detector Wavelength: | 220 nm |

Typical Procedures and Characterization of Selected Examples:

Preparation of Precursors:

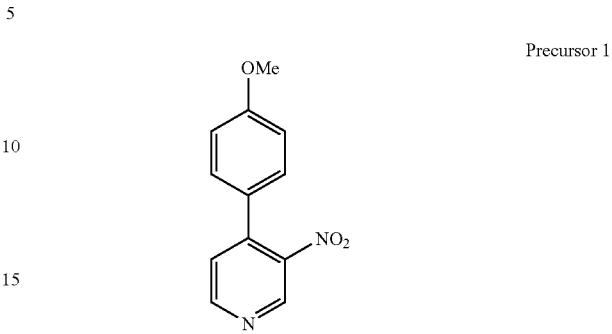

Precursor 1

4-Methoxyphenylboronic acid (24.54 g), 4-chloro-3-nitro-pyridine hydrochloride (26.24 g), $Pd(Ph_3P)_4$ (4 g) and $K_2CO_3$ (111 g) were combined in DME (500 mL). The reaction was heated to reflux for 10 hours. After the mixture cooled down to room temperature, it was poured into saturated aqueous $NH_4OAc$ (500 mL) solution. The aqueous phase was extracted with EtOAc (3×200 mL). The combined extract was concentrated to give a residue which was purified using silica gel chromatography (10% to 30% EtOAc/PE) to afford 10.6 g of Precursor 1, 3-Nitro-4-(4-methoxyphenyl)pyridine. MS m/z: $(M+H)^+$ calcd for $C_{12}H_{11}N_2O_3$: 231.08; found 231.02. HPLC retention time: 1.07 minutes (column B).

Precursor 1a
Alternate route to 5-azaindoles:

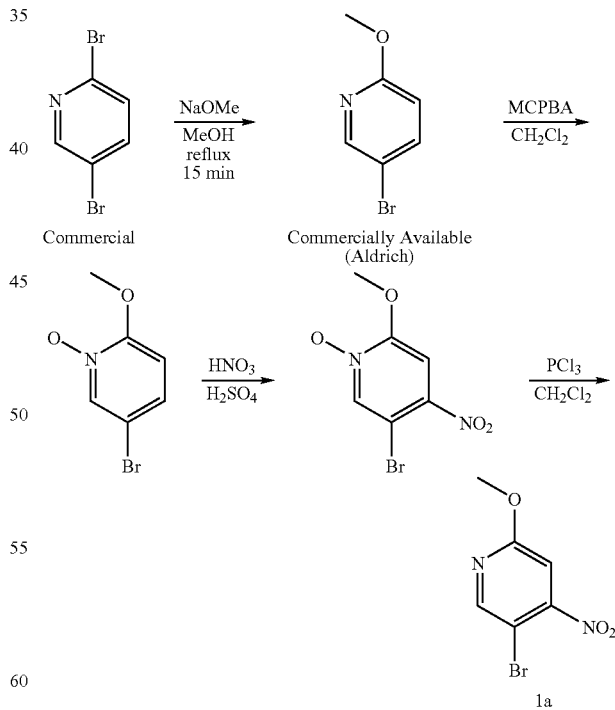

2-methoxy-5-bromo pyridine can be purchased from Aldrich (or others) or prepared. Oxidation with 1.1 eq of MCPBA in dichloromethane (20 ml per 10.6 mmol bromide) in the presence of anhydrous MgSO4 (0.4 g per mL dichloromethane)

with stirring from 0° to ambient temperature for approximately 14 h provided the N-oxide after workup and flash chromatographic purification over silica gel using a 5% Etoac/Hexane gradient of increasing EtOAc. The N-oxide (1.6 g) was dissolved in 10 mL 98% sulfuric acid and cooled to 0°. 10 mL of 69% nitric acid was added and then allowed to warm to ambient temp with stirring. The reaction was then heated and stirred at 80° C. for 14 h and then poured over ice, extracted with dichloromethane, washed with water, and concentrated to give a yellow solid which was purified by flash chromatography over Silica gel using 1:1 EtOAc/hexane and then a gradient to provide a yellow crystalline solid). $^1$H NMR (CDCl3) δ 8.50 (s, 1H), 7.59 (s, 1H), 4.12 (3H, s). LC MS showed desired M+H. The N-oxide was reduced by dissolving the starting material in dichloromethane (0.147M substrate) and cooling to 0°. A solution of 1.2 eq $PCl_3$ (0.44M) in dichloromethane was added slowly to keep the reaction at 0°. Warm to ambient temp and stir for 72 h. Aqueous workup and concentration provided a yellow solid which could be used in subsequent reactions or purified by chromatography. Note: a similar sequence could be used with 2-methoxy-5-chloro-pyridine as starting material.

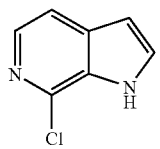

Precursor 2a

Typical procedure for preparing azaindole from nitropyridine: Preparation of 7-chloro-6-azaindole, Precursor 2a, is an example of Step A of Scheme 1. 2-chloro-3-nitropyridine (5.0 g, 31.5 mmol) was dissolved in dry THF (200 mL). After the solution was cooled to −78° C., vinyl magnesium bromide (1.0M in THF, 100 mL) was added dropwise. The reaction temperature was maintained at −78° C. for 1 h, and then at −20° C. for another 12 h before it was quenched by addition of 20% $NH_4Cl$ aqueous solution (150 mL). The aqueous phase was extracted with EtOAc (3×150 mL). The combined organic layer was dried over $MgSO_4$, filtered and the filtrate was concentrated in vacuo to give a residue which was purified by silica gel column chromatography (EtOAc/Hexane, 1/10) to afford 1.5 g (31%) of 7-chloro-6-azaindole, Precursor 2a. $^1$H NMR (500 MHz, $CD_3OD$) δ 7.84 (d, 1H, J=10.7 Hz), 7.55 (dd, 1H, J=10.9, 5.45 Hz), 6.62 (d, 1H, J=5.54 Hz), 4.89 (s, 1H). MS m/z: (M+H)$^+$ calcd for $C_7H_6ClN_2$: 153.02; found 152.93. HPLC retention time: 0.43 minutes (column A).

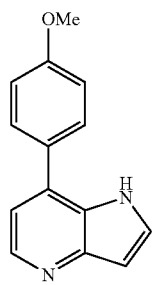

Precursor 2b

Precursor 2b, 7-(4-Methoxyphenyl)-4-azaindole, was prepared by the same method as Precursor 2a starting from 3-Nitro-4-(4-methoxyphenyl)pyridine, Precursor 1. MS m/z: (M+H)$^+$ calcd for $C_{14}H_{13}N_2O$: 225.10; found 225.02. HPLC retention time: 1.39 minutes (column B).

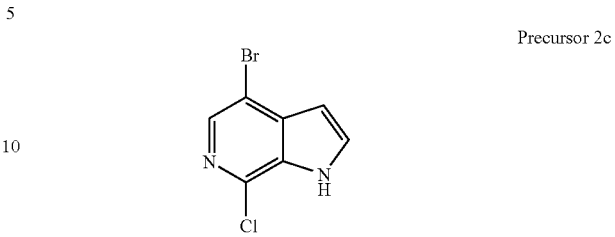

Precursor 2c

Precursor 2c, 4-bromo-7-chloro-6-azaindole, was prepared by the same method as Precursor 2a, starting from 2-Chloro-3-nitro-5-bromo-pyridine (available from Aldrich, Co.). MS m/z: (M+H)$^+$ calcd for $C_7H_5BrClN_2$: 230.93; found 231.15. HPLC retention time: 1.62 minutes (column B).

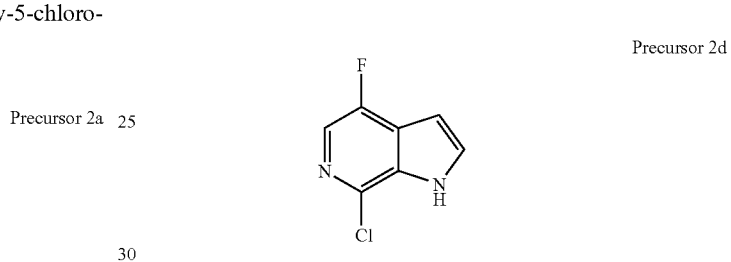

Precursor 2d

Precursor 2d, 4-fluoro-7-chloro-6-azaindole (above), was prepared according to the following scheme:

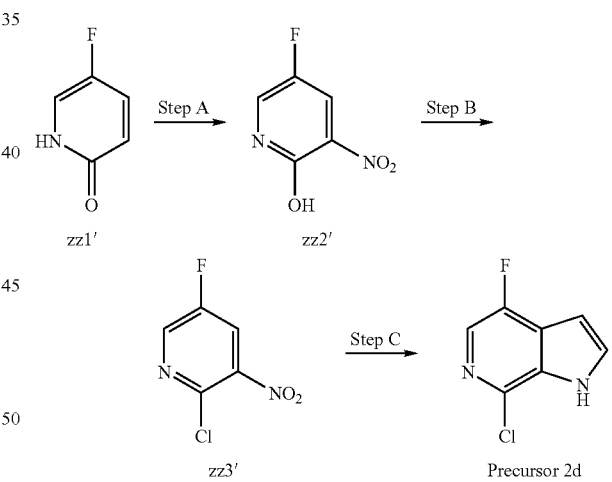

A) fuming $HNO_3$, $H_2SO_4$;
B) $POCl_3$/DMF, 110° C.;
C) vinylmagnesium bromide, THF, -78° C. ~ -20° C.

It should be noted that 2-chloro-5-fluoro-3-nitro pyridine, zz3', may be prepared by the method in example 5B of the reference Marfat, A.; and Robinson, R. P.; "Azaoxindole Derivatives" U.S. Pat. No. 5,811,432 1998. The preparation below provides some details which enhance the yields of this route.

In Step A, compound zz1' (1.2 g, 0.01 mol) was dissolved in sulfuric acid (2.7 mL) at room temperature. Premixed fuming nitric acid (1 mL) and sulfuric acid was added dropwise at 5-10° C. to the solution of compound zz1'. The reaction mixture was then heated at 85° C. for 1 hour, then was cooled to room temperature and poured into ice (20 g). The yellow solid precipitate was collected by filtration, washed with water and air dried to provide 1.01 g of compound zz2'.

In Step B, compound zz2' (500 mg, 3.16 mmol) was dissolved in phosphorous oxychloride (1.7 mL, 18.9 mmol) and dimethoxyethane at room temperature. The reaction was heated to 110° C. for 5 hours. The excess phosphorous oxychloride was then removed by concentrating the reaction mixture in vacuo. The residue was chromatographed on silica gel, eluted with chloroform (100%) to afford 176 mg of product zz3'.

In Step C, compound zz3' (140 mg, 0.79 mmol) was dissolved in THF (5 mL) and cooled to −78° C. under a nitrogen atmosphere. To this solution was added dropwise a solution of vinyl magnesium bromide (1.2 mmol, 1.0 M in diethyl ether, 1.2 mL). The reaction mixture was then kept at −20° C. for 15 hours. The reaction mixture was then quenched with saturated ammonium chloride, and extracted with ethyl acetate. The combined organic layers were washed with brine, dried over magnesium sulfate, filtered, and the filtrate was concentrated in vacuo. The residue was chromatographed on silica to provide 130 mg of precursor 2d $^1$H NMR (500 MHz, CD$_3$OD) δ 7.78 (s, 1H), 7.60 (d, 1H, J=3.0 Hz), 6.71 (d, 1H, J=3.05 Hz). MS m/z: (M+H)$^+$ calcd for C$_7$H$_5$ClFN$_2$: 171.10; found 171.00. HPLC retention time: 1.22 minutes (column A).

Precursor 2d, 4-fluoro-7-chloro-6-azaindole, was prepared by the same method as Precursor 2a, starting from 2-Chloro-3-nitro-5-fluoro-pyridine which was prepared according to the procedure above. Experimental details for this preparation are contained in Wang et. al. PCT WO 01/62255. $^1$H NMR (500 MHz, CD$_3$OD) δ 7.78 (s, 1H), 7.60 (d, 1H, J=3.0 Hz), 6.71 (d, 1H, J=3.05 Hz). MS m/z: (M+H)$^+$ calcd for C$_7$H$_5$ClFN$_2$: 171.10; found 171.00. HPLC retention time: 1.22 minutes (column A).

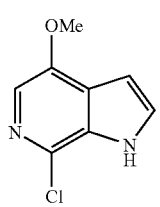

Precursor 2e

Precursor 2e was prepared by either Method A or Method B, below:

Method A: A mixture of 4-bromo-7-chloro-6-azaindole (1 g), CuI (0.65 g) and NaOMe (4 mL, 25% in methanol) in MeOH (16 mL) was heated at 110-120° C. for 16 hours in a sealed tube. After cooling to room temperature, the reaction mixture was neutralized with 1N HCl to pH 7. The aqueous solution was extracted with EtOAc (3×30 mL). Then the combined organic layer was dried over MgSO$_4$, filtered and the filtrate was concentrated in vacuo to afford a residue, which was purified by using silica gel chromatography to give 0.3 g of 4-methoxy-7-chloro-6-azaindole, Precursor 2e. MS m/z: (M+H)$^+$ calcd for C$_8$H$_8$ClN$_2$O: 183.03; found 183.09. HPLC retention time: 1.02 minutes (column B).

Method B: A mixture of 4-bromo-7-chloro-6-azaindole (6 g), CuBr (3.7 g) and NaOMe (30 mL, 5% in MeOH) was heated at 110° C. for 24 hours in a sealed tube. After cooling to room temperature, the reaction mixture was added to saturated aqueous NH$_4$Cl. The resulting aqueous solution was extracted with EtOAc (3×30 mL). The combined organic layer was dried over MgSO$_4$, filtered and the filtrate was concentrated in vacuo to afford a residue, which was purified by using silica gel chromatography to give 1.8 g of 4-methoxy-7-chloro-6-azaindole, Precursor 2e.

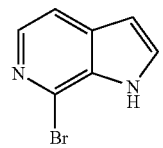

Precursor 2f

Precursor 2f, 7-bromo-6-azaindole was prepared by the same method as Precursor 2a, starting from 2-Bromo-3-nitro-pyridine (available from Aldrich, Co.). MS m/z: (M+H)$^+$ calcd for C$_7$H$_6$BrN$_2$: 197.97; found 197.01. HPLC retention time: 0.50 minutes (column A).

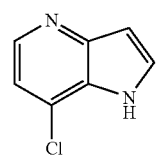

Precursor 2g

Precursor 2g, 7-chloro-4-azaindole was prepared by the same method as Precursor 2a, starting from 4-Chloro-3-nitro-pyridine (HCl salt, available from Austin Chemical Company, Inc.). MS m/z: (M+H)$^+$ calcd for C$_7$H$_6$ClN$_2$: 153.02; found 152.90. HPLC retention time: 0.45 minutes (column A).

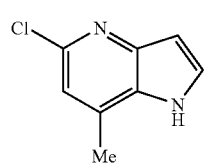

Precursor 2h

Precursor 2h, 5-chloro-7-methyl-4-azaindole was prepared by the same method as Precursor 2a, starting from 2-Chloro-4-methyl-5-nitro-pyridine (available from Aldrich, Co.). MS m/z: (M+H)$^+$ calcd for C$_8$H$_8$ClN$_2$: 167.04; found 166.99. HPLC retention time: 1.22 minutes (column B).

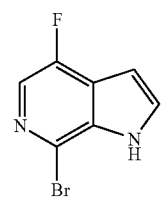

Precursor 2i

Precursor 2i, 4-fluoro-7-bromo-6-azaindole, was prepared by the same method as Precursor 2e, using POBr$_3$ in the step B instead of POCl$_3$. MS m/z: (M+H)$^+$ calcd for C$_7$H$_5$BrFN$_2$: 214.96; found 214.97. HPLC retention time: 1.28 minutes (column G).

Precursor 2j

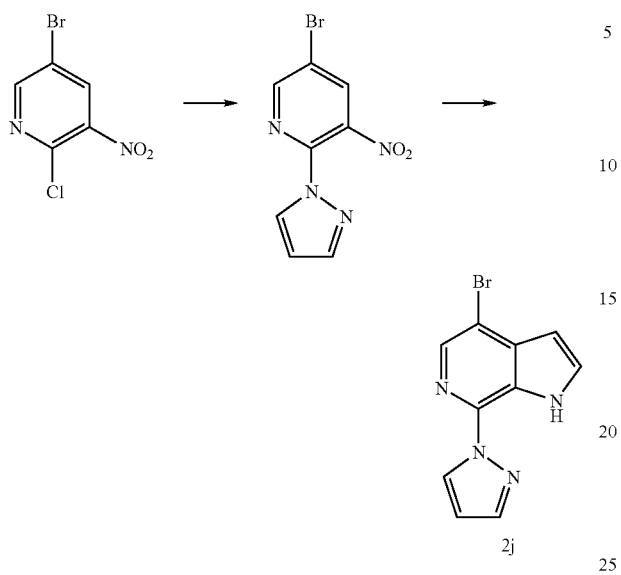

2j

To a mixture of 5-bromo-2-chloro-3-nitropyridine (10 g, 42 mmol) in 1,4-dioxane (100 ml) was added pyrazole (5.8 g, 85 mmol). The resulting mixture was stirred at 120° C. for 26.5 h., and then evaporated after cooling to r.t. The crude material was purified by flash chromatography (0 to 5% EtOAc/Hexanes) to give the desired product 5-Bromo-3-nitro-2-pyrazol-1-yl-pyridine. $^1$H NMR: (CD$_3$OD) δ 8.77 (s, 1H), 8.56 (s, 1H), 8.45 (s, 1H), 7.73 (s, 1H), 6.57 (s, 1H); LC/MS: (ES+) m/z (M+H)$^+$=269, 271, HPLC R$_t$=1.223.

To a 250 mL round bottom flask was charged 5-Bromo-3-nitro-2-pyrazol-1-yl-pyridine (1.02 g, 3.8 mmol) and THF (30 ml). The mixture was then cooled to −78° C., and added a THF solution of vinylmagnesium bromide (23 mL, 18.4 mmol, 0.8 M). After three minutes, the reaction mixture was warmed to −45° C. and remained stirring for 1 h. The reaction was then quenched with ammonium chloride, and the resulting mixture extracted with EtOAc. The combined extracts were evaporated in vacuo, and the residue purified by flash column chromatography (5% EtOAc/Hexanes) to give compound 2 (which by HPLC contained about 50% of a side product, presumably 3-vinylamino of compound 1); $^1$H NMR: (CDCl$_3$) δ 10.75 (b s, 1H), 8.73 (s, 1H), 8.10 (s, 1H), 7.82 (s, 1H), 7.52 (s, 1H), 6.67 (s, 1H), 6.53 (s, 1H); LC/MS: (ES+) m/z (M+H)=262, 264; HPLC R$_t$=1.670.

Precursor 2k

2k

To a solution of 2-bromo-5-chloro-3-nitropyridine 5 (20 g, 84 mmol, prepared in 2 steps from 2-amino-5-chloropyridine as described in WO9622990) in THF (300 ml) at −78° C. was charged a THF solution of vinylmagnesium bromide (280 ml, 252 mmol, 0.9 M). The resulting mixture was stirred at −78° C. for one hour, followed by quenching with aqueous ammonium chloride (500 ml, sat.) and extracted with EtOAc (5×500 ml). The combined organic extracts were washed with aqueous ammonium chloride (2×500 ml, sat.) and water (3×500 ml), dried (MgSO$_4$) and evaporated to give a brownish residue. The crude material was triturated with CH$_2$Cl$_2$, and the solid formed filtered to give compound 6 as a yellow solid (8.0 g, 41%); $^1$H NMR: (DMSO-d$_6$) 12.30 (b s, 1H), 7.99 (s, 1H), 7.80 (d, J=3.0, 1H), 6.71 (d, J=3.0, 1H); LC/MS: (ES+) m/z (M+H)$^+$=231, 233, 235; HPLC R$_t$=1.833.

Precursor 2m

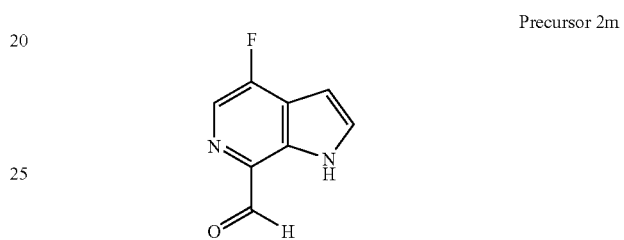

4-Fluoro-7-Bromo-6-azaindole (500 mg, 1.74 mmol) was dissolved in THF (5 ml) and cooled to −78° C. and n-BuLi (2.5 M, 2.1 ml) was added dropwise. The reaction mixture was stirred at −78° C. for 15 min, then stirred at 0° C. for 30 min. The reaction was cooled to −78° C. again, and DMF(0.7 ml, 8.7 mmol) was added. After stirring for 30 min, water was added to quench the reaction. The reaction mixture was extracted with ethylacetate. The organic layer was dried over MgSO$_4$, filtered, concentrated and chromatographed to afford 208 mg of precursor 2m. LC/MS: (ES$^+$) m/z (M+H)$^+$=164.98. Rt=0.44 min.

Precursor 2n

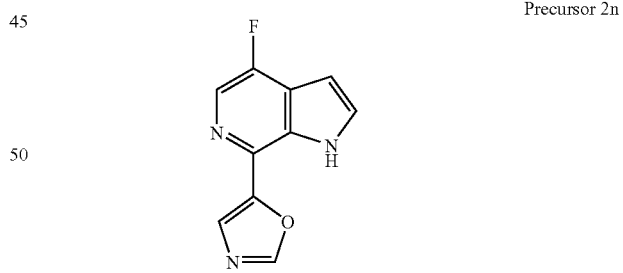

A mixture of precursor 2 m (50 mg, 0.30 mmol), potassium carbonate (42 mg, 0.30 mmol) and tosylmethyl isocyanide (60 mg, 0.30 mmol) in MeOH(3 ml) was heated to reflux for about 2 hr. The solvent was removed in vacuum and the residue was treated with ice water and extracted with ether. The organic layer was washed with an aqueous solution of HCl (2%), water and dried over magnesium sulfate. After filtration and evaporation of the solvent, the residue was purified on silica to afford the title compound (60 mg). LC/MS: (ES$^+$) m/z (M+H)$^+$=204. Rt=0.77 min.

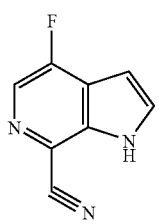
Precursor 2o

4-Fluoro-7-Bromo-6-azaindole (510 mg, 2.39 mmol) in anhydrous DMF (5 mL) was treated with copper cyanide (430 mg, 4.8 mmol) at 150° C. in a seal tube for 1 h. An aqueous solution of NH$_4$OH (10 mL) was added and the reaction was extracted with diethylether (2×50 mL) and ethylacetate (2×50 mL). The organic phases were combined and dried over sodium sulfate, filtered, concentrated in vacuum and chromatographed on silica gel (gradient elution AcOEt/Hexanes 0-30%) to afford the title compound as a brownish solid (255 mg, 66%) LC/MS: (ES$^+$) m/z (M+H)$^+$=162.

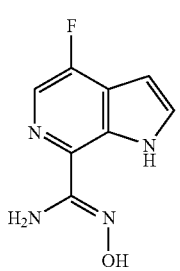
Precursor 2p

Precursor 2o (82 mg, 0.51 mmol) was dissolved in absolute ethanol (200% proof, 5 mL) and treated with hydroxylamine hydrochloride (53 mg, 0.76 mmol) and triethylamine (140 μL, 1.0 mmol) and the reaction mixture was heated up at 80° C. in a seal tube for 2 h. The solvent was removed in vacuum and the pale yellow solid residue was washed with water to afford the title compound. LC/MS: (ES$^+$) m/z (M+H)$^+$=195. This compound was taken to the next step without further purification.

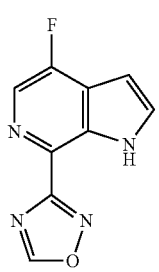
Precursor 2q

Precursor 2p was dissolved in trimethylorthoformate (1 mL) and heated at 85° C. in a seal tube for 1 h, then it was cooled to rt, the solvent was removed in vacuum and the residue was chromatographed on silica gel (AcOEt/Hexanes, gradient elution 10-60%) to afford the title compound (54 mg, LC/MS: (ES$^+$) m/z (M+H)$^+$=205).

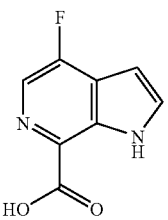
Precursor 2r

Precursor 2q (100 mg, 0.62 mmol, crude) in ethanol (5 mL) was treated with an aqueous solution of sodium hydroxide (50%, 2 mL) and the reaction mixture was heated at 110° C. overnight in a seal tube. The pH was adjusted to 2 with HCl (6N) and a brown precipitate was filtered off. The solution was concentrated to dryness to afford the title compound as a pale yellow solid LC/MS: (ES$^+$) m/z (M+H)$^+$=181. This compound was used without further purification.

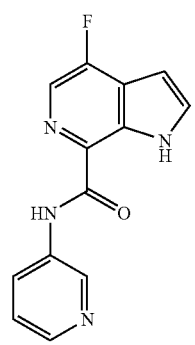
Precursor 2s

Precursor 2r (0.62 mmol) was dissolved in DMF (1 mL) and treated with 3-aminopyridine (58.3 mg, 0.62 mmol), DEBT (185 mg, 0.62) and Hunig's base (216 μL, 1.26 mmol) and the reaction mixture was stirred at room temperature for 18 h. Water was added and the reaction was extracted with AcOEt (2×25 mL) and CHCl$_3$ (2×25 mL), dried over sodium sulfate, concentrated and chromatographed on silica gel (AcOEt/Hexanes gradient elution 0-50%) to afford the title compound as a brownish solid LC/MS: (ES$^+$) m/z (M+H)$^+$=257.

Precursor 2s'

Precursor 2h, 4-methoxy-7-bromo-5-azaindole was prepared by the same method as Precursor 2a, starting from 2-methoxy-5-bromo-4-nitro-pyridine (precursor 1a). $^1$H NMR (CDCl3) δ 8.52 (s, 1H), 7.84 (s, 1H), 7.12 (t, 1H), 6.68 (d, 1H), 3.99 (s, 3H). LC MS showed desired M+H.

Precursor 2t

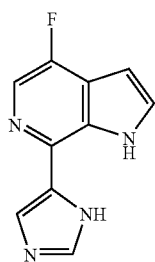

A mixture of aldehyde precursor 2m (150 mg, 0.91 mmol), sodium cyanide (44 mg, 0.091 mmol) and tosylmethyl isocyanide (177 mg, 0.91 mmol) in EtOH (3 ml) was stirred at room temperature for 30 min, then filtered and the crystals were washed with ether-hexane (1:1) and dried. The obtained crystals, and a saturated solution of ammonia in dry methanol (8 ml) were heated between 100-110° C. for 16 hr. The mixture was concentrated and chromatographed to provide 20 mg of precursor 2. LC/MS: (ES$^+$) m/z (m+H)$^+$=203. Rt=0.64 min.

Precursor 3a

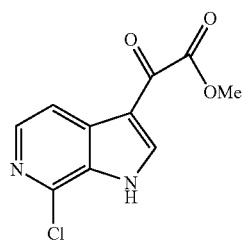

*Typical procedure for acylation of azaindole*: Preparation of Methyl (7-chloro-6-azaindol-3-yl)-oxoacetate, Precursor 3a is an example of Step B of Scheme 1. 7-Chloro-6-azaindole, Precursor 2a (0.5 g, 3.3 mmol) was added to a suspension of AlCl$_3$ (2.2 g, 16.3 mmol) in CH$_2$Cl$_2$ (100 mL). Stirring was continued at rt for 10 minutes before methyl chlorooxoacetate (2.0 g, 16.3 mmol) was added dropwise. The reaction was stirred for 8 h. The reaction was quenched with iced aqueous NH$_4$OAc solution (10%, 200 mL). The aqueous phase was extracted with CH$_2$Cl$_2$ (3×100 mL). The combined organic layer was dried over MgSO$_4$, filtered and the filtrate was concentrated in vacuo to give a residue which was carried to the next step without further purification. Precursor 2, Methyl (7-chloro-6-azaindol-3-yl)-oxoacetate: MS m/z: (M+H)$^+$ calcd for C$_{10}$H$_8$ClN$_2$O$_3$: 239.02; found 238.97. HPLC retention time: 1.07 minutes (column A).

Precursor 3b

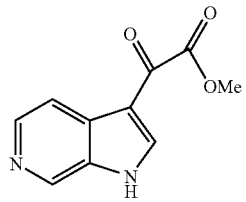

Precursor 3b, Methyl (6-azaindol-3-yl)-oxoacetate, was prepared by the same method as Precursor 3a, starting from 6-azaindole. MS m/z: (M+H)$^+$ calcd for C$_{10}$H$_9$N$_2$O$_3$: 205.06; found 205.14. HPLC retention time: 0.49 minutes (column A).

Precursor 3c

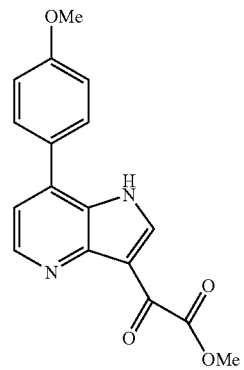

Precursor 3c, Methyl (7-(4-methoxyphenyl)-4-azaindol-3-yl)-oxoacetate, was prepared by the same method as Precursor 3a, starting from 7-(4-methoxyphenyl)-4-azaindole (Precursor 2b). MS m/z: (M+H)$^+$ calcd for C$_{17}$H$_{15}$N$_2$O$_4$: 311.10; found 311.04. HPLC retention time: 1.15 minutes (column A).

Precursor 3d

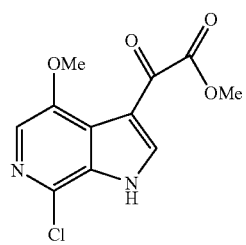

Precursor 3d, methyl (7-chloro-4-methoxy-6-azaindol-3-yl)-oxoacetate was prepared by the same method as Precursor 3a, starting from Precursor 2e, 4-methoxy-7-chloro-6-azaindole. MS m/z: (M+H)$^+$ calcd for C$_{12}$H$_{12}$ClN$_2$O$_4$: 283.05; found 283.22. HPLC retention time: 1.37 minutes (column B).

Precursor 3e

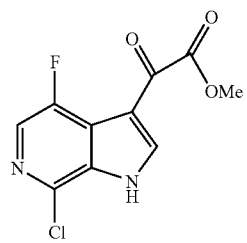

Precursor 3e, Methyl (7-chloro-4-fluoro-6-azaindol-3-yl)-oxoacetate was prepared by the same method as Precursor 3a starting from Precursor 2d, 4-fluoro-7-chloro-6-azaindole. $^1$H NMR (500 MHz, CD$_3$OD) δ 8.63 (s, 1H), 8.00 (s, 1H), 3.95 (s, 3H). MS m/z: (M+H)$^+$ calcd for C$_{10}$H$_7$ClFN$_2$O$_3$: 257.01; found 257.00. HPLC retention time: 1.26 minutes (column A).

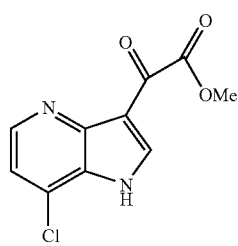

Precursor 3f

Precursor 3f, Methyl (7-chloro-4-azaindol-3-yl)-oxoacetate was prepared by the same method as Precursor 3a, starting from Precursor 2g, 7-chloro-4-azaindole. MS m/z: (M+H)+ calcd for $C_{10}H_8ClN_2O_3$: 239.02; found 238.97. HPLC retention time: 0.60 minutes (column A).

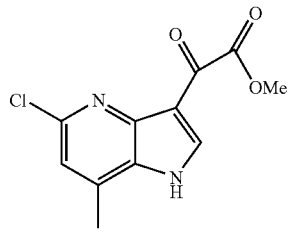

Precursor 3g

Precursor 3g, Methyl (5-chloro-7-methyl-4-azaindol-3-yl)-oxoacetate was prepared by the same method as Precursor 3a, starting from Precursor 2h, 5-chloro-7-methyl-4-azaindole. MS m/z: (M+H)+ calcd for $C_{11}H_{10}ClN_2O_3$: 253.04; found 252.97. HPLC retention time: 1.48 minutes (column B).

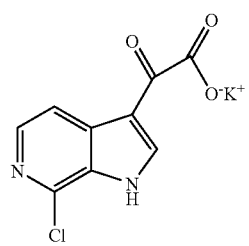

Precursor 4a

Typical procedure of hydrolysis of ester: Preparation of Potassium (7-chloro-6-azaindol-3-yl)-oxoacetate, Precursor 4a, is an example of Step C of Scheme 1. Crude methyl (7-chloro-6-azaindol-3-yl)-oxoacetate, Precursor 3a, and an excess of $K_2CO_3$ (2 g) were dissolved in MeOH (20 mL) and $H_2O$ (20 mL). After 8 h, the solution was concentrated and the residue was purified by silica gel column chromatography to provide 200 mg of Potassium (7-chloro-6-azaindol-3-yl)-oxoacetate. MS m/z: (M+H)+ of the corresponding acid was observed. Calc'd for $C_9H_6ClN_2O_3$: 225.01; found 225.05. HPLC retention time: 0.83 minutes (column A).

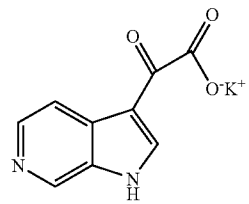

Precursor 4b

Potassium (6-azaindol-3-yl)oxoacetate, Precursor 4b, was prepared by the same method as Precursor 4a, starting from Methyl (6-azaindol-3-yl)oxoacetate, Precursor 3b. MS m/z: (M+H)+ of the corresponding acid was observed. Calc'd for $C_9H_7N_2O_3$: 191.05; Found 190.99. HPLC retention time: 0.12 minutes (column A).

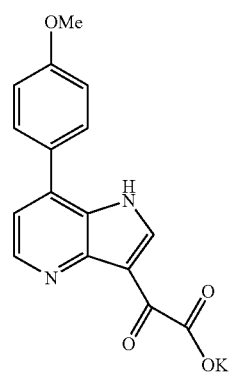

Precursor 4c

Precursor 4c, Potassium (7-(4-methoxyphenyl)-4-azaindol-3-yl)-oxoacetate, was prepared by the same method as Precursor 4a, starting from Methyl (7-(4-methoxyphenyl)-4-azaindol-3-yl)-oxoacetate, Precursor 3c. MS m/z: (M−K+H)+ calcd for $C_{16}H_{13}N_2O_4$: 297.07; found 297.04. HPLC retention time: 1.00 minutes (column A).

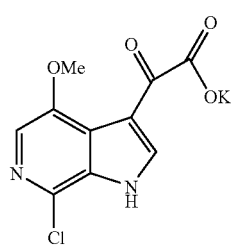

Precursor 4d

Precursor 4d, Potassium (7-chloro-4-methoxy-6-azaindol-3-yl)-oxoacetate was prepared by the same method as Precursor 4a starting from Methyl (7-chloro-4-methoxy-6-azaindol-3-yl)-oxoacetate, Precursor 3d. MS m/z: (M+H)+ of the corresponding acid of compound 4d (M−K+H)+ calcd for $C_{10}H_8ClN_2O_4$: 255.02; found 255.07. HPLC retention time: 0.74 minutes (column A).

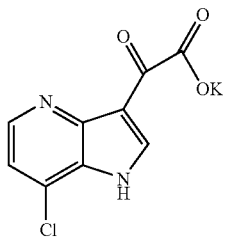

Precursor 4e

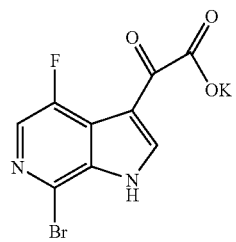

Precursor 4h

Precursor 4e, Potassium (7-chloro-4-azaindol-3-yl)-oxoacetate was prepared by the same method as Precursor 4a, starting from Methyl (7-chloro-4-azaindol-3-yl)-oxoacetate, Precursor 3f. MS m/z: (M+H)$^+$ of the corresponding acid of compound 4e (M−K+H)$^+$ calcd for $C_9H_6ClN_2O_3$: 225.01; found 225.27. HPLC retention time: 0.33 minutes (column A).

Precursor 4h, Potassium (7-bromo-4-fluoro-6-azaindol-3-yl)-oxoacetate was prepared by the same method as Precursor 4a, starting from Methyl (7-bromo-4-fluoro-6-azaindol-3-yl)-oxoacetate (prepared according to the method of Precursor 3a from 7-Bromo-4-fluoro-6-azaindole, Precursor 2i). MS m/z: (M+H)$^+$ of the corresponding acid of compound 4g (M−K+H)$^+$ calcd for $C_9H_5BrFN_2O_3$: 286.95; found 286.94. HPLC retention time: 0.94 minutes (column A).

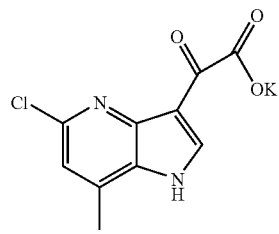

Precursor 4f

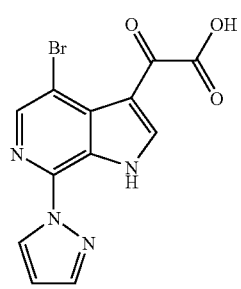

Precursor 4i

4g

Precursor 4f, Potassium (5-chloro-7-methyl-4-azaindol-3-yl)-oxoacetate was prepared by the same method as Precursor 4a, starting from Methyl (5-chloro-7-methyl-4-azaindol-3-yl)-oxoacetate, Precursor 3g. MS m/z: (M+H)$^+$ of the corresponding acid of compound 4f (M−K+H)$^+$ calcd for $C_{10}H_8ClN_2O_3$: 239.02; found 238.94. HPLC retention time: 1.24 minutes (column B).

1-ethyl-3-methylimidazolium chloride (0.172 g, 1.1 mmol) was added to aluminum chloride (0.560 g, 4.2 mmol), and the mixture vigorously stirred. Upon formation of a liquid, precursor 2j was added, followed by ethyl chlorooxoacetate (0.12 ml, 1.1 mmol). The mixture was allowed to stir at r.t. for 16 h, after which additional chlorooxoacetate was added (0.12 ml, 1.1 mmol). Following this addition, the reaction was allowed to stir at r.t. for another 24 h. The flask was cooled to 0° C. and water added, upon which precipitates were formed. The solid material was filtered, washed with water and methanol, and dried under high vacuum to give compound 3; LC/MS: (ES+) m/z (M+H)=334, 336; HPLC $R_t$=1.390.

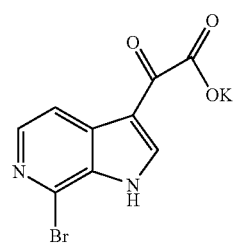

Precursor 4g

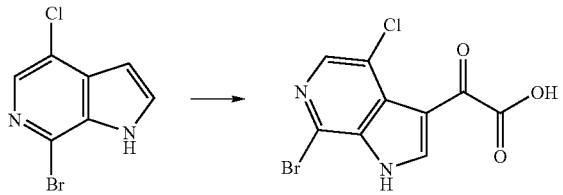

Precursor 4j

Precursor 4g, Potassium (7-bromo-6-azaindol-3-yl)-oxoacetate was prepared by the same method as Precursor 4a, starting from Methyl (7-bromo-6-azaindol-3-yl)-oxoacetate (prepared according to the method of Precursor 3a from 7-Bromo-6-azaindole, Precursor 2f). $^1$H NMR (500 MHz, DMSO-$d_6$) δ 8.59 (s, 1H), 8.16 (d, 1H, J=5.3 Hz), 8.08 (d, 1H, J=5.45 Hz); $^{13}$C NMR (125 MHz, DMSO-$d_6$) δ 180.5, 164.0, 141.6, 140.4, 132.4, 125.3, 115.5, 113.0.

To 1-ethyl-3-methylimidazolium chloride (2.54 g, 17.3 mmol) was added aluminum chloride (6.91 g, 51.8 mmol). The mixture was stirred vigorously at ambient temperature for ten minutes. To the resulting yellow liquid was added precursor 2k (2.0 g, 8.64 mmol) and ethyl chlorooxoacetate (2.0 ml, 17.3 mmol), and was stirred at ambient temperature for 16 h. The reaction mixture was then added ice/water (300 ml) to give precipitates, which were filtered and washed with water to give the title compound as a yellow solid (1.98 g). The aqueous solution was extracted with EtOAc (3×300 ml), and the extracts evaporated in vacuo to give a second batch of compound 8 as a yellow solid (439 mg, total yield 92%); $^1$H NMR: (DMSO-$d_6$) 14.25 (b s, 1H), 13.37 (s, 1H), 8.56 (s, 1H), 8.18 (s, 1H); LC/MS: (ES+) m/z (M+H)$^+$=303, 305, 307; HPLC $R_t$=1.360.

Precursor 4k

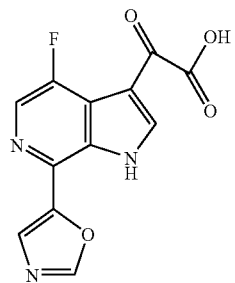

1-Ethyl-3-methylimidazolium chloride (82 mg, 0.56 mmol) was added to a flask which contained precursor 2n (56 mg, 0.28 mmol) and the mixture was cooled to 0° C. Aluminum chloride (336 mg, 2.52 mmol) was added in one portion followed by ClCOCOOEt (58 µL, 0.56 mmol) and the reaction mixture was stirred at room temperature for 2 days. Ice water was added to quench the reaction. The reaction mixture was filtered. The solid was washed with water and diethylether and dried in air to afford the title compound (58 mg). LC/MS: (ES$^+$) m/z (M+H)$^+$=276. Rt=0.85 min.

Precursor 4m

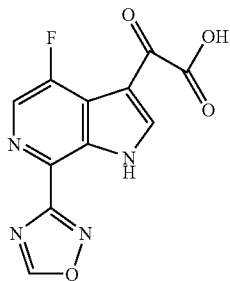

1-Ethyl-3-methylimidazolium chloride (73 mg, 0.52 mmol) and aluminum chloride (198 mg, 1.56 mmol) were stirred together under nitrogen for 1 h. To this solution was added intermediate 2q (54 mg, 0.26 mmol) and ethyloxalylchloride (58 µL, 0.52 mmol) and the reaction mixture was stirred at rt for 18 h. The reaction was quenched with water and the mixture was stirred for 15 min. The solid was collected by filtration and washed with water and diethylether. LC/MS (ES$^+$) m/z (M+H)$^+$=276. This compound was used without further purification.

Precursor 4n

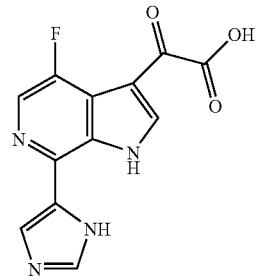

1-Ethyl-3-methylimidazolium chloride (26 mg, 0.18 mmol) was added to a flask which contained precursor 2t (18 mg, 0.09 mmol) and the mixture was cooled to 0° C. Aluminum chloride (92 mg, 0.54 mmol) was added in one portion followed by ClCOCOOEt (20 µL, 0.18 mmol) and the reaction mixture was stirred at room temperature for 2 days. Ice water was added to quench the reaction. The reaction mixture was filtered. The solid was washed with water and diethylether and dried in air to afford compound D (18 mg). LC/MS: (ES$^+$) m/z (m+H)$^+$=275. Rt=0.49 min.

Precursor 5a

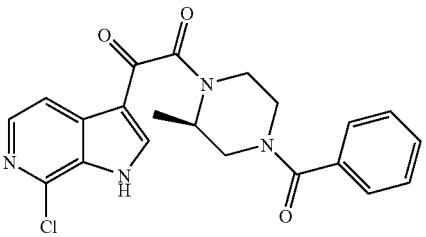

Typical procedure for coupling piperazine derivative and azaindole acid: Preparation of 1-benzoyl-3-(R)-methyl-4-[(7-chloro-6-azaindol-3-yl)-oxoacetyl]piperazine, Precursor 5, is an example of Step D of Scheme 1. Potassium 7-chloro-6-azaindole 3-glyoxylate, Precursor 4a, (100 mg, 0.44 mmol), 3-(R)-methyl-1-benzoylpiperazine (107 mg, 0.44 mol), 3-(diethoxyphosphoryloxy)-1,2,3-benzotriazin-4(3H)-one (DEPBT) (101 mg, 0.44 mol) and Hunig's Base (diisopropylethylamine, 0.5 mL) were combined in 5 mL of DMF. The mixture was stirred at rt for 8 h. DMF was removed via evaporation at reduced pressure and the residue was purified using a Shimadzu automated preparative HPLC System to give 1-(benzoyl)-3-(R)-methyl-4-[(7-chloro-6-azaindol-3-yl)-oxoacetyl]-piperazine (70 mg, 39%). MS m/z: (M+H)$^+$ Calc'd for $C_{21}H_{20}ClN_4O_3$: 411.12; Found 411.06. HPLC retention time: 1.32 minutes (column A).

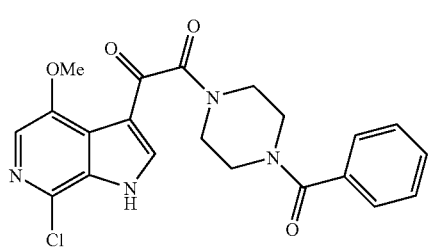

Precursor 5b

Precursor 5b, 1-benzoyl-4-[(7-chloro-4-methoxy-6-azaindol-3-yl)-oxoacetyl]piperazine was prepared by the same method as Precursor 5a starting from Potassium (7-chloro-4-methoxy-6-azaindol-3-yl)-oxoacetate, Precursor 4d, and 1-benzoylpiperazine. MS m/z: $(M+H)^+$ calcd for $C_{21}H_{20}ClN_4O_4$: 427.12; found 427.12. HPLC retention time: 1.28 minutes (column A).

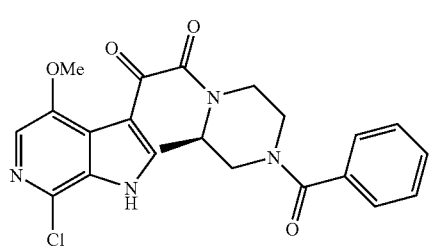

Precursor 5c

Precursor 5c, 1-benzoyl-3-(R)-methyl-4-[(7-chloro-4-methoxy-6-azaindol-3-yl)-oxoacetyl]piperazine was prepared by the same method as Precursor 5a starting from Potassium (7-chloro-4-methoxy-6-azaindol-3-yl)-oxoacetate, Precursor 4d, and 1-benzoylpiperazine. $^1$H NMR (500 MHz, CDCl$_3$) δ 8.10 (s, 1H), 7.72 (s, 1H), 7.40 (s, 5H), 3.89 (s, 3H), 3.71-3.40 (m, 8H). MS m/z: $(M+H)^+$ calcd for $C_{22}H_{22}ClN_4O_4$: 441.13; found 441.17. HPLC retention time: 1.33 minutes (column A).

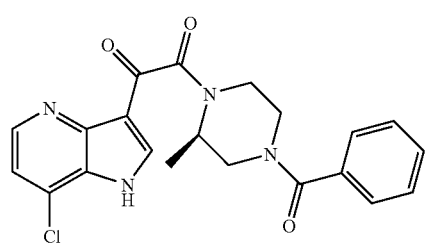

Precursor 5d

Precursor 5d, 1-benzoyl-3-(R)-methyl-4-[(7-chloro-4-azaindol-3-yl)-oxoacetyl]piperazine was prepared by the same method as Precursor 5a, starting from Potassium (7-chloro-4-azaindol-3-yl)-oxoacetate, Precursor 4e, and 1-benzoyl-3-(R)-methyl piperazine. MS m/z: $(M+H)^+$ calcd for $C_{21}H_{20}ClN_4O_3$ 411.12, found 411.04. HPLC retention time: 1.10 minutes (column A).

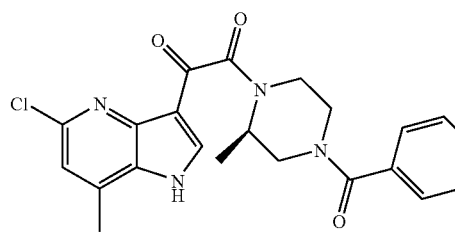

Precursor 5e

Precursor 5e, 1-benzoyl-3-(R)-methyl-4-[(5-chloro-7-methyl-4-azaindol-3-yl)-oxoacetyl]piperazine was prepared by the same method as Precursor 5a, starting from Potassium (5-chloro-7-methyl-4-azaindol-3-yl)-oxoacetate, Precursor 4f, and 1-benzoyl-3-(R)-methyl piperazine. MS m/z: $(M+H)^+$ calcd for $C_{22}H_{22}ClN_4O_3$ 425.24, found 425.04. HPLC retention time: 1.72 minutes (column B).

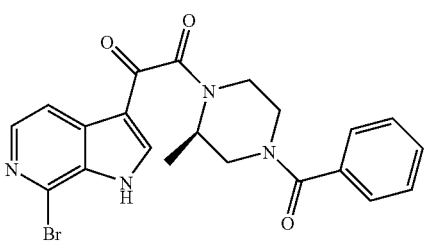

Precursor 5f

Precursor 5f, 1-benzoyl-3-(R)-methyl-4-[(7-bromo-6-azaindol-3-yl)-oxoacetyl]piperazine was prepared by the same method as Precursor 5a, starting from (7-bromo-6-azaindol-3-yl)-oxoacetic acid potassium salt, Precursor 4g, and 1-benzoyl-3-(R)-methylpiperazine. MS m/z: $(M+H)^+$ calcd for $C_{21}H_{20}BrN_4O_3$: 455.07; found 455.14. HPLC retention time: 1.45 minutes (column B).

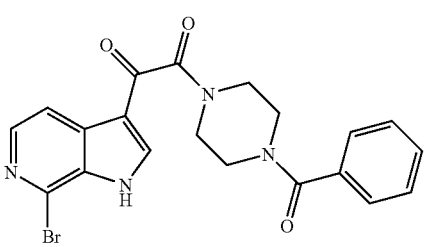

Precursor 5g

Precursor 5g, 1-benzoyl-4-[(7-bromo-6-azaindol-3-yl)-oxoacetyl]piperazine was prepared by the same method as Precursor 5a, starting from (7-bromo-6-azaindol-3-yl)-oxoacetic acid potassium salt, Precursor 4g, and 1-benzoylpiperazine. MS m/z: $(M+H)^+$ calcd for $C_{20}H_{18}BrN_4O_3$: 441.06; found 441.07. HPLC retention time: 1.43 minutes (column B).

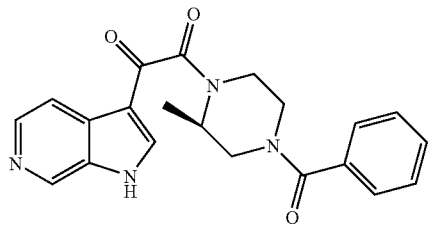

Precursor 5h

Precursor 5h, 1-benzoyl-3-(R)-methyl-4-[(6-azaindol-3-yl)-oxoacetyl]piperazine was prepared by the same method as Precursor 5a starting from Potassium (6-azaindol-3-yl) oxoacetate, Precursor 4b, and 1-benzoyl-3-(R)-methylpiperazine. MS m/z: (M+H)$^+$ Calc'd for $C_{21}H_{21}N_4O_3$: 377.16; Found 377.10. HPLC retention time: 0.88 minutes (column A).

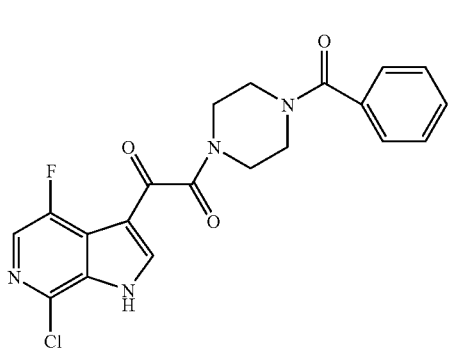

Precursor 5i

Addition of precursor 2d to a solution of aluminum trichloride in dichloromethane stirring at ambient temperature followed 30 minutes later with chloromethyl or chloroethyl oxalate (according to the method described for precursor 3a) provides either the methyl or ethyl ester, respectively. Hydrolysis with KOH (as in the standard hydrolysis procedure described for precursor 4a) provided potassium (7-chloro-4-fluoro-6-azaindol-3-yl)oxoacetate. Potassium (7-chloro-4-fluoro-6-azaindol-3-yl)oxoacetate was then reacted with 1-benzoyl piperazine in the presence of DEPBT under the standard conditions (as described for precursor 5a) to provide 1-benzoyl-4-[(4-fluoro-7-chloro-6-azaindol-3-yl)-oxoacetyl]piperazine, precursor 5i. $^1$H NMR (500 MHz, CD$_3$OD) δ 8.40 (s, 1H), 8.04 (s, 1H), 7.46 (bs, 5H), 3.80-3.50 (m, 8H); LC/MS (ES$^+$) m/z (M+H)$^+$ 415 observed; retention time 1.247 minutes; LC/MS method: YMC ODS-A C18 S7 3.0×50 mm column; Start % B=0, Final % B=100, Gradient time=2 minutes; Flow rate=5 mL/min; detector wavelength=220 nm.

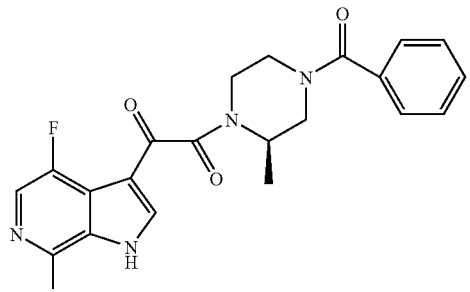

Precursor 5j 1-benzoyl-3-(R)-methyl-4-[(4-fluoro-7-chloro-6-azaindol-3-yl)-oxoacetyl]-piperazine was prepared by coupling potassium (7-chloro-4-fluoro-6-azaindol-3-yl)oxoacetate, prepared as described above for precursor 5i, with 1-benzoyl-3-(R)-methylpiperazine in the presence of DEPBT under the standard conditions (as described for precursor 5a) to provide 1-benzoyl-3-(R)-methyl-4-[(4-fluoro-7-chloro-6-azaindol-3-yl)-oxoacetyl]piperazine, precursor 5j. $^1$H NMR (500 MHz, CD$_3$OD) δ 8.42, 8.37 (s, s, 1H), 8.03 (s, 1H), 7.71-7.45 (m, 5H), 4.72-3.05 (m, 7H), 1.45-1.28 (m, 3H); LC/MS (ES$^+$) m/z (M+H)$^+$ 429 observed; retention time 1.297 minutes; LC/MS method: YMC ODS-A C18 S7 3.0×50 mm column; Start % B=0, Final % B=100, Gradient time=2 minutes; Flow rate=5 mL/min; detector wavelength=220 nm.

Precursor 5k

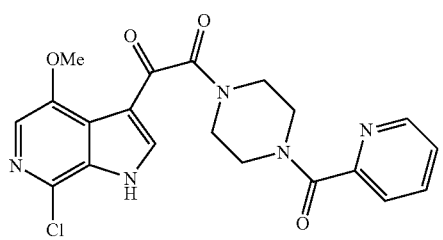

Precursor 5k, 1-benzoyl-4-[(7-chloro-6-azaindol-3-yl)-oxoacetyl]piperazine was prepared by the same method as Precursor 5a, starting from (7-chloro-6-azaindol-3-yl)-oxoacetic acid potassium salt, Precursor 4a, and 1-benzoylpiperazine. MS m/z: (M+H)$^+$ calcd for $C_{20}H_{18}ClN_4O_3$: 397.11; found 396.97. HPLC retention time: 2.37 minutes (column F, gradient time=3 min, flow rate=4 ml/min).

Precursor 5l

Precursor 5l, 1-picolinoyl-4-[(4-methoxy-7-chloro-6-azaindol-3-yl)-oxoacetyl]piperazine was prepared by the same method as Precursor 5a starting from Potassium (4-methoxy- 7-chloro-6-azaindol-3-yl)oxoacetate, Precursor 4d, and picolinoyl-piperazine. ¹H NMR (500 MHz, DMSO-d₆) δ 8.63-7.45 (m, 7H), 3.94 (s, 3H), 3.82-2.50 (m, 8H). MS m/z: (M+H)⁺ Calc'd for C₂₀H₁₉ClN₅O₄: 428.11; Found 428.11. HPLC retention time: 1.09 minutes (column A).

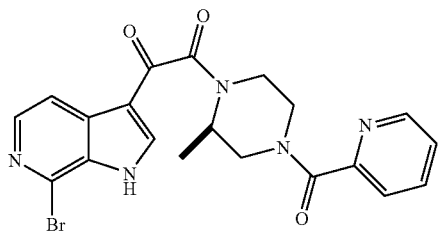

Precursor 5m

Precursor 5m, (R)-1-picolinoyl-3-methyl-4-[(7-bromo-6-azaindol-3-yl)-oxoacetyl]piperazine was prepared by the same method as Precursor 5a starting from Potassium (7-bromo-6-azaindol-3-yl)oxoacetate, Precursor 4g, and (R)-3-methyl-1-picolinoyl-piperazine. MS m/z: (M+H)⁺ Calc'd for C₂₀H₁₉BrN₅O₃: 456.07; Found 456.11. HPLC retention time: 1.12 minutes (column A).

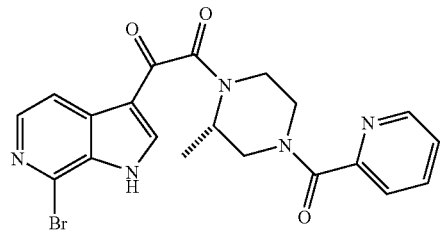

Precursor 5n

Precursor 5n, (S)-1-picolinoyl-3-methyl-4-[(7-bromo-6-azaindol-3-yl)-oxoacetyl]piperazine was prepared by the same method as Precursor 5a starting from Potassium (7-bromo-6-azaindol-3-yl)oxoacetate, Precursor 4g, and (S)-3-methyl-1-picolinoyl-piperazine. ¹H NMR (500 MHz, CDCl₃) δ 8.63-7.36 (m, 7H), 5.02-3.06 (m, 7H), 1.42-1.26 (m, 3H).

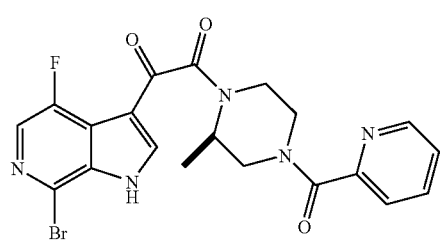

Precursor 5o

Precursor 5o, (R)-1-picolinoyl-3-methyl-4-[(7-bromo-4-fluoro-6-azaindol-3-yl)-oxoacetyl]piperazine was prepared by the same method as Precursor 5a starting from Potassium (7-bromo-4-fluoro-6-azaindol-3-yl)oxoacetate, Precursor 4h, and (R)-3-methyl-1-picolinoyl-piperazine. ¹H NMR (500 MHz, CD₃OD) δ8.68-7.52 (m, 6H), 4.94-2.69 (m, 7H), 1.48-1.24 (m, 3H). MS m/z: (M+H)⁺ Calc'd for C₂₀H₁₈BrFN₅O₃: 474.06; Found 474.23. HPLC retention time: 1.20 minutes (column A).

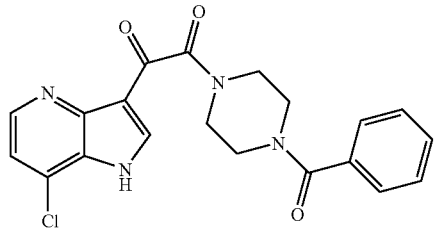

Precursor 5o

Precursor 5p, 1-benzoyl-4-[(7-chloro-4-azaindol-3-yl)-oxoacetyl]piperazine was prepared by the same method as Precursor 5a starting from Potassium (7-chloro-4-fluoro-4-azaindol-3-yl)oxoacetate, Precursor 4e, and 1-benzoyl-piperazine. ¹H NMR (500 MHz, CD₃OD) δ8.83 (s, 1H), 8.63 (d, 1H, J=5.35 Hz), 7.91 (d, 1H, J=5.75 Hz), 7.47 (m, 5H), 3.80-3.30 (m, 3H). MS m/z: (M+H)⁺ Calc'd for C₂₀H₁₈ClN₄O₃: 397.11; Found 397.02. HPLC retention time: 1.20 minutes (column A).

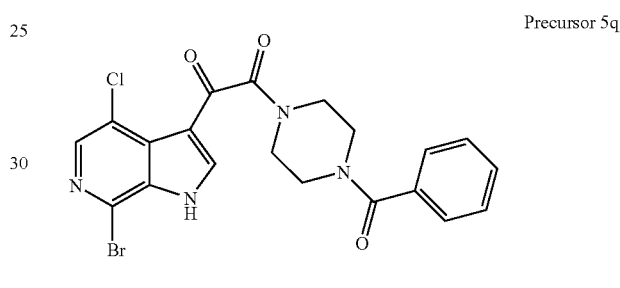

Precursor 5q

Precursor 5q, 1-(4-Benzoyl-piperazin-1-yl)-2-(7-bromo-1H-pyrrolo[2,3-c]pyridin-3-yl)-ethane-1,2-dione To a solution of acid precursor 4j (2.4 g, 7.9 mmol) in DMF (40 ml) was added 3-(diethoxyphosphoryloxy)-1,2,3-benzotriazin-4(3H)-one (DEPBT, 5.96 g, 19.9 mmol), benzoylpiperazine hydrochloride (2.71 g, 11.9 mmol), and N,N-diisopropylethylamine (14 ml, 80.4 mmol). The mixture was stirred at ambient temperature for 16 h. The reaction mixture was then added water (400 ml) and extracted with EtOAc (4×300 ml). The combined extracts were evaporated in vacuo to give a brownish residue, which was triturated with MeOH to provide the title compound as a white solid (2.8 g, 74%); ¹H NMR: (DMSO-d₆) 13.41 (s, 1H), 8.48 (s, 1H), 8.19 (s, 1H), 7.45 (b s, 5H), 3.80-3.35 (b m, 8H); LC/MS: (ES+) m/z (M+H)⁺=475, 477, 479; HPLC (alternate conditions B, column G) R_t=1.953.

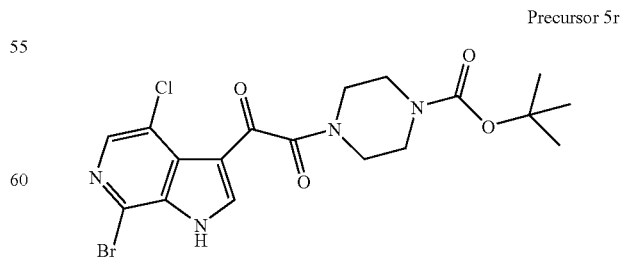

Precursor 5r

Precursor 5r was prepared by procedure used for 5q using mono N-Boc piperazine. ¹H NMR: (CDCl₃) δ 8.26 (s, 1H), 8.19 (s, 1H), 3.71 (b s, 2H), 3.53 (b m, 6H), 1.48 (s, 9H);

LC/MS: (ES+) m/z (M+H)+=471, 473, 475; HPLC (alternate conditions B, column G) R$_t$=1.543.

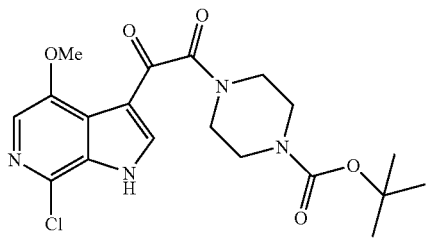

Precursor 5s

Precursor 5s was prepared by procedure used for 5b using mono N-Boc piperazine. MS m/z: (M+H)+ Calc'd for C$_{19}$H$_{24}$ClN$_4$O$_5$: 423.14; Found 423.07 HPLC retention time: 1.44 minutes (column L).

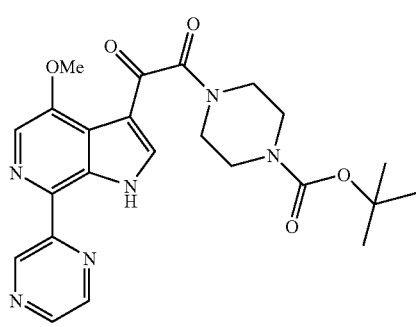

Precursor 5t

Precursor 5t, was prepared from Precursor 5s and the pyrazin-2-yl stannane, via the procedure described in the later section Preparation of Compounds of Formula I. MS m/z: (M+H)+ Calc'd for C$_{23}$H$_{27}$N$_6$O$_5$: 467.20; found 467.47. HPLC retention time: 1.57 minutes (column C).

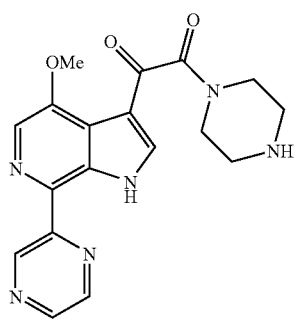

Precursor 5u

Preparation of precursor 5u: Precursor 5t (30 mg) was dissolved in TFA (0.5 g). After the reaction was stirred for 30 minutes, the mixture was concentrated in vacuo to give the desired intermediate 5u which was used in further reactions without any purification. MS m/z: (M+H)+ Calc'd for C$_{18}$H$_{19}$N$_6$O$_5$: 367.15; found 367.06. HPLC retention time: 0.91 minutes (column M).

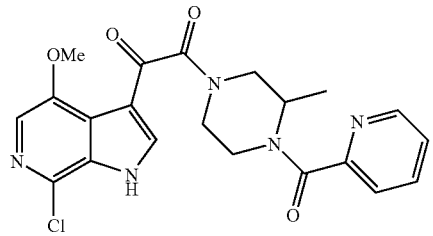

Precursor 5v

Precursor 5v was prepared by procedure used for 5b using 2-methyl-1-picolinoylpiperazine. MS m/z: (M+H)+ Calc'd for C$_{21}$H$_{21}$ClN$_5$O$_4$: 442.13; Found 442.11. HPLC retention time: 1.01 minutes (column G).

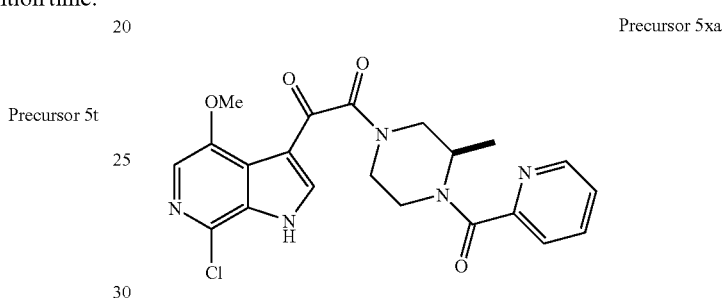

Precursor 5xa

Precursor 5xa was prepared by procedure used for 5b using (R)-2-methyl-1-picolinoylpiperazine. MS m/z: (M+H)+ Calc'd for C$_{21}$H$_{21}$ClN$_5$O$_4$: 442.13; Found 442.23. HPLC retention time: 1.12 minutes (column L).

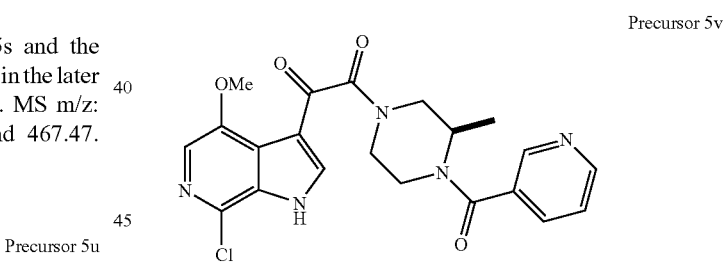

Precursor 5y

Precursor 5y was prepared by procedure used for 5b using (R)-2-methyl-1-nicotinoylpiperazine. MS m/z: (M+H)+ Calc'd for C$_{21}$H$_{21}$ClN$_5$O$_4$: 442.13; Found 442.15. HPLC retention time: 0.87 minutes (column C).

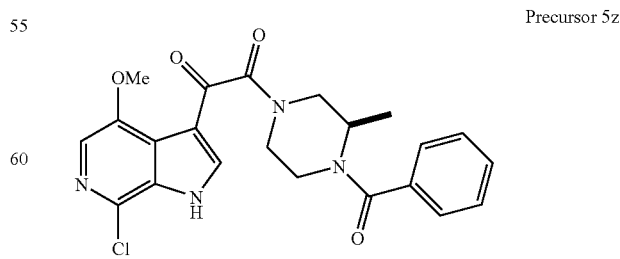

Precursor 5z

Precursor 5z was prepared by procedure used for 5b using (R)-2-methyl-1-benzoylpiperazine. MS m/z: (M+H)+ Calc'd for $C_{22}H_{22}ClN_4O_4$: 441.13; Found 441.46. HPLC retention time: 1.27 minutes (column C).

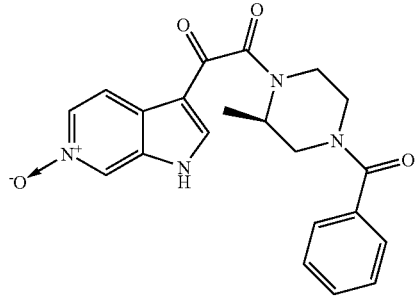

Precursor 6

Typical procedure for N-Oxide formation: Preparation of 1-benzoyl-3-(R)-methyl-4-[(6-oxide-6-azaindol-3-yl)-oxoacetyl]piperazine, Precursor 6. 20 mg of 1-benzoyl-3-(R)-methyl-4-[(6-azaindol-3-yl)-oxoacetyl]piperazine, Precursor 5h, (0.053 mmol) was dissolved in $CH_2Cl_2$ (2 mL). 18 mg of mCPBA (0.11 mmol) was then added into the solution and the reaction was stirred for 12 h at rt. $CH_2Cl_2$ was removed via evaporation at reduced pressure and the residue was purified using a Shimadzu automated preparative HPLC System to give the compound shown above (5.4 mg, 26%). MS m/z: $(M+H)^+$ Calc'd for $C_{21}H_{21}N_4O_4$: 393.16; Found 393.11. HPLC retention time: 0.90 minutes (column A).

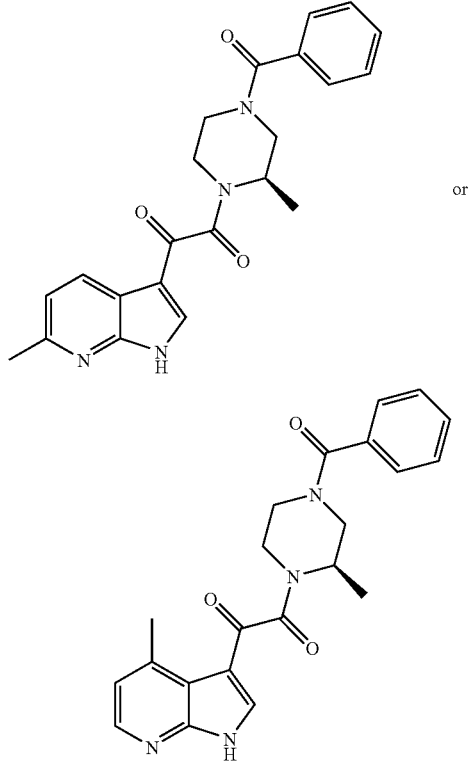

Precursor 7

Preparation of 1-benzoyl-3-(R)-methyl-4-[(6-methyl-7-azaindol-3-yl)-oxoacetyl]-piperazine or 1-benzoyl-3-(R)-methyl-4-[(4-methyl-7-azaindol-3-yl)-oxoacetyl]-piperazine. An excess of MeMgI (3M in THF, 0.21 ml, 0.63 mmol) was added into a solution of 1-benzoyl-3-(R)-methyl-4-[(6-oxide-6-azaindol-3-yl)-oxoacetyl]piperazine, Precursor 6, (25 mg, 0.064 mmol). The reaction mixture was stirred at rt and then quenched with MeOH. The solvents were removed under vacuum, the residue was diluted with MeOH and purified using a Shimadzu automated preparative HPLC System to give a compound shown above which was a single isomer but regiochemistry was not definitively assigned. (6.7 mg, 27%). MS m/z: $(M+H)^+$ Calc'd for $C_{22}H_{23}N_4O_3$: 391.18; Found 391.17. HPLC retention time: 1.35 minutes (column B).

Precursor 8

1-benzoyl-3-(R)-methyl-4-[(6-phenyl-7-azaindol-3-yl)-oxoacetyl]piperazine or 1-benzoyl-3-(R)-methyl-4-[(4-phenyl-7-azaindol-3-yl)-oxoacetyl]piperazine (regiochemistry was not definitively assigned) were prepared by the method described for Example 7 starting with 1-benzoyl-3-(R)-methyl-4-[(6-oxide-6-azaindol-3-yl)-oxoacetyl]piperazine, Precursor 6, and phenyl magnesium bromide (phenyl Grignard reagent). MS m/z: $(M+H)^+$ Calc'd for $C_{27}H_{25}N_4O_3$: 453.19; Found 454.20. HPLC retention time: 1.46 minutes (column B).

Precursor 9

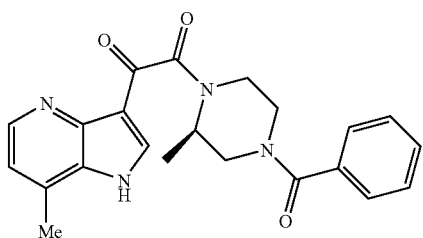

A mixture of Pd (10% on carbon, 100 mg), trifluoroacetic acid (1 mL) and 1-benzoyl-3-(R)-methyl-4-[(5-chloro-7-methyl-4-azaindol-3-yl)-oxoacetyl]piperazine, Precursor 5e (1.5 g) in MeOH (50 mL) and EtOAc (50 mL) was shaken in a Parr reactor under a hydrogen atmosphere (45 psi) for 48 hours. After solids were removed via filtration, the filtrate was concentrated in vacuo to afford precursor 9 (1 g) which was used without further purification. MS m/z: (M+H)$^+$ calcd for $C_{21}H_{21}N_4O_3$ 391.18, found 391.15. HPLC retention time: 1.15 minutes (column A).

Precursors 10 and 11

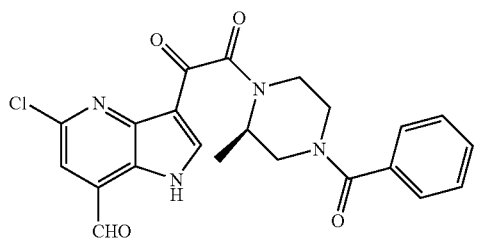

10

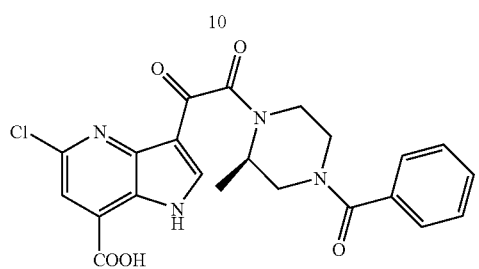

11

Preparation of Precursor 10, 1-benzoyl-3-(R)-methyl-4-[(5-chloro-7-carbonyl-4-azaindol-3-yl)-oxoacetyl]-piperazine and Precursor 11, 1-benzoyl-3-(R)-methyl-4-[(5-chloro-7-hydroxycarbonyl-4-azaindol-3-yl)-oxoacetyl]-piperazine: A mixture of 1-benzoyl-3-(R)-methyl-4-[(5-chloro-7-methyl-4-azaindol-3-yl)-oxoacetyl]piperazine (1.78 g) and SeO$_2$ (4.7 g) in dioxane/water (100:1) was refluxed for 10 hours. After cooling to room temperature, the mixture was concentrated in vacuo to provide a residue. The residue was purified by using silica gel chromatography with EtOAc and MeOH as eluting solvents to afford precursor 10 (350 mg) and precursor 11 (410 mg).

Precursor 10, 1-benzoyl-3-(R)-methyl-4-[(5-chloro-7-carbonyl-4-azaindol-3-yl)-oxoacetyl]-piperazine: MS m/z: (M+H)$^+$ calcd for $C_{22}H_{20}ClN_4O_4$: 439.12, found 439.01. HPLC retention time: 1.37 minutes (column A); Precursor 11, 1-benzoyl-3-(R)-methyl-4-[(5-chloro-7-hydroxycarbonyl-4-azaindol-3-yl)-oxoacetyl]-piperazine: MS m/z: (M+H)$^+$ calcd for $C_{22}H_{20}ClN_4O_5$: 455.11, found 455.10. HPLC retention time: 1.44 minutes (column A).

Precursors 12 and 13

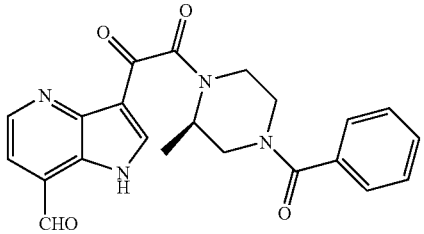

12

13

Precursor 12, 1-benzoyl-3-(R)-methyl-4-[(7-carbonyl-4-azaindol-3-yl)-oxoacetyl]-piperazine and Precursor 13, 1-benzoyl-3-(R)-methyl-4-[(7-hydroxycarbonyl-4-azaindol-3-yl)-oxoacetyl]-piperazine were made according to the same procedure of preparing Precursors 10 and 11, by using Precursor 9 as a starting material. Precursor 12, 1-benzoyl-3-(R)-methyl-4-[(7-carbonyl-4-azaindol-3-yl)-oxoacetyl]-piperazine: MS m/z: (M+H)$^+$ calcd for $C_{22}H_{21}N_4O_4$: 405.16, found 405.14. HPLC retention time: 0.91 minutes (column A); Precursor 13, 1-benzoyl-3-(R)-methyl-4-[(7-hydroxycarbonyl-4-azaindol-3-yl)-oxoacetyl]-piperazine: MS m/z: (M+H)$^+$ calcd for $C_{22}H_{21}N_4O_5$: 421.15, found 421.09. HPLC retention time: 1.02 minutes (column A).

Precursors 14a-1-14a-21

The following tin agents and boron agents can be purchased from commercial resources and used without any further treatment (Table I-1).

TABLE I-1

| Precursor Number | Structure | Company |
| --- | --- | --- |
| 14a-1 | SnBu$_3$ (pyrazine) | Frontier Scientific, Inc. |

TABLE I-1-continued

| Precursor Number | Structure | Company |
|---|---|---|
| 14a-2 | 3-(SnBu$_3$)pyridine | Maybridge Chem. Co. |
| 14a-3 | 4-(SnBu$_3$)pyridine | Frontier Scientific, Inc. |
| 14a-4 | 2,4-dimethoxy-5-(B(OH)$_2$)pyrimidine | Matrix Scientific |
| 14a-5 | 3,5-dimethyl-4-(B(OH)$_2$)isoxazole | Matrix Scientific |
| 14a-6 | 2-(Bu$_3$Sn)furan | Aldrich, Co. |
| 14a-7 | 2-(Bu$_3$Sn)thiophene | Aldrich, Co. |
| 14a-8 | 2-(B(OH)$_2$)benzofuran | Aldrich, Co. |
| 14a-9 | 4-fluorophenyl-B(OH)$_2$ | Aldrich, Co. |
| 14a-10 | 4-chlorophenyl-B(OH)$_2$ | Aldrich, Co. |
| 14a-11 | 3-(B(OH)$_2$)-4-methyl-aniline | Lancaster |
| 14a-12 | 4-(B(OH)$_2$)benzoic acid | Aldrich, Co. |
| 14a-13 | 5-(B(OH)$_2$)benzo[1,3]dioxole | Aldrich, Co. |
| 14a-14 | 8-(B(OH)$_2$)quinoline | Frontier Scientific, Inc. |
| 14a-15 | 1-methyl-2-(Bu$_3$Sn)pyrrole | Matrix Scientific |
| 14a-16 | 5-(B(OH)$_2$)indole | Frontier Scientific, Inc. |
| 14a-17 | 5-(Cyclohexyl$_3$Sn)-1H-1,2,4-triazole | Riedel-de Haen AG |
| 14a-18 | 2-(B(OH)$_2$)benzothiophene | Lancaster |
| 14a-19 | 2-(SnBu$_3$)pyridine | Lancaster |
| 14a-20 | 2-(Ph$_3$Sn)benzothiazole | Aldrich, Co. |
| 14a-21 | 2-(Bu$_3$Sn)thiazole | Frontier Scientific, Inc. |

Preparation of Tin Agents:

Precursors 14-1-14-65

The following known tin agents and boron agents could be prepared according to the documented procedures indicated without any modification (Table I-2):

TABLE I-2

| Precursor Number | Structure | Reference |
|---|---|---|
| 14-1 | 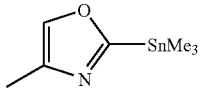 | Dondoni, A., et al Synthesis, 1987, 693 |
| 14-2 | 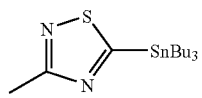 | Aldous, D. J., et al U.S. Pat. No. 5,453,433 |
| 14-3 | 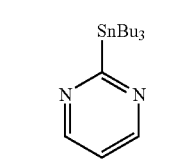 | Sandosham, J., et al Tetrahedron 1994, 50, 275. |
| 14-4 | 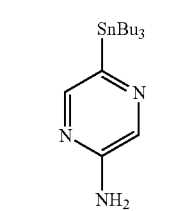 | Lehn, L. M., et al. Chem. Eur. J. 2000, 6, 4133. |
| 14-5 | 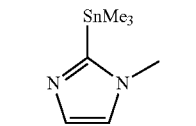 | Jutzi, P., et al J. Organometallic Chem. 1983, 246, 163. |
| 14-6 | 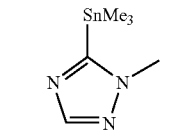 | Jutzi, P., et al J. Organometallic Chem. 1983, 246, 163. |
| 14-7 | 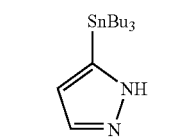 | Graybill, T. L., et al Bioorg. Med. Chem. Lett. 1995, 5(4), 387. |
| 14-8 | 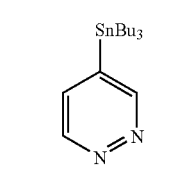 | Heldmann, D. K., et al Tetrahedron Lett. 1997, 38, 5791. |
| 14-9 | 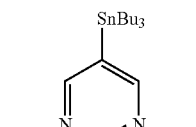 | Kennedy, G., et al Tetrahedron Lett. 1996, 37, 7611. |
| 14-10 | 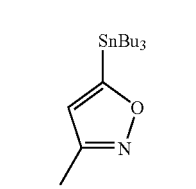 | Kondo, Y., et al Tetrahedron Lett. 1989, 30, 4249 |

TABLE I-2-continued

| Precursor Number | Structure | Reference |
|---|---|---|
| 14-11 | 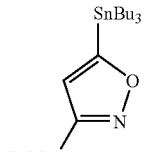 | Kondo, Y., et al Tetrahedron Lett. 1989, 30, 4249 |
| 14-12 | 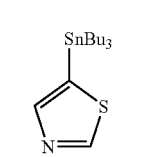 | Or, Y. S., et al U.S. Pat. No. 6,054,435 |
| 14-13 | 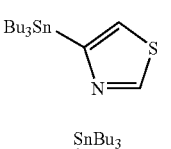 | Or, Y. S., et al U.S. Pat. No. 6,054,435 |
| 14-14 | 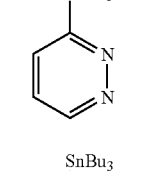 | Okada, T., et al WO-0123383 |
| 14-15 | 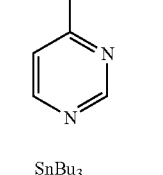 | Okada, T., et al WO-0123383 |
| 14-16 | 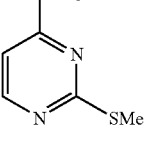 | Sandosham, J., et al Tetrahedron 1994, 50, 275 |
| 14-17 | 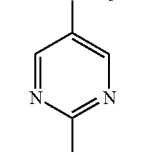 | Sandosham, J., et al Acta Chem. Scand. 1989, 43, 684. |
| 14-18 | 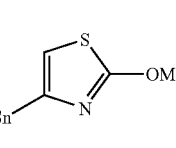 | Nicolaou, K. C., et al WO-9967252 |
| 14-19 | 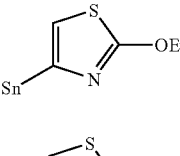 | Nicolaou, K. C., et al WO-9967252 |
| 14-20 | 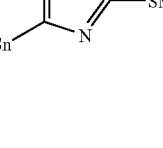 | Nicolaou, K. C., et al WO-9967252 |

TABLE I-2-continued

| Precursor Number | Structure | Reference |
|---|---|---|
| 14-21 | Bu₃Sn-thiazole-NHCO-O-tBu | Benheda, R., et al Tetrahedron Lett. 1999, 40, 5701. |
| 14-22 | 2-SnBu₃ oxazole | Collins, I., et al Tetrahedron Lett. 1999, 40, 4069. |
| 14-23 | Et-thiadiazole-B(OH)₂ | Fuss, R. W., et al DE-19502178 |
| 14-24 | SnBu₃ pyrimidine, 2-Cl | Bunnage, M. E. et. al PCT Int. Appl. WO 0024745 A1 (2000); and Sandosham, J. et. A1 Tetrahedron (1994), 50(1), 275-84. |
| 14-25 | SnBu₃ pyrimidine, 2-F | From 5-iodo2-chloro-1,3 pyrimidine. Fluoropyrimidines are obtained by fluorination of chloropyrimidines with CsF in N-methyl-2-pyrrolidinone or DMF 2.5-63 h at 80-150° C. The iodo is then converted to the lithium reagent with tBuLi and trapped with Bu₃SnCl. See Sandosham above. |
| 14-26 | SnBu₃ pyrimidine, 2-SO₂Me | Arukwe, J.; Benneche, T.; Undheim, K. J. Chem. Soc., Perkin Trans. 1 (1989), (2), 255-9. |
| 14-27 | SnBu₃ pyrazine, C(S)NHtBu | Fruit, C.; et. al. Heterocycles (1999), 51(10), 2349-2365. |
| 14-28 | SnMe₃ pyrimidine, NH₂ | Ziener, U.; et. al. Chem.-Eur. J. (2000), 6(22), 4132-4139. |
| 14-29 | SnBu₃ 3,5-dichloropyrazine | Turck, A.; et. al Lab. J. Organomet. Chem. (1991), 412(3), 301-10. Metallation of 2,6-dicloropyrazine and quench with Bu₃SnCl. |
| 14-30 | SnBu₃ pyridine-C≡C-Et | Ueno, K.; Sasaki, A.; Kawano, K.; Okabe, T.; Kitazawa, N.; Takahashi, K.; Yamamoto, N.; Suzuki, Y.; Matsunaga, M.; Kubota, A. PCT Int. Appl. WO 9918077 A1 (1999). |
| 14-31 | SnMe₃ pyridine-CN | Fensome, A.; Miller, L. L.; Ullrich, J. W.; Bender, R. H. W.; Zhang, P.; Wrobel, J. E.; Zhi, L.; Jones, T. K.; Marschke, K. B.; Tegley, C. M. PCT Int. Appl. WO 0066556 A1 (2000). |
| 14-32 | SnBu₃ pyridine-CN | Maw, G. N.; Middleton, D. S. Jpn. Kokai Tokkyo Koho JP 2000016984 A2 (2000). |
| 14-33 | SnBu₃ pyridine-Cl | Chem. Pharm. Bull. (1998), 46(3), 400-412. |
| 14-34 | SnBu₃ pyridine-CH₂COCH₃ | Hayashi, K.; Kito, T.; Mitsuyama, J.; Yamakawa, T.; Kuroda, H.; Kawafuchi, H. PCT Int. Appl. WO 9951588 A1 (1999). |
| 14-35 | SnBu₃ pyridine-COOH | Brown, A. D.; Dickinson, R. P.; Wythes, M. J. PCT Int. Appl. WO 9321178 A1 (1993). |
| 14-36 | SnBu₃ pyridine-CONH₂ | Brown, A. D.; Dickinson, R. P.; Wythes, M. J. PCT Int. Appl. WO 9321178 A1 (1993). |

TABLE I-2-continued

| Precursor Number | Structure | Reference |
|---|---|---|
| 14-37 | 5-SnBu₃, 3-CONHMe pyridine | Zalutsky, M. R. PCT Int. Appl. WO 0032240 A2 (2000). |
| 14-38 | 5-SnBu₃, 3-CONMe₂ pyridine | Brown, A. D.; Dickinson, R. P.; Wythes, M. J. PCT Int. Appl. WO 9321178 A1 (1993). |
| 14-39 | 5-SnMe₃, 3-(azetidin-1-ylcarbonyl) pyridine | North, P. C.; Wadman, S. N. PCT Int. Appl. WO 9408993 A1 (1994). |
| 14-40 | 5-SnMe₃, 3-(morpholin-4-ylcarbonyl) pyridine | North, P. C.; Wadman, S. N. PCT Int. Appl. WO 9408993 A1 (1994). |
| 14-41 | 2,6-dichloro-3-SnMe₃ pyridine | Achab, S.; Guyot, M.; Potier, P. Tetrahedron Lett. (1993), 34(13), 2127-30. |
| 14-42 | 2-MeO, 3-SnMe₃ pyridine | Muratake, H.; Tonegawa, M.; Natsume, M. Chem. Pharm. Bull. (1998), 46(3), 400-412. Dehmlow, E. V.; Sleegers, A. Liebigs Ann. Chem. (1992), (9), 953-9. |
| 14-43 | 2-F, 3-SnBu₃ pyridine | Proudfoot, J. R.; Hargrave, K.; Kapadia, S. PCT Int. Appl. WO 9907379 A1 (1999); and Chem. Pharm. Bull. (1998), 46(3), 400-412. |
| 14-44 | 2-Br, 3-SnBu₃ pyridine | Cruskie, M. P. Jr.; Zoltewicz, J. A.; Abboud, K. A. J. Org. Chem. (1995), 60(23), 7491-5. |
| 14-45 | 2-Br, 3-SnMe₃ pyridine | Muratake, H.; et. al Chem. Pharm. Bull. (1998), 46(3), 400-412. |
| 14-46 | 2-Cl, 3-SnBu₃ pyridine | Muratake, H.; Tonegawa, M.; Natsume, M. Chem. Pharm. Bull. (1998), 46(3), 400-412. Dolle, R. E.; Graybill, T. L.; Osifo, I. K.; Harris, A. L.; Miller, M. S.; Gregory, J. S. U.S. U.S. Pat. No. 5622967 (1997). |
| 14-47 | 2-Br, 5-SnMe₃ pyridine | Henze, O.; Lehmann, U.; Schlueter, A. D. Synthesis (1999), (4), 683-687. |
| 14-48 | 2-CH₃, 5-SnBu₃ pyridine | Hayashi, K.; Kito, T.; Mitsuyama, J.; Yamakawa, T.; Kuroda, H.; Kawafuchi, H. PCT Int. Appl. WO 9951588 A1 (1999); Reuman, M.; Daum, S. J.; Singh, B.; Wentland, M. P.; Perni, R. B.; Pennock, P.; Carabateas, P. M.; Gruett, M. D.; Saindane, M. T.; et al. J. Med. Chem. (1995), 38(14), 2531-40. |
| 14-49 | 2-Cl, 5-SnBu₃ pyridine | Barros, M. T.; Maycock, C. D.; Ventura, M. R. Tetrahedron Lett. (1999), 40(3), 557-560. Sirisoma, N. S.; Johnson, C. R. Tetrahedron Lett. (1998), 39(15), 2059-2062. Trost, B. M.; Cook, G. R Tetrahedron Lett. (1996), 37(42), 7485-7488. |
| 14-50 | 8-SnBu₃-imidazo[1,2-a]pyridine | Bunnage, M. E.; Maw, G. N.; Rawson, D. J.; Wood, A.; Mathias, J. P.; Street, S. D. A. PCT Int. Appl. WO 0024745 A1 (2000). |
| 14-51 | 2-Et, 5-SnBu₃ pyridine | Bunnage, M. E.; Maw, G. N.; Rawson, D. J.; Wood, A.; Mathias, J. P.; Street, S. D. A. PCT Int. Appl. WO 0024745 A1 (2000). |

TABLE I-2-continued

| Precursor Number | Structure | Reference |
|---|---|---|
| 14-52 | 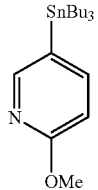 | Hayashi, K.; Kito, T.; Mitsuyama, J.; Yamakawa, T.; Kuroda, H.; Kawafuchi, H. PCT Int. Appl. WO 9951588 A1 (1999); and Sirisoma, N. S.; Johnson, C. R. Tetrahedron Lett. (1998), 39(15), 2059-2062. |
| 14-53 | 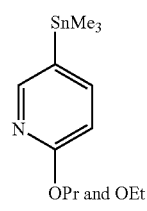 | Schnatterer, S.; Kern, M.; Sanft, U. PCT Int. Appl. WO 9965901 A1 (1999). |
| 14-54 | 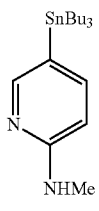 | Hayashi, K.; Kito, T.; Mitsuyama, J.; Yamakawa, T.; Kuroda, H.; Kawafuchi, H. PCT Int. Appl. WO 9951588 A1 (1999). |
| 14-55 | 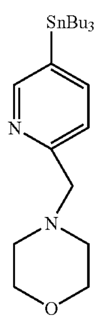 | Betageri, R.; Breitfelder, S.; Cirillo, P. F.; Gilmore, T. A.; Hickey, E. R.; Kirrane, T. M.; Moriak, M. H.; Moss, N.; Patel, U. R.; Proudfoot, J. R.; Regan, J. R.; Sharma, R.; Sun, S.; Swinamer, A. D.; Takahashi, H. PCT Int. Appl. WO 0055139 A2 (2000). |
| 14-56 | 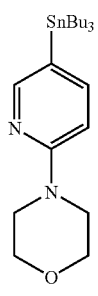 | Ueno, K.; Sasaki, A.; Kawano, K.; Okabe, T.; Kitazawa, N.; Takahashi, K.; Yamamoto, N.; Suzuki, Y.; Matsunaga, M.; Kubota, A. PCT Int. Appl. WO 9918077 A1 (1999). |
| 14-57 | 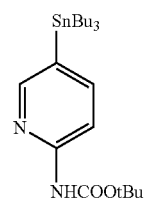 | Calderwood, D.; Arnold, L. D.; Mazdiyasni, H.; Hirst, G.; Deng, B. B. PCT Int. Appl. WO 0017202 A1 (2000). |

TABLE I-2-continued

| Precursor Number | Structure | Reference |
|---|---|---|
| 14-58 | 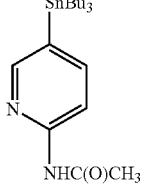 | Hayashi, K.; Kito, T.; Mitsuyama, J.; Yamakawa, T.; Kuroda, H.; Kawafuchi, H. PCT Int. Appl. WO 9951588 A1 (1999). |
| 14-59 | 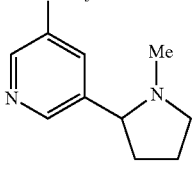 | Saji, H.; Watanabe, A.; Magata, Y.; Ohmono, Y.; Kiyono, Y.; Yamada, Y.; Iida, Y.; Yonekura, H.; Konishi, J.; Yokoyama, A. Chem. Pharm. Bull. (1997), 45(2), 284-290. |
| 14-60 | 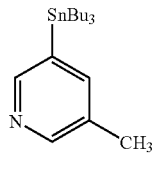 | Hayashi, K.; Kito, T.; Mitsuyama, J.; Yamakawa, T.; Kuroda, H.; Kawafuchi, H. PCT Int. Appl. WO 9951588 A1 (1999); Reuman, M.; Daum, S. J.; Singh, B.; Wentland, M. P.; Perni, R. B.; Pennock, P.; Carabateas, P. M.; Gruett, M. D.; Saindane, M. T.; et al. J. Med. Chem. (1995), 38(14), 2531-40. |
| 14-61 | 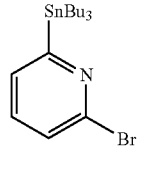 | Iino, Y.; Fujita, K.; Kodaira, A.; Hatanaka, T.; Takehana, K.; Kobayashi, T.; Konishi, A.; Yamamoto, T. PCT Int. Appl. WO 0102359 A1 (2001). |
| 14-62 | 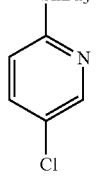 | Iino, Y.; Fujita, K.; Kodaira, A.; Hatanaka, T.; Takehana, K.; Kobayashi, T.; Konishi, A.; Yamamoto, T. PCT Int. Appl. WO 0102359 A1 (2001). |
| 14-63 | 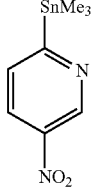 | Torrado, A.; Imperiali, B. J. Org. Chem. (1996), 61(25), 8940-8948. |
| 14-64 | 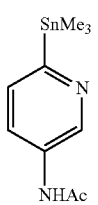 | Iino, Y.; Fujita, K.; Kodaira, A.; Hatanaka, T.; Takehana, K.; Kobayashi, T.; Konishi, A.; Yamamoto, T. PCT Int. Appl. WO 0102359 A1 (2001). |

TABLE I-2-continued

| Precursor Number | Structure | Reference |
|---|---|---|
| 14-65 | SnBu₃ pyridine OMe | Gros, P.; Fort, Y. Synthesis (1999), (5), 754-756 and Gros, P.; Fort, Y.; Caubere, P. J. Chem. Soc., Perkin Trans. 1 (1997), (20), 31 3071-3080. |

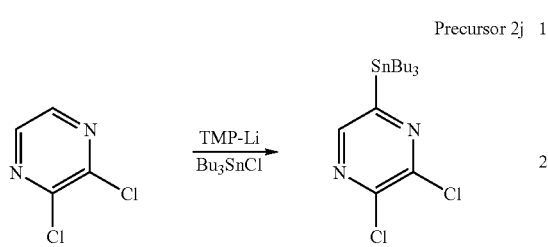

Precursor 2j

Preparation of 2,3-dichloro-5-(tri-n-butylstannyl)pyrazine (An example of general procedure Tin-01, below): TMP-Li (2,2,6,6-tetramethylpiperidinyl lithium) was prepared by addition of n-butyl lithium (1.6 M, 6.25 mL) to a solution of 2,2,4,4-tetramethylpiperidine (1.4 g) in dry THF (180 mL) at −78° C. The solution was then allowed to warm to 0° C., was stirred at 0° C. for 15 minutes, then was cooled to −78° C. To the solution was added 2,3-dichloropyrazine (1.35 g), and followed by an addition of tri-n-butyltin chloride (3.25 g) in another 2 hours. The reaction was quenched with aqueous ammonium chloride solution. The organic layer was separated, and aqueous layer was extracted with ethyl acetate (3×100 mL). The combined organic extract was dried over magnesium sulfate, filtered and the filtrate concentrated in vacuo. The residue was purified by silica gel chromatography to afford 2,3-dichloro-5-(tri-n-butylstannyl)pyrazine (1 g).

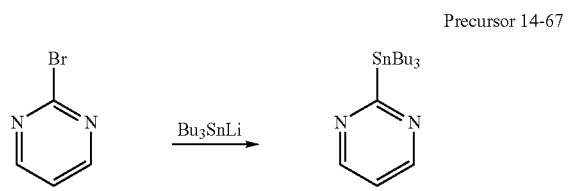

Precursor 14-67

Preparation of 2-(tri-n-butylstannyl)-pyrimidine: (Example of the general procedure Tin-03, below) Tri-n-butylstannyl lithium was prepared at 0° C. in dry THF (20 mL) from tri-butyltin hydride (2.2 mL) and LDA (lithium diisopropylamide, 2M, 4.09 mL). The tri-n-butylstannyl lithium solution was then cooled to −78° C. and to it was added 2-bromopyrimidine (1 g). The reaction mixture was then allowed to warm up to room temperature over 8 hours. The reaction was then quenched with aqueous ammonium chloride solution. The organic layer was separated, and aqueous layer was extracted with ethyl acetate (3×20 mL). The combined organic layer was dried over magnesium sulfate, filtered and the filtrate concentrated in vacuo. The residue was purified by silica gel chromatography to afford 2-(tri-n-butylstannyl)-pyrimidine (190 mg).

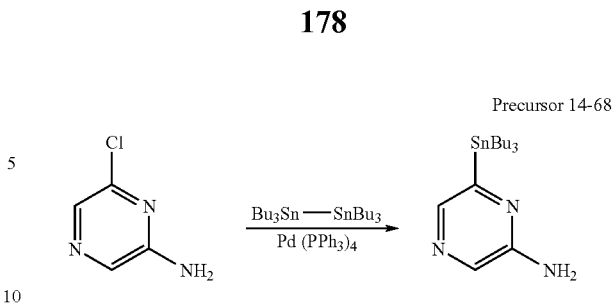

Precursor 14-68

Preparation of 2-amino-6-(tri-n-butylstannyl)pyrazine (Example of the general procedure Tin-04, below): To a sealed tube, 2-amino-6-chloro-pyrazine (1 g), bis(tri-butyltin) (3.92 mL) and tetrakis-triphenylphosphine palladium, Pd(Ph₃P)₄ (100 mg) were combined in dioxane (10 mL). The reaction was heated at 110-120° C. for 10 h. After the mixture cooled down to room temperature, it was poured into 20 mL of water. The solution was extracted with EtOAc (4×20 mL). The combined extract was concentrated in vacuo to give a residue which was purified by silica gel chromatography to afford 2-amino-6-(tri-n-butylstannyl)pyrazine (0.5 g)

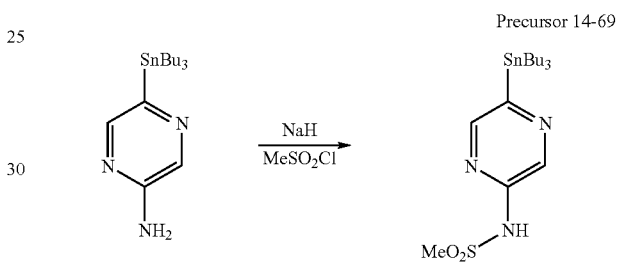

Precursor 14-69

Preparation of 2-methylsulfonylamino-5-(tri-n-butylstannyl)pyrazine (Example of general procedure Tin-05, below): NaH (60%, 20 mg) was added into a solution of 2-amino-5-(tri-n-butylstannyl)pyrazine (0.2 g) in THF (30 mL) at room temperature. After the mixture stirred at room temperature for 30 minutes, to it was added methylsulfonyl chloride (63 mg). The reaction mixture was stirred at room temperature over 8 hours. The reaction was quenched with aqueous ammonium chloride solution. The organic layer was separated, and the aqueous layer was extracted with ethyl acetate (3×100 mL). The combined organic extract was dried over magnesium sulfate, filtered and the filtrate was concentrated in vacuo. The residue was purified by silica gel chromatography to afford 2-methylsulfonylamino-5-(tri-n-butylstannyl)pyrazine (20 mg).

Precursors 14-70-14-129

The precursors 14-70-14-129 were prepared according to the following general procedures designated Tin-01 through Tin-05 (Table I-3).

General Procedure Tin-01:

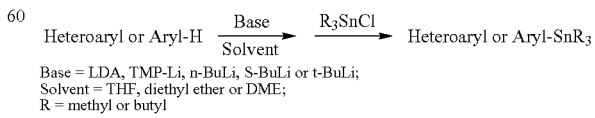

Base = LDA, TMP-Li, n-BuLi, S-BuLi or t-BuLi;
Solvent = THF, diethyl ether or DME;
R = methyl or butyl To a solution of a base (1.1 equivalents) selected from lithium diisopropylamide, 2,2,6,6-tetramethylpiperidinyl lithium, n-butyl lithium, sec-butyl lithium or tert-butyl lithium in a solvent selected from tetrahydrofuran, diethyl ether or dimethoxyethane (concentration of approximately 0.05 mmol base/mL of solvent) at −78° C. was added an appropriate aryl or heteroaryl substrate (1.0 equivalents) followed by an addition of tri-n-butyltin chloride or trimethyltin chloride (1.1 equivalents) in another 2 hours. The reaction was quenched with aqueous ammonium chloride solution. The organic layer was separated, and aqueous layer was extracted with ethyl acetate. The combined organic extract was dried over magnesium sulfate, filtered and the filtrate concentrated in vacuo. The residue was purified by silica gel chromatography to afford the desired stannane.

General Procedure Tin-02:

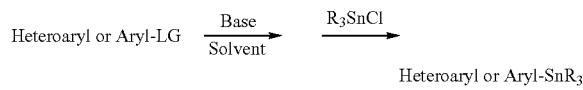

LG = Br or I; Base = n-BuLi, S-BuLi, or t-BuLi; Solvent = THF, ether or DME;
R = methyl or butyl To a solution of a base (1.1 equivalents) selected from n-butyl lithium, sec-butyl lithium or tert-butyl lithium in a solvent selected from tetrahydrofuran, diethyl ether or dimethoxyethane (concentration of approximately 0.05 mmol base/mL of solvent) at −78° C. was added an appropriate aryl or heteroaryl bromide or aryl or heteroaryl iodide substrate (1.0 equivalents). The reaction mixture was stirred at −78° C. for a period suitable to generate the anion via metal-halogen exchange then to it was added tri-n-butyltin chloride or trimethyltin chloride (1.1 equivalents). The reaction was quenched with aqueous ammonium chloride solution. The organic layer was separated, and aqueous layer was extracted with ethyl acetate. The combined organic extract was dried over magnesium sulfate, filtered and the filtrate concentrated in vacuo. The residue was purified by silica gel chromatography to afford the desired stannane.

General Procedure Tin-03:

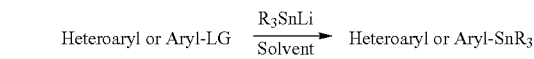

LG = F, Cl, Br, I; Solvent = THF, diethyl ether or DME; R = methyl or butyl

Tri-n-butylstannyl lithium or trimethylstannyl lithium (1.3 equivalents) was prepared at 0° C. in dry solvent selected from THF, diethyl ether or dimethoxyethane (20 mL) from tri-n-butyltin hydride or trimethyltin hydride, respectively (1.3 equivalents) and LDA (lithium diisopropylamide, 1.3 equivalents) at a concentration of approximately 0.4 mmol of alkylstannyl lithium/mL of solvent. The tri-n-butylstannyl lithium or trimethylstannyl lithium solution was then cooled to −78° C. and to it was added an appropriate haloaryl or haloheteroaryl substrate (1.0 equivalent). The reaction mixture was then allowed to warm up to room temperature over 8 hours. The reaction was then quenched with aqueous ammonium chloride solution. The organic layer was separated, and aqueous layer was extracted with ethyl acetate (3×20 mL). The combined organic layer was dried over magnesium sulfate, filtered and the filtrate concentrated in vacuo. The residue was purified by silica gel chromatography to afford the desired stannane precursor.

General Procedure Tin-04:

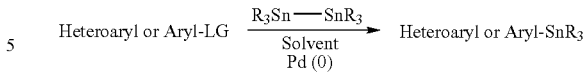

LG = Cl, Br, I or OTf; Solvent = Dioxane or Toluene; R = methyl or butyl

To a sealed tube, an appropriate aryl or heteroaryl substrate (1.0 equivalent), bis(tri-butyltin) or hexamethylditin (1.0 equivalent) and tetrakis-triphenylphosphine palladium, Pd(Ph$_3$P)$_4$ (1.0 mol %) were combined in dioxane or toluene (10 mL). The reaction was heated at 110-120° C. for 10 h. After the mixture cooled down to room temperature, it was poured into water. The solution was extracted with ethyl acetate and the combined extracts were concentrated in vacuo to give a residue which was purified by silica gel chromatography to afford the desired stannane product.

General Procedure Tin-05:

The following general reaction scheme depicts the derivatization of stannane precursors in which the stannane has a reactive ring NH group or reactive exocyclic amino, hydroxy or thiol group. The starting stannane is treated with base in an appropriate solvent then is reacted with suitable electrophiles such as alkyl halides, acid chlorides, sulfonyl chlorides, isocyanates and the like.

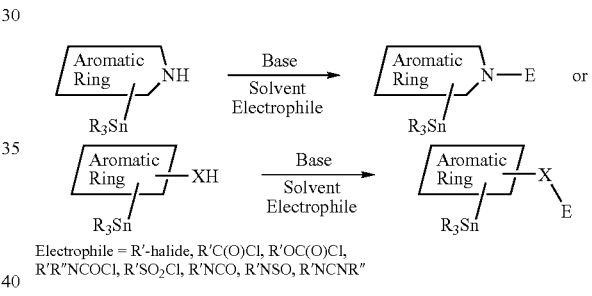

Electrophile = R′-halide, R′C(O)Cl, R′OC(O)Cl, R′R″NCOCl, R′SO$_2$Cl, R′NCO, R′NSO, R′NCNR″

E = R′——, R′C(O)——, R′OC(O)——, R′R″NC(O)——, R′SO$_2$——, R′NC(O)——, R′NS(O)——, R′NCNR″

Solvent = CH$_2$Cl$_2$, THF, diethyl ether, DMF

R = methyl or butyl; X = NH, O or S

Base = NaH, BuLi, LDA, K$_2$CO$_3$, Et$_3$N, DBU, DMAP, NaHMDS

An appropriate base selected from sodium hydride, n-butyl lithium, lithium diisopropylamide, potassium carbonate, triethylamine, DBU, DMAP or sodium hexamethyldisilazide (1.0 equivalent) was added into a solution of an appropriate stannane substrate (as depicted above, 1.0 equivalent) in an appropriate solvent selected from dichloromethane, THF, diethyl ether or N,N-dimethylformamide at a temperature between −78° C. and room temperature. After the mixture stirred for a period sufficient to allow deprotonation, typically for 5 to 30 minutes, then to it was added an appropriate electrophile such as an alkyl halide, acid chloride, sulfonyl (1.0 equivalent). The reaction mixture was stirred, typically at room temperature, over a period of 2 to 8 hours. The reaction was quenched with aqueous ammonium chloride solution. The organic layer was separated, and the aqueous layer was extracted with ethyl acetate (3×100 mL). The combined organic extract was dried over magnesium sulfate, filtered and the filtrate was concentrated in vacuo. The residue was purified by silica gel chromatography to afford the desired stannane precursor.

General Procedure Tin-06

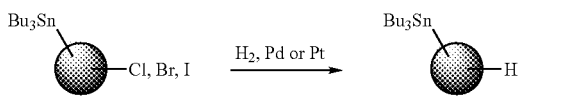

An aryl hilide stannane agent was dissolved in appropriate alcohol, either methanol or ethanol. After a catalyst (pt or pd) was added into the solvent, the reaction mixture is placed in an environment of hydrogen under normal or raised pressure. After reaction finishes, the catalyst is filtered, and, concentration of the mother solution provides a residue which is used in the further reactions without any purification.

TABLE I-3

| Intermed. Number | Structure | Starting Material | Method Applied | Identification |
|---|---|---|---|---|
| 14-70 | 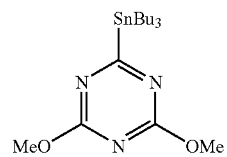 | | Tin-04 | $R_f$ = 2.33 min (Column A) $^1$H NMR (500 MHz, CDCl3) δ 4.00 (s, 6 H), 1.63-0.85 (m, 27 H) |
| 14-71 | 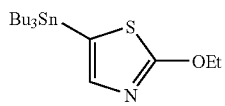 | | Tin-01 | $R_f$ = 2.52 min (Column A) $^1$H NMR (300 MHz, CDCl$_3$) δ 7.02 (s, 1 H), 4.44 (q, 2 H, J = 7.02 Hz), 1.63-0.85 (m, 30 H) |
| 14-72 | 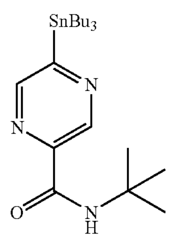 | | Tin-01 | $R_f$ = 2.84 min (Column B) $^1$H NMR (500 MHz, CDCl3) δ 9.48 (s, 1 H), 8.45 (s, 1 H), 2.03-0.88 (m, 36 H) |
| 14-73 | 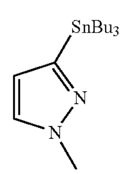 | | Tin-05 | $R_f$ = 2.27 min (Column A) $^1$H NMR (500 MHz, CDCl$_3$) δ 7.53 (m, 1 H), 6.29 (m, 1 H), 3.94 (s, 3 H), 1.56-0.87 (m, 27 H) |
| 14-74 | 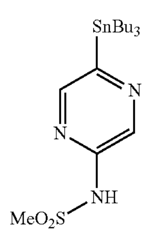 | | Tin-05 | $R_f$ = 2.22 min (Column A) |
| 14-75 | 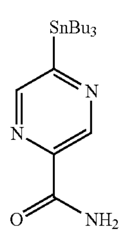 | | Tin-01 | $R_f$ = 2.44 min (Column B) $^1$H NMR (500 MHz, CDCl$_3$) δ 8.89 (s, 1 H), 8.34 (s, 1 H), 1.61-0.85 (m, 27 H) |

TABLE I-3-continued

| Intermed. Number | Structure | Starting Material | Method Applied | Identification |
|---|---|---|---|---|
| 14-76 | 3-chloro-2-(tributylstannyl)pyrazine | 2-chloropyrazine | Tin-01 | R$_f$ = 3.41 min (Column A, flow rate = 4 ml/min) $^1$H NMR (300 MHz, CDCl3) δ 8.58 (d, 1 H, J = 2.52 Hz), 8.13 (d, 1 H, J = 2.52 Hz), 1.63-0.85 (m, 27 H) |
| 14-77 | 3,5-dichloro-2-(tributylstannyl)pyrazine | 2,6-dichloropyrazine | Tin-01 | R$_f$ = 3.89 min (Column A, flow rate = 4 ml/min) $^1$H NMR (300 MHz, CDCl3) δ 8.63 (s, 1 H), 1.61-0.85 (m, 27 H) |
| 14-78 | 5,6-dichloro-2-(tributylstannyl)pyrazine | 2,3-dichloropyrazine | Tin-01 | R$_f$ = 3.86 min (Column A, flow rate = 4 ml/min) $^1$H NMR (300 MHz, CDCl3) δ 8.24 (s, 1 H), 1.61-0.85 (m, 27 H) |
| 14-79 | 6-(tributylstannyl)pyrazin-2-amine | 6-chloropyrazin-2-amine | Tin-04 | R$_f$ = 2.10 min (Column B) $^1$H NMR (500 MHz, CDCl3) δ 7.90 (s, 1 H), 7.26 (s, 1 H), 1.58-0.87 (m, 27 H) |
| 14-80 | 1-methyl-5-(tributylstannyl)-1H-imidazole | 5-bromo-1-methyl-1H-imidazole | Tin-04 | R$_f$ = 1.83 min (Column A) |
| 14-81 | 1-methyl-4-(tributylstannyl)-1H-imidazole | 4-bromo-1-methyl-1H-imidazole | Tin-04 | R$_f$ = 1.84 min (Column A) |
| 14-82 | 3-methoxy-6-(tributylstannyl)pyridazine | 3-chloro-6-methoxypyridazine | Tin-04 | R$_f$ = 1.84 min (Column A) |
| 14-83 | 2,6-dimethoxy-4-(tributylstannyl)pyrimidine | 4-chloro-2,6-dimethoxypyrimidine | Tin-04 | R$_f$ = 1.90 min (Column A) |

TABLE I-3-continued

| Intermed. Number | Structure | Starting Material | Method Applied | Identification |
|---|---|---|---|---|
| 14-84 | pyrazine with SnBu₃ and COOH | pyrazine with COOH | Tin-01 | R_f = 2.23 min (Column A) |
| 14-85 | thiazole with SnBu₃ and NEt₂ | thiazole with Br and NEt₂ | Tin-04 | R_f = 1.92 min (Column A) |
| 14-86 | pyrimidine with SnBu₃ | pyrimidine with Br | Tin-03 | R_f = 2.01 min (Column A) |
| 14-87 | thiazole with SnBu₃ | thiazole | Tin-01 | R_f = 2.45 min (Column A) |
| 14-88 | bithiazole with SnBu₃ | bithiazole | Tin-01 | R_f = 2.67 min (Column C) |
| 14-89 | thiazole with Bu₃Sn and SH | thiazole with SH | Tin-01 | R_f = 2.31 min (Column C) |
| 14-90 | pyrimidine with SnBu₃ and pyrrole | pyrimidine with Br and pyrrole | Tin-04 | R_f = 2.71 min (Column D) |

TABLE I-3-continued

| Intermed. Number | Structure | Starting Material | Method Applied | Identification |
|---|---|---|---|---|
| 14-91 | 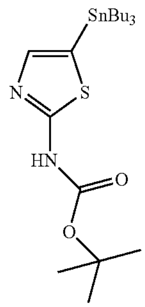 | | Tin-01 | $R_f$ = 2.49 min (Column C) |
| 14-92 | 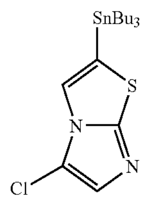 | | Tin-01 | $R_f$ = 2.42 min (Column C) |
| 14-93 | 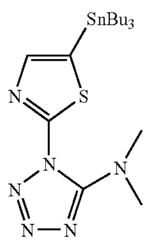 | | Tin-01 | $R_f$ = 3.49 min (Column C) Flow Rate = 4 ml/min |
| 14-94 | 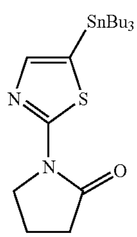 | | Tin-01 | $R_f$ = 2.46 min (Column C) |
| 14-95 | 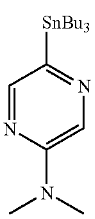 | | Tin-05 | $R_f$ = 2.15 min (Column A) |
| 14-96 | 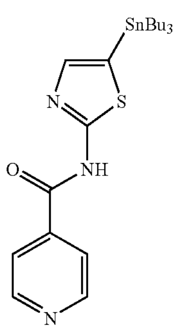 | | Tin-01 | $R_f$ = 2.28 min (Column C) |

TABLE I-3-continued

| Intermed. Number | Structure | Starting Material | Method Applied | Identification |
|---|---|---|---|---|
| 14-97 | 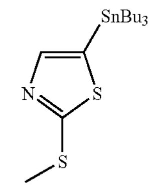 | | Tin-01 | $R_f$ = 2.60 min (Column C) |
| 14-98 | 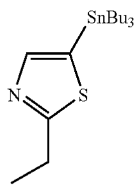 | | Tin-01 | $R_f$ = 2.37 min (Column A) |
| 14-99 | 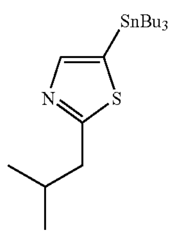 | | Tin-01 | $R_f$ = 2.59 min (Column A) |
| 14-100 | 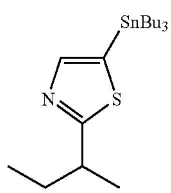 | | Tin-01 | $R_f$ = 2.49 min (Column C) |
| 14-101 | 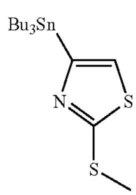 | | Tin-04 | $R_f$ = 2.41 min (Column A) |
| 14-102 | 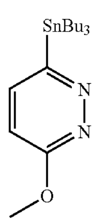 | | Tin-04 | $R_f$ = 1.88 min (Column E) |
| 14-103 | 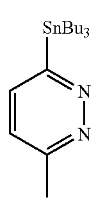 | | Tin-04 | $R_f$ = 1.92 min (Column E) |

TABLE I-3-continued

| Intermed. Number | Structure | Starting Material | Method Applied | Identification |
|---|---|---|---|---|
| 14-104 | 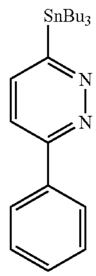 | | Tin-04 | $R_f$ = 2.01 min (Column E) |
| 14-105 | 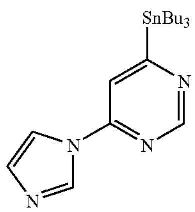 | | Tin-04 | $R_f$ = 2.15 min (Column E) |
| 14-106 | 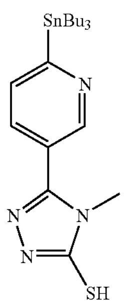 | | Tin-04 | $R_f$ = 1.91 min (Column E) |
| 14-107 | 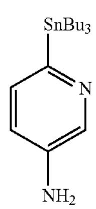 | | Tin-04 | Rf = 1.95 min (Column A) |
| 14-108 | 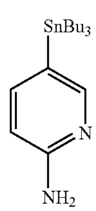 | | Tin-04 | Rf = 1.93 min (Column A) |
| 12-109 | 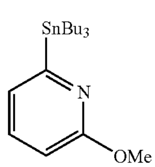 | | Tin-01 | Rf = 1.95 min (Column A) |

TABLE I-3-continued

| Intermed. Number | Structure | Starting Material | Method Applied | Identification |
|---|---|---|---|---|
| 14-110 | pyridazine-SnBu₃ | pyridazine | Tin-01 | Rf = 1.83 min (Column A) ¹H NMR (500 MHz, CDCl3) δ 9.03 (d, 1 H, J = 5.15 Hz), 7.49 (d, 1 H, J = 7.95 Hz), 7.26 (m, 1 H), 1.61-0.86 (m, 27 H); ¹³C NMR (125 MHz, CDCl3) δ 175.3, 149.8, 133.2, 123.7, 29.0, 27.3, 13.6, 10.1. |
| 14-111 | pyrimidine-SnBu₃ | pyrimidine | Tin-01 | Rf = 2.18 min (Column E) ¹H NMR (500 MHz, CDCl3) δ 9.22 (s, 1 H), 8.46 (d, 1 H, J = 4.80 Hz), 7.42 (d, 1 H, J = 4.75 Hz), 1.56-0.86 (m, 27 H); ¹³C NMR (125 MHz, CDCl3) δ 185.4, 158.0, 153.2, 130.6, 28.9, 27.2, 13.5, 9.9. |
| 14-112 | 4-SnBu₃-6-MeO-pyrimidine | 4-Cl-6-MeO-pyrimidine | Tin-04 | Rf = 1.96 min (Column A) |
| 14-113 | 4-SnBu₃-2-Cl-pyrimidine | 2-Cl-pyrimidine | Tin-01 | Rf = 2.61 min (Column A) |
| 14-114 | 4-SnBu₃-2,6-diCl-pyrimidine | 2,4-diCl-pyrimidine | Tin-01 | Rf = 2.85 min (Column A) |
| 14-115 | 5-SnBu₃-2-(NHMe)-pyrazine | 5-SnBu₃-2-NH₂-pyrazine | Tin-05 | Rf = 2.09 min (Column A) ¹H NMR (500 MHz, CDCl3) δ 8.12 (s, 1 H), 7.95 (s, 1 H), 4.11 (s, 1 H), 2.95 (s, 3 H), 2.03-0.85 (m, 27 H) |

TABLE I-3-continued

| Intermed. Number | Structure | Starting Material | Method Applied | Identification |
|---|---|---|---|---|
| 14-116 | [pyrazine with SnBu₃ and NHEt] | [pyrazine with SnBu₃ and NH₂] | Tin-05 | Rf = 2.16 min (Column A) $^1$H NMR (500 MHz, CDCl3) δ 8.08 (s, 1 H), 7.92 (s, 1 H), 4.49 (s, 1 H), 3.35 (m, 2 H), 1.63-0.85 (m, 30 H) |
| 14-117 | [pyrazine with SnBu₃, OMe, NHMe] | [pyrazine with Br, OMe, NHMe] | Tin-04 | Rf = 2.19 min (Column A) |
| 14-118 | [pyrazine with SnBu₃, OMe, NH₂] | [pyrazine with Br, OMe, NH₂] | Tin-04 | Rf = 2.18 min (Column A) |
| 14-119 | [pyrazine with SnBu₃, Cl, NH₂] | [pyrazine with Br, Cl, NH₂] | Tin-04 | Rf = 2.47 min (Column A) $^1$H NMR (500 MHz, CDCl3) δ 7.85 (s, 1 H), 4.91 (s, 2 H), 2.16-0.87 (m, 27 H) |
| 14-120 | [pyrazine with SnBu₃, Cl, NHMe] | [pyrazine with Br, Cl, NHMe] | Tin-04 | Rf = 2.61 min (Column A) |
| 14-121 | [pyrazine with SnBu₃, Cl, NHPr] | [pyrazine with Br, Cl, NHPr] | Tin-04 | Rf = 2.92 min (Column A) |
| 14-122 | [pyrimidine with SnBu₃, NHMe] | [pyrimidine with Cl, NHMe] | Tin-04 | Rf = 1.93 min (Column A) |

TABLE I-3-continued

| Intermed. Number | Structure | Starting Material | Method Applied | Identification |
|---|---|---|---|---|
| 14-123 | 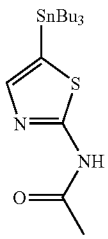 | | Tin-01 | Rf = 2.20 min (Column A) |
| 14-124 | 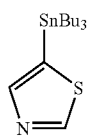 | | Tin-01 | Rf = 2.50 min (Column A) $^1$H NMR (500 MHz, CDCl3) δ 9.07 (s, 1 H), 7.87 (s, 1 H), 1.59-0.85 (m, 27 H) |
| 12-125 | 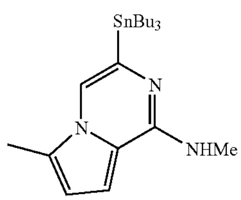 | | Tin-04 | Rf = 1.97 min (Column A) |
| 14-126 | 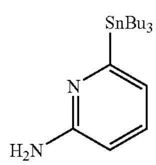 | | Tin-04 | Rf = 1.97 min (Column A) |
| 14-127 | 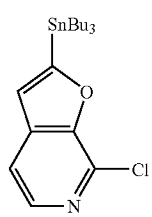 | | Tin-01 | Rf = 2.70 min (Column E) $^1$H NMR (500 MHz, CDCl3) δ 8.11 (d, 1 H, J = 5.2 Hz), 7.41 (d, 1 H, J = 5.2 Hz), 6.94 (s, 1 H), 1.62-0.89 (m, 27 H) |
| 14-128 | 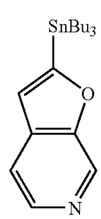 | | Tin-06 | $^1$H NMR (500 MHz, CDCl3) δ 8.12 (d, 1 H, J = 5.2 Hz), 7.78 (s, 1 H), 7.46 (d, 1 H, J = 5.2 Hz), 6.84 (s, 1 H), 1.98-0.85 (m, 27 H) |
| 14-129 | 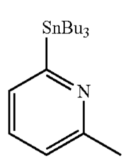 | | Tin-01 | Rf = 1.86 min (Column A) |

Rf = retention time

The following Table I-4 contains novel stannane reagents which can be prepared by the methodology described above and then could be used to prepare compounds of formula I.

TABLE I-4

| Precursor Number | Structure | Reference |
|---|---|---|
| | 5-SnBu₃, 2-F pyrimidine | From 5-iodo2-chloro-1,3 pyrimidine. Fluoropyrimidines are obtained by fluorination of chloropyrimidines with CsF in N-methyl-2-pyrrolidinone or DMF 2.5-63 h at 80-150° C. The iodo is then converted to the lithium reagent with tBuLi and trapped with Bu3SnCl. See Sandosham above. |
| | 3-SnBu₃, 6-NH₂ pyridazine | |
| | 3-SnBu₃, 6-OMe pyridazine | |
| | 3-SnBu₃, 6-Cl pyridazine | |
| | 3-SnBu₃, 6-F pyridazine | |
| | 3-SnBu₃, 6-NHMe pyridazine | |
| | 4-SnBu₃, 2-Cl pyrimidine | |

TABLE I-4-continued

| Precursor Number | Structure | Reference |
|---|---|---|
| | 4-SnBu₃, 2-F pyrimidine | |
| | 4-SnBu₃, 6-F pyrimidine | |
| | 4-SnBu₃, 6-C(O)OCH₃, 2-CH₃ pyrimidine | |
| | 4-SnBu₃, 6-CH₃, 2-CH₃ pyrimidine | |
| | 3-SnBu₃, 2-F pyrazine | |
| | 2-SnBu₃, 6-F pyrazine | |
| | 2-SnBu₃, 5-F pyrazine | |
| | 5-SnMe₃, 2-NHC(O)CH₃ pyrazine | |

TABLE I-4-continued

| Precursor Number | Structure | Reference |
|---|---|---|
| | 5-SnMe₃-pyrazin-2-yl-NHC(O)(CH₂)₄CH₃ | |
| | 5-SnBu₃-pyrazin-2-yl-C(O)NH₂ | |
| | 5-SnBu₃-pyrazin-2-yl-C(O)NHMe | |
| | 5-SnBu₃-pyrazin-2-yl-C(O)NMe₂ | |
| | 5-SnBu₃-pyrazin-2-yl-C(O)(pyrrolidin-1-yl) | |
| | 5-SnBu₃-pyrazin-2-yl-C(O)NEt₂ | |
| | 5-SnMe₃-pyrazin-2-yl-F | |
| | 5-SnMe₃-pyrazin-2-yl-OMe | |
| | 5-SnMe₃-pyrazin-2-yl-OH | |
| | 6-SnMe₃-pyrazin-2-yl-F | |
| | 5-SnMe₃-pyrazin-2-yl-CN | |
| | 3,5-dichloro-6-SnBu₃-pyrazine | Turck, A.; et. al Lab. J. Organomet. Chem. (1991), 412(3), 301-10. Metallation of 2,6-dicloropyrazine and quench with Bu3SnCl |
| | 5-SnBu₃-pyrazin-2-yl-NHMe | Analogous to Lehn, L. M., et al. Chem. Eur. J. 2000, 6, 4133. |
| | 5-SnBu₃-pyrazin-2-yl-NMe₂ | |

TABLE I-4-continued

| Precursor Number | Structure | Reference |
|---|---|---|

(5-SnBu3-pyrazin-2-yl)-NEt2

5-SnBu3-2-Me-pyridine

5-SnBu3-2-Cl-pyridine

5-SnBu3-2-OH-pyridine

5-SnBu3-2-Br-pyridine

5-SnBu3-2-Ph-pyridine

3-SnBu3-5-F-pyridine

3-SnBu3-2-F-pyridine

5-SnBu3-2-SMe-pyridine

3-SnBu3-5-NHC(O)CH3-pyridine

2-SnBu3-5-Cl-pyridine

2-SnBu3-5-F-pyridine

2-SnBu3-5-NH2-pyridine

2-SnBu3-5-Me-pyridine

2-SnBu3-6-CH3-pyridine

TABLE I-4-continued

| Precursor Number | Structure | Reference |
|---|---|---|

[Structures shown:
- 6-SnBu3-pyridine-2-CH2OH
- 6-SnBu3-pyridine-2-NH2 (pyrimidine)
- 6-SnBu3-pyridine-2-SO2Me
- 6-SnBu3-pyridine-2-NHAc
- 4-SnBu3-3-CH3-6-CH3-pyridazine
- 2-SnBu3-4,6-bis(NEt2)-1,3,5-triazine
- 2-SnBu3-pyrimidine

- 6-SnBu3-3-Cl-1,2,4-triazine
- 6-SnBu3-3-OMe-1,2,4-triazine
- 6-SnBu3-3-CF3-1,2,4-triazine
- 6-SnBu3-3-OCF3-1,2,4-triazine
- 6-SnBu3-3-F-1,2,4-triazine
- 6-SnBu3-1,2,4-triazine
- 2-F-1-Trityl-5-SnBu3-imidazole]

Reference for last entry: Metallation of 1-trityl-4-iodo imidazole (prepared in Takahashi, Kazuyuki; Kirk, Kenneth L.; Cohen, Louis A. Lab. Chem., Natl. Inst. Arthritis Diabetes Dig. Kidney Dis., Bethesda, MD, U.S.A. J. Labelled Compd. Radiopharm. (1986), 23(1), 1-8) using tBuLi in THF at −78 and quenching with Bu$_3$SnCl. Detritylate with TFA or aq HCl after coupling to azaindole core.

TABLE I-4-continued

| Precursor Number | Structure | Reference |
|---|---|---|
| | ![structure: 2-F, 1-NMe, 5-SnBu3 imidazole] | Metallation of 1-methyl-4-iodo imidazole (prepared in Takahashi, Kazuyuki; Kirk, Kenneth L.; Cohen, Louis A. Lab. Chem., Natl. Inst. Arthritis Diabetes Dig. Kidney Dis., Bethesda, MD, U.S.A. J. Labelled Compd. Radiopharm. (1986), 23(1), 1-8) using tBuLi in THF at −78 and quenching with Bu₃SnCl. El Borai, M.; Moustafa, A. H.; Anwar, M.; Abdel Hay, F. I. The bromo derivative is described in Pol. J. Chem. (1981), 55(7-8), 1659-65 and can be used to generate the tin reagent via transmetallation. |
| | ![structure: 2-F, NH, SnBu3 imidazole] | |
| | ![structure: 2-SnBu3, NH, 4,5-F imidazole] | 4,5difluoroimidazole prepared as in Dolensky, Bohumil; et. al, U.S.A. J. Fluorine Chem. (2001), 107(1), 147-148. |
| | ![structure: 2-SnBu3, NMe, 4,5-F imidazole] | Dolensky, Bohumil; et. al, U.S.A. J. Fluorine Chem. (2001), 107(1), 147-148. |
| | ![structure: 2-SnBu3, NMe, 4-F, 5-NH2 imidazole] | |

Select General Procedures, Via $S_NAr$ Reactions, for the Preparation of Starting Materials for Tin Agents a. Preparation of 2-bromo-5-substituted-pyrazine, 5-bromo-2-substituted-thiazole, 2-substituted-thiazaole, 4-chloro-6-substituted-pyrimidine and 5-bromo-2-substituted-pyrimidine

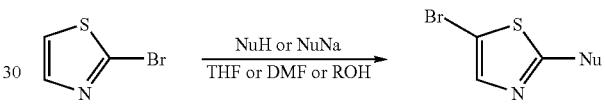

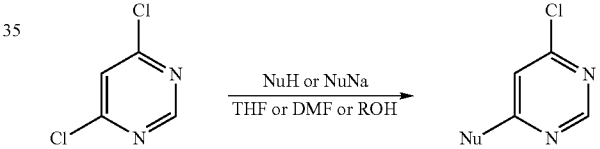

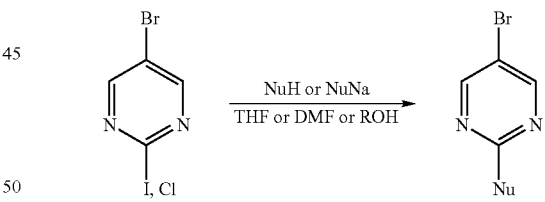

To a flask, an appropriate pyrazine, pyrimidine or thiazole (1.0 equivalent) and a nucleophile (Nu), such as amine, alcohol or thio-derivatives in one equivalence or an exess amount were combined in a solvent such as THF, DMF or alcohol, with or without an addition of NaH. The reaction was either stirred at room temperature or under heating for one to three days. After all the solvents were removed, the residue was partitioned between saturated NaHCO₃ and EtOAc. The aqueous layer was extracted with ethyl acetate and the combined extracts were concentrated in vacuo to give a residue, which was purified by silica gel chromatography to afford the desired product.

| Starting Material | Product | Reaction Condition | Rf (minutes) | MS (M + H)+ Calcd. | MS (M + H)+ Obsv. |
|---|---|---|---|---|---|
| 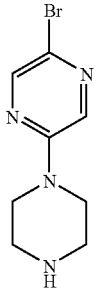 SM-01 | 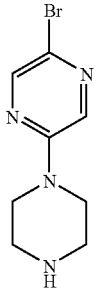 | SM-01 (2 g) Piperazine (10 g), THF (50 ml), r.t. | 0.56 (column G) | 243.02 | 243.03 |
| 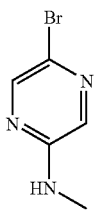 SM-01 | 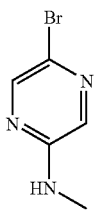 | SM-01 (1 g), MeNH$_2$ (2 M in THF, 100 ml), r.t. | 0.89 (column E) | 187.93 | 187.98 |
| 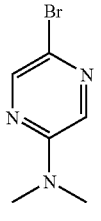 SM-01 | 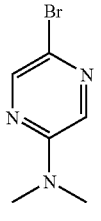 | SM-01 (1 g), Me$_2$NH (2 M in THF, 100 ml), r.t. | 1.19 (column E) | 201.92 | 202.00 |
| 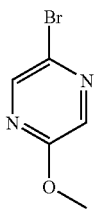 SM-01 | 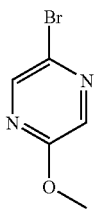 | SM-01 (1 g), MeONa (0.5 M in MeOH, 100 ml), r.t. | 1.05 (column E) | 188.91 | 188.97 |
| 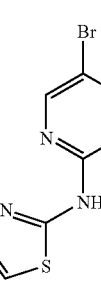 SM-01 | 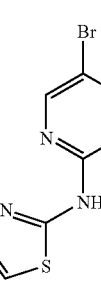 | SM-01 (50 mg), NaH (17 mg), 2-amino-1,3,4-thiadiazole (25 mg), DMF 5 ml) r.t. | 1.21 (column E) | 257.94 | 257.89 |

-continued

| Starting Material | Product | Reaction Condition | Rf (minutes) | MS (M + H)+ Calcd. | MS (M + H)+ Obsv. |
|---|---|---|---|---|---|
| SM-01 (5-bromo-2-bromopyrazine) | 5-bromo-2-(4-benzylpiperazin-1-yl)pyrazine | SM-01 (50 mg), NaH (17 mg), N-benzyl-piperazine (25 mg), DMF 5 ml) r.t. | 1.04 (column E) | 333.07 | 332.99 |
| SM-01 | 2-((5-bromopyrazin-2-yl)oxy)-N,N-diethylethanamine | SM-01 (50 mg), NaH (17 mg), N,N-diethyl-amino-ethanol (0.033 ml), DMF 5 ml) r.t. | 0.72 (column E) | 274.06 | 273.97 |
| SM-02 (2,5-dibromothiazole) | 5-bromo-2-(piperazin-1-yl)thiazole | SM-02 (2 g) Piperazine (10 g), THF (50 ml), r.t. | 0.89 (column E) | 247.99 | 247.97 |
| SM-02 | 5-bromo-N,N-dimethylthiazol-2-amine | SM-05 (1 g), Me₂NH (2 M in THF, 100 ml), r.t. | 0.65 (column E) | 206.89 | 206.96 |
| SM-02 | 5-bromo-2-methoxythiazole | SM-02 (1 g), MeONa (0.5 M in MeOH, 100 ml), r.t. | 1.35 (column E) | 193.93 | 193.84 |

-continued

| Starting Material | Product | Reaction Condition | Rf (minutes) | MS (M + H)+ Calcd. | MS (M + H)+ Obsv. |
|---|---|---|---|---|---|
| SM-02 | | SM-03 (50 mg), NaH (16 mg), imidazole (77 mg), DMF 5 ml) r.t. | 0.89 (column E) | 229.94 | 229.83 |
| SM-02 | | SM-02 (50 mg), NaH (16 mg), N-benzyl-piperazine (30 mg), DMF 5 ml) r.t. | 1.02 (column E) | 338.03 | 337.98 |
| SM-02 | | SM-02 (50 mg), NaH (16 mg), N,N-diethyl-amino-ethanol (0.033 ml), DMF 5 ml) r.t. | 0.83 (column E) | 279.02 | 278.95 |
| SM-03 | | SM-03 (50 mg), NaH (25 mg), imidazole (25 mg), DMF 5 ml) r.t. | 0.31 (column E) | 151.91 | 152.03 |
| SM-03 | | SM-03 (50 mg), NaH (25 mg), N-benzyl-piperazine (37 mg), DMF 5 ml) r.t. | 0.66 (column E) | 260.07 | 260.12 |

-continued

| Starting Material | Product | Reaction Condition | Rf (minutes) | MS (M + H)+ Calcd. | MS (M + H)+ Obsv. |
|---|---|---|---|---|---|
|  SM-03 |  | SM-03 (50 mg), NaH (25 mg), N,N-diethyl-amino-ethanol (0.05 ml), DMF 5 ml) r.t. | 0.46 (column E) | 201.11 | 201.02 |
| 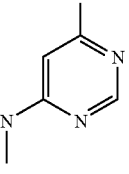 SM-04 |  | SM-04 (1 g), MeONa (0.5 M in MeOH, 13.52 ml), r.t. | 0.86 (column E) | 145.02 | 144.99 |
|  SM-04 |  | SM-04 (1 g), MeNH$_2$ (2 M in THF, 100 ml), r.t. | 0.46 (column E), | 144.03 | 143.96 |
| Br / N / N / Cl SM-05 | Br / N / N / OMe | SM-05 (1 g), MeONa (0.5 M in MeOH, 100 ml), 1 day, r.t. | 0.91 (column E) | 188.97 | 188.91 |
| Br / N / N / Cl SM-05 | Br / N / N / NHMe | SM-05 (1 g), MeNH$_2$ (2 M in THF, 100 ml), r.t. | 0.84 (column E) | 187.99 | 187.94 |
| Br / N / N / Cl SM-05 | Br / N / N / NMe$_2$ | SM-05 (1 g), Me$_2$NH (2 M in THF, 100 ml), r.t. | 1.24 (column E) | 202.00 | 201.98 | b. Preparation of 2-bromo-5,6-disubstituted-pyrazine

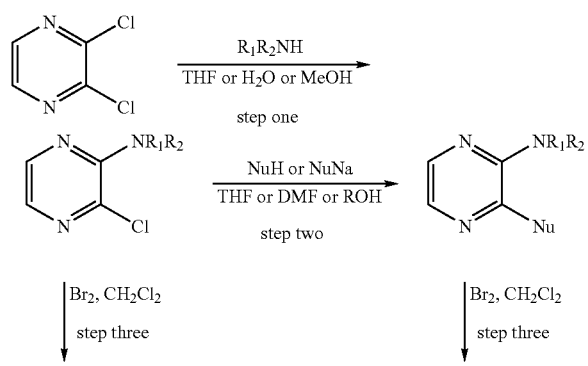

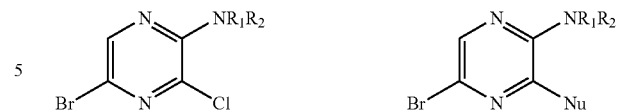

Step One

To a flask, an appropriate pyrazine (1.0 equivalent) and a nucleophile, such as amine or sodium alkoxide in an exess amount were combined in a solvent such as water or THF or without solvent. The reaction was either stirred at room temperature or under heating for one to three days. After all the solvents were removed, a residue was collected and used in the further steps without any purification.

| Starting Material | Product | Reaction Condition | Rf (minutes) | MS (M + H)+ Calcd. | MS (M + H)+ Obsv. |
|---|---|---|---|---|---|
| SM-06 (2,3-dichloropyrazine) | 3-chloro-N-propylpyrazin-2-amine | SM-06 (100 mg), propylamine (2 ml), r.t. | 1.28 (column C) | 172.06 | 172.09 |
| SM-06 | 3-chloro-N,N-dimethylpyrazin-2-amine | SM-06 (100 mg), Me₂NH (2 M in THF, 10 ml) or Me₂NH (40% in water, 10 ml), r.t. | 1.21 (column C) | 158.05 | 158.07 |
| SM-06 | N²,N²,N³,N³-tetramethylpyrazine-2,3-diamine | SM-06 (100 mg), Me2NH (40% in water, 10 ml), 100° C. | 0.49 (column C) | 167.13 | 167.19 |
| SM-06 | 3-chloro-N-methylpyrazin-2-amine | SM-06 (100 mg), MeNH₂ (2 M in THF, 10 ml), r.t. | 0.72 (column C) | 144.03 | 144.07 |
| SM-06 | 3-chloropyrazin-2-amine | SM-06 (100 mg), NH₄OH (10 ml), 100° C. | 0.41 (column C) | 162.04 (M + MeOH + H)⁺ | 162.06 (M + MeOH + H)⁺ |

Step Two

To a flask, the crude pyrazine derivative obtained from the step one (1.0 equivalent) and a nucleophile, such as amine or sodium alkoxide in an exess amount were combined in a solvent such as water or THF or without solvent. The reaction was either stirred at room temperature or under heating for one to three days. After all the solvents were removed, a residue was collected and used in the further steps without any purification.

| Starting Material | Product | Reaction Condition | Rf (minutes) | MS (M + H)+ Calcd. | MS (M + H)+ Obsv. |
|---|---|---|---|---|---|
| SM-07 | | SM-07 (2 g), MeONa (12.5 wt %, 100 ml), 100° C. | 0.28 (column C) | 140.08 | 140.14 |
| SM-08 | | SM-08 (2 g), MeONa (12.5 wt %, 20 ml), 100° C. | 0.28 (column C) | 158.13 | 158.09 |
| SM-07 | | SM-07 (2 g), MeNH$_2$ (40% in water, 100 ml), 110° C. | 0.34 (column C) | 139.10 | 139.13 |

Step Three

To a flask, the crude pyrazine derivative obtained from the step two (1.0 equivalent) was dissolved in methylene chloride. A slightly excess of bromine was then added into the mixed solution. The reaction was stirred at room temperature for ten hours. After all the solvents were removed, a residue was collected and purified by silica gel chromatography to afford the desired product.

| Starting Material | Product | Reaction Condition | Rf (minutes) | MS (M + H)+ Calcd. | MS (M + H)+ Obsv. |
|---|---|---|---|---|---|
| SM-09 | | SM-09 (5 g), bromine (1.34 ml), CH$_2$Cl$_2$ (100 ml) | 1.77 (column C) | 249.97 | 250.02 |

-continued

| Starting Material | Product | Reaction Condition | Rf (minutes) | MS (M + H)+ Calcd. | MS (M + H)+ Obsv. |
|---|---|---|---|---|---|
| SM-10 | 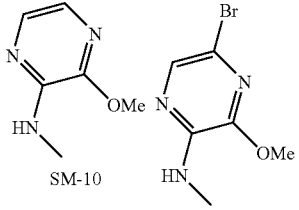 | SM-10 (2 g), bromine (0.72 ml), CH₂Cl₂ (20 ml) | 1.13 (column C) | 217.99 | 217.98 |
| SM-11 | 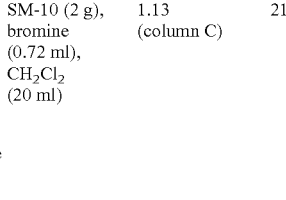 | SM-11 (2 g), bromine (0.72 ml), CH₂Cl₂ (20 ml) | 0.98 (column C) | 203.98 | 203.99 |

General Procedure of the Preparation of 2-alkyl-5-bromopyrimide:

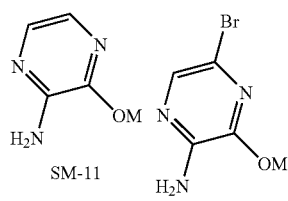

To a sealed tube, 5-bromo-2-iodopyrimidine (1.0 equivalent), tri-alkylaluminum (1.5 equivalent) and tetrakis-triphenylphosphine palladium, $Pd(Ph_3P)_4$ (1.0 mol %) were combined in dioxane (10 mL). The reaction was heated at 110-120° C. for 10 h. After the mixture cooled down to room temperature, it was poured into water. The solution was extracted with ethyl acetate and the combined extracts were concentrated in vacuo to give a residue which was purified by silica gel chromatography to afford the desired 2-alkyl-5-bromopyrimidine product.

| R3Al | Product | Rf (minutes) | MS (M + H)+ Calcd. | MS (M + H)+ Obsv. |
|---|---|---|---|---|
| Me₃Al | 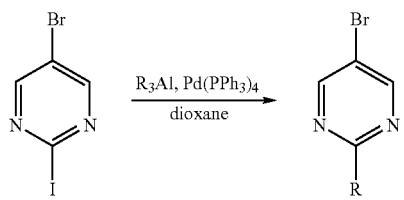 | 0.90 (column E) | 172.94 | 172.97 |
| (i-Bu)₃Al | 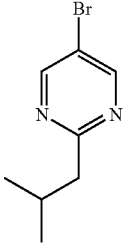 | 1.45 (column E) | 215.02 | 214.99 |

Prep of triazine stannane for Stille coupling to prepare examples of claim 1. (the sulfur can then be removed with Raney Nickel to give additional desulfurized triazines).

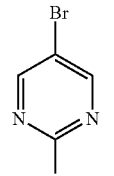

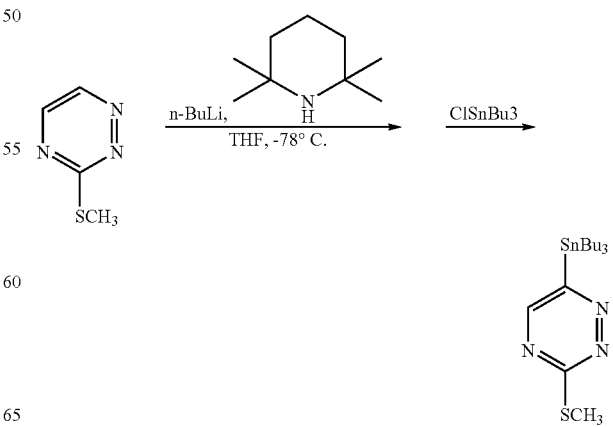

2,2,6,6-tetramethylpiperidine (2.0 ml, 11.81 mmol) in 30 ml of THF was cooled to −78° C. and treated with n-butyllithium (4.7 ml, 11.81 mmol, 2.5M in hexane). After stirring 30 min at 0° C., the reaction was cooled to −78° C. again and 3-methylthio-1,2,4-triazine (1.0 g, 7.87 mmol) was added. The resulting solution was stirred at −78° C. for 30 min before tributyltin chloride (2.1 ml, 7.87 mmol) was added. The reaction was kept at −78° C. for 1 hr, then quenched with water. The THF solvent was removed on rotarory evaporator and the remaining solution was extracted with ethylacetate. The organic layer was dried over MgSO4, filtered and the filtrate was concentrated. The residue was chromatographed to afford 96 mg of 3-methylthio-6-tributyltin-1,2,4-triazine.

1H NMR (300 Hz, CHCl3): 8.83 (s, 1H); 2.62 (s, 3H); 2.04-0.79 (m, 27H).

LC/MS: (ES+) M/Z (M+H)+=418, RT=2.29 min.

Precursor 13a

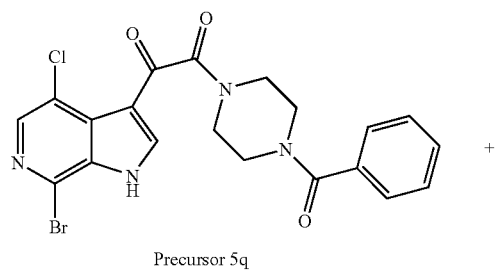

Precursor 5q

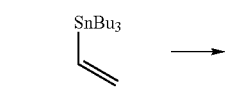

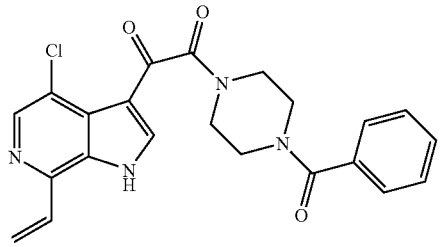

Precursor 13a

To a mixture of 5q (50 mg, 105 μmol) and Pd(PPh$_3$)$_4$ (25 mg, 21 μmol) was added 1,4-dioxane (1 ml) and vinyl tributylstannane (50 mg, 158 μmol). The reaction mixture was heated in a sealed tube at 145° C. for 3 hours. After cooling to ambient temperature, the reaction mixture was added MeOH (4 ml) and then filtered. The filtrate was purified by preparative reverse phase HPLC to give the TFA salt of Precursor 13a using the method: Start % B=30, Final % B=75, Gradient time=20 min, Flow Rate=25 ml/min, Column: YMC C18 5 um 20×100 mm, Fraction Collection: 7.92-8.58 min. $^1$H NMR: (CD$_3$OD) δ 8.61 (s, 1H), 8.37 (s, 1H), 7.47 (b s, 5H), 7.31 (dd, J=17.3, 11.3, 1H), 6.50 (d, J=17.3, 1H), 5.97 (d, J=11.3, 1H), 3.97-3.38 (b m, 8H); LC/MS: (ES+) m/z (M+H)$^+$=423, 425; HPLC R$_t$=1.887.

Precursor 14

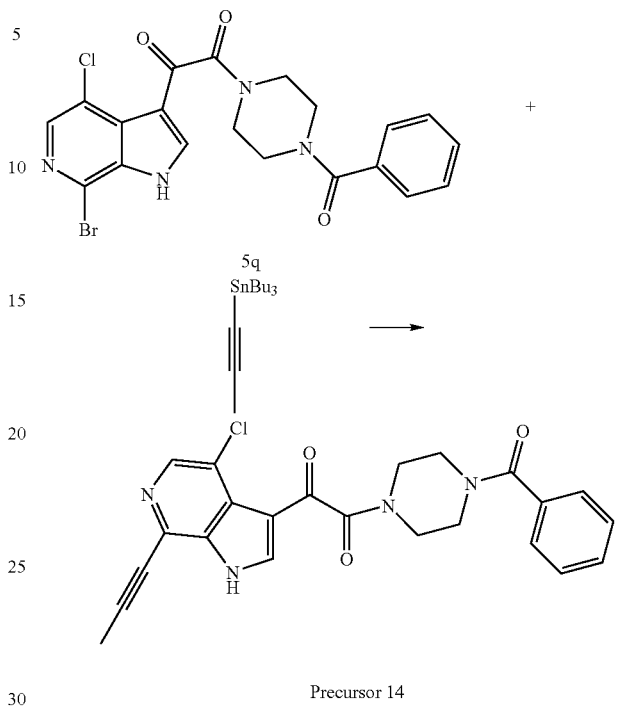

Precursor 14

To a mixture of precursor 5q (30 mg, 63 μmol) and Pd(PPh$_3$)$_4$ (20 mg, 17 μmol) was added 1,4-dioxane (1 ml) and 1-tributylstannyl propyne (40 mg, 122 μmol). The reaction mixture was heated in a sealed tube at 145° C. for 2 hours. After cooling to ambient temperature, the reaction mixture was added MeOH (4 ml) and then filtered. The filtrate was purified by preparative reverse phase HPLC to give the TFA salt of precursor 14 (1-(4-Benzoyl-piperazin-1-yl)-2-(4-chloro-7-prop-1-ynyl-1H-pyrrolo[2,3-c]pyridin-3-yl)-ethane-1,2-dione) using the method: Start % B=20, Final % B=80, Gradient time=20 min, Flow Rate=25 ml/min, Column: YMC C18 5 um 20×100 mm, Fraction Collection: 8.74-9.00 min. $^1$H NMR: (CD$_3$OD) δ 8.47 (s, 1H), 8.27 (s, 1H), 7.46 (b s, 5H), 3.82-3.34 (b m, 8H), 2.26 (s, 3H); LC/MS: (ES+) m/z (M+H)$^+$=435, 437; HPLC (alternate conditions B, column G) R$_t$=2.123.

Precursor 15

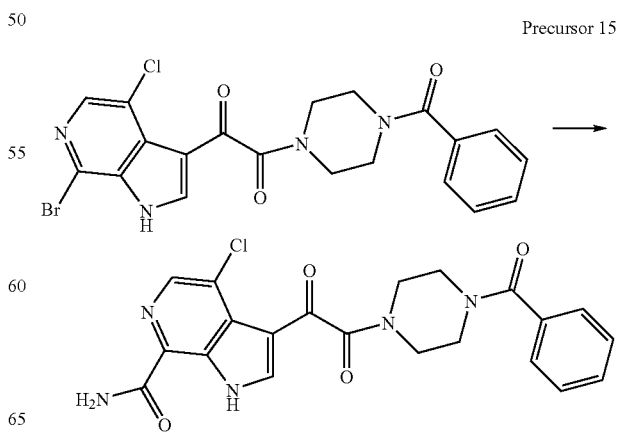

To a solution of precursor 5q (50 mg, 0.11 mmol) in DMF (1 ml) was added CuCN (30 mg, 0.335 mmol). The reaction mixture was heated at 170° C. for 30 min. After cooling to ambient temperature, the reaction mixture was diluted with MeOH (15 ml), filtered under gravity, and the filtrate evaporated in vacuo to afforded a brownish residue. To the residue in EtOH (3 ml) at ambient temperature was bubbled hydrogen chloride gas for 10 minutes to give a yellow solution, which was purified by preparative reverse phase HPLC using the method: Start % B=15, Final % B=85, Gradient time=15 min, Flow Rate=40 ml/min, Column: XTERRA C18 5 um 30×100 mm, Fraction Collection: 10.40-10.85 min; $^1$H NMR: (CD$_3$OD) 8.35 (s, 1H), 8.33 (s, 1H), 7.42 (b s, 5H), 3.95-3.41 (b m, 8H); LC/MS: (ES+) m/z (M+H)$^+$=440, 442; HPLC (alternate conditions B, column G) R$_t$=1.820.

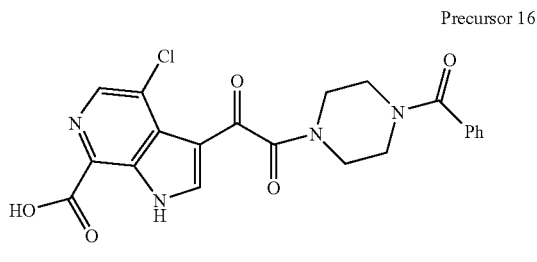

Precursor 16

Preparation of Precursor 16:

To a suspension of precursor 15 (6 mg, 13 μmol) in a mixture of AcOH (0.5 ml) and Ac$_2$O (1.0 ml) at 0° C. was charged with sodium nitrite (17 mg, 246 μmol). The reaction mixture was stirred at 0° C. for 30 min. and then at ambient temperature for 1 hour. After addition of MeOH (4 ml), the reaction mixture was purified by preparative reverse phase HPLC to give the TFA solvate of the title compound using the method: Start % B=15, Final % B=80, Gradient time=15 min, Flow Rate=25 ml/min, Column: YMC C18 5 um 20×100 mm, Fraction Collection: 9.48-10.03 min. $^1$H NMR: (DMSO-d$_6$) δ 12.76 (s, 1H), 8.48 (s, 1H), 8.32 (d, J=3.0, 1H), 7.44 (b s, 5H), 3.97-3.47 (b m, overlapping with water peak, 8H); LC/MS: (ES+) m/z (M+H)$^+$=441, 443; HPLC (alternate conditions B, column G) R$_t$=1.530. Ref: Amide hydrolysis: Evans, D. A.; Carter, P. H.; Dinsmore, C. J.; Barrow, J. C.; Katz, J. L.; Kung, D. W. *Tetrahedron Lett.* 1997, 38, 4535 and references cited therein.

Additional Piperazine Precursors

N-(Benzoyl)-2-methylpiperazine, Precursor 17a, was prepared according to the procedure described in Ref. 90(b). $^1$H NMR (300 MHz, CD$_3$OD) δ 7.47 (m, 5H), 3.30-2.70 (m, 7H), 1.36 (d, 3H, J=6.90 Hz); $^{13}$C NMR (75 MHz, CD$_3$OD) δ171.0, 135.4, 129.7, 128.5, 126.3, 48.5, 44.3, 14.5;[2] HRMS m/z: (M+H)$^+$ calcd for C$_{12}$H$_{17}$N$_2$O: 205.1341, found 205.1341.

[2] Some carbon peaks are missing due to the overlap of signals.

(R)—N-(Benzoyl)-2-methylpiperazine, Precursor 17b, was prepared according to the procedure described in Ref. 90(b). $^1$H NMR (300 MHz, CD$_3$OD) δ7.41 (m, 5H), 3.31-2.70 (m, 7H), 1.35 (d, 3H, J=6.90 Hz). MS m/z: (M+H)$^+$ Calc'd for C$_{12}$H$_{17}$N$_2$O: 205.13; Found 205.16. HPLC retention time: 0.51 minutes (column L).

(S)—N-(Benzoyl)-2-methylpiperazine, Precursor 17c, was prepared according to the procedure described in Ref. 90(b). $^1$H NMR (300 MHz, CD$_3$OD) δ7.41 (m, 5H), 3.31-2.72 (m, 7H), 1.35 (d, 3H, J=6.90 Hz). MS m/z: (M+H)$^+$ Calc'd for C$_{12}$H$_{17}$N$_2$O: 205.13; Found 205.16. HPLC retention time: 0.50 minutes (column L).

N-(Benzoyl)-2-ethylpiperazine, Precursor 17d, was prepared according to the procedure described in Ref. 90(b). $^1$H NMR (300 MHz, CD$_3$OD) δ7.49 (m, 5H), 3.34-2.80 (m, 7H), 2.10-1.70 (m, 2H), 0.85 (b, 3H); $^{13}$C NMR (75 MHz, CD$_3$OD) δ171.5, 135.1, 129.8, 128.5, 126.5, 48.5, 46.0, 43.9, 21.8, 9.6;[2] HRMS m/z: (M+H)$^+$ calcd for C$_{13}$H$_{19}$N$_2$O 219.1497, found 219.1501.

Preparation of Compounds of Formula I

EXAMPLE 1

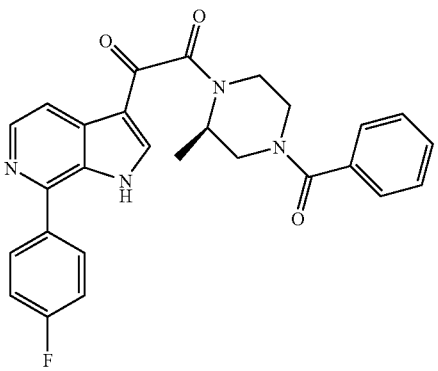

Typical procedure for coupling azaindole with aromatic boron reagent (An example of the general procedure described below for examples 2-14): Preparation of 1-benzoyl-3-(R)-methyl-4-[(7-(4-fluorophenyl)-6-azaindol-3-yl)-oxoacetyl]-piperazine is an example of Step E as described in Scheme 15. To a sealed tube, 1-(benzoyl)-3-(R)-methyl-4-[(7-chloro-6-azaindol-3-yl)-oxoacetyl]piperazine, Precursor 5a, (20 mg, 0.049 mmol), 4-fluorophenylboronic acid, Precursor 14a-9, (8.2 mg, 0.059 mmol), Pd(Ph$_3$P)$_4$ (5 mg) and K$_2$CO$_3$ (20 mg, 0.14 mmol) were combined in 1.5 mL of DMF and 1.5 mL of water. The reaction was heated at 110-120° C. for 10 h. After the mixture cooled down to rt, it was poured into 20 mL of water. The solution was extracted with EtOAc (4×20 mL). The combined extract was concentrated to give a residue which was purified using a Shimadzu automated preparative HPLC System to give compound 1-benzoyl-3-(R)-methyl-4-[(7-(4-fluorophenyl)-6-azaindol-3-yl)-oxoacetyl]piperazine (1.8 mg, 7.9%). MS m/z: (M+H)$^+$ Calc'd for C$_{27}$H$_{24}$FN$_4$O$_3$: 471.18; found 471.08. HPLC retention time: 1.12 minutes (column A).

EXAMPLES 2-14

Examples 2-14 were prepared according to the following general method in a manner analogous to the preparation of Example 1.

Typical procedure for coupling azaindole with aromatic boron reagent: To a sealed tube, an appropriately substituted azaindole precursor (0.049 mmol), an appropriate boronic acid derivative (0.059 mmol), Pd(Ph$_3$P)$_4$ (5 mg) and K$_2$CO$_3$ (20 mg, 0.14 mmol) were combined in 1.5 mL of DMF and 1.5 mL of water. The reaction was heated at 110-120° C. for 10 h. After the mixture cooled down to rt, it was poured into 20 mL of water. The solution was extracted with EtOAc (4×20 mL). The combined extract was concentrated in vacuo to give a residue which was purified using a Shimadzu automated preparative HPLC System to provide the desired compound.

EXAMPLE 2

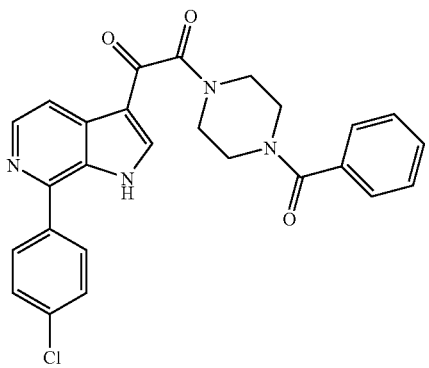

Example 2, was prepared according to the general method described above starting from Precursor 5g and 4-chlorophenyl boronic acid, Precursor 14a-10, to provide 1-benzoyl-4-[(7-(4-chlorophenyl)-6-azaindol-3-yl)-oxoacetyl]piperazine. MS m/z: (M+H)$^+$ Calc'd for $C_{27}H_{24}FN_4O_3$: 473.14; found 473.13. HPLC retention time: 1.43 minutes (column B).

EXAMPLE 3

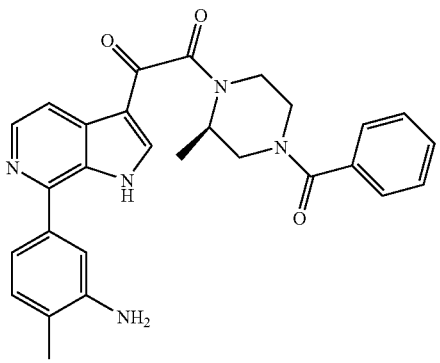

Example 3, was prepared according to the general method described above starting from Precursor 5a and 3-amino-4-methylphenyl boronic acid, Precursor 14a-11, to provide 1-benzoyl-3-®-methyl-4-[(7-(3-amino-4-methylphenyl)-6-azaindol-3-yl)-oxoacetyl]piperazine. MS m/z: (M+H)$^+$ Calc'd for $C_{27}H_{24}ClN_4O_3$: 482.22; found 482.25. HPLC retention time: 1.35 minutes (column B).

EXAMPLE 4

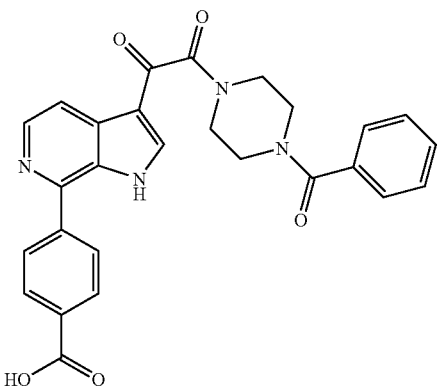

Example 4, was prepared according to the general method described above starting from Precursor 5g and 4-hydroxycarbonylphenyl boronic acid, Precursor 14a-12, to provide 1-benzoyl-4-[(7-(4-carboxy-phenyl)-6-azaindol-3-yl)-oxoacetyl]piperazine. MS m/z: (M+H)$^+$ Calc'd for $C_{27}H_{24}ClN_4O_3$: 483.17; found 483.10. HPLC retention time: 1.00 minutes (column A).

EXAMPLE 5

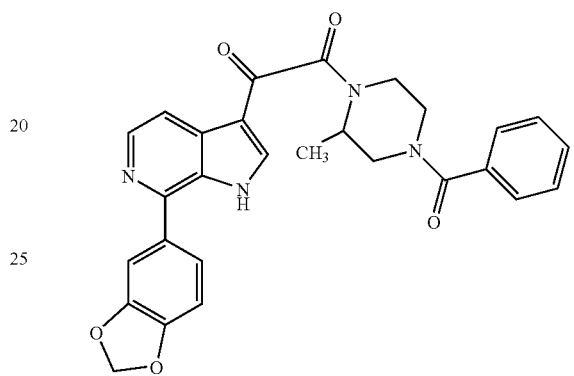

Example 5, was prepared according to the general method described above from 1-benzoyl-3-methyl-4-[(7-chloro-6-azaindol-3-yl)-oxoacetyl]piperazine and 3,4-methylenedioxyphenyl boronic acid, Precursor 14a-13, to provide 1-benzoyl-3-methyl-4-[(7-(3,4-methylenedioxyphenyl)-6-azaindol-3-yl)-oxoacetyl]piperazine. MS m/z: (M+H)$^+$ Calc'd for $C_{28}H_{25}N_4O_5$: 497.18; found 497.03. HPLC retention time: 1.41 minutes (column B).

EXAMPLE 6

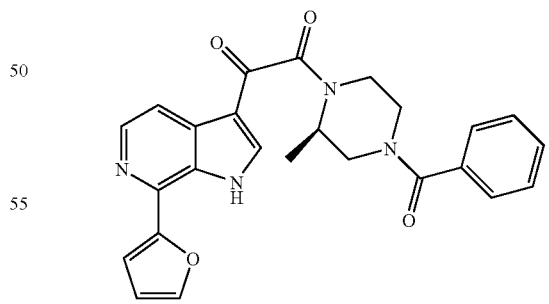

Example 6, was prepared according to the general method described above starting from Precursor 5a and furan-2-yl boronic acid to provide 1-benzoyl-3-®-methyl-4-[(7-(furan-2-yl)-6-azaindol-3-yl)-oxoacetyl]piperazine; MS m/z: (M+H)$^+$ Calc'd for $C_{25}H_{23}N_4O_4$: 443.17; found 443.12. HPLC retention time: 1.20 minutes (column A).

EXAMPLE 7

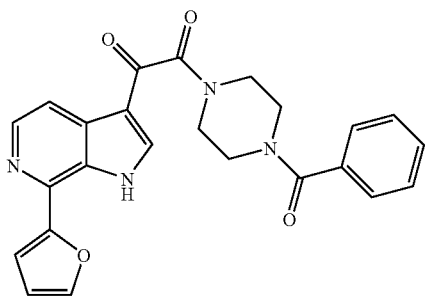

Example 7, was prepared according to the general method described above starting from Precursor 5g and furan-2-yl boronic acid to provide 1-benzoyl-4-[(7-(furan-2-yl)-6-azaindol-3-yl)-oxoacetyl]piperazine MS m/z: (M+H)+ Calc'd for $C_{24}H_{21}N_4O_4$: 429.16; found 428.98. HPLC retention time: 1.36 minutes (column A).

EXAMPLE 8

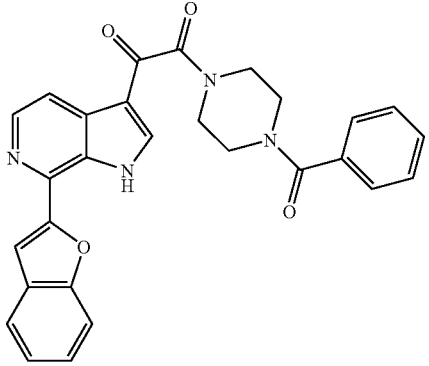

Example 8, was prepared according to the general method described above starting from Precursor 5g and benzofuran-2-yl boronic acid to provide 1-benzoyl-4-[(7-(benzofuran-2-yl)-6-azaindol-3-yl)-oxoacetyl]piperazine MS m/z: (M+H)+ Calc'd for $C_{28}H_{23}N_4O_4$: 479.17; found 479.09. HPLC retention time: 1.67 minutes (column B).

EXAMPLE 9

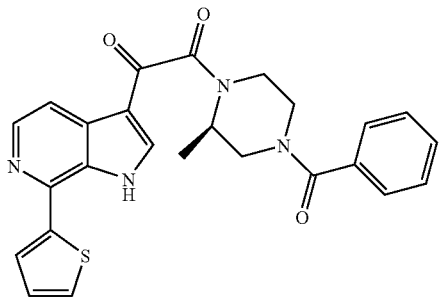

Example 9, was prepared according to the general method described above starting from Precursor 5a and thien-2-yl boronic acid to provide 1-(benzoyl)-3-®-methyl-4-[(7-(thien-2-yl)-6-azaindol-3-yl)-oxoacetyl]piperazine MS m/z: (M+H)+ Calc'd for $C_{25}H_{23}N_4O_3S$: 459.15; found 459.10. HPLC retention time: 1.20 minutes (column A).

EXAMPLE 10

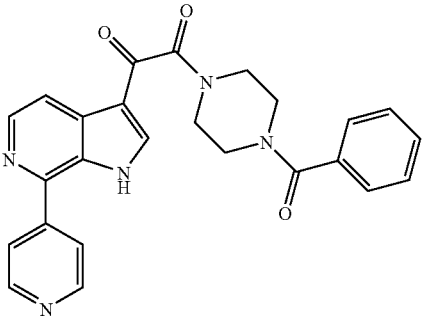

Example 10, was prepared according to the general method described above starting from Precursor 5g and pyridin-4-yl boronic acid to provide 1-(benzoyl)-4-[(7-(pyridin-4-yl)-6-azaindol-3-yl)-oxoacetyl]piperazine MS m/z: (M+H)+ Calc'd for $C_{25}H_{22}N_5O_3$: 440.17; found 440.10. HPLC retention time: 0.97 minutes (column A).

EXAMPLE 11

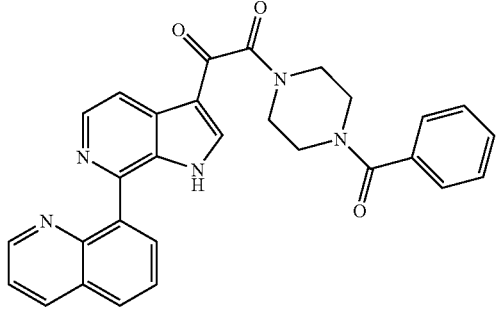

Example 11, was prepared according to the general method described above starting from Precursor 5g and quinolin-8-yl boronic acid, Precursor 14a-14, to provide 1-benzoyl-4-[(7-(quinolin-8-yl)-6-azaindol-3-yl)-oxoacetyl]piperazine MS m/z: (M+H)+ Calc'd for $C_{25}H_{22}N_5O_3$: 490.19; found 490.09. HPLC retention time: 1.34 minutes (column B).

EXAMPLE 12

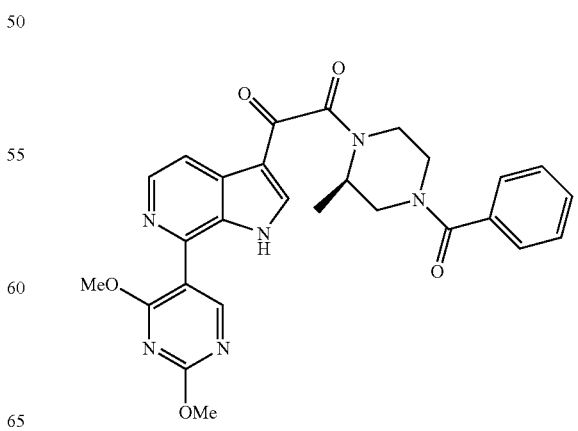

Example 12, was prepared according to the general method described above starting from Precursor 5a and 2,4-dimethoxypyrimidin-5-yl boronic acid, Precursor 14a-4, to provide 1-benzoyl-3-®-methyl-4-[(7-(2,4-dimethoxy-pyrimidin-5-yl)-6-azaindol-3-yl)-oxoacetyl]piperazine MS m/z: (M+H)$^+$ Calc'd for $C_{27}H_{27}N_6O_5$: 515.20; found 515.28. HPLC retention time: 1.17 minutes (column B).

EXAMPLE 13

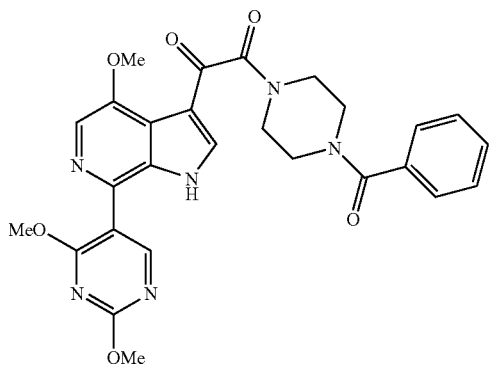

Example 13, was prepared according to the general method described above starting from Precursor 5b and 2,4-dimethoxypyrimidin-5-yl boronic acid, Precursor 14a-4, to provide 1-benzoyl-4-[(4-methoxy-7-(2,4-dimethoxy-pyrimidin-5-yl)-6-azaindol-3-yl)-oxoacetyl]piperazine $^1$H NMR (500 MHz, CD$_3$OD) δ 8.71 (s, 1H), 8.64 (s, 1H), 8.21 (s, 1H), 7.48 (s, 5H), 4.15 (s, 3H), 4.13 (s, 3H), 3.84 (s, 3H), 3.64-3.34 (m, 8H). MS m/z: (M+H)$^+$ Calc'd for $C_{29}H_{35}N_6O_6$: 531.20; found 531.26. HPLC retention time: 1.09 minutes (column A).

EXAMPLE 14

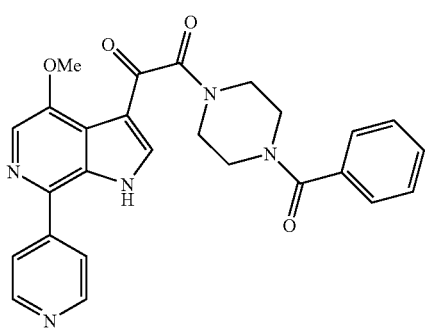

Example 14, was prepared according to the general method described above starting from Precursor 5b and pyridin-4-yl boronic acid to provide 1-benzoyl-4-[(4-methoxy-7-(pyridin-4-yl)-6-azaindol-3-yl)-oxoacetyl]piperazine MS m/z: (M+H)$^+$ Calc'd for $C_{26}H_{24}N_5O_4$: 470.18; found 470.32. HPLC retention time: 1.02 minutes (column A).

EXAMPLE 15

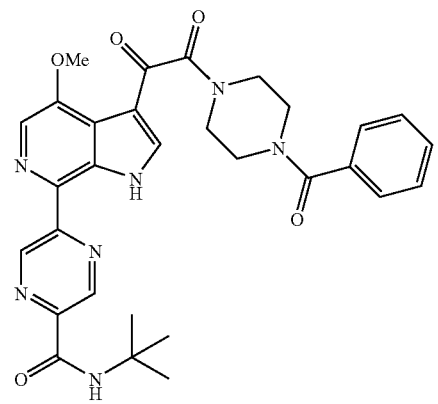

Typical Procedure for Coupling Azaindole with Aromatic Tin Reagent (an Example of the General Procedure Described Below for Examples 16-53):

Preparation of Example 15, 1-benzoyl-4-[(4-methoxy-7-(2-(1,1-dimethylethylaminocarbonyl)-pyrazin-5-yl)-6-azaindol-3-yl)-oxoacetyl]piperazine is an example of Step E as described in Scheme 15. To a sealed tube, 1-benzoyl-4-[(7-chloro-4-methoxy-6-azaindol-3-yl)-oxoacetyl]piperazine, Precursor 5b, (20 mg), 2-(1,1-dimethylethylaminocarbonyl)-5-tributylstannyl-pyrazine (1.2 equivalents, 27 mg.) and Pd(Ph$_3$P)$_4$ (1 mg) were combined in 1.5 mL of dioxane. The reaction was heated at 110-120° C. for 10 h. After the mixture cooled down to room temperature, it was poured into 5 mL of water. The solution was extracted with EtOAc (4×5 mL). The combined extract was concentrated in vacuo to give a residue which was purified using a Shimadzu automated preparative HPLC System to give compound 1-benzoyl-4-[(4-methoxy-7-(2-(1,1-dimethylethylaminocarbonyl)-pyrazin-5-yl)-6-azaindol-3-yl)-oxoacetyl]piperazine (1 mg); MS m/z: (M+H)$^+$ Calc'd for $C_{30}H_{32}N_7O_5$: 570.25; found 570.43. HPLC retention time: 1.83 minutes (column B).

EXAMPLES 16-54

Examples 16-54 were prepared according to the following general procedure by a method analogous to the method described for the preparation of Example 15.

Typical procedure for coupling azaindole with aromatic tin reagent: To a sealed tube, an appropriate azaindole (0.049 mmol), an appropriate stannane (0.059 mmol) and Pd(Ph$_3$P)$_4$ (1 mg) were combined in 1.5 mL of dioxane. The reaction was heated at 110-120° C. for 10 h. After the mixture cooled down to rt, it was poured into 5 mL of water. The solution was extracted with EtOAc (4×5 mL). The combined extract was concentrated to give a residue which was purified using a Shimadzu automated preparative HPLC System to provide the desired compound.

EXAMPLE 16

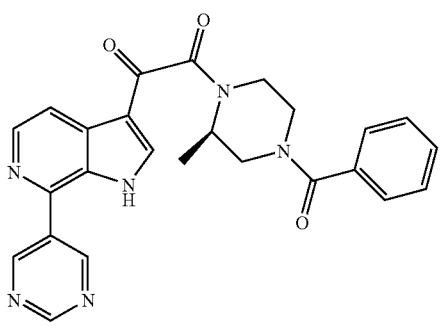

Example 16, was prepared according to the general method described above starting from Precursor 5a and pyrimidin-5-yl tributyltin, Precursor 14-9, to provide 1-benzoyl-3-(R)-methyl-4-[(7-(pyrimidin-5-yl)-6-azaindol-3-yl)-oxoacetyl]piperazine; MS m/z: (M+H)$^+$ Calc'd for $C_{25}H_{23}N_6O_3$: 455.18; found 455.17. HPLC retention time: 1.33 minutes (column B).

EXAMPLE 17

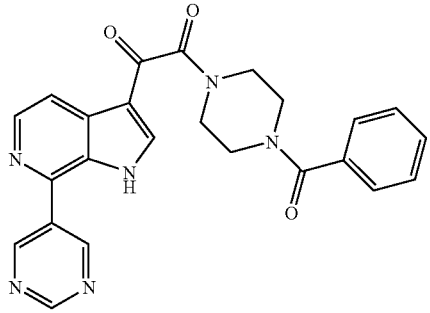

Example 17, was prepared according to the general method described above starting from Precursor 5g and pyrimidin-5-yl tributyltin, Precursor 14-9, to provide 1-benzoyl-4-[(7-(pyrimidin-5-yl)-6-azaindol-3-yl)-oxoacetyl]piperazine MS m/z: (M+H)$^+$ Calc'd for $C_{25}H_{23}N_6O_3$: 441.17; found 441.07. HPLC retention time: 1.30 minutes (column B).

EXAMPLE 18

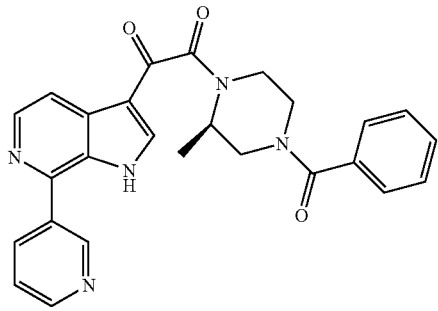

Example 18, was prepared according to the general method described above starting from Precursor 5a and pyridin-3-yl tributyltin, Precursor 14a-2, to provide 1-benzoyl-3-(R)-methyl-4-[(7-(pyridin-3-yl)-6-azaindol-3-yl)-oxoacetyl]piperazine MS m/z: (M+H)$^+$ Calc'd for $C_{26}H_{24}N_5O_3$: 454.19; found 454.17. HPLC retention time: 1.11 minutes (column A).

EXAMPLE 19

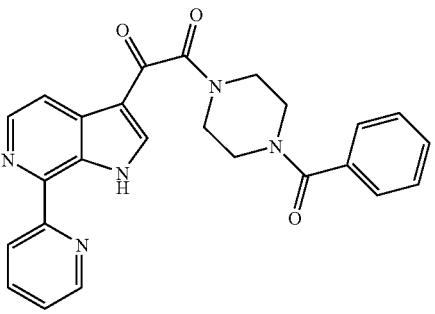

Example 19, was prepared according to the general method described above starting from Precursor 5g and pyridin-2-yl tributyltin, Precursor 14a-19, to provide 1-benzoyl-4-[(7-(pyridin-2-yl)-6-azaindol-3-yl)-oxoacetyl]piperazine MS m/z: (M+H)$^+$ Calc'd for $C_{25}H_{22}N_5O_3$: 440.17; found 440.07. HPLC retention time: 1.40 minutes (column B).

EXAMPLE 20

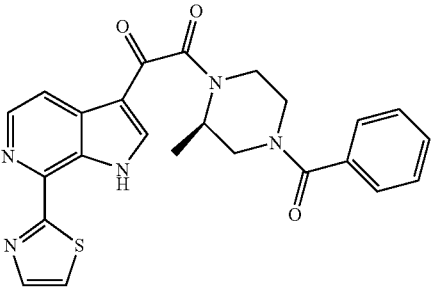

Example 20, was prepared according to the general method described above starting from Precursor 5a and thiazol-2-yl tributyltin, Precursor 14a-21, to provide 1-benzoyl-3-(R)-methyl-4-[(7-(thiazol-2-yl)-6-azaindol-3-yl)oxoacetyl]piperazine; MS m/z: (M+H)$^+$ Calc'd for $C_{24}H_{22}N_5O_3S$: 460.14; found 460.15. HPLC retention time: 1.48 minutes (column B).

EXAMPLE 21

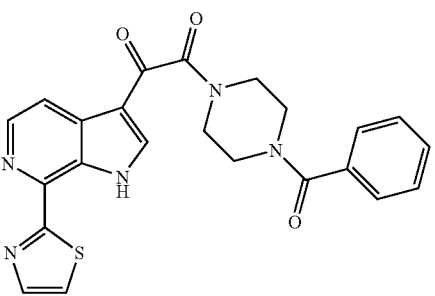

Example 21, was prepared according to the general method described above starting from Precursor 5g and thiazol-2-yl tributyltin, Precursor 14a-21, to provide 1-benzoyl-4-[(7-

(thiazol-2-yl)-6-azaindol-3-yl)-oxoacetyl]piperazine; MS m/z: (M+H)$^+$ Calc'd for $C_{23}H_{20}N_5O_3S$: 446.13; found 446.03. HPLC retention time: 1.44 minutes (column B).

EXAMPLE 22

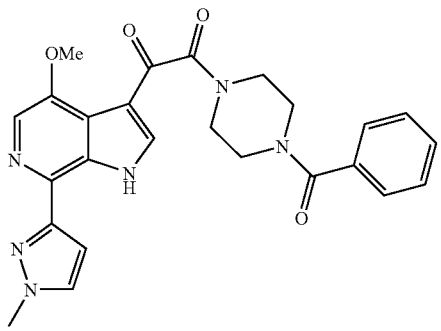

Example 22, was prepared according to the general method described above starting from Precursor 5b and 1-methylpyrazol-3-yl tributyltin, to provide 1-benzoyl-4-[(4-methoxy-7-(1-methyl-pyrazol-3-yl)-6-azaindol-3-yl)-oxoacetyl]piperazine; MS m/z: (M+H)$^+$ Calc'd for $C_{25}H_{25}N_6O_4$: 473.19; found 473.28. HPLC retention time: 1.18 minutes (column B).

EXAMPLE 23

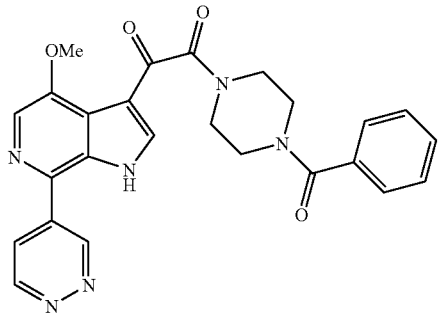

Example 23, was prepared according to the general method described above starting from Precursor 5b and Intermediate 14-9 to provide 1-benzoyl-4-[(4-methoxy-7-(pyridazin-4-yl)-6-azaindol-3-yl)-oxoacetyl]piperazine; MS m/z: (M+H)$^+$ Calc'd for $C_{25}H_{23}N_6O_4$: 471.18; found 471.26. HPLC retention time: 1.20 minutes (column B).

EXAMPLE 24

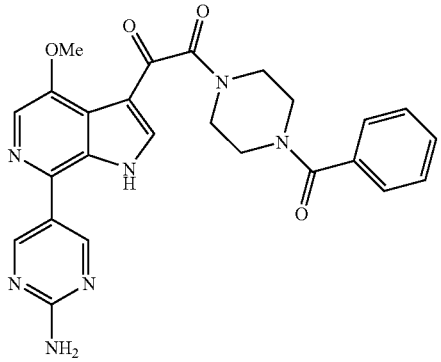

Example 24, was prepared according to the general method described above starting from Precursor 5b and 2-aminopyrimidin-5-yl tributyltin, to provide 1-benzoyl-4-[(4-methoxy-7-(2-amino-pyrimidin-5-yl))-6-azaindol-3-yl)-oxoacetyl]piperazine MS m/z: (M+H)$^+$ Calc'd for $C_{25}H_{24}N_7O_4$: 486.19: found 486.24. HPLC retention time: 1.19 minutes (column A).

EXAMPLE 25

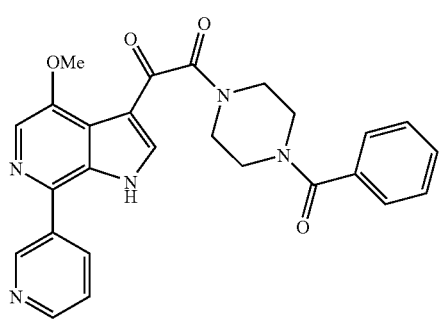

Example 25, was prepared according to the general method described above starting from Precursor 5b and pyridin-3-yl tributyltin, Precursor 14a-2, to provide 1-benzoyl-4-[(4-methoxy-7-(pyridin-3-yl)-6-azaindol-3-yl)-oxoacetyl]piperazine; MS m/z: (M+H)$^+$ Calc'd for $C_{26}H_{24}N_5O_4$: 470.18; found 470.19. HPLC retention time: 1.04 minutes (column A).

EXAMPLE 26

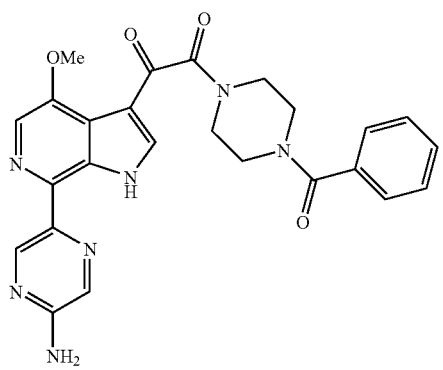

Example 26, was prepared according to the general method described above starting from Precursor 5b and 2-aminopyrazin-5-yl trimethyltin, Precursor 14-28, to provide 1-benzoyl-4-[(4-methoxy-7-(2-amino-pyrazin-5-yl))-6-azaindol- 3-yl)-oxoacetyl]piperazine; MS m/z: (M+H)+ Calc'd for C$_{25}$H$_{24}$N$_7$O$_4$: 486.19; found 470.19. HPLC retention time: 1.13 minutes (column B).

EXAMPLE 27

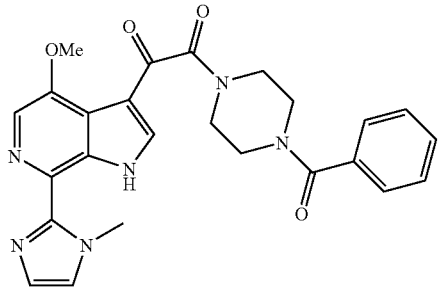

Example 27, was prepared according to the general method described above starting from Precursor 5b and 1-methylimidazol-2-yl trimethyltin, Precursor 14-5, to provide 1-benzoyl-4-[(4-methoxy-7-(1-methyl-imidazol-2-yl)-6-azaindol-3-yl)-oxoacetyl]piperazine; MS m/z: (M+H)+ Calc'd for C$_{25}$H$_{25}$N$_6$O$_4$: 473.18; found 473.27. HPLC retention time: 1.07 minutes (column B).

EXAMPLE 28

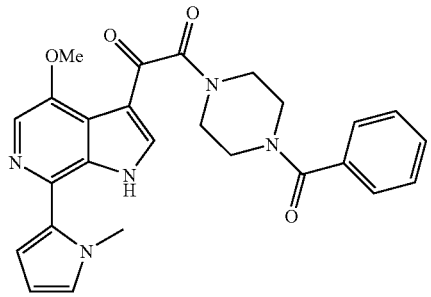

Example 28, was prepared according to the general method described above starting from Precursor 5b and 1-methylpyrrol-2-yl tributyltin, Precursor 14a-15, to provide 1-benzoyl-4-[(4-methoxy-7-(1-methyl-pyrrol-2-yl)-6-azaindol-3-yl)-oxoacetyl]piperazine; MS m/z: (M+H)+ Calc'd for C$_{26}$H$_{26}$N$_5$O$_4$: 472.20; found 470.26. HPLC retention time: 1.11 minutes (column A).

EXAMPLE 29

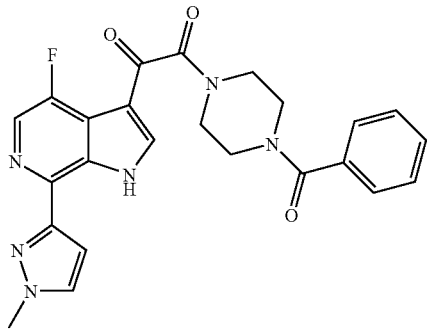

Example 29, was prepared according to the general method described above starting from Precursor 5i and 1-methylpyrazol-3-yl tributyltin, to provide 1-benzoyl-4-[(4-fluoro-7-(1-methyl-pyrazol-3-yl)-6-azaindol-3-yl)-oxoacetyl]piperazine; MS m/z: (M+H)+ Calc'd for C$_{24}$H$_{22}$FN$_6$O$_3$: 461.17; found 461.24. HPLC retention time: 1.36 minutes (column A).

EXAMPLE 30

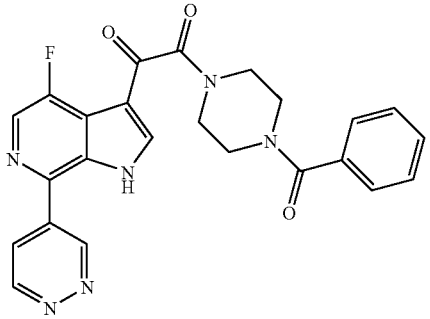

Example 30, was prepared according to the general method described above starting from Precursor 5i and pyridazin-4-yl tributyltin, Precursor 14-8, to provide 1-benzoyl-4-[(4-fluoro-7-(pyridazin-4-yl)-6-azaindol-3-yl)-oxoacetyl]piperazine $^1$H NMR (500 MHz, CD$_3$OD) δ 9.72 (s, 1H), 9.39 (s, 1H), 8.42 (m, 2H), 8.22 (s, 1H), 7.47 (s, 5H), 3.84-3.38 (m, 8H). MS m/z: (M+H)+ Calc'd for C$_{24}$H$_{20}$FN$_6$O$_3$: 459.16; found 459.25. HPLC retention time: 1.26 minutes (column A).

EXAMPLE 32

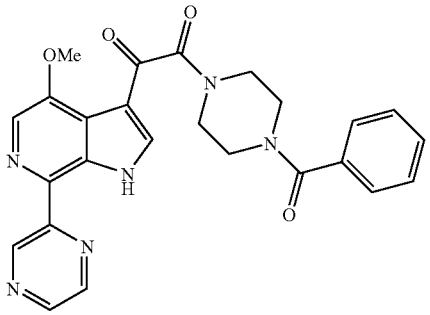

Example 32, was prepared according to the general method described above starting from Precursor 5b and pyrazin-2-yl tributyltin, Precursor 14a-1, to provide 1-benzoyl-4-[(4-methoxy-7-(pyrazin-2-yl)-6-azaindol-3-yl)-oxoacetyl]piperazine; MS m/z: (M+H)+ Calc'd for C$_{25}$H$_{23}$N$_6$O$_3$: 471.18; found 471.17. HPLC retention time: 1.35 minutes (column A).

EXAMPLE 33

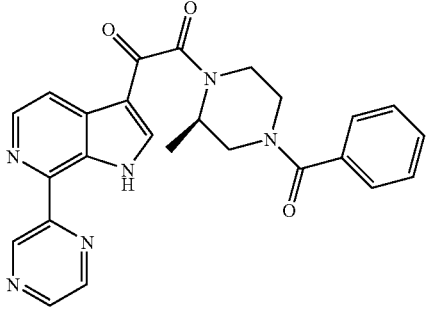

Example 33, was prepared according to the general method described above starting from Precursor 5a and pyrazin-2-yl tributyltin, Precursor 14a-1, to provide 1-benzoyl-3-(R)-methyl-4-[(7-(pyrazin-2-yl)-6-azaindol-3-yl)-oxoacetyl]piperazine; MS m/z: (M+H)+ Calc'd for $C_{25}H_{23}N_6O_3$: 455.18; found 455.26. HPLC retention time: 1.46 minutes (column A).

EXAMPLE 34

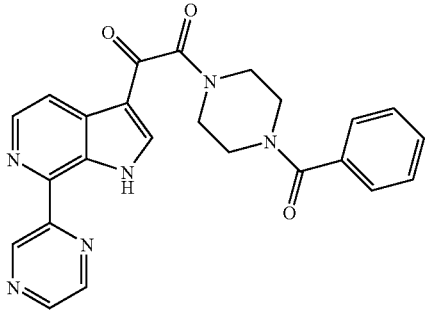

Example 34, was prepared according to the general method described above starting from Precursor 5g and pyrazin-2-yl tributyltin, Precursor 14a-1, to provide 1-benzoyl-4-[(7-(pyrazin-2-yl)-6-azaindol-3-yl)-oxoacetyl]piperazine; MS m/z: (M+H)+ Calc'd for $C_{24}H_{21}N_6O_3$: 441.17; found 441.22. HPLC retention time: 1.22 minutes (column A).

EXAMPLE 35

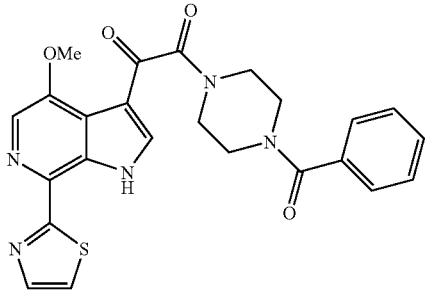

Example 35, was prepared according to the general method described above starting from Precursor 5b and thiazol-2-yl tributyltin, Precursor 14a-21, to provide 1-(benzoyl)-4-[(4-methoxy-7-(thiazol-2-yl)-6-azaindol-3-yl)-oxoacetyl]piperazine; MS m/z: (M+H)+ Calc'd for $C_{24}H_{22}N_5O_3S$: 476.14; found 476.20. HPLC retention time: 1.25 minutes (column B).

EXAMPLE 36

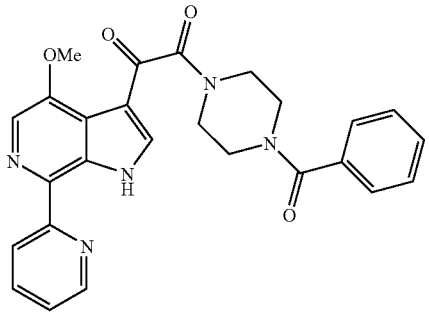

Example 36, was prepared according to the general method described above starting from Precursor 5b and pyridin-2-yl tributyltin, Precursor 14a-19, to provide 1-benzoyl-4-[(4-methoxy-7-(pyridin-2-yl)-6-azaindol-3-yl)-oxoacetyl]piperazine; MS m/z: (M+H)+ Calc'd for $C_{26}H_{24}N_5O_4$: 470.18; found 470.17. HPLC retention time: 1.04 minutes (column A).

EXAMPLE 37

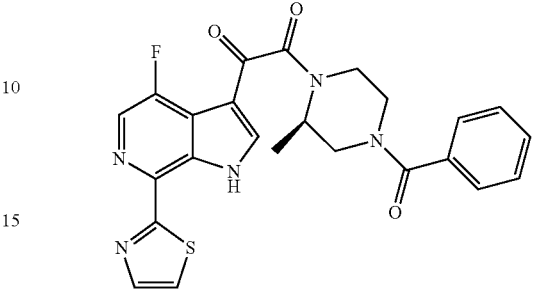

Example 37, was prepared according to the general method described above starting from Precursor 5j and thiazol-2-yl tributyltin, Precursor 14a-21, to provide 1-benzoyl-3-(R)-methyl-4-[(4-fluoro-7-(thiazol-2-yl)-6-azaindol-3-yl)-oxoacetyl]piperazine; MS m/z: (M+H)+ Calc'd for $C_{24}H_{21}FN_5O_3S$: 478.13; found 478.13. HPLC retention time: 1.34 minutes (column A).

EXAMPLE 38

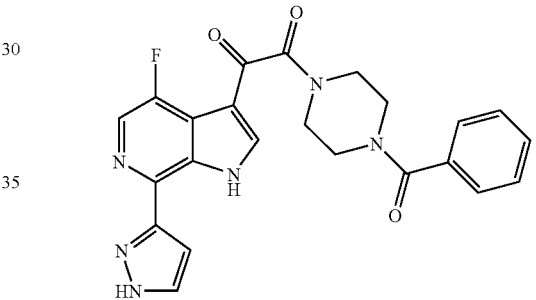

Example 38, was prepared according to the general method described above starting from Precursor 5i and pyrazol-3-yl tributyltin, to provide 1-benzoyl-4-[(4-fluoro-7-(pyrazol-3-yl)-6-azaindol-3-yl)-oxoacetyl]piperazine MS m/z: (M+H)+ Calc'd for $C_{23}H_{20}FN_6O_3$: 447.16; found 447.15. HPLC retention time: 1.26 minutes (column A).

EXAMPLE 39

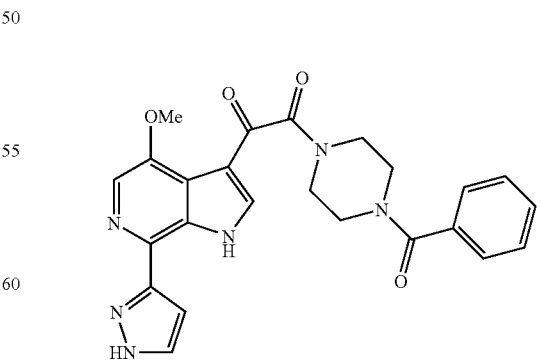

Example 39, was prepared according to the general method described above starting from Precursor 5b and pyrazol-3-yl tributyltin, to provide 1-benzoyl-4-[(4-methoxy-7-(pyrazol- 3-yl)-6-azaindol-3-yl)-oxoacetyl]piperazine; MS m/z: (M+H)+ Calc'd for $C_{24}H_{23}N_6O_4$: 459.18; found 459.21. HPLC retention time: 1.11 minutes (column A).

EXAMPLE 40

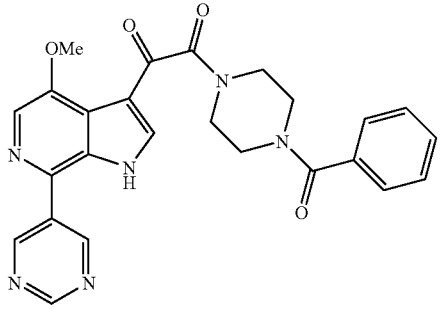

Example 40, was prepared according to the general method described above starting from Precursor 5b and pyrimidin-5-yl tributyltin, Precursor 14-9, to provide 1-benzoyl-4-[(4-methoxy-7-(pyrimidin-5-yl)-6-azaindol-3-yl)-oxoacetyl]piperazine MS m/z: (M+H)+ Calc'd for $C_{25}H_{23}N_6O_4$: 471.18; found 471.20. HPLC retention time: 1.61 minutes (column A).

EXAMPLE 41

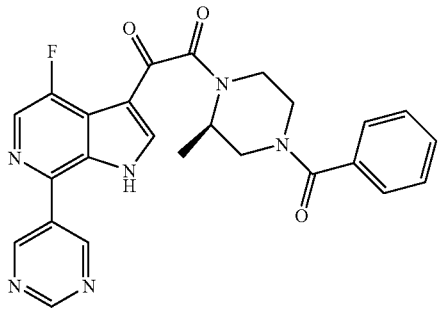

Example 41, was prepared according to the general method described above starting from Precursor 5j and pyrimidin-5-yl tributyltin, Precursor 14-9, to provide 1-benzoyl-3-(R)-methyl-4-[(4-fluoro-7-(pyrimidin-5-yl)-6-azaindol-3-yl)-oxoacetyl]piperazine; $^1$H NMR (500 MHz, CD$_3$OD) δ 9.26 (m, 3H), 8.39 (m, 2H), 7.56 (m, 5H), 4.72-3.12 (m, 7H), 1.40-0.91 (m, 3H). MS m/z: (M+H)+ Calc'd for $C_{25}H_{22}FN_6O_3$: 473.17; found 473.17. HPLC retention time: 1.34 minutes (column A).

EXAMPLE 42

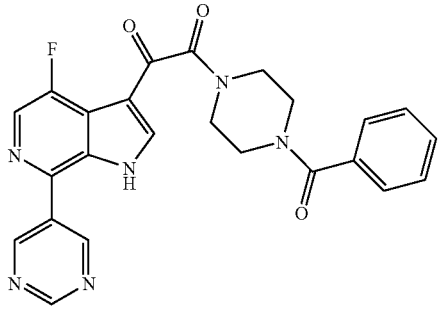

Example 42, was prepared according to the general method described above starting from Precursor 5i and pyrimidin-5-yl tributyltin, Precursor 14-9, to provide 1-benzoyl-4-[(4-fluoro-7-(pyrimidin-5-yl)-6-azaindol-3-yl)-oxoacetyl]piperazine; MS m/z: (M+H)+ Calc'd for $C_{24}H_{20}FN_6O_3$: 459.16; found 459.14. HPLC retention time: 1.28 minutes (column A).

EXAMPLE 43

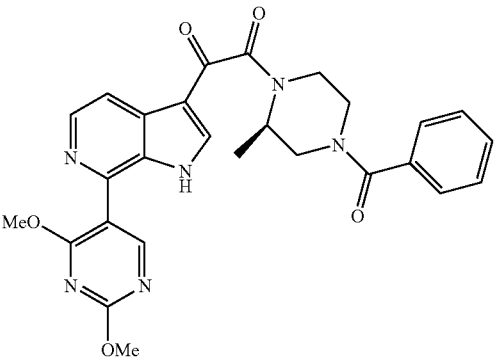

Example 43, (R)-1-(benzoyl)-3-methyl-4-[(7-(2,4-dimethoxy-pyrimidin-5-yl)-6-azaindol-3-yl)-oxoacetyl]piperazine MS m/z: (M+H)+ Calc'd for $C_{27}H_{27}N_6O_5$: 515.20; found 515.28. HPLC retention time: 1.17 minutes (column B).

EXAMPLE 44

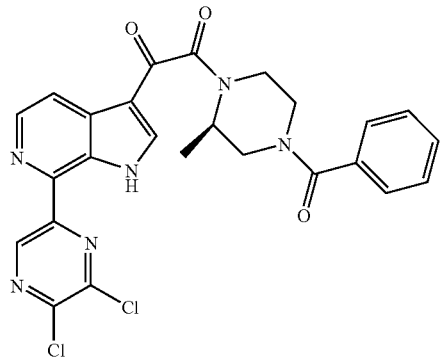

Example 44, was prepared according to the general method described above starting from Precursor 5a and 2,3-dichloro-pyrazin-5-yl tributyltin, Precursor 14-66, to provide 1-benzoyl-3-(R)-methyl-4-[(7-(2,3-dichloro-pyrazin-5-yl)-6-azaindol-3-yl)-oxoacetyl]piperazine; MS m/z: (M+Na)+ Calc'd for $C_{25}H_{20}Cl_2NaN_6O_3$: 545.09; found 545.29. HPLC retention time: 1.87 minutes (column B).

EXAMPLE 45

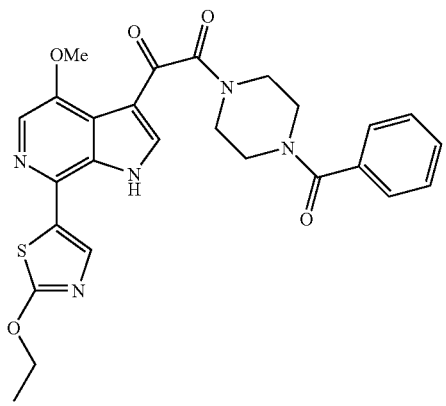

Example 45, was prepared according to the general method described above starting from Precursor 5b and 2-ethoxythiazol-5-yl tributyltin, Precursor 14-71, to provide 1-benzoyl-4-[(4-methoxy-7-(2-ethoxy-thiazol-5-yl)-6-azaindol-3-yl)-oxoacetyl]piperazine; MS m/z: (M+H)+ Calc'd for $C_{26}H_{26}N_5O_5S$: 520.17; found 520.24. HPLC retention time: 1.32 minutes (column A).

EXAMPLE 46

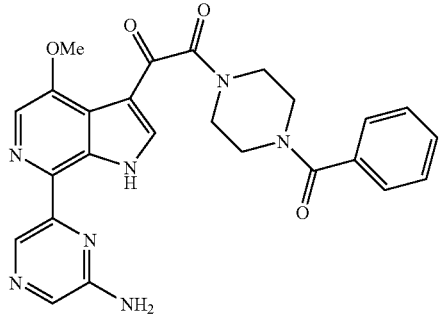

Example 46, was prepared according to the general method described above starting from Precursor 5b and the 2-aminopyrazin-6-yl stannane, Precursor 14-68, to provide 1-benzoyl-4-[(4-methoxy-7-(2-amino-pyrazin-6-yl)-6-azaindol-3-yl)-oxoacetyl]piperazine; MS m/z: (M+H)+ Calc'd for $C_{25}H_{24}N_7O_4$: 486.19; found 486.31. HPLC retention time: 1.22 minutes (column B).

EXAMPLE 47

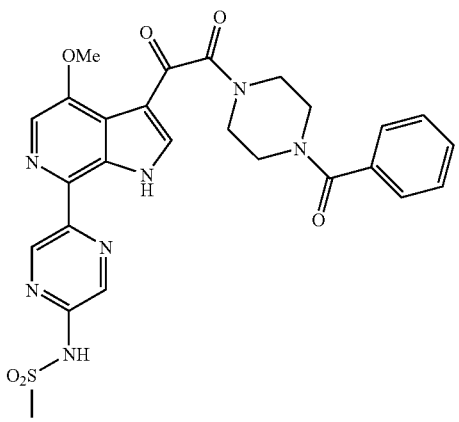

Example 47, was prepared according to the general method described above starting from Precursor 5b and 2-methylsulfonylamino-5-(tri-n-butylstannyl)pyrazine, Precursor 14-69, to provide 1-benzoyl-4-[(7-(2-methylsulfonylamino-pyrazin-5-yl)-6-azaindol-3-yl)-oxoacetyl]piperazine MS m/z: (M+H)+ Calc'd for $C_{26}H_{26}N_7O_6S$: 564.17; found 564.21. HPLC retention time: 1.24 minutes (column A).

EXAMPLE 48

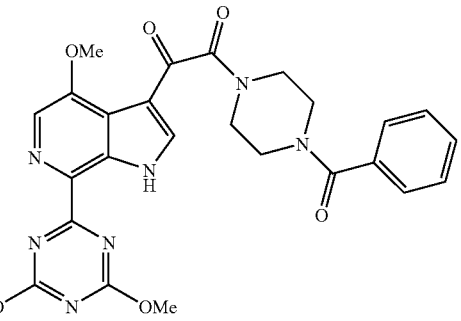

Example 48, was prepared according to the general method described above starting from Precursor 5b and 2,4-dimethoxy-1,3,5-triazin-6-yl tributyltin, Precursor 14-70, to provide 1-benzoyl-4-[(7-(2,4-dimethoxy-1,3,5-triazin-6-yl)-6-azaindol-3-yl)-oxoacetyl]piperazine; MS m/z: (M+H)+ Calc'd for $C_{26}H_{26}N_7O_6$: 532.19; found 532.12. HPLC retention time: 1.28 minutes (column A).

EXAMPLE 49

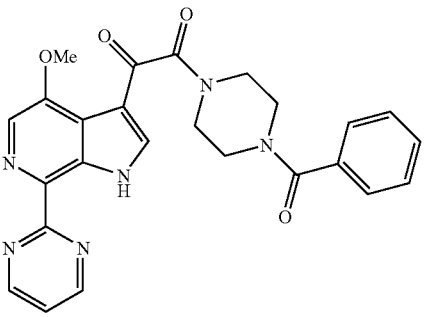

Example 49, was prepared according to the general method described above starting from Precursor 5b and pyrimidin-2-yl tributyltin, Precursor 14-67, to provide 1-benzoyl-4-[(4-methoxy-7-(pyrimidin-2-yl)-6-azaindol-3-yl)-oxoacetyl]piperazine; MS m/z: (M+H)+ Calc'd for $C_{25}H_{23}N_6O_4$: 471.18; found 471.29. HPLC retention time: 1.21 minutes (column A).

EXAMPLE 50

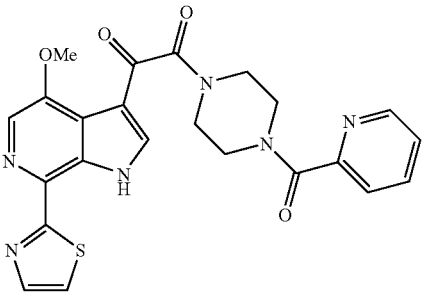

Example 50, was prepared from 1-(pyridin-2-yl)-4-[(4-methoxy-7-chloro-6-azaindol-3-yl)-oxoacetyl]piperazine and thiazol-2-yl tributyltin, Precursor 14a-21, according to the general method above to provide 1-(pyridin-2-yl)-4-[(4-methoxy-7-(thiazol-2-yl)-6-azaindol-3-yl)-oxoacetyl]piperazine MS m/z: (M+H)+ Calc'd for $C_{24}H_{25}N_6O_4S$: 477.13; found 477.22. HPLC retention time: 0.98 minutes (column A).

EXAMPLE 51

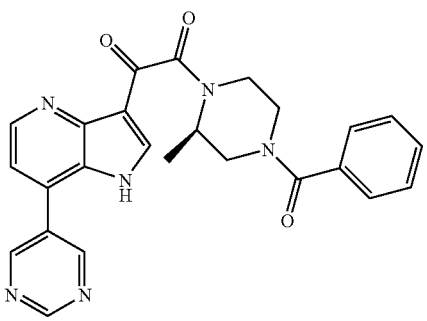

Example 51, was prepared according to the general method described above starting from Precursor 5d and pyrimidin-5-yl tributyltin, Precursor 14-9, to provide 1-benzoyl-3-(R)-methyl-4-[(7-(pyrimidin-5-yl)-4-azaindol-3-yl)-oxoacetyl]piperazine; MS m/z: (M+H)+ Calc'd for $C_{25}H_{23}N_6O_3$: 455.18; found 455.16. HPLC retention time: 0.98 minutes (column A).

EXAMPLE 52

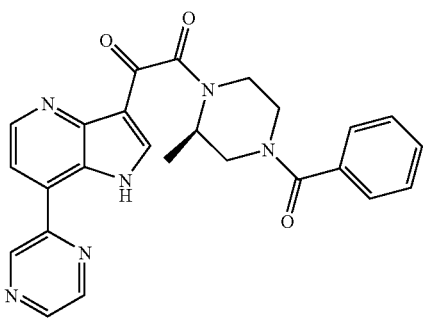

Example 52, was prepared according to the general method described above starting from Precursor 5d and pyrimidin-2-yl tributyltin, Precursor 14a-1, to provide 1-benzoyl-3-(R)-methyl-4-[(7-(pyrazin-2-yl)-4-azaindol-3-yl)-oxoacetyl]piperazine; MS m/z: (M+H)+ Calc'd for $C_{25}H_{23}N_6O_3$: 455.18; found 455.16. HPLC retention time: 1.09 minutes (column A).

EXAMPLE 53

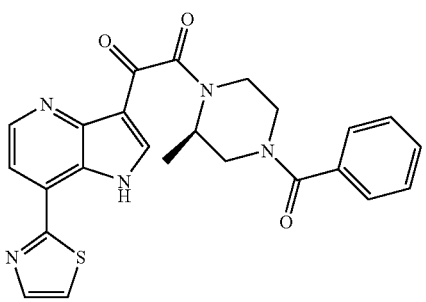

Example 53, was prepared according to the general method described above starting from Precursor 5d and thiazol-2-yl tributyltin, Precursor 14a-21, to provide 1-benzoyl-3-(R)-methyl-4-[(7-(thiazol-2-yl)-4-azaindol-3-yl)-oxoacetyl]piperazine; MS m/z: (M+H)+ Calc'd for $C_{24}H_{22}N_5O_3S$: 460.14; found 460.26. HPLC retention time: 1.02 minutes (column A).

EXAMPLE 54

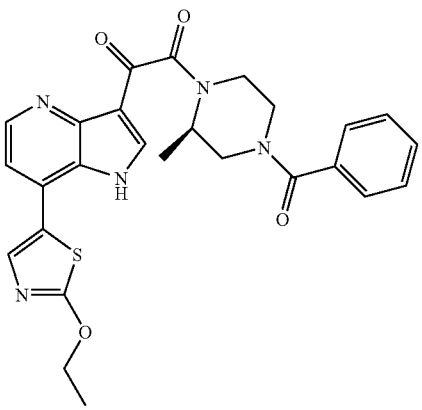

Example 54, was prepared according to the general method described above starting from Precursor 5d and 2-ethoxythiazol-5-yl tributyltin, Precursor 14-71, to provide 1-benzoyl-3-(R)-methyl-4-[(7-(2-ethoxy-thiazol-5-yl)-4-azaindol-3-yl)-oxoacetyl]piperazine; MS m/z: (M+H)+ Calc'd for $C_{26}H_{26}N_5O_4S$: 504.17; found 4504.18. HPLC retention time: 1.26 minutes (column A).

EXAMPLE 55

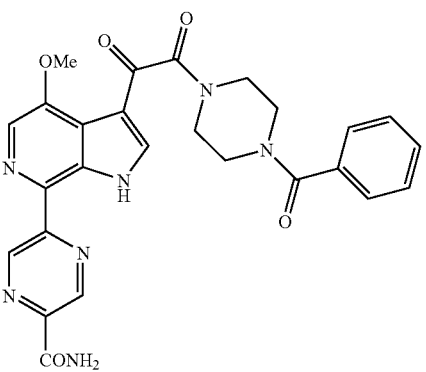

The compound of Example 15, 1-benzoyl-4-[(4-methoxy-7-(2-(1,1-dimethylethylaminocarbonyl)-pyrazin-5-yl)-6-azaindol-3-yl)-oxoacetyl]piperazine (20 mg) was dissolved in 1 drop of concentrated sulfuric acid. After 30 minutes, the mixture was diluted with 2 mL of methanol. The resulting solution was injected into a Shimadzu automated preparative HPLC System and the HPLC purification afforded the compound of Example 55, 1-benzoyl-4-[(4-methoxy-7-(2-aminocarbonyl-pyrazin-5-yl)-6-azaindol-3-yl)-oxoacetyl]piperazine (1 mg); MS m/z: (M+H)+ Calc'd for $C_{26}H_{24}N_7O_5$: 514.78; found 514.22. HPLC retention time: 1.44 minutes (column B).

EXAMPLE 56

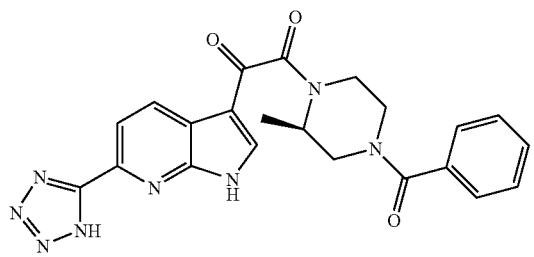

An excess of $NH_4Cl$ (27 mg) was added into a solution of 1-(benzoyl)-3-(R)-methyl-4-[(6-cyano-7-azaindol-3-yl)-oxoacetyl]piperazine (20 mg) and $NaN_3$ (16 mg) in DMF. The reaction was heated to reflux for 12 h. After cooling down, the mixture was concentrated under reduced pressure and the residue was purified using Shimadzu automated preparative HPLC System to give 1-benzoyl-3-(R)-methyl-4-[(6-(tetrazol-1-yl)-7-azaindol-3-yl)-oxoacetyl]piperazine (6.3 mg). MS m/z: (M+H)+ Calc'd for $C_{22}H_{21}N_8O_3$: 445.17; Found 3445.16. HPLC retention time: 1.42 minutes (column B); Column B: PHX-LUNA C18 4.6×30 mm.

EXAMPLE 57

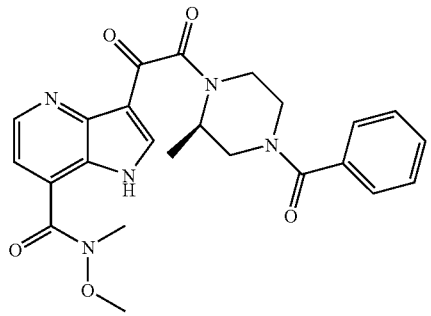

Preparation of 1-benzoyl-3-(R)-methyl-4-[(7-(methoxymethylamino)carbonyl)-4-azaindol-3-yl)-oxoacetyl]piperazine: A mixture of Precursor 13 (267 mg), N,O-dimethylhydroxylamine hydrogen chloride (248 mg), carbon tetrabromide (844 mg), pyridine (202 mg) and triphenylphosphine (668 mg) in dichloromethane (10 mL) was stirred at room temperature for 10 hours. After solvent was removed under vacuum, the residue was purified by using silica gel chromatography to afford 1-(benzoyl)-3-(R)-methyl-4-[(7-(methoxymethylamino)carbonyl)-4-azaindol-3-yl)- oxoacetyl]piperazine (56 mg); MS m/z: (M+H)+ Calc'd for $C_{24}H_{26}N_5O_5$: 464.19; found 464.25. HPLC retention time: 1.02 minutes (column A).

EXAMPLE 58

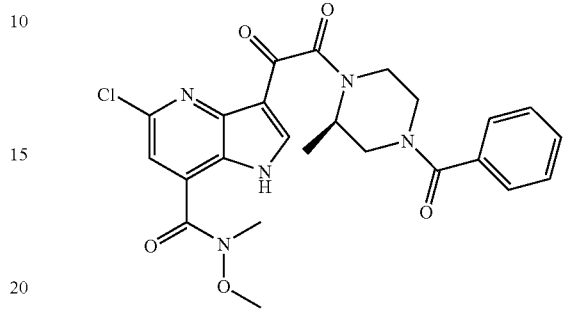

Example 58 was prepared according to the same procedure used in preparing Example 57 with the exception of using Precursor 11 as a starting material instead of Precursor 13. The procedure provided 1-benzoyl-3-(R)-methyl-4-[(5-chloro-(7-(methoxymethylamino)carbonyl)-4-azaindol-3-yl)-oxoacetyl]piperazine; MS m/z: (M+H)+ Calc'd for $C_{24}H_{25}ClN_5O_5$: 498.15; found 498.12. HPLC retention time: 1.39 minutes (column A).

General Procedure A to Prepare CO—NR1R2 from COOH

EXAMPLE 59

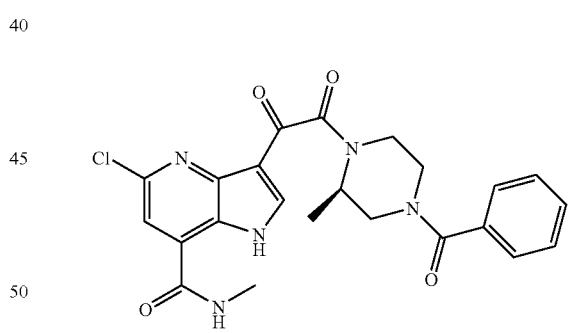

Preparation of 1-benzoyl-3-(R)-methyl-4-[(5-chloro-7-(methylamino)carbonyl)-4-azaindol-3-yl)-oxoacetyl]piperazine: A mixture of Precursor 11 (25 mg), methylamine (2M in THF, 0.08 mL), EDC (26 mg), HOBT (11.2 mg) and diisopropylethylamine (43 mg) in tetrahydrofuran (5 mL) was stirred at room temperature for 10 hours. After the solvent was removed under vacuum, the residue was purified by using silica gel chromatography to afford 1-benzoyl-3-(R)-methyl-4-[(5-chloro-7-(methylamino)carbonyl)-4-azaindol-3-yl)-oxoacetyl]piperazine (13.6 mg); MS m/z: (M+H)+ Calc'd for $C_{23}H_{23}ClN_5O_4$: 468.14; found 468.03. HPLC retention time: 1.33 minutes (column A).

This general procedure A is applied to prepare examples 94 and 135:

EXAMPLE 94

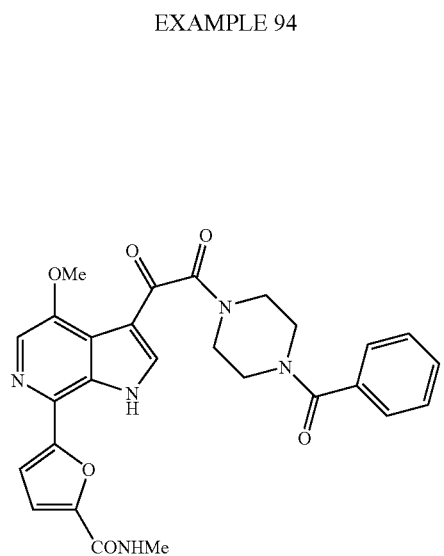

Example 94, 1-benzoyl-4-[(4-methoxy-7-(2-methylaminocarbonyl-furan-5-yl)-6-azaindol-3-yl)-oxoacetyl]piperazine. $^1$H NMR (500 MHz, CD$_3$OD) δ8.37 (s, 1H), 8.06 (s, 1H), 7.48-7.26 (m, 7H), 4.08 (s, 3H), 3.83-3.44 (m, 8H), 2.96 (s, 3H). MS m/z: (M+H)$^+$ Calc'd for C$_{29}$H$_{26}$N$_5$O$_6$: 516.19; found 516.14. HPLC retention time: 1.35 minutes (column A).

EXAMPLE 135

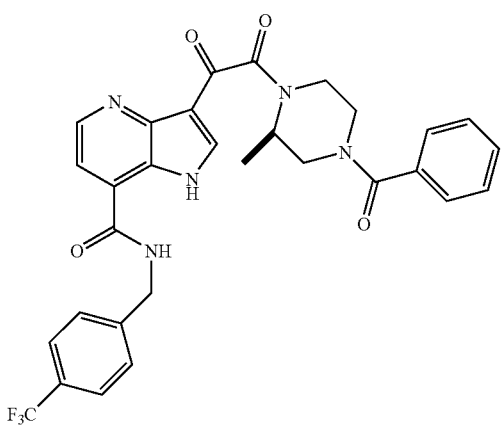

Example 135, (R)-1-benzoyl-3-methyl-4-[(7-(4-trifluoromethylbenzylamino) carbonyl-4-azaindol-3-yl)-oxoacetyl]piperazine. MS m/z: (M+H)$^+$ Calc'd for C$_{30}$H$_{27}$F$_3$N$_5$O$_4$: 578.20; found 578.39. HPLC retention time: 1.47 minutes (column G).

General Procedure B to Prepare CO—NR1R2 from COOH

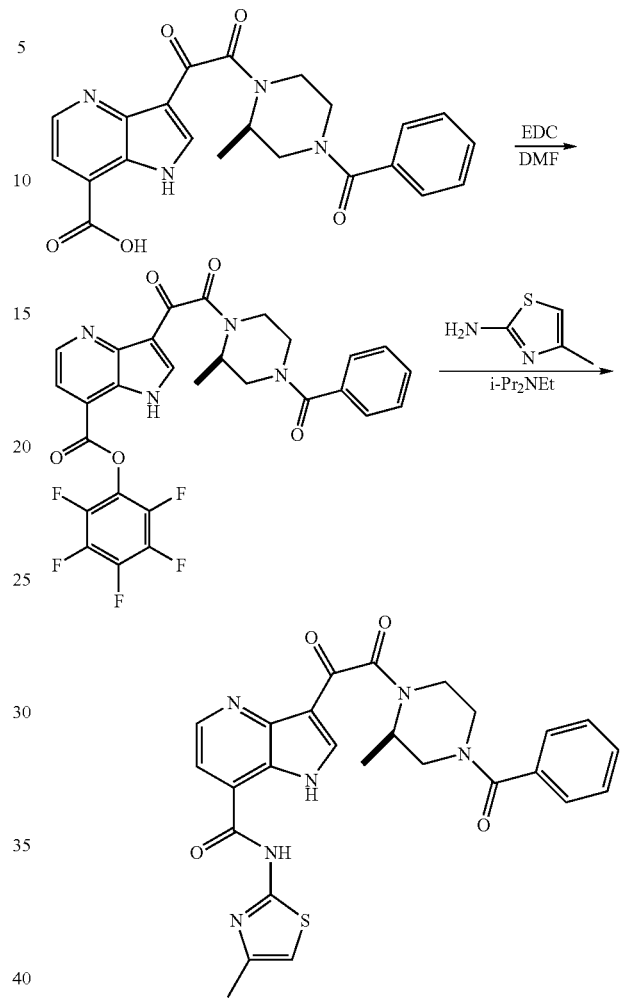

Preparation of Example 136, (R)-1-benzoyl-3-methyl-4-[(7-(4-methylthiazol-2-yl)aminocarbonyl-4-azaindol-3-yl)-oxoacetyl]piperazine.

To a solution of (R)-1-benzoyl-3-methyl-4-[(7-hydroxylcarbonyl-4-azaindol-3-yl)-oxoacetyl]piperazine (146 mg) in DMF (5 ml) at room temperature was added pentafluorophenyl (70.3 mg) followed by EDC (73.23 mg). The reaction mixture was stirred at room temperature for 8 hours. The crude product was diluted with methylene chloride and was washed with water, 0.1N HCl and brine. The organic phase was dried over MgSO4, filtered and concentrated. The pentafluorophenyl ester was used in the following reaction without further purification.

To a stirred solution of 4-methyl-2-amino-thiazole (39.6 mg) and Hunig's base (49.4 mg) in DMF (5 ml) at room temperature was added a solution of pentafluorophenyl ester (⅓ of the product obtained in the previous step described above) in DMF (2 ml). The reaction mixture was stirred at room temperature for 16 hours. The crude product was diluted with methylene chloride and was washed with Na2CO3 (sat.) and brine. The organic phase was dried over MgSO4, filtered and concentrated. The residue was purified using Shimadzu automated preparative HPLC System to give (R)-1-benzoyl-3-methyl-4-[(7-(4-methylthiazol-2-yl)aminocarbonyl-4-azaindol-3-yl)-oxoacetyl]piperazine (3.6 mg).

MS m/z: (M+H)+ Calc'd for C26H25N6O4S: 517.17; found 517.41. HPLC retention time: 1.25 minutes (column A).

This general procedure B is applied to prepare example 137:

EXAMPLE 137

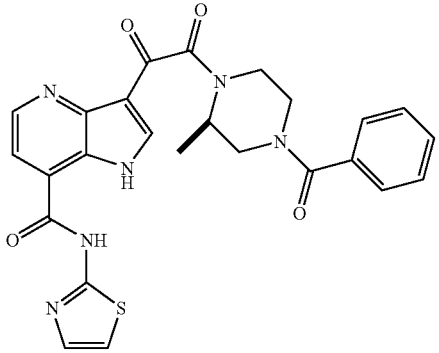

Example 137, (R)-1-benzoyl-3-methyl-4-[(7-(thiazol-2-yl)aminocarbonyl-4-azaindol-3-yl)-oxoacetyl]piperazine. MS m/z: (M+H)+ Calc'd for C25H23N6O4S: 503.15; found 503.29. HPLC retention time: 1.33 minutes (column A).

EXAMPLE 60

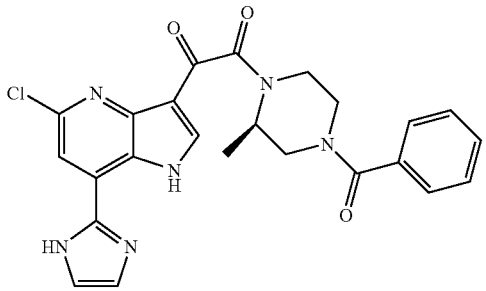

Preparation of 1-benzoyl-3-(R)-methyl-4-[(5-chloro-7-(imidazol-2-yl)-4-azaindol-3-yl)-oxoacetyl]piperazine: A mixture of Precursor 10 (34 mg), glyoxal (40% in water, 0.2 mL) and ammonia acetate (139 mg) in methanol was heated up to reflux for 10 hours. After cooling down, the mixture was concentrated under reduced pressure and the residue was purified using Shimadzu automated preparative HPLC System to provide 1-benzoyl-3-(R)-methyl-4-[(5-chloro-7-(imidazol-2-yl)-4-azaindol-3-yl)-oxoacetyl]piperazine (1.8 mg); MS m/z: (M+H)+ Calc'd for C24H22ClN6O3: 477.14; found 477.13. HPLC retention time: 1.17 minutes (column A).

EXAMPLE 61

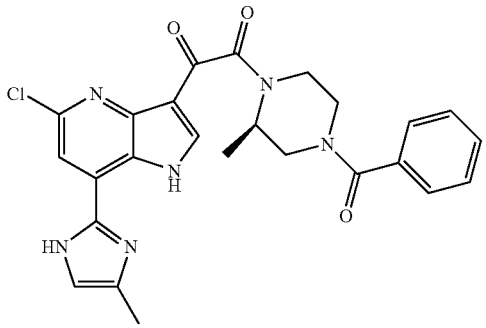

Example 61 was prepared according to the same procedure used for preparing Example 60 with the exception of using methylglyoxal as a starting material instead of glyoxal to provide 1-benzoyl-3-(R)-methyl-4-[(5-chloro-7-(4-methyl-imidazol-2-yl)-4-azaindol-3-yl)-oxoacetyl]piperazine MS m/z: (M+H)+ Calc'd for C25H24ClN6O3: 491.16; found 491.13. HPLC retention time: 1.26 minutes (column A).

EXAMPLE 62

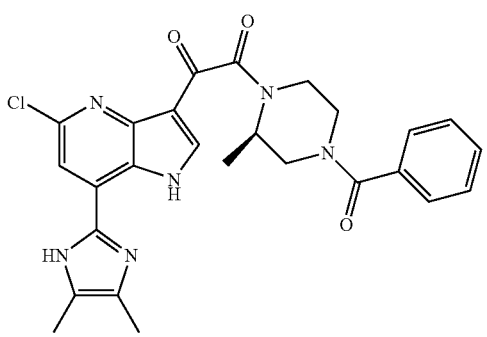

Example 62 was prepared according to the same procedure used for preparing Example 60 with the exception of using dimethylglyoxal as a starting material instead of glyoxal to provide 1-benzoyl-3-(R)-methyl-4-[(5-chloro-7-(4,5-dimethyl-imidazol-2-yl)-4-azaindol-3-yl)-oxoacetyl]piperazine; MS m/z: (M+H)+ Calc'd for C26H26ClN6O3: 505.18; found 505.10. HPLC retention time: 1.24 minutes (column A).

EXAMPLE 63

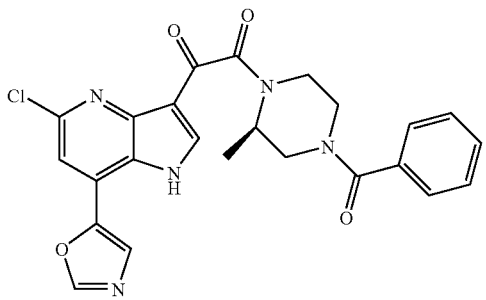

Preparation of 1-benzoyl-3-(R)-methyl-4-[(5-chloro-7-(oxazol-5-yl)-4-azaindol-3-yl)-oxoacetyl]piperazine: A mixture of Precursor 10 (27.6 mg), tosylmethyl isocyanide (12.3 mg) and K2CO3 (8.7 mg) in MeOH was heated up to reflux for 10 hours. After cooling down, the mixture was concentrated under reduced pressure and the residue was purified using Shimadzu automated preparative HPLC System to provide 1-(benzoyl)-3-(R)-methyl-4-[(5-chloro-7-(oxazol-5-yl)-4-azaindol-3-yl)-oxoacetyl]piperazine (17.7 mg); MS m/z: (M+H)+ Calc'd for C24H21ClN5O4: 478.13; found 478.03. HPLC retention time: 1.48 minutes (column A).

EXAMPLE 64

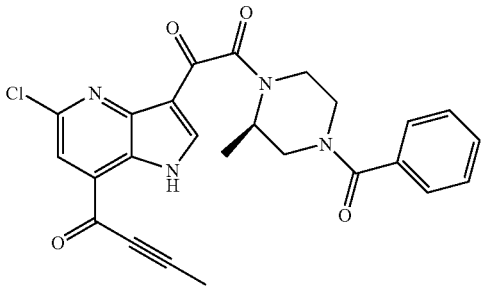

Step 1: Preparation of 1-64, 1-benzoyl-3-(R)-methyl-4-[(7-(2-propynyl)carbonyl-4-azaindol-3-yl)-oxoacetyl]piperazine: Propynyllithium (21 mg) was added to a solution of Example 52 (41 mg) in tetrahydrofuran (5 ml) at −78° C. The reaction was quenched with methanol at −25° C. in 2 hours. After solvents were removed under vacuum, the residue was carried to the further reactions without any purification.

1-64, 1-benzoyl-3-(R)-methyl-4-[(7-(2-propynyl)carbonyl-4-azaindol-3-yl)-oxoacetyl]piperazine MS m/z: (M+H)+ Calc'd for $C_{25}H_{22}ClN_4O_4$: 477.13; found 477.17. HPLC retention time: 1.46 minutes (column A).

Step 2: Preparation of Example 64:

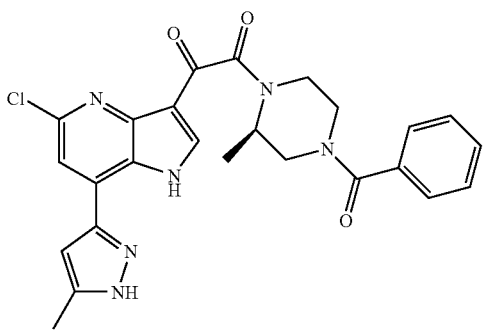

EXAMPLE 64

Preparation of Example 64, 1-benzoyl-3-(R)-methyl-4-[(5-chloro-7-(3-methyl-pyrazol-5-yl)-4-azaindol-3-yl)-oxoacetyl]piperazine: A mixture of 1-64 (crude product from Step 1) and hydrazine (0.22 mL) in EtOAc (2 mL) and water (2 mL) was stirred at room temperature for 24 hours. Then solvents were removed under vacuum, and the residue was purified using Shimadzu automated preparative HPLC System to give 1-benzoyl-3-(R)-methyl-4-[(5-chloro-7-(3-methyl-pyrazol-5-yl)-4-azaindol-3-yl)-oxoacetyl]piperazine (9 mg); MS m/z: (M+H)+ Calc'd for $C_{25}H_{24}ClN_6O_3$: 491.16; found 491.19. HPLC retention time: 1.42 minutes (column A).

EXAMPLES 65-67

The procedure for the preparation of Examples 65-67 is the same as that described previously for the preparation of Precursor 5a and is as follows: Potassium 7-(4-methoxyphenyl)-4-azaindole-3-glyoxylate, Precursor 4c (147 mg, 0.44 mmol), an appropriate 1-benzoylpiperazine derivative (0.44 mmol), 3-(diethoxyphosphoryloxy)-1,2,3-benzotriazin-4(3H)-one (DEPBT) (101 mg, 0.44 mol) and Hunig's Base (0.5 mL) were combined in 5 mL of DMF. The mixture was stirred at rt for 8 h. DMF was removed via evaporation at reduced pressure and the residue was purified using a Shimadzu automated preparative HPLC System to give the corresponding 1-benzoyl-4-[(7-(4-methoxyphenyl)-4-azaindol-3-yl)-oxoacetyl]-piperazine derivative.

EXAMPLE 65

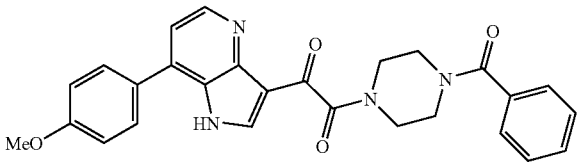

Example 19, 1-(benzoyl)-4-[(7-(4-methoxy)-4-azaindol-3-yl)-oxoacetyl]piperazine was prepared from potassium 7-(4-methoxyphenyl)-4-azaindole-3-glyoxylate and 1-(benzoyl)piperazine according to the above general procedure. MS m/z: (M+H)+ Calc'd for $C_{27}H_{25}N_4O_4$: 469.19; found 469.16. HPLC retention time: 1.26 minutes (column A).

EXAMPLE 66

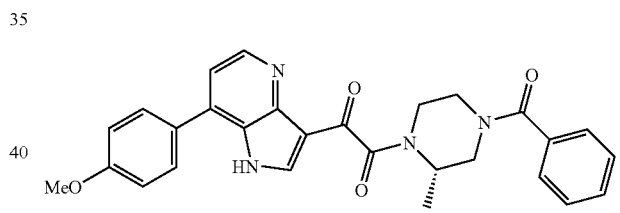

Example 66, 1-benzoyl-3-(S)-methyl-4-[(7-(4-methoxy)-4-azaindol-3-yl)-oxoacetyl]piperazine was prepared from potassium 7-(4-methoxyphenyl)-4-azaindole-3-glyoxylate and the corresponding 1-(benzoyl)-3-methylpiperazine according to the above general procedure. MS m/z: (M+H)+ Calc'd for $C_{28}H_{27}N_4O_4$: 483.20; found 483.17. HPLC retention time: 1.30 minutes (column A).

EXAMPLE 67

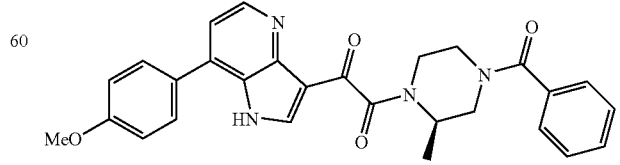

Example 67, 1-benzoyl-3-(R)-methyl-4-[(7-(4-methoxyphenyl)-4-azaindol-3-yl)oxoacetyl]piperazine was prepared from potassium 7-(4-methoxyphenyl)-4-azaindole-3-glyoxylate and the corresponding 1-benzoyl-3-methylpiperazine according to the above general procedure. MS m/z: (M+H)$^+$ Calc'd for $C_{28}H_{27}N_4O_4$: 483.20; found 483.16. HPLC retention time: 1.28 minutes (column A).

EXAMPLES 68-79 AND 81

Examples 68-79 and 81 were prepared according to the same general method as previously described for Examples 16-54.

EXAMPLE 68

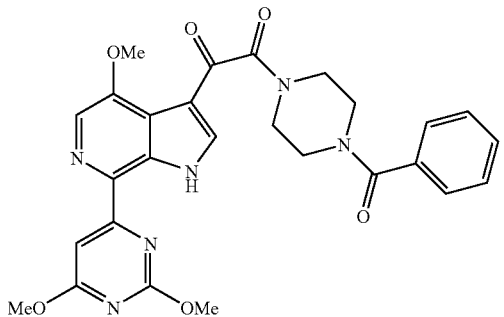

Example 68, was prepared from Precursor 5b and the 2,4-dimethoxypyrimidin-6-yl stannane to provide 1-benzoyl-4-[(4-methoxy-7-(2,6-dimethoxy-pyrimidin-4-yl)-6-azaindol-3-yl)-oxoacetyl]piperazine. $^1$H NMR (500 MHz, CDCl$_3$) δ 8.20 (s, 1H), 8.13 (s, 1H), 7.52 (s, 1H), 7.42 (m, 5H), 4.11 (s, 3H), 4.06 (s, 3H), 4.00-3.40 (m, 8H). MS m/z: (M+H)$^+$ Calc'd for $C_{27}H_{27}N_6O_6$: 531.20; found 531.24. HPLC retention time: 1.54 minutes (column A).

EXAMPLE 69

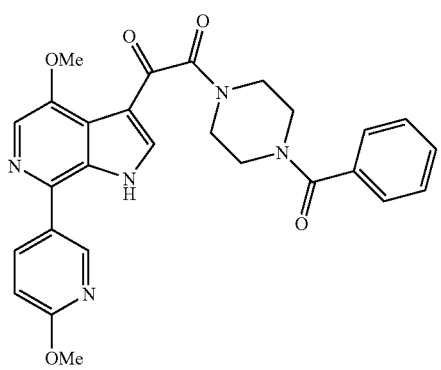

Example 69, was prepared from Precursor 5b and the 6-methoxypyridin-3-yl stannane to provide 1-benzoyl-4-[(4-methoxy-7-(6-methoxy-pyridin-3-yl)-6-azaindol-3-yl)-oxoacetyl]piperazine. $^1$H NMR (500 MHz, CD$_3$OD) δ 8.69 (s, 1H), 8.63 (s, 1H), 8.11 (m, 2H), 7.49 (m, 5H), 7.10 (d, 1H, J=8.65 Hz), 4.16 (s, 3H), 4.06 (s, 3H), 4.00-3.40 (m, 8H). MS m/z: (M+H)$^+$ Calc'd for $C_{27}H_{26}N_5O_5$: 500.09; found 500.20. HPLC retention time: 1.11 minutes (column A).

EXAMPLE 70

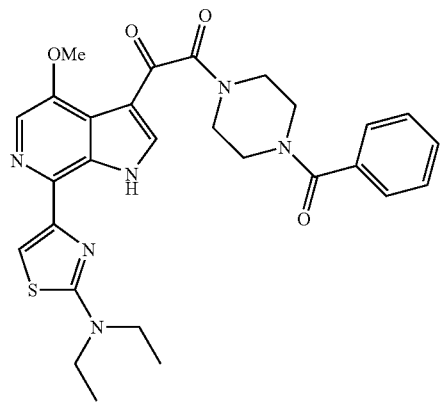

Example 70, was prepared from Precursor 5b and the 2-diethylamino-thiazol-4-yl stannane to provide 1-benzoyl-4-[(4-methoxy-7-(2-diethylamino-thiazol-4-yl)-6-azaindol-3-yl)-oxoacetyl]piperazine. $^1$H NMR (500 MHz, CD$_3$OD) δ 8.47 (s, 1H), 7.97 (m, 2H), 7.49 (m, 5H), 4.08 (s, 3H), 3.64 (m, 12H), 1.35 (m, 6H). MS m/z: (M+H)$^+$ Calc'd for $C_{28}H_{31}N_6O_4S$: 547.21; found 547.22. HPLC retention time: 1.35 minutes (column A).

EXAMPLE 71

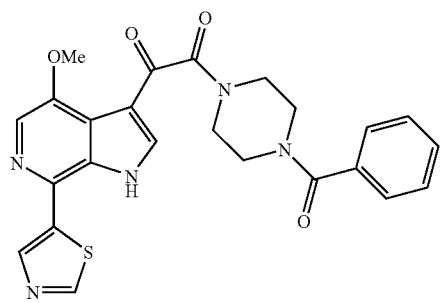

Example 71, was prepared from Precursor 5b and the thiazol-5-yl stannane to provide 1-benzoyl-4-[(4-methoxy-7-(thioazol-5-yl)-6-azaindol-3-yl)-oxoacetyl]piperazine. $^1$H NMR (500 MHz, DMSO-d$_6$) δ 9.19 (s, 1H), 8.64 (s, 1H), 8.34 (s, 1H), 8.11 (s, 1H), 7.46 (m, 5H), 4.00 (s, 3H), 3.55 (m, 8H). MS m/z: (M+H)$^+$ Calc'd for $C_{24}H_{22}N_5O_4S$: 476.14; found 476.17. HPLC retention time: 1.13 minutes (column A).

EXAMPLE 72

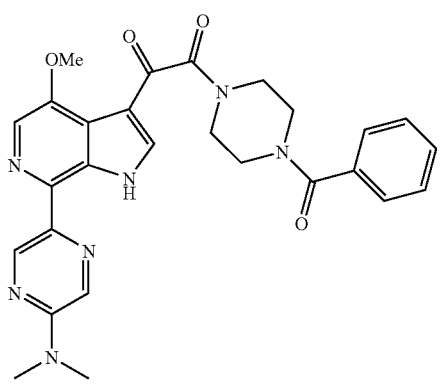

Example 72, was prepared from Precursor 5b and the 2-dimethylamino-pyrazin-5-yl stannane to provide 1-(benzoyl)-4-[(4-methoxy-7-(2-dimethylamino-pyrazin-5-yl)-6-azaindol-3-yl)-oxoacetyl]piperazine. MS m/z: (M+H)$^+$ Calc'd for $C_{27}H_{28}N_7O_4$: 514.22; found 514.29. HPLC retention time: 1.27 minutes (column A).

EXAMPLE 73

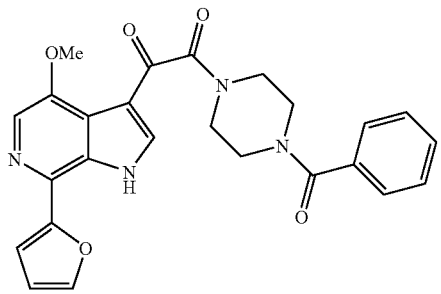

Example 73, was prepared from Precursor 5b and the furan-2-yl stannane to provide 1-(benzoyl)-4-[(4-methoxy-7-(furan-2-yl)-6-azaindol-3-yl)-oxoacetyl]piperazine. MS m/z: (M+H)$^+$ Calc'd for $C_{25}H_{23}N_4O_5$: 459.17; found 459.25. HPLC retention time: 1.15 minutes (column A).

EXAMPLE 74

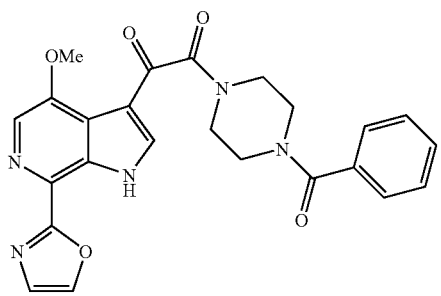

Example 74, was prepared from Precursor 5b and the oxazol-2-yl stannane to provide 1-benzoyl-4-[(4-methoxy-7-(oxazol-2-yl)-6-azaindol-3-yl)-oxoacetyl]piperazine. $^1$H NMR (500 MHz, DMSO-d$_6$) δ 9.19 (s, 1H), 8.64 (s, 1H), 8.34 (s, 1H), 8.11 (s, 1H), 7.46 (m, 5H), 4.00 (s, 3H), 3.55 (m, 8H). MS m/z: (M+H)$^+$ Calc'd for $C_{24}H_{22}N_5O_5$: 460.16; found 460.23. HPLC retention time: 1.22 minutes (column A).

EXAMPLE 75

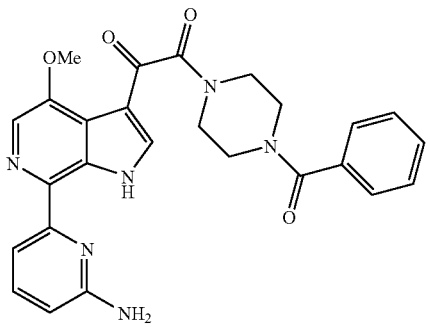

Example 75, was prepared from Precursor 5b and the 6-aminopyridin-2-yl stannane to provide 1-benzoyl-4-[(4-methoxy-7-(2-aminopyridin-6-yl)-6-azaindol-3-yl)-oxoacetyl]piperazine. MS m/z: (M+H)$^+$ Calc'd for $C_{26}H_{25}N_6O_4$: 485.19; found 485.24. HPLC retention time: 1.15 minutes (column A).

EXAMPLE 76

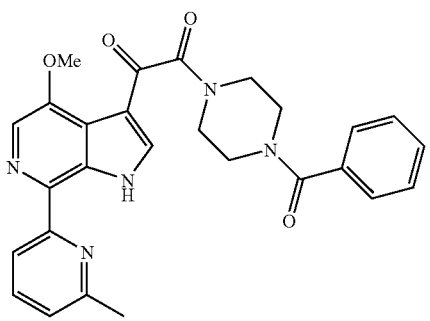

Example 76, was prepared from Precursor 5b and the 6-methylpyridin-2-yl stannane to provide 1-benzoyl-4-[(4-methoxy-7-(2-methyl-pyridin-6-yl)-6-azaindol-3-yl)-oxoacetyl]piperazine. MS m/z: (M+H)$^+$ Calc'd for $C_{27}H_{26}N_5O_4$: 484.20; found 484.22. HPLC retention time: 1.24 minutes (column A).

EXAMPLE 77

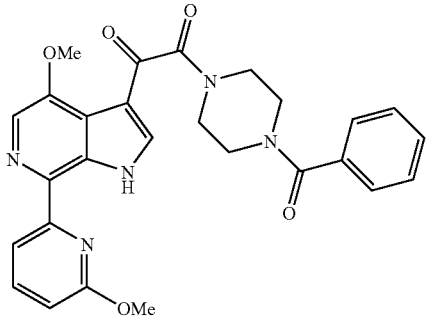

Example 77, was prepared from Precursor 5b and the 6-methoxypyridin-2-yl stannane to provide 1-benzoyl-4-[(4-methoxy-7-(2-methoxy-pyridin-6-yl)-6-azaindol-3-yl)-oxoacetyl]piperazine. MS m/z: (M+H)+ Calc'd for $C_{27}H_{26}N_5O_5$: 500.19; found 500.23. HPLC retention time: 1.26 minutes (column A).

EXAMPLE 78

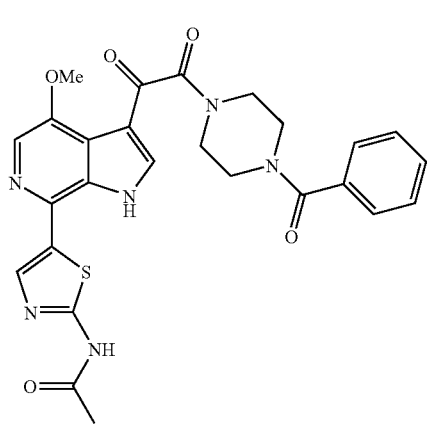

Example 78, was prepared from Precursor 5b and the 2-acetylamino-thiazol-5-yl stannane to provide 1-benzoyl-4-[(4-methoxy-7-(2-acetylamino-thiazol-5-yl)-6-azaindol-3-yl)-oxoacetyl]piperazine. MS m/z: (M+H)+ Calc'd for $C_{26}H_{25}N_6O_5S$: 533.16; found 533.18. HPLC retention time: 1.21 minutes (column A).

EXAMPLE 79

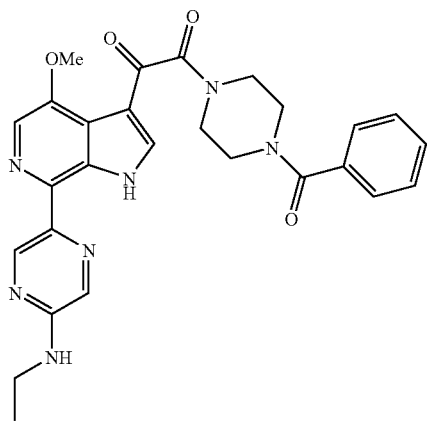

Example 79, was prepared from Precursor 5b and the 2-ethylamino-pyrazin-5-yl stannane to provide 1-benzoyl-4-[(4-methoxy-7-(2-ethylamino-pyrazin-5-yl)-6-azaindol-3-yl)-oxoacetyl]piperazine. MS m/z: (M+H)+ Calc'd for $C_{27}H_{28}N_7O_4$: 514.22; found 514.18. HPLC retention time: 1.31 minutes (column A).

EXAMPLE 88

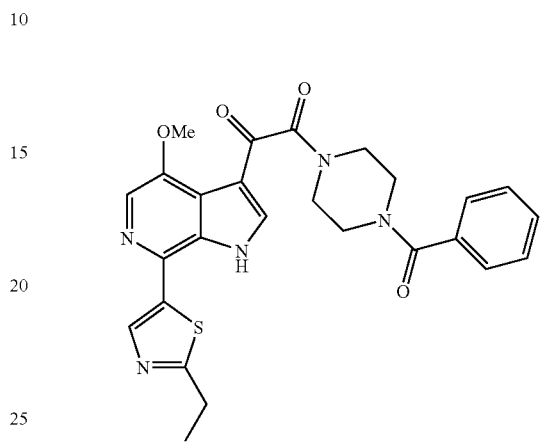

Example 88, was prepared from Precursor 5b and the 2-ethyl-thiazol-5-yl stannane to provide 1-benzoyl-4-[(4-methoxy-7-(2-ethyl-thiazol-5-yl)-6-azaindol-3-yl)-oxoacetyl]piperazine. MS m/z: (M+H)+ Calc'd for $C_{26}H_{26}N_5O_4S$: 504.17; found 514.32. HPLC retention time: 1.50 minutes (column A).

EXAMPLE 89

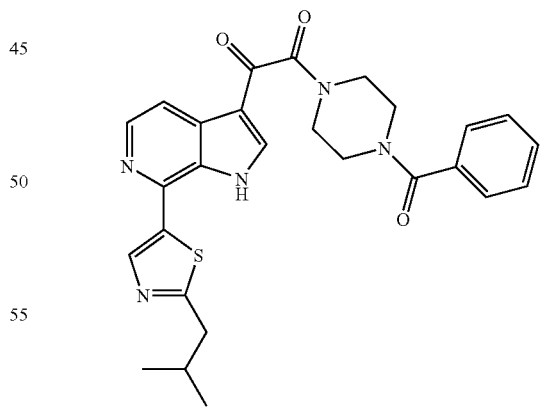

Example 89, was prepared from Precursor 5k and the 2-isobutyl-thiazol-5-yl stannane to provide 1-benzoyl-4-[(7-(2-isobutyl-thiazol-5-yl)-6-azaindol-3-yl)-oxoacetyl]piperazine. MS m/z: (M+H)+ Calc'd for $C_{27}H_{28}N_5O_3S$: 502.19; found 502.26. HPLC retention time: 1.56 minutes (column E).

EXAMPLE 90

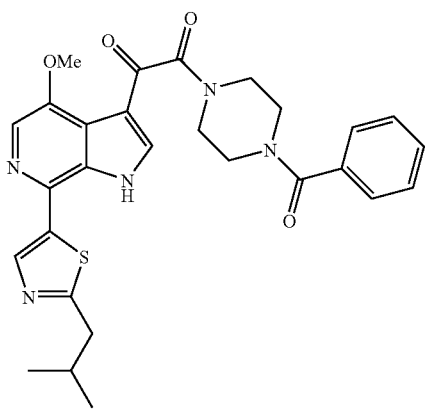

Example 90, was prepared from Precursor 5b and the 2-isobutyl-thiazol-5-yl stannane to provide 1-benzoyl-4-[(4-methoxy-7-(2-isobutyl-thiazol-5-yl)-6-azaindol-3-yl)-oxoacetyl]piperazine. MS m/z: (M+H)+ Calc'd for $C_{28}H_{30}N_5O_4S$: 532.20; found 532.27. HPLC retention time: 1.57 minutes (column E).

EXAMPLE 91

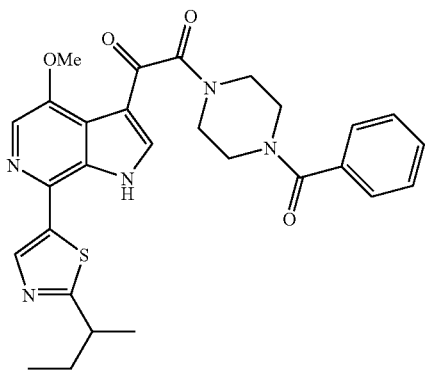

Example 91, was prepared from Precursor 5b and the 2-(2-butyl)-thiazol-5-yl stannane to provide 1-benzoyl-4-[(4-methoxy-7-(2-(2-butyl)-thiazol-5-yl)-6-azaindol-3-yl)-oxoacetyl]piperazine. MS m/z: (M+H)+ Calc'd for $C_{28}H_{30}N_5O_4S$: 532.20; found 532.27. HPLC retention time: 1.57 minutes (column E).

EXAMPLE 92

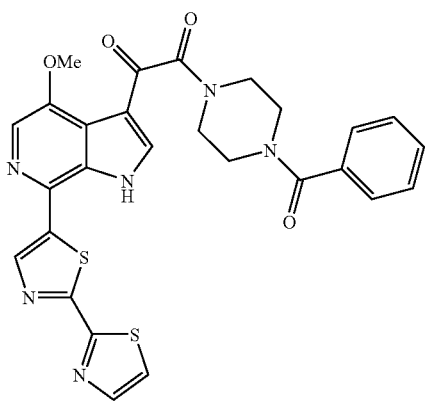

Example 92, was prepared from Precursor 5b and the 2-(thiazol-2-yl)-thiazol-5-yl stannane to provide 1-benzoyl-4-[(4-methoxy-7-(2-(thiazol-2-yl)-thiazol-5-yl)-6-azaindol-3-yl)-oxoacetyl]piperazine. MS m/z: (M+H)+ Calc'd for $C_{27}H_{23}N_6O_4S_2$: 559.12; found 559.18. HPLC retention time: 1.55 minutes (column E).

EXAMPLE 93

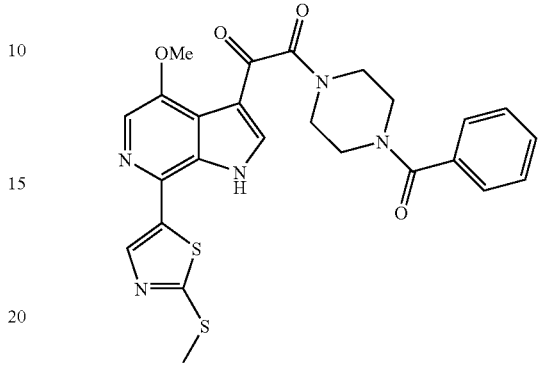

Example 93, was prepared from Precursor 5b and the 2-methylthio-thiazol-5-yl stannane to provide 1-benzoyl-4-[(4-methoxy-7-(2-methylthio-thiazol-5-yl)-6-azaindol-3-yl)-oxoacetyl]piperazine. MS m/z: (M+H)+ Calc'd for $C_{25}H_{24}N_5O_4S_2$: 522.13; found 522.17. HPLC retention time: 1.45 minutes (column E).

EXAMPLE 95

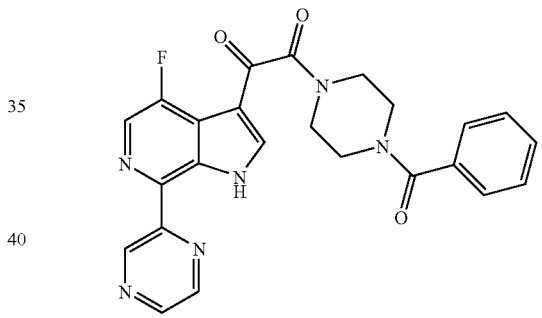

Example 95, was prepared from Precursor 5i and the pyrazin-2-yl stannane to provide 1-benzoyl-4-[(4-fluoro-7-(pyrazin-2-yl)-6-azaindol-3-yl)-oxoacetyl]piperazine. $^1$H NMR (500 MHz, CDCl$_3$) δ9.89 (s, 1H), 8.70-8.34 (m, 4H), 7.46 (m, 5H), 3.80-3.50 (m, 8H). MS m/z: (M+H)+ Calc'd for $C_{24}H_{20}FN_6O_3$: 459.16; found 459.33. HPLC retention time: 1.46 minutes (column G).

EXAMPLE 100

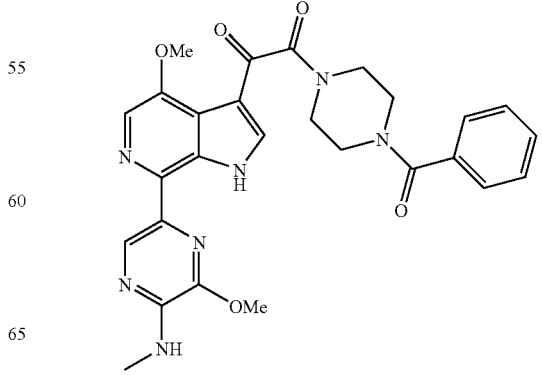

Example 100, was prepared from Precursor 5b and the 2-methylamino-3-methoxy-pyrazin-5-yl stannane to provide 1-benzoyl-4-[(4-methoxy-7-(2-methylamino-3-methoxy-pyrazin-5-yl)-6-azaindol-3-yl)-oxoacetyl]piperazine. $^1$H NMR (500 MHz, CD$_3$OD) δ8.65 (s, 1H), 8.43 (s, 1H), 7.95 (s, 1H), 7.45 (m, 5H), 4.21 (s, 3H), 4.12 (s, 3H), 3.89-3.32 (m, 8H), 3.06 (s, 3H). MS m/z: (M+H)$^+$ Calc'd for C$_{27}$H$_{28}$N$_7$O$_5$: 530.22; found 530.19. HPLC retention time: 1.31 minutes (column A).

EXAMPLE 101

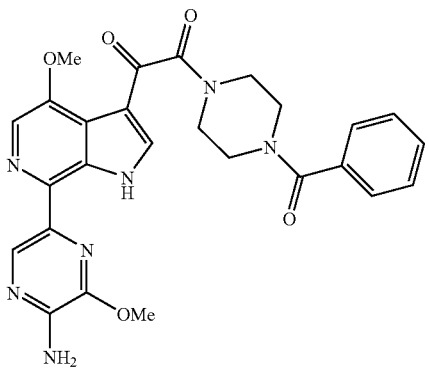

Example 101, was prepared from Precursor 5b and the 2-amino-3-methoxy-pyrazin-5-yl stannane to provide 1-benzoyl-4-[(4-methoxy-7-(2-amino-3-methoxy-pyrazin-5-yl)-6-azaindol-3-yl)-oxoacetyl]piperazine. $^1$H NMR (500 MHz, CD$_3$OD) δ8.67 (s, 1H), 8.34 (s, 1H), 7.96 (s, 1H), 7.48 (m, 5H), 4.22 (s, 3H), 4.12 (s, 3H), 3.92-3.32 (m, 8H). MS m/z: (M+H)$^+$ Calc'd for C$_{26}$H$_{26}$N$_7$O$_5$: 516.20; found 516.23. HPLC retention time: 1.27 minutes (column A).

EXAMPLE 102

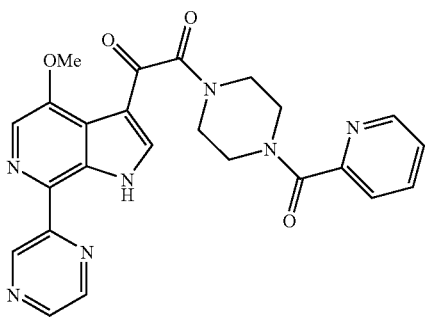

Example 102, was prepared from Precursor 51 and the pyrazin-2-yl stannane to provide 1-picolinoyl-4-[(4-methoxy-7-(pyrazin-2-yl)-6-azaindol-3-yl)-oxoacetyl]piperazine. $^1$H NMR (500 MHz, CD$_3$OD) δ9.59 (s, 1H), 8.79-7.51 (m, 8H), 4.13 (s, 3H), 3.95-3.34 (m, 8H). MS m/z: (M+H)$^+$ Calc'd for C$_{24}$H$_{22}$N$_7$O$_4$: 472.17; found 472.25. HPLC retention time: 1.15 minutes (column A).

EXAMPLE 103

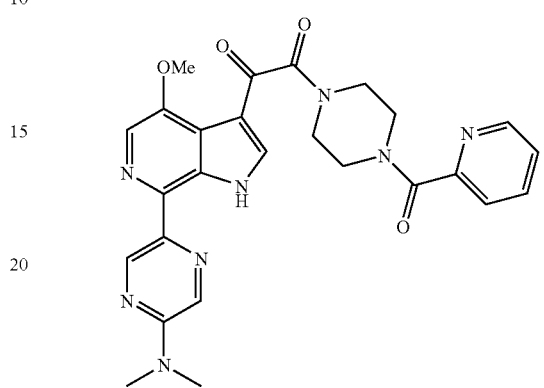

Example 103, was prepared from Precursor 51 and the 2-dimethylamino-pyrazin-5-yl stannane to provide 1-picolinoyl-4-[(4-methoxy-7-(2-dimethylamino-pyrazin-5-yl)-6-azaindol-3-yl)-oxoacetyl]piperazine. MS m/z: (M+H)$^+$ Calc'd for C$_{26}$H$_{27}$N$_8$O$_4$: 515.22; found 515.16. HPLC retention time: 1.29 minutes (column A).

EXAMPLE 104

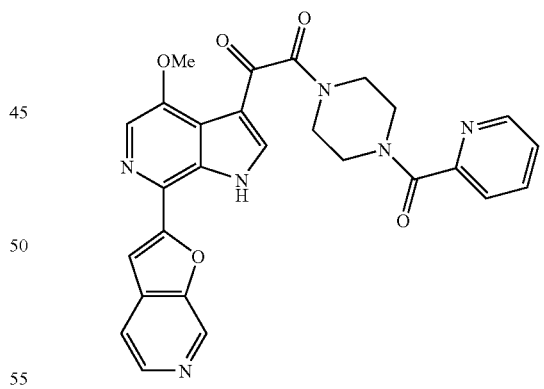

Example 104, was prepared from Precursor 5b and the 6-aza-benzofuran-2-yl stannane to provide 1-benzoyl-4-[(4-methoxy-7-(6-aza-benzofuran-2-yl)-6-azaindol-3-yl)-oxoacetyl]piperazine. $^1$H NMR (500 MHz, CDCl$_3$) δ8.48 (d, 1H, J=8.5 Hz), 8.36 (s, 1H), 8.30 (s, 1H), 8.02 (s, 1H), 7.64 (d, 1H, J=8.55 Hz), 7.41 (m, 4H), 6.92 (s, 1H), 4.12 (s, 3H), 3.87-3.38 (m, 8H). MS m/z: (M+H)$^+$ Calc'd for C$_{28}$H$_{24}$N$_5$O$_5$: 510.18; found 510.33. HPLC retention time: 1.33 minutes (column A).

EXAMPLE 105

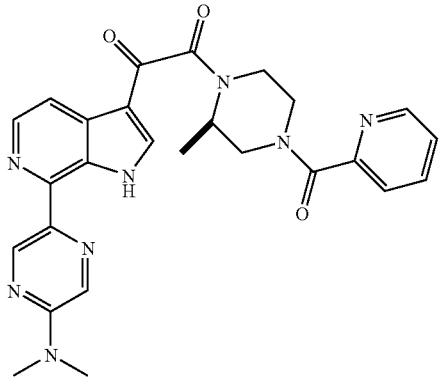

Example 105, was prepared from Precursor 5m and the 2-dimethylamino-pyrazin-5-yl stannane to provide (R)-1-picolinoyl-3-methyl-4-[(7-(2-dimethylamino-pyrazin-5-yl)-6-azaindol-3-yl)-oxoacetyl]piperazine. MS m/z: (M+H)$^+$ Calc'd for $C_{26}H_{27}N_8O_3$: 499.22; found 499.27. HPLC retention time: 1.17 minutes (column A).

EXAMPLE 106

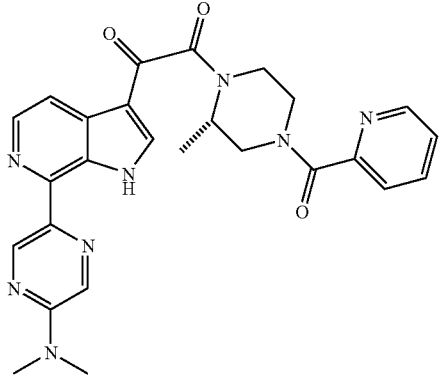

Example 106, was prepared from Precursor 5n and the 2-dimethylamino-pyrazin-5-yl stannane to provide (S)-1-picolinoyl-3-methyl-4-[(7-(2-dimethylamino-pyrazin-5-yl)-6-azaindol-3-yl)-oxoacetyl]piperazine. $^1$H NMR (500 MHz, CD$_3$OD) δ9.08-7.49 (m, 9H), 5.00-3.15 (m, 13H), 1.44-1.27 (m, 3H). MS m/z: (M+H)$^+$ Calc'd for $C_{26}H_{27}N_8O_3$: 499.22; found 499.27. HPLC retention time: 1.19 minutes (column A).

EXAMPLE 109

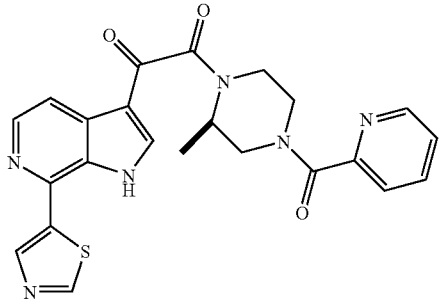

Example 109, was prepared from Precursor 5m and the thiazol-5-yl stannane to provide (R)-1-picolinoyl-3-methyl-4-[(7-(thiazol-5-yl)-6-azaindol-3-yl)-oxoacetyl]piperazine.
$^1$H NMR (500 MHz, CD$_3$OD) δ9.42-7.49 (m, 9H), 4.98-3.14 (m, 7H), 1.43-1.26 (m, 3H). MS m/z: (M+H)$^+$ Calc'd for $C_{23}H_{21}N_6O_3S$: 4611.14; found 461.28. HPLC retention time: 1.11 minutes (column A).

EXAMPLE 110

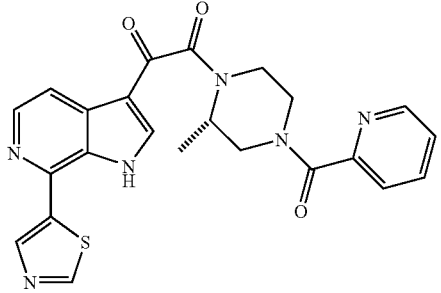

Example 110, was prepared from Precursor 5n and the thiazol-5-yl stannane to provide (S)-1-picolinoyl-3-methyl-4-[(7-(thiazol-5-yl)-6-azaindol-3-yl)-oxoacetyl]piperazine.
$^1$H NMR (500 MHz, CD$_3$OD) δ9.44-7.48 (m, 9H), 4.98-3.15 (m, 7H), 1.43-1.26 (m, 3H). MS m/z: (M+H)$^+$ Calc'd for $C_{23}H_{21}N_6O_3S$: 461.14; found 461.27. HPLC retention time: 1.13 minutes (column A).

EXAMPLE 111

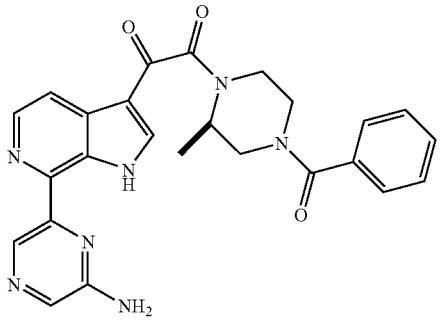

Example 111, was prepared from Precursor 5f and the 2-amino-pyrazin-6-yl stannane to provide (R)-1-benzoyl-3-methyl-4-[(7-(2-amino-pyrazin-6-yl)-6-azaindol-3-yl)-oxoacetyl]piperazine. $^1$H NMR (500 MHz, CD$_3$OD) δ8.68-7.45 (m, 10H), 4.89-3.13 (m, 7H), 1.39-0.99 (m, 3H). MS m/z: (M+H)$^+$ Calc'd for $C_{25}H_{24}N_7O_3$: 470.19; found 470.31. HPLC retention time: 1.30 minutes (column A).

EXAMPLE 112

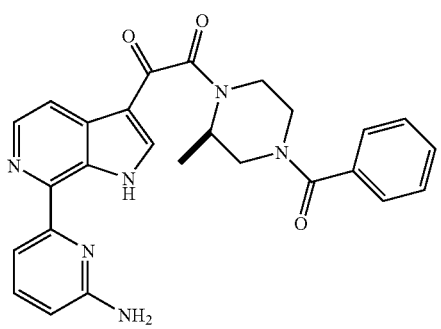

Example 112, was prepared from Precursor 5f and the 2-amino-pyridin-6-yl stannane to provide (R)-1-benzoyl-3-methyl-4-[(7-(2-amino-pyridin-6-yl)-6-azaindol-3-yl)-oxoacetyl]piperazine. ¹H NMR (500 MHz, CD₃OD) δ8.65-6.89 (m, 1H), 4.90-3.12 (m, 7H), 1.39-0.99 (m, 3H). MS m/z: (M+H)⁺ Calc'd for C$_{26}$H$_{25}$N$_6$O$_3$: 469.20; found 469.32. HPLC retention time: 1.26 minutes (column A).

EXAMPLE 113

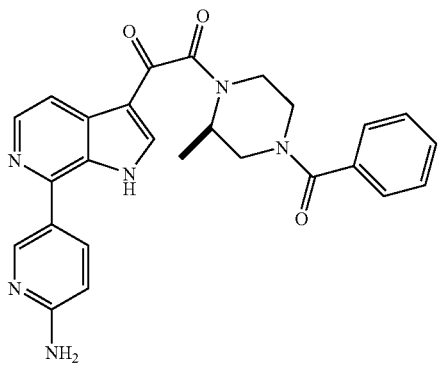

Example 113, was prepared from Precursor 5f and the 2-amino-pyridin-5-yl stannane to provide (R)-1-benzoyl-3-methyl-4-[(7-(2-amino-pyridin-5-yl)-6-azaindol-3-yl)-oxoacetyl]piperazine. ¹H NMR (500 MHz, CD₃OD) δ8.75-7.19 (m, 11H), 4.91-3.12 (m, 7H), 1.38-1.25 (m, 3H). MS m/z: (M+H)⁺ Calc'd for C$_{26}$H$_{25}$N$_6$O$_3$: 469.20; found 469.34. HPLC retention time: 1.05 minutes (column A).

EXAMPLE 114

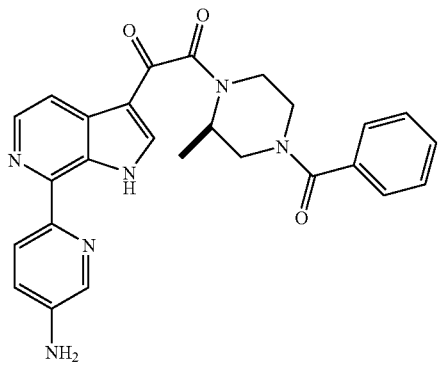

Example 114, was prepared from Precursor 5f and the 5-amino-pyridin-2-yl stannane to provide (R)-1-benzoyl-3-methyl-4-[(7-(5-amino-pyridin-2-yl)-6-azaindol-3-yl)-oxoacetyl]piperazine. ¹H NMR (500 MHz, CD₃OD) δ8.67-7.20 (m, 11H), 4.88-3.13 (m, 7H), 1.39-1.25 (m, 3H). MS m/z: (M+H)⁺ Calc'd for C$_{26}$H$_{25}$N$_6$O$_3$: 469.20; found 469.33. HPLC retention time: 1.22 minutes (column A).

EXAMPLE 115

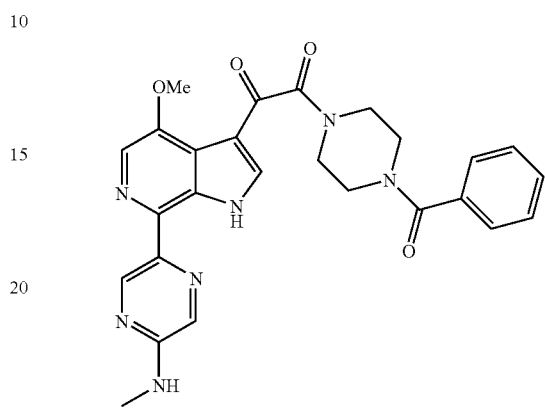

Example 115, was prepared from Precursor 5b and the 2-methylamino-pyrazin-5-yl stannane to provide 1-benzoyl-4-[(4-methoxy-7-(2-methylamino-pyrazin-5-yl)-6-azaindol-3-yl)-oxoacetyl]piperazine. ¹H NMR (500 MHz, CD₃OD) δ8.90 (s, 1H), 8.61 (s, 1H), 8.18 (s, 1H), 7.92 (s, 1H), 7.46 (m, 5H), 4.12 (s, 3H), 3.85-3.40 (m, 8H), 3.02 (s, 3H). MS m/z: (M+H)⁺ Calc'd for C$_{26}$H$_{26}$N$_7$O$_4$: 500.20; found 500.23. HPLC retention time: 1.24 minutes (column A).

EXAMPLE 116

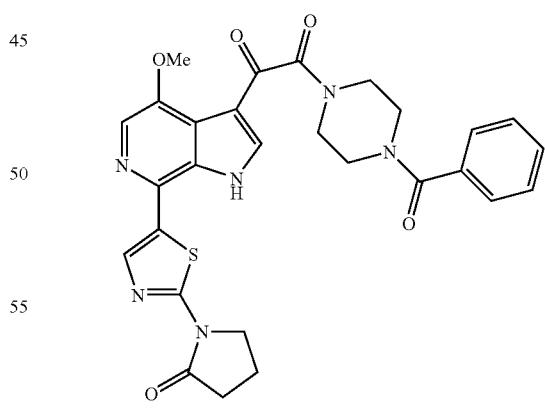

Example 116, was prepared from Precursor 5b and the 2-(2-pyrrolidinon-1-yl)-thiazol-5-yl stannane to provide 1-benzoyl-4-[(4-methoxy-7-((2-pyrrolidinon-1-yl)-thiazol-5-yl)-6-azaindol-3-yl)-oxoacetyl]piperazine. MS m/z: (M+H)⁺ Calc'd for C$_{28}$H$_{27}$N$_6$O$_5$S$_2$: 559.18; found 559.11. HPLC retention time: 1.39 minutes (column E).

EXAMPLE 117

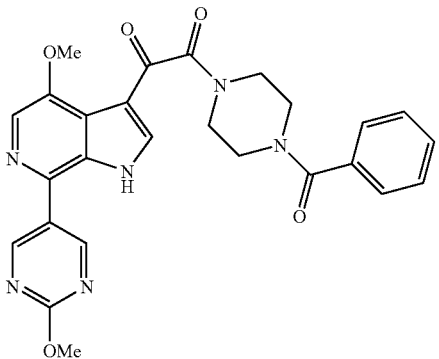

Example 117, was prepared from Precursor 5b and the 2-methoxy-pyrimidin-5-yl stannane to provide 1-benzoyl-4-[(4-methoxy-7-(2-methoxy-pyrimidin-5-yl)-6-azaindol-3-yl)-oxoacetyl]piperazine. MS m/z: (M+H)+ Calc'd for $C_{26}H_{25}N_6O_5$: 501.19; found 501.12. HPLC retention time: 1.21 minutes (column E).

EXAMPLE 118

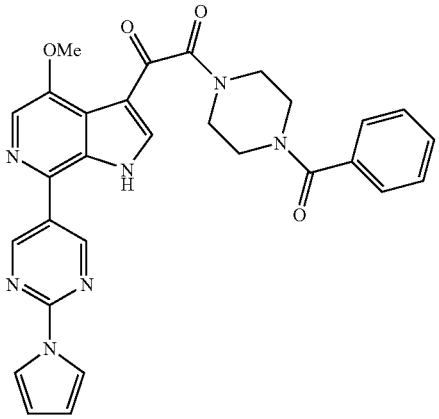

Example 118, was prepared from Precursor 5b and the 2-(pyrrol-1-yl)-pyrimidin-5-yl stannane to provide 1-benzoyl-4-[(4-methoxy-7-(2-(pyrrol-1-yl)-pyrimidin-5-yl)-6-azaindol-3-yl)-oxoacetyl]piperazine. MS m/z: (M+H)+ Calc'd for $C_{29}H_{26}N_7O_4$: 536.20; found 536.33. HPLC retention time: 1.44 minutes (column C).

EXAMPLE 119

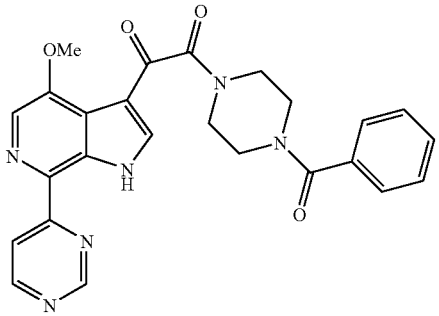

Example 119, was prepared from Precursor 5b and the pyrimidin-4-yl stannane to provide 1-benzoyl-4-[(4-methoxy-7-(pyrimidin-5-yl)-6-azaindol-3-yl)-oxoacetyl]piperazine. $^1$H NMR (500 MHz, CD$_3$OD) δ9.29 (s, 1H), 8.88 (d, 1H, J=5.4 Hz), 8.48 (d, 1H, J=5.25 Hz), 8.26 (s, 1H), 8.18 (s, 1H), 7.43 (m, 5H), 4.13 (s, 3H), 3.85-3.47 (m, 8H). MS m/z: (M+H)+ Calc'd for $C_{25}H_{23}N_6O_4$: 471.18; found 471.32. HPLC retention time: 1.35 minutes (column G).

EXAMPLE 120

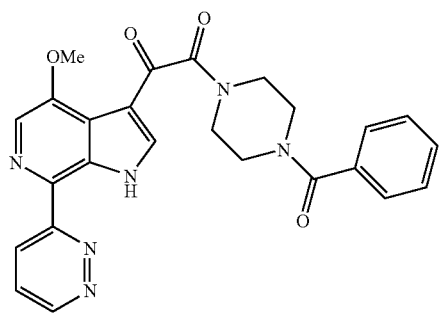

Example 119, was prepared from Precursor 5b and the pyridazin-3-yl stannane to provide 1-benzoyl-4-[(4-methoxy-7-(pyridazin-3-yl)-6-azaindol-3-yl)-oxoacetyl]piperazine. $^1$H NMR (500 MHz, CD$_3$OD) δ9.16 (s, 1H), 8.77 (d, 1H, J=8.5 Hz), 8.26 (d, 1H, J=3.05 Hz), 8.18 (s, 1H), 7.68 (m, 1H), 7.43 (m, 5H), 4.13 (s, 3H), 3.85-3.47 (m, 8H). MS m/z: (M+H)+ Calc'd for $C_{25}H_{23}N_6O_4$: 471.18; found 471.16. HPLC retention time: 1.35 minutes (column G).

EXAMPLE 125

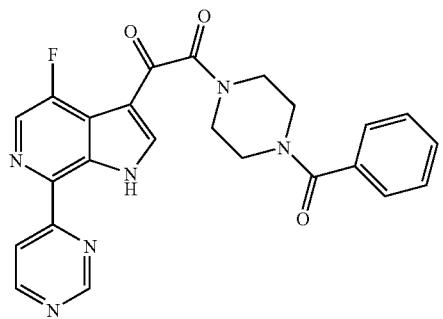

Example 125, was prepared from Precursor 5i and the pyrimidin-4-yl stannane to provide 1-benzoyl-4-[(4-fluoro-7-(pyrimidin-5-yl)-6-azaindol-3-yl)-oxoacetyl]piperazine. $^1$H NMR (500 MHz, CD$_3$OD) δ9.36 (s, 1H), 8.96 (d, 1H, J=5.35 Hz), 8.58 (d, 1H, J=5.10 Hz), 8.43 (s, 1H), 8.38 (s, 1H), 7.43 (m, 5H), 3.85-3.47 (m, 8H). MS m/z: (M+H)+ Calc'd for $C_{24}H_{20}FN_6O_2$: 459.16; found 459.15. HPLC retention time: 1.48 minutes (column A).

EXAMPLE 126

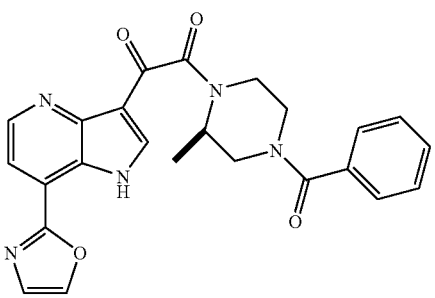

Example 126, was prepared from Precursor 5i and the oxazol-2-yl stannane to provide (R)-1-benzoyl-3-Methyl-4-[7-(oxazol-2-yl)-4-azaindol-3-yl)-oxoacetyl]piperazine. MS m/z: (M+H)$^+$ Calc'd for $C_{24}H_{22}N_5O_4$: 444.17; found 444.25. HPLC retention time: 1.13 minutes (column A).

EXAMPLE 131

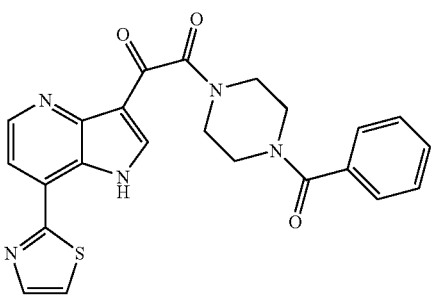

Example 131, was prepared from Precursor 5p and the thiazol-2-yl stannane to provide 1-benzoyl-4-[7-(thiazol-2-yl)-4-azaindol-3-yl)-oxoacetyl]piperazine. MS m/z: (M+H)$^+$ Calc'd for $C_{23}H_{20}N_5O_3S$: 446.13; found 446.04. HPLC retention time: 1.12 minutes (column A).

EXAMPLE 80

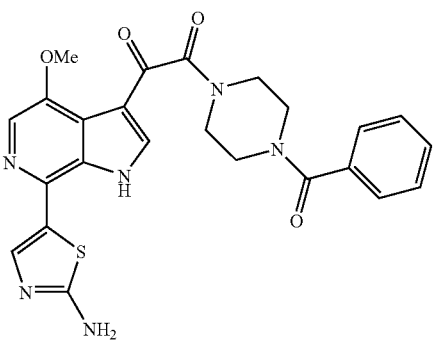

Preparation of Example 80, 1-benzoyl-4-[(4-methoxy-7-(2-amino-thioazol-5-yl)-6-azaindol-3-yl)-oxoacetyl]piperazine: A mixture of Example 78 (9 mg), TFA (3 mL) and water (1 mL) was stirred at 80° C. for 10 hours. After solvent was removed under vacuum, the residue was purified by using silica gel chromatography to afford 1-benzoyl-4-[(4-methoxy-7-(2-amino-thioazol-5-yl)-6-azaindol-3-yl)-oxoacetyl]piperazine (3 mg); MS m/z: (M+H)$^+$ Calc'd for $C_{24}H_{23}N_6O_5S$: 491.15; found 491.21. HPLC retention time: 1.20 minutes (column A).

EXAMPLE 81

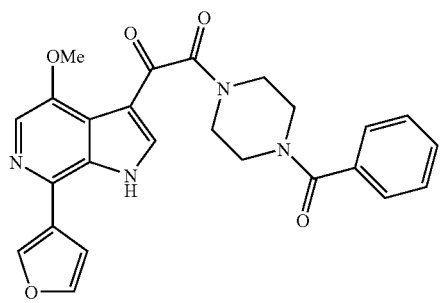

Example 81, was prepared from Precursor 5b and the furan-3-yl stannane to provide 1-benzoyl-4-[(4-methoxy-7-(furan-3-yl)-6-azaindol-3-yl)-oxoacetyl]piperazine. MS m/z: (M+H)$^+$ Calc'd for $C_{25}H_{23}N_4O_5$: 459.17; found 459.24. HPLC retention time: 1.13 minutes (column A).

EXAMPLE 150

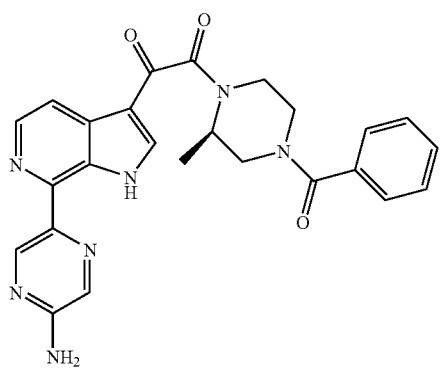

Example 150, was prepared from Precursor 5f and the 5-amino-pyrazin-2-yl stannane to provide (R)-1-benzoyl-3-methyl-4-[(7-(5-amino-pyrazin-2-yl)-6-azaindol-3-yl)-oxoacetyl]piperazine. MS m/z: (M+H)$^+$ Calc'd for $C_{25}H_{24}N_7O_3$: 470.19; found 470.19. HPLC retention time: 1.14 minutes (column G).

EXAMPLE 153

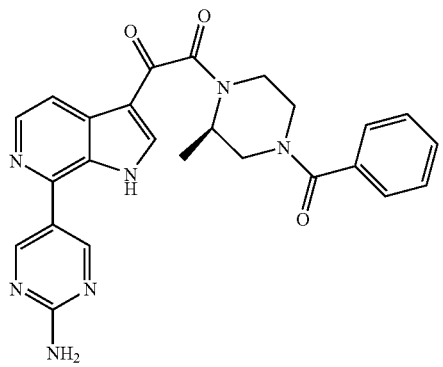

Example 153, was prepared from Precursor 5f and the 2-amino-pyrimidin-5-yl stannane to provide (R)-1-benzoyl-3-methyl-4-[(7-(2-amino-pyrimidin-5-yl)-6-azaindol-3-yl)-oxoacetyl]piperazine. MS m/z: (M+H)+ Calc'd for $C_{25}H_{24}N_7O_3$: 470.19; found 470.22. HPLC retention time: 1.07 minutes (column G).

EXAMPLE 170

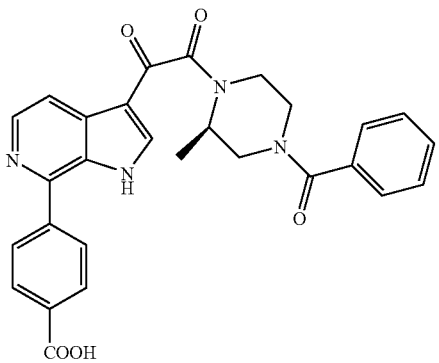

Example 170, was prepared from Precursor 5f and the 4-borono-bezoic acid to provide (R)-1-benzoyl-3-methyl-4-[(7-(hydroxylcarbonyl-benzen-4-yl)-6-azaindol-3-yl)-oxoacetyl]piperazine. MS m/z: (M+H)+ Calc'd for $C_{28}H_{25}N_4O_5$: 497.18; found 497.10. HPLC retention time: 1.25 minutes (column H).

EXAMPLE 171

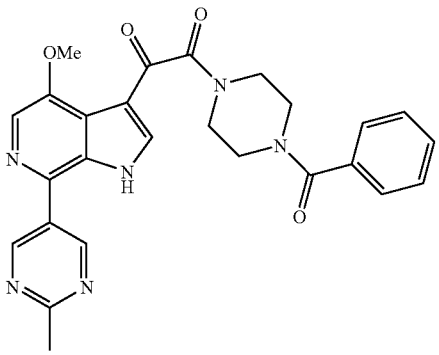

Example 171, was prepared from Precursor 5b and the 2-methyl-pyrimidin-5-yl stannane to provide 1-benzoyl-4-[(4-methoxy-7-(2-methyl-pyrimidin-5-yl)-6-azaindol-3-yl)-oxoacetyl]piperazine. MS m/z: (M+H)+ Calc'd for $C_{26}H_{25}N_6O_4$: 485.19; found 485.20. HPLC retention time: 1.14 minutes (column C).

EXAMPLE 172

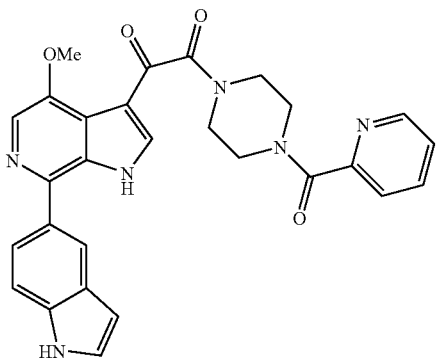

Example 172, was prepared from Precursor 5l and the 5-indole boronic acid to provide 1-picolinoyl-4-[(4-methoxy-7-(indol-5-yl)-6-azaindol-3-yl)-oxoacetyl]piperazine. MS m/z: (M+H)+ Calc'd for $C_{28}H_{25}N_6O_4$: 509.19; found 509.33. HPLC retention time: 1.14 minutes (column J).

EXAMPLE 173

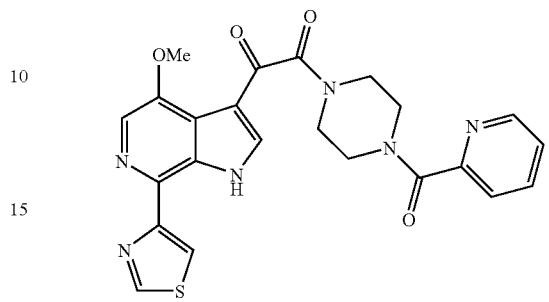

Example 173, was prepared from Precursor 5l and the thiazol-4-yl stannane to provide 1-picolinoyl-4-[(4-methoxy-7-(thiazol-4-yl)-6-azaindol-3-yl)-oxoacetyl]piperazine. MS m/z: (M+H)+ Calc'd for $C_{23}H_{21}N_6O_4S$: 477.13; found 477.06. HPLC retention time: 0.92 minutes (column G).

EXAMPLE 174

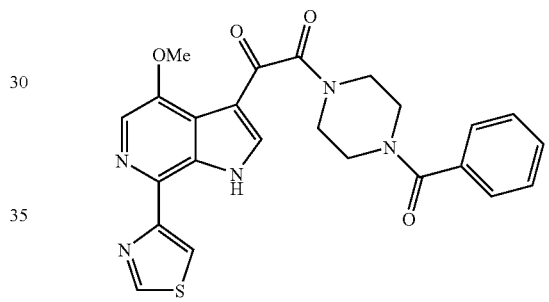

Example 174, was prepared from Precursor 5b and the thiazol-4-yl stannane to provide 1-benzoyl-4-[(4-methoxy-7-(thiazol-4-yl)-6-azaindol-3-yl)-oxoacetyl]piperazine. MS m/z: (M+H)+ Calc'd for $C_{24}H_{22}N_5O_4S$: 476.14; found 476.13. HPLC retention time: 1.12 minutes (column G).

EXAMPLE 175

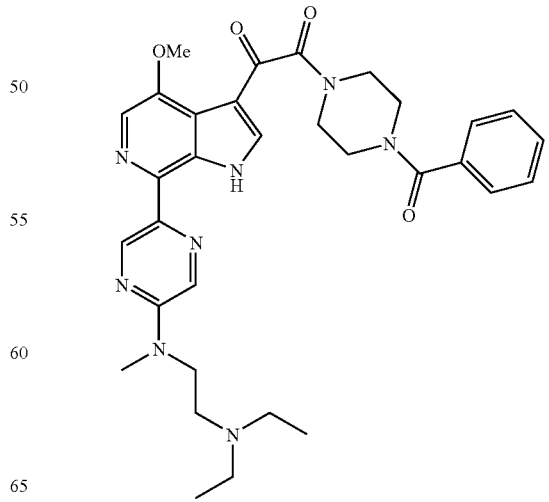

Example 175, was prepared from Precursor 5b and the 2-(N-diethylaminoethyl-N-methyl)aminopyrazin-5-yl stannane to provide 1-benzoyl-4-[(4-methoxy-7-(2-(N-diethylaminoethyl-N-methyl)aminopyrazin-5-yl)-6-azaindol-3-yl)-oxoacetyl]piperazine. MS m/z: (M+H)+ Calc'd for $C_{32}H_{39}N_8O_4$: 599.31; found 599.29. HPLC retention time: 1.11 minutes (column G).

EXAMPLE 176

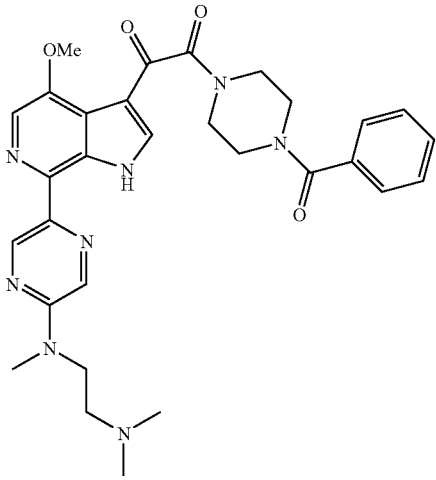

Example 176, was prepared from Precursor 5b and the 2-(N-dimethylaminoethyl-N-methyl)aminopyrazin-5-yl stannane to provide 1-benzoyl-4-[(4-methoxy-7-(2-(N-dimethylaminoethyl-N-methyl)aminopyrazin-5-yl)-6-azaindol-3-yl)-oxoacetyl]piperazine. MS m/z: (M+H)+ Calc'd for $C_{30}H_{35}N_8O_4$: 571.28; found 571.23. HPLC retention time: 1.06 minutes (column G).

EXAMPLE 177

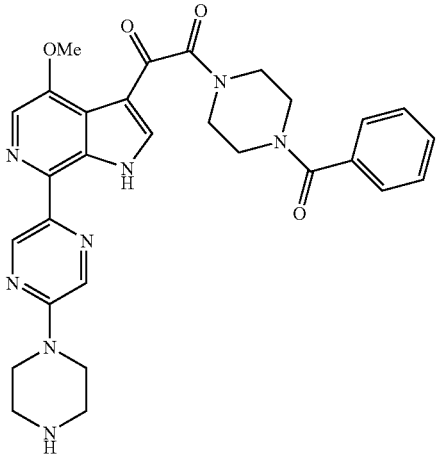

Example 177, was prepared from Precursor 5b and the 2-(N-piperazinyl)-pyrazin-5-yl stannane to provide 1-benzoyl-4-[(4-methoxy-7-(2-(N-piperazinyl)-pyrazin-5-yl)-6-azaindol-3-yl)-oxoacetyl]piperazine. MS m/z: (M+H)+ Calc'd for $C_{29}H_{31}N_8O_4$: 555.25; found 555.19. HPLC retention time: 1.05 minutes (column G).

EXAMPLE 178

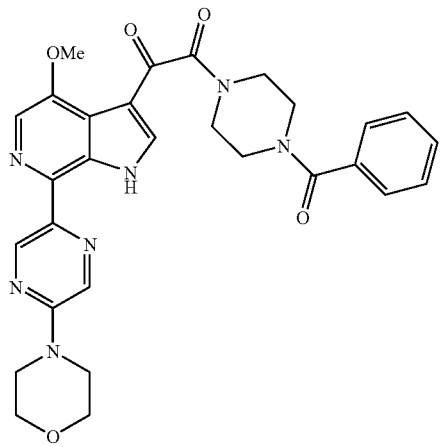

Example 178, was prepared from Precursor 5b and the 2-(4-morpholinyl)-pyrazin-5-yl stannane to provide 1-benzoyl-4-[(4-methoxy-7-(2-(4-morpholinyl)-pyrazin-5-yl)-6-azaindol-3-yl)-oxoacetyl]piperazine. MS m/z: (M+H)+ Calc'd for $C_{29}H_{30}N_7O_5$: 556.23; found 556.18. HPLC retention time: 1.27 minutes (column G).

EXAMPLE 179

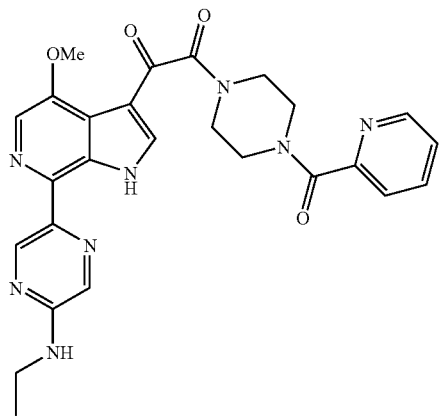

Example 179, was prepared from Precursor 51 and the 2-ethylaminopyrazin-5-yl stannane to provide 1-picolinoyl-4-[(4-methoxy-7-(2-ethylaminopyrazin-5-yl)-6-azaindol-3-yl)-oxoacetyl]piperazine. MS m/z: (M+H)+ Calc'd for $C_{26}H_{27}N_8O_4$: 515.22; found 515.14. HPLC retention time: 1.13 minutes (column G).

EXAMPLE 180

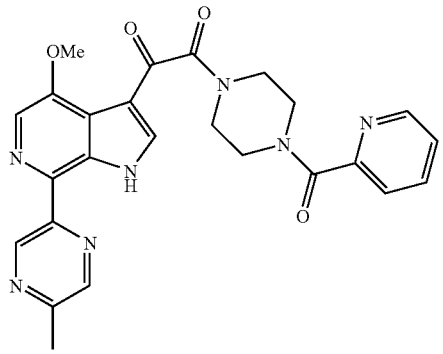

Example 180, was prepared from Precursor 5i and the 2-methylpyrazin-5-yl stannane to provide 1-picolinoyl-4-[(4-methoxy-7-(2-methylpyrazin-5-yl)-6-azaindol-3-yl)-oxoacetyl]piperazine. MS m/z: (M+H)$^+$ Calc'd for $C_{25}H_{24}N_7O_4$: 486.19; found 486.16. HPLC retention time: 1.08 minutes (column G).

EXAMPLE 181

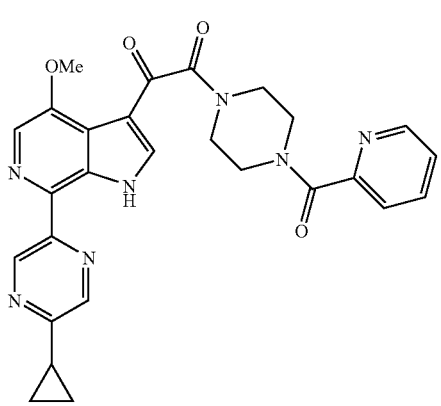

Example 181, was prepared from Precursor 51 and the 2-cyclopropanyl-pyrazin-5-yl stannane to provide 1-picolinoyl-4-[(4-methoxy-7-(2-cyclopropanyl-pyrazin-5-yl)-6-azaindol-3-yl)-oxoacetyl]piperazine. MS m/z: (M+H)$^+$ Calc'd for $C_{27}H_{26}N_7O_4$: 512.20; found 512.12. HPLC retention time: 1.35 minutes (column G).

EXAMPLE 182

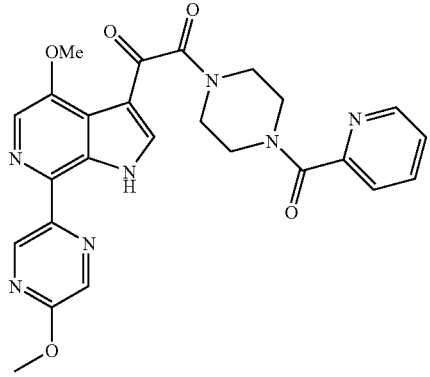

Example 182, was prepared from Precursor 51 and the 2-methoxy-pyrazin-5-yl stannane to provide 1-picolinoyl-4-[(4-methoxy-7-(2-methoxy-pyrazin-5-yl)-6-azaindol-3-yl)-oxoacetyl]piperazine. MS m/z: (M+H)$^+$ Calc'd for $C_{25}H_{24}N_7O_5$: 502.18; found 502.08. HPLC retention time: 1.15 minutes (column G).

EXAMPLE 183

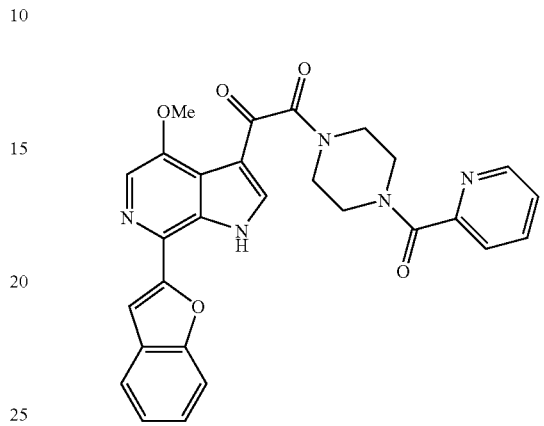

Example 183, was prepared from Precursor 51 and the 2-benzofuran boronic acid to provide 1-picolinoyl-4-[(4-methoxy-7-(benzofuran-2-yl)-6-azaindol-3-yl)-oxoacetyl]piperazine. MS m/z: (M+H)$^+$ Calc'd for $C_{28}H_{24}N_5O_5$: 510.18; found 510.08. HPLC retention time: 1.33 minutes (column G).

EXAMPLE 184

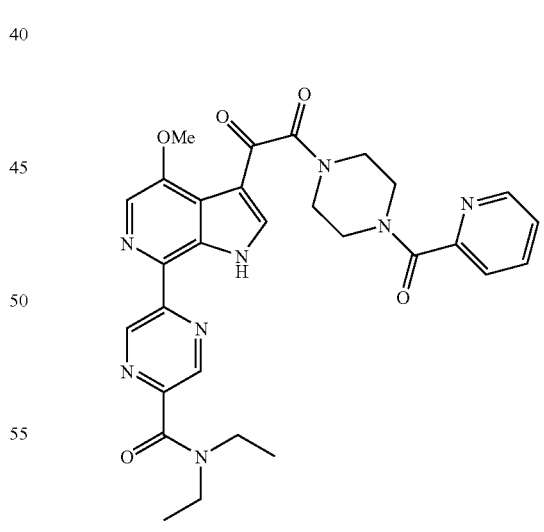

Example 184, was prepared from Precursor 51 and the 2-diethylaminocarbonyl-pyrazin-5-yl stannane to provide 1-picolinoyl-4-[(4-methoxy-7-(2-diethylaminocarbonyl-pyrazin-5-yl)-6-azaindol-3-yl)-oxoacetyl]piperazine. MS m/z: (M+H)$^+$ Calc'd for $C_{29}H_{31}N_8O_5$: 571.24; found 571.19. HPLC retention time: 1.55 minutes (column J).

EXAMPLE 185

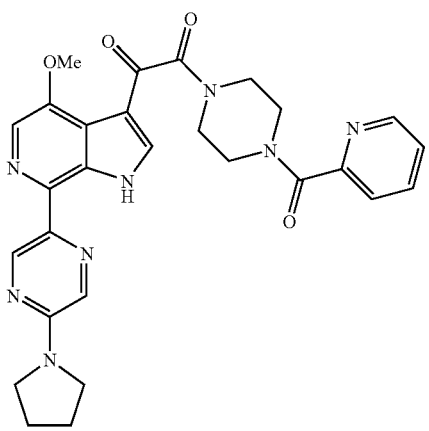

Example 185, was prepared from Precursor 51 and the 2-(N-pyrrolinyl)-pyrazin-5-yl stannane to provide 1-picolinoyl-4-[(4-methoxy-7-(2-(N-pyrrolinyl)-pyrazin-5-yl)-6-azaindol-3-yl)-oxoacetyl]piperazine. MS m/z: (M+H)$^+$ Calc'd for $C_{28}H_{29}N_8O_4$: 541.23; found 541.18. HPLC retention time: 1.30 minutes (column J).

EXAMPLE 186

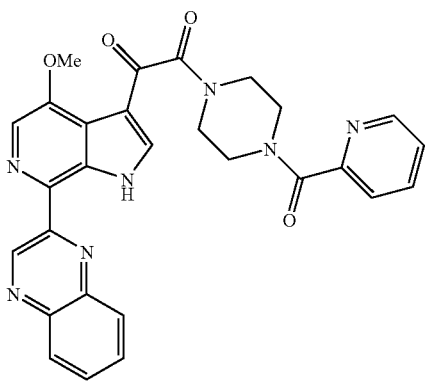

Example 186, was prepared from Precursor 51 and the quinoxalin-2-yl stannane to provide 1-picolinoyl-4-[(4-methoxy-7-(quinoxakin-2-yl)-6-azaindol-3-yl)-oxoacetyl]piperazine. MS m/z: (M+H)$^+$ Calc'd for $C_{28}H_{24}N_7O_4$: 522.19; found 522.14. HPLC retention time: 1.68 minutes (column J).

EXAMPLE 194

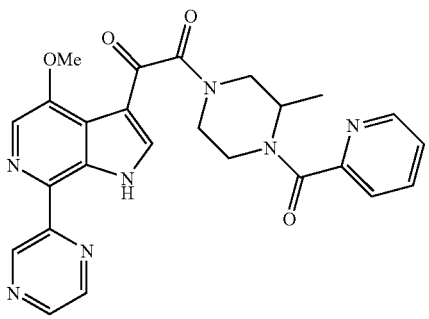

Example 194, was prepared from Precursor 5v and the pyrazin-2-yl stannane to provide 2-methyl-1-picolinoyl-4-[(4-methoxy-7-(pyrazin-2-yl)-6-azaindol-3-yl)-oxoacetyl] piperazine. MS m/z: (M+H)$^+$ Calc'd for $C_{25}H_{24}N_7O_4$: 486.19; found 486.14. HPLC retention time: 1.50 minutes (column G).

EXAMPLE 147

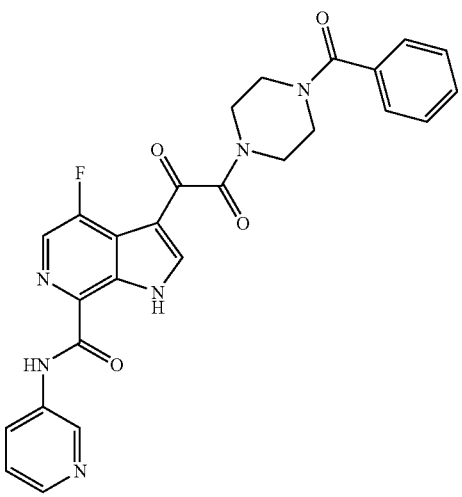

Precursor 5i (16.5 mg, 0.05 mmol) in DMF (1 mL) was treated with N-benzoylpiperazine hydrochloride, DEBPT (15 mg, 0.05 mmol) and Hunig's base (34 µL, 0.2 mmol) at rt for 18 h. The solvent was removed in vacuum and the residue was purified by reverse phase preparative HPLC. The fractions showing the right LC/MS (ES$^+$) m/z (M+H)$^+$=501 were collected, concentrated and purified again using a preparative TLC (5% MeOH/CH$_2$Cl$_2$) to afford the title compound as a white solid. $^1$H-NMR (500 MHz, CDCl$_3$) δ 11.2 (s, 1H), 10.0 (s, 1H), 9.21 (s, 1H), 8.51 (s, 1H), 8.41 (s, 1H), 8.40 (m, 1H), 8.32 (s, 1H), 7.62 (m, 1H), 7.45 (m, 5H), 3.90-3.50 (bm, 8H).

EXAMPLE 156

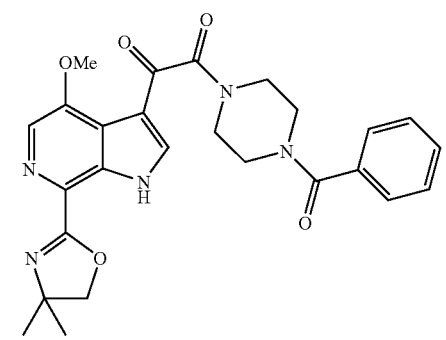

Example 156, was prepared from Precursor 5b and the 4,4-dimethyloxazolin-2-yl stannane to provide 1-benzoyl-4-[(7-(4,4-dimethyloxazolin-2-yl)-6-azaindol-3-yl)-oxoacetyl]piperazine. MS m/z: (M+H)$^+$ Calc'd for $C_{27}H_{28}N_5O_5$: 490.21; found 490.22. HPLC retention time: 1.20 minutes (column C).

EXAMPLE 169

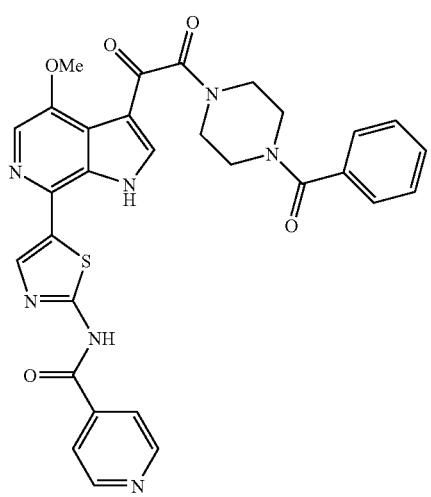

Example 169, was prepared from Precursor 5b and the 2-(4-pyridinecarboxamido)-thiazol-5-yl stannane to provide 1-benzoyl-4-[(7-(2-(4-pyridinecarboxamido)-thiazol-5-yl)-6-azaindol-3-yl)-oxoacetyl]piperazine. MS m/z: (M+H)+ Calc'd for $C_{30}H_{26}N_7O_5S$: 596.17; found 596.14. HPLC retention time: 1.32 minutes (column C).

EXAMPLES 82-86, 98, 107, 108, 129, 130, 132, 133, 134

Examples 82-86, 98, 107, 108, 127, 128, 129, 130, 132, 133 and 134 were prepared according to the general procedure as previously described for Examples 2-14.

EXAMPLE 82

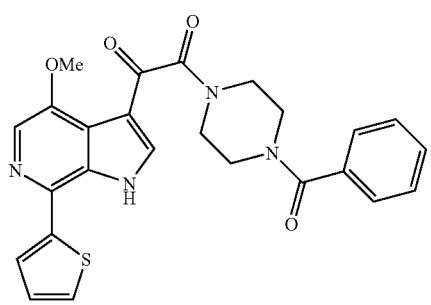

Example 82, was prepared from Precursor 5b and thien-2-yl boronic acid to provide 1-benzoyl-4-[(4-methoxy-7-(thiophen-2-yl)-6-azaindol-3-yl)-oxoacetyl]piperazine. MS m/z: (M+H)+ Calc'd for $C_{25}H_{23}N_4O_4S$: 475.14; found 475.31. HPLC retention time: 1.14 minutes (column A).

EXAMPLE 83

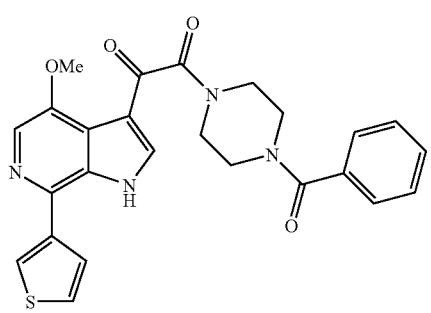

Example 83, was prepared from Precursor 5b and thien-2-yl boronic acid to provide 1-benzoyl-4-[(4-methoxy-7-(thiophen-3-yl)-6-azaindol-3-yl)-oxoacetyl]piperazine. MS m/z: (M+H+ Calc'd for $C_{25}H_{23}N_4O_4S$: 475.14; found 475.33. HPLC retention time: 1.16 minutes (column A).

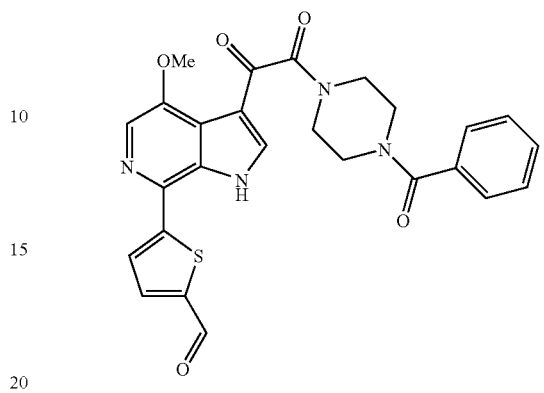

Example 84, was prepared from Precursor 5b and 5-carbonylthien-2-yl boronic acid to provide 1-benzoyl-4-[(4-methoxy-7-(5-carbonyl-thiophen-2-yl)-6-azaindol-3-yl)-oxoacetyl]piperazine. MS m/z: (M+H)+ Calc'd for $C_{26}H_{23}N_4O_5S$: 503.14; found 503.23. HPLC retention time: 1.31 minutes (column A).

EXAMPLE 85

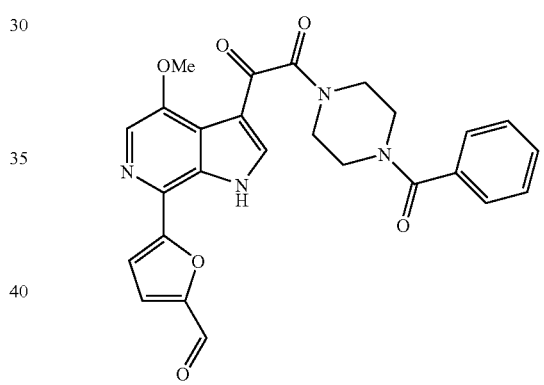

Example 76, was prepared from Precursor 5b and 5-carbonylfuran-2-yl boronic acid to provide 1-(benzoyl)-4-[(4-methoxy-7-(5-carbonyl-furan-2-yl)-6-azaindol-3-yl)-oxoacetyl]piperazine. MS m/z: (M+H)+ Calc'd for $C_{26}H_{23}N_4O_6$: 487.16; found 487.28. HPLC retention time: 1.44 minutes (column A).

EXAMPLE 86

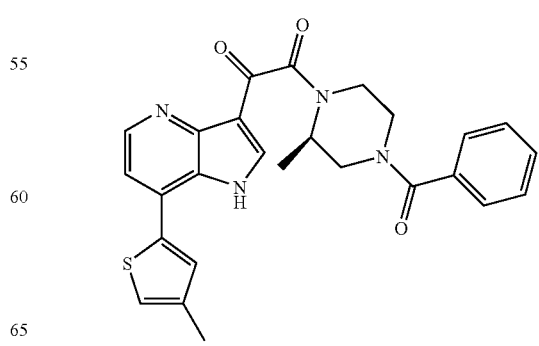

Example 86, was prepared from Precursor 5d and 4-methylthien-2-yl boronic acid to provide 1-benzoyl-3-(R)-methyl-4-[(7-(4-methyl-thiophen-2-yl)-4-azaindol-3-yl)-oxoacetyl]piperazine. MS m/z: (M+H)$^+$ Calc'd for $C_{26}H_{25}N_4O_3S$: 473.16; found 473.26. HPLC retention time: 1.28 minutes (column A).

EXAMPLE 98

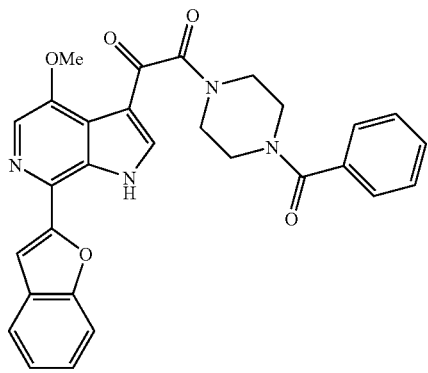

Example 98, was prepared from Precursor 5d and 2-benzofuranyl boronic acid to provide 1-benzoyl-3-(R)-methyl-4-[(7-(benzofuran-2-yl)-4-azaindol-3-yl)-oxoacetyl]piperazine. $^1$H NMR (500 MHz, CDCl$_3$) δ 8.24 (s, 1H), 8.09 (s, 1H), 7.70-7.26 (m, 10H), 4.03 (s, 3H), 3.97-3.49 (m, 8H). MS m/z: (M+H)$^+$ Calc'd for $C_{29}H_{25}N_4O_5$: 509.18; found 509.18. HPLC retention time: 1.50 minutes (column A).

EXAMPLE 107

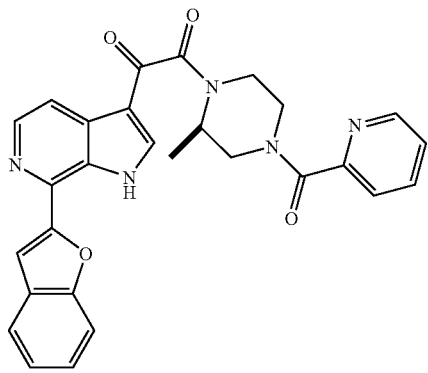

Example 107, was prepared from Precursor 5m and 2-benzofuranyl boronic acid to provide (R)-1-picolinoyl-3-methyl-4-[(7-(benzofuran-2-yl)-6-azaindol-3-yl)-oxoacetyl]piperazine. $^1$H NMR (500 MHz, CD$_3$OD) δ8.77-7.38 (m, 12H), 4.99-3.16 (m, 7H), 1.44-1.27 (m, 3H). MS m/z: (M+H)$^+$ Calc'd for $C_{28}H_{24}N_5O_4$: 494.18; found 494.24. HPLC retention time: 1.35 minutes (column A).

EXAMPLE 108

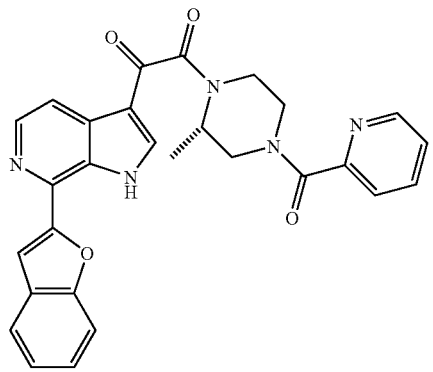

Example 108, was prepared from Precursor 5n and 2-benzofuranyl boronic acid to provide (S)-1-picolinoyl-3-methyl-4-[(7-(benzofuran-2-yl)-6-azaindol-3-yl)-oxoacetyl]piperazine. MS m/z: (M+H)$^+$ Calc'd for $C_{28}H_{24}N_5O_4$: 494.18; found 494.23. HPLC retention time: 1.37 minutes (column A).

EXAMPLE 127

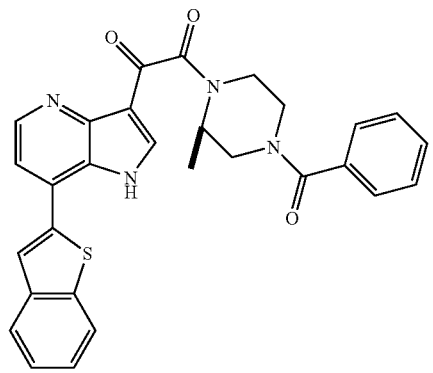

Example 127, was prepared from Precursor 5i and the benzothiophen-2-yl boronic acid to provide (R)-1-benzoyl-3-Methyl-4-[7-(benzothiophen-2-yl)-4-azaindol-3-yl)-oxoacetyl]piperazine. MS m/z: (M+H)$^+$ Calc'd for $C_{29}H_{25}N_4O_3S$: 509.16; found 509.21. HPLC retention time: 1.42 minutes (column A).

EXAMPLE 128

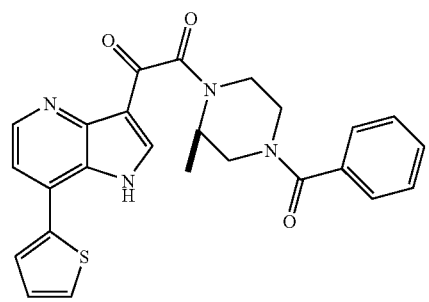

Example 128, was prepared from Precursor 5i and the thiophen-2-yl boronic acid to provide (R)-1-benzoyl-3-Methyl-4-[7-(thiophen-2-yl)-4-azaindol-3-yl)-oxoacetyl]piperazine. MS m/z: (M+H)+ Calc'd for C$_{25}$H$_{23}$N$_4$O$_3$S: 459.15; found 459.27. HPLC retention time: 1.22 minutes (column A).

EXAMPLE 129

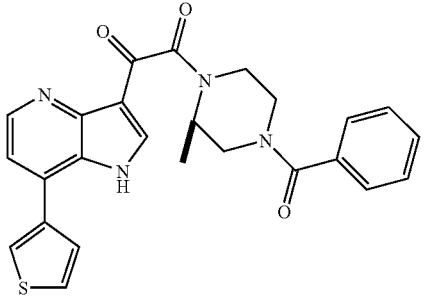

Example 129, was prepared from Precursor 5i and the thiophen-3-yl boronic acid to provide (R)-1-benzoyl-3-Methyl-4-[7-(thiophen-3-yl)-4-azaindol-3-yl)-oxoacetyl]piperazine. MS m/z: (M+H)+ Calc'd for C$_{25}$H$_{23}$N$_4$O$_3$S: 459.15; found 459.34. HPLC retention time: 1.31 minutes (column A).

EXAMPLE 130

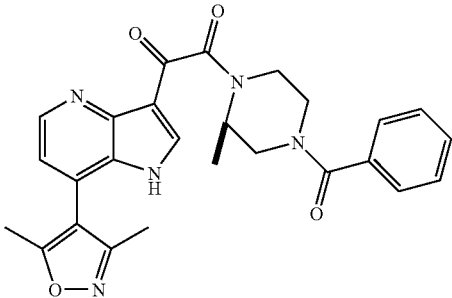

Example 130, was prepared from Precursor 5i and the 2,5-dimethyl-isoxazol-4-yl boronic acid to provide (R)-1-benzoyl-3-Methyl-4-[7-(2,5-dimethyl-isoxazol-4-yl)-4-azaindol-3-yl)-oxoacetyl]piperazine. MS m/z: (M+H)+ Calc'd for C$_{26}$H$_{26}$N$_5$O$_4$: 472.20; found 472.28. HPLC retention time: 1.14 minutes (column A).

EXAMPLE 132

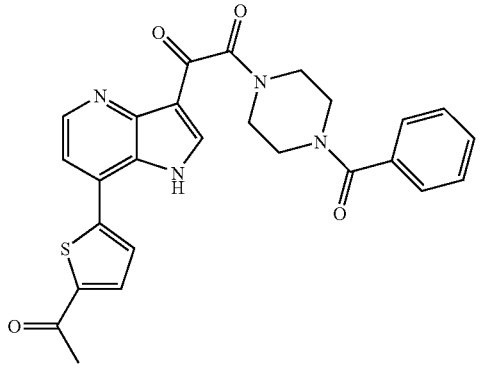

Example 132, was prepared from Precursor 5p and the 2-methylcarbonyl-thiophen-5-yl boronic acid to provide 1-benzoyl-4-[7-(2-methylcarbonyl-thiophen-5-yl)-4-azaindol-3-yl)-oxoacetyl]piperazine. MS m/z: (M+H)+ Calc'd for C$_{26}$H$_{23}$N$_4$O$_4$S: 487.14; found 487.20. HPLC retention time: 1.14 minutes (column A).

EXAMPLE 133

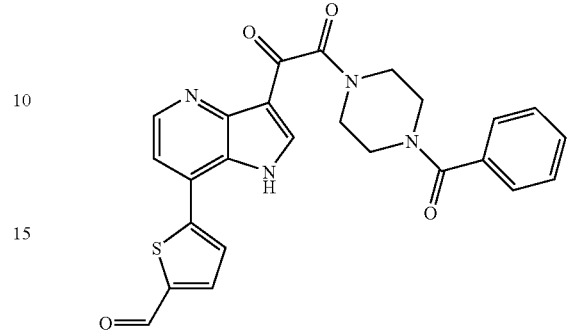

Example 133, was prepared from Precursor 5p and the 2-carbonyl-thiophen-5-yl boronic acid to provide 1-benzoyl-4-[7-(2-carbonyl-thiophen-5-yl)-4-azaindol-3-yl)-oxoacetyl]piperazine. MS m/z: (M+H)+ Calc'd for C$_{25}$H$_{21}$N$_4$O$_4$S: 473.13; found 473.11. HPLC retention time: 1.14 minutes (column A).

EXAMPLE 134

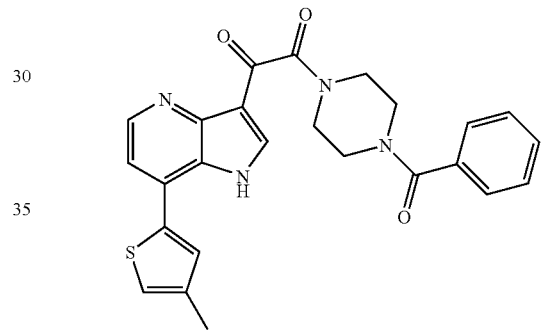

Example 134, was prepared from Precursor 5p and the 4-methyl-thiophen-2-yl boronic acid to provide 1-benzoyl-4-[7-(4-methyl-thiophen-2-yl)-4-azaindol-3-yl)-oxoacetyl] piperazine. MS m/z: (M+H)+ Calc'd for C$_{25}$H$_{23}$N$_4$O$_3$S: 459.15; found 459.08. HPLC retention time: 1.26 minutes (column G).

EXAMPLE 152

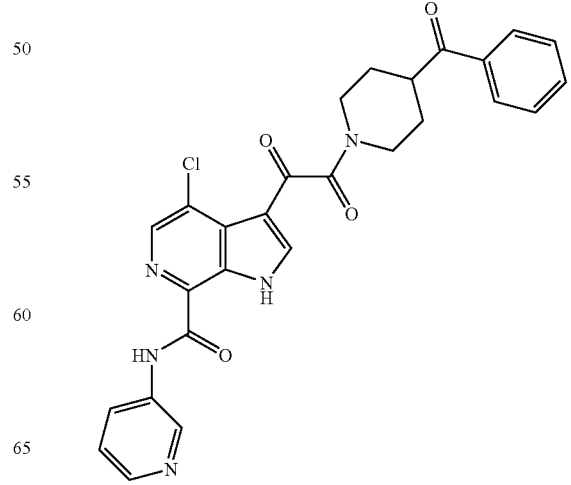

Preparation of Example 152:

To a mixture of acid precursor 16 (30 mg, 68 μmol), 3-aminopyridine (26 mg, 0.27 mmol) and DMAP (50 mg, 0.41 mmol) was added THF (2 ml), and then EDC (60 mg, 0.31 mmol). The reaction mixture was stirred at ambient temperature for 16 hours. The LC/MS analysis indicated that the major product was the activated ester. The reaction mixture was then added into a DMF (2 ml) solution of 3-aminopyridine (400 mg, 4.25 mmol) and stirred at ambient temperature for 16 hours. After addition of MeOH (4 ml), the reaction mixture was purified by preparative reverse phase HPLC to give the TFA salt of the title compound using the method: Start % B=30, Final % B=75, Gradient time=25 min, Flow Rate=25 ml/min, Column: YMC C18 5 um 20×100 mm, Fraction Collection: 10.41-11.08 min. $^1$H NMR: (DMSO-$d_6$) δ 13.04 (s, 1H), 11.17 (s, 1H), 9.17 (s, 1H), 8.53 (s, 1H), 8.35 (m, 3H), 7.44 (b s, 6H), 3.75-3.37 (b m, 8H); LC/MS: (ES+) m/z (M+H)$^+$=517, 519; HPLC $R_t$=1.653.

EXAMPLE 143

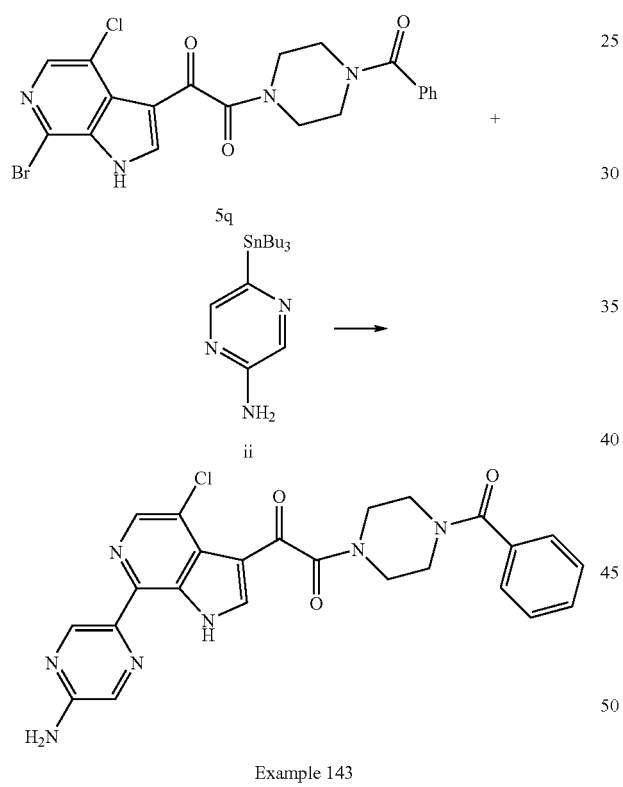

Example 143

Prep of Example 143:

To a mixture of precursor 5q (31 mg, 65 μmol) and Pd(PPh$_3$)$_4$ (20 mg, 17 μmol) was added 1,4-dioxane (1 ml) and ii (30 mg, 78 μmol). The reaction mixture was heated in a sealed tube at 145° C. for 4 hours. After cooling to ambient temperature, the reaction mixture was added MeOH (4 ml) and then filtered. The filtrate was purified by preparative reverse phase HPLC to give the TFA salt of the title compound using the method: Start % B=25, Final % B=90, Gradient time=20 min, Flow Rate=25 ml/min, Column: YMC C18 5 um 20×100 mm, Fraction Collection: 11.14-11.92 min. $^1$H NMR: (DMSO-$d_6$) δ 12.71 (s, 1H), 9.01 (s, 1H), 8.36 (s, 1H), 8.27 (s, 1H), 8.08 (s, 1H), 7.44 (b s, 5H), 7.44 (b s, 2H), 3.75-3.37 (b m, 8H); LC/MS: (ES+) m/z (M+H)$^+$=490, 492; HPLC $R_t$=2.250.

EXAMPLE 149

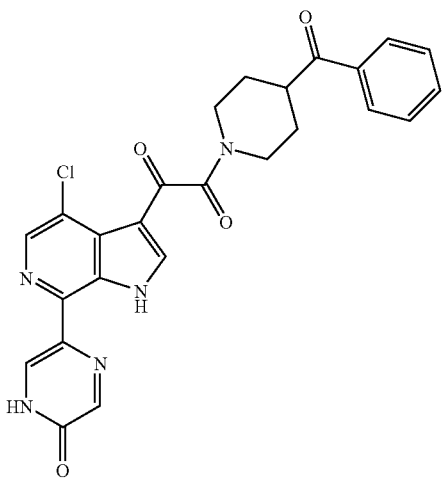

Preparation of Example 49:

To a suspension of compound of Example 143 (12 mg, 24 μmol) in sulfuric acid (5%, 2 ml), was charged sodium nitrite (22 mg, 0.32 mol) at 0° C. The reaction mixture was stirred at 0° C. for 30 minutes and then at ambient temperature for 1 hour. After addition of MeOH (4 ml), the reaction mixture was purified by preparative reverse phase HPLC to give a TFA solvate of title compound using the method: Start % B=20, Final % B=85, Gradient time=15 min, Flow Rate=25 ml/min, Column: YMC C18 5 um 20×100 mm, Fraction Collection: 10.67-11.36 min. $^1$H NMR: (DMSO-$d_6$) δ 12.62 (s, 1H), 8.45 (s, 1H), 8.35 (s, 1H), 8.29 (s, 1H), 8.18 (s, 1H), 7.44 (b s, 5H), 3.80-3.30 (b m, 8H); LC/MS: (ES+) m/z (M+H)$^+$=491, 493; HPLC $R_t$=2.193.

EXAMPLE 144

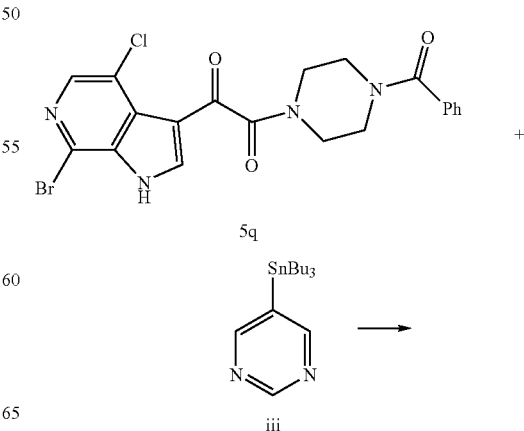

-continued

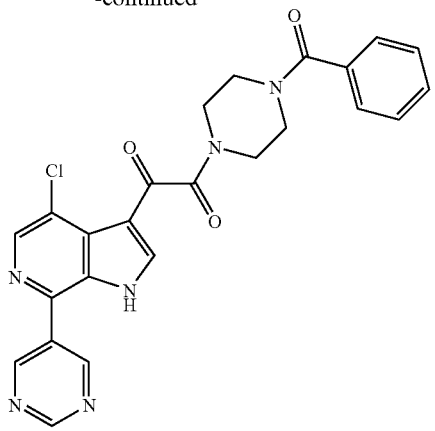

Preparation of Example 144:

To a mixture of precursor 5q (50 mg, 105 μmol) and Pd(PPh₃)₄ (50 mg, 43 μmol) was added 1,4-dioxane (1 ml) and iii (77 mg, 210 μmol). The reaction mixture was heated in a sealed tube at 145° C. for 16 hours. After cooling to ambient temperature, the reaction mixture was added MeOH (4 ml) and then filtered. The filtrate was purified by reverse phase HPLC to give the TFA salt of the title compound of using the method: Start % B=15, Final % B=100, Gradient time=20 min, Flow Rate=25 ml/min, Column: YMC C18 5 um 20×100 mm, Fraction Collection: 11.80-12.31 min. $^1$H NMR: (CD₃OD) δ 9.32 (s, 1H), 9.25 (s, 2H), 8.50 (s, 1H), 8.44 (s, 1H), 7.47 (b s, 5H), 4.00-3.44 (b m, 8H); LC/MS: (ES+) m/z (M+H)⁺=475, 477; HPLC $R_t$=1.833.

EXAMPLE 87

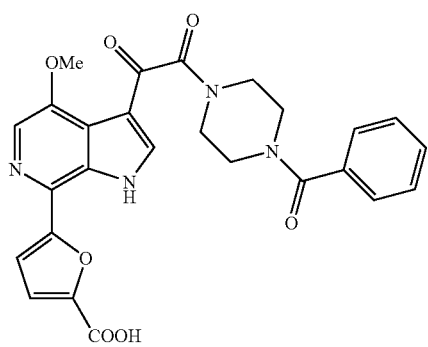

Preparation of Example 87, 1-benzoyl-4-[(4-methoxy-7-(2-hydroxycarbonyl-furan-5-yl)-6-azaindol-3-yl)-oxoacetyl]piperazine: A mixture of the compound of Example 85 (19 mg), NaClO₂ (9.2 mg) in a mixed solution of CH₃CN (3 mL) and water (0.5 mL) was stirred at room temperature for 24 hours. After the reaction was quenched by 1N NaOH solution (1 ml), the mixture was extracted with diethyl ether (3×10 mL). The aqueous phase was acidified with 1N HCl to give a yellow solid precipitate (5 mg) which was the product shown. MS m/z: (M+H)⁺ Calc'd for C₂₆H₂₃N₆O₇: 503.16; found 503.19. HPLC retention time: 1.37 minutes (column A).

General Procedure of Converting —NH₂ Group to —NH-COR Group

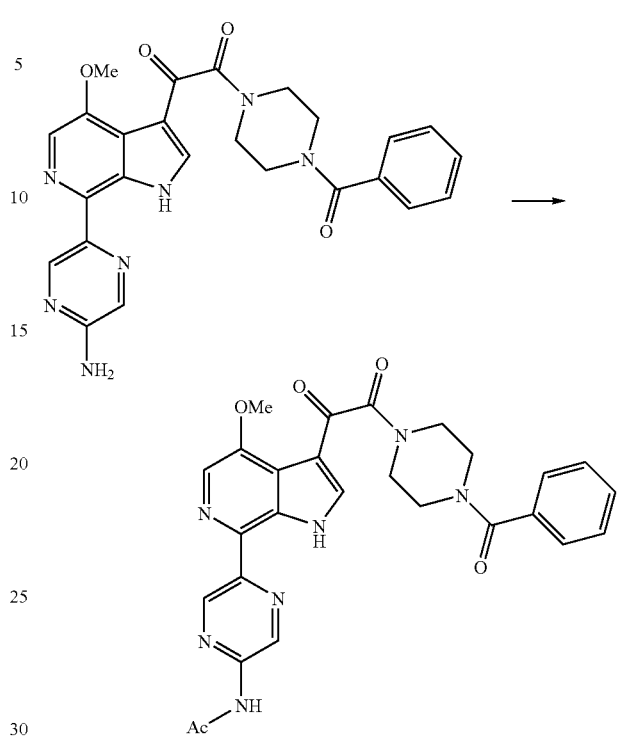

Preparation of Example 99, 1-(benzoyl)-4-[(4-methoxy-7-(2-acetylamino-pyrazin-5-yl)-6-azaindol-3-yl)-oxoacetyl] piperazine: 1-(benzoyl)-4-[(4-methoxy-7-(2-amino-pyrazin-5-yl)-6-azaindol-3-yl)-oxoacetyl]piperazine (4 mg) and acetic anhydride (20 mg) were dissolved in pyridine (0.5 ml). The reaction was stirred for three hours at room temperature. After reaction was quenched with MeOH (1 ml), solvents were concentrated to give a residue which was purified using a Shimadzu automated preparative HPLC System to provide 3.0 mg of the desired compound, 1-(benzoyl)-4-[(4-methoxy-7-(2-acetylamino-pyrazin-5-yl)-6-azaindol-3-yl)-oxoacetyl] piperazine. $^1$H NMR (500 MHz, CD₃OD) δ9.58 (s, 1H), 9.25 (s, 1H), 8.45 (s, 1H), 8.10 (s, 1H), 7.49 (m, 5H), 4.12 (s, 3H), 3.84-3.35 (m, 8H), 2.27 (s, 3H). MS m/z: (M+H)⁺ Calc'd for C₂₇H₂₆N₇O₅: 528.20; found 528.22. HPLC retention time: 1.33 minutes (column A).

General Procedure of Converting —NH₂ Group to —OH Group

Preparation of Example 97, 1-(benzoyl)-4-[(4-methoxy-7-(2-hydroxyl-pyrazin-5-yl)-6-azaindol-3-yl)-oxoacetyl]piperazine: 1-(benzoyl)-4-[(4-methoxy-7-(2-amino-pyrazin-5-yl)-6-azaindol-3-yl)-oxoacetyl]piperazine (15 mg) and NaNO₂ (10 mg) was added into a H₂SO₄ solution (0.1 ml of concentrated H₂SO₄ diluted with 0.3 ml of water). The reaction was stirred at room temperature for one hour. Then, the reaction mixture was neutralized with a saturated Na₂CO₃ solution (10 ml). The solvents were concentrated to give a residue which was purified using a Shimadzu automated preparative HPLC System to provide 4.2 mg of the desired compound, 1-(benzoyl)-4-[(4-methoxy-7-(2-hydroxyl-pyrazin-5-yl)-6-azaindol-3-yl)-oxoacetyl]piperazine. $^1$H NMR (500 MHz, CD₃OD) δ8.55 (s, 1H), 8.44 (s, 1H), 8.31 (s, 1H), 8.01 (s, 1H), 7.49 (m, 5H), 4.12 (s, 3H), 3.84-3.64 (m, 8H). MS m/z: (M+H)⁺ Calc'd for C₂₅H₂₃N₆O₅: 487.17; found 487.22. HPLC retention time: 1.13 minutes (column A).

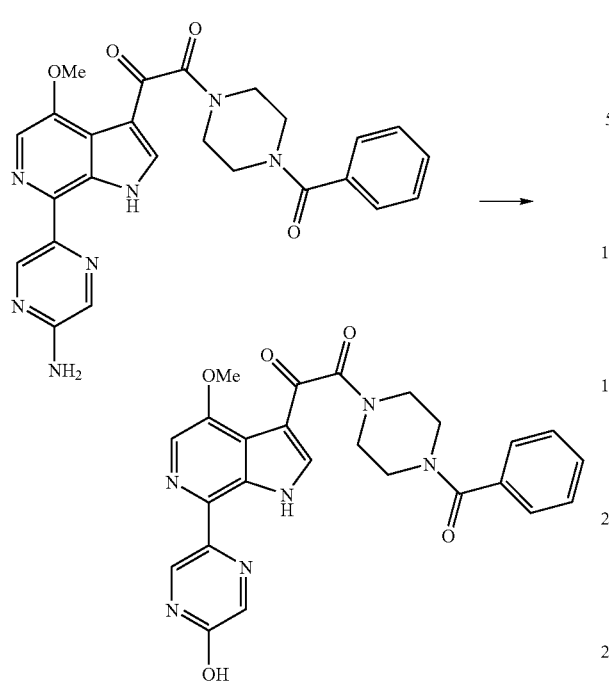

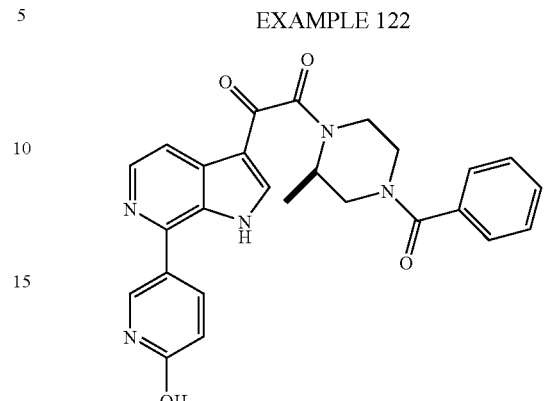

oxoacetyl]piperazine was isolated during the preparation of Example 121. MS m/z: (M+H)+ Calc'd for $C_{25}H_{23}N_6O_5$: 487.17; found 487.17. HPLC retention time: 1.08 minutes (column G).

EXAMPLE 122

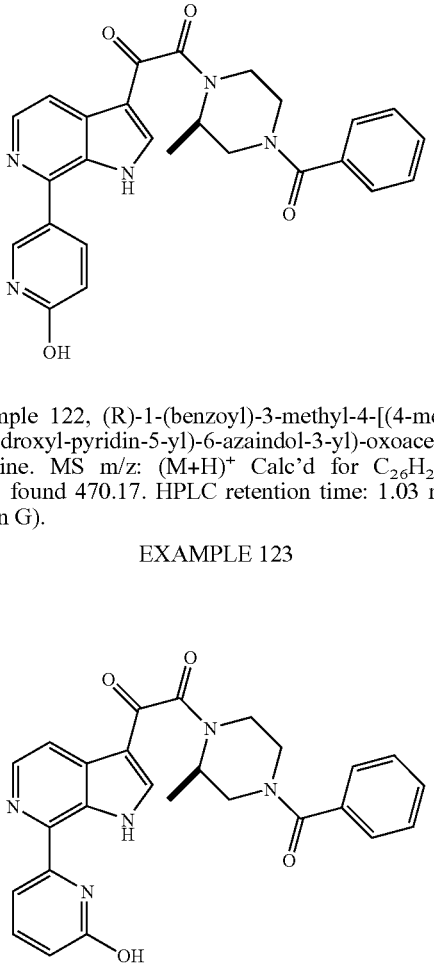

This general procedure is applied to prepare examples 121, 122, 123, 124, 155, 157, and 162.

EXAMPLE 121

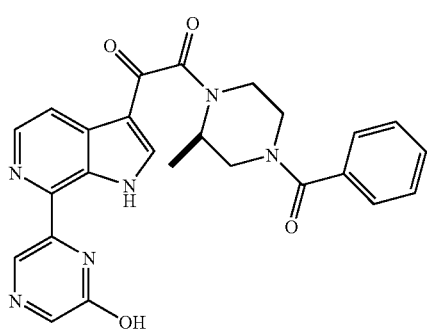

Example 121, (R)-1-(benzoyl)-3-methyl-4-[(4-methoxy-7-(2-hydroxyl-pyrazin-6-yl)-6-azaindol-3-yl)-oxoacetyl]piperazine. MS m/z: (M+H)+ Calc'd for $C_{25}H_{23}N_6O_4$: 471.18; found 471.17. HPLC retention time: 1.39 minutes (column G).

EXAMPLE 121-2

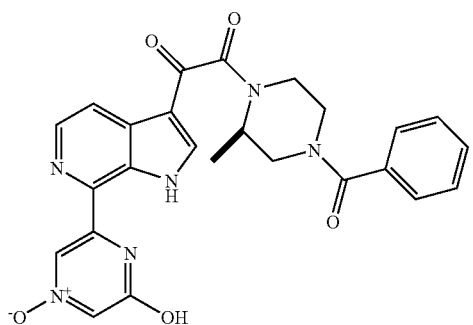

Example 121-2, (R)-1-(benzoyl)-3-methyl-4-[(4-methoxyl-7-(2-hydroxyl-4-oxo-pyrazin-6-yl)-6-azaindol-3-yl)-

Example 122, (R)-1-(benzoyl)-3-methyl-4-[(4-methoxy-7-(2-hydroxyl-pyridin-5-yl)-6-azaindol-3-yl)-oxoacetyl]piperazine. MS m/z: (M+H)+ Calc'd for $C_{26}H_{24}N_5O_4$: 470.18; found 470.17. HPLC retention time: 1.03 minutes (column G).

EXAMPLE 123

Example 123, (R)-1-(benzoyl)-3-methyl-4-[(4-methoxy-7-(2-hydroxyl-pyridin-6-yl)-6-azaindol-3-yl)-oxoacetyl]piperazine. MS m/z: (M+H)+ Calc'd for $C_{26}H_{24}N_5O_4$: 470.18; found 470.14. HPLC retention time: 1.28 minutes (column G).

EXAMPLE 124

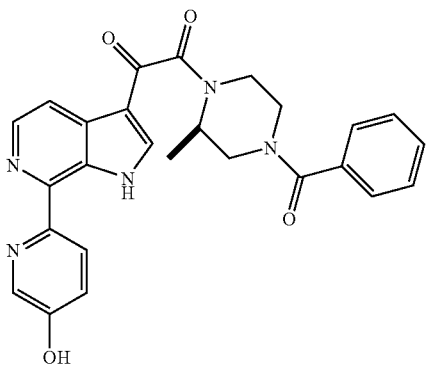

Example 124, (R)-1-(benzoyl)-3-methyl-4-[(4-methoxy-7-(5-hydroxyl-pyridin-2-yl)-6-azaindol-3-yl)-oxoacetyl]piperazine. MS m/z: (M+H)$^+$ Calc'd for $C_{26}H_{24}N_5O_4$: 470.18; found 470.13. HPLC retention time: 1.21 minutes (column G).

Preparation of Example 138

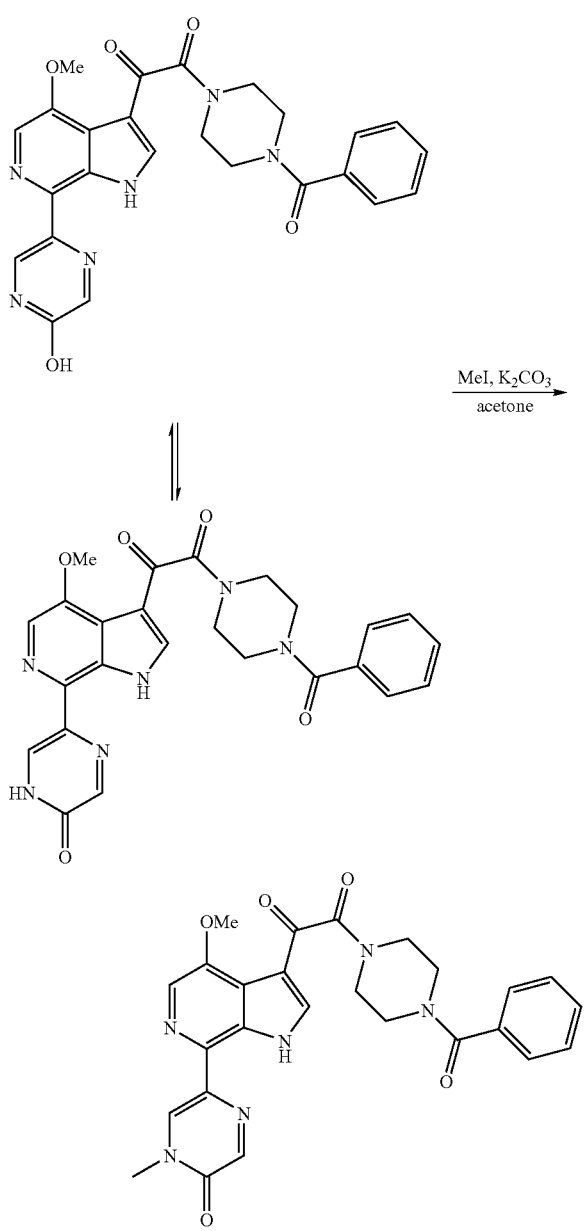

Preparation of Example 138, 1-(benzoyl)-4-[(4-methoxy-7-(1-methylpyrazin-2-on-5-yl)-6-azaindol-3-yl)-oxoacetyl]piperazine: 1-(benzoyl)-4-[(4-methoxy-7-(2-hydroxyl-pyrazin-5-yl)-6-azaindol-3-yl)-oxoacetyl]piperazine (6 mg), MeI (5 mg) and K$_2$CO$_3$ (4 mg) were dissolved in acetone (5 ml). The reaction was stirred for four hours at room temperature. After solid was filtered away, the mother liquid was concentrated to give a residue which was purified using a Shimadzu automated preparative HPLC System to provide 3.0 mg of the desired compound, 1-(benzoyl)-4-[(4-methoxy-7-(1-methylpyrazin-2-on-5-yl)-6-azaindol-3-yl)-oxoacetyl]piperazine. MS m/z: (M+H)$^+$ Calc'd for $C_{26}H_{25}N_6O_5$: 501.19; found 501.14. HPLC retention time: 1.08 minutes (column G).

EXAMPLE 139

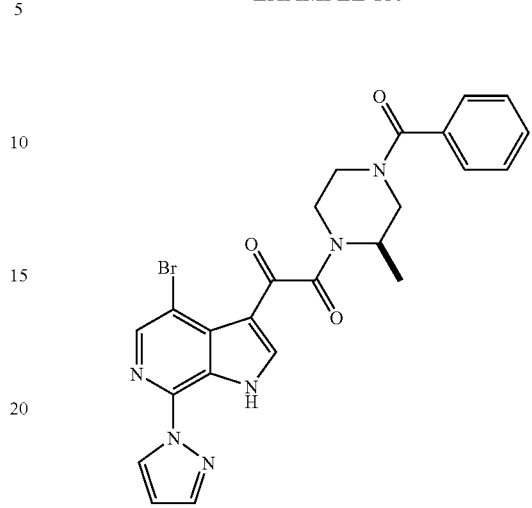

Precursor 4i was dissolved in DMF (2 ml), and to which N-benzoyl-(R)-methylpiperazine hydrochloride (0.092 g, 0.45 mmol) and 3-(diethoxyphosphoryloxy)-1,2,3-benzotriazin-4(3H)-one (DEPBT, 0.180 g, 0.60 mmol) were added, followed by N,N-diisopropylethylamine (0.15 ml, 0.87 mmol). The reaction mixture was stirred for 2 h at r.t., and then the volatile evaporated under high vacuum. Water was added to the mixture to induce precipitation, and the solids were filtered and dried in vacuo. Purification of the crude solid by preparative thin layer chromatography (5% MeOH/CH$_2$Cl$_2$), and subsequent washing with ether gave the title compound; $^1$H NMR: (CDCl$_3$) δ 8.78 (s, 1H), 8.32 (s, 1H), 8.28 (s, 1H) 7.84 (s, 1H), 7.44 (b s, 5H), 6.56 (s, 1H), 5.00-3.00 (b m, 7H), 1.45-1.20 (b s, 3H); LC/MS: (ES+) m/z (M+H)$^+$=521, 523; HPLC R$_t$=1.677.

Preparation of N-linked Azaindole Heterocylic Derivatives from the Corresponding Bromide or Chloride. An Example of a Typical Procedure:

A general reaction condition is shown with the preparation of example 187. Other analogs, examples 188-193, were prepared via the same reaction condition.

EXAMPLE 187

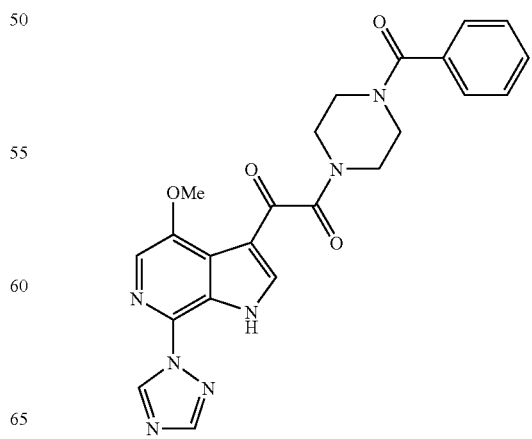

Preparation of compound of Example 187: Precursor 5b (30 mg), 1,2,4-triazole (145 mg), Cu (4.4 mg) and K2CO3 (9.6 mg) were combined in a sealed tube which was degassed before being sealed. The mixture was heated to 160° C. for 8 hours. After being allowed to cool down to ambient temperature, the mixture was diluted with MeOH (14 ml) and dichloromethane (7 ml). After filtration, the filtrate was concentrated to give a residue which was purified using a Shimadzu automated preparative HPLC System to provide 12.9 mg of the desired compound 187, 1-benzoyl-4-[(4-methoxy-7-(1,2,4-triazol-1-yl)-6-azaindol-3-yl)-oxoacetyl]piperazine. MS m/z: (M+H)+ Calc'd for $C_{23}H_{22}N_7O_4$: 460.17; found 460.33. HPLC retention time: 1.45 minutes (column J).

EXAMPLE 188 AND EXAMPLE 188A

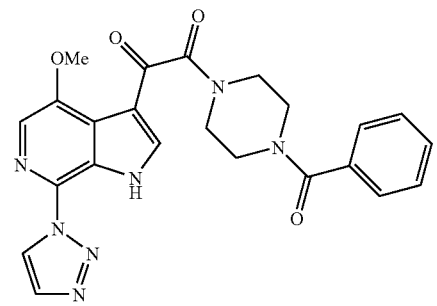

Example 188 and

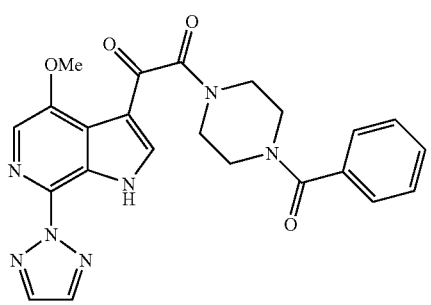

Example-188A

Example 188 and 188A, were prepared according to the general method described above starting from Precursor 5z and 1,2,3-triazole to provide Example 188 and Example 188A.

Precursor 5z (0.050 g), 0.050 g Cu powder, 0.025 g K2CO3 and 6 equivalents of 1,2,3 triazole were heated at 150 C for 16 hrs. The reaction was allow to cool to ambient temperature and was dissolved in MeOH and purified by Prep HPLC as described above in the general methods to provide Example 188 (0.0237 g brown solid, yield 44%) and the other isomer Example 188a.

Example 188, 1-benzoyl-4-[(4-methoxy-7-(1,2,3-triazol-1-yl)-6-azaindol-3-yl)-oxoacetyl]piperazine. MS m/z: (M+H)+ Calc'd for $C_{23}H_{22}N_7O_4$: 460.17; found 460.34. HPLC retention time: 1.50 minutes (column J); 1.29 minutes (column L). $^1$H NMR (500 MHz, CD$_3$OD) δ8.86 (s, 1H), 8.34 (s, 1H), 7.97 (m, 2H), 7.48 (b, 5H), 4.08 (s, 3H), 3.89-3.56 (m, 8H).

Example 188A, 1-benzoyl-4-[(4-methoxy-7-(1,2,3-triazol-2-yl)-6-azaindol-3-yl)-oxoacetyl]piperazine. MS m/z: (M+H)+ Calc'd for $C_{23}H_{22}N_7O_4$: 460.17; found 460.34. HPLC retention time: 1.39 minutes (column J). $^1$H NMR (500 MHz, CD$_3$OD) δ8.32 (s, 1H), 7.76 (s, 1H), 7.45 (b, 7H), 4.07 (s, 3H), 3.80-3.30 (m, 8H).

EXAMPLE 189

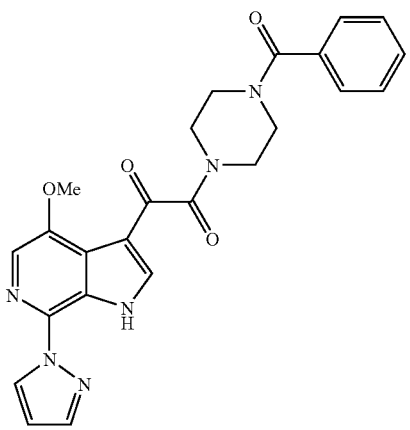

Example 189, was prepared from Precursor 5b and pyrazole to provide 1-benzoyl-4-[(4-methoxy-7-(1-pyrazolyl)-6-azaindol-3-yl)-oxoacetyl]piperazine. MS m/z: (M+H)+ Calc'd for $C_{24}H_{23}N_6O_4$: 459.18; found 459.01. HPLC retention time: 0.92 minutes (column G).

EXAMPLE 190

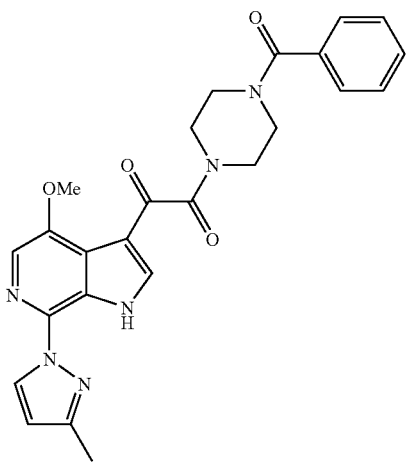

Example 190, was prepared from Precursor 5b and 3-methylpyrazole to provide 1-benzoyl-4-[(4-methoxy-7-(3-methylpyrazol-1-yl)-6-azaindol-3-yl)-oxoacetyl]piperazine. MS m/z: (M+H)+ Calc'd for $C_{25}H_{25}N_6O_4$: 473.19; found 473.09. HPLC retention time: 1.49 minutes (column G).

EXAMPLE 191

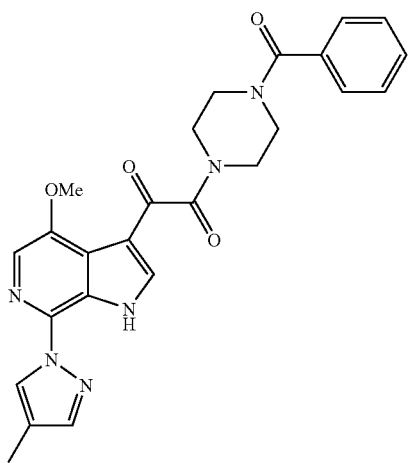

Example 191, was prepared from Precursor 5b and 4-methylpyrazole to provide 1-benzoyl-4-[(4-methoxy-7-(4-methylpyrazol-1-yl)-6-azaindol-3-yl)-oxoacetyl]piperazine. MS m/z: (M+H)$^+$ Calc'd for $C_{25}H_{25}N_6O_4$: 473.19; found 473.09. HPLC retention time: 1.52 minutes (column G).

EXAMPLE 192

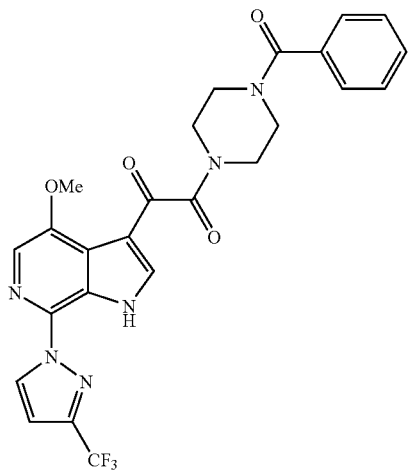

Example 192, was prepared from Precursor 5b and 3-trifluoromethylpyrazole to provide 1-benzoyl-4-[(4-methoxy-7-(3-trifluoromethylpyrazol-1-yl)-6-azaindol-3-yl)-oxoacetyl]piperazine. MS m/z: (M+H)$^+$ Calc'd for $C_{25}H_{22}F_3N_6O_4$: 527.17; found 527.09. HPLC retention time: 1.64 minutes (column G).

EXAMPLE 193

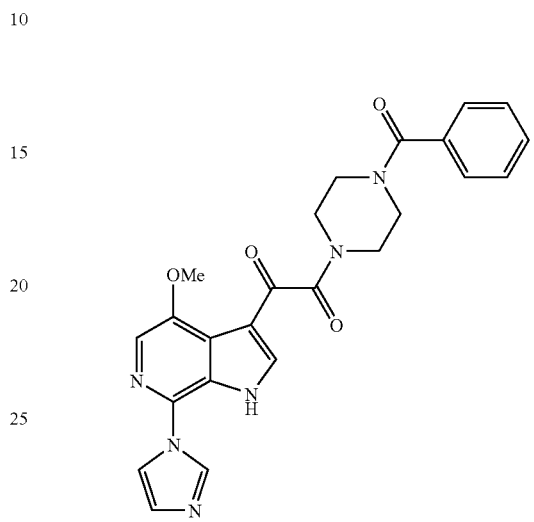

Example 193, was prepared from Precursor 5b and imidazole to provide 1-benzoyl-4-[(4-methoxy-7-(1-imidazolyl)-6-azaindol-3-yl)-oxoacetyl]piperazine. MS m/z: (M+H)$^+$ Calc'd for $C_{24}H_{23}N_6O_4$: 459.18; found 459.26. HPLC retention time: 1.22 minutes (column G).

EXAMPLE 140

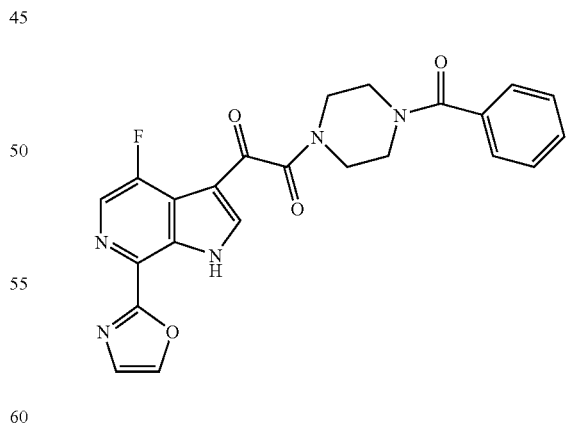

The title compound was prepared according to general procedures described before (Sn-coupling). H NMR: 8.41 (m, 1H); 8.33 (m, 1H); 8.16 (m, 1H); 7.53 (m, 1H); 7.47 (bs, 5H); 3.97-3.54 (m, 8H). LC/MS: (ES$^+$) m/z (m+H)$^+$=448, Rt=1.28 min.

EXAMPLE 141

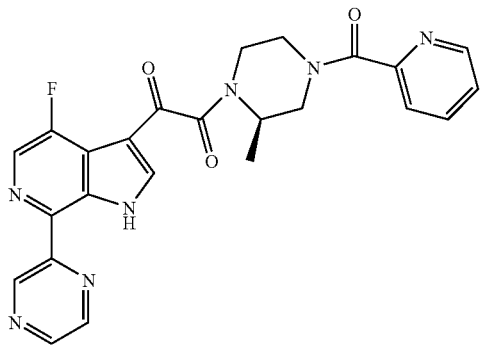

The title compound was prepared according to general procedures described before (Sn-coupling). ¹H-NMR: 9.71-9.70 (m, 1H); 8.80-8.79 (m, 1H); 8.66-8.42 (m, 2H); 8.41-8.35 (m, 2H); 7.99-7.92 (m, 1H); 7.69-7.53 (m, 1H); 7.48-7.44 (m, 1H); 5.05-3.15 (m, 8H). LC/MS: (ES$^+$) m/z (m+H)$^+$=474. Rt=1.26 min.

EXAMPLE 144

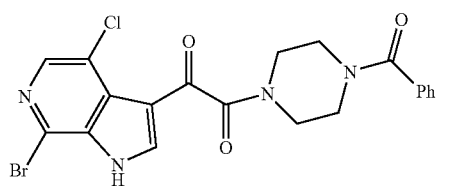

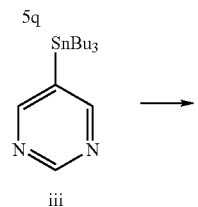

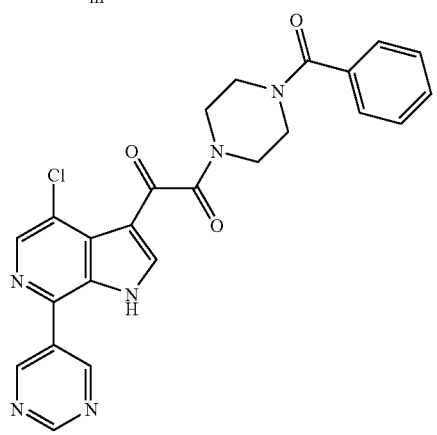

Preparation of Example 144:

To a mixture of precursor 5q (50 mg, 105 μmol) and Pd(PPh$_3$)$_4$ (50 mg, 43 μmol) was added 1,4-dioxane (1 ml) and iii (77 mg, 210 μmol). The reaction mixture was heated in a sealed tube at 145° C. for 16 hours. After cooling to ambient temperature, the reaction mixture was added MeOH (4 ml) and then filtered. The filtrate was purified by reverse phase HPLC to give the TFA salt of the title compound of using the method: Start % B=15, Final % B=100, Gradient time=20 min, Flow Rate=25 ml/min, Column: YMC C18 5 um 20×100 mm, Fraction Collection: 11.80-12.31 min. ¹H NMR: (CD$_3$OD) δ 9.32 (s, 1H), 9.25 (s, 2H), 8.50 (s, 1H), 8.44 (s, 1H), 7.47 (b s, 5H), 4.00-3.44 (b m, 8H); LC/MS: (ES+) m/z (M+H)$^+$=475, 477; HPLC R$_t$=1.833.

EXAMPLE 145

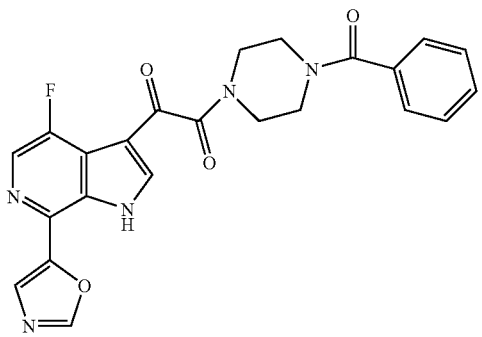

The title compound was prepared following the procedure described before for example 146 and precursor 4k. ¹H NMR: 8.35-8.33 (m, 2H); 8.11 (s, 1H); 7.89 (s, 1H); 7.43 (bs, 5H); 3.89-3.49 (m, 8H). LC/MS: (ES$^+$) m/z (M+H)$^+$=448. Rt=1.18 min.

EXAMPLE 146

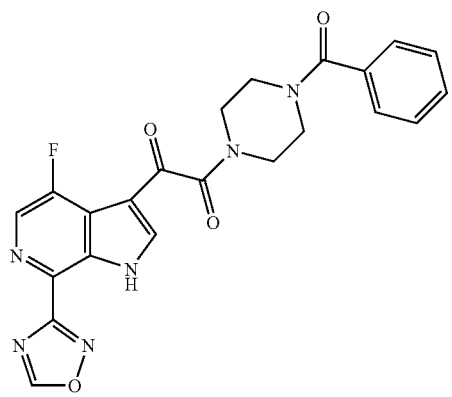

Precursor 4m (0.26 mmol) was dissolved in DMF (1 mL) and treated with N-benzoylpiperazine hydrochloride (59 mg, 0.26 mmol), DEBPT (79 mg, 0.26 mmol) and Hunig's base (90 μL, 0.52 mmol) and the reaction mixture was stirred at rt for 18 h. The solvent was removed in vacuum and the residue was purified by reverse phase preparative HPLC. The fractions showing the right LC/MS: (ES$^+$) m/z (M+H)$^+$=449 were collected, concentrated and purified again using a preparative TLC (5% MeOH/CH$_2$Cl$_2$) to afford the title compound as a white solid. $^1$H-NMR (500 MHz, CDCl$_3$) δ 10.7 (s, 1H), 9.00 (s, 1H), 8.54 (s, 1H), 8.39 (s, 1H), 7.45 (m, 5H), 3.9-3.5 (bm, 8H).

EXAMPLE 148

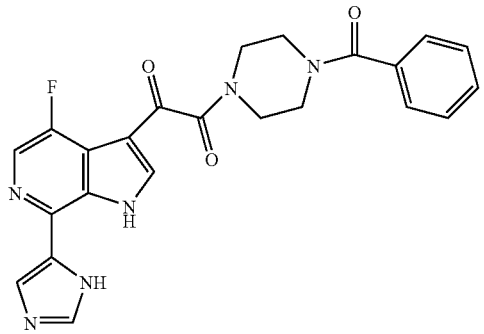

The title compound was prepared from precursor 4n using the same coupling conditions described for the last step of the preparation of precursor 5i. $^1$H NMR: 8.82 (m, 1H); 8.48-8.45 (m, 1H); 8.37-8.33 (m, 1H); 8.26-8.23 (m, 1H); 7.47 (bs, 5H); 3.97-3.54 (m, 8H). LC/MS: (ES$^+$) m/z (m+H)$^+$=447 Rt=0.94 min.

EXAMPLE 151

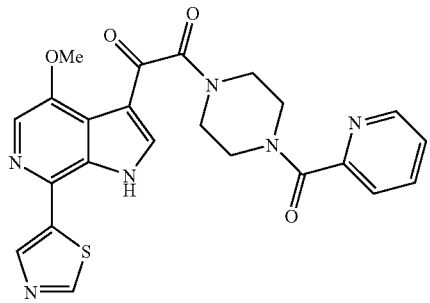

Example 151, was prepared from Precursor 5l and the thiazol-5-yl stannane to provide 1-picolinoyl-4-[(4-methoxy-7-(thiazol-5-yl)-6-azaindol-3-yl)-oxoacetyl]piperazine. MS m/z: (M+H)$^+$ Calc'd for C$_{23}$H$_{21}$N$_6$O$_4$S: 477.13; found 477.13. HPLC retention time: 0.94 minutes (column G).

EXAMPLE 154

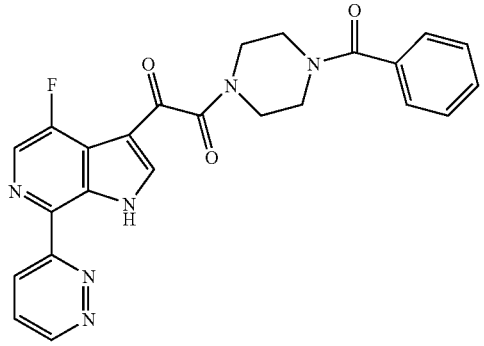

The title compound was prepared according to general procedures described before (Sn-coupling). $^1$H-NMR: 9.23-

9.22 (m, 1H); 8.83-8.81 (m, 1H); 8.43 (m, 1H); 8.36 (m, 1H); 7.75-7.73 (m, 1H), 7.44 (bs, 5H); 3.85-3.49 (m, 8H). LC/MS: (ES$^+$) m/z (M+H)$^+$=459. Rt=1.39 min.

EXAMPLE 155

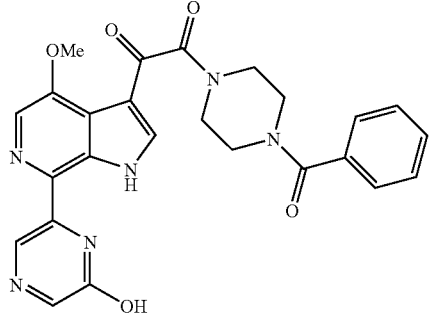

Example 155, 1-(benzoyl)-4-[(4-methoxy-7-(2-hydroxyl-pyrazin-5-yl)-6-azaindol-3-yl)-oxoacetyl]piperazine. MS m/z: (M+H)$^+$ Calc'd for C$_{25}$H$_{23}$N$_6$O$_5$: 487.17; found 487.14. HPLC retention time: 1.30 minutes (column G).

EXAMPLE 157

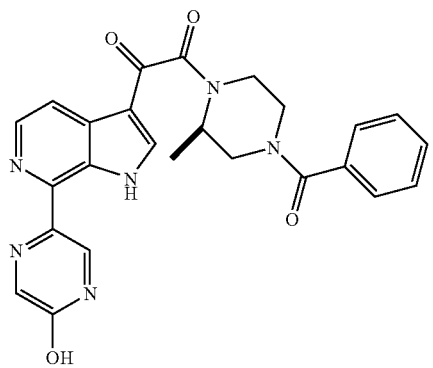

Example 157, (R)-1-(benzoyl)-3-methyl-4-[(4-methoxy-7-(5-hydroxy-pyrazin-2-yl)-6-azaindol-3-yl)-oxoacetyl]piperazine. MS m/z: (M+H)$^+$ Calc'd for C$_{25}$H$_{23}$N$_6$O$_4$: 471.18; found 471.16. HPLC retention time: 1.09 minutes (column G).

EXAMPLE 161

A

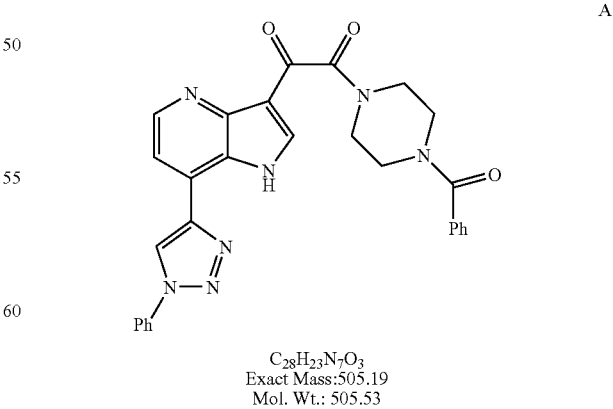

C$_{28}$H$_{23}$N$_7$O$_3$
Exact Mass:505.19
Mol. Wt.: 505.53

Example 161 was prepared from precursor 5p and 3-phenyl-5-tributylstannyl-1,2,3-triazole using the general tin coupling procedure provided earlier: ¹H NMR (500 MHz, DMSO) δ 9.67 (s, 1H), 8.81 (s, 1H), 8.72 (d, J=5.4 Hz, 1H), 8.25 (d, J=6.1 Hz, 1H), 8.00 (dd, J=8.2, 1.8 Hz, 1H), 7.68 (dd, J=8.2, 7.4 Hz, 2H), 7.60 (tt, J=7.4, 1.8 Hz, 2H), 7.48 (br s, 5H), 4.04-3.46 (m, 8H). MS m/z: (M+H)⁺ calcd for $C_{28}H_{24}N_7O_3$: 506.19; found 506.15. HPLC retention time: 1.21 minutes (XTERRA C18 S7 3.0×50 mm)).

EXAMPLE 162

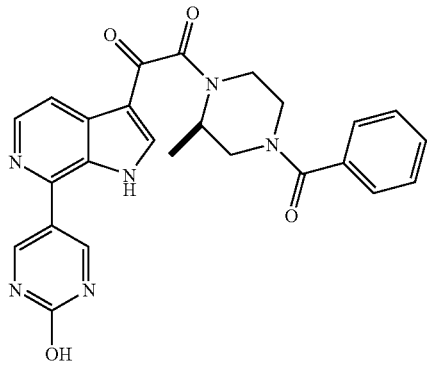

Example 162, (R)-1-(benzoyl)-3-methyl-4-[(4-methoxy-7-(2-hydroxyl-pyrimidin-5-yl)-6-azaindol-3-yl)-oxoacetyl]piperazine. MS m/z: (M+H)⁺ Calc'd for $C_{25}H_{23}N_6O_4$: 471.18; found 471.13. HPLC retention time: 0.95 minutes (column G).

EXAMPLE 163

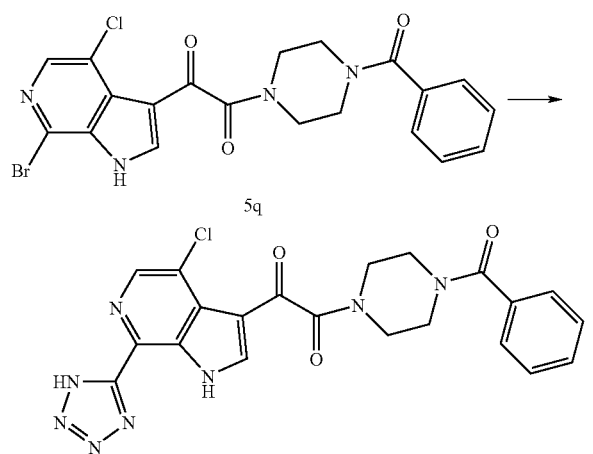

To a solution of precursor 5q (50 mg, 0.11 mmol) in DMF (1 ml) was added CuCN (30 mg, 0.335 mmol). The reaction mixture was heated at 170° C. for 30 min. After cooling to ambient temperature, the reaction mixture was diluted with MeOH (15 ml), filtered under gravity, and the filtrate evaporated in vacuo to afforded a brownish residue which is a cyanoprecursor. To the residue in DMF (1 ml) was added sodium azide (61 mg, 0.95 mmol) and ammonium chloride (50 mg, 0.95 mmol). The mixture was heated at 90° C. for one hour. The reaction mixture was then diluted with MeOH (4 ml), filtered, and the filtrate purified by preparative reverse phase HPLC using the method: Start % B=20, Final % B=80, Gradient time=15 min, Flow Rate=40 ml/min, Column: XTERRA C18 5 um 30×100 mm, Fraction Collection: 11.26-11.71 min. The material was homogenous by ¹H NMR and HPLC, although the mass spectrum indicated an extra peak at (M+H)⁺=431; ¹H NMR: (CD₃OD) 8.41 (s, 1H), 8.12 (s, 1H), 7.47 (b s, 5H), 3.97-3.47 (b m, 8H); LC/MS: (ES+) m/z (M+H)⁺=465, 467; HPLC $R_t$=1.937

EXAMPLE 164

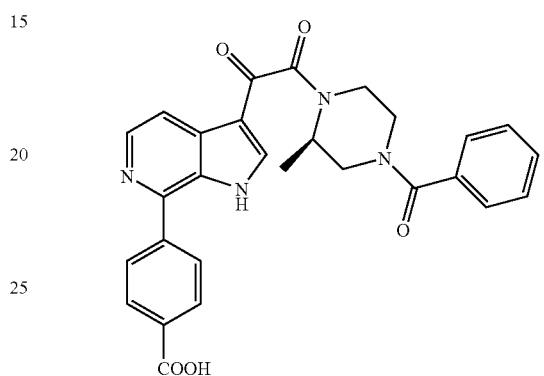

Example 164, was prepared from Precursor 5a and the 4-hydroxycarbonylphenyl boronic acid to provide 1-benzoyl-4-[7-(4-hydroxycarbonylphenyl)-4-azaindol-3-yl)-oxoacetyl]piperazine. MS m/z: (M+H)⁺ Calc'd for $C_{28}H_{25}N_4O_5$: 497.18; found 497.22. HPLC retention time: 1.20 minutes (column C).

EXAMPLE 165

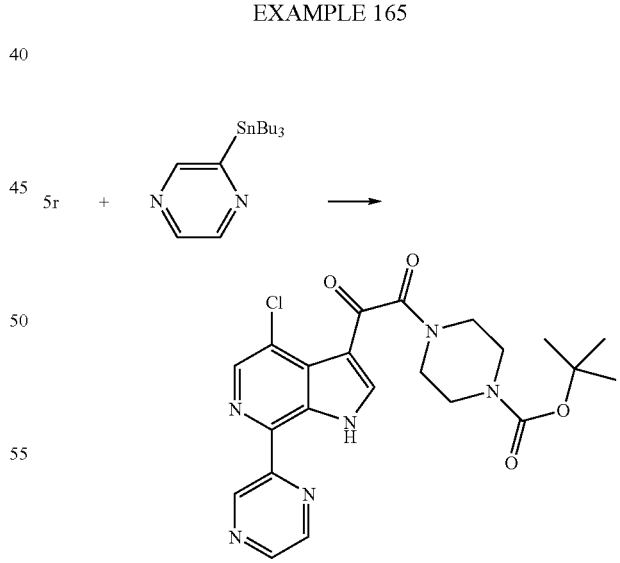

Compound of Example 165 was prepared in a similar manner to compound of Example 143 starting with precursor 5r, but at 125° C. for 22 hours and purification by preparative thin layer chromatography (4% MeOH/CH₂Cl₂). ¹H NMR: (CDCl₃) δ 11.85 (s, 1H), 9.91 (d, J=1.6 Hz, 1H), 8.70 (d, J=2.6 Hz, 1H), 8.65 (dd, J=1.6, 2.6 Hz, 1H), 8.52 (s, 1H), 8.35 (d, J=3.1 Hz, 1H), 3.73 (b m, 2H), 3.56 (b m, 4H), 3.53 (b m, 2H), 1.48 (s, 9H); LC/MS: (ES+) m/z (M+H)+=471, 473; HPLC R$_f$=1.690.

EXAMPLE 167

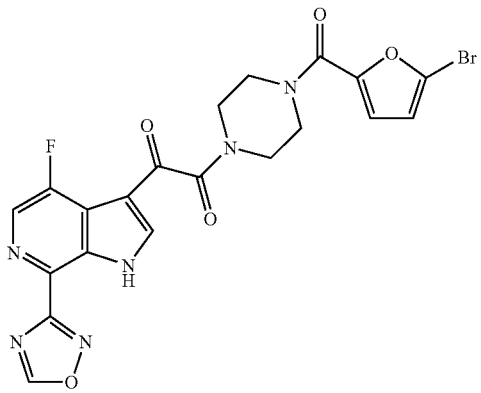

Precursor 4m (0.098 mmol) was dissolved in DMF (1 mL) and treated with N-[5-(2-Bromofuroyl)]piperazine hydrochloride (30 mg, 0.098 mmol), DEBPT (60 mg, 0.19 mmol) and Hunig's base (70 µL, 0.19 mmol) and the reaction mixture was stirred at rt for 18 h. The solvent was removed in vacuum and the residue was purified by reverse phase preparative HPLC. The fractions showing the right LC/MS: (ES+) m/z (M+H)+=518,520 were collected, concentrated and purified again using a preparative TLC (5% MeOH/CH$_2$Cl$_2$) to afford the title compound as a white solid. $^1$H-NMR (500 MHz, CDCl$_3$) δ 10.7 (s, 1H), 9.00 (s, 1H), 8.54 (s, 1H), 8.40 (s, 1H), 7.06 (d, J=3.4 Hz, 1H), 6.46 06 (d, J=3.4 Hz, 1H), 3.90-3.66 (bm, 8H).

EXAMPLE 168

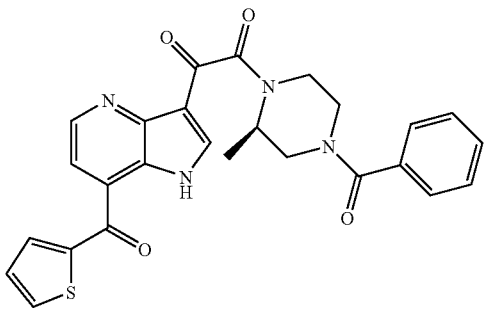

Example 168, 1-benzoyl-3-(R)-methyl-4-[(7-(2-thienylcarbonyl)-4-azaindol-3-yl)-oxoacetyl]piperazine, was prepared from a reaction 1-benzoyl-3-(R)-methyl-4-[(7-(methoxymethylamino)carbonyl)-4-azaindol-3-yl)-oxoacetyl]piperazine and 2-thienyl lithium by using the same procedure for the preparation of 1-64, 1-benzoyl-3-(R)-methyl-4-[(7-(2-propynyl)carbonyl-4-azaindol-3-yl)-oxoacetyl]piperazine. MS m/z: (M+H)+ Calc'd for C$_{26}$H$_{23}$N$_4$O$_4$S: 487.14; found 487.11. HPLC retention time: 1.31 minutes (column A).

General Procedure for the Preparation of Piperazine Amides or Carbamides:

The free nitrogen atom of piperazine could be masked as amides or carbamides via reactions of piperazine with acyl halides, acyl acids or acyl halo formates, which are shown in the following schemes 80 and 81.

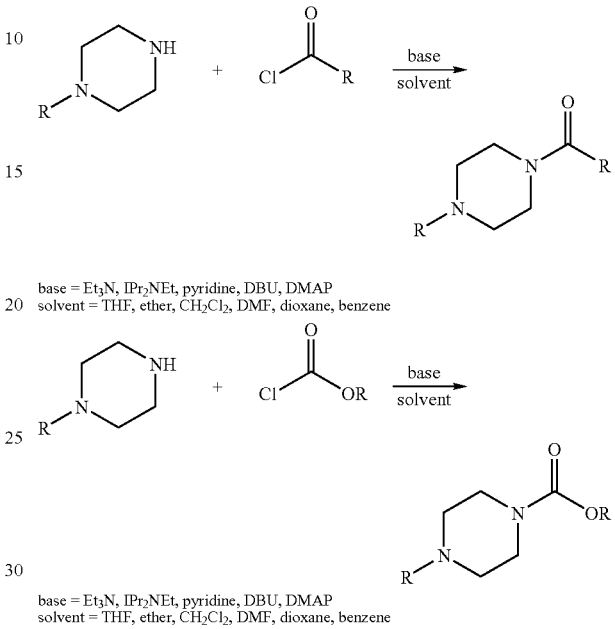

Example 195-199 were prepared via a procedure demonstrated in Scheme 80. The typical procedure is presented in the synthesis of Example 195.

EXAMPLE 195

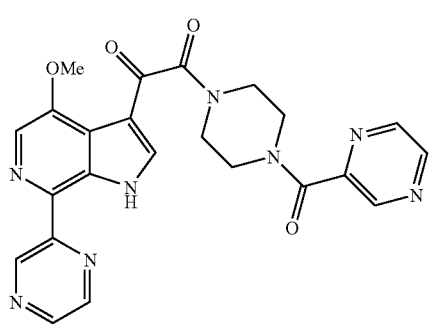

Example 195: Precursor 5u (40 mg), pyrazine carbonyl chloride (50 mg) and I—Pr$_2$NEt (0.2 g) were combined in 1 ml of THF. After the reaction was stirred at room temperature for 16 h, the mixture was concentrated in vacuo to give a residue which was purified using a Shimadzu automated preparative HPLC System to provide the desired compound 195 (4.7 mg). MS m/z: (M+H)$^+$ Calc'd for C$_{23}$H$_{21}$N$_8$O$_4$: 473.17; found 473.42. HPLC retention time: 1.14 minutes (column C).

EXAMPLE 196

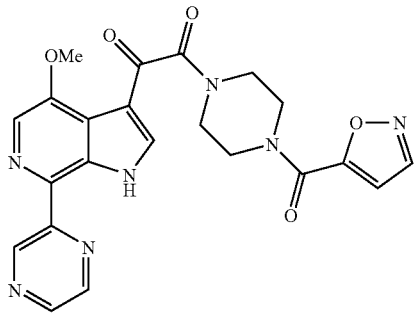

Example 196, was prepared from Precursor 5u and 4-isoxazole carbonyl chloride. MS m/z: (M+H)$^+$ Calc'd for C$_{22}$H$_{20}$N$_7$O$_5$: 462.15; found 462.41. HPLC retention time: 1.09 minutes (column C).

EXAMPLE 197

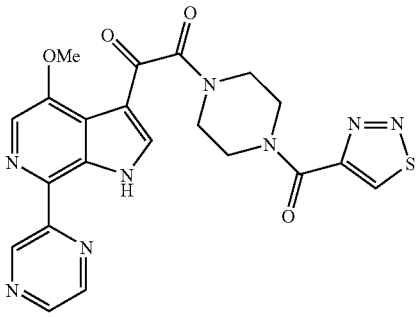

Example 197, was prepared from Precursor 5u and 4-(1,2,3-thiodiazole)-carbonyl chloride. MS m/z: (M+H)$^+$ Calc'd for C$_{21}$H$_{19}$N$_8$O$_4$S: 479.12; found 479.31. HPLC retention time: 1.17 minutes (column C).

EXAMPLE 198

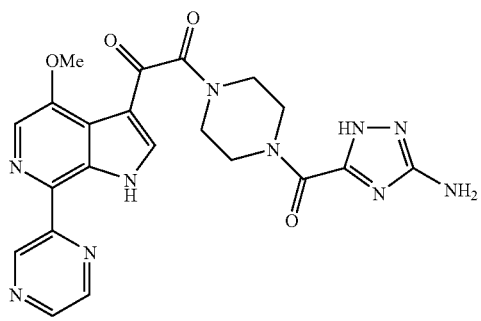

Example 198, was prepared from Precursor 5u and 5-(3-amino-1,2,4-triazole)-carbonyl chloride. MS m/z: (M+H)$^+$ Calc'd for C$_{21}$H$_{21}$N$_{10}$O$_4$: 477.17; found 477.36. HPLC retention time: 0.97 minutes (column C).

EXAMPLE 199

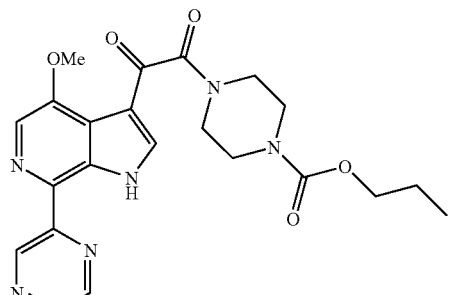

Example 199, was prepared from Precursor 5u and propanyl chloro formate. MS m/z: (M+H)$^+$ Calc'd for C$_{22}$H$_{25}$N$_6$O$_5$: 453.19; found 453.17. HPLC retention time: 1.53 minutes (column M).

Example 200-201 were prepared via a procedure demonstrated in Scheme 81. The typical procedure is presented in the synthesis of Example 200.

EXAMPLE 200

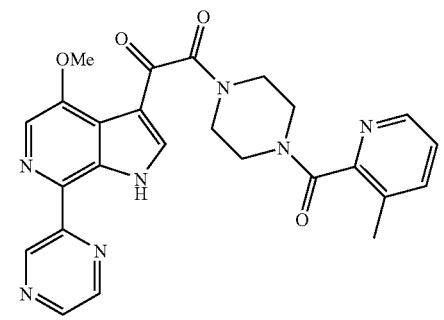

Example 200: 3-methyl-2-picolinic acid (140 mg), EDAC (190 mg) pentafluorophenol (180 mg) were combined in DMF, and, the reaction was stirred for 12 hours. Precursor 3u was then added and resulted mixture was stirred at room temperature for another 16 hours. Solvents were removed in vacuo to give a residue which was purified using a Shimadzu automated preparative HPLC System to provide the desired compound 200 (28 mg). MS m/z: (M+H)$^+$ Calc'd for C$_{25}$H$_{24}$N$_7$O$_4$: 486.19; found 486.14. HPLC retention time: 1.08 minutes (column G).

EXAMPLE 201

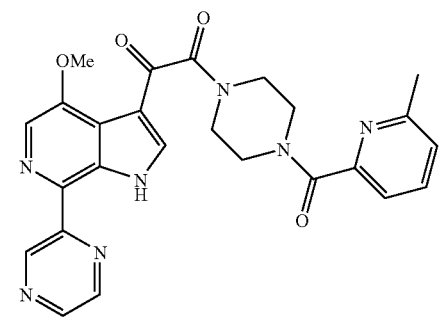

309

Example 201, was prepared from Precursor 5u and 6-methyl-2-picolinic acid. MS m/z: (M+H)+ Calc'd for C25H24N7O4: 486.19; found 486.28. HPLC retention time: 1.44 minutes (column G).

EXAMPLE 202

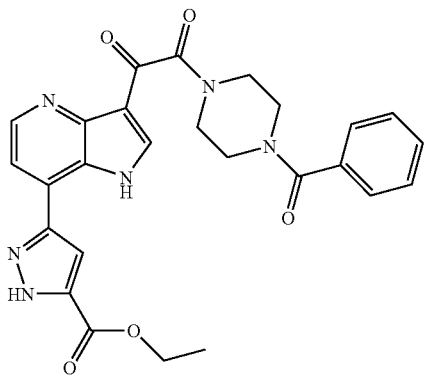

Example 202, was prepared from Precursor 5p and the ethyl pyrazol-5-yl stannane carboxylate to provide 5-{3-[2-(4-Benzoyl-piperazin-1-yl)-2-oxo-acetyl]-1H-pyrrolo[3,2-b]pyridin-7-yl}-2H-pyrazole-3-carboxylic acid ethyl ester. MS m/z: (M+H)+ Calc'd for C26H25N6O5: 501.18; found 501.13. HPLC retention time: 1.14 minutes (column G).

EXAMPLE 203

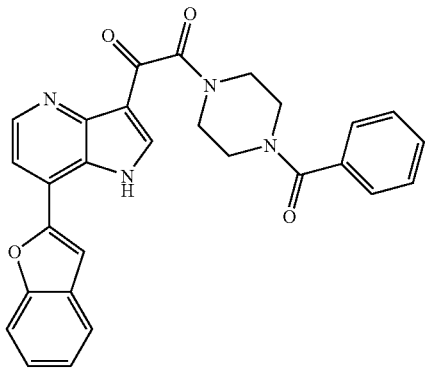

Example 202, was prepared from Precursor 5p and the benzofuran-2-yl stannane to provide 1-(7-benzofuran-2-yl-1H-pyrrolo[3,2-b]pyridin-3-yl)-2-(4-benzoyl-piperazin-1-yl)-ethane-1,2-dione. MS m/z: (M+H)+ Calc'd for C28H21N4O4: 479.16; found 479.07. HPLC retention time: 1.31 minutes (column G).

310

EXAMPLE 204

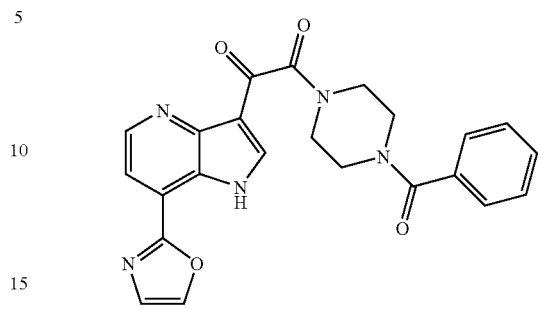

Example 204, was prepared from Precursor 5p and the oxazol-2-yl stannane to provide 1-benzoyl-4-[7-(oxazol-2-yl)-4-azaindol-3-yl)-oxoacetyl]piperazine MS m/z: (M+H)+ Calc'd for C23H20N5O4: 430.14; found 430.07. HPLC retention time: 2.08 minutes (column F, 10 minute gradient).

EXAMPLE 205 AND EXAMPLE 206

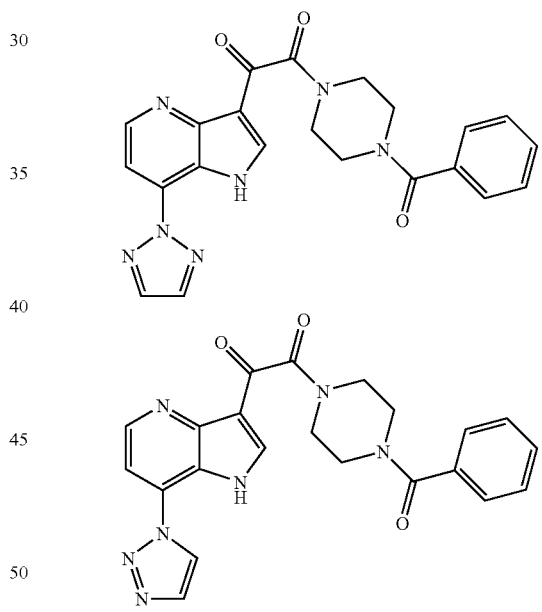

Example 205 and 206. In a sealed tube -(4-benzoyl-piperazin-1-yl)-2-(7-chloro-1H-pyrrolo[3,2-b]pyridin-3-yl)-ethane-1,2-dione (30 mg, 0.076 mmol), 1H-1,2,3-triazole (160 mg, 2.3 mmol), Cu (0) (10 mg, 0.16 mmol) and K2CO3 (11 mg, 0.080 mmol) were heated at 160° C. for 16 h. The reaction mixture was diluted with MeOH, filtered through celite and concentrated. The reaction mixture was diluted with MeOH, filtered through celite and concentrated. The residue was purified by preparative HPLC to provide 1-(4-benzoyl-piperazin-1-yl)-2-(7-[1,2,3]triazol-2-yl-1H-pyrrolo[3,2-b]pyridin-3-yl)-ethane-1,2-dione: 1H NMR (300 MHz, CD3OD) δ 8.79 (d, J=6.6 Hz, 1H), 8.79 (s, 1H), 8.48 (d, J=6.6 Hz, 1H), 8.40 (s, 2H), 7.48 (br s, 5H), 4.00-3.55 (m, 8H). MS m/z (M+H)+ calcd for C22H20N7O3: 430.15; found 430.29. HPLC retention time 0.91 min (Column G); and 1-(4-benzoyl-piperazin-1-yl)-2-(7-[1,2,3]triazol-1-yl-1H-pyrrolo[3,2-b]pyridin-3-yl)-ethane-1,2-dione: 1H NMR (300 MHz, CD3OD) δ 8.97 (d, J=61.2 Hz, 1H), 8.70 (d, J=5.6 Hz, 1H), 8.48 (s, 1H), 8.06 (d, J=1.2 Hz, 1H), 7.80 (d, J=5.6 Hz, 1H), 7.47 (br s, 5H), 4.00-3.45 (m, 8H). MS m/z (M+H)+ calcd for C22H20N7O3: 430.15; found 430.29. HPLC retention time 0.90 min (Column G).

EXAMPLE 207

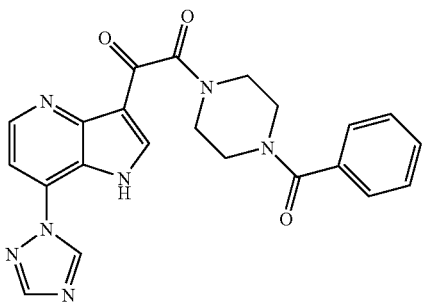

Example 207, was prepared as in Example 205 from Precursor 5p and 1,2,4-triazole to provide 1-(4-benzoyl-piperazin-1-yl)-2-(7-[1,2,4]triazol-1-yl-1H-pyrrolo[3,2-b]pyridin-3-yl)-ethane-1,2-dione. 1H NMR (300 MHz, CD3OD) δ 9.73 (s, 1H), 8.82 (d, J=6.6 Hz, 1H), 8.77 (s, 1H), 8.55 (s, 1H), 8.32 (d, J=6.6 Hz, 1H), 7.48 (br s, 5H), 4.00-3.45 (m, 8H). MS m/z (M+H)+ calcd for C22H20N7O3: 430.15; found 430.27. HPLC retention time 0.87 min (Column G).

EXAMPLE 208

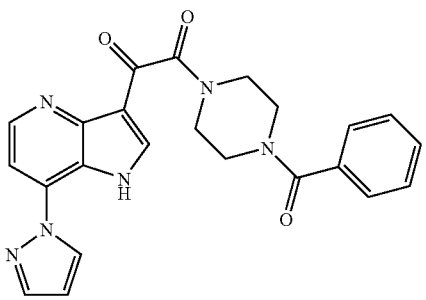

Example 208, was prepared as in Example 205 from Precursor 5p and pyrazole to provide 1-(4-Benzoyl-piperazin-1-yl)-2-(7-pyrazol-1-yl-1H-pyrrolo[3,2-b]pyridin-3-yl)-ethane-1,2-dione. 1H NMR (300 MHz, CD3OD) δ 8.87 (d, J=2.7 Hz, 1H), 8.70 (s, 1H), 8.68 (d, J=6.6 Hz, 1H), 8.18 (d, J=1.5 Hz, 1H), 8.14 (d, J=6.6 Hz, 1H), 7.48 (br s, 5H), 6.85 (dd, J=2.7, 1.5 Hz, 1H), 4.00-3.50 (m, 8H). MS m/z (M+H)+ calcd for C23H21N6O3: 429.16; found 429.23. HPLC retention time 0.87 min (Column G).

EXAMPLE 209

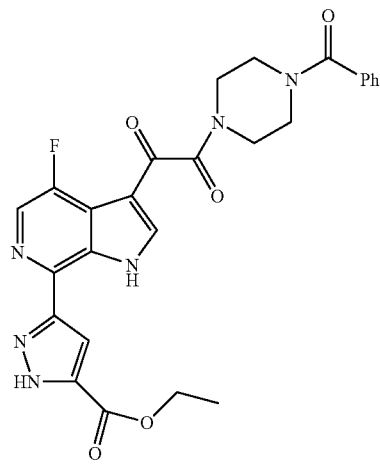

The compound of Example 209 was prepared according to the general method described above starting from Precursor 5i and pyrazol-3-carboxylic ethyl ester-5-tributyltin prepared as described in the following reference: Heterocycles, 1992, 33(2), 813-18. After cooling to ambient temperature, the reaction mixture was concentrated in vacuum. The residue was filtered through filter paper and washed with methanol. The resulting yellow solid was dried in air to provide Compound X; 1H NMR (500 MHz, CDCl3): 8.33 (s, 1H); 8.31 (s, 1H); 7.66 (s, 1H); 7.46-7.39 (m, 5H); 4.47-4.42 (q, 2H); 3.98-3.45 (m, 8H); 1.43-1.40 (t, 3H). LC/MS: (ES+) m/z (M+H)+=519. Rt=1.43 min.

EXAMPLES 210-213

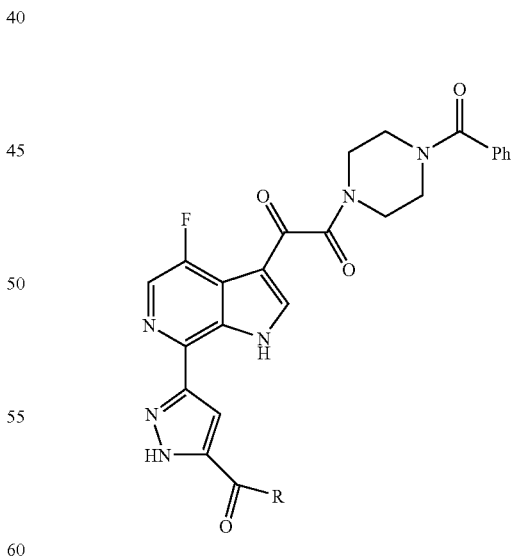

General Procedure for the Preparation of Examples 210-213

The compound of Example 209 was treated with an excess (>5 eq.) of the corresponding amine and stirred in a sealed tube at ambient temperature or 70° C. (R=NH2) for 20 hr. The resulting solution was concentrated on a rotary evaporator and purified by reverse phase preparative HPLC.

EXAMPLES 210 AND 214

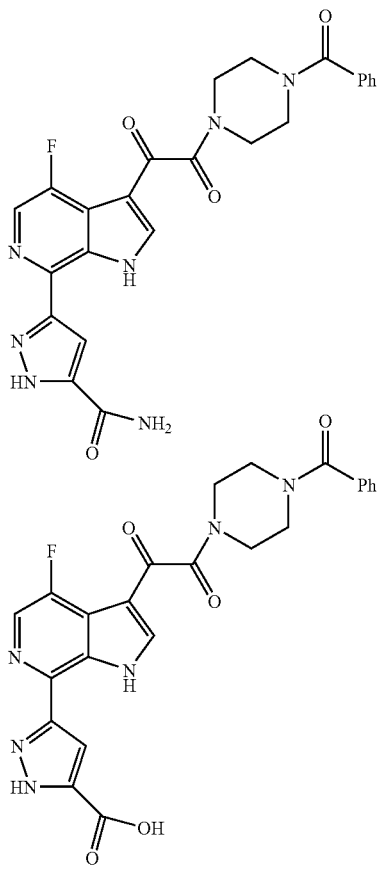

Compounds of Example 210 and 214 were prepared from compound of Example 209 and ammonium hydroxide following the procedure described above. X1a: $^1$H NMR (500 MHz, CD$_3$OD$_3$): 8.40-8.37 (m, 1H); 8.28-8.27 (m, 1H); 7.58-7.39 (m, 6H); 3.97-3.43 (m, 8H). LC/MS: (ES$^+$) m/z (M+H)$^+$=490. Rt=1.14 min. X1b: 8.43 (s, 1H); 8.29 (s, 1H); 7.56 (s, 1H); 7.45-7.55 (m, 5H); 3.99-3.45 (m, 8H). LC/MS: (ES$^+$) m/z (M+H)$^+$=491. Rt=1.12 min.

EXAMPLE 211

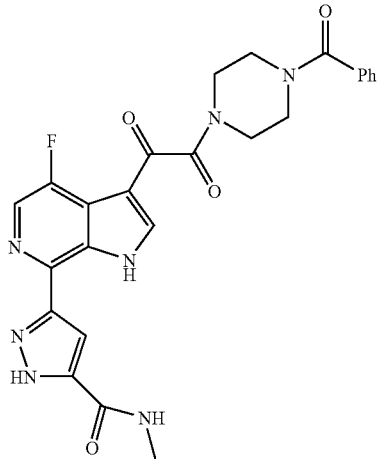

The compound of Example 211 was prepared from the compound of Example 209 and methylamine following the procedure described above. $^1$H NMR (500 MHz, CD$_3$OD$_3$): 8.43 (s, 1H); 8.31 (s, 1H); 7.49 (bs, 5H); 7.45 (s, 1H) 3.97-3.48 (m, 8H); 2.97 (s, 3H). LC/MS: (ES$^+$) m/z (M+H)$^+$=504. Rt=1.31 min.

EXAMPLE 212

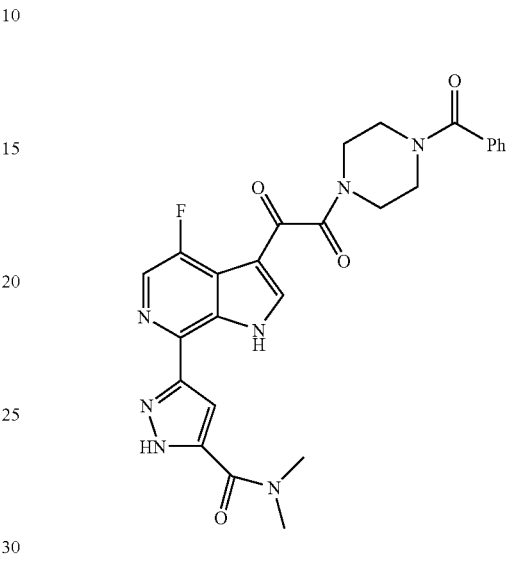

The compound of example 212 was prepared from the compound of example 209 and dimethylamine following the procedure described above. LC/MS: (ES$^+$) m/z (M+H)$^+$=518. Rt=122 min.

COMPOUND 213

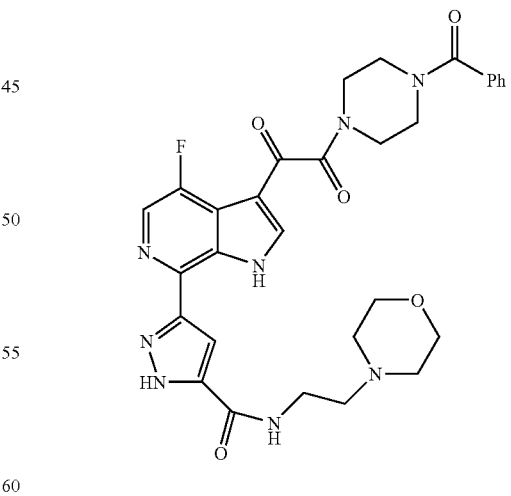

The compound of Example 213 was prepared from the compound of Example 209 and N-aminoethylmorpholine following the procedure described above. $^1$H NMR (500 MHz, CD$_3$OD$_3$): 8.41 (s, 1H); 8.31 (s, 1H); 7.52-7.49 (m, 6H); 4.19-3.20 (m, 20H); LC/MS: (ES$^+$) m/z (M+H)$^+$=603. Rt=1.03 min.

COMPOUNDS Of EXAMPLES 215-222

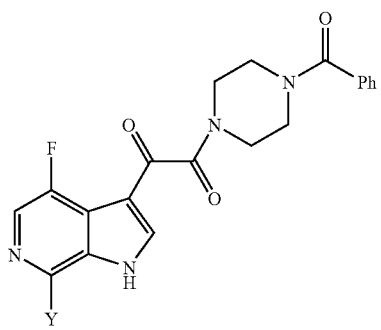

General Procedure for the Preparation of Compounds of Examples 215-222

A mixture of precursor 5i, 30 equivalents of the corresponding amine, 1 equivalent of copper powder and 1 equivalent of potassium carbonate was heated at 160° C. for 4-7 hr in a sealed tube. The reaction was cooled to room temperature and filtered through filter paper. The filtrate was diluted with methanol and purified by preparative HPLC.

EXAMPLE 215

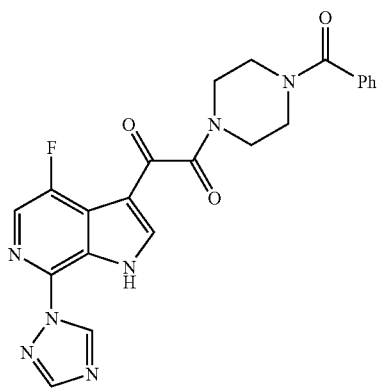

Example 215 was prepared from precursor 5i and 1,2,4-triazole following the procedure described above. $^1$H NMR (500 MHz, CDCl$_3$): 11.15 (bs, 1H); 9.28 (s, 1H); 8.33-8.34 (m, 1H); 8.22 (s, 1H); 8.10 (s, 1H); 7.46-7.42 (m, 5H); 3.90-3.48 (m, 8H). LC/MS: (ES$^+$) m/z (M+H)$^+$=448. Rt=1.21 min.

EXAMPLE 216

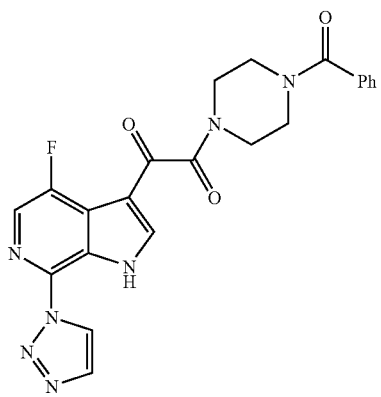

Example 216 was prepared from precursor 5i and 1,2,3-triazole following the procedure described above. $^1$H NMR (500 MHz, CDCl$_3$): 11.16 (bs, 1H); 8.75 (s, 1H); 8.37-8.37 (s, 1H); 8.15 (s, 1H); 7.92 (s, 1H); 7.43 (bs, 5H); 3.99-3.48 (m, 8H). LC/MS: (ES$^+$) m/z (M+H)$^+$=448. Rt=1.28 min.

EXAMPLE 217

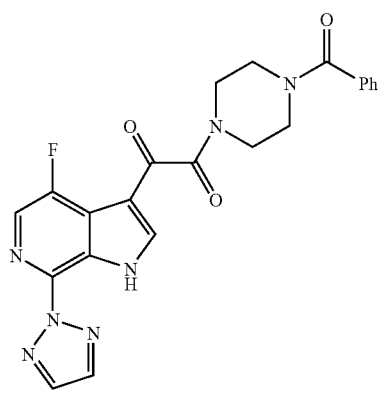

Example 217 was prepared from precursor 5i and 1,2,3-triazole following the procedure described above. $^1$H NMR (500 MHz, CDCl$_3$): 11.12 (bs, 1H); 8.78-8.77 (m, 1H); 8.37-8.36 (m, 1H); 8.02-8.0 (m, 2H); 7.45-7.41 (m, 5H); 4.11-3.45 (m, 8H). LC/MS: (ES+) m/z (M+H)$^+$=448. Rt=1.03 min.

EXAMPLE 218

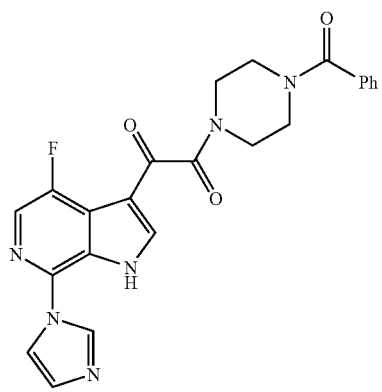

Example 218 was prepared from precursor 5i and imidazole following the procedure described above. $^1$H NMR (500 MHz, CDCl$_3$): 13.35 (bs, 1H); 9.49 (s, 1H); 8.35-8.30 (m, 1H); 8.20 (s, 1H); 7.97 (s, 1H); 7.56-7.53 (m, 1H); 7.46-7.41 (m, 5H); 3.98-3.40 (m, 8H). LC/MS: (ES⁺) m/z (M+H)⁺=447. Rt=1.25 min.

EXAMPLE 219

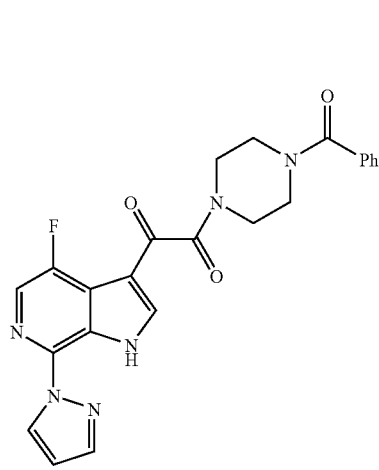

Example 219 was prepared from precursor 5i and pyrazole following the procedure described above. ¹H NMR (500 MHz, CDCl₃): 11.52 (bs, 1H); 8.65-8.64 (m, 1H); 8.27-8.26 (m, 1H); 8.05-8.04 (m, 1H); 7.81-7.80 (m, 1H); 7.50-7.35 (m, 5H); 6.54-6.53 (m, 1H); 4.01-3.47 (m, 8H). LC/MS: (ES⁺) m/z (M+H)⁺=447. Rt=1.25 min.

EXAMPLE 220

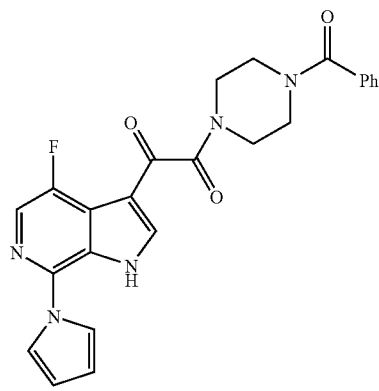

Example 220 was prepared from precursor 5i and pyrrole following the procedure described above. ¹H NMR (300 MHz, CD₃OD₃): 8.33-8.29 (m, 2H); 7.49-7.40 (m, 5H); 7.38-7.37 (m, 2H); 6.42-6.41 (m, 2H); 3.91-3.40 (m, 8H). LC/MS: (ES⁺) m/z (M+H)⁺=446. Rt=1.34 min.

EXAMPLE 221

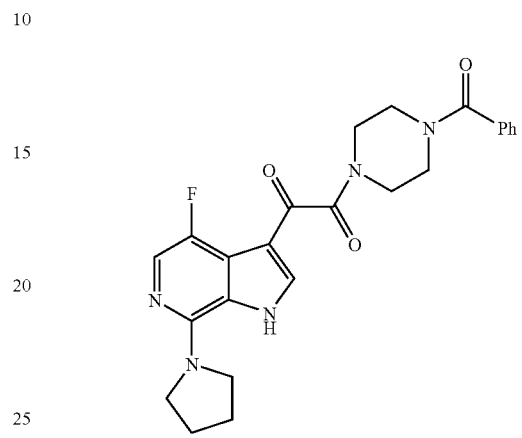

Example 221 was prepared from precursor 5i and pyrrolidine following the procedure described above. ¹H NMR (300 MHz, CD₃OD₃): 8.37 (s, 1H); 7.61-7.59 (m, 1H); 7.51-7.38 (m, 5H); 4.08-3.23 (m, 12H); 2.25-2.15 (m, 4H). LC/MS: (ES⁺) m/z (M+H)⁺=450. Rt=0.89 min.

EXAMPLE 222

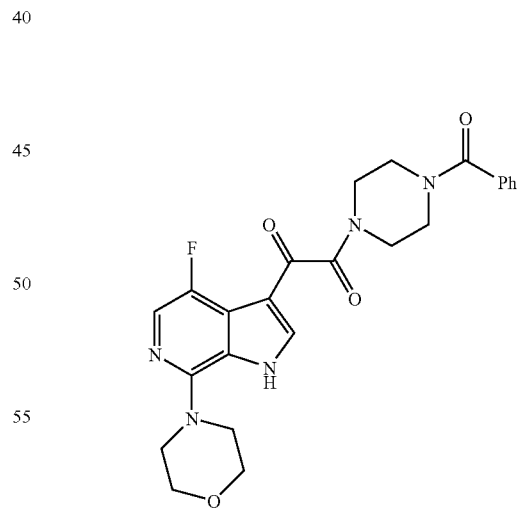

Compound of example 222 was prepared from precursor 5i and morpholine following the procedure described above. ¹H NMR (300 MHz, CD₃OD₃): 8.38 (s, 1H); 7.86-7.84 (m, 1H); 4.14-3.25 (m, 16H). LC/MS: (ES⁺) m/z (M+H)⁺=466. Rt=0.988 min.

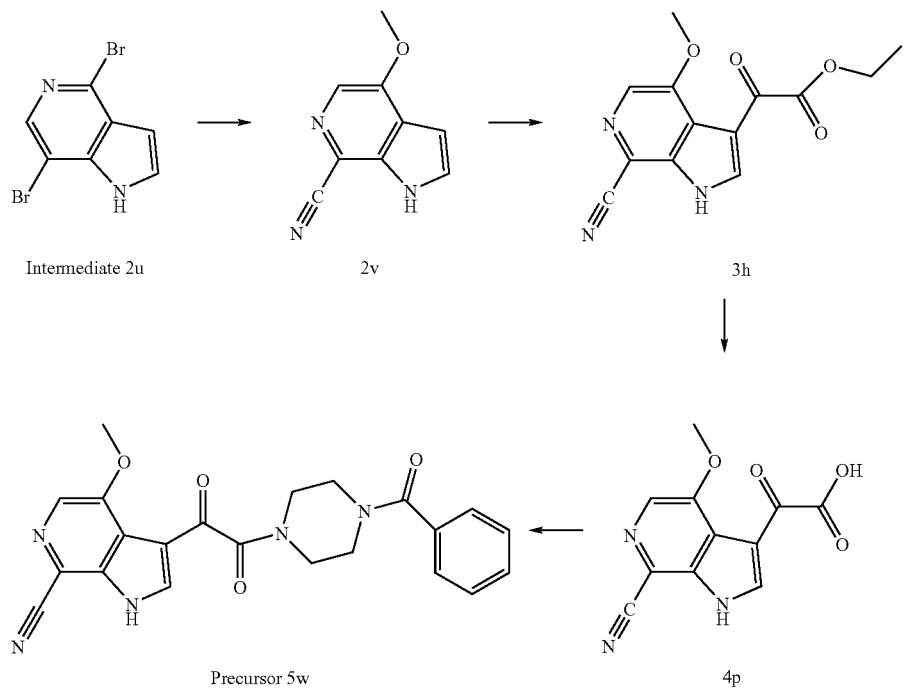

Preparation of Precursor 5w:

To a mixture of 2u (2.0 g, 7.3 mmol) and CuCN (1.0 g, 11 mmol) was added DMF (20 ml). The reaction mixture was heated at 150° C. for 1 hour. After cooling to room temperature, the reaction mixture was added NaOMe (20 ml, 25 wt. % solution in MeOH), and was heated at 110° C. for 10 minutes. After cooling to room temperature, the reaction mixture was poured into an aqueous solution of ammonium acetate (sat. 500 ml). The resulting mixture was filtered through a short Celite® pad. The filtrate was extracted with EtOAc (500 ml×4). The combined extracts were dried over MgSO$_4$ and evaporated in vacuo to give a brownish residue, which was triturated with MeOH (5 ml×3) to provide precursor 2v as a yellow solid (317 mg, 25%). The structure was supported by NOE experiments. $^1$H NMR: (DMSO-d$_6$) 12.47 (s, 1H), 8.03 (s, 1H), 7.65 (t, J=2.8, 1H), 6.70 (dd, J=2.8, 1.8, 1H), 4.08 (s, 3H); LC/MS: (ES+) m/z (M+H)$^+$=174; HPLC (alternate conditions B, column G) R$_t$=1.320.

Preparation of Precursor 3h:

To 1-ethyl-3-methylimidazolium chloride (85 mg, 0.58 mmol) in a capped vial was quickly added aluminum chloride (231 mg, 1.73 mmol). The mixture was vigorously stirred at room temperature until the formation of the ionic liquid. After cooling to room temperature, the ionic liquid was added compound 2v (50 mg, 0.29 mmol) and ethyl chlorooxoacetate (0.2 ml, 1.79 mmol). The reaction mixture was stirred at room temperature for three hours, cooled to 0° C. and quenched by carefully adding ice-water (15 ml). The precipitates were filtered, washed with water (5 ml×3) and dried in vacuo to give 3 h as a grayish yellow solid (50 mg, 63%). $^1$H NMR: (DMSO-d$_6$) 13.73 (s, 1H), 8.54 (s, 1H), 8.26 (s, 1H), 4.35 (q, J=7.0, 2H), 4.06 (s, 3H), 1.29 (t, J=7.0, 3H); LC/MS: (ES+) m/z (M+H)$^+$=274; HPLC (alternate conditions B, column G) R$_t$=1.527.

Preparation of Precursor 4p:

To a mixture of 3 h (200 mg, 0.73 mmol) in MeOH (1 ml) was added NaOH (2.5 ml, 1N aqueous). The reaction mixture was stirred at room temperature for 30 minutes, and then acidified with hydrochloric acid (1N, ~3 ml) to pH about 2. The solid was filtered, washed with water (5 ml×4), and dried in vacuo to give 4p as a brownish solid (160 mg, 89%). Compound 4p was used directly in the following reaction without further purification. LC/MS: (ES+) m/z (M+H)$^+$=246; HPLC (alternate conditions B, column G) R$_t$=0.777.

Preparation of Precursor 5w:

To a mixture of 4p (160 mg, 0.65 mmol), DEPBT (390 mg, 1.31 mmol) and benzoylpiperazine hydrochloride (222 mg, 0.98 mmol) was added DMF (2 ml) and N,N-diisopropylethylamine (1.2 ml, 6.9 mmol). The reaction mixture was stirred at room temperature for 16 hours, and concentrated to remove most of the solvent. The residue was diluted with MeOH (10 ml) and then filtered. The filtrate was purified by preparative reverse phase HPLC using the method: Start % B=15, Final % B=70, Gradient time=30 min, Flow Rate=40 ml/min, Wavelength=220 nm, Column XTERRA C18 5 μm 30×100 mm, A=10% MeOH, —90% H$_2$O—0.1% TFA, B=90% MeOH—10% H$_2$O—0.1% TFA, Fraction Collection: 14.03-15.43 min. The structure was supported by NOE experiments. $^1$H NMR: (DMSO-d$_6$) 13.66 (s, 1H), 8.45 (s, 1H), 8.25 (s, 1H), 7.45 (s, 5H), 4.07 (s, 3H), 3.80-3.40 (b m, 8H); LC/MS: (ES+) m/z (M+H)$^+$=418 HPLC (alternate conditions B, column G) R$_t$=1.447.

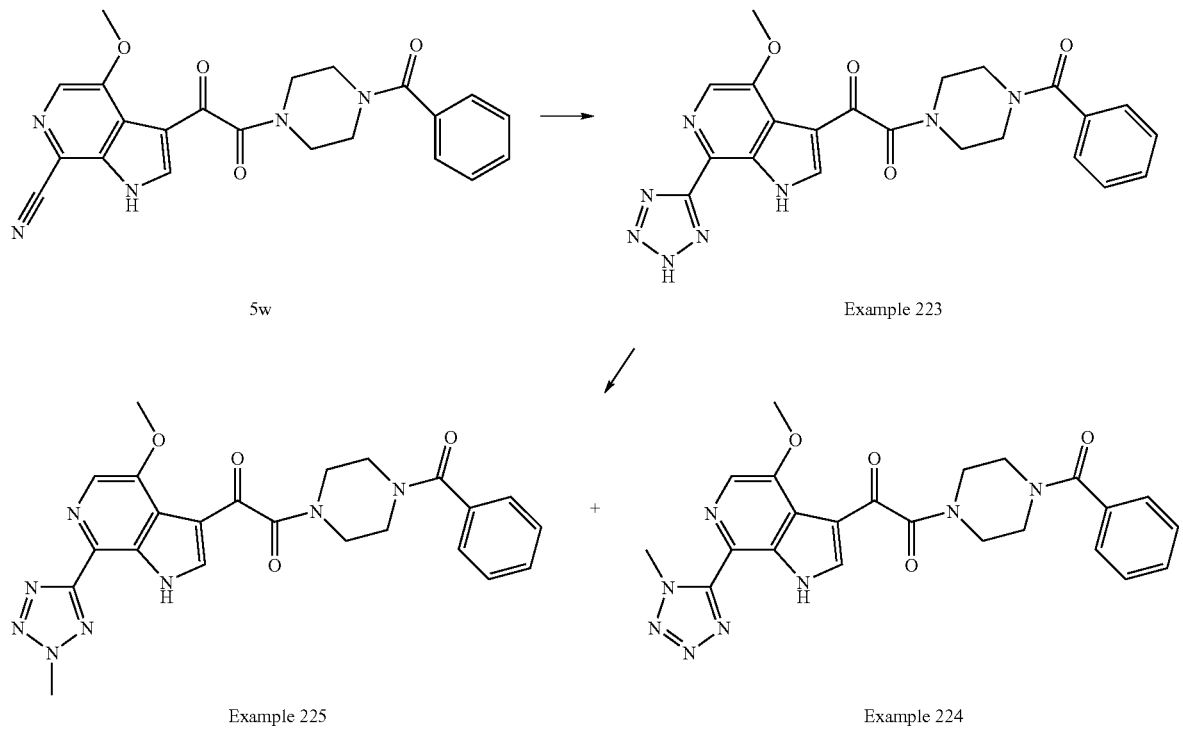

5w

Example 223

Example 225

Example 224

Preparation of Example 223:

To a mixture of 5w (15 mg, 0.036 mmol), NaN$_3$ (24 mg, 0.36 mmol), and NH$_4$Cl (19 mg, 0.36 mmol) was added DMF (1 ml). The reaction mixture was heated at 100° C. for three hours. After cooling to room temperature, the reaction mixture was added MeOH (4 ml) and then filtered. The filtrate was purified by preparative reverse phase HPLC using the method: Start % B=15, Final % B=75, Gradient time=15 min, Flow Rate=40 ml/min, Wavelength=220 nm, Column: XTERRA C18 5 μm 30×100 mm, A=10% MeOH, —90% H$_2$O—0.1% TFA, B=90% MeOH—10% H$_2$O—0.1% TFA, Fraction Collection: 8.48-9.78 min. $^1$H NMR: (DMSO-d$_6$) 12.68 (b s, 1H), 8.26 (s, 1H), 8.24 (s, 1H), 7.46 (s, 5H), 4.09 (s, 3H), 3.86-3.30 (b m, overlapping with broad water peak, 8H), one exchangeable proton was not observed due to the presence of water in the sample. LC/MS: (ES+) m/z (M+H)$^+$=461 HPLC (alternate conditions B, column G) R$_t$=1.392.

Preparation of Examples 224 and 225:

To the mixture of 5w (10 mg, 0.022 mmol) in MeOH (0.2 ml) and benzene (0.4 ml) was added TMSCHN$_2$ (0.4 ml, 0.1 M*). The reaction mixture was stirred at room temperature for 1.5 hours, followed by purification on preparative TLC (1×20×20 cm, 500 microns) with 10% MeOH/CH$_2$Cl$_2$ to give the two compounds as white solids. Example 224 (2.7 mg, 26%); $^1$H NMR: (DMSO-d$_6$) 12.60 (b s, 1H), 8.31 (s, 1H), 8.23 (s, 1H), 7.46 (s, 5H), 4.50 (s, 3H), 4.15 (s, 3H), 3.80-3.30 (b m, 8H); LC/MS: (ES+) m/z (M+H)$^+$=475, HPLC (alternate conditions B, column G) R$_t$=1.672. Example 225 (1.4 mg, 13%), $^1$H NMR: (DMSO-d$_6$) 12.40 (b s, 1H), 8.22 (s, 1H), 8.20 (s, 1H), 7.46 (s, 5H), 4.52 (s, 3H), 4.04 (s, 3H), 3.80-3.30 (b m, 8H); LC/MS: (ES+) m/z (M+H)$^+$=475, HPLC (alternate conditions B, column G) R$_t$=1.373. These two structures were further supported by nitrogen HMBC analysis. *TMSCHN$_2$ (0.1 M) was prepared by diluting commercially available TMSCHN$_2$ (0.2 ml, 2.0 M) with hexane (3.8 ml).

EXAMPLE 226

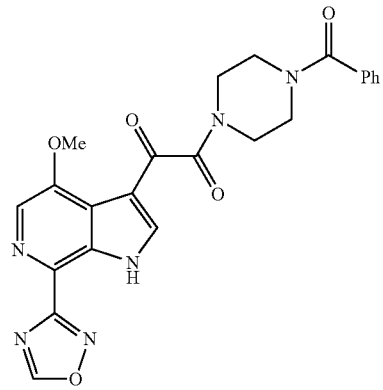

Reaction scheme for prep of example 226

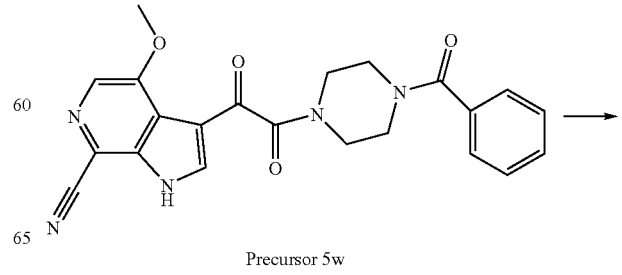

Precursor 5w

323

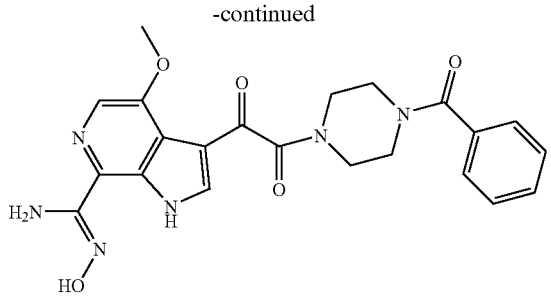

Precursor 5x
↓

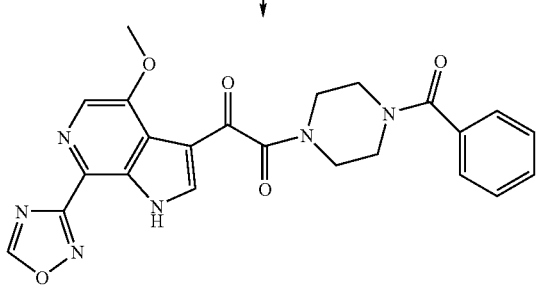

Example 226

Preparation of Example 226

To a mixture of 5w (85 mg, 0.204 mmol) and hydroxylamine hydrochloride (22 mg, 0.305 mmol) in anhydrous ethanol (3 ml, 200 proof) was added triethylamine (60 μl, 0.4 mmol). The reaction mixture was heated in a capped vial at 100° C. for 6 hours. Removal of solvent gave precursor 5x as a white solid, to which was added triethyl orthoformate (3 ml). The mixture was then heated in a capped vial at 100° C. for 12 hours. After removal of most of the excess triethyl orthoformate, the residue was diluted with MeOH (6 ml), followed by filtration. The filtrate was purified by preparative reverse phase HPLC using the method: Start % B=30, Final % B=50, Gradient time=20 min, Flow Rate=40 ml/min, Column: XTERRA C18 5 μm 30×100 mm, Fraction Collection: 7.57-7.98 min. $^1$H NMR: (DMSO-$d_6$) 12.41 (s, 1H), 9.87 (s, 1H), 8.27 (s, 1H), 8.24 (s, 1H), 7.45 (s, 5H), 4.06 (s, 3H), 3.68-3.20 (b m, overlapping with broad water peak, 8H); The following HPLC conditions for the analytical LCMS were used: Column: Xterra C18 S7 3×50 mm; Gradient Time=3 min; Flow rate=4 ml/min. LC/MS: (ES+) m/z (M+H)$^+$=461 HPLC $R_t$=1.390. Product from a similar run provided the following $^1$H NMR spectra (methanol-d6) δ 9.32 (s, 1H), 8.28 (s, 2H), 7.83 (s, 1H), 7.45 (narrow multiplet, 6H), 4.05 (s, 3H), 3.80 (bm, 4H), 3.56 (bm, 4H).

EXAMPLES 227 to 229

Examples 227 to 230 (Table 2-1) were prepared analogously to Example 194 except that the appropriate substituted piperazine was utilized. The preparation of the appropriate substituted piperazines is described for precursors 17a-d or in reference 90b.

324

General Procedures for the Preparation of Pyrazoles

3-Substituted pyrazoles can be prepared via the following routes:

Route P-A

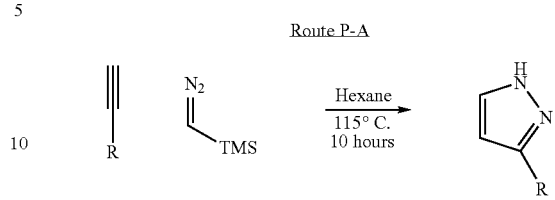

Alkyne (1 eq.) was dissolved in a 2M solution of diazomethane (5-10 eq.) in hexane and resulting mixture was heated to 110-115° C. for 12 hours. After reaction was quenched with MeOH, removal of solvents provided a residue which was used in the next step without any purification.

Route P-B

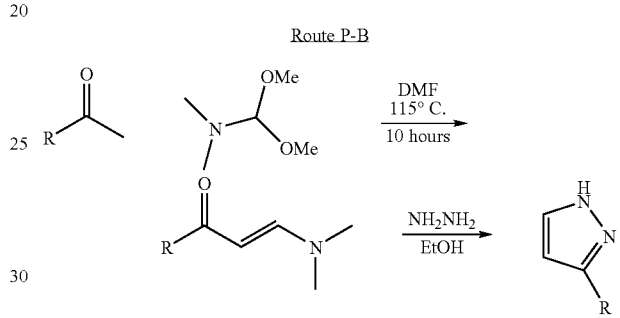

Methyl ketone (1 eq.) was added into a solution of dimethoxy-DMF (5-10 eq.) in DMF and the resulting mixture was heated to 110-115° C. for 12 hours. Solvents were then removed under vacuum to provide a residue.

The above residue was mixed with hydrazine (5-10 eq.) in ethanol and the reaction was kept in refluxing for 12 hours. Removal of solvents in vacco gave a residue, which was carried onto further reactions without purification.

Route P-C

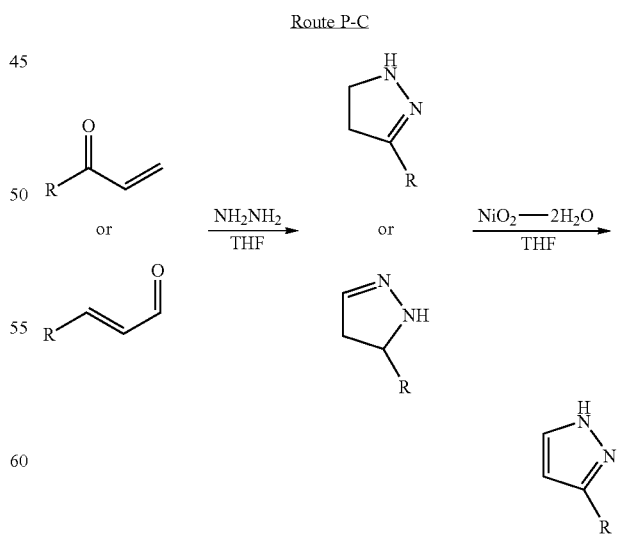

Hydrazine (10-20 eq.) was added into a solution of alkenone or alkenal (1 eq.) in THF and the resulting mixture was heated to 1110-115° C. for 12 hours. After the mixture cooled down to room temperature, an excess of NiO2-2H2O (5-10 eq.) was then added into the reaction mixture and the reaction was stirred at room temperature for another 12 hours. Insoluble materials were then filtered away and concentration under vacuum provided a residue that was used in the further reactions without purification.

TABLE I-5

Preparation of Pyrazoles

| Compound# | Structure | Method Used | HPLC R$_f$ (column)/MS (M + H)$^+$ or (M + Na)$^+$ |
|---|---|---|---|
| Pyrazole-001 | 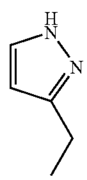 | P-A | 0.35 min (column L) |
| Pyrazole-002 | 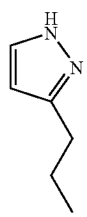 | P-A | 0.59 min (column L) |
| Pyrazole-003 | 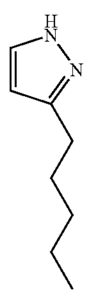 | P-A | 1.07 min (column L)/ MS(M + H)$^+$: Calc'd 139.12 Found 139.18 |
| Pyrazole-004 | 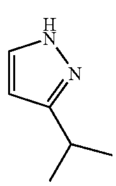 | P-A, P-B, P-C | 0.53 min (column L) |
| Pyrazole-005 | 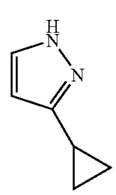 | P-B | 0.48 min (column L) |
| Pyrazole-006 | 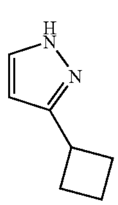 | P-A | 0.63 min (column L) |
| Pyrazole-007 | | P-A | 0.21 min (cloumn G) |
| Pyrazole-008 | | P-A | 0.81 min (column L)/ MS(M + H)$^+$: Calc'd 197.13 Found 197.18 |
| Pyrazole-009 | | P-A | |
| Pyrazole-010 | | P-A | 0.34 min (column L) |
| Pyrazole-011 | | P-A | 0.47 min (column L)/ MS(M + H)$^+$: Calc'd 155.08 Found 155.06 |
| Pyrazole-012 | | P-A | 0.38 min (column G) |

TABLE I-5-continued

Preparation of Pyrazoles

| Compound# | Structure | Method Used | HPLC R$_f$(column)/MS (M + H)$^+$ or (M + Na)$^+$ |
|---|---|---|---|
| Pyrazole-013 | (structure) | P-A | |
| Pyrazole-014 | (structure) | P-A | |
| Pyrazole-015 | (structure) | P-A | 0.26 min (column L)/ MS(M + Na)$^+$: Calc'd 149.07 Found 149.11 |
| Pyrazole-016 | (structure) | P-A | 0.31 min (column L)/ MS(M + H)$^+$: Calc'd 141.10 Found 141.17 |
| Pyrazole-017 | (structure) | P-A | 0.27 min (column L)/ MS(M + Na)$^+$: Calc'd 149.07 Found 149.13 |
| Pyrazole-018 | (structure) | P-A | 0.22 min (column L) |
| Pyrazole-019 | (structure) | P-A | 0.61 min (column L)/ MS(M + Na)$^+$: Calc'd 175.08 Found 175.14 |
| Pyrazole-020 | (structure) | P-A | 0.79 min (column L)/ MS(M + Na)$^+$: Calc'd 189.10 Found 189.17 |
| Pyrazole-021 | (structure) | P-A | 0.59 min (column L)/ MS(M + H)$^+$: Calc'd 141.10 Found 141.18 |
| Pyrazole-022 | (structure) | P-A | 0.22 (column L) |
| Pyrazole-023 | (structure) | P-A | 0.34 min (column L)/ MS(M + Na)$^+$: Calc'd 193.10 Found 193.14 |
| Pyrazole-024 | (structure) | P-A | 1.05 min (column L)/ MS(M + H)$^+$: Calc'd 228.08 Found 228.14 |

General Procedure Si—Cu

Silicon Masked General Procedure for Attaching Pyrazoles, Imidazoles and Triazoles with Melting-points Higher than 160° C. to C-7 Position of Azaindoles:

In cases where the melting points of the nitrogen heterocycle to be attached to the azaindole have melting points higher than 160° C., an excess of the heterocycle (usually greater than 3 equivalents) is heated with a larger excess of hexamethydisilazane or chloro trimethylsilane (>10 equivalents) at temperatures up to 140° C. for approximately 12 h. The excess silylating reagent is removed in vacuo and the mixture is combined with the azaindole halide and the copper catalyzed reaction is conducted as below.

A mixture of halo-indole or halo-azaindole intermediate, 1-2 equivalents of copper powder, with 1 equivalent preferred for the 4-F,6-azaindole series and 2 equivalents for the 4-methoxy,6-azaindole series; 1-2 equivalents of potassium carbonate, and the corresponding silylated heterocyclic reagent as prepared above, was heated at 135-160° C. for 4 to 9 hours, with 5 hours at 160° C. preferred for the 4-F,6-azaindole series and 7 hours at 135° C. preferred for the 4-methoxy,6-azaindole series. The reaction mixture was cooled to room temperature and filtered through filter paper. The filtrate was diluted with methanol and purified either by preparative HPLC or silica gel. In many cases no chromatography is necessary, the product can be obtained by crystallization with methanol.

TABLE I-6

N-containing Heterocycles Applied under General Procedure Si—Cu (Silicon-Masking Conditions)

| Entry | N-Containing Heterocycle |
|---|---|
| HM-01 | |
| HM-02 | |
| HM-03 | |
| HM-04 | |

TABLE I-6-continued

N-containing Heterocycles Applied under General Procedure Si—Cu (Silicon-Masking Conditions)

| Entry | N-Containing Heterocycle |
|---|---|
| HM-05 | |
| HM-06 | |
| HM-07 | |

Examples 230 Through Example 258, were Prepared Using the Same Conditions and Method Used for Synthesizing Example 187:

EXAMPLE 230

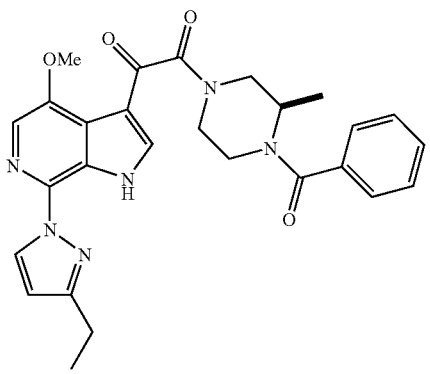

Example 230, was prepared according to the general method described above starting from Precursor 5z and Pyrazole-001 to provide (R)-1-benzoyl-2-methyl-4-[(4-methoxy-7-(3-ethyl-pyrazol-1-yl)-6-azaindol-3-yl)-oxoacetyl]piperazine; MS m/z: (M+H)$^+$ Calc'd for $C_{27}H_{29}N_6O_4$: 501.23;

found 501.17. HPLC retention time: 2.30 minutes (column G, flow rate 4 ml/min, gradient time 3 min).

EXAMPLE 231

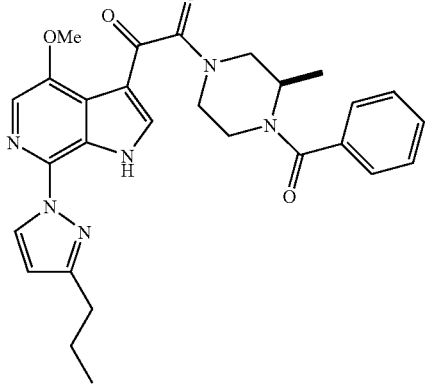

Example 231, was prepared according to the general method described above starting from Precursor 5z and Pyrazole-002 to provide (R)-1-benzoyl-2-methyl-4-[(4-methoxy-7-(3-propyl-pyrazol-1-yl)-6-azaindol-3-yl)-oxoacetyl]piperazine; MS m/z: (M+H)$^+$ Calc'd for $C_{28}H_{31}N_6O_4$: 515.24; found 515.19. HPLC retention time: 2.47 minutes (column G, flow rate 4 ml/min, gradient time 3 min).

EXAMPLE 232

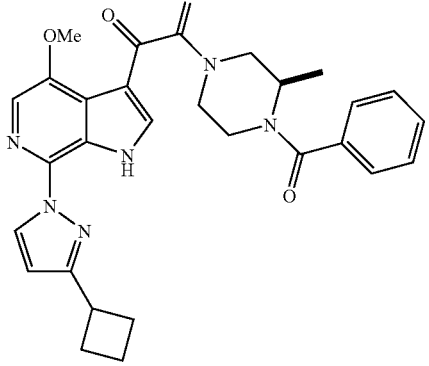

Example 232, was prepared according to the general method described above starting from Precursor 5z and Pyrazole-006 to provide (R)-1-benzoyl-2-methyl-4-[(4-methoxy-7-(3-cycloputyl-pyrazol-1-yl)-6-azaindol-3-yl)-oxoacetyl]piperazine; MS m/z: (M+H)$^+$ Calc'd for $C_{29}H_{31}N_6O_4$: 527.24; found 527.16. HPLC retention time: 2.53 minutes (column G, flow rate 4 ml/min, gradient time 3 min).

EXAMPLE 233

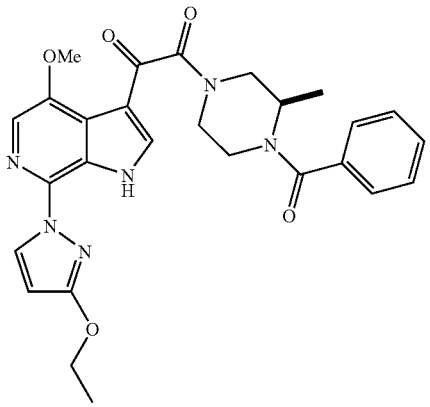

Example 233, was prepared according to the general method described above starting from Precursor 5z and Pyrazole-012 to provide (R)-1-benzoyl-2-methyl-4-[(4-methoxy-7-(3-ethoxy-pyrazol-1-yl)-6-azaindol-3-yl)-oxoacetyl]piperazine; MS m/z: (M+H)$^+$ Calc'd for $C_{27}H_{29}N_6O_5$: 517.22; found 517.17. HPLC retention time: 2.26 minutes (column G, flow rate 4 ml/min, gradient time 3 min).

EXAMPLE 234

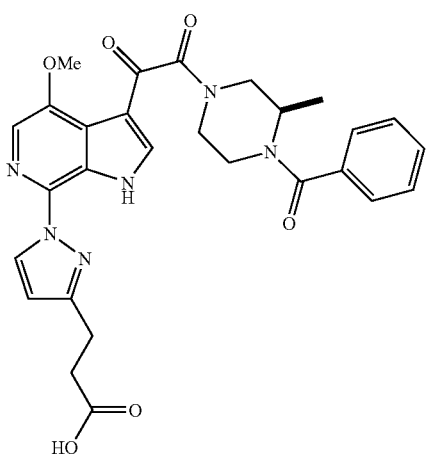

Example 234, was prepared according to the general method described above starting from Precursor 5z and Pyrazole-011 to provide (R)-1-benzoyl-2-methyl-4-[(4-methoxy-7-(3-(2-hydroxylcarbonylethan-1-yl)-pyrazol-1-yl)-6-azaindol-3-yl)-oxoacetyl]piperazine; MS m/z: (M+H)$^+$ Calc'd for $C_{28}H_{29}N_6O_4$: 545.21; found 545.15. HPLC retention time: 2.08 minutes (column G, flow rate 4 ml/min, gradient time 3 min).

EXAMPLE 235

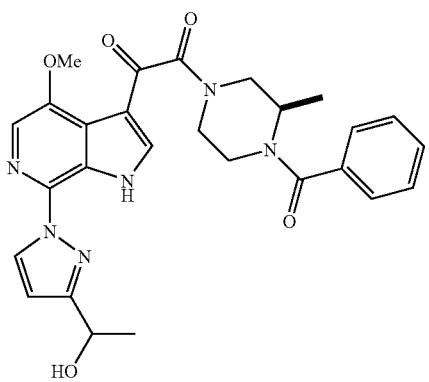

Example 235, was prepared according to the general method described above starting from Precursor 5z and Pyrazole-009 to provide (R)-1-benzoyl-2-methyl-4-[(4-methoxy-7-(3-(1-hydroxylethyl)-pyrazol-1-yl)-6-azaindol-3-yl)-oxoacetyl]piperazine; MS m/z: (M+H)$^+$ Calc'd for $C_{27}H_{29}N_6O_5$: 517.22; found 517.15. HPLC retention time: 1.43 minutes (column G).

EXAMPLES 236 AND 237

Example 236

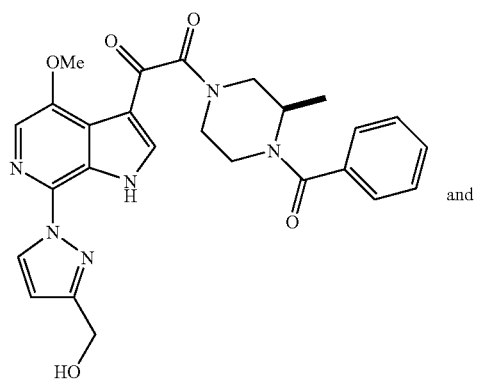

and

Example 237

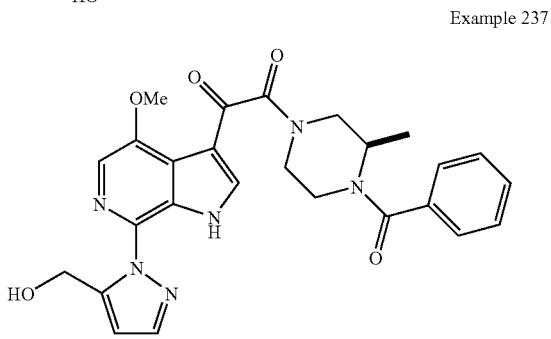

Examples 236 and 237, were prepared according to the general method described above starting from Precursor 5z and Pyrazole-007 to provide Example 236, (R)-1-benzoyl-2-methyl-4-[(4-methoxy-7-(3-hydroxylmethyl-pyrazol-1-yl)-6-azaindol-3-yl)-oxoacetyl]piperazine and Example 237, (R)-1-benzoyl-3-methyl-4-[(4-methoxy-7-(4-hydroxylmethyl-pyrazol-1-yl)-6-azaindol-3-yl)-oxoacetyl]piperazine.

Example 236, (R)-1-benzoyl-3-methyl-4-[(4-methoxy-7-(3-hydroxylmethyl-pyrazol-1-yl)-6-azaindol-3-yl)-oxoacetyl]piperazine: MS m/z: (M+H)$^+$ Calc'd for $C_{26}H_{27}N_6O_5$: 503.20; found 503.20. HPLC retention time: 1.87 minutes (column G, flow rate 4 ml/min, gradient time 3 min).

Example 237, (R)-1-benzoyl-3-methyl-4-[(4-methoxy-7-(4-hydroxylmethyl-pyrazol-1-yl)-6-azaindol-3-yl)-oxoacetyl]piperazine: MS m/z: (M+H)$^+$ Calc'd for $C_{26}H_{27}N_6O_5$: 503.20; found 503.25. HPLC retention time: 1.31 minutes (column G, flow rate 4 ml/min, gradient time 3 min).

EXAMPLE 238

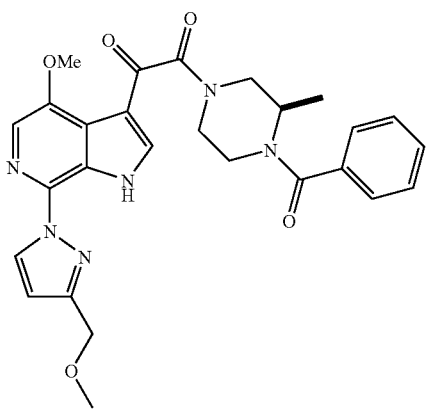

Example 238, was prepared according to the general method described above starting from Precursor 5z and Pyrazole-013 to provide (R)-1-benzoyl-2-methyl-4-[(4-methoxy-7-(3-methoxymethyl-pyrazol-1-yl)-6-azaindol-3-yl)-oxoacetyl]piperazine; MS m/z: (M+H)$^+$ Calc'd for $C_{27}H_{29}N_6O_5$: 517.22; found 517.23. HPLC retention time: 1.95 minutes (column G, flow rate 4 ml/min, gradient time 3 min).

EXAMPLE 239

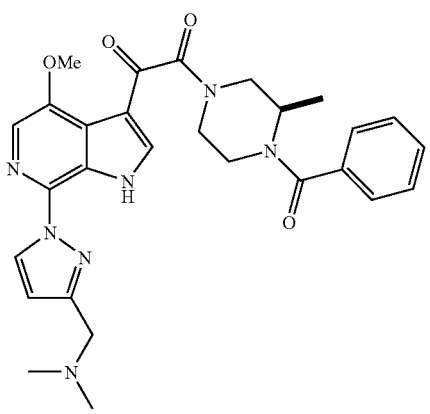

Example 239, was prepared according to the general method described above starting from Precursor 5z and Pyrazole-014 to provide (R)-1-benzoyl-2-methyl-4-[(4-methoxy-7-(3-(N,N-dimethylamino)methyl-pyrazol-1-yl)-6-azaindol-3-yl)-oxoacetyl]piperazine; MS m/z: (M+H)+ Calc'd for $C_{28}H_{32}N_7O_4$: 530.25; found 530.25. HPLC retention time: 1.45 minutes (column G, flow rate 4 ml/min, gradient time 3 min).

EXAMPLES 190 AND 240

Example-190

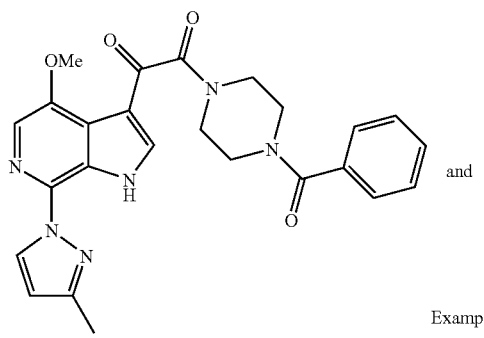

and

Example 240

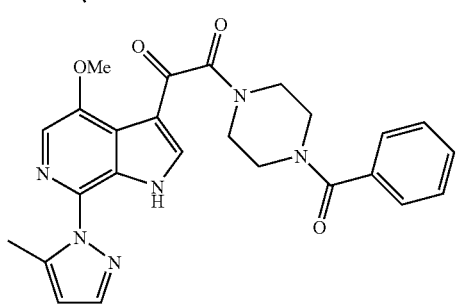

Examples 190 and 240, were prepared according to the general method described above starting from Precursor 5b and 3-methylpyrazole to provide example Example 190 and Example 240.

Example 240, 1-benzoyl-4-[(4-methoxy-7-(5-methyl-pyrazol-1-yl)-6-azaindol-3-yl)-oxoacetyl]piperazine; MS m/z: (M+H)+ Calc'd for $C_{25}H_{25}N_6O_4$: 473.19; found 473.19. HPLC retention time: 1.35 minutes (column G).

Example 190, 1-benzoyl-4-[(4-methoxy-7-(3-methyl-pyrazol-1-yl)-6-azaindol-3-yl)-oxoacetyl]piperazine; MS m/z: (M+H)+ Calc'd for $C_{25}H_{25}N_6O_4$: 473.19; found 473.17. HPLC retention time: 1.50 minutes (column G).

EXAMPLES 241 AND 242

Example 241

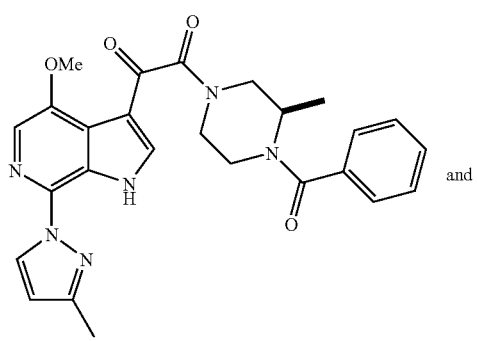

and

Example 242

-continued

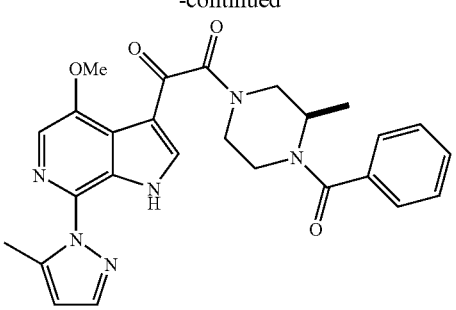

Examples 241 and 242, were prepared according to the general method described above starting from Precursor 5z and 3-methylpyrazole.

Example 241, (R)-1-benzoyl-2-methyl-4-[(4-methoxy-7-(3-methyl-pyrazol-1-yl)-6-azaindol-3-yl)-oxoacetyl]piperazine; MS m/z: (M+H)+ Calc'd for $C_{26}H_{26}N_6O_4$: 487.21; found 486.20. HPLC retention time: 1.54 minutes (column G).

Example 242, (R)-1-benzoyl-2-methyl-4-[(4-methoxy-7-(5-methyl-pyrazol-1-yl)-6-azaindol-3-yl)-oxoacetyl]piperazine; MS m/z: (M+H)+ Calc'd for $C_{26}H_{27}N_6O_4$: 487.21; found 486.20. HPLC retention time: 1.41 minutes (column G).

EXAMPLE 243

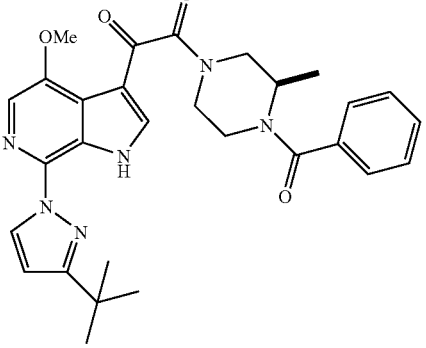

Example 243, was prepared according to the general method described above starting from Precursor 5z and 3-t-butylpyrazole to provide (R)-1-benzoyl-2-methyl-4-[(4-methoxy-7-(3-t-butyl-pyrazol-1-yl)-6-azaindol-3-yl)-oxoacetyl]piperazine; MS m/z: (M+H)+ Calc'd for $C_{29}H_{30}N_6O_4$: 529.26; found 529.29. HPLC retention time: 1.86 minutes (column G).

EXAMPLE 244

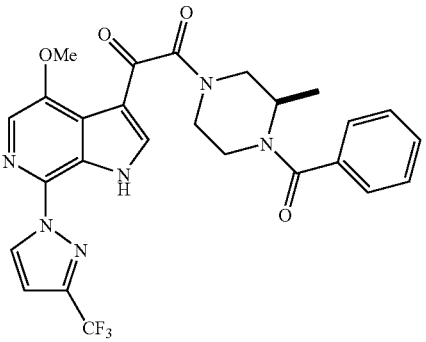

Example 244, was prepared according to the general method described above starting from Precursor 5z and 3-trifluoromethylpyrazole to provide (R)-1-benzoyl-2-methyl-4-[(4-methoxy-7-(3-trifluoromethyl-pyrazol-1-yl)-6-azaindol-3-yl)-oxoacetyl]piperazine; MS m/z: (M+H)+ Calc'd for $C_{26}H_{24}F_3N_6O_4$: 541.18; found 541.25. HPLC retention time: 1.71 minutes (column G).

EXAMPLE 245

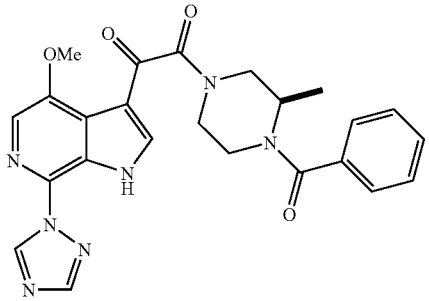

Example 245, was prepared according to the general method described above starting from Precursor 5z and 1,2,4-triazole to provide (R)-1-benzoyl-2-methyl-4-[(4-methoxy-7-(1,2,4-triazol-1-yl)-6-azaindol-3-yl)-oxoacetyl]piperazine; MS m/z: (M+H)+ Calc'd for $C_{24}H_{24}N_7O_4$: 474.19; found 474.23. HPLC retention time: 1.29 minutes (column G).

EXAMPLE 246

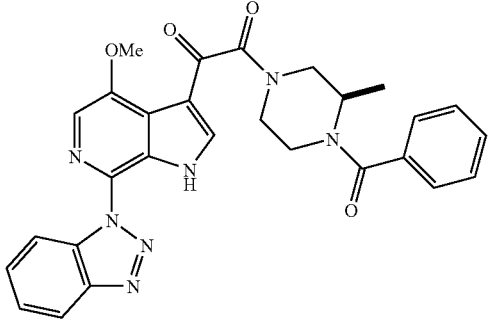

Example 246, was prepared according to the general method described above starting from Precursor 5z and 1,2,3-benzotriazole to provide (R)-1-benzoyl-2-methyl-4-[(4-methoxy-7-(1,2,3-benzotriazol-1-yl)-6-azaindol-3-yl)-oxoacetyl]piperazine; MS m/z: (M+H)+ Calc'd for $C_{28}H_{26}N_7O_4$: 524.20; found 524.27. HPLC retention time: 1.68 minutes (column G).

EXAMPLE 247

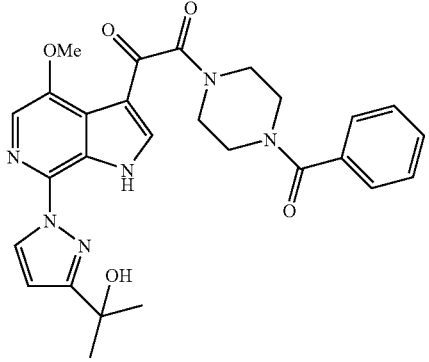

Example 247, was prepared according to the general method described above starting from Precursor 5b and Pyrazole-010 to provide 1-benzoyl-4-[(4-methoxy-7-(3-(1-hydroxyl-1-methylethyl)-pyrazol-1-yl)-6-azaindol-3-yl)-oxoacetyl]piperazine; MS m/z: (M+H)+ Calc'd for $C_{27}H_{29}N_6O_5$: 517.22; found 517.37. HPLC retention time: 1.38 minutes (column L).

EXAMPLE 248

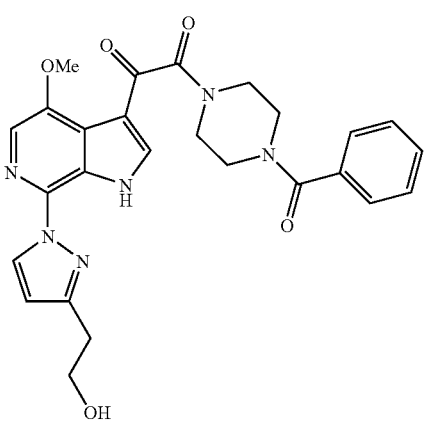

Example 248, was prepared according to the general method described above starting from Precursor 5b and Pyrazole-008 to provide 1-benzoyl-4-[(4-methoxy-7-(3-(3-hydroxylethyl)-pyrazol-1-yl)-6-azaindol-3-yl)-oxoacetyl]piperazine; MS m/z: (M+H)+ Calc'd for $C_{26}H_{27}N_6O_5$: 503.20; found 503.27. HPLC retention time: 1.16 minutes (column L).

EXAMPLE 249

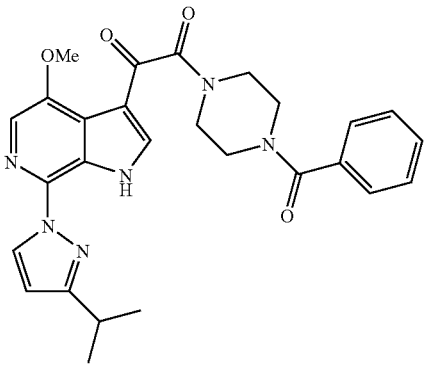

Example 249, was prepared according to the general method described above starting from Precursor 5b and Pyrazole-004 to provide 1-benzoyl-4-[(4-methoxy-7-(3-iso-propyl-pyrazol-1-yl)-6-azaindol-3-yl)-oxoacetyl]piperazine; MS m/z: (M+H)+ Calc'd for $C_{27}H_{29}N_6O_4$: 501.23; found 501.34. HPLC retention time: 1.74 minutes (column L).

EXAMPLE 250

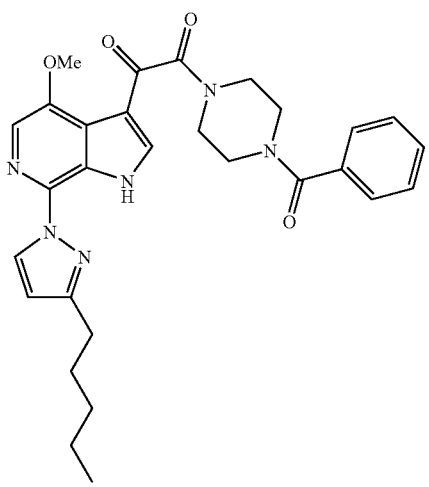

Example 250, was prepared according to the general method described above starting from Precursor 5b and Pyrazole-003 to provide 1-benzoyl-4-[(4-methoxy-7-(3-n-pentyl-pyrazol-1-yl)-6-azaindol-3-yl)-oxoacetyl]piperazine; MS m/z: (M+H)$^+$ Calc'd for $C_{29}H_{33}N_6O_4$: 529.26; found 529.34. HPLC retention time: 1.96 minutes (column L).

EXAMPLES 251 AND APP 252

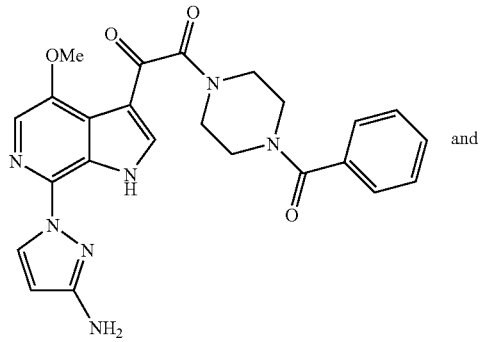

Example 251 and

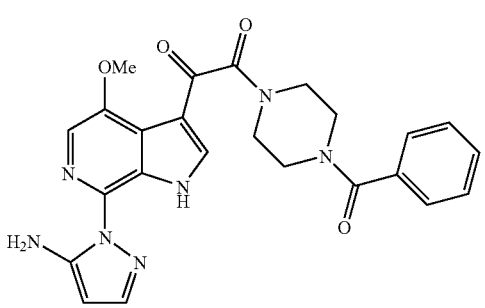

Example 252

Examples 251 and 252, were prepared according to the general method described above starting from Precursor 5b and 3-aminopyrazole.

Example 251, 1-benzoyl-4-[(4-methoxy-7-(3-amino-pyrazol-1-yl)-6-azaindol-3-yl)-oxoacetyl]piperazine; MS m/z: (M+H)$^+$ Calc'd for $C_{24}H_{24}N_7O_4$: 474.29; found 474.24. HPLC retention time: 1.58 minutes (column G).

Example 252, 1-benzoyl-4-[(4-methoxy-7-(5-amino-pyrazol-1-yl)-6-azaindol-3-yl)-oxoacetyl]piperazine; MS m/z: (M+H)$^+$ Calc'd for $C_{24}H_{24}N_7O_4$: 474.29; found 474.22. HPLC retention time: 1.59 minutes (column G).

EXAMPLES 253 AND 254

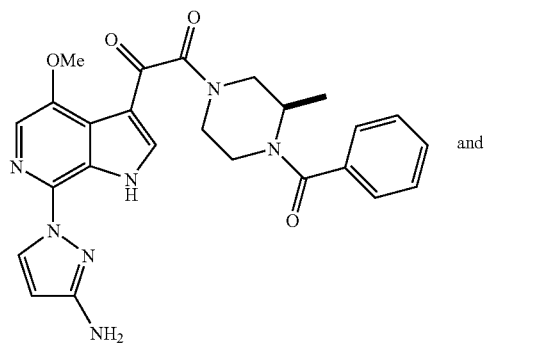

Example 253 and

Example 254

Examples 253 and 254, were prepared according to the general method described above starting from Precursor 5z and 3-aminopyrazole.

Example 253, (R)-1-benzoyl-2-methyl-4-[(4-methoxy-7-(3-amino-pyrazol-1-yl)-6-azaindol-3-yl)-oxoacetyl]piperazine; MS m/z: (M+H)$^+$ Calc'd for $C_{25}H_{26}N_7O_4$: 488.20; found 488.25. HPLC retention time: 1.65 minutes (column G, flow rate=4 ml/min, gradient time=3 min).

Example 254, (R)-1-benzoyl-2-methyl-4-[(4-methoxy-7-(5-amino-pyrazol-1-yl)-6-azaindol-3-yl)-oxoacetyl]piperazine; MS m/z: (M+H)$^+$ Calc'd for $C_{25}H_{26}N_7O_4$: 488.20; found 488.25. HPLC retention time: 1.74 minutes (column G, flow rate=4 ml/min, gradient time=3 min).

EXAMPLES 255 AND 256

Example 255

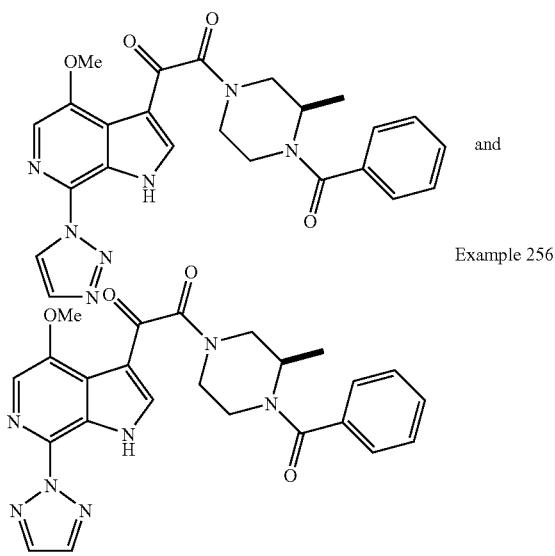

Example 256

Examples 255 and 256, were prepared according to the general method described above starting from Precursor 5z and 1,2,3-triazole. Precursor 5z (0.056 g), 0.056 g Cu powder, 0.025 g K2CO3 and 10 equivalents of 1,2,3 triazole were heated at 155-170 C for 4 hrs. The reaction was allowed to cool to ambient temperature and the residue was dissolved in MeOH and purified by Prep HPLC. as described above in the general methods to provide Example 255 (0.020 g) as a brown solid, yield 34% and the other isomer Example 256.

Example 255, (R)-1-benzoyl-2-methyl-4-[(4-methoxy-7-(1,2,3-triazol-1-yl)-6-azaindol-3-yl)-oxoacetyl]piperazine; MS m/z: $(M+H)^+$ Calc'd for $C_{24}H_{24}N_7O_4$: 474.19; found 474.21. HPLC retention time: 1.84 minutes (column G, flow rate=4 ml/min, gradient time=3 min). $^1$H NMR (500 MHz, CD$_3$OD) δ8.85 (s, 1H), 8.32 (ss, 1H), 7.94 (m, 2H), 7.48 (m, 5H), 4.07 (ss, 3H), 4.00-3.00 (m, 7H), 1.33 (m, 3H).

Example 256, (R)-1-benzoyl-2-methyl-4-[(4-methoxy-7-(1,2,3-triazol-2-yl)-6-azaindol-3-yl)-oxoacetyl]piperazine; MS m/z: $(M+H)^+$ Calc'd for $C_{24}H_{24}N_7O_4$: 474.19; found 474.21. HPLC retention time: 1.66 minutes (column G, flow rate=4 ml/min, gradient time=3 min). $^1$H NMR (500 MHz, CD$_3$OD) δ8.33 (ss, 1H), 8.13 (s, 1H), 7.46 (m, 7H), 4.07 (ss, 3H), 4.00-3.00 (m, 7H), 1.32 (m, 3H).

EXAMPLE 257

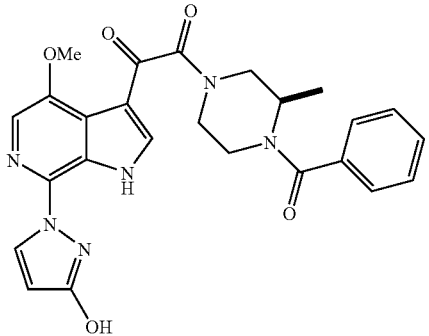

Example 257, was prepared according to the general method described above starting from Precursor 5z and 3-hydroxylpyrazole to provide (R)-1-benzoyl-2-methyl-4-[(4-methoxy-7-(3-hydroxylpyrazol-1-yl)-6-azaindol-3-yl)-oxoacetyl]piperazine; MS m/z: $(M+H)^+$ Calc'd for $C_{25}H_{25}N_6O_5$: 489.19; found 489.15. HPLC retention time: 1.38 minutes (column G).

EXAMPLE 258

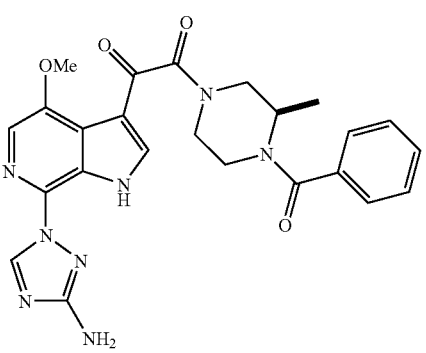

Example 258, was prepared according to the general method described above starting from Precursor 5z and 3-amino-1,2,4-triazole to provide (R)-1-benzoyl-2-methyl-4-[(4-methoxy-7-(3-amino-1,2,4-triazol-1-yl)-6-azaindol-3-yl)-oxoacetyl]piperazine; MS m/z: $(M+H)^+$ Calc'd for $C_{24}H_{25}N_8O_4$: 489.20; found 489.24. HPLC retention time: 1.69 minutes (column G).

Examples 259 Through 265, were Prepared According to the General Procedure Si—Cu (Silicon-Masking Conditions) Described Above:

EXAMPLE 259

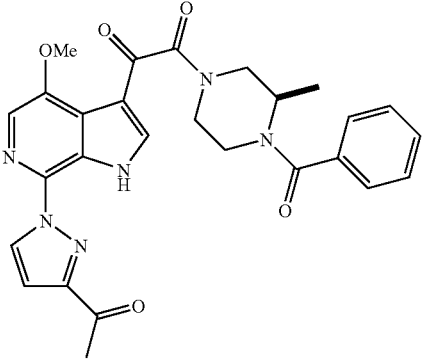

Example 259, was prepared according to the general method Si—Cu (Silicon-Masking) described above starting from Precursor 5z and 3-methylcarbonylpyrazole to provide (R)-1-benzoyl-2-methyl-4-[(4-methoxy-7-(3-methylcarbonyl-pyrazol-1-yl)-6-azaindol-3-yl)-oxoacetyl]piperazine;

MS m/z: (M+H)+ Calc'd for $C_{27}H_{27}N_6O_5$: 515.20; found 515.15. HPLC retention time: 1.51 minutes (column G).

EXAMPLE 260

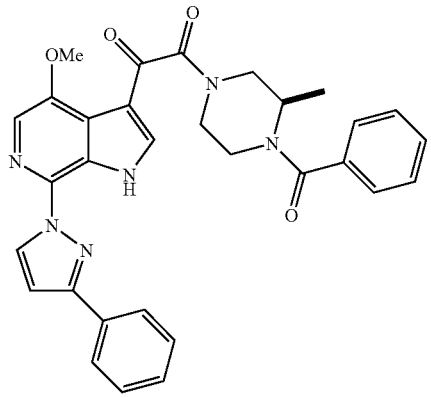

Example 260, was prepared according to the general method Si—Cu (Silicon-Masking) described above starting from Precursor 5z and 3-phenylpyrazole to provide (R)-1-benzoyl-2-methyl-4-[(4-methoxy-7-(3-phenyl-pyrazol-1-yl)-6-azaindol-3-yl)-oxoacetyl]piperazine; MS m/z: (M+H)+ Calc'd for $C_{31}H_{29}N_6O_4$: 549.23; found 549.18. HPLC retention time: 1.82 minutes (column G).

EXAMPLE 261

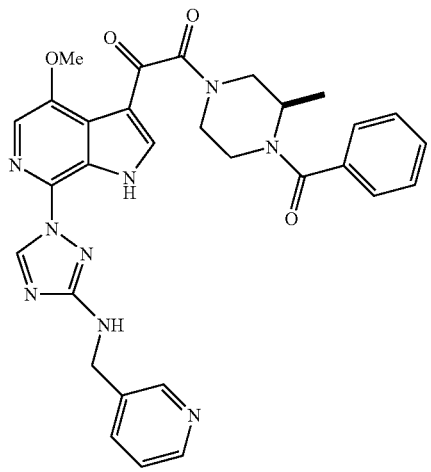

Example 261, was prepared according to the general method Si—Cu (Silicon-Masking) described above starting from Precursor 5z and 3-(3-pyridinemethylamino)-1,2,4-triazole to provide (R)-1-benzoyl-2-methyl-4-[(4-methoxy-7-(3-(3-pyridinemethylamino)-1,2,4-triazol-1-yl)-6-azaindol-3-yl)-oxoacetyl]piperazine; MS m/z: (M+H)+ Calc'd for $C_{30}H_{30}N_9O_4$: 580.24; found 580.14. HPLC retention time: 1.15 minutes (column G).

EXAMPLE 262

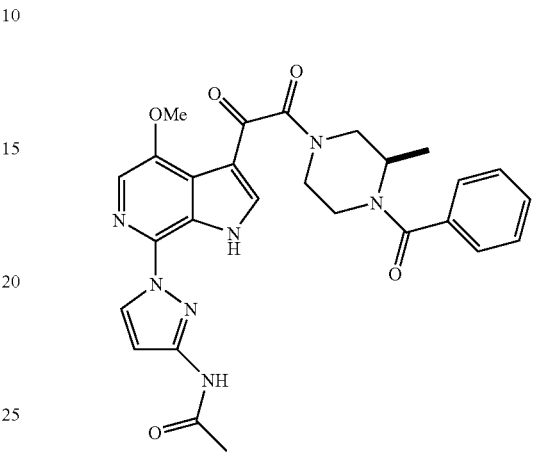

Example 262, was prepared according to the general method Si—Cu (Silicon-Masking) described above starting from Precursor 5z and 3-acetylaminopyrazole to provide (R)-1-benzoyl-2-methyl-4-[(4-methoxy-7-(3-acetylamino-pyrazol-1-yl)-6-azaindol-3-yl)-oxoacetyl]piperazine; MS m/z: (M+H)+ Calc'd for $C_{27}H_{28}N_7O_5$: 530.22; found 530.15. HPLC retention time: 1.41 minutes (column G).

EXAMPLE 263

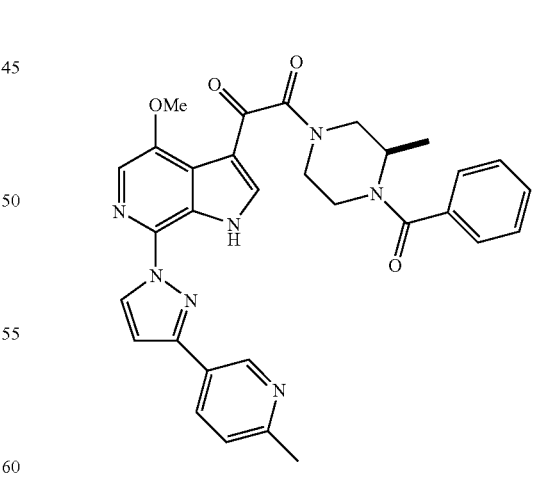

Example 263 was prepared according to the general method Si—Cu (Silicon-Masking) described above starting from Precursor 5z and 3-(2-methylpyridin-5-yl)pyrazole to provide (R)-1-benzoyl-2-methyl-4-[(4-methoxy-7-(3-(2-methylpyridin-5-yl)pyrazol-1-yl)-6-azaindol-3-yl)-oxoacetyl]

piperazine; MS m/z: (M+H)+ Calc'd for $C_{31}H_{30}N_7O_4$: 564.24; found 564.26. HPLC retention time: 1.22 minutes (column C).

EXAMPLE 264

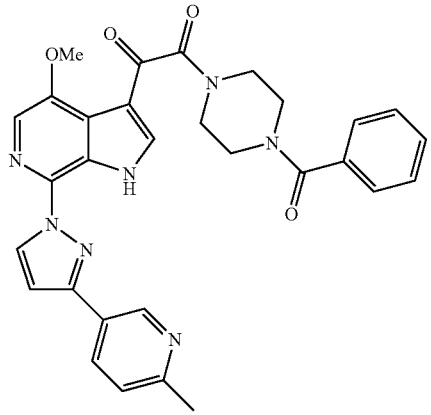

Example 264 was prepared according to the general method Si—Cu (Silicon-Masking) described above starting from Precursor 5b and 3-(2-methylpyridin-5-yl)pyrazole to provide 1-benzoyl-4-[(4-methoxy-7-(3-(2-methylpyridin-5-yl)pyrazol-1-yl)-6-azaindol-3-yl)-oxoacetyl]piperazine; MS m/z: (M+H)+ Calc'd for $C_{30}H_{28}N_7O_4$: 550.22; found 550.26. HPLC retention time: 1.20 minutes (column C).

EXAMPLE 265

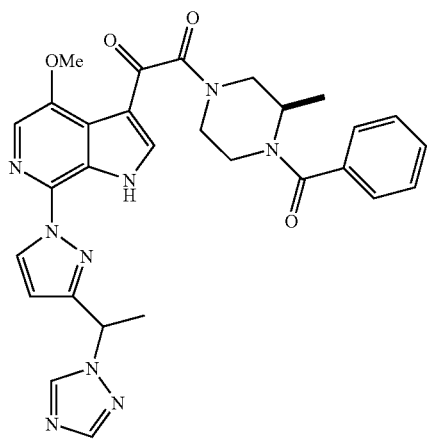

Example 265 was prepared according to the general method Si—Cu (Silicon-Masking) described above starting from Precursor 5z and 3-(1,2,4-triazol-1-yl)ethyl-pyrazole to provide (R)-1-benzoyl-2-methyl-4-[(4-methoxy-7-(3-(1,2,4-triazol-1-yl)ethyl-pyrazol-1-yl)-6-azaindol-3-yl)-oxoacetyl] piperazine; MS m/z: (M+H)+ Calc'd for $C_{29}H_{30}N_9O_4$: 568.24; found 568.13. HPLC retention time: 1.44 minutes (column G).

Examples 266 to 270, were Prepared According to a Procedure an Analogous to the Procedure Used Synthesize Example 15:

EXAMPLE 266

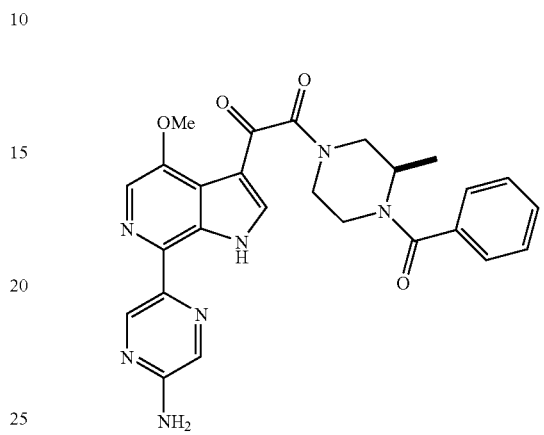

Example 266, was prepared according to the general method described above starting from Precursor 5z and 2-amino-pyrazin-5-yl tributyltin, to provide (R)-1-benzoyl-2-methyl-4-[(7-(2-amino-pyrazin-5-yl)-6-azaindol-3-yl)-oxoacetyl]piperazine; MS m/z: (M+H)+ Calc'd for $C_{26}H_{26}N_7O_4$: 500.20; found 500.26. HPLC retention time: 1.11 minutes (column G).

EXAMPLE 267

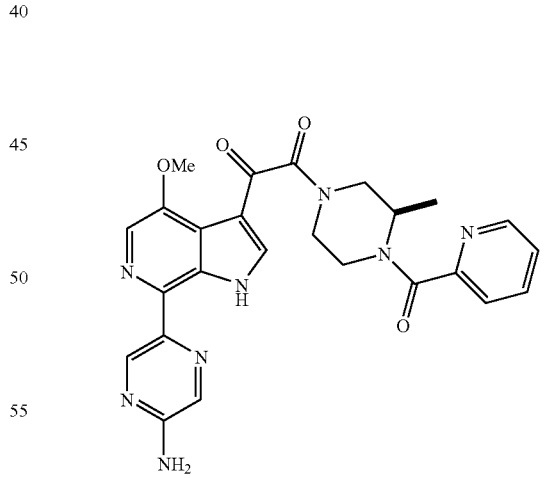

Example 267, was prepared according to the general method described above starting from Precursor 5za and 2-amino-pyrazin-5-yl tributyltin, to provide (R)-1-picolinoyl-2-methyl-4-[(7-(2-amino-pyrazin-5-yl)-6-azaindol-3-yl)-oxoacetyl]piperazine; MS m/z: (M+H)+ Calc'd for $C_{25}H_{25}N_8O_4$: 501.20; found 501.30. HPLC retention time: 1.04 minutes (column J).

EXAMPLE 268

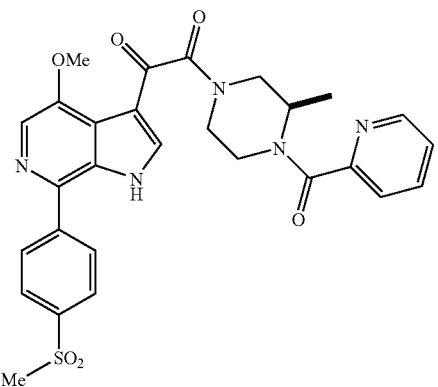

Example 268, was prepared according to the general method described above starting from Precursor 5xa and 4-methylsulfonylphenyl boronic acid, to provide (R)-1-picolinoyl-2-methyl-4-[(7-(4-methylsulfonyl-phenyl-1-yl)-6-azaindol-3-yl)-oxoacetyl]piperazine; MS m/z: (M+H)$^+$ Calc'd for $C_{28}H_{28}N_5O_6S$: 562.18; found 562.19. HPLC retention time: 0.86 minutes (column G).

EXAMPLE 269

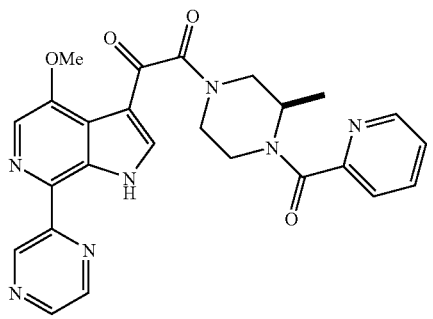

Example 269, was prepared according to the general method described above starting from Precursor 5xa and tributylstannyl pyrazine, to provide (R)-1-picolinoyl-2-methyl-4-[(7-pyrazinyl-6-azaindol-3-yl)-oxoacetyl]piperazine; MS m/z: (M+H)$^+$ Calc'd for $C_{25}H_{24}N_7O_4$: 486.19; found 486.32. HPLC retention time: 1.07 minutes (column G).

EXAMPLE 270

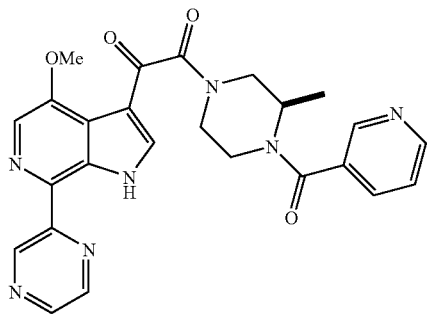

Example 270, was prepared according to the general method described above starting from Precursor 5y and tributylstannyl pyrazine, to provide (R)-1-nicotinoyl-2-methyl-4-[(7-pyrazinyl-6-azaindol-3-yl)-oxoacetyl]piperazine; MS m/z: (M+H)$^+$ Calc'd for $C_{25}H_{24}N_7O_4$: 486.19; found 486.10. HPLC retention time: 0.96 minutes (column L).

Examples 271 Through 272, were Prepared Using the "General Procedure of Converting —NH$_2$ Group to —OH Group", Examplified by the Preparation of Example 97:

EXAMPLE 271

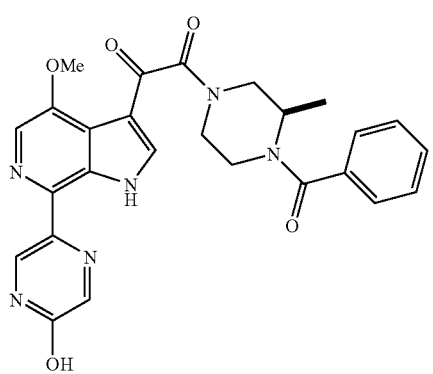

Example 271, was prepared according to the general method described above starting from Example 266 to provide (R)-1-benzoyl-2-methyl-4-[(7-(5-hydroxyl-pyrazin-1-yl)-6-azaindol-3-yl)-oxoacetyl]piperazine; MS m/z: (M+H)$^+$ Calc'd for $C_{26}H_{25}N_6O_5$: 501.19; found 501.21. HPLC retention time: 1.08 minutes (column G).

EXAMPLE 272

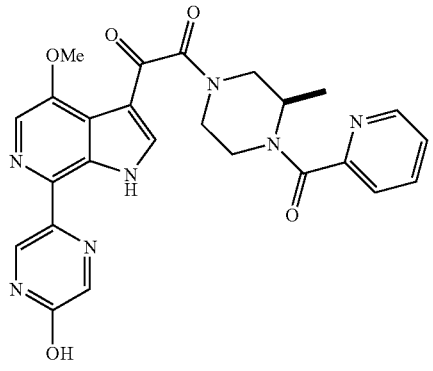

Example 272, was prepared according to the general method described above starting from Example 267 to provide (R)-1-picolinoyl-2-methyl-4-[(7-(5-hydroxyl-pyrazin-1-yl)-6-azaindol-3-yl)-oxoacetyl]piperazine; MS m/z: (M+H)$^+$ Calc'd for $C_{25}H_{24}N_7O_5$: 502.18; found 502.19. HPLC retention time: 0.88 minutes (column G).

EXAMPLE 273

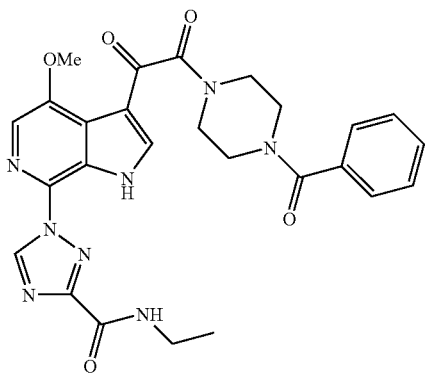

Example 273, was prepared from Precursor 5b and 1H-[1,2,4]-triazole-3-carboxylic acid ethylamide to provide 1-benzoyl-4-[(4-methoxy-7-(3-ethylaminocarbonyl-1,2,4-triazol-1-yl)-6-azaindol-3-yl)-oxoacetyl]piperazine. MS m/z: (M+H)$^+$ Calc'd for $C_{26}H_{27}N_8O_5$: 531.21; found 531.221. HPLC retention time: 1.75 minutes (column G). $^1$H NMR (500 MHz, $CD_3OD$) δ9.35 (s, 1H), 8.34 (s, 1H), 7.86 (s, 1H), 7.48 (b, 5H), 4.06 (s, 3H), 4.00-3.49 (m, 10H), 1.30 (t, 3H, J=7.5 Hz).

EXAMPLE 274

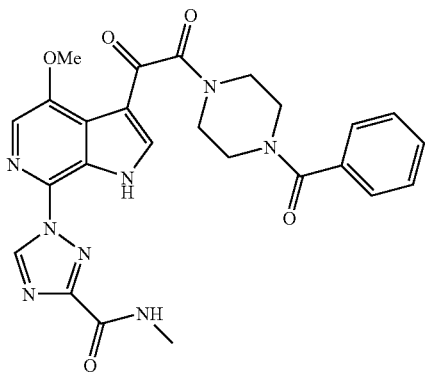

Example 274, was prepared from Precursor 5b and 1H-[1,2,4]-triazole-3-carboxylic acid methylamide to provide 1-benzoyl-4-[(4-methoxy-7-(3-methylaminocarbonyl-1,2,4-triazol-1-yl)-6-azaindol-3-yl)-oxoacetyl]piperazine. MS m/z: (M+H)$^+$ Calc'd for $C_{25}H_{25}N_8O_5$: 517.19; found 517.18. HPLC retention time: 1.67 minutes (column G). $^1$H NMR (500 MHz, $CD_3OD$) δ9.36 (s, 1H), 8.35 (s, 1H), 7.88 (s, 1H), 7.48 (b, 5H), 4.06 (s, 3H), 3.80-3.60 (m, 8H), 3.02 (s, 3H).

EXAMPLE 275

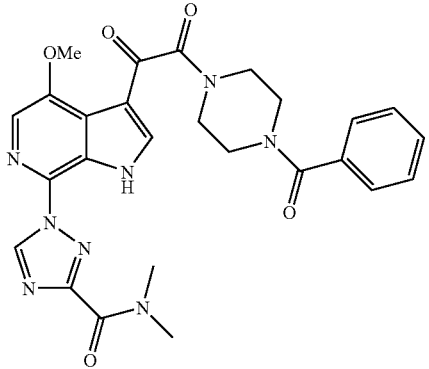

Example 275, was prepared from Precursor 5b and 1H-[1,2,4]-triazole-3-carboxylic acid dimethylamide to provide 1-benzoyl-4-[(4-methoxy-7-(3-dimethylaminocarbonyl-1,2,4-triazol-1-yl)-6-azaindol-3-yl)-oxoacetyl]piperazine. MS m/z: (M+H)$^+$ Calc'd for $C_{26}H_{27}N_8O_5$: 531.21; found 531.28. HPLC retention time: 1.71 minutes (column G).

EXAMPLE 276

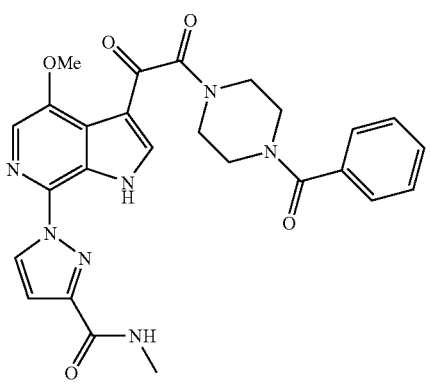

Example 276, was prepared from Precursor 5b and 1H-pyrazole-3-carboxylic acid methylamide to provide 1-benzoyl-4-[(4-methoxy-7-(3-methylaminocarbonyl-pyrazol-1-yl)-6-azaindol-3-yl)-oxoacetyl]piperazine. MS m/z: (M+H)$^+$ Calc'd for $C_{26}H_{26}N_7O_5$: 516.20; found 516.27. HPLC retention time: 1.86 minutes (column G).

EXAMPLE 277

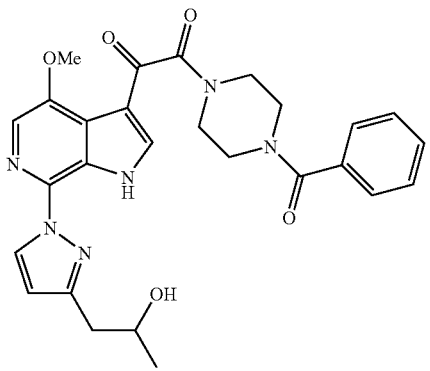

Example 277, was prepared from Precursor 5b and 1-(1H-pyrazol-3-yl)-propan-2-ol to provide 1-benzoyl-4-[(4-methoxy-7-(3-(2-hydroxylpropyl)-pyrazol-1-yl)-6-azaindol-3-yl)-oxoacetyl]piperazine. MS m/z: (M+H)$^+$ Calc'd for $C_{27}H_{29}N_6O_5$: 517.22; found 517.38. HPLC retention time: 1.42 minutes (column L).

EXAMPLE 278

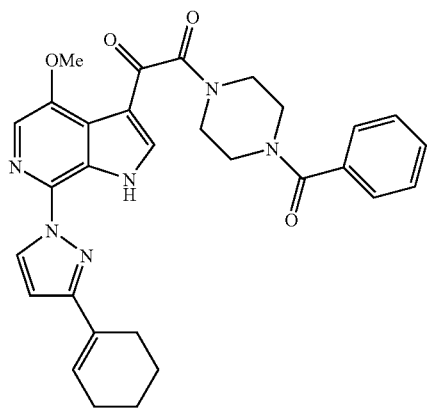

Example 278, was prepared from Precursor 5b and 3-cyclohex-1-enyl-1H-pyrazole to provide 1-benzoyl-4-[(4-methoxy-7-(3-(cyclohexen-1-yl)-pyrazol-1-yl)-6-azaindol-3-yl)-oxoacetyl]piperazine. MS m/z: (M+H)$^+$ Calc'd for $C_{30}H_{31}N_6O_4$: 539.24; found 539.26. HPLC retention time: 1.96 minutes (column L).

EXAMPLE 279

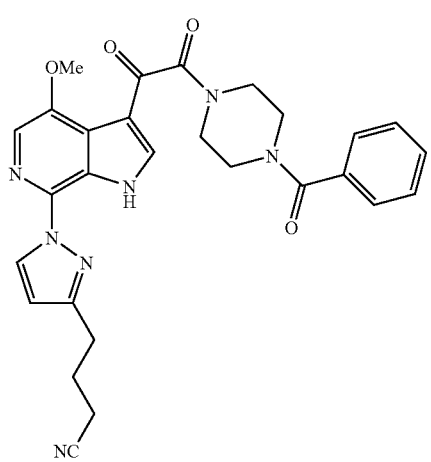

Example 279, was prepared from Precursor 5b and 4-(1H-pyrazol-3-yl)-butyronitrile to provide 1-benzoyl-4-[(4-methoxy-7-(3-(3-cyano-propan-1-yl)-pyrazol-1-yl)-6-azaindol-3-yl)-oxoacetyl]piperazine. MS m/z: (M+H)$^+$ Calc'd for $C_{28}H_{28}N_7O_4$: 526.22; found 526.35. HPLC retention time: 1.51 minutes (column L).

EXAMPLE 280

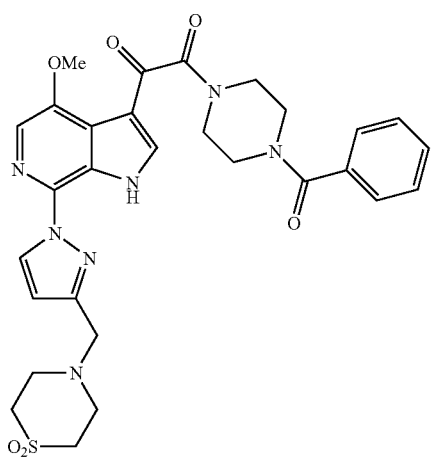

Example 280, was prepared from Precursor 5b and 4-(1H-pyrazol-3-ylmethyl)-thiomorpholine 1,1-dioxide to provide 1-benzoyl-4-[(4-methoxy-7-(3-(1,1-dioxo-thiomorpholin-4-yl)methyl-pyrazol-1-yl)-6-azaindol-3-yl)-oxoacetyl]piperazine. MS m/z: (M+H)$^+$ Calc'd for $C_{29}H_{32}N_7O_6S$: 606.21; found 606.34. HPLC retention time: 1.01 minutes (column L).

EXAMPLE 281

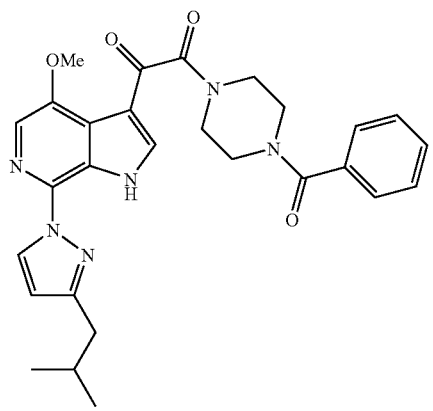

Example 281, was prepared from Precursor 5b and 3-isobutyl-1H-pyrazole to provide 1-benzoyl-4-[(4-methoxy-7-(3-isobutyl-pyrazol-1-yl)-6-azaindol-3-yl)-oxoacetyl]piperazine. MS m/z: (M+H)$^+$ Calc'd for $C_{28}H_{31}N_6O_4$: 515.24; found 515.35. HPLC retention time: 1.90 minutes (column L).

EXAMPLE 282

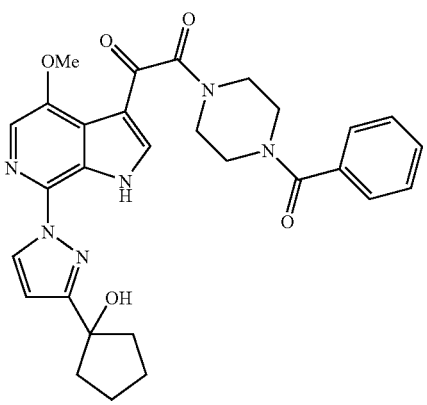

Example-282, was prepared from Precursor 5b and 1-(1H-pyrazol-3-yl)-cyclopentanol to provide 1-benzoyl-4-[(4-methoxy-7-(3-(1-hydroxy-cyclopentyl)-pyrazol-1-yl)-6-azaindol-3-yl)-oxoacetyl]piperazine. MS m/z: (M+H)$^+$ Calc'd for $C_{29}H_{31}N_6O_5$: 543.24; found 543.43. HPLC retention time: 1.51 minutes (column L).

EXAMPLE 283

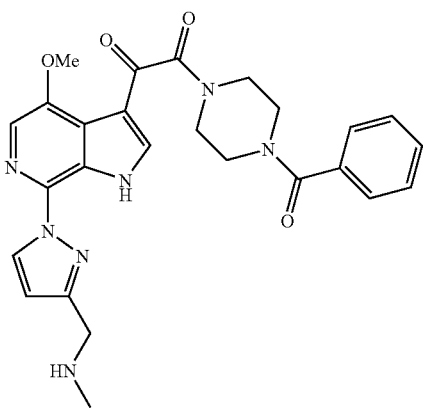

Example 283, was prepared from Precursor 5b and methyl-(1H-pyrazol-3-ylmethyl)-amine to provide 1-benzoyl-4-[(4-methoxy-7-(3-methylaminomethyl-pyrazol-1-yl)-6-azaindol-3-yl)-oxoacetyl]piperazine. MS m/z: (M+H)$^+$ Calc'd for $C_{26}H_{28}N_7O_4$: 502.22; found 502.31. HPLC retention time: 1.51 minutes (column L).

EXAMPLE 284

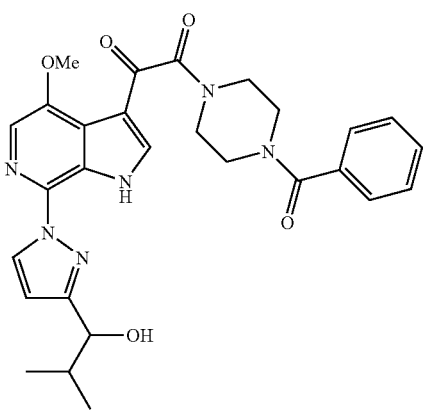

Example 284, was prepared from Precursor 5b and 2-methyl-1-(1H-pyrazol-3-yl)-propan-1-ol to provide 1-benzoyl-4-[(4-methoxy-7-(3-(1-hydroxy-2-methyl-propyl)-pyrazol-1-yl)-6-azaindol-3-yl)-oxoacetyl]piperazine. MS m/z: (M+H)$^+$ Calc'd for $C_{28}H_{31}N_6O_5$: 531.24; found 531.43. HPLC retention time: 1.63 minutes (column L).

EXAMPLE 285

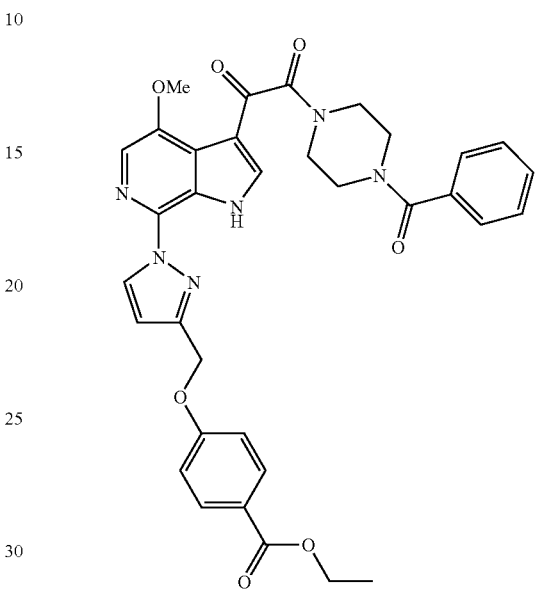

Example 285, was prepared according to the general method described above starting from Precursor 5b and Pyrazole-025 to provide 1-benzoyl-4-[(4-methoxy-7-(3-(4-ethoxycarbonyl-phenyl)oxymethyl-pyrazol-1-yl)-6-azaindol-3-yl)-oxoacetyl]piperazine; MS m/z: (M+H)$^+$ Calc'd for $C_{34}H_{33}N_6O_7$: 637.24; found 637.34. HPLC retention time: 1.87 minutes (column G). $^1$H NMR (500 MHz, CDCl$_3$) δ 8.61 (s, 1H), 8.16 (s, 1H), 8.02 (d, 2H, J=15 Hz), 7.76 (s, 1H), 7.43 (b, 5H), 7.05 (d, 2H, J=14.5 Hz), 6.60 (s, 1H), 5.29 (s, 2H), 4.33 (q, 2H, J=12 Hz), 4.03 (s, 3H), 3.80-3.57 (m, 8H), 1.38 (t, 3H, J=12.0 Hz).

EXAMPLE 286

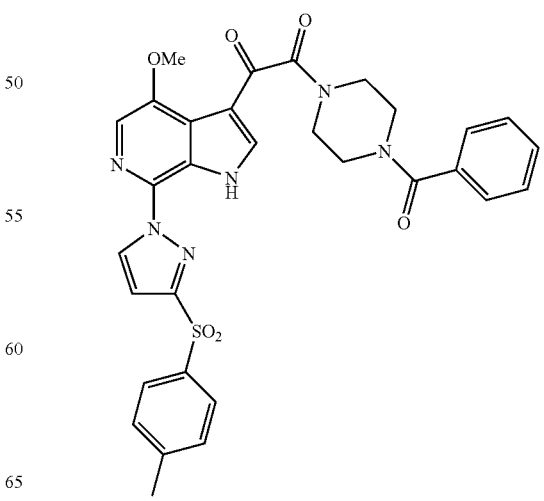

Example 286, was prepared according to the general method described above starting from Precursor 5b and 3-(toluene-4-sulfonyl)-1H-pyrazole to provide 1-benzoyl-4-[(4-methoxy-7-(3-(toluene-4-sulfonyl)-pyrazol-1-yl)-6-aza-indol-3-yl)-oxoacetyl]piperazine; MS m/z: (M+H)+ Calc'd for $C_{31}H_{29}N_6O_6S$: 613.19; found 613.28. HPLC retention time: 1.69 minutes (column G). $^1$H NMR (500 MHz, CDCl$_3$) δ8.64 (s, 1H), 8.21 (s, 1H), 7.94 (d, 2H, J=8.00 Hz), 7.74 (s, 1H), 7.43 (b, 5H), 7.34 (d, 2H, J=8.00 Hz), 6.94 (s, 1H), 4.04 (s, 3H), 4.00-3.40 (m, 8H), 2.42 (s, 3H).

EXAMPLE 287

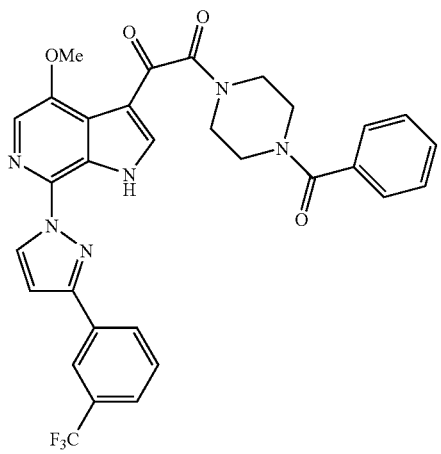

Example 287, was prepared according to the general method described above starting from Precursor 5b and 3-(3-trifluoromethyl-phenyl)-1H-pyrazole to provide 1-benzoyl-4-[(4-methoxy-7-(3-(3-trifluoromethyl-phenyl)-pyrazol-1-yl)-6-azaindol-3-yl)-oxoacetyl]piperazine; MS m/z: (M+H)+ Calc'd for $C_{31}H_{26}F_3N_6O_4$: 603.20; found 603.32. HPLC retention time: 1.94 minutes (column G). $^1$H NMR (500 MHz, CDCl$_3$) δ8.67 (s, 1H), 8.26 (s, 1H), 8.09-7.42 (m, 10H), 6.87 (s, 1H), 4.01 (s, 3H), 4.00-3.62 (m, 8H).

EXAMPLE 288

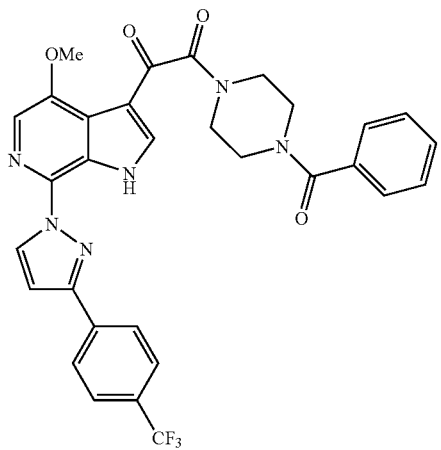

Example 288, was prepared according to the general method described above starting from Precursor 5b and 3-(4-trifluoromethyl-phenyl)-1H-pyrazole to provide 1-benzoyl-4-[(4-methoxy-7-(3-(4-trifluoromethyl-phenyl)-pyrazol-1-yl)-6-azaindol-3-yl)-oxoacetyl]piperazine; MS m/z: (M+H)+ Calc'd for $C_{31}H_{26}F_3N_6O_4$: 603.20; found 603.32. HPLC retention time: 1.96 minutes (column G). $^1$H NMR (500 MHz, CDCl$_3$) δ8.69 (s, 1H), 8.26 (s, 1H), 8.09-7.43 (m, 10H), 6.87 (s, 1H), 4.01 (s, 3H), 4.00-3.62 (m, 8H).

EXAMPLE 289

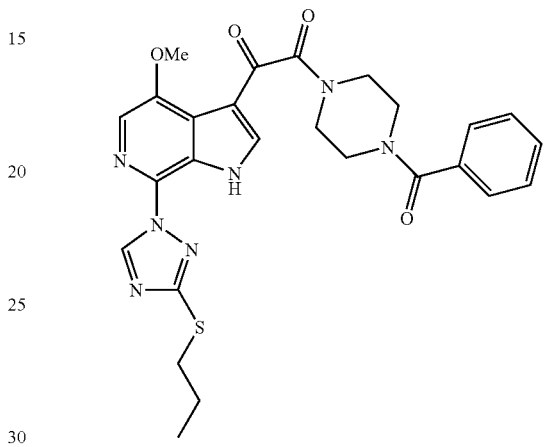

Example 289, was prepared according to the general method described above starting from Precursor 5b and 3-propylsulfanyl-1H-[1,2,4]triazole to provide 1-benzoyl-4-[(4-methoxy-7-(3-propylsulfanyl-[1,2,4]triazol-1-yl)-6-azaindol-3-yl)-oxoacetyl]piperazine; MS m/z: (M+H)+ Calc'd for $C_{26}H_{28}N_7O_4S$: 534.19; found 534.32. HPLC retention time: 1.65 minutes (column G). $^1$H NMR (500 MHz, CDCl$_3$) δ9.09 (s, 1H), 8.18 (s, 1H), 7.70 (s, 1H), 7.37 (m, 5H), 4.05 (s, 3H), 3.90-3.30 (m, 8H), 3.18 (t, 2H, J=11.5 Hz), 1.74 (m, 2H), 1.02 (t, 3H, J=12.5 Hz).

EXAMPLE 290

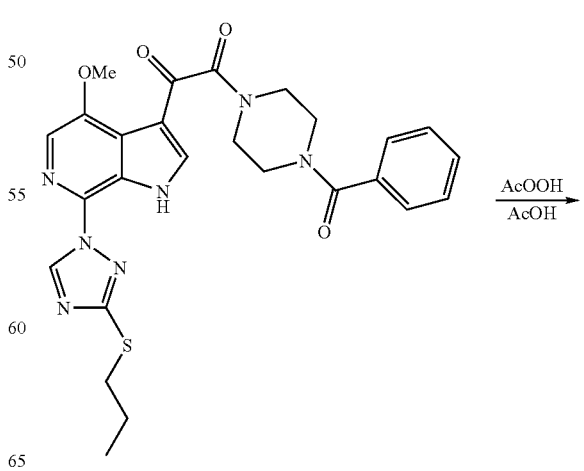

Example 289

357 / 358

-continued

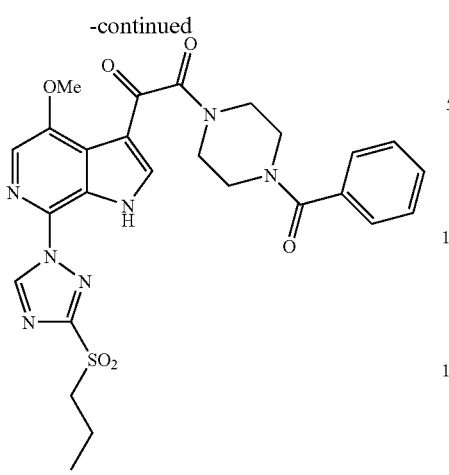

Example 290

Example 290 (18 mg) was dissolved in 1 ml of AcOOH (37% in ACOH) at room temperature and the mixture was kept stirring for 10 hours. Removal of solvents under vacuum provided a redicue, which was purified using Shimadzu automated preparative HPLC System to provide Example 290, 1-benzoyl-4-[(4-methoxy-7-(3-(propane-1-sulfonyl)-[1,2,4]triazol-1-yl)-6-azaindol-3-yl)-oxoacetyl]piperazine; MS m/z: (M+H)$^+$ Calc'd for $C_{26}H_{28}N_7O_6S$: 566.18; found 566.30. HPLC retention time: 1.44 minutes (column G). $^1$H NMR (500 MHz, CDCl$_3$) δ 9.33 (s, 1H), 8.24 (s, 1H), 7.80 (s, 1H), 7.43 (m, 5H), 4.08 (s, 3H), 3.90-3.50 (m, 8H), 3.42 (t, 2H, J=8.00 Hz), 1.90 (m, 2H), 1.09 (t, 3H, J=7.50 Hz).

EXAMPLE 291

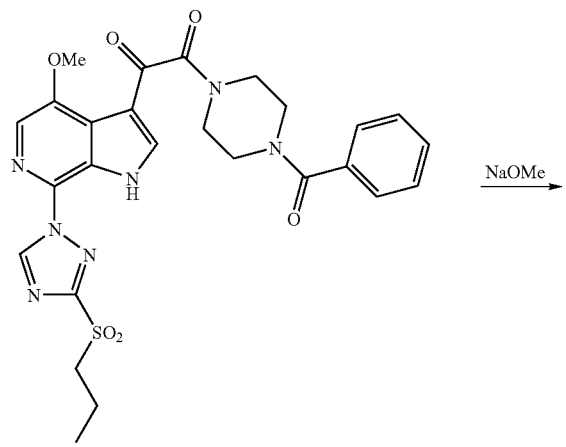

Example 290 and Example 291

Example 290, obtained from the previous stage, was dissolved in 5 ml of MeONa (8 wt % in MeOH) at room temperature and the mixture was heated to 90° C. for 10 hours to form 291, 1-benzoyl-4-[(4-methoxy-7-(3-methoxy-[1,2,4]triazol-1-yl)-6-azaindol-3-yl)-oxoacetyl]piperazine; MS m/z: (M+H)$^+$ Calc'd for $C_{24}H_{24}N_7O_5$: 490.18; found 490.29. HPLC retention time: 1.36 minutes (column G).

EXAMPLE 292

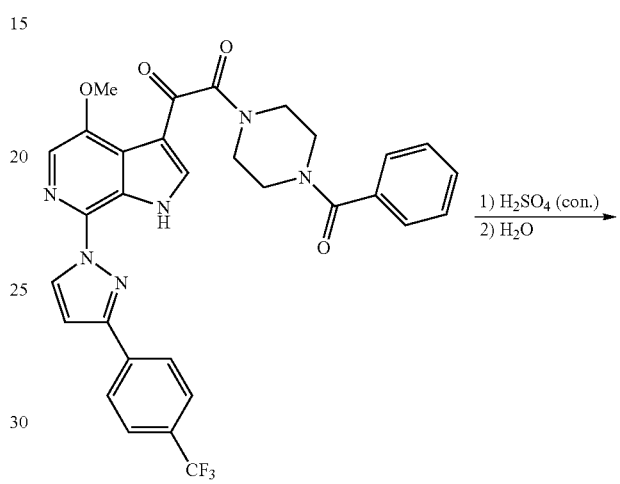

Example 288

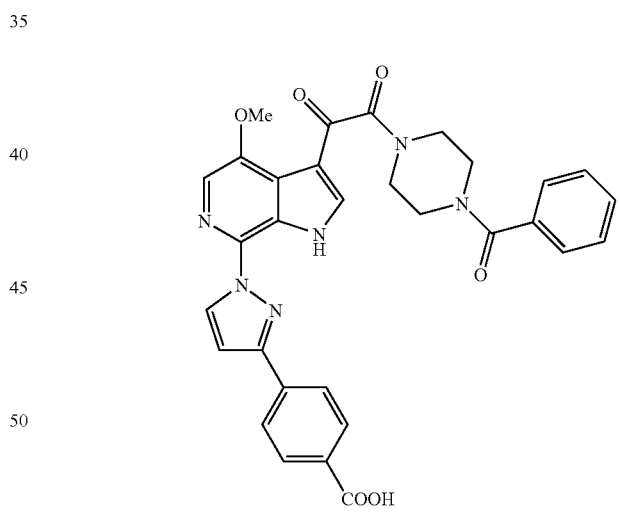

Example 288

Example 288 (8 mg) was dissolved in 0.2 ml of concentrated at room temperature and the mixture was heated to 70° C. for 6 hours. Then the mixture was quenched with water (2 ml) to form Example 292, which was purified using Shimadzu automated preparative HPLC System (2.1 mg of Example 292 obtained). Example 292, 1-benzoyl-4-[(4-methoxy-7-(3-(4-hydroxylcarbonylphenyl)-pyrazol-1-yl)-6-azaindol-3-yl)-oxoacetyl]piperazine; MS m/z: (M+H)$^+$ Calc'd for $C_{31}H_{27}N_6O_6$: 579.20; found 579.28. HPLC retention time: 1.72 minutes (column G).

$^1$H NMR (500 MHz, CDCl$_3$) δ8.71 (s, 1H), 8.29 (s, 1H), 8.15 (d, 2H, J=8.00 Hz), 7.97 (d, 2H, J=8.00 Hz), 7.80 (s, 1H), 7.45 (m, 5H), 6.90 (s, 1H), 4.05 (s, 3H), 4.02-3.49 (m, 8H).

EXAMPLE 293

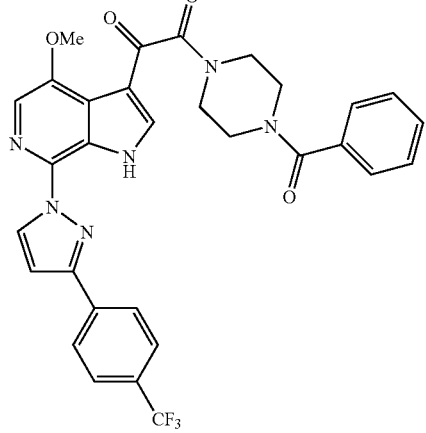

Example 288

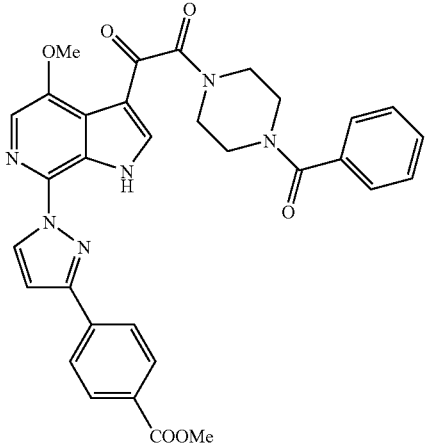

Example 293

EXAMPLE 294

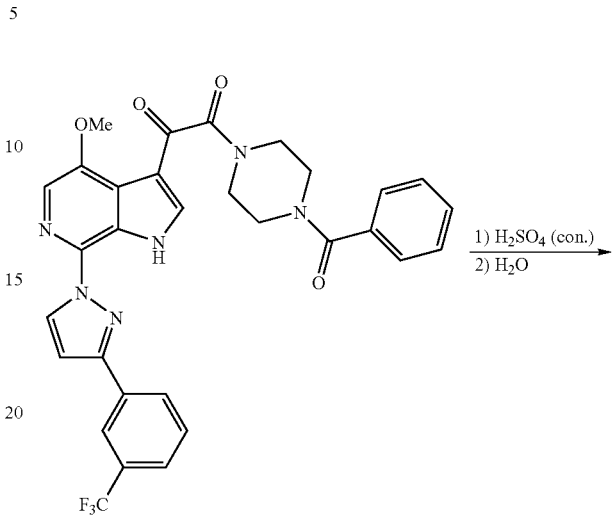

Example 287

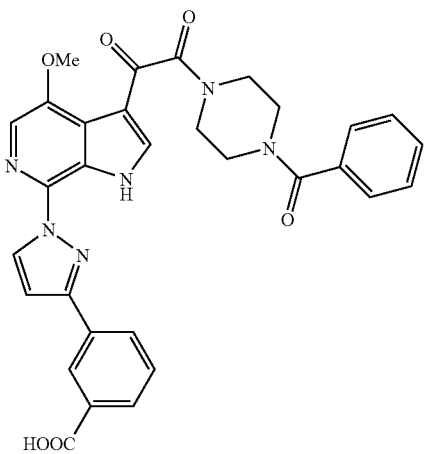

Example 294

Example 288 (8 mg) was dissolved in 0.2 ml of concentrated at room temperature and the mixture was heated to 70° C. for 6 hours. Then the mixture was quenched with MeOH (2 ml) to form Example 293, which was purified using Shimadzu automated preparative HPLC System (1.1 mg of Example 293 obtained). Example 293, 1-benzoyl-4-[(4-methoxy-7-(3-(4-methoxycarbonylphenyl)-pyrazol-1-yl)-6-azaindol-3-yl)-oxoacetyl]piperazine; MS m/z: (M+H)$^+$ Calc'd for C$_{32}$H$_{29}$N$_6$O$_6$: 593.21; found 593.32. HPLC retention time: 1.84 minutes (column G). $^1$H NMR (500 MHz, CDCl$_3$) δ8.74 (s, 1H), 8.29 (s, 1H), 8.16 (d, 2H, J=8.00 Hz), 7.94 (d, 2H, J=8.00 Hz), 7.79 (s, 1H), 7.44 (m, 5H), 6.89 (s, 1H), 4.05 (s, 3H), 3.96 (s, 3H), 3.90-3.40 (m, 8H).

Example 287 (6 mg) was dissolved in 0.2 ml of concentrated at room temperature and the mixture was heated to 70° C. for 6 hours. Then the mixture was quenched with water (2 ml) to form Example 294, which was purified using Shimadzu automated preparative HPLC System (2.7 mg of Example 294 obtained). Example 294, 1-benzoyl-4-[(4-methoxy-7-(3-(3-hydroxylcarbonylphenyl)-pyrazol-1-yl)-6-azaindol-3-yl)-oxoacetyl]piperazine; MS m/z: (M+H)$^+$ Calc'd for C$_{31}$H$_{27}$N$_6$O$_6$: 579.20; found 579.28. HPLC retention time: 1.74 minutes (column G).

$^1$H NMR (500 MHz, CDCl$_3$) δ8.76 (s, 1H), 8.56 (s, 1H), 8.30 (s, 1H), 8.10 (m, 2H), 7.77 (m, 1H), 7.80 (s, 1H), 7.45 (m, 5H), 6.87 (s, 1H), 4.04 (s, 3H), 4.00-3.40 (m, 8H).

EXAMPLE 295

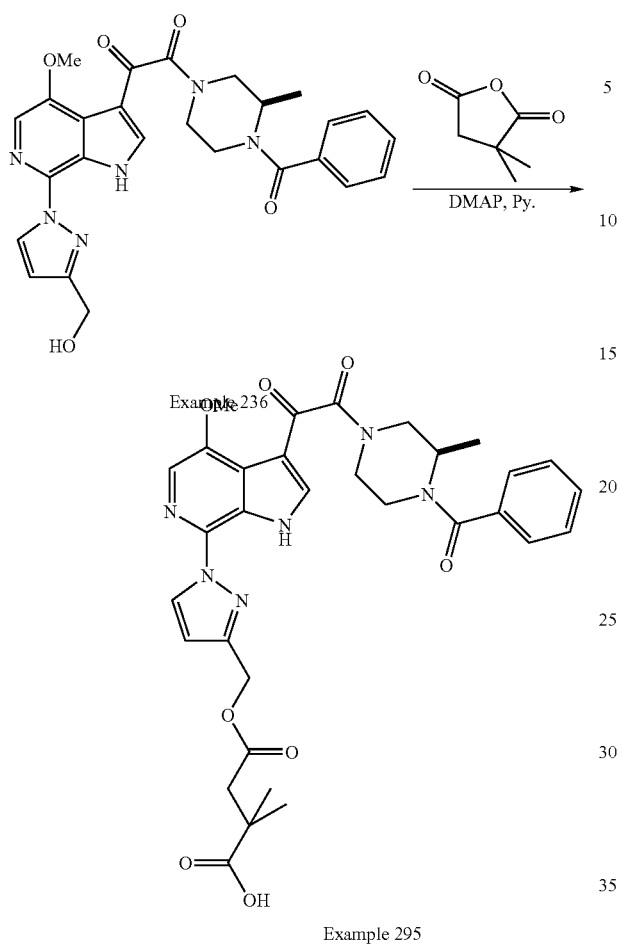

Example 295

Example 136 (6 mg), succinic anhydride (20 mg) and DMAP (5 ml) were dissolved in 5 ml of anhydrous pyridine at room temperature and the mixture was heated to reflux for 10 hours. Then the mixture was quenched with MeOH and solvents were removed under vacuum to provide a residue, which was purified using Shimadzu automated preparative HPLC System to give Example 295 (2.4 mg), 2,2-Dimethyl-succinic acid 4-(1-{3-[2-(4-benzoyl-3-methyl-piperazin-1-yl)-2-oxo-acetyl]-4-methoxy-1H-pyrrolo[2,3-c]pyridin-7-yl}-1H-pyrazol-3-ylmethyl)ester; MS m/z: (M+H)+ Calc'd for $C_{32}H_{35}N_6O_8$: 631.25; found 631.34. HPLC retention time: 1.64 minutes (column G).

EXAMPLE 296

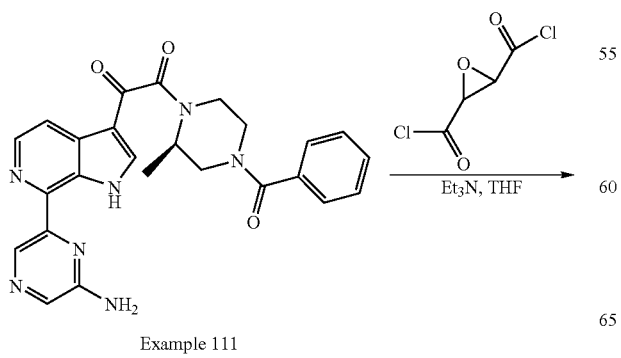

Example 111

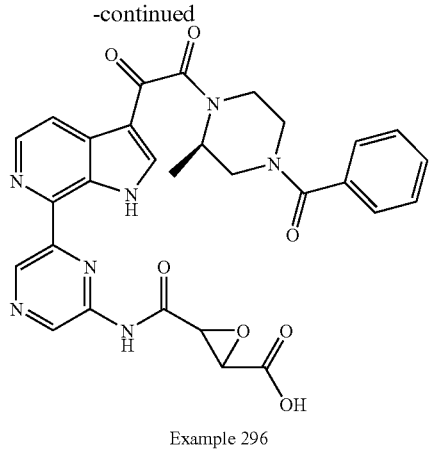

Example 296

Example 111 (10 mg), trans-epoxysuccinyl chloride (20 mg) and $Et_3N$ (0.2 ml) were dissolved in 2 ml of anhydrous THF at room temperature and the mixture was kept stirring for 10 hours. Then the mixture was quenched with water and solvents were removed under vacuum to provide a residue, which was purified using Shimadzu automated preparative HPLC System to give Example 296 (2 mg), 3-(6-{3-[2-(4-Benzoyl-2-methyl-piperazin-1-yl)-2-oxo-acetyl]-1H-pyrrolo[2,3-c]pyridin-7-yl}-pyrazin-2-ylcarbamoyl)-oxirane-2-carboxylic acid; MS m/z: (M+H)+ Calc'd for $C_{29}H_{26}N_7O_7$: 584.19; found 584.36. HPLC retention time: 1.44 minutes (column G).

EXAMPLE 297

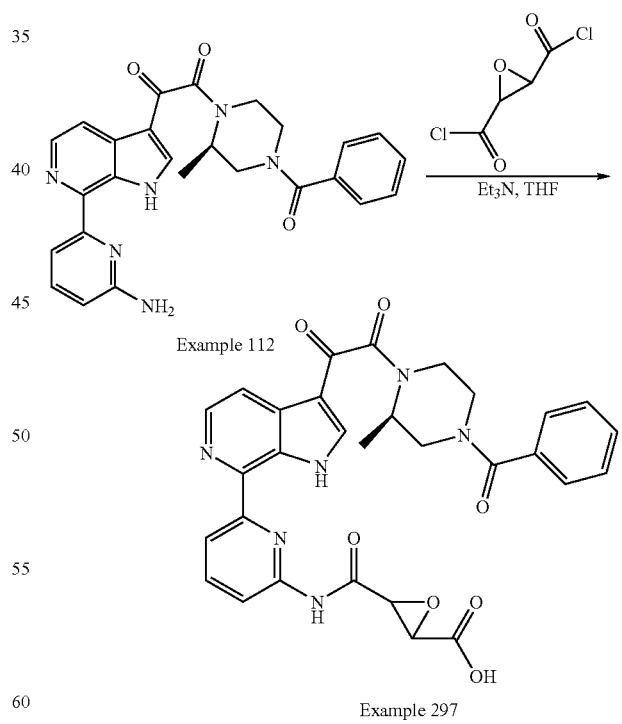

Example 112

Example 297

Example 112 (10 mg), trans-epoxysuccinyl chloride (20 mg) and $Et_3N$ (0.2 ml) were dissolved in 2 ml of anhydrous THF at room temperature and the mixture was kept stirring for 10 hours. Then the mixture was quenched with water and solvents were removed under vacuum to provide a residue, which was purified using Shimadzu automated preparative HPLC System to give Example 297 (5 mg), 3-(6-{3-[2-(4-Benzoyl-2-methyl-piperazin-1-yl)-2-oxo-acetyl]-1H-pyrrolo[2,3-c]pyridin-7-yl}-pyridin-2-ylcarbamoyl)-oxirane-2-carboxylic acid; MS m/z: (M+H)$^+$ Calc'd for $C_{30}H_{27}N_6O_7$: 583.19; found 583.34. HPLC retention time: 1.31 minutes (column G).

Precursor 4p was prepared from precursor 2u following the procedure described to prepare precursor 4m. LC/MS: (ES$^+$) m/z (M+H)$^+$=306. Taken to next step without further purification.

EXAMPLE 298

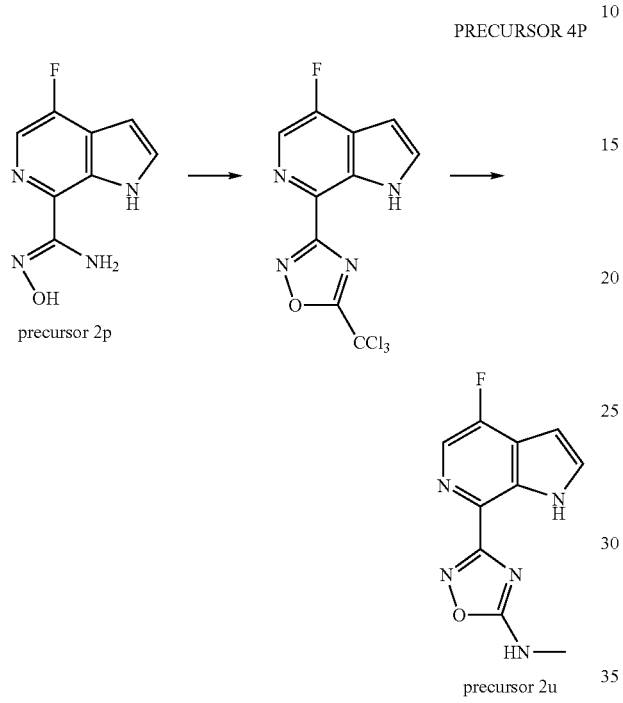

Precursor 2p (200 mg, 1.0 mmol) was dissolved in trichloroacetic anhydride (1.2 mL) and heated at 80° C. for 3 h. MeOH (10 mL) was added and the mixture was stirred at rt for 30 min. The volatiles were removed in vacuo. The residue was diluted with AcOEt (25 mL) and washed with water (2×25 mL). The organic layer was dried over $Na_2SO_4$, filtered and concentrated. The resulting crude oil was dissolved in DMF (1 mL) and treated with a 2M solution of $MeNH_2$ in MeOH (2 mL). The reaction mixture was stirred at rt for 18 h. LC/MS: (ES$^+$) m/z (M+H)$^+$=234. The volatiles were removed in vacuo and the crude (134 mg) was taken to next step without further purification.

PRECURSOR 4P

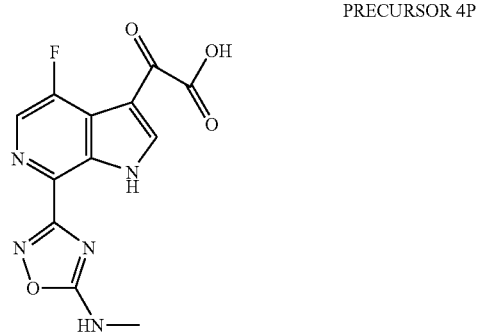

Example 298 was prepared from precursor 4p by treatment with EDC (434 mg, 2.3 mmol), HOBt (308 mg, 2.3 mmol) and benzoylpiperazine (304 mg, 1.36 mmol) in DMF (2 mL). The mixture was stirred at rt for 18 h and then concentrated in vacuo and purified using reverse phase HPCL to afford the title compound. LC/MS: (ES$^+$) m/z (M+H)$^+$=478; rt=1.25 min.

PRECURSORS 2V AND 2VV

To a diethylether (10 mL) solution of trimethylsilyldiazomethane (2 M in hexane, 5.3 mL) was added n-BuLi (2.5 M in hexane, 4.2 mL) at 0° C. After stirring for 20 min, the resulting mixture was added into a diethylether (5 ml) solution of 4-fluoro-7-bromo-6-azaindole (340 mg, 2.1 mmol). The reaction was stirred at 0° C. for 60 min and then, quenched with water (20 mL). The reaction mixture was extracted with ethyl acetate (2×40 mL). The organic layers were combined, dried over MgSO$_4$, filtered and concentrated. The residue was triturated with ethyl acetate. The solid was filtered and dried in air to give precursor 2v as a white solid (35 mg). $^1$H NMR (300 MHz, CD$_3$OD): 8.43 (bs, 1H); 8.09-8.08 (m, 1H); 7.64-7.63 (m, 1H); 6.72-6.71 (m, 1H). LC/MS: (ES$^+$) m/z (M+H)$^+$=204. Rt=0.50 min. The filtrate was concentrated and purified on silica gel column eluting with 5-10% of ethyl acetate/hexane to afford precursor 2vv as a yellow solid (422 mg). $^1$H NMR (300 MHz, CDCl$_3$): 8.09-8.08 (m, 1H); 7.47-7.45 (m, 1H); 6.69-6.67 (m, 1H); 0.45 (s, 9H). LC/MS: (ES$^+$) m/z (M+H)$^+$=276. Rt=1.39 min.

PRECURSOR 4Q

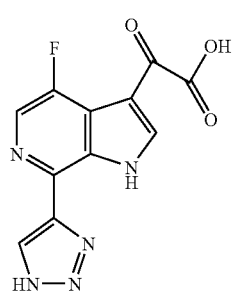

Precursor 4q was prepared following the procedure described before for compound 4m. LC/MS: (ES$^+$) m/z (M+H)$^+$=276. Rt=0.42 min.

EXAMPLE 299

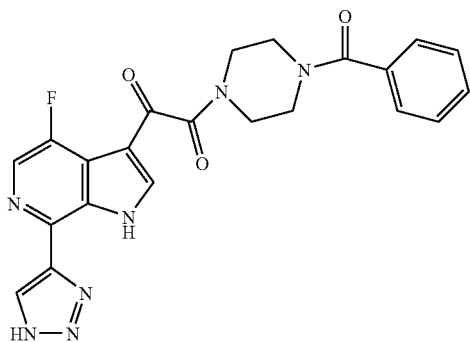

The title compound was prepared following the coupling procedure previously described before for precursor 5a $^1$H NMR (300 MHz, DMSO): 8.44 (m, 1H); 8.33-8.31 (m, 2H); 7.44 (m, 5H); 3.87-3.40 (m, 8H). LC/MS: (ES$^+$) m/z (M+H)$^+$=448. Rt=1.04 min.

N-Hydroxy-Acetamidine

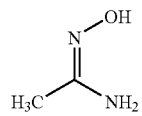

N-Hydroxy-acetamidine

Sodium ethoxide solution (32.5 mL, 21% w/v) was added over 1 h to a solution of hydrochloride (3.5 g, 0.05 mol) and phenolphthalein (5 mg) in ethanol (20 mL). After stirring for 3 hr at room temperature, acetonitrile (1.4 g) was added. The reaction was stirred for 2 h and then heated at 40° C. for 48 h. The reaction mixture was cooled to room temperature and concentrated under vacuum. The residue was kept at room temperature for 48 h, purified on silica gel column eluting with 9:1 dichloromethane:methanol to give N-Hydroxy-acetamidine (1.8 g, 73%). $^1$H NMR (300 MHz, DMSO): 8.60 (s, 1H); 5.51 (bs, 2H); 1.60 (s, 3H).

PRECURSOR 2Y

A solution of 4-fluoro-7-bromo-6-azaindole (100 mg, 0.46 mmol), N-Hydroxy-acetamidine (170 mg, 2.3 mmol), tetrakis(triphenylphosphine)palladium (200 mg, 0.17 mmol) and triethylamine (0.2 mL, 1.4 mmol) in toluene (2.5 mL) was heated at reflux under an atmosphere of carbon monoxide for 18 h. The reaction mixture was cooled to room temperature and concentrated under vacuum. The residue was diluted with ethyl acetate (10 mL) and washed with water (2×25 mL). The organic layer was concentrated and purified on preparative HPLC to give precursor 2y (5 mg, 5%). $^1$H NMR (300 MHz, CDCl$_3$): 10.22 (bs, 1H); 8.32-8.31 (m, 1H); 7.55-7.53 (m, 1H); 6.81-6.79 (m, 1H); 2.55 (s, 3H). LC/MS: (ES$^+$) m/z (M+H)$^+$=219. Rt=1.15 min.

PRECURSOR 4R

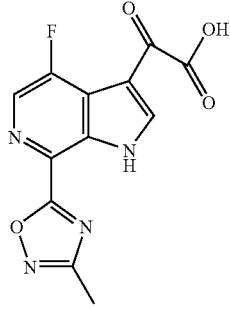

Precursor 4r was prepared following the procedure previously described for compound 4k LC/MS: (ES⁺) m/z (M+H)⁺=291. Rt=0.87 min.

EXAMPLE 300

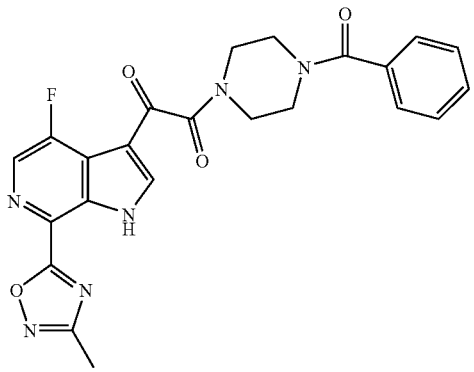

The title compound was prepared following the general coupling procedure described before for precursor 5a and using precursor 4k and benzoyl piperazine as the inputs. $^1$H NMR (300 MHz, CDCl$_3$): 10.92 (bs, 1H); 8.51-8.50 (m, 1H); 8.41-8.40 (m, 1H); 7.43 (m, 5H); 3.97-3.50 (m, 8H); 2.58 (s, 3H). LC/MS: (ES⁺) m/z (m+H)⁺=463. Rt=1.24 min.

PRECURSOR 2Z

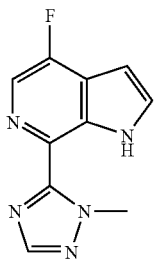

1-Methyl-1,2,4-triazole (249 mg, 3 mmol) was dissolved in anhydrous THF (3 mL) and cooled to −78° C. n-BuLi (2.5 M in hexane, 1.2 ml) was added via a syringe. After stirring for 10 min, ZnCl$_2$ (0.5 M in hexane, 6 mL) was added. The reaction mixture was stirred at −78° C. for 20 min, then warmed to room temperature. The resulting mixture was transferred via a syringe into a pressure flask which contained a mixture of 4-fluoro-7-bromo-6-azaindole (215 mg, 1.0 mmol), tetrakis(triphenylphosphine)palladium (127 mg, 0.11 mmol) and dioxane (6 mL). The reaction mixture was heated at 120° C. in the sealed flask for 15 h, and then cooled to room temperature. Ethyl acetate (100 mL) was added to quench the reaction. The resulting mixture was washed with water (2×20 mL). The organic layer was concentrated and purified on preparative HPLC. Final crystallization in methanol/water gave Precursor 2z (80 mg, 37%). $^1$H NMR (300 MHz, CDCl$_3$): 11.10 (bs, 1H); 8.18-8.17 (m, 1H); 8.02-8.01 (m, 1H); 7.50-7.48 (m, 1H); 6.74-6.72 (m, 1H); 4.52 (s, 3H). LC/MS: (ES⁺) m/z (M+H)⁺=218. Rt=1.23 min.

PRECURSOR 4S

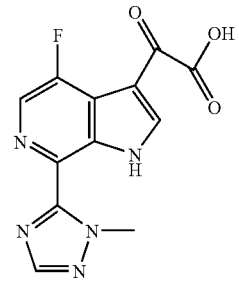

Precursor 4s was prepared following the procedure described before for precursor 4m. LC/MS: (ES⁺) m/z (M+H)⁺=293. Rt=0.92 min.

EXAMPLE 301

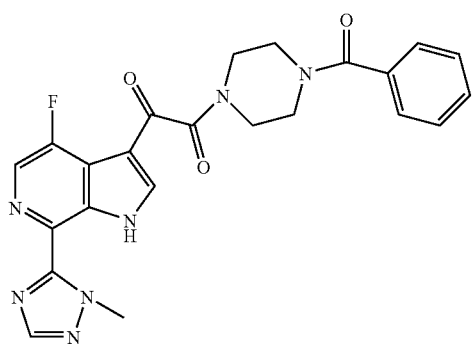

The title compound was prepared following the example coupling procedure described before for precursor 5a and using precursor 4s and (benzoyl piperazine as inputs. $^1$H NMR (300 MHz, CDCl$_3$): 11.86 (bs, 1H); 8.37-8.36 (m, 1H); 8.32-8.31 (m, 1H); 8.02-8.01 (m, 1H); 7.42 (m, 5H); 4.51 (s, 3H); 3.95-3.51 (m, 8H). LC/MS: (ES⁺) m/z (M+H)⁺=462 Rt=1.32 min.

Preparation of Precursor 4T

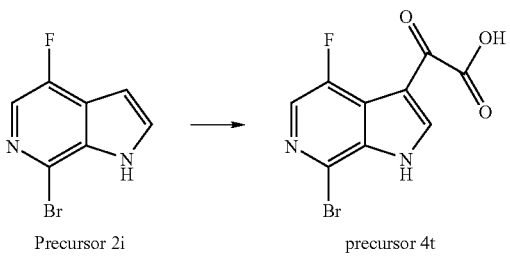

Precursor 2i      precursor 4t

To a solution of 1-ethyl-3-methyl imidazolium chloride (2.7 g, 18.6 mmol) and aluminum chloride (7.5 g, 55.8 mmol) was added precursor 2i (2.0 g, 9.3 mmol) followed by slow addition of ethyloxalylacetate (2.1 ml, 18.6 mmol) at room temperature. The reaction was then stirred at room temperature for 20 h, and quenched by slow addition of ice water (20 mL). A light brown solid precipitated out and was collected by filtration and dried in air to provide compound precursor 4t (2.2 g, 82%). LC/MS: (ES+) m/z (M+H)+=289. Rt=0.85 min.

Preparation of Precursor 5ab

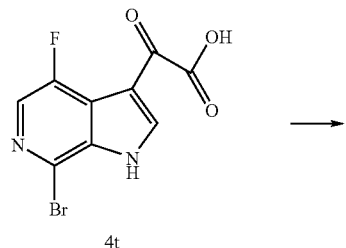

4t

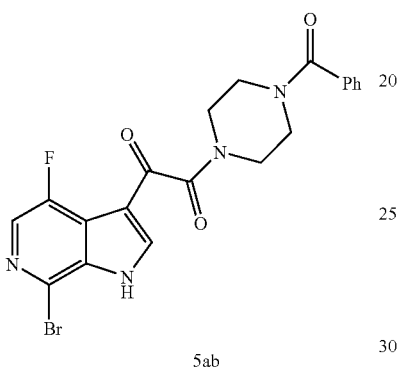

5ab

A mixture of compound precursor 4t (500 mg, 1.74 mmol), benzylpiperazine hydrochloride (395 mg, 1.74 mmol), DEBPT (520 mg, 1.74 mg) and diisopropylethylamine (0.61 ml, 3.48 mmol) in 3 ml of DMF was stirred at rt for 20 h. The reaction mixture was diluted with EtOAc (50 ml) and washed with water (50 ml). The aqueous layer was extracted with EtOAc (3×50 ml). The organic extracts were combined and dried over Mg$_2$SO$_4$, filtered and concentrated to dryness. The residue was redissolved in EtOAc and precursor 5ab crystallized out as a pale brownish solid and was collected by filtration (221 mg, 27%). $^1$H NMR (d, MeOD): 8.4 (s, 1H), 8.1 (s, 1H), 7.5 (bs, 5H), 3.82-3.53 (m, 8H); MS m/z 461 (MH); Rt=1.24 min.

GENERAL PROCEDURE FOR PREPARING EXAMPLES 302-315

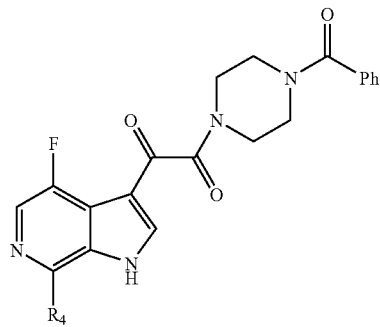

General Procedure for the Preparation of 7-N-Linked Heterocycles

A mixture of precursor 5ab for examples 302-313 or 5ac for Examples 314-315, 15-30 equivalents of the corresponding amine, preferably 30 equivalents were used, 1 equivalent of copper powder and 1 equivalent of potassium carbonate was heated at 160° C. for 4-7 hr in a sealed tube. The reaction was cooled to room temperature, diluted with EtOAc and filtered through filter paper. The solvent was removed in vacuo and the residue was diluted with methanol and purified by preparative HPLC.

EXAMPLE 303

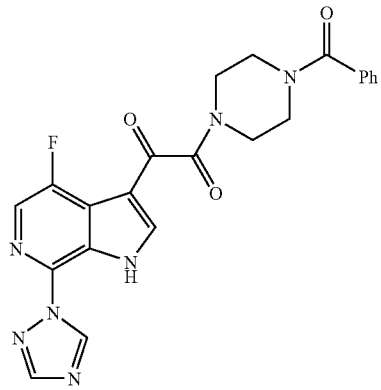

Example 303 was prepared from precursor 5ab and 1,2,4-triazole following the procedure described above. $^1$H NMR (500 MHz, CDCl$_3$): 11.15 (bs, 1H); 9.28 (s, 1H); 8.33-8.34 (m, 1H); 8.22 (s, 1H); 8.10 (s, 1H); 7.46-7.42 (m, 5H); 3.90-3.48 (m, 8H). LC/MS: (ES+) m/z (M+H)+=448. Rt=1.21 min.

EXAMPLE 304

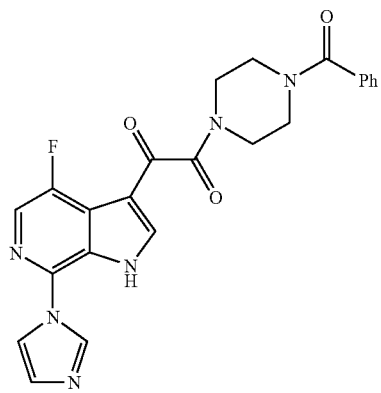

Example 304 was prepared from precursor 5ab and imidazole following the procedure described above. $^1$H NMR (500 MHz, CDCl$_3$): 13.35 (bs, 1H); 9.49 (s, 1H); 8.35-8.30 (m, 1H); 8.20 (s, 1H); 7.97 (s, 1H); 7.56-7.53 (m, 1H); 7.46-7.41 (m, 5H); 3.98-3.40 (m, 8H). LC/MS: (ES$^+$) m/z (M+H)$^+$=447. Rt=1.25 min.

EXAMPLE 305

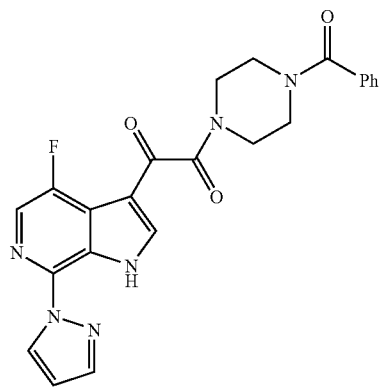

Example 305 was prepared from precursor 5ab and pyrazole following the procedure described above. $^1$H NMR (500 MHz, CDCl$_3$): 11.52 (bs, 1H); 8.65-8.64 (m, 1H); 8.27-8.26 (m, 1H); 8.05-8.04 (m, 1H); 7.81-7.80 (m, 1H); 7.50-7.35 (m, 5H); 6.54-6.53 (m, 1H); 4.01-3.47 (m, 8H). LC/MS: (ES$^+$) m/z (M+H)$^+$=447. Rt=1.25 min. Compound of example 222 was prepared from precursor 5i and morpholine following the procedure described above. $^1$H NMR (300 MHz, CD$_3$OD$_3$): 8.38 (s, 1H); 7.86-7.84 (m, 1H); 4.14-3.25 (m, 16H). LC/MS: (ES$^+$) m/z (M+H)$^+$=466. Rt=0.988 min.

EXAMPLES 306 AND 307

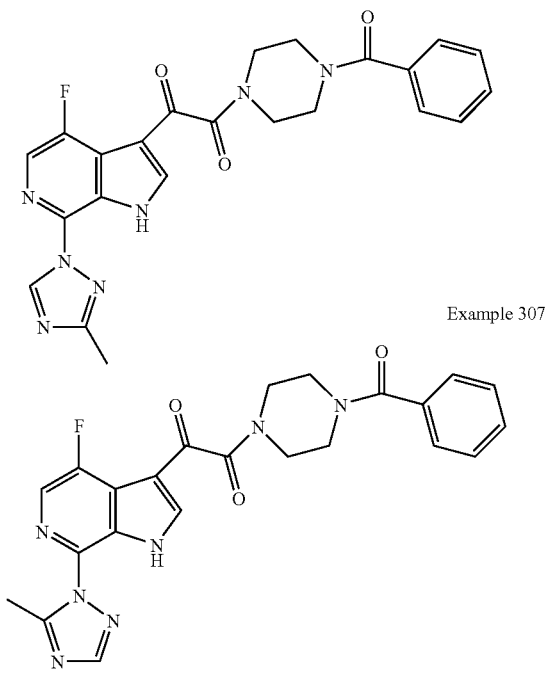

Example 306

Example 307

Examples 306 and 307 were prepared from precursor 5ab using the general procedure previously described above using 3-methyltriazole. Example 306: $^1$H NMR (500 MHz, CDCl$_3$): 9.14 (s, 1H); 8.32 (s, 1H); 8.06 (s, 1H); 7.42 (m, 5H); 3.75-3.85 (m, 4H); 3.55-3.70 (m, 4H); 2.57 (s, 3H). LC/MS: (ES$^+$) m/z (M+H)$^+$=462; rt=1.27 min. Example 307: $^1$H NMR (500 MHz, CDCl$_3$): 8.29 (s, 1H); 8.17 (s, 1H); 8.05 (s, 1H); 7.42 (m, 5H); 4.75-4.85 (m, 4H); 4.55-5.70 (m, 4H); 3.02 (s, 3H). LC/MS: (ES$^+$) m/z (M+H)$^+$=462; rt=1.27 min.

EXAMPLE 308

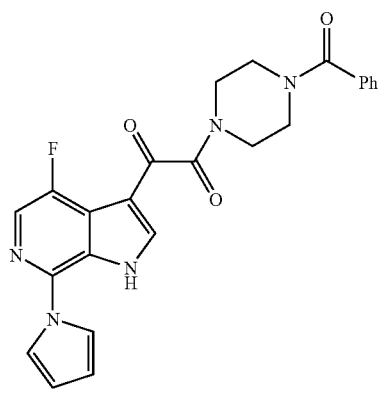

Example 308 was prepared from precursor 5ab and pyrrole following the procedure described above. $^1$H NMR (300 MHz, CD$_3$OD$_3$): 8.33-8.29 (m, 2H); 7.49-7.40 (m, 5H); 7.38-7.37 (m, 2H); 6.42-6.41 (m, 2H); 3.91-3.40 (m, 8H). LC/MS: (ES$^+$) m/z (M+H)$^+$=446. Rt=1.34 min.

EXAMPLE 309

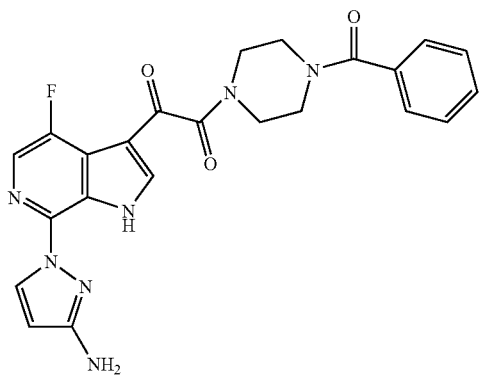

The title compound was prepared from precursor 5ab using the general procedure previously described using 3-aminopyrazole. $^1$H NMR (300 MHz, DMSO): 12.42 (bs, 1H); 8.34-8.33 (m, 1H); 8.31-8.30 (m, 1H); 8.04-8.03 (m, 1H); 7.44 (bs, 5H); 5.93-5.92 (m, 1H); 3.80-3.16 (m, 8H). LC/MS: (ES$^+$) m/z (M+H)$^+$=462. Rt=1.26 min.

EXAMPLE 310

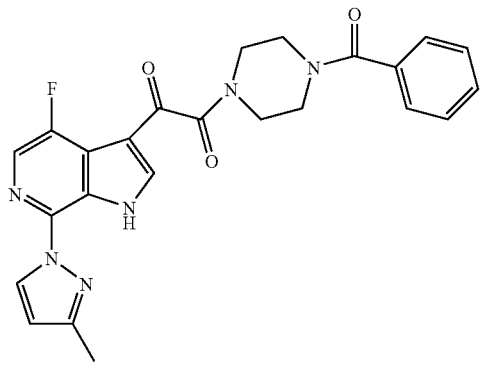

The title compound was prepared from precursor 5ab according to the general procedure previously described using 3-methylpyrazole. $^1$H NMR (500 MHz, CDCl$_3$): 11.59 (bs, 1H); 8.53-8.52 (m, 1H); 8.27-8.26 (m, 1H); 8.02-8.01 (m, 1H); 7.46-7.42 (m, 5H); 6.32-6.31 (m, 1H); 3.82-3.48 (m, 8H); 2.43 (s, 3H). LC/MS: (ES$^+$) m/z (M+H)$^+$=461. Rt=1.50 min.

EXAMPLE 311

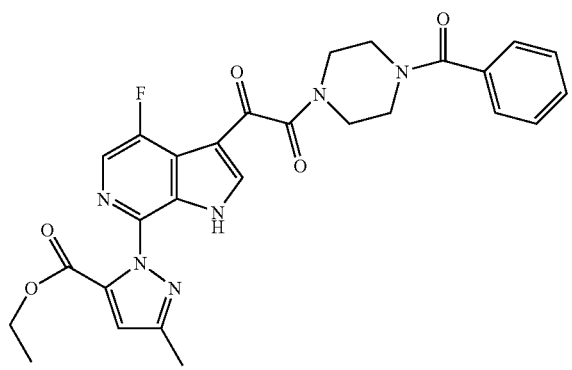

The title compound was prepared from precursor 5ab according to the general procedures previously described. $^1$H NMR (500 MHz, CDCl$_3$): 11.92 (bs, 1H); 8.28-8.27 (m, 1H); 8.08-8.07 (m, 1H); 7.47-7.42 (m, 5H); 6.73-6.72 (m, 1H); 4.45-4.38 (m, 2H); 4.0-3.49 (m, 8H); 2.84 (s, 3H); 1.44-1.37 (m, 3H). LC/MS: (ES$^+$) m/z (m+H)$^+$=533. Rt=1.67 min.

EXAMPLE 312

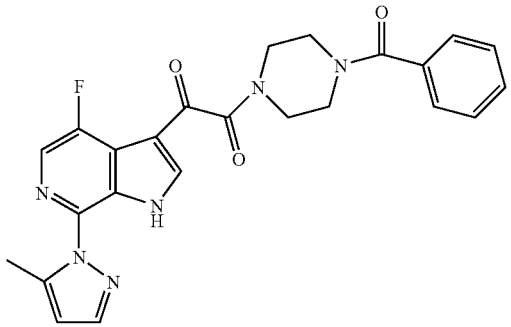

Example 312 was prepared from precursor 5ab according to the general procedure previously described using 3-methylpyrazole. $^1$H NMR (300 MHz, CDCl$_3$): 11.61 (bs, 1H); 8.23-8.22 (m, 1H); 8.06-8.05 (m, 1H); 7.67-7.66 (m, 1H); 7.42 (m, 5H); 6.25 (m, 1H); 3.89-3.48 (m, 8H); 2.82 (s, 3H). LC/MS: (ES$^+$) m/z (M+H)$^+$=461. Rt=1.41 min.

EXAMPLE 313

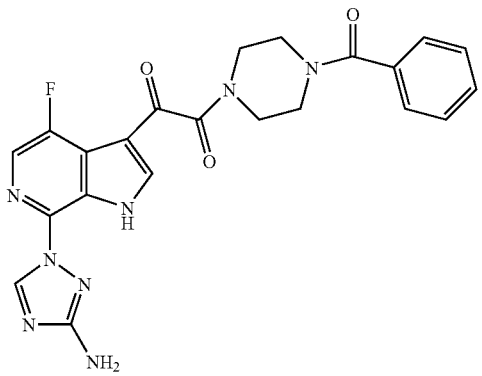

Example 313 was prepared from precursor 5ab according to the general procedure previously described using 3-amino-1,2,4-triazole. $^1$H NMR (500 MHz, CDCl$_3$): 11.12 (bs, 1H); 8.89-8.88 (m, 1H); 8.29-8.28 (m, 1H); 8.03-8.02 (m, 1H); 7.58-7.51 (m, 5H); 3.87-3.50 (m, 8H). LC/MS: (ES$^+$) m/z (M+H)$^+$=463. Rt=1.16 min.

Precursor 5ac

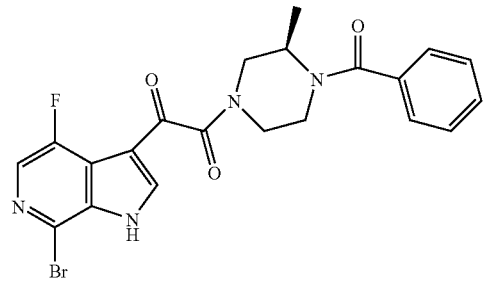

Precursor 5ac was prepared from precursor 4t following the procedure described for precursor 5ab using 1-benzoyl-3-(R)-methylpiperazine instead of benzylpiperazine. LC/MS: (ES$^+$) m/z (M+H)$^+$=474-475. Rt=1.20 min.

EXAMPLE 314

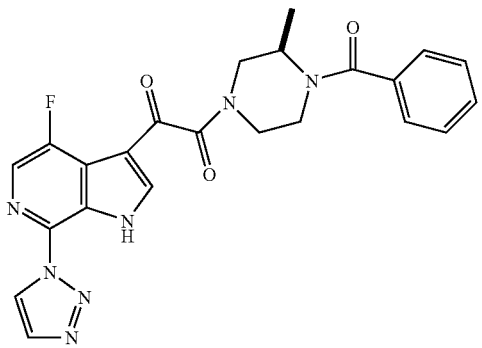

Example 314 was prepared from Precursor 5ac following the general procedure described above for 7-N-linked heterocycles. $^1$H NMR (500 MHz, CDCl$_3$): 8.75 (s, 1H); 8.36 (m, 1H); 8.08 (m, 1H); 7.45-7.38 (m, 5H); 4.75-2.947 (series of multiplets, 7H); 1.37-1.30 (m, 3H).

EXAMPLE 315

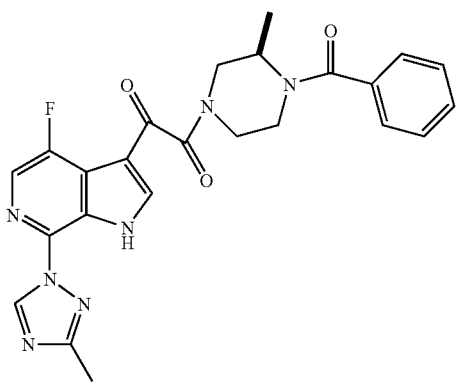

Example 315 was prepared from Precursor 5ac following the general procedure described above for 7-N-linked heterocycles. $^1$H NMR (500 MHz, CDCl$_3$): 9.15 (s, 1H); 8.32 (d, J=3.0 Hz, 1H); 8.16 (m, 1H); 7.92 (s, 1H); 7.45-7.38 (m, 5H); 4.72-2.94 (series of multiplets, 7H); 2.57 (s, 3H); 1.37-1.30 (m, 3H); LC/MS: (ES$^+$) m/z (M+H)$^+$=476. Rt=1.29 min.

Example 216

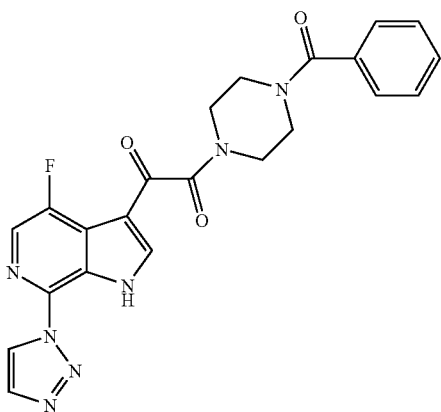

Synthetic Experimental Procedures for Best Preparation of Example 216 (Scheme 80)

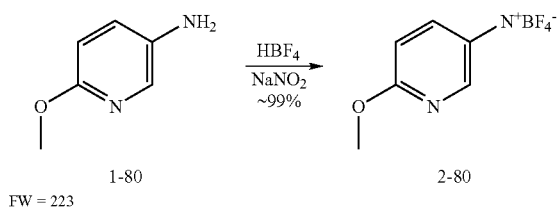

5-Amino 2 methoxypyridine (50 g, 0.4 mol) was added to a stirring mixture of absolute ethanol (280 ml) and HBF$_4$ (48% in water, 172 ml) and cooled to 0° C. Sodium nitrite (129 g) was dissolved in water (52 ml) and added portionwise over 1 h). The stirring was continued at 0° C. for 2 hr. The reaction mixture was diluted with ether (1 L). The solid product was collected by filtration and washed with 500 ml of 50:50 EtOH/ether and subsequently several times with ether until the product was slightly pinkish in color. The pale pink solid 90 g (~100% yield) was kept in a dessicator over P$_2$O$_5$.

The same procedure was followed to perform the reaction on larger scale:

(1) (200 g, 1.6 mol); HBF$_4$ (688 ml); NaNO$_2$ (116 g); EtOH (1.12 L); H$_2$O (208 ml)

The reaction was run 4 times (total 800 grams (1-80)). The product was dried over P$_2$O$_5$ for 48 hr. (only 24 hr for first batch).

A total of 1,293 g of (2-80) was obtained, (91% yield).

Ref: J. Heterocyclic Chem., 10, 779, 1973 (for above reactions, including analytical data)

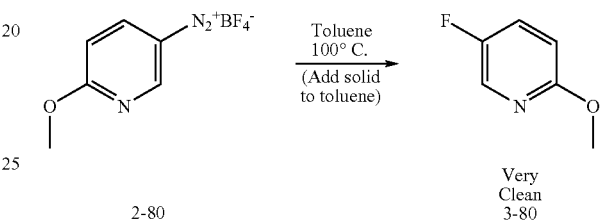

The decomposition of the diazonium salt was run in 3 batches of:

206 g, 219 g and 231 g using 1.3 L, 1.4 L and 1.6 L of anhydrous toluene respectively.

The toluene was preheated under nitrogen to 100° C. (internal temperature) in a 2 L 3-neck round bottom flask provided with a mechanical stirrer. The solid was added solid portionwise via a scoop through a powder funnel which was attached to an adapter with slight outward positive nitrogen flow. During addition, the temperature was maintained between 99-102° C. (set at 100° C.) and stirred vigorously. Total addition time was 60 min. for the smaller two batches and 70 min. for the last one. After the addition was finished, each stirring reaction was heated at 110° C. for 1 hr. The heating mantle was removed and stirring was stopped. The reactions were allowed to stand for 2 hr (ambient temp achieved). Safety Note: The reaction contains BF3 so working with the reaction hot exposes vapors which caused skin irritation with some people. No incidents were noted at ambient temperature (6 different people). The hot toluene from the reaction was poured into a 4 L Erlenmeyer (a dark brown oil and residue remained in the flask). The residue was washed with 50 ml of toluene and poured into the original toluene extracts.

Add 1.5 L of 1N NaOH to toluene layer, extract and wash with ~100 ml of sat aq. NaCl.

Combine NaCl with NaOH layer, re-extract with 150 ml of toluene, wash with 50 ml of sat NaCl.

Combine toluene layers.

Add 1 L of 1N NaOH to residue in reaction flask and swirl to dissolve as much residue as possible then add 500 ml Et2O and pour into Erlenmeyer.

Add ~500 ml more of 1 N NaOH to reaction flask and swirl ~500 ml of Et2O.

Combine dark Et2O and NaOH washings in erlenmyer flask.

Et2O/NaOH mixture was poured through powder funnel containing plug of glass wool to collect dark viscous solid. (Add ~500 ml more ether to wash) into 6 L sep funnel.

Extract. Wash ether layer with ~200 ml of $H_2O$ and then 100 ml of sat NaCl.

Combine all washings with original NaOH aq. Layer and re-extract with 500 ml of ether. Wash with 100 ml $H_2O$ and 100 ml of NaCl.

Combine ether extracts. Toluene and ether extracts were checked by LC/MS clean product.

The ether was concentrated on a rotovap and the residue was combined with the toluene extracts to make a homogeneous solution which is taken to next step as is.

The other two rxns were combined and worked up in the same way.

All aqueous layers were checked by LC/MS=no product.

Ref: J. Heterocyclic Chem., 10, 779, 1973 (for above reactions, including analytical data)

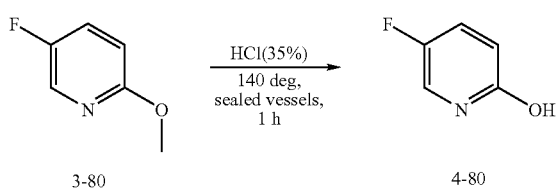

A total of 4.6 L of toluene solution containing 3-80 was placed in several sealed tubes and treated with 900 ml of 35% HCl at 145° C. for 2 hr. LC/MS showed no starting material, only 4. The toluene solution was decanted and discarded. The aqueous phase was washed with EtOAc and concentrated down to remove volatiles to afford a brown solid containing the desired fluoro-hydroxypyridine 4-80. A total of 244 g of this solid was collected and taken to next step as is (it was not completely dry).

Note: We have subsequently run this by decanting the toluene layer first prior to heating to reduce volumes. Same reaction was carried out using HBr (48% in H2O) at 100° C. for 6 h with similar result to the literature procedure 49% yield.

Ref: J. Heterocyclic Chem., 10, 779, 1973 (for above reactions, including analytical data)

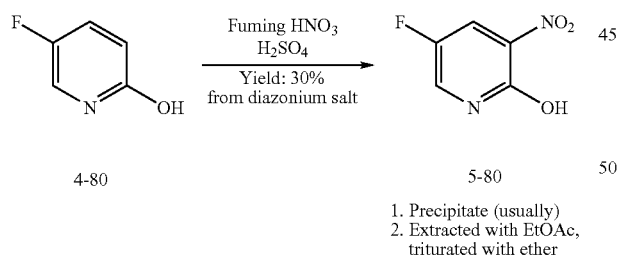

1. Precipitate (usually)
2. Extracted with EtOAc, triturated with ether

The solid from above containing (4-80) was divided in 4 batches and treated with $H_2SO_4$ and fuming $HNO_3$ as shown below. The amounts used were:

|  | batch 1 | batch 2 | batch 3 | batch 4 |
| --- | --- | --- | --- | --- |
| (1) | 25 g | 54 g | 75 g | 90 g |
| fuming $HNO_3$ | 20.8 ml | 45 ml | 62.4 ml | 75 ml |
| $H_2SO_{4,\ (for\ addition)}$ | 5.6 ml+ | 12 ml+ | 16.8 ml+ | 20 ml+ |
| (for soln) | 56 ml | 120 ml | 168 ml | 200 ml |

Compound 4-80 was dissolved in sulfuric acid (the larger amounts indicated above) at rt and then heated to 65° C. A preformed solution of fuming nitric acid and sulfuric acid (the smaller amount indicated above) was added dropwise. The temperature was kept between 65° C. and 80° C. (rxn is exothermic and although the bath is at 65° C., temperature goes higher, usually 75, sometimes 80° C.). After the addition was complete, the reaction mixture was heated at 65° C. for an additional hr. The reaction mixture was then cooled to rt and poured in a flask containing ice) (20 g of ice/gr compound, evolution of gas occurred). A solid precipitated out and it was collected by filtration ([1]HNM" showed 4-80 and something else (discarded)).

The aqueous layer was extracted with AcOEt several times (3-5) and concentrated on a rotary evaporator under vacuum to afford a solid that was triturated with ether to afford 5-80 as a bright yellow solid. A total of 117 g of desired product was collected in the first crop (27% yield from diazonium salt). A portion did not crystallize: this oil was triturated with MeOH and $Et_2O$ to afford 3.6 g of 5-80; another precipitation from the mother liquid afforded an additional 6.23 g of the desired product 5-80

Total: 117.0+3.6+6.23=126.83. 30.4%). Yield for 3 steps (decomposition of diazonium salt; deprotection and nitration).

Analytical data from Notebook: 53877-115: $^1$H NMR (δ, MeOD): 8.56-8.27 (dd, J=7.5, 3.3 Hz, 1H), 8.01 (d, J=3.3 Hz, 1H); LC/MS (M+1)$^+$=158.9; rt=0.15 min.

Note: A portion of the aqueous acidic solution was taken and neutralized with $Na_2CO_3$ until effervescence stopped and then it was extracted with AcOEt=⟹A different product was obtained. No desired product in these extracts.

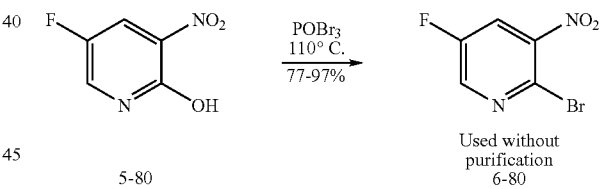

Used without purification
6-80

A total of 117 g of 5-80 was divided in 4 batches of 30 g×3 and 27 g×1 and treated with $POBr_3$ (3 equiv.; 163 g×3 and 155 g×1) and a catalytic amount of DMF (15 ml) at rt (DMF was added carefully ⟹gas evolution). After 5 min. at room temperature, the solutions were heated at 110° C. for 3 hr. LC/MS showed starting material had been consumed. The reaction mixtures were allowed to cool to rt. The reaction flasks were placed in an ice bath; and then ice was added very slowly and carefully portionwise into the flask, gas evolution was due to HBr formation; the liquid and black solid that formed was poured into a beaker with ice. EtOAc was added and the mixture was then extracted several times with EtOAc. The organic layer was washed with saturated aq. $NaHCO_3$; $H_2O$ and brine; dried over $Na_2SO_4$ and filtered. The product was dried in the pump overnight to provide 123 g of 6-80 as a brown solid (77% yield).

Note: Reaction is completed within 1 h.
$^1$H NMR (δ, CDCl$_3$): 8.52 (m, 1H), 7.93 (m, 1H).

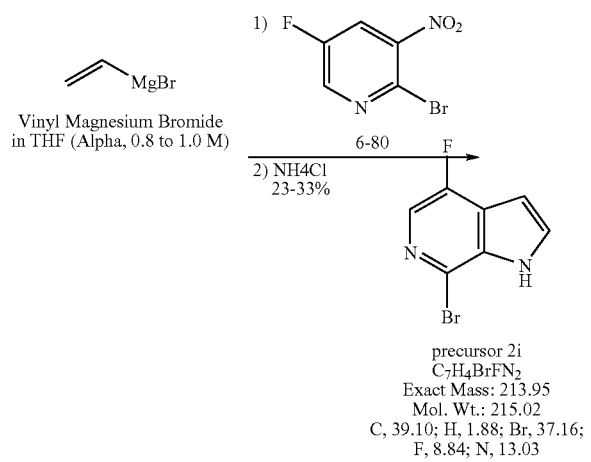

precursor 2i
C$_7$H$_4$BrFN$_2$
Exact Mass: 213.95
Mol. Wt.: 215.02
C, 39.10; H, 1.88; Br, 37.16; F, 8.84; N, 13.03

800 ml of vinyl magnesium bromide (1M in THF, Aldrich) was cooled below −60° C. with vigorous stirring under N$_2$. 2-bromo-5-fluoro-3-nitro pyridine (43.3 g, 0.196 mol) in 200 ml THF was added dropwise via addition funnel at such a rate that the temp was kept below −60° C. This took ~1.25 hr. The reaction mixture was warmed to −40 to −50° C. and stirred for 1 hr more. Then 1L of saturated aqueous NH$_4$Cl was added slowly and cautiously. At first, foaming occurred and considerable solid was present, but this essentially dissolved as the addition was completed and the material warmed to rt. The layers were separated and the aqueous layer extracted 3 times with ethyl acetate. The organic extracts were washed with brine, dried over Na$_2$SO$_4$, filtered and concentrated to afford ~50 g of a black gummy solid. HPLC indicated 57-58% product. To this was added CH$_2$Cl$_2$ and the solid was collected by filtration and washed with CH$_2$Cl$_2$ to afford 12.5 g of product as a brown solid. The reaction was repeated on exactly the same scale and worked up in the same manner. From CH$_2$Cl$_2$ trituration there was obtained 12.4 g of Precursor 2i (HPLC ~97% pure). The crude was recovered and allowed to stand in dichloromethane. Upon standing 3.6 g of additional product separated and was recovered by filtration.

Total yield=29.5 g (35%).

$^1$H NMR (δ, CDCl$_3$): 8.69 (bs, 1H), 7.92 (d, J=1.8 Hz, 1H), 7.41 (m, 1H), 6.77 (m, 1H); LC/MS (M+1)$^+$=216-217.9; rt=1.43 min.

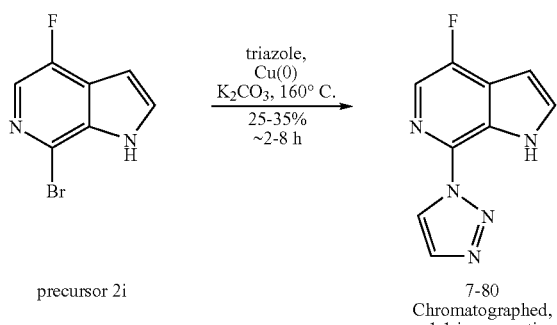

Reaction was carried in a 250 ml flask (foaming occurred upon heating and the big size flask is more convenient). A mixture of precursor 2i (3 g, 13.95 mmol), 1,2,3-triazole (15 g, 217.6 mmol, 15 eq), K$_2$CO$_3$ (1.9 g, 13.95 mmol, 1 eq) and Cu(0) (0.9 g, 13.9 mmol, 1 eq) was heated at 160° C. for 7 hr (from rt to 160° C. total 7 hr) under N$_2$ (depending on the Cu(0) lot, reaction time may vary from 2 hr to 7 hr). The resulting mixture was diluted with MeOH, filtered through filter paper (to remove the copper). Washed with MeOH (20 ml) and water (30 ml).

The filtrate was concentrated (remove solvent in rotovap) and diluted with ethylacetate. The aqueous layer was extracted with ethylacetate. The combined organic layer was dried over sodium sulfate, filtered and concentrated. The residue was dissolved in MeOH (20 ml), 7-80 (750 mg) crystallized from the methanol as a white solid and was collected by filtration. (Slow gradient volume, silica gel hex/AcOEt (0→18%) of the mother liquids usually affords 5-10% more of 7-80.

$^1$H NMR (δ, CDCl$_3$): 10.47 (bs, 1H), 8.76 (s, 1H), 7.94 (s, 1H), 7.89 (s, 1H), 7.53 (m, 1H), 6.78 (m, 1H); LCMS (M+1)$^+$=204; rt=1.29 min.

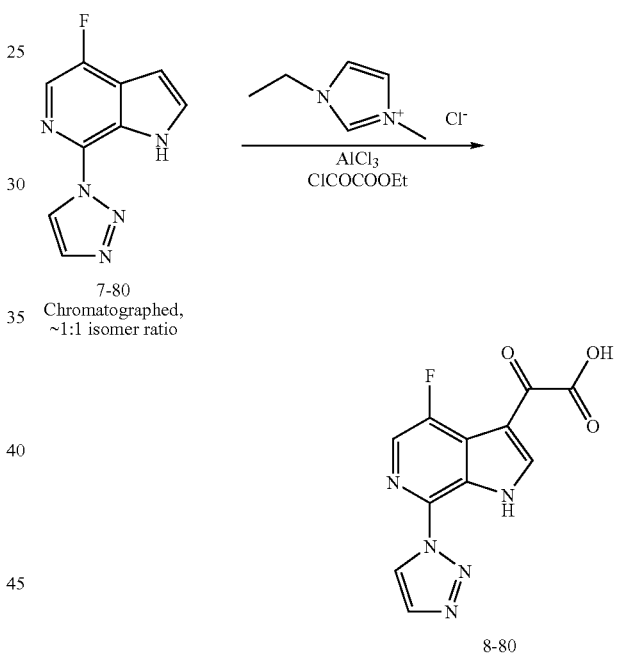

Ethyl methylimidazolium chloride (4.3 g, 29.6 mmol, 3 eq) was placed in a 250 ml flask. AlCl$_3$ (11-8 g, 88.6 mmol, 9 eq) was added into the flask in one portion. A liquid suspension was formed (some of AlCl$_3$ remained as solid). After stirring for 5-10 min. compound (I) (2.0 g, 9.85 mmol) was added in one portion followed by slow addition (via a syringe) of ethyl chlorooxalacetate (3.3 ml, 29.6 mmol, 3 eq). The reaction was stirred at room temperature for 20 hr. LCMS indicated compound 8-80:compound 7-80=6:2. (Compound I has strong UV absorption) The reaction was quenched by carefully adding ice water (~75 ml) at 0° C. A yellow solid precipitated at this point. The resulting suspension was filtered and the solid was washed with water. MeOH and ethyl acetate (to remove unreacted SM) and the solid was dried in air. (LCMS purity 70%~80%) 2 g of solid containing 8-80 was obtained and taken to the next step without further purification. LCMS (M+1)$^+$=276; rt=0.97 min.

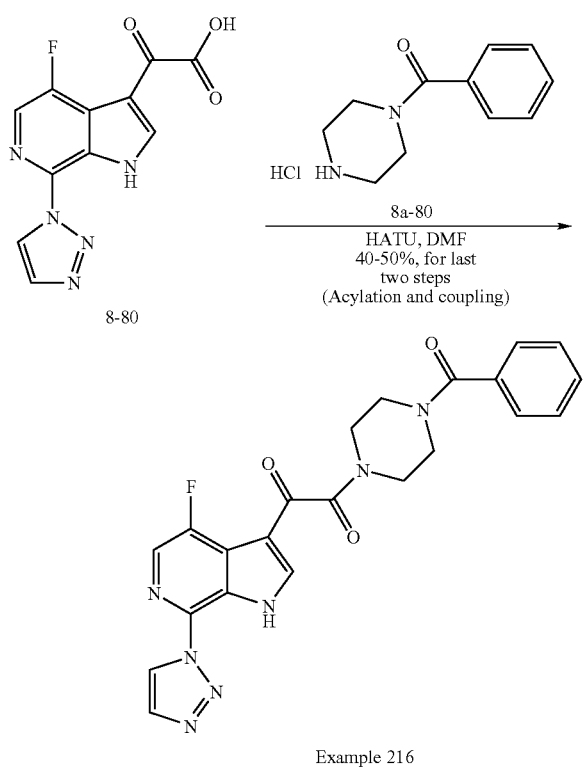

Example 216

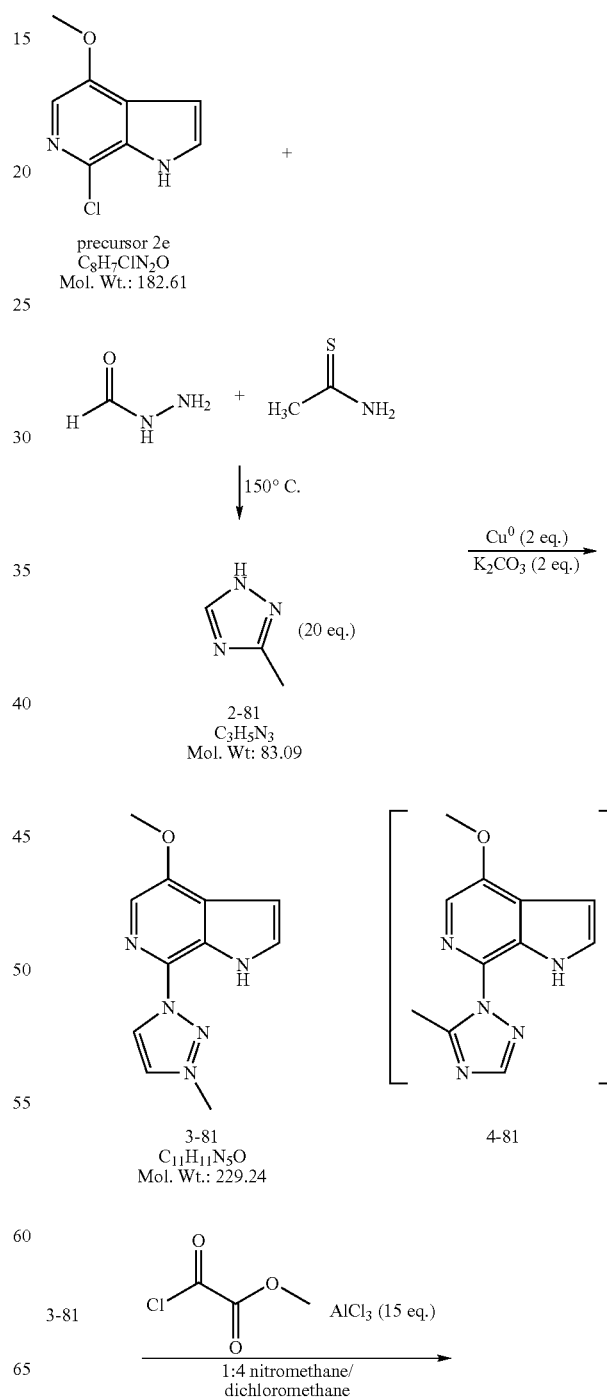

Scheme 81 precursor 2e
C₈H₇ClN₂O
Mol. Wt.: 182.61

2-81
C₃H₅N₃
Mol. Wt: 83.09

3-81
C₁₁H₁₁N₅O
Mol. Wt.: 229.24

4-81

A mixture of compound 8-80 (4.9 g, 17.8 mmol) & N-benzoylpiperazine hydrochloride 8a-80 (HCl salt; 6.0 g, 26.7 mmol, 1.5 eq) in DMF (30 ml) was stirred at RT overnight (16 hr). A slurry was formed. An additional 20 ml of DMF was added into the slurry. Then HATU (12.2 g, 26.7 mmol, 1.5 eq) was added followed by DMAP (4.3 g, 35.6 mmol, 2 eq). The reaction mixture was stirred for 30 min. LCMS indicated the starting material 8-80 was completely converted to product (EXAMPLE 216). The resulting mixture was filtered and the solid washed with water. The filtrate was concentrated in vacuo. Water was added to the residue and the solid was collected by filtration. The solids were combined and washed with water, MeOH and EtOAc. Then the solid was dried in air. LCMS & HPLC showed BMS-585248, >99% pure. The solid product was further purified by precipitation and crystallization in 5~10% CH₃OH/CHCl₃.

PURIFICATION Of EXAMPLE 216

Crude compound of Example 216 obtained as above (15.3 g) was dissolved in 10% MeOH/CHCl₃ (600 ml). A light brown suspension was formed, filtered through filter paper and washed with MeOH a twice. The brownish solid was discarded (~1.2 g). Example 216 was crystallized in the filtrate, the solid was collected by filtration and the white solid was dried in air. The filtrate was used to repeat the crystallization several times. The solid obtained from each filtration was analyzed by HPLC. All the pure fractions were combined. The not so pure fractions were resubjected to crystallization with MeOH & CHCl₃. A total of 12.7 g of Example 216 was obtained from recrystallization and precipitation. The mother liquid was concentrated and purified on silica gel column (EtOAc, then CHCl₃/MeOH (0-2%)) to provide 506 mg of product) as a white solid.

¹H NMR (d, DMSO) 13.1 (bs, 1H), 9.0 (s, 1H), 8.4 (s, 1H), 8.3 (s, 1H), 8.2 (s, 1H), 7.4 (bs, 5H), 3.7 (bs, 4H), 3.5 (bs, 4H); MS m/z 448 (MH). Anal: Calc for C₂₂H₁₈FN₇O₃; C, 59.05; H, 4.05; N, 21.91; F 4.24. Found; C, 57.28; H, 4.14; N, 21.22; F 4.07%.

Scheme 81 is a preferred method for making compounds of Formula I and Ia where R² is methoxy. This is specifically exemplified for the preparation of compound Example 316 and 317.

-continued

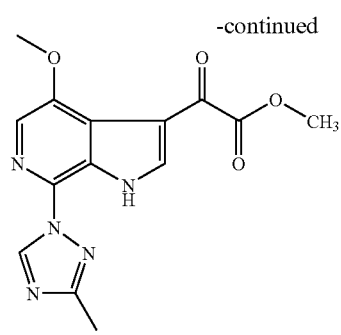

5-81
C₁₄H₁₃N₅O₄
Mol. Wt.: 315.28

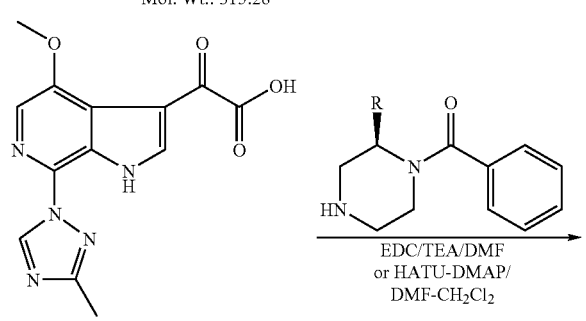

6-81
C₁₃H₁₁N₅O₄
Mol. Wt.: 301.26

Example 316,
R = H
C₂₄H₂₃N₇O₄
Mol. Wt.: 473.48
Example 317,
R = Me
C₂₅H₂₅N₇O₄
Mol. Wt.: 487.51

Preparation of 3-methyl-1,2,4-triazole (2-81)

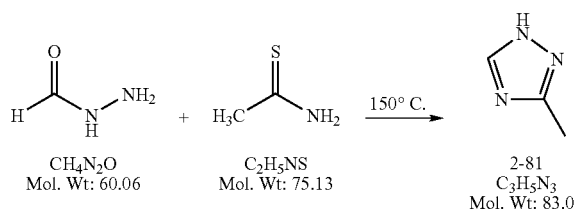

Procedure: A solid mixture of formic hydrazide (68 g, 1.13 mol) and thioacetamide (85 g, 1.13 mol) in a 500 mL-RBF was heated with stirring at 150° C. (oil bath temp.) for 1.5 hrs with a gentle stream of nitrogen, removing H₂S and water (about 18 mL of liquid collected) formed during the reaction. The reaction mixture was distilled under reduced pressure, collecting 60.3 g (0.726 mol, Y. 63.3%) of the title compound at 102° C./0.35-1 mmHg as white solid after removing a liquid forerun.: ¹H NMR (CDCl₃) δ ppm 2.51 (3H, s, 3-Me), 8.03 (1H, s, 5-H), 9.5 (1H, br, NH); TLC Rf (10% MeOH/CH₂Cl₂)=0.3 (phosphomolybdate-charring, white spot).

Reference: Vanek, T.; Velkova, V.; Gut, Jiri *Coll. Czech. Chem. Comm.* 1985, 49, 2492.

Preparation of 3-81

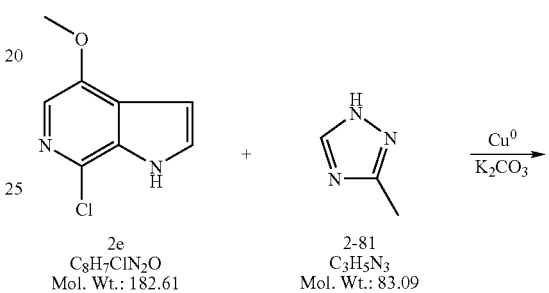

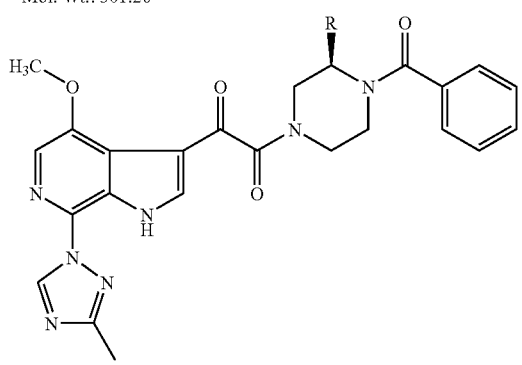

3-81
C₁₁H₁₁N₅O
Mol. Wt.: 229.24

4-81
C₁₁H₁₁N₅O
Mol. Wt.: 229.24

Procedure: A 500 mL round bottom flask was loaded with 4-methoxy-7-chloro-6-azaindole precursor 2e (9.1 g, 50 mmol; dried in vacuo), potassium carbonate (13.8 g, 100 mmol, 2 eq.), copper powder (6.35 g, 100 mmol, 2 eq.), and 3-methyl-1,2,4-triazole (83 g, 1.0 mol, 20 eq.). The solid mixture was heated to melt at 170-175° C. (external oil bath temperature) under gentle stream of anhydrous nitrogen for 12 h, by which time HPLC analysis indicates the amount of the peak for the starting material becomes 5-30% and the desired product peak becomes about 45% with isomeric by-product peak becomes 15%. As the reaction mixture cools, MeOH (150 mL) was added slowly to the stirred warm mixture. Upon cooling, the insoluble material (copper powder) was filtered through a Celite pad, and rinsed with methanol. The filtrate was concentrated in vacuo to a thick paste which was diluted with water (1 L) and extracted with EtOAc (3×150 mL). The EtOAc extracts were dried (MgSO₄), filtered and concentrated to obtain about 8 g of crude residue which was crystallized by dissolving in hot CH₃CN (50 mL), followed by diluting with water (100 mL) and cooling at 0° C. to collect 1.45 g (12.7%) of the title compound as white solid. The filtrate was purified by C-18 reverse phase silica gel (YMC ODS-A 75 μm) eluted with 15-30% CH$_3$CN/H$_2$O. Appropriate fractions were combined and the aqueous solution after removing CH$_3$CN by rotary evaporator was lyophilized to give additional 1.15 g of the title compound 3-81. The crude aqueous layer was further extracted with EtOAc several times. The ethyl acetate extracts were dried (MgSO4), filtered, concentrated, and crystallized from MeOH to give additional 200 mg of the title compound 3-81. The total yield: 2.8 g (12.2 mmol, Y. 24.5%); MS m/z 230 (MH), HRMS (ESI) m/z calcd for C$_{11}$H$_{12}$N$_5$O (M+H), 230.1042, found 230.1038 (Δ-1.7 ppm); $^1$H NMR (CDCl$_3$) δ ppm 2.54 (3H, s, CH$_3$), 4.05 (3H, s, OCH$_3$), 6.73 (1H, s, H-3), 7.40 (1H, s, H-2), 7.56 (1H, s, H-5), 9.15 (1H, s, triazole-H-5); $^{13}$C NMR (CDCl$_3$, 125.7 MHz) δ ppm 14.2 (triazole-Me), 56.3 (OMe), 100.5 (C-3), 116.9 (C-5), 123.5, 127.2, 127.5 (C-2), 129.5 (C-7), 141.2 (C-5'), 149.5 (C-4), 161.8 (C-3'); Anal. Calcd for C$_{11}$H$_{11}$N$_5$O: C, 57.63; H, 4.83; N, 30.55. found C, 57.37; H, 4.64; N, 30.68.

The structure was confirmed by a single X-ray crystallographic analysis using crystals obtained from C-18 column fractions. A portion of C-18 column fractions containing a mixture of the desired 3-methyl-1,2,4-triazolyl analog 3-81 and isomeric 5-methyl-1,2,4-triazolyl analog 4-81 was further purified by C-18 reverse phase column eluting with 8-10% CH$_3$CN/H$_2$O. Appropriate fractions were extracted with CH$_2$Cl$_2$, and slow evaporation of the solvent gave crystalline material of the isomeric 7-(5-methyl-1,2,4-triazolyl)-4-methoxy-6-azaindole (4-81): MS m/z 230 (MH), $^1$H NMR (CDCl$_3$) δ ppm 3.05 (3H, s, CH$_3$), 4.07 (3H, s, OCH$_3$), 6.74 (1H, q, J=2.4, H-2), 7.37 (1H, t, J=2.4, H-3), 7.65 (1H, s, H-5), 8.07 (1H, s, triazole-H-3). The structure was confirmed by a single X-ray crystallographic analysis.

Preparation of 5-81

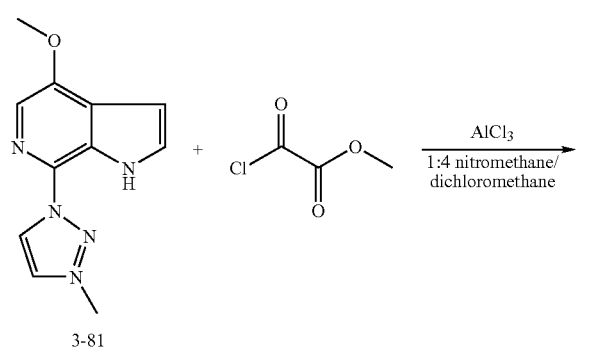

3-81

-continued

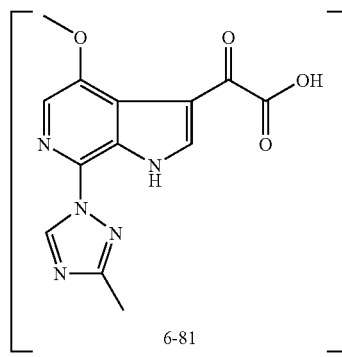

6-81

Procedure: AlCl$_3$ (40 g, 0.3 mol, 15 eq.) was dissolved in a solution of CH$_2$Cl$_2$ (100 mL) and nitromethane (20 mL) under dry nitrogen. To this solution was added compound 3-81 (4.58 g, 0.02 mol) under stirring and under N$_2$, followed by methyl chlorooxoacetate (9.8 g, 0.08 mol, 4 eq.). The mixture was stirred under N$_2$ at room temperature for 1.5 h. The mixture was added drop-wise to a cold and stirred solution of 20% aqueous ammonium acetate solution (750 mL). The mixture was stirred for 20 min and the resultant precipitate was filtered, washed thoroughly with water and dried in vacuo to obtain 4.7 g (0.015 mol, Y. 75%) of the title compound 5-81 as white solid: MS m/z 316 (MH); HRMS (ESI) m/z calcd for C$_{14}$H$_{14}$N$_5$O$_4$ (M+H), 316.1046; found 316.1041 (Δ-1.6 ppm); $^1$H NMR (CDCl$_3$, 500 MHz) δ ppm 2.58 (3H, s, CH$_3$), 3.96 (3H, s, OCH$_3$), 4.05 (3H, s, OCH$_3$), 7.76 (1H, s, H-5), 8.34 (1H, d, J=3 Hz, H-2), 9.15 (1H, s, triazole-H-5), 11.0 (1H, brs, NH). More title compound 5-81 and hydrolyzed acid 6-81 can be obtained from the filtrate by acid-base extraction with EtOAc.

Preparation of 6-81

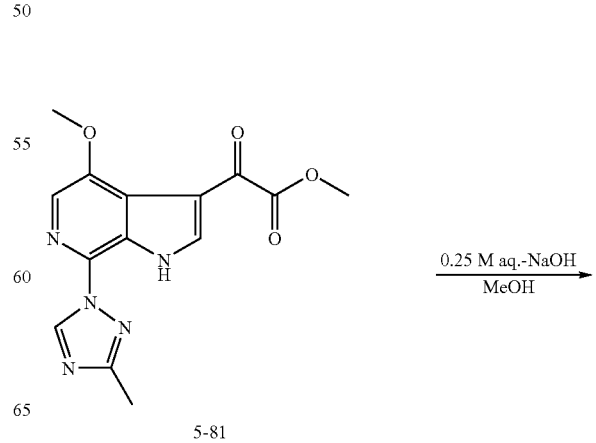

5-81

-continued

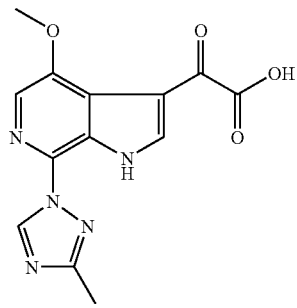

6-81

Procedure: To a suspension of the methyl ester 5-81 (2.2 g, 7.0 mmol) in MeOH (50 mL) was added 0.25M NaOH solution in water (56 mL, 14 mmol, 2 eq.) at room temperature and the mixture stirred for 15 min by which time HPLC indicated the hydrolysis was complete. The mixture was concentrated in vacuo quickly to remove MeOH, and to the residual solution was added water (100 mL) and 1N HCl (14 mL) with stirring to neutralize the mixture. The resultant fine precipitate was filtered, washed with water and dried in vacuo to obtain 1.98 g (6.58 mmol, Y. 94%) of the title compound 6-81 as off-white solid: MS m/z 302 (MH); $^1$H NMR (DMSO-d$_6$, 500 MHz) δ ppm 2.50 (3H, s, overlapped with DMSO peaks), 3.98 (3H, s, CH$_3$O), 7.87 (1H, s, H-5), 8.29 (1H, d, J=3.5 Hz, H-2), 9.25 (1H, s, triazole-H-5), 12.37 (1H, s, NH).

Alternative procedure: To a suspension of the methyl ester 5-81 (10.7 g, 34 mmol) in MeOH (150 mL) was added 0.25M NaOH solution in water (272 mL, 68 mmol, 2 eq.) at room temperature and the mixture stirred for 20 min by which time HPLC indicated the hydrolysis was complete. The mixture was concentrated in vacuo quickly to remove MeOH, and the residual solution was extracted with EtOAc to remove any neutral impurities. To the aqueous phase was added 1N HCl (68 mL, 68 mmol) to neutralize the product. The resultant mixture was frozen and lyophilized to obtain 14.1 g (33.7 mmol, Y. 99.2%) of the title compound 6-81, containing 2 mole equivalents of NaCl as off-white solid. This material was used in the subsequent reaction without further purification. The sodium salt of the title compound 6-81 was obtained by C-18 reverse phase column chromatography after sodium bicarbonate treatment: HPLC >97% (AP, uv at 254 nm); HRMS (Na salt, ESI$^-$) m/z calcd for C$_{13}$H$_{10}$N$_5$O$_4$ (M–H), 300.0733; found 300.0724 (Δ-3 ppm); $^1$H NMR (Na salt, DMSO-d$_6$, 500 MHz) δ ppm 2.37 (3H, s, Me), 3.83 (3H, s, CH$_3$O), 7.56 (1H, s, H-5), 8.03 (1H, s, H-2), 9.32 (1H, s, triazole-H-5); $^{13}$C NMR (Na salt, DMSO-d$_6$, 125.7 MHz) δ ppm 13.8 (triazole-Me), 57.2 (OMe), 114.8 (C-3), 120.0 (C-5), 125.1, 143.5 (C-5'), 149.8 (C-4), 160.0 (C-3'), 171.7, 191.3.

PREPARATION OF EXAMPLE 316

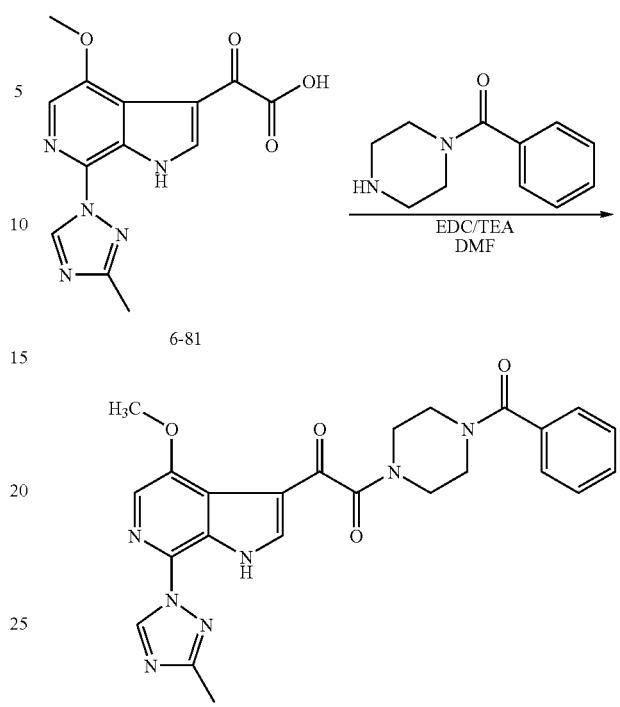

Example 316

Procedure: To a solution of the acid 6-81 (3.01 g, 10 mmol) and benzoylpiperazine hydrochloride (3.39 g, 15 mmol) in DMF (50 mL) was added triethylamine (10.1 g, 100 mmol, 10 eq.), followed by 1-[3-(dimethylamino)propyl]-3-ethylcarbodiimide hydrochloride (EDC; 5.75 g, 30 mmol) under N$_2$ and the mixture stirred at room temperature for 22 h after sonication and at 40° C. for 2 h. The mixture was concentrated in vacuo to remove DMF and TEA, and to the residual solution was added water (200 mL) under stirring and sonication. The precipitates formed were collected, washed with water and dried in vacuo to obtain 2.8 g (5.9 mmol, Y. 59%) of the title compound Example 316 as off-white solid. The filtrate was extracted with CH$_2$Cl$_2$ (x2). The CH$_2$Cl$_2$ extracts were dried (Na$_2$SO$_4$), filtered and concentrated to gum which was triturated with Et$_2$O to obtain a solid. This solid was suspended and triturated with MeOH to obtain 400 mg of the title compound Example 316 as off-white solid. Total yield: 3.2 g (6.8 mmol, Y. 68%): MS m/z 474 (MH); HRMS (ESI) m/z calcd for C$_{24}$H$_{24}$N$_7$O$_4$ (M+H) 474.1890, found 474.1884 (Δ-1.2 ppm); $^1$H NMR (DMSO-d6) δ ppm 2.50 (3H, s, overlapped with DMSO peaks), 3.43 (4H, br, CH$_2$N), 3.68 (4H, br, CH$_2$N), 3.99 (3H, s, CH$_3$O), 7.46 (5H, br. s, Ar—Hs), 7.88 (1H, s, indole-H-5), 8.25 (1H, s, indole-H-2), 9.25 (1H, s, triazole-H-5), 12.40 (1H, s, NH); $^{13}$C-NMR (DMSO-d6) δ ppm 13.78, 40.58, 45.11, 56.78, 114.11, 120.95, 122.71, 123.60, 126.98, 128.34, 129.6, 135.43, 138.52, 142.10, 149.15, 161.29, 166.17, 169.22, 185.42; UV (MeOH) λmax 233.6 nm (ε 3.43×10$^4$), 314.9 nm (ε 1.73×10$^4$); Anal: Calc for C$_{24}$H$_{24}$N$_7$O$_4$.1/5H$_2$O; C, 60.42; H, 4.94; N, 20.55. Found; C, 60.42; H, 5.03; N, 20.65; KF (H$_2$O) 0.75%.

This reaction can also be performed by use of HATU and DMAP to provide more consistent yield of the title compound: To a suspension of the acid 6-81 (15.6 mmol) and HATU [O-(7-azabenzotriazol-1-yl)-N,N,N',N'-tetramethyluronium hexafluorophosphonate] (8.90 g, 23.4 mmol; 1.5 eq.) in DMF (60 mL) and CH$_2$Cl$_2$ (60 mL) was added a mixture of DMAP (5.72 g, 46.8 mmol, 3 eq.) and benzoylpiperazine hydrochloride (5.30 g, 23.4 mmol; 1.5 eq.) in DMF (60 mL) at room temperature and the mixture was stirred under nitrogen atmosphere for 4 hrs. The mixture was concentrated in vacuo to remove CH$_2$Cl$_2$ and most of DMF, and to the residual solution was added water under stirring and sonication. The precipitates formed were collected, washed with water and dried in vacuo to obtain 5.38 g (11.4 mmol, Y. 72.8%) of the title compound Example 316 as off-white solid: HPLC >95% (AP, uv at 254 nm).

PREPARATION OF EXAMPLE 317

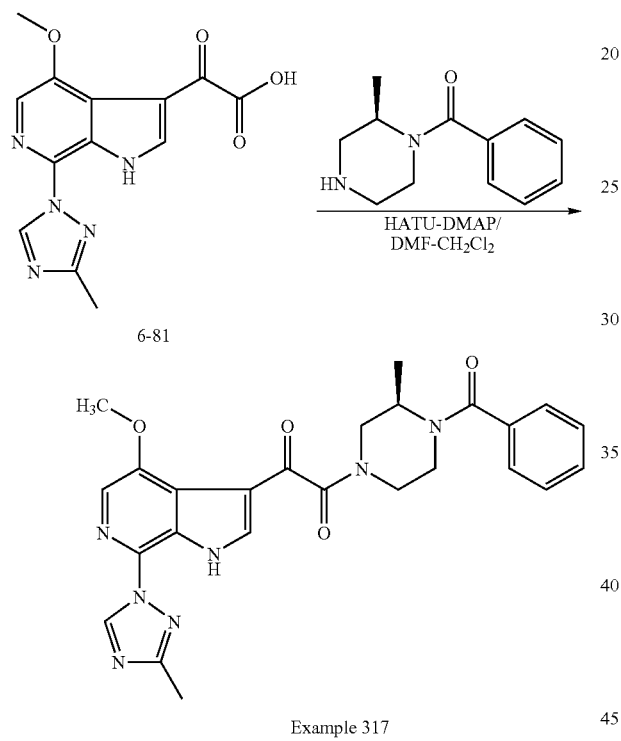

6-81

Example 317

Procedure: To a solution of the acid 6-81, containing 2 mole equivalent of NaCl (4.1 g, 9.8 mmol) in CH$_2$Cl$_2$ (30 mL) and DMF (30 mL) was added at −10° C. under anhydrous nitrogen HATU [O-(7-azabenzotriazol-1yl)-N,N,N',N'-tetramethyluronium hexafluorophosphate] (5.59 g, 14.7 mmol; 1.5 eq.), and stirred at −10° C. for 30 min. To this mixture was added a solution of 2-(R)-methyl-N-benzoylpiperazine trifluoroacetate (4.7 g, 14.7 mmol; 1.5 eq.) and dimethylaminopyridine (3.5 g, 29 mmol; 3 eq.) in DMF (30 mL) and CH$_2$Cl$_2$ (30 mL) and the mixture stirred at room temperature overnight, by which time HPLC analysis indicated reaction was essentially complete. The mixture was concentrated in vacuo to remove valatiles and DMF, and to the residue was added water (~150 mL) under stirring and sonication. The precipitates formed were collected, washed with water and dried in vacuo to obtain 4.3 g of the title compound Example 317 as off-white solid. This was dissolved in 20% MeOH in CH$_2$Cl$_2$ (about 250 mL), removing any insoluble material, and the filtrate was concentrated in vacuo to remove more volatile CH$_2$Cl$_2$. The resultant precipitate was collected, washed with MeOH and then with Et$_2$O to obtain 3.5 g (7.18 mmol, Y. 73.2%; AP>99%) of the title compound Example 317 as off-white solid: LC/MS m/z 488 (MH); $^1$H NMR (DMSO-d6) δ ppm 1.15, 1.22 (3H, 2d, J=7 Hz), 2.50 (3H, s, overlapped with DMSO peaks), 3-4.3 (8H, m, CH$_2$N), 3.98, 4.00 (3H, s, CH$_3$O), 7.45 (5H, m, Ar—Hs), 7.89 (1H, s, indole-H-5), 8.19, 8.26 (1H, 2s, indole-H-2), 9.24, 9.25 (1H, 2s, triazole-H-5), 12.40 (1H, br.s, NH); Anal: Calc for C$_{25}$H$_{25}$N$_7$O$_4$; C, 61.59; H, 5.16; N, 20.11. Found; C, 61.69; H, 5.27; N, 20.10; KF (H$_2$O)<0.1%.

Notes:

The following compounds, Examples 187, 245, and 241, were also prepared by the method described above using appropriate azoles (1,2,4-triazole for Example 187, and Example 245; 3-methylpyrazole for Example 241.

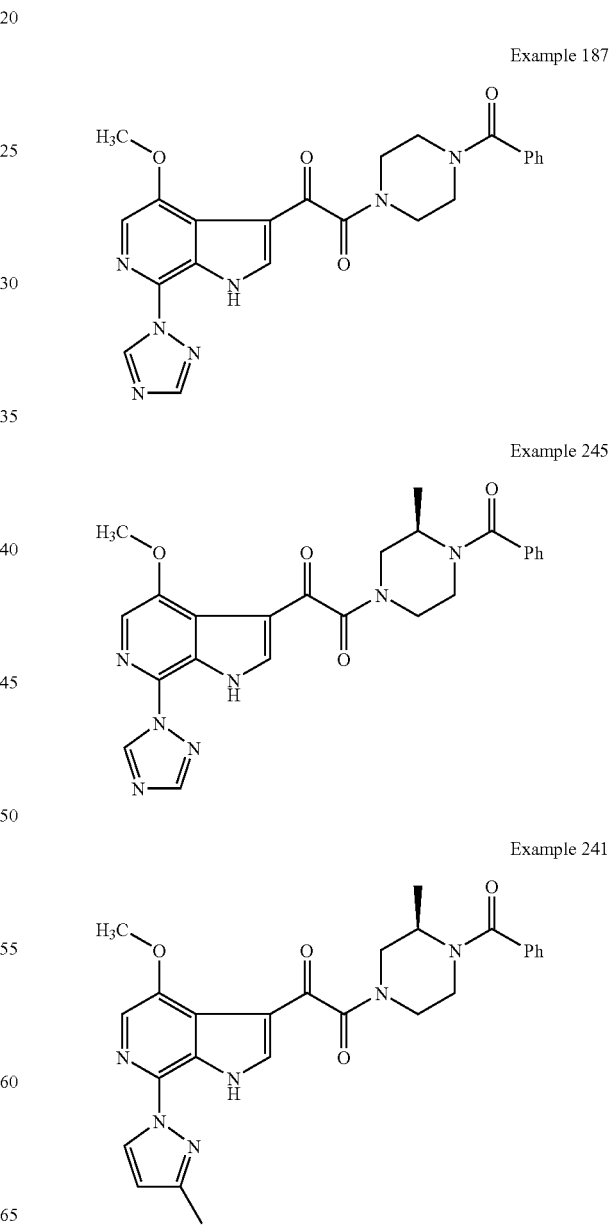

Example 187

Example 245

Example 241

PREPARATION OF EXAMPLE 316

ALTERNATE PREPARATION OF EXAMPLE 316

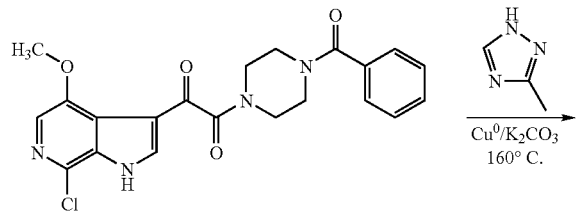

Precursor 5b

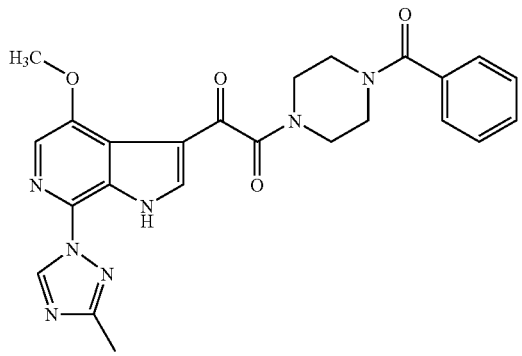

Example 316

A mixture of compound precursor 5b (150 mg, 0.35 mmol), 3-methyl-1,2,4-triazole (581 mg, 7 mmol; 20 eq.; prepared by the method described in *Coll Czech. Chem. Comm.* 1985, 49, 2492), copper powder (45 mg, 0.7 mmol; 2 eq.), potassium carbonate (97 mg, 0.7 mmol; 2 eq.) was flushed with anhydrous nitrogen and heated in a sealed tube at 160° C. for 11 h. Upon cooling, to the mixture was added MeOH, and the insoluble material was filtered. The filtrate was concentrated in vacuo and purified by C-18 reverse phase column (Prep. System eluting with MeOH-water containing 0.1% TFA) to obtain 19 mg (0.040 mmol, Y. 11%) of the title compound Example 216 as amorphous powder (TFA salt): MS m/e 474 (MH); $^1$H NMR (DMSO-d6) δ ppm 2.50 (3H, s, overlapped with DMSO peaks), 3.44 (4H, br, $CH_2N$), 3.68 (4H, br, $CH_2N$), 4.00 (3H, s, $CH_3O$), 7.46 (5H, br. s, Ar—Hs), 7.89 (1H, s), 8.25 (1H, s), 9.24 (1H, s), 12.41 (1H, s, NH).

ALTERNATE PREPARATION OF EXAMPLE 317

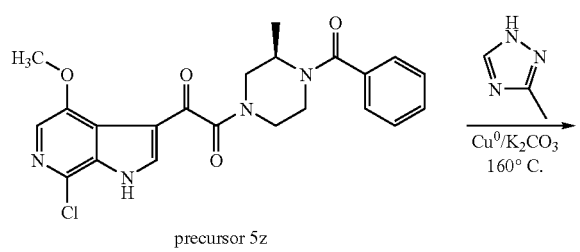

precursor 5z

-continued

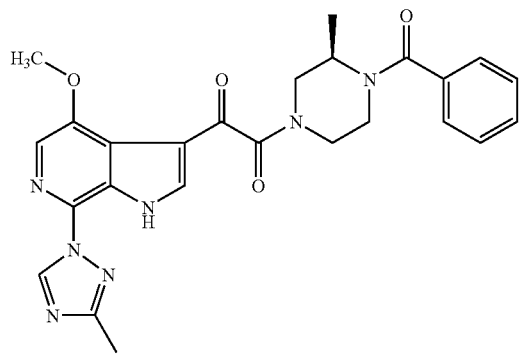

Example 317

A mixture of compound 5z (220 mg, 0.5 mmol), 3-methyl-1,2,4-triazole (830 mg, 10 mmol; 20 eq.; prepared by the method described in *Coll Czech. Chem. Comm.* 1985, 49, 2492), copper powder (63.5 mg, 1 mmol; 2 eq.), potassium carbonate (138 mg, 1 mmol; 2 eq.) was flushed with anhydrous nitrogen and heated in a sealed tube at 160° C. for 11 h. Upon cooling, to the mixture was added MeOH, and the insoluble material was filtered. The filtrate was concentrated in vacuo and purified by C-18 reverse phase column (Prep. System eluting with gradient 0-70% MeOH-water containing 0.1% TFA) to obtain 24 mg (0.049 mmol, Y. 9.8%) of the title compound Example 317 as amorphous powder (TFA salt): MS m/e 488 (MH); $^1$H NMR ($CD_3OD$) δ ppm 1.30, 1.35 (3H, 2d, J=7 Hz), 2.54 (3H, s, $CH_3$), 3-4.5 (8H, m, $CH_2N$), 4.04, 4.05 (3H, 2s, $CH_3O$), 7.46, 7.47 (5H, 2s, Ar—Hs), 7.85, 7.86 (1H, 2s), 8.28, 8.31 (1H, 2s), 9.22 (1H, s).

PREPARATION OF EXAMPLE 318

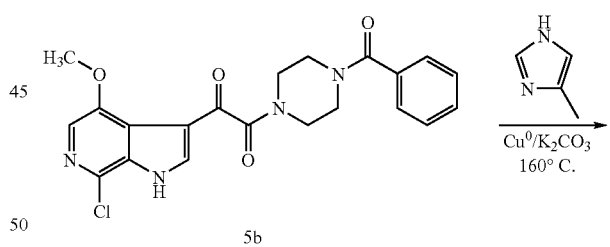

5b

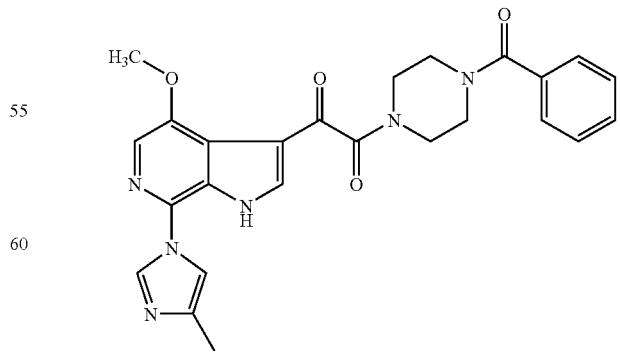

Example 318

A mixture of compound 5b (150 mg, 0.35 mmol), 4-methylimidazole (517 mg, 6.2 mmol; 18 eq.; Aldrich), copper powder (26 mg, 0.42 mmol; 1.2 eq.), potassium carbonate (57 mg, 0.42 mmol; 1.2 eq.) was flushed with anhydrous nitrogen and heated in a sealed tube at 160° C. for 6 h. Upon cooling, to the mixture was added MeOH, and the insoluble material was filtered. The filtrate was concentrated in vacuo and purified by C-18 reverse phase column eluting with 15% CH$_3$CN-water containing 0.1% TFA to obtain 32 mg (0.068 mmol, Y. 19%) of the title compound Example 318 as amorphous powder (TFA salt). $^1$H-NMR indicates contamination of about 30% of the isomeric product, 5-methylimidazolyl analog: MS (ES) m/e 473 (MH); $^1$H NMR (CD$_3$OD) δ ppm 2.25 (s), 2.51 (3H, s, CH$_3$), 3.63 (4H, br, CH$_2$N), 3.9 (4H, br, CH$_2$N), 4.13 (3H, s, CH$_3$O), 4.15 (s), 7.50 (5H, br. s, Ar—Hs), 7.60 (s), 7.89 (1H, s), 8.03 (1H, s), 8.11 (s), 8.43 (1H, s), 9.35 (s), 9.42 (1H, s).

PREPARATION OF EXAMPLE 319

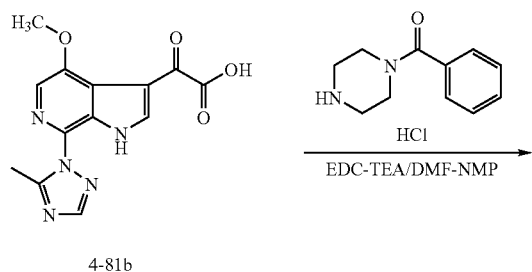

4-81b

Example 319

A mixture of precursor 4-81b (30 mg, 0.11 mmol; prepared from 7-(5-methyl-1,2,4-triazolyl)-4-methoxy-6-azaindole by the method used for the best mode-preparation of Example 316), benzoylpiperazine hydrochloride (39 mg, 0.17 mmol), triethylamine (200 mg, 1.9 mmol; 18 eq.), 1-[3-(dimethylamino)propyl]-3-ethylcarbodiimide hydrochloride (EDC; 77 mg, 0.45 mmol) in 1:1 DMF-NMP (1 mL) was stirred under N$_2$ at room temperature for 20 h. The mixture was concentrated in vacuo to remove DMF and to the residue was added water and the mixture stirred to form precipitates which were collected and dried to obtain 14 mg (0.030 mmol, Y. 27%) of the title compound Example 319 as amorphous powder: MS m/e 474 (MH); $^1$H NMR (DMSO-d6) δ ppm 2.67 (3H, s, CH$_3$), 3.44 (4H, br, CH$_2$N), 3.68 (4H, br, CH$_2$N), 4.02 (3H, s, CH$_3$O), 7.46 (5H, br. s, Ar—Hs), 7.98 (1H, s), 8.21 (1H, s), 8.24 (1H, s), 12.57 (1H, s, NH).

PREPARATION OF EXAMPLE 320

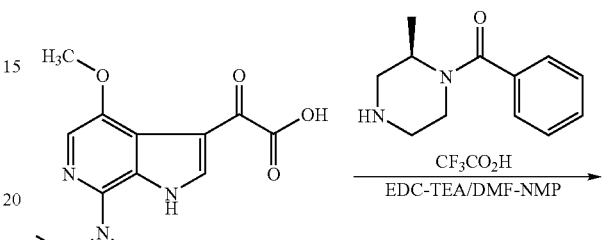

4-81b

Example 320

A mixture of compound 4-81b (30 mg, 0.11 mmol; prepared from 7-(5-methyl-1,2,4-triazolyl)-4-methoxy-6-azaindole by the method used for the best mode-preparation of Example 316), 2R-methyl-1-benzoylpiperazine trifluoroacetate (54 mg, 0.17 mmol), triethylamine (200 mg, 1.9 mmol; 18 eq.), 1-[3-(dimethylamino)propyl]-3-ethylcarbodiimide hydrochloride (EDC; 77 mg, 0.45 mmol) in 1:1 DMF-NMP (1 mL) was stirred under N$_2$ at room temperature for 20 h. More EDC (20 mg) was added to the mixture and stirred for additional 6 h. The mixture was concentrated in vacuo to remove DMF and to the residue was added water and the product was extracted with EtOAc twice. The EtOAc extracts were dried (MgSO$_4$), filtered and concentrated. The residue was purified by silica gel column chromatography eluting with 5% MeOH—CH$_2$Cl$_2$ to obtain 10 mg (0.021 mmol, Y. 19%) of the title compound Example 320 as amorphous powder: MS m/e 488 (MH); $^1$H NMR (CDCl$_3$) δ ppm 1.33, 1.36 (3H, 2d, J=7 Hz), 3.00 (3H, s, CH$_3$), 3-4.6 (8H, m, CH$_2$N), 4.05 (3H, s, CH$_3$O), 7.38-7.44 (5H, m, Ar—Hs), 7.81 (1H, s), 8.02 (1H, s), 8.16, 8.17, 8.18, 8.19 (1H, 4s), 11.10 (1H, s, NH).

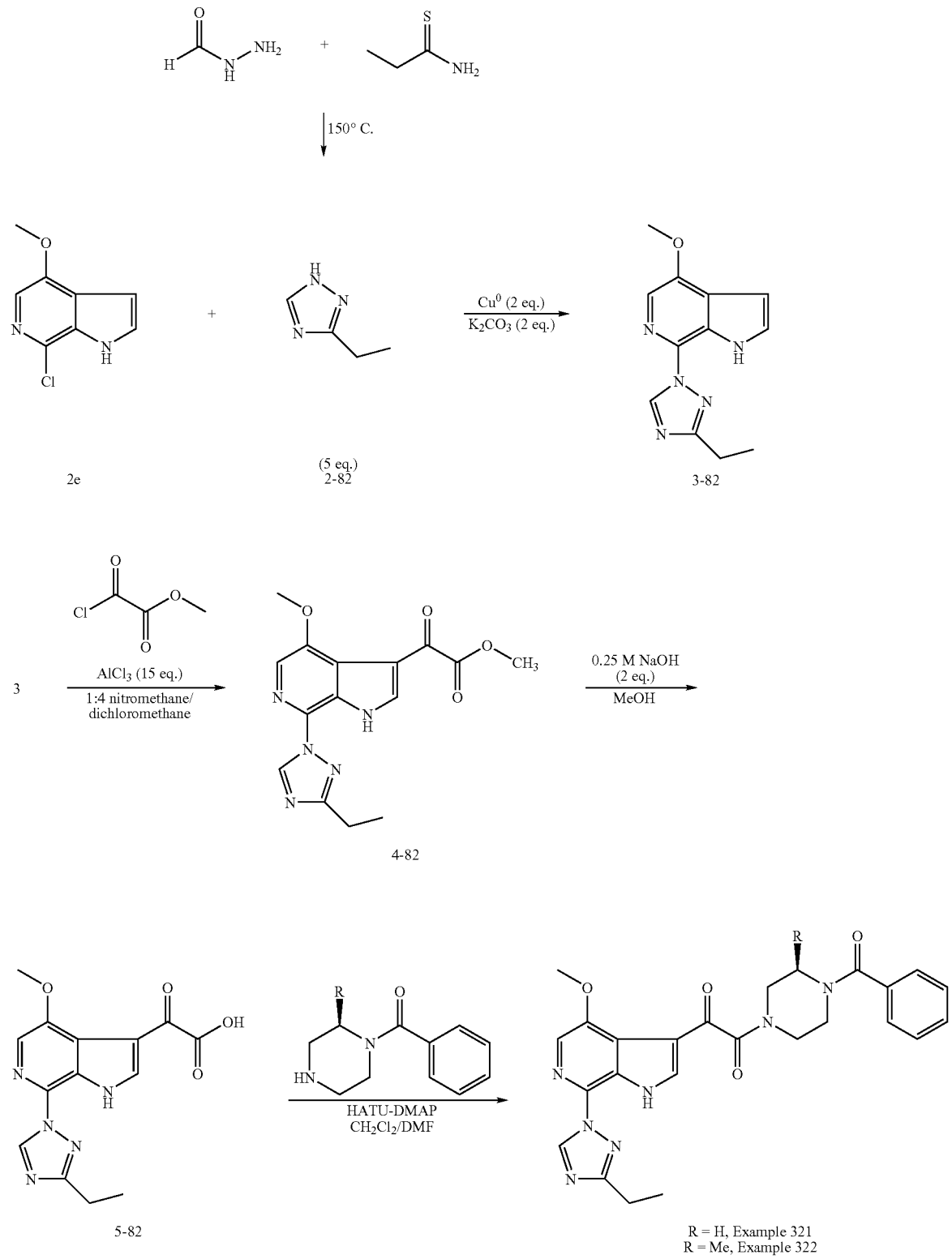

Preparation of 3-methyl-1,2,4-triazole (2-82)

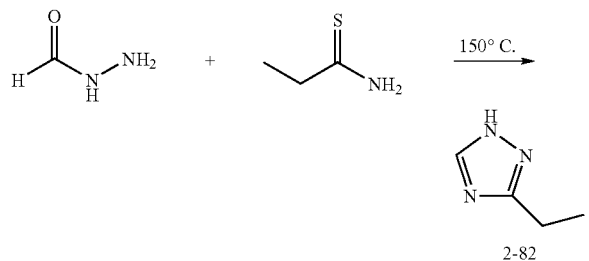

Procedure: A solid mixture of formic hydrazide (6.0 g, 0.1 mol; Aldrich) and thiopropionamide (8.92 g, 0.1 mol; TCI) was heated with stirring at 150° C. (oil bath temp.) for 2 hrs with a gentle stream of nitrogen. It was cooled and stored at room temperature overnight. The solid reaction mixture was suspended in 20% EtOAc/$CH_2Cl_2$, removing insoluble solid and the filtrate was concentrated. The residue was purified by column chromatography, eluting first with 50-80% EtOAc/$CH_2Cl_2$, removing by-products, and then with 10% MeOH/$CH_2Cl_2$, collecting 5.4 g (0.056 mol, Y. 56%) of the title compound as a solid: MS (ESI−) m/z 96 (M−H); $^1$H NMR (CDCl$_3$) δ ppm 1.37 (3H, t, J=7.5 Hz), 2.88 (2H, q, J=7.5 Hz), 8.06 (1H, s, 5-H), 9.4 (1H, br, NH).

Reference: Vanek, T.; Velkova, V.; Gut, Jiri *Coll Czech. Chem. Comm.* 1985, 49, 2492.

Preparation of 3-82

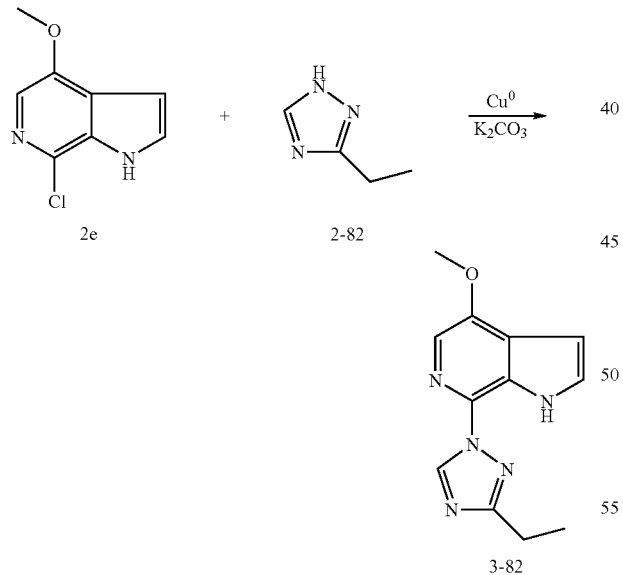

Procedure: A mixture of 4-methoxy-7-chloro-6-azaindole 2e (910 mg, 5.0 mmol), potassium carbonate (1.38 g, 10 mmol, 2 eq.), copper powder (635 mg, 10 mmol, 2 eq.), and 3-ethyl-1,2,4-triazole (2.4 g, 25 mmol, 5 eq.) in a sealed tube was heated at 145-150° C. (external oil bath temperature) for 52 h, by which time HPLC analysis indicated no more reaction progressed. After cooling, MeOH was added, the insoluble material (copper powder) was filtered through a Celite pad, and rinsed with methanol. The filtrate was concentrated in vacuo. The residue was purified by silica gel column chromatography (50% EtOAc/$CH_2Cl_2$) to obtain 450 mg of the products as an about 4:1 mixture of two regioisomers. This was further separated by C-18 reverse phase silica gel (YMC, ODS-A 75 μm) eluted with 15% $CH_3CN$/$H_2O$ containing 0.1% TFA. The fractions containing the major isomer were concentrated in vacuo to remove acetonitrile and the aqueous solution was extracted with $CH_2Cl_2$ after neutralizing with aqueous sodium bicarbonate to obtain the title compound 3-82 (305 mg, 1.25 mmol; Y. 25%): HPLC >97% (AP at 254 nm); MS (LC/MS) m/z 244 (M+H); $^1$H NMR (CDCl$_3$) δ ppm 1.43 (3H, t, J=7.5 Hz; $CH_3$), 2.91 (2H, q, J=7.5 Hz; $CH_2$), 4.05 (3H, s, $OCH_3$), 6.71 (1H, dd, J=6, 2.4 Hz, H-3), 7.57 (1H, t, J=3 Hz, H-2), 7.57 (1H, s, H-5), 9.16 (1H, s, triazole-H-5), 10.3 (1H, br, NH).

Preparation of 4-82

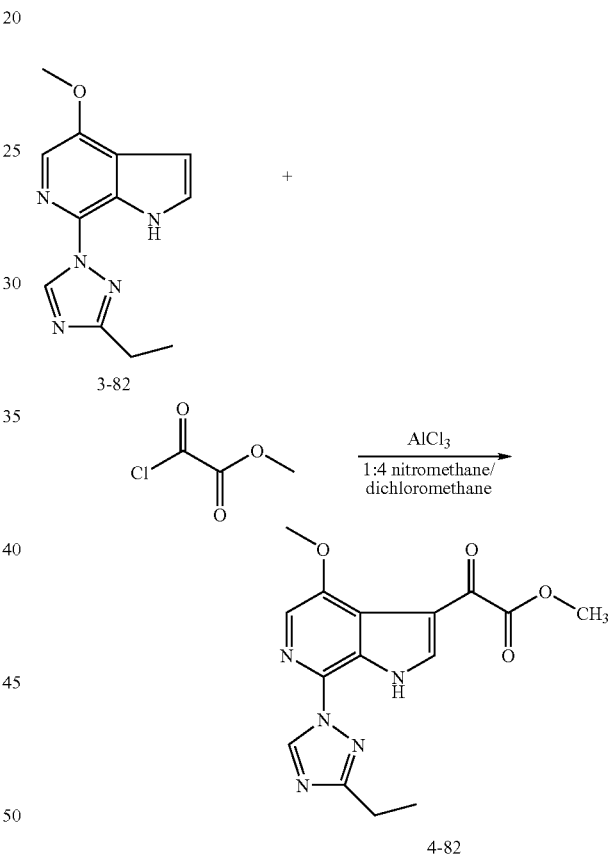

Procedure: AlCl$_3$ (2.50 g, 18.8 mmol, 15 eq.) was dissolved in a solution of $CH_2Cl_2$ (8 mL) and nitromethane (2 mL) under dry nitrogen. To this solution was added compound 3-82 (305 mg, 1.26 mmol) under stirring and under N$_2$, followed by methyl chlorooxoacetate (612 mg, 5.0 mol, 4 eq.). The mixture was stirred under N$_2$ at room temperature for 1.5 h. The mixture was added drop-wise to a cold and stirred solution of 20% aqueous ammonium acetate solution (120 mL). The mixture was stirred for 30 min and the resultant precipitate was filtered, washed thoroughly with water and dried in vacuo to obtain 320 mg (0.97 mmol, Y. 77%) of the title compound 5-82 as a solid: HPLC purity 97% (AP at 254 nm); LC/MS m/z 330 (M+H); $^1$H NMR (DMSO-d$_6$) δ ppm 1.35 (3H, t, J=7.5 Hz, $CH_3$), 2.85 (2H, q, J=7.5 Hz, $CH_2$), 3.89

(3H, s, OCH₃), 3.99 (3H, s, OCH₃), 7.90 (1H, s, H-5), 8.35 (1H, s, H-2), 9.25 (1H, s, triazole-H-5), 12.4 (1H, brs, NH).

Preparation of 5-82

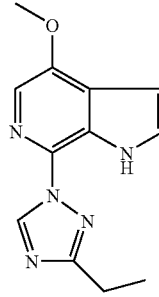

4-82

0.25M aq.-NaOH / MeOH →

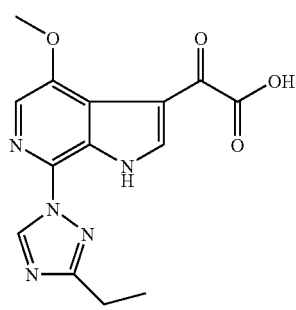

5-82

Procedure: To a suspension of the methyl ester 4-82 (315 mg, 0.957 mmol) in MeOH (8 mL) was added 0.25M NaOH solution in water (7.6 mL, 1.9 mmol, 2 eq.) at room temperature and the mixture stirred for 15 min by which time HPLC indicated the hydrolysis was complete. The mixture was concentrated in vacuo quickly to remove MeOH, and to the residual solution was added water (~10 mL) and 1N HCl (2 mL) with stirring to neutralize the mixture. The resultant fine precipitate was filtered, washed with water and dried in vacuo to obtain 285 mg (0.904 mmol, Y. 94%) of the title compound 5-82 as off-white solid: HPLC purity >96% (AP at 254 nm); LC/MS m/z 316 (M+H); ¹H NMR (DMSO-d₆) δ ppm 1.35 (3H, t, J=7.5 Hz, Me), 2.85 (2H, q, J=7.5 Hz, CH₂), 3.97 (3H, s, CH₃O), 7.88 (1H, s, H-5), 8.30 (1H, d, J=3 Hz, H-2), 9.24 (1H, s, triazole-H-5), 12.28 (1H, s, NH).

PREPARATION OF EXAMPLE 321

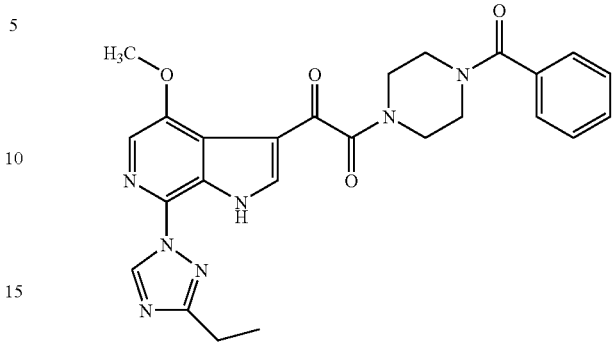

Example 321

Procedure: A mixture of the acid 5-82 (126 mg, 0.4 mmol) and HATU (O-(7-azabenzotriazol-1-yl)-N,N,N',N'-tetramethyluronium hexafluorophosphonate, 228 mg, 0.6 mmol; 1.5 eq.) in a mixture of CH₂Cl₂ (2 mL) and DMF (2 mL) was stirred for 30 min under N₂. To this mixture was added a mixture of benzoylpiperazine hydrochloride (136 mg, 0.60 mmol; 1.5 eq.) and DMAP (dimethylaminipyridine, 147 mg, 1.2 mmol; 3 eq.) in DMF (2 mL), and the mixture was stirred at room temperature under N₂ for 15 min, by which time HPLC indicated the reaction was complete. The mixture was quickly concentrated in vacuo to remove DMF and all volatile materials, and to the residue was added water (50 mL) under stirring and sonication. The precipitates formed were collected, washed with water and dried in vacuo to obtain 160 mg (0.328 mmol, Y. 82%) of the title compound Example 321 as off-white solid: HPLC purity 100% (AP, at 254 nm); LC/MS m/z 488 (M+H); ¹H NMR (DMSO-d6) δ ppm 1.35 (3H, t, J=7.5 Hz, Me), 2.85 (2H, q, J=7.5 Hz, CH₂), 3.43 (4H, br, CH₂N), 3.68 (4H, br, CH₂N), 4.00 (3H, s, CH₃O), 7.46 (5H, br. s, Ar—Hs), 7.89 (1H, s, indole-H-5), 8.26 (1H, s, indole-H-2), 9.25 (1H, s, triazole-H-5), 12.32 (1H, br.s, NH).

PREPARATION OF EXAMPLE 322

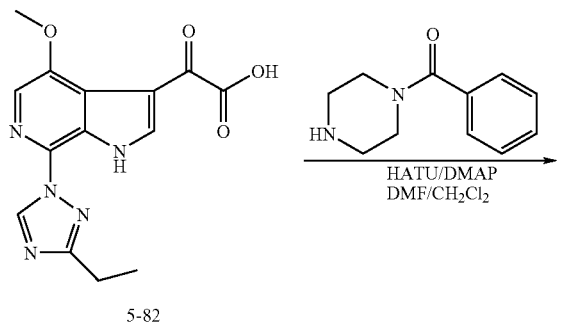

5-82

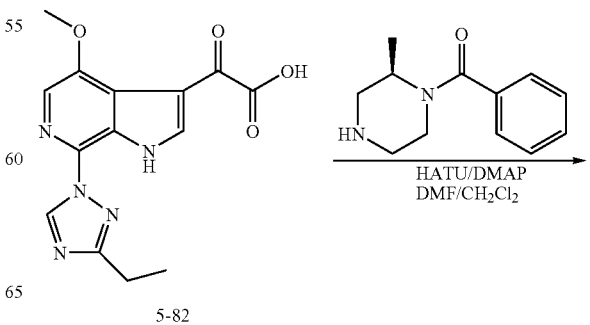

5-82

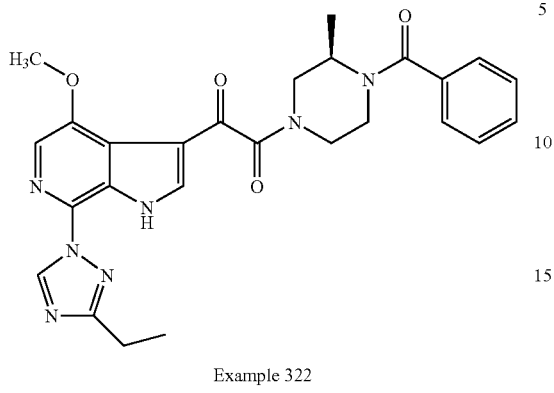

Example 322

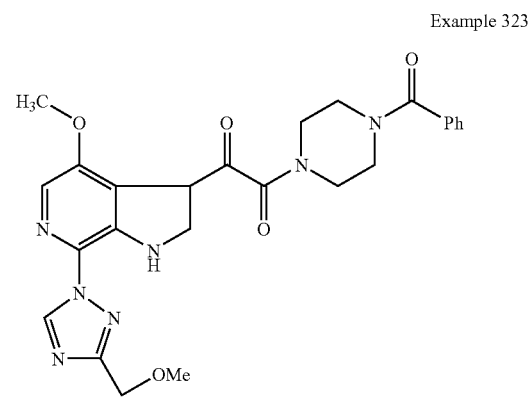

Example 323

Procedure: A mixture of the acid 5-82 (79 mg, 0.25 mmol) and HATU (O-(7-azabenzotriazol-1-yl)-N,N,N',N'-tetramethyluronium hexafluorophosphonate, 142 mg, 0.375 mmol; 1.5 eq.) in a mixture of CH$_2$Cl$_2$ (1 mL) and DMF (1 mL) was stirred for 30 min under N$_2$. To this mixture was added a mixture of benzoylpiperazine hydrochloride (136 mg, 0.60 mmol; 1.5 eq.) and DMAP (dimethylaminipyridine, 92 mg, 0.75 mmol; 3 eq.) in DMF (1 mL), and the mixture was stirred at room temperature under N$_2$ for 15 min, by which time HPLC indicated the reaction was complete. The mixture was quickly concentrated in vacuo to remove all solvents, CH$_2$Cl$_2$ and DMF, and to the residue was added water (~25 mL) under stirring and sonication. The resultant gum were further washed with water and collected by decantation. The residual gum was dried in vacuo. The solution of this gum in isopropanol was concentrated in vacuo to remove any residual water. Addition of anhydrous diethyl ether and trituration gave 90 mg (0.18 mmol, Y. 72%) of the title compound Example 322 as off-white solid: HPLC purity ~95% (AP, at 254 nm); LC/MS m/z 502 (M+H); $^1$H NMR (DMSO-d6) δ ppm 1.15, 1.22 (3H, 2d, J=6.6 Hz, Me), 1.35 (3H, t, J=7.5 Hz, Me), 2.85 (2H, q, J=7.5 Hz, CH$_2$), 2.9-4.4 (7H, m, CH$_2$N, CHN), 3.99, 4.00 (3H, 2s, CH$_3$O), 7.45 (5H, br. s, Ph-Hs), 7.89 (1H, s, indole-H-5), 8.20, 8.25 (1H, 2s, indole-H-2), 9.24, 9.25 (1H, 2s, triazole-H-5), 12.29, 12.32 (1H, 2br.s, NH).

The following compounds, Example 323, and Example 324, were prepared by the method described above using 3-(methoxymethyl)-1,2,4-triazole (10-83).

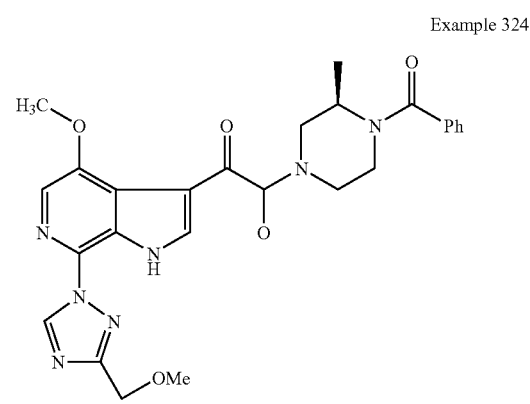

Example 324

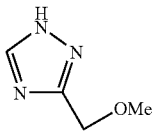

10-83

Synthetic Scheme

Scheme 83

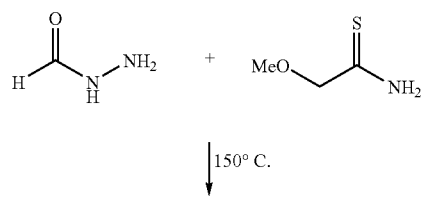

↓ 150° C.

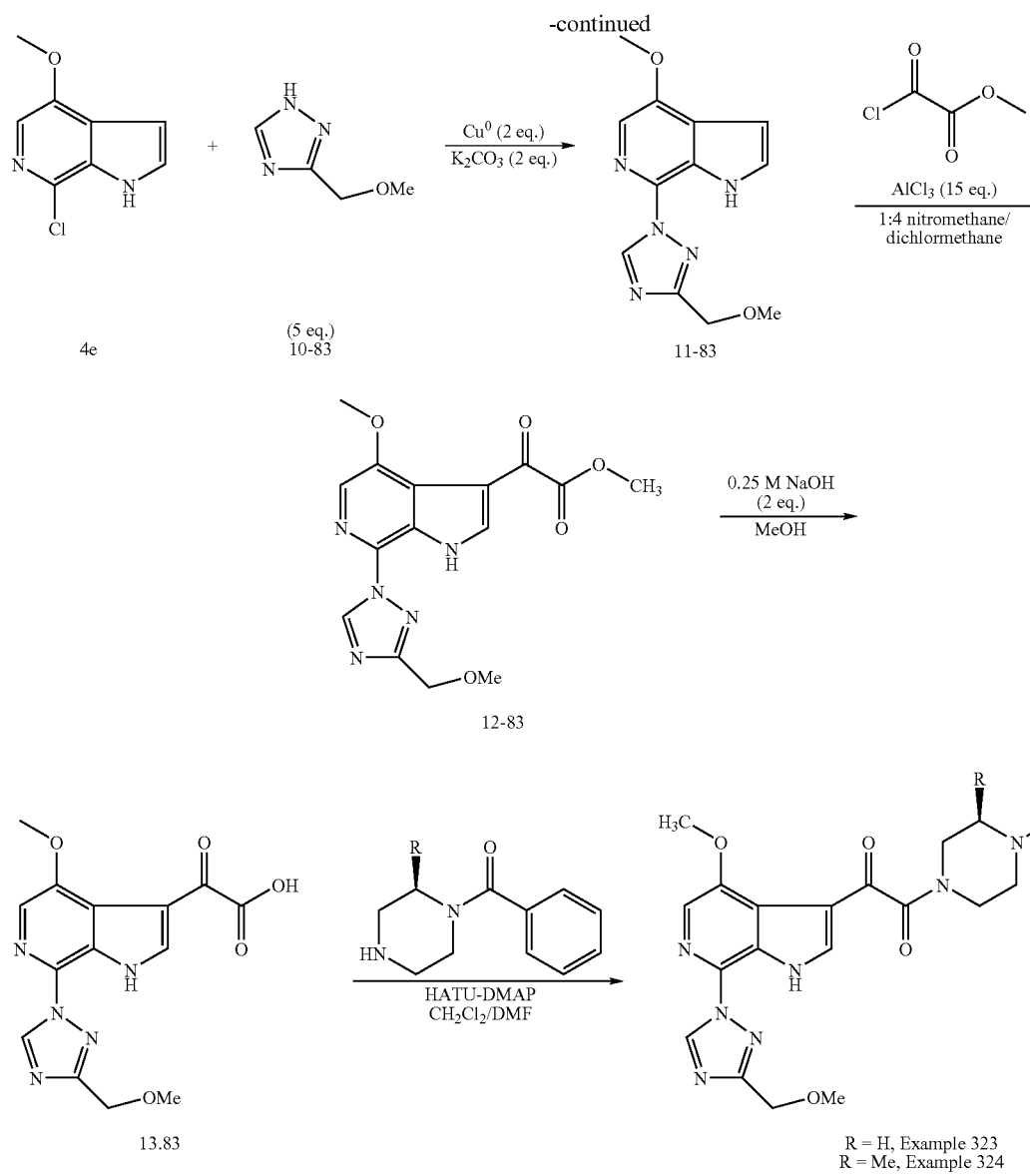

Preparation of 3-methoxymethyl-1,2,4-triazole (10-83)

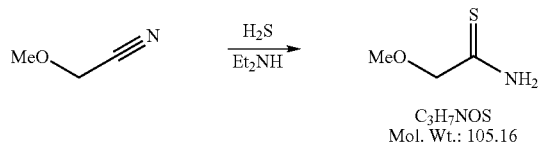

Procedure: To a mixture of methoxyacetonitrile (25 g, 0.35 mol: Aldrich) and diethylamine (1 g, 8.6 mmol) was condensed $H_2S$ (50 mL), and the mixture was sealed, and heated at 50° C. for 14 hrs. After cooling volatile materials were evaporated and the residue was dissolved in water, extracted with EtOAc several times. The combined organic extracts were washed with brine, dried over anhydrous $Na_2SO_4$, and concentrated in vacuo. The residue was purified by column chromatography (EtOAc:$CH_2Cl_2$=1:10) to obtain 13 g (0.12 mol, Y. 35%) of the title compound as a dark oil: GC/MS m/z 105 (M); $^1H$ NMR (CDCl$_3$) δ ppm 3.43 (3H, s, CH$_3$), 4.26 (2H, s, CH$_2$).

Preparation of 3-methoxymethyl-1,2,4-triazole (10-83)

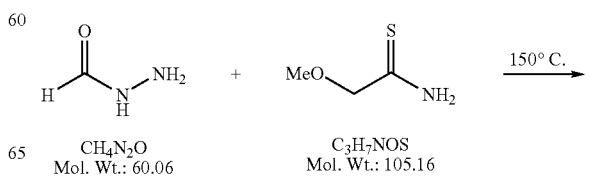

-continued

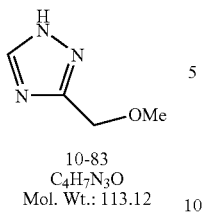

10-83
C₄H₇N₃O
Mol. Wt.: 113.12

Procedure: A solid mixture of formic hydrazide (4.58 g, 0.0763 mol) and methoxythioacetamide (8.92 g, 0.1 mol) was heated with stirring at 150° C. (oil bath temp.) for 2 hrs with a gentle stream of nitrogen. It was cooled and stored at room temperature overnight. The solid reaction mixture was suspended in 20% EtOAc/CH₂Cl₂, removing insoluble solid and the filtrate was concentrated. The residue was purified by column chromatography, eluting first with 50-80% EtOAc/CH₂Cl₂, removing by-products, and then with 10% MeOH/CH₂Cl₂, collecting 3.8 g (0.034 mol, Y. 44%) of the title compound 10-83 as a solid: $^1$H NMR (CDCl₃) δ ppm 3.48 (3H, s, MeO), 4.67 (2H, s, CH₂), 8.10 (1H, s, 5-H).

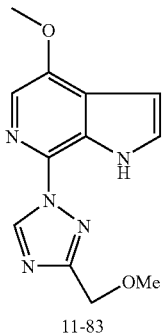

Compund 11-83

11-83

Y. 9%: HPLC >98% (AP at 254 nm); MS (LC/MS) m/z 260 (M+H); $^1$H NMR (CDCl₃) δ ppm 3.53 (3H, s, MeO), 4.06 (3H, s, 4-OCH₃), 4.69 (2H, s, CH₂), 6.73 (1H, dd, J=3, 2.4 Hz, H-3), 7.40 (1H, t, J=2.7 Hz, H-2), 7.58 (1H, s, H-5), 9.16 (1H, s, triazole-H-5), 10.2 (1H, br, NH).

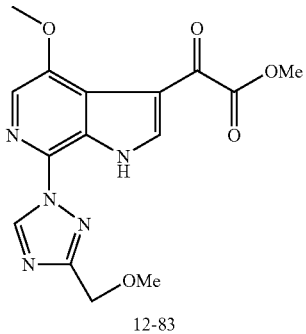

Compound 12-83

12-83

Y. 78%: HPLC 100% (AP at 254 nm); MS (LC/MS) m/z 346 (M+H); $^1$H NMR (CD₃OD) δ ppm 3.51 (3H, s, MeO), 3.94 (3H, s, MeO), 4.05 (3H, s, MeO), 4.71 (2H, s, CH₂), 7.87 (1H, s), 8.35 (1H, s), 9.33 (1H, s, triazole-H-5).

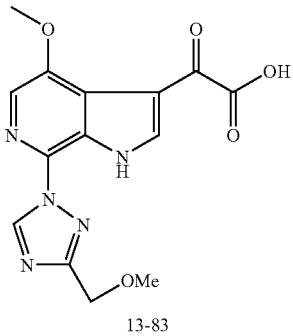

Compound 13-83

13-83

Y. 97%: HPLC 98% (AP at 254 nm); MS (LC/MS) m/z 332 (M+H); $^1$H NMR (CDCl₃) δ ppm 3.49 (1H, s, OH), 3.55 (3H, s, MeO), 4.10 (3H, s, MeO), 4.72 (2H, s, CH₂), 7.84 (1H, s, H-5), 9.13 (1H, d, J=3.3 Hz), 9.21 (1H, s, triazole-H-5), 11.15 (1H, br, NH).

EXAMPLE 323

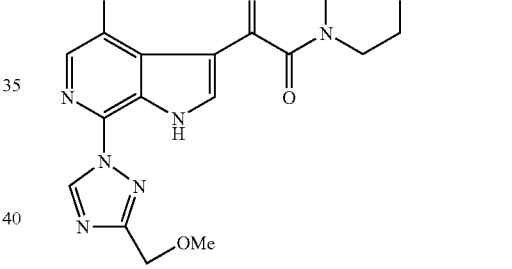

Example 323

Y. 79%: HPLC 100% (AP at 254 nm); MS (LC/MS) m/z 504 (M+H); $^1$H NMR (DMSO-d₆) δ ppm 3.39 (3H, s, MeO), 3.42 (4H, br, CH₂N), 3.68 (4H, br, CH₂N), 4.01 (3H, s, 4-MeO), 4.61 (2H, s, CH₂), 7.46 (5H, s, Ph-Hs), 7.92 (1H, s), 8.27 (1H, s), 9.36 (1H, s, triazole-H-5), 12.42 (1H, br.s, NH).

EXAMPLE 324

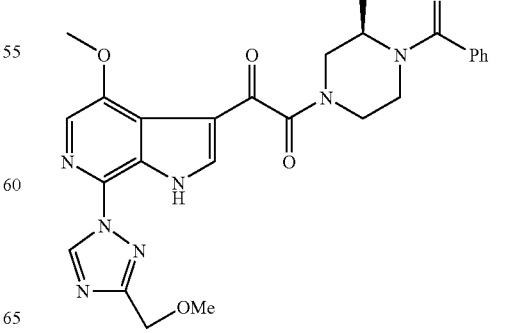

Example 324

Y. 69%: HPLC >97% (AP at 254 nm); MS (LC/MS) m/z 518 (M+H); $^1$H NMR (DMSO-d$_6$) δ ppm 1.15, 1.22 (3H, 2d, J=7 Hz, Me), 2.9-4.4 (7H, m, CH$_2$N, CHN), 3.39 (3H, s, MeO), 4.00, 4.01 (3H, 2s, CH$_3$O), 4.61 (2H, s, CH$_2$), 7.4-7.5 (5H, m, Ph-Hs), 7.92 (1H, s, indole-H-5), 8.21, 8.29 (1H, 2s, indole-H-2), 9.35, 9.36 (1H, 2s, triazole-H-5), 12.4 (1H, br, NH).
The following compounds, Examples 325, 326, 327, and 328, were prepared by the method described above using 4-methyl-1,2,3-triazole (19-84).
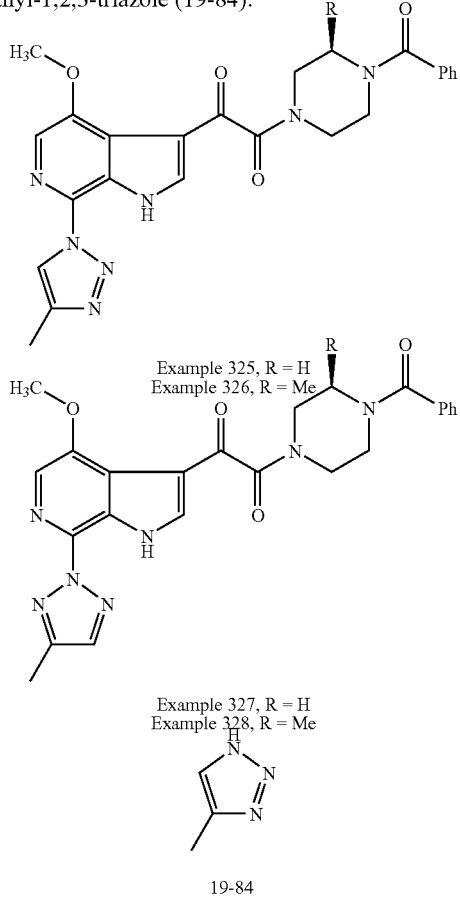
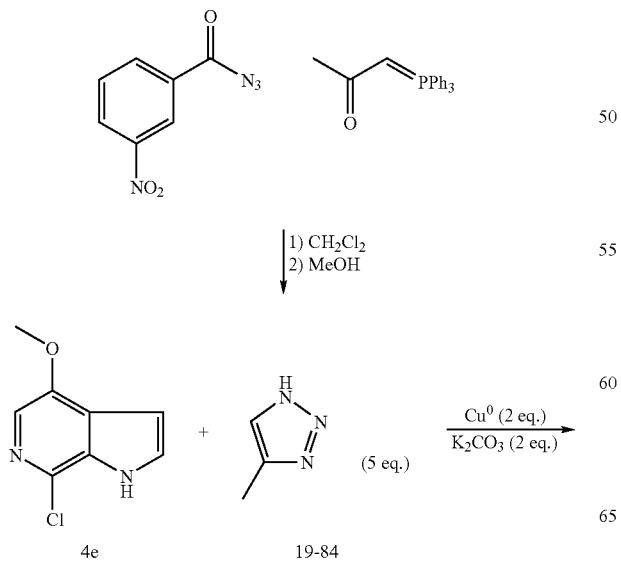
Scheme 84
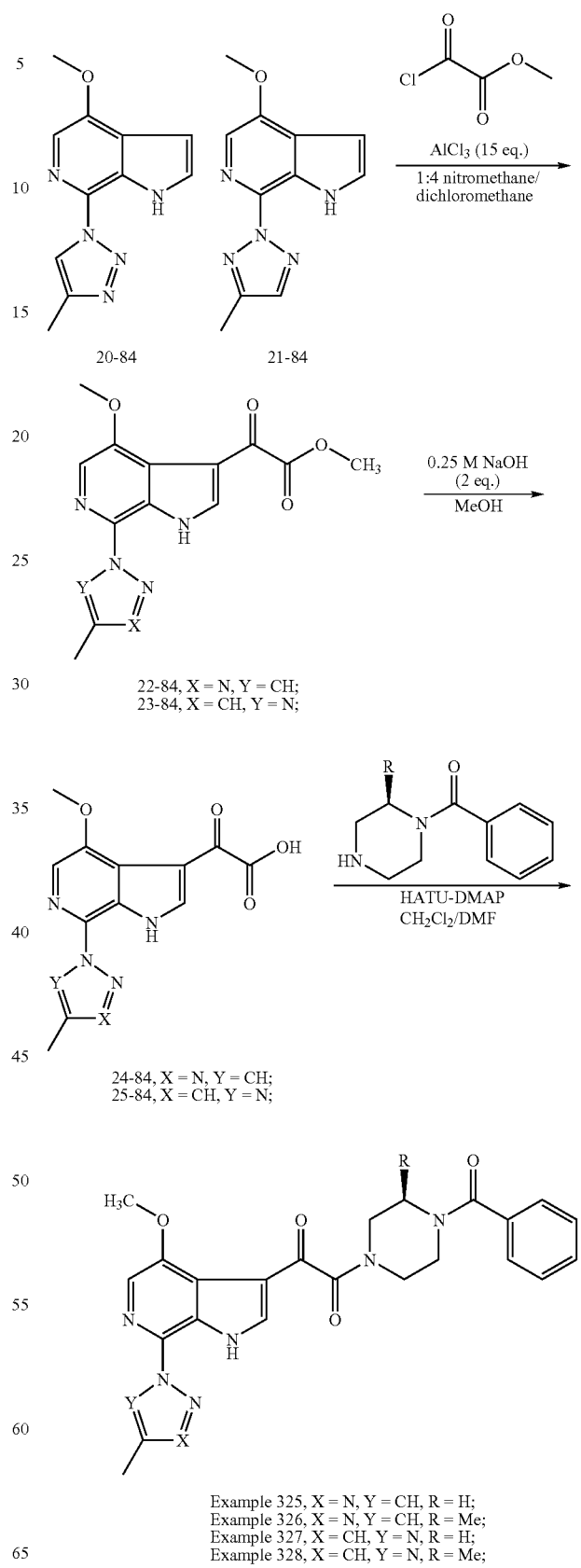

Preparation of 4-methyl-1,2,3-triazole (19-84)

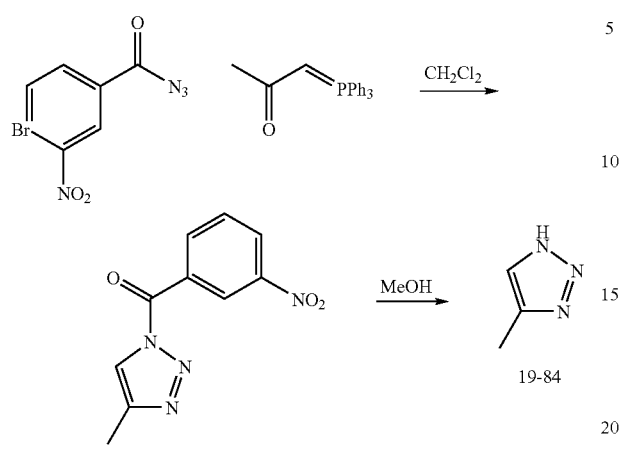

Procedure:

This compound 19-84 was prepared by the method described in M. Begtrup *J. Chem. Soc., Perkin Transactions II*, 1976, 736.

A mixture of m-nitrobenzoyl azide (38.4 g, 0.200 mol; prepared from m-nitrobenzoyl chloride and sodium azide following the procedure described in *Org. Syn. Coll*. Vol. IV, 1963, p. 715) and 1-triphenylphosphoranylidene-2-propanone (63.6 g, 0.200 mol: Aldrich) in $CH_2Cl_2$ (300 mL) was stirred at room temperature for 2 hrs. The mixture was concentrated in vacuo to obtain a solid. This solid was dissolved in MeOH, and the solution was stirred at room temperature for 30 min, and the precipitates formed were removed. The filtrate was concentrated in vacuo, and the residue was extracted with water (500 mL) containing TFA (17 mL). This solution was washed once with a small amount of $CH_2Cl_2$ to remove the most of triphenylphosphine, and the aqueous phase neutralized with NaHCO3 to pH 7 and extracted five times with $CH_2Cl_2$ (total of 500 mL). The combined extracts were dried over Na2SO4, concentrated to obtain 7.6 g (0.091 mol, Y. 46%) of the title compound 19-84 as a yellow oil: $^1$H NMR ($CDCl_3$) δ ppm 2.37 (3H, s, Me), 7.50 (1H, s, 5-H), 10.41 (1H, br, NH).

Compound 20-84

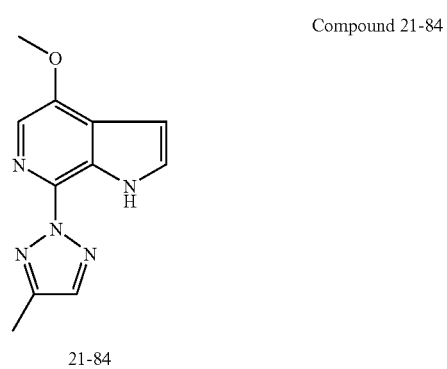

20-84

Yield 5-9%: HPLC purity 100% (RT1.89 min, AP at 254 nm); MS (LC/MS) m/z 230 (M+H); $^1$H NMR ($CDCl_3$) δ ppm 2.47 (3H, s, Me), 4.07 (3H, s, 4-$OCH_3$), 6.74 (1H, t, J=2.7 Hz, H-3), 7.42 (1H, t, J=2.7 Hz, H-2), 7.62 (1H, s, H-5), 8.41 (1H, s, triazole-H-5), 10.3 (1H, br, NH).

The structure was confirmed by a single X-ray crystallographic analysis.

Compound 21-84

21-84

Yield 11-14%: HPLC purity 100% (RT1.36 min, AP at 254 nm); MS (LC/MS) m/z 230 (M+H); $^1$H NMR ($CDCl_3$) δ ppm 2.48 (3H, s, Me), 4.06 (3H, s, 4-$OCH_3$), 6.74 (1H, dd, J=3, 2.4 Hz, H-3), 7.39 (1H, t, J=3 Hz, H-2), 7.68 (1H, s, H-5), 7.72 (1H, br, triazole-H-5), 10.25 (1H, br, NH).

Compound 22-84

22-84

Yield 79%: HPLC purity 94% (AP at 254 nm); MS (LC/MS) m/z 316 (M+H); $^1$H NMR ($CDCl_3$) δ ppm 2.49 (3H, s, Me), 3.96 (3H, s, OMe), 4.07 (3H, s, OMe), 7.81 (1H, s, H-5), 8.38 (1H, d, J=3.3 Hz, H-2), 8.42 (1H, s, triazole-H-5), 11.07 (1H, br, NH).

Compound 23-84

23-84

Yield 81%: HPLC purity >95% (AP at 254 nm); MS (LC/MS) m/z 316 (M+H); $^1$H NMR ($CDCl_3$) δ ppm 2.49 (3H, s, Me), 4.00 (3H, s, OMe), 4.05 (3H, s, OMe), 7.72 (1H, s, H-5), 7.89 (1H, br.s, triazole-H-5), 8.33 (1H, d, J=3 Hz, H-2), 11 (1H, br, NH).

Compound 24-84

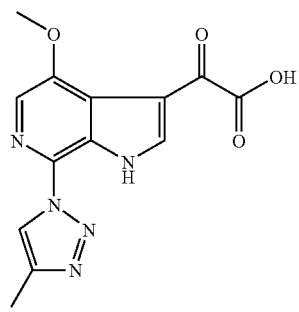

24-84

Yield 83%: HPLC purity 98% (AP at 254 nm); MS (LC/MS) m/z 302 (M+H); $^1$H NMR (CD$_3$OD) δ ppm 2.46 (3H, s, Me), 4.06 (3H, s, OMe), 7.89 (1H, s, H-5), 8.39 (1H, d, J=3.3 Hz, H-2), 8.58 (1H, s, triazole-H-5).

Compound 25-84

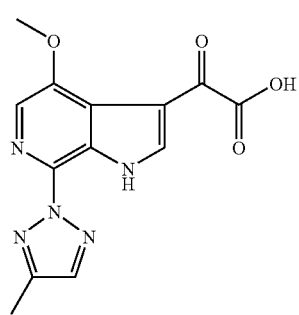

25-84

Yield 74%: HPLC purity 100% (AP at 254 nm); MS (LC/MS) m/z 302 (M+H); $^1$H NMR (CD$_3$OD) δ ppm 2.50 (3H, s, Me), 4.05 (3H, s, OMe), 7.84 (1H, s), 7.90 (1H, s), 8.39 (1H, s).

EXAMPLE 325

Example 325

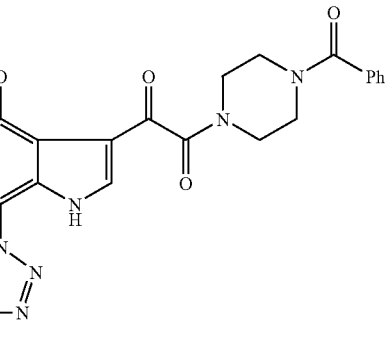

Y. 76%: HPLC 98% (AP at 254 nm); MS (LC/MS) m/z 474 (M+H); $^1$H NMR (DMSO-d$_6$) δ ppm 2.40 (3H, s, Me), 3.44 (4H, br, CH$_2$N), 3.68 (4H, br, CH$_2$N), 4.02 (3H, s, 4-MeO), 7.46 (5H, s, Ph-Hs), 7.96 (1H, s), 8.21 (1H, s), 8.68 (1H, s, triazole-H-5), 12.72 (1H, br.s, NH).

EXAMPLE 326

Example 326

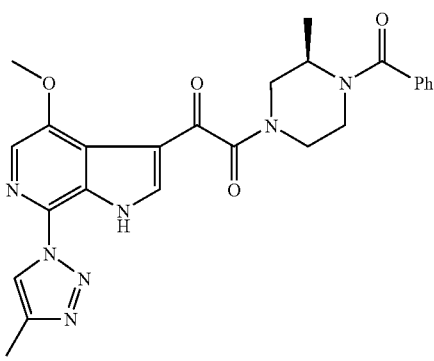

Y. 62%: HPLC 97% (AP at 254 nm); MS (LC/MS) m/z 488 (M+H); $^1$H NMR (DMSO-d$_6$) δ ppm 1.14, 1.21 (3H, 2d, J=7 Hz, Me), 2.40 (3H, s, Me), 2.9-4.4 (7H, m, CH$_2$N, CHN), 4.01, 4.02 (3H, 2s, CH$_3$O), 7.46 (5H, s, Ph-Hs), 7.96 (1H, s), 8.16, 8.23 (1H, 2s), 8.675, 8.68 (1H, 2d, J=2.5 Hz), 12.72 (1H, br.s, NH).

COMPOUND EXAMPLE 327

Example 327

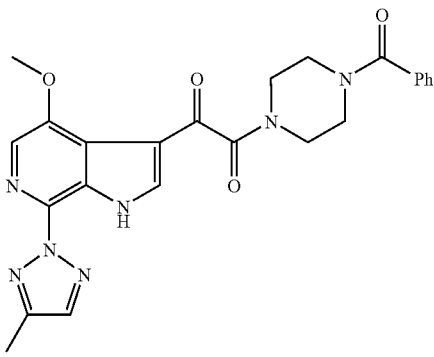

Y. 73%: HPLC 96% (AP at 254 nm); MS (LC/MS) m/z 474 (M+H); $^1$H NMR (DMSO-d$_6$) δ ppm 2.45 (3H, s, Me), 3.44 (4H, br, CH$_2$N), 3.68 (4H, br, CH$_2$N), 4.01 (3H, s, 4-MeO), 7.46 (5H, s, Ph-Hs), 7.93 (1H, s), 8.04 (1H, s), 8.24 (1H, d, J=3 Hz, H-2), 12.51 (1H, br.s, NH).

EXAMPLE 328

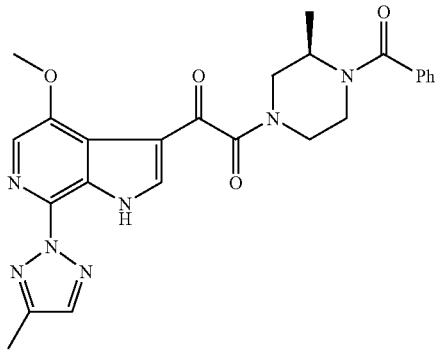
Example 328

Y. 74%: HPLC 99% (AP at 254 nm); MS (LC/MS) m/z 488 (M+H); $^1$H NMR (DMSO-d$_6$) δ ppm 1.15, 1.22 (3H, 2d, J=7 Hz, Me), 2.45 (3H, s, Me), 2.9-4.4 (7H, m, CH$_2$N, CHN), 4.00, 4.01 (3H, 2s, CH$_3$O), 7.45 (5H, s, Ph-Hs), 7.92 (1H, s), 8.03 (1H, s), 8.18, 8.26 (1H, 2s), 12.5 (1H, br.s, NH).

PREPARATION OF EXAMPLE 329

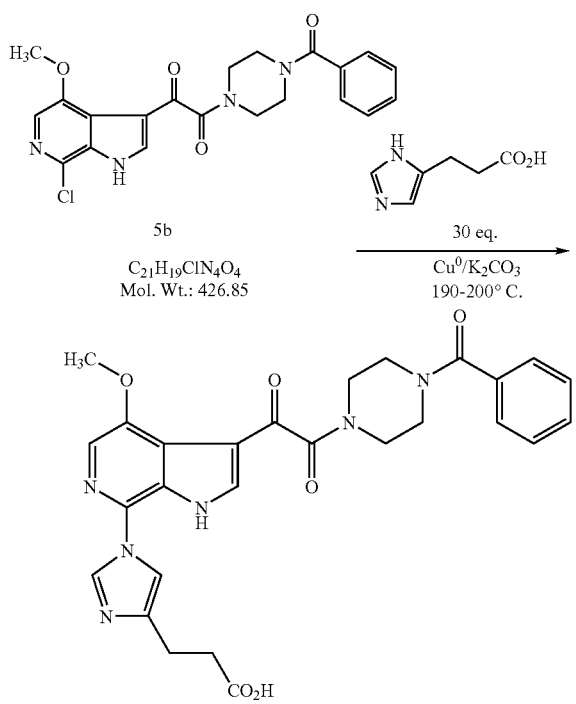
Example 329
C$_{27}$H$_{26}$N$_6$O$_6$
Mol. Wt.: 530.53

A mixture of compound 5b (128 mg, 0.3 mmol), imidazole-4-propionic acid (1.26 g, 9 mmol; 30 eq.; prepared from urocanic acid by catalytic hydrogenation using 10% Pd—C in acetic acid, following the procedure described in J. Altman, N. Shoef, M. Wilchek, and A. Warshawsky *J. Chem. Soc., Perkin Trans. I,* 1984, 59), copper powder (38 mg, 0.6 mmol; 2 eq.), potassium carbonate (83 mg, 0.6 mmol; 2 eq.) was flushed with anhydrous nitrogen and heated in a sealed tube at 190°-200° C. (oil bath temp.) for 2 h. Upon cooling, to the mixture was added MeOH, and the insoluble material was filtered. The filtrate was concentrated in vacuo and purified by C-18 reverse phase column (YMC, eluting with 15% CH$_3$CN-water containing 0.1% TFA) to obtain 12 mg (0.023 mmol, Y. 7.5%) of the title compound Example 329 as amorphous powder (about 1:1 mixture of two regio-isomers): HPLC purity 96% (AP, at 254 nm); MS (LC/MS) m/z 531 (M+H); $^1$H NMR (CD$_3$OD) δ ppm 2.74, 3.00 (2H, 2t, J=7 Hz), 2.82, 3.11 (2H, 2t, J=7 Hz), 3.59 (4H, br, CH$_2$N), 3.79 (4H, br, CH$_2$N), 3.79, 4.10 (3H, 2s, CH$_3$O), 6.73 (s), 7.33 (s), 7.48 (5H, br. s, Ar—Hs), 7.93 (br.s), 8.00 (s), 8.10 (s), 8.40 (s), 8.77 (s), 9.43 (br.s).

The following compounds, Examples 330 and 331 were similarly prepared by following the above procedure.

EXAMPLE 330

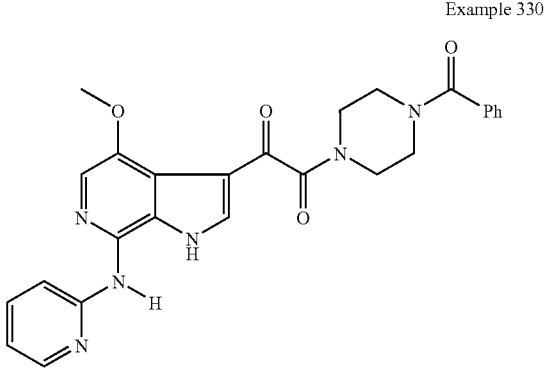
Example 330

Y. 10% (150° C., 7 h): HPLC 93% (AP at 254 nm); MS (LC/MS) m/z 485 (M+H); $^1$H NMR (CD$_3$OD, 500 MHz) δ ppm 3.63 (4H, br, CH$_2$N), 3.84 (4H, br, CH$_2$N), 4.05 (3H, s, 4-MeO), 7.32 (2H, m, pyr-Hs), 7.52 (5H, s, Ph-Hs), 7.71 (1H, s), 8.06 (1H, t, J=7.5 Hz, pyr-H), 8.48 (1H, d, J=4.5 Hz), 8.60 (1H, s).

EXAMPLE 331

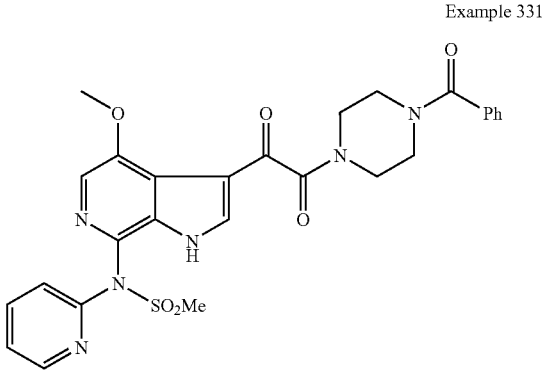
Example 331

Y. 10% (150° C., 7 h): HPLC 93% (AP at 254 nm); MS (LC/MS) m/z 563 (M+H); $^1$H NMR (CDCl$_3$) δ ppm 2.76 (3 h. S, Me), 3.55 (4H, br, CH$_2$N), 3.78 (4H, br, CH$_2$N), 4.09 (3H, s, 4-MeO), 6.71 (1H, t, J=7 Hz, pyr-H), 7.43 (5H, s, Ph-Hs), 7.68 (1H, t, J=7 Hz, pyr-H), 7.82 (1H, t, J=7 Hz, pyr-H), 7.91 (1H, s), 8.15 (1H, s), 10.84 (1H, br, NH).

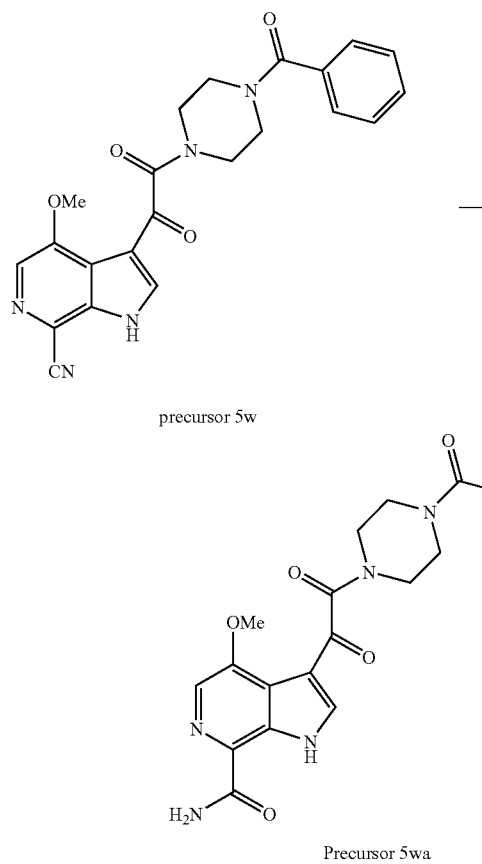

precursor 5w

Precursor 5wa

A mixture of precursor 5w (71.5 mg, 0.17 mmol) in MeOH (1.5 mL) was cooled to 0° C., and saturated with hydrogen chloride gas over the course of 10 min. The volatiles were then evaporated via blowing $N_2$ overnight to provide precursor 5wa. $^1$H NMR: (DMSO-$d_6$) δ 12.45 (s, 1H), 8.12 (s, 2H), 8.07 (s, 1H), 7.65 (s, 1H), 7.45 (s, 5H), 4.04 (s, 3H), 3.80-3.30 (b m, 8H); LC/MS: (ES+) m/z (M+H)$^+$=436, HPLC $R_t$=1.357 (Column G).

To a mixture of precursor 5wa (10 mg, 23 μmol) in acetic acid (0.4 mL) and acetic anhydride (0.75 mL) at 0° C., was added NaNO$_2$ (30 mg, 0.43 mmol). The reaction mixture was stirred at 0° C. for 30 min, and allowed to warm to ambient temperature. After stirring for an additional 1.5 hr, the mixture was filtered and the residue dried under vacuum to give the desired compound 5wb an off-white solid. $^1$H NMR: (CD$_3$OD) δ 8.44 (s, 1H), 8.08 (s, 1H), 7.48 (b s, 5H), 4.14-3.27 (m, 8H), 4.14 (s, 3H); LC/MS: (ES+) m/z (M+H)$^+$=437, HPLC $R_t$=0.750 (Column G).

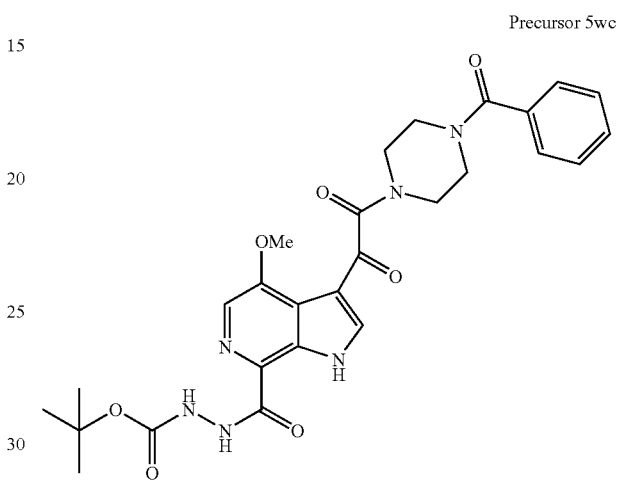

Precursor 5wc

A flask was charged with precursor 5wb (2.6 mg, 6.0 μmol), DMF (0.5 mL), tert-butyl carbazate (1.2 mg, 8.9 μmol), DEPBT (5.4 mg, 18 μmol), and N,N-diisopropylethylamine (10 μL, 30 μmol). The reaction mixture was allowed to stir at ambient temperature overnight. The product 5wc was separated using the following reverse phase preparative HPLC method: Start % B=0, Final % B=100, Gradient time=6 min, Flow Rate=30 mL/min, Column: Xerra Prep MS C18 5 μm 19×50 mm, Fraction Collection: 4.38-4.59 min. $^1$H NMR: (CD$_3$OD) δ 8.29 (s, 1H), 8.11 (s, 1H), 7.47 (b s, 5H), 4.11-3.28 (m, 8H), 4.10 (s, 3H), 1.50 (b s, 9H); LC/MS: (ES+) m/z (M+H)$^+$=551, HPLC $R_t$=1.203 (Column G).

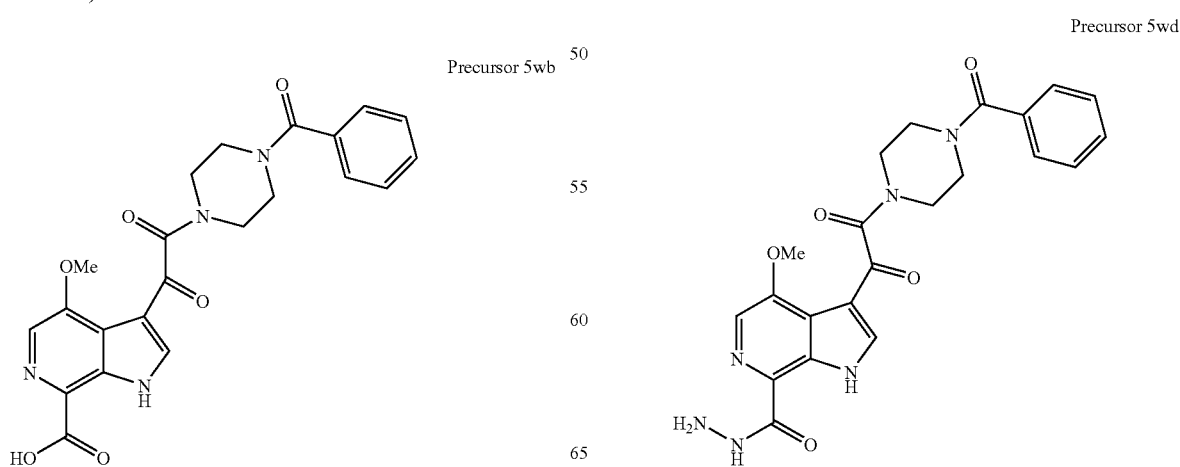

Precursor 5wb

Precursor 5wd

To precursor 5wc (57 mg, 0.104 mmol) was added a solution of HCl in 1,4-dioxane (4 M, 0.25 mL), and the reaction mixture was stirred overnight at room temperature. The deprotection afforded the desired product precursor 5wd cleanly. The excess reagent and solvent were evaporated via blowing $N_2$, and the product dried under vacuum. LC/MS: (ES+) m/z $(M+H)^+$=451, HPLC $R_t$=0.803 (Column G).

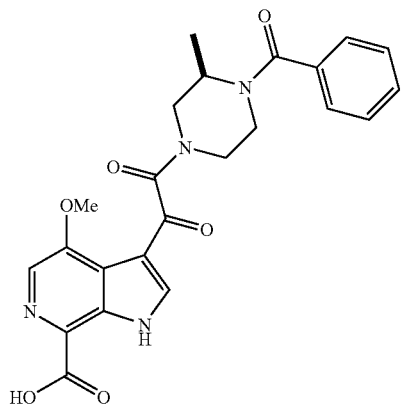

Precursor 5wg

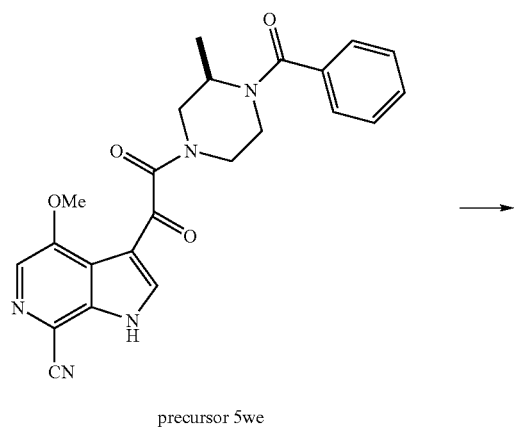

precursor 5we

To a solution of precursor 5wf (65 mg, 0.14 mmol) in MeOH (1 mL) was added NaOH (1.5 mL, 1 N aq.). The mixture was stirred for 2 hours, and upon which time HCl (1.5 mL, 1 N aq.) was added to quench the reaction. The volatiles were evaporated in vacuo to give precursor 5wg. $^1$H NMR: (TFA solvate, $CD_3OD$) δ 8.54, 8.51 (s, 1H), 8.11 (b s, 1H), 7.57-7.48 (b s, 5H), 4.60-3.10 (b m, 7H), 4.17, 4.16 (s, 3H), 1.37, 1.33 (d, J=6.5, 6.0, 3H); LC/MS: (ES+) m/z $(M+H)^+$=451, HPLC $R_t$=0.837 (Column G).

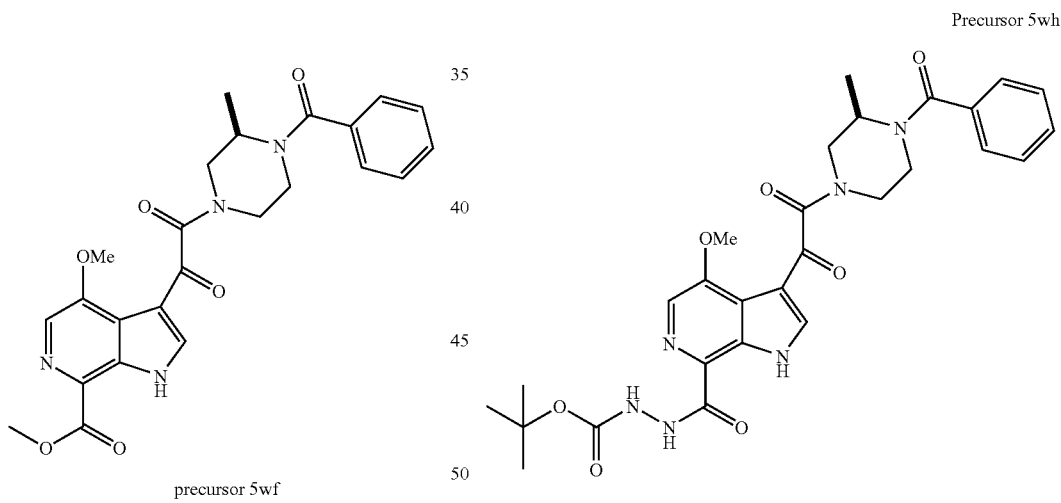

precursor 5wf

Precursor 5wh

A solution of precursor 5we (106 mg, 0.25 mmol) in MeOH (2.5 mL) in a sealed tube at 0° C. was flushed with $N_2$, and saturated with HCl gas for 10 min. The tube was closed and the reaction mixture was stirred at 70° C. for 50 minutes. After cooling to ambient temperature, the volatiles were evaporated in vacuo to give precursor 5wf. $^1$H NMR: ($CD_3OD$) δ 8.33, 8.30 (s, 1H), 8.13, 8.12 (s, 1H), 7.48-7.44 (m, 5H), 4.60-3.10 (b m, 7H), 4.12, 4.11 (s, 3H) 4.06 (s, 3H), 1.35, 1.29 (d, J=6.5, 7.0, 3H); LC/MS: (ES+) m/z $(M+H)^+$=465, HPLC $R_t$=0.993 (Column G).

To a mixture of precursor 5wg (22 mg, 0.048 mmol) in DMF (1 mL) were added tert-butyl carbazate (14 mg, 0.11 mmol), DEPBT (53 mg, 0.18 mmol), and N,N-diisopropylethylamine (40 µL, 0.23 mmol). The reaction mixture was stirred overnight, and the desired compound precursor 5wh was isolated via preparative reverse phase HPLC using the following conditions: Start % B=0, Final % B=100, Gradient time=6 min, Flow Rate=30 mL/min, Column: Xerra Prep MS C18 5 µm 19×50 mm, Fraction Collection: 4.37-4.98 min. $^1$H NMR: ($CD_3OD$) δ 8.28, 8.26 (s, 1H), 8.08 (b s, 1H), 7.47-7.43 (m, 5H), 4.75-3.26 (m, 7H), 4.10 (s, 3H), 1.50 (b s, 9H), 1.36-1.27 (m, 3H); LC/MS: (ES+) m/z $(M+H)^+$=565, HPLC $R_t$=1.207 (Column G).

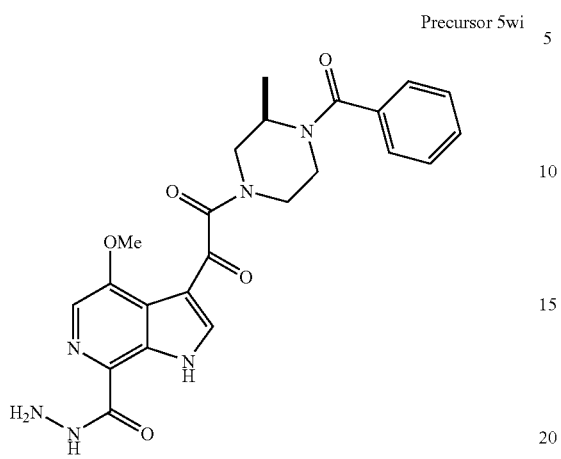

Precursor 5wi

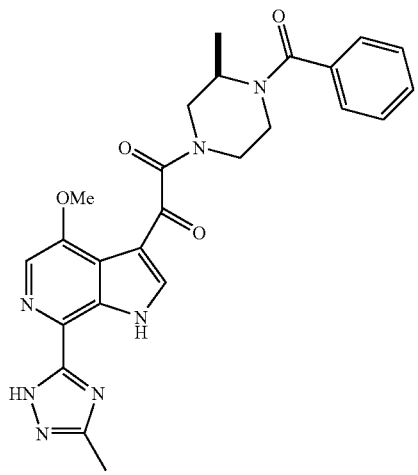

Example 334

A mixture of precursor 5wh in a solution of HCl in 1,4-dioxane (0.2 mL, 4 M) was stirred for 3.5 hr at ambient temperature. The volatiles were evaporated in vacuo, and the crude mixture was purified via reverse phase preparative HPLC using the following method: Start % B=0, Final % B=100, Gradient time=6 min, Flow Rate=30 mL/min, Column: Xerra Prep MS C18 5 μm 19×50 mm, Fraction Collection: 3.20-3.80 min. $^1$H NMR: (CD$_3$OD) δ 8.74, 8.71 (s, 1H), 8.31, 8.28 (s, 1H), 7.47-7.44 (m, 5H), 4.46-3.35 (m, 7H), 4.18, 4.10 (s, 3H), 1.38-1.22 (m, 3H); LC/MS: (ES+) m/z (M+H)$^+$=465, HPLC R$_t$=0.850 (Column G).

EXAMPLE 333 AND EXAMPLE 334

Thioacetamide (2 mg, 22 μmol) was added to Example 333 (10 mg, 20 μmol, HCl salt) in a round-bottom flask. The mixture was heated to 150° C. for 20 minutes, after which it was cooled to ambient temperature, and diluted with MeOH. Purification of the desired compound Example 334 was performed via preparative reverse phase HPLC using the following method: Start % B=0, Final % B=100, Gradient time=6 min, Flow Rate=30 mL/min, Column: Xerra Prep MS C18 5 μm 19×50 mm, Fraction Collection: 3.47-3.86 min. $^1$H NMR: (CD$_3$OD) δ 8.64, 8.62 (s, 1H), 8.04 (b s, 1H), 7.49-7.44 (m, 5H), 4.37-3.44 (m, 7H), 4.16, 4.14 (s, 3H), 2.63 (s, 3H), 1.36-1.32 (m, 3H); LC/MS: (ES+) m/z (M+H)$^+$=488, HPLC R$_t$=0.973 (column G).

The following examples were prepared in a similar manner as above.

EXAMPLE 335

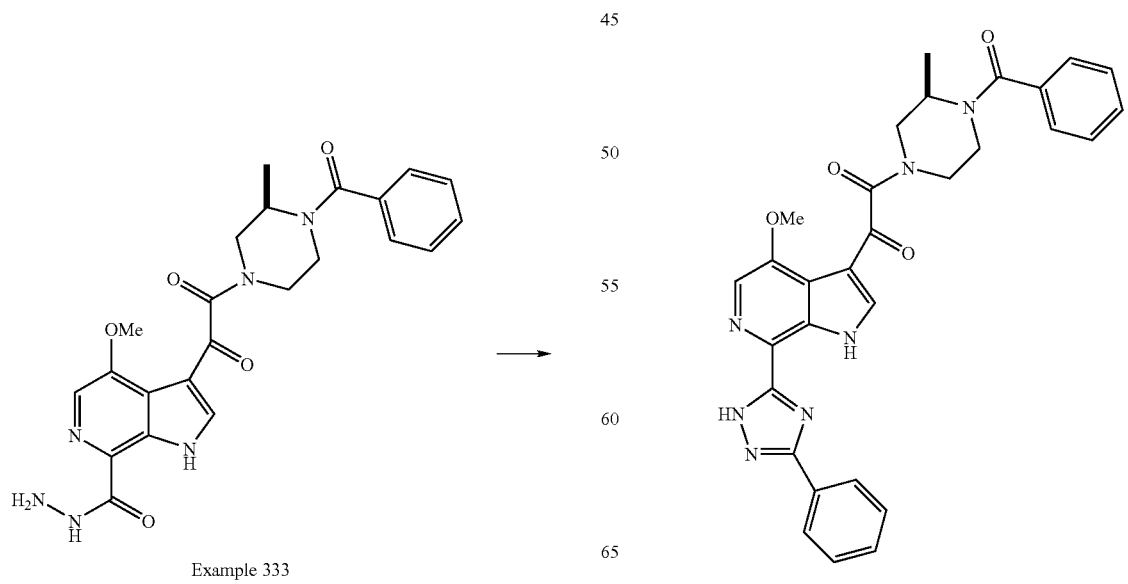

Example 333

PREPARATION OF EXAMPLE 335

$^1$H NMR: (CD$_3$OD) δ 8.60, 8.58 (s, 1H), 8.12 (d, J=3, 1H), 7.71-7.67 (m, 1H), 7.59-7.54 (m, 4H), 7.50-7.46 (m, 5H), 4.37-3.44 (m, 7H), 4.16, 4.14 (s, 3H), 1.37, 1.33 (d, J=6.5, 3H); LC/MS: (ES+) m/z (M+H)$^+$=550, HPLC R$_t$=1.283 (column G).

EXAMPLE 336

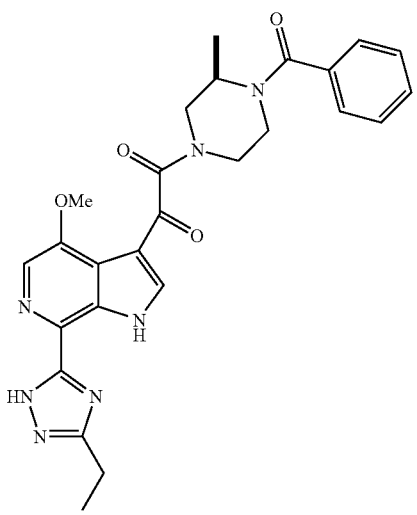

EXAMPLE 336

$^1$H NMR: (CD$_3$OD) δ 8.66, 8.64 (s, 1H), 8.04 (d, J=3, 1H), 7.49-7.40 (m, 5H), 4.41-3.44 (m, 7H), 4.16, 4.14 (s, 3H), 3.00 (q, J=7.5, 2H), 1.46 (t, J=7.5, 3H), 1.36-1.32 (m, 3H); LC/MS: (ES+) m/z (M+H)$^+$=502, HPLC R$_t$=1.007 (column G).

EXAMPLE 337

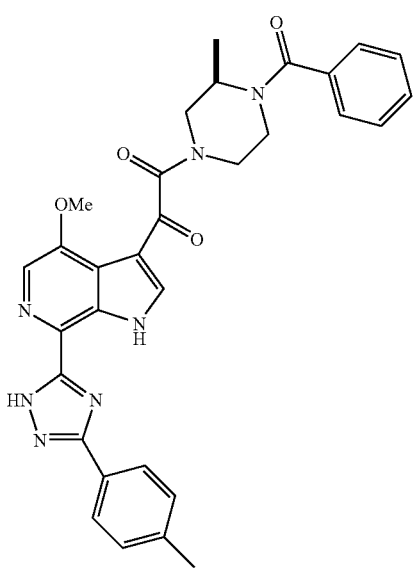

EXAMPLE 337

$^1$H NMR: (CD$_3$OD) δ 8.59, 8.57 (s, 1H), 8.11 (b d, 1H), 7.48-7.40 (m, 9H), 4.46-3.39 (m, 7H), 4.16, 4.14 (s, 3H), 2.45 (s, 3H), 1.40-1.29 (m, 3H); LC/MS: (ES+) m/z (M+H)$^+$=564, HPLC R$_t$=1.363 (column G).

EXAMPLE 338

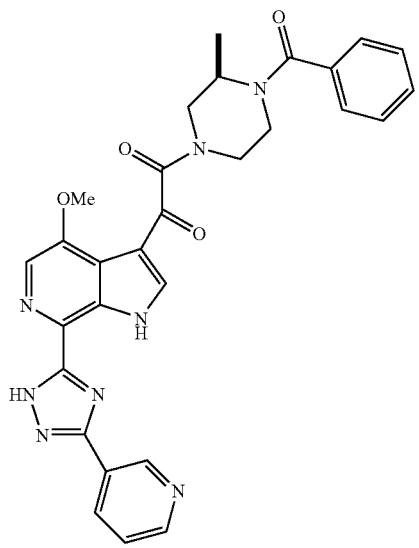

EXAMPLE 338

$^1$H NMR: (CD$_3$OD) δ 9.62 (s, 1H), 9.11 (s, 1H), 8.82 (d, J=5.5, 1H), 8.47 (d, J=8.5, 1H), 8.19 (s, 1H), 7.98 (s, 1H), 7.49-7.46 (m, 5H), 4.64-3.35 (m, 7H), 4.14, 4.13 (s, 3H), 1.37, 1.32 (d, J=7, 3H); LC/MS: (ES+) m/z (M+H)$^+$=551, HPLC R$_t$=1.090 (column G).

EXAMPLE 339

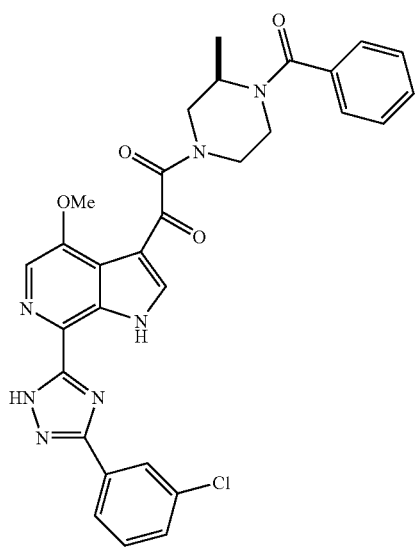

EXAMPLE 339

¹H NMR: (CD₃OD) δ 8.50 (s, 1H), 8.17 (b d, 1H), 7.53-7.45 (m, 9H), 4.64-3.35 (m, 7H), 4.14, 4.13 (s, 3H), 1.37, 1.32 (d, J=6.5, 7, 3H); LC/MS: (ES+) m/z (M+H)⁺=584, HPLC R$_t$=1.427 (column G).

EXAMPLE 340

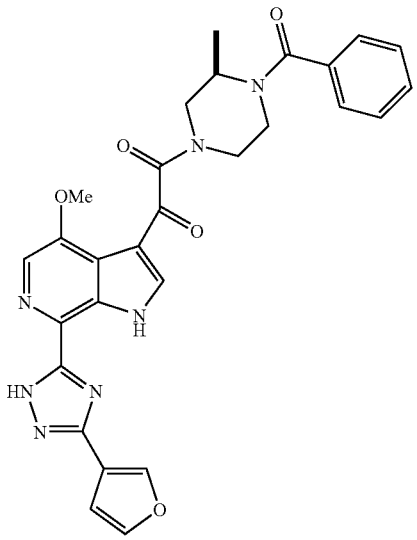

EXAMPLE 340

¹H NMR: (CD₃OD) δ 8.56, 8.55 (s, 1H), 8.36 (s, 1H), 8.10 (s, 1H), 7.72 (s, 1H), 7.48-7.45 (m, 5H), 7.09 (s, 1H), 4.64-3.44 (m, 7H), 4.15, 4.14 (s, 3H), 1.36-1.32 (m, 3H); LC/MS: (ES+) m/z (M+H)⁺=540, HPLC R$_t$=1.133 (column G).

EXAMPLE 341

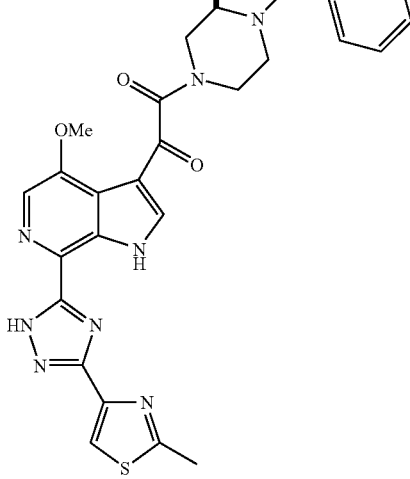

EXAMPLE 341

¹H NMR: (CD₃OD) δ 8.54, 8.51 (s, 1H), 8.20 (s, 1H), 8.14 (s, 1H), 7.48-7.39 (m, 5H), 4.71-3.44 (m, 7H), 4.14, 4.13 (s, 3H), 2.85 (s, 3H), 1.37-1.29 (m, 3H); LC/MS: (ES+) m/z (M+H)⁺=571, HPLC R$_t$=1.450 (column G).

EXAMPLE 342

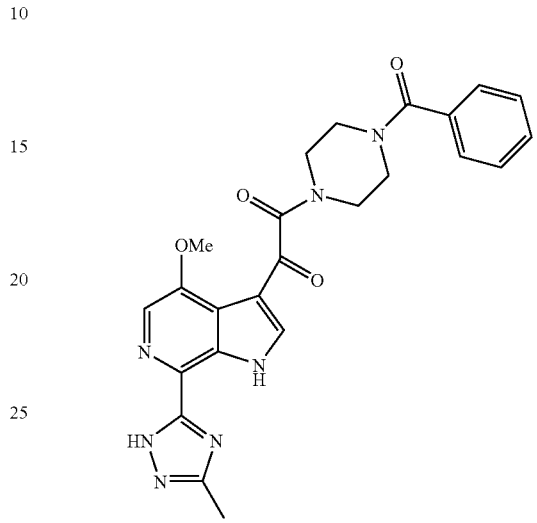

EXAMPLE 342

¹H NMR: (CD₃OD) δ 8.64 (s, 1H), 8.04 (s, 1H), 7.48 (s, 5H), 4.16 (s, 3H), 3.92-3.39 (m, 8H), 2.64 (s, 3H); LC/MS: (ES+) m/z (M+H)⁺=474, HPLC R$_t$=0.903 (column G).

EXAMPLES 343 AND 344

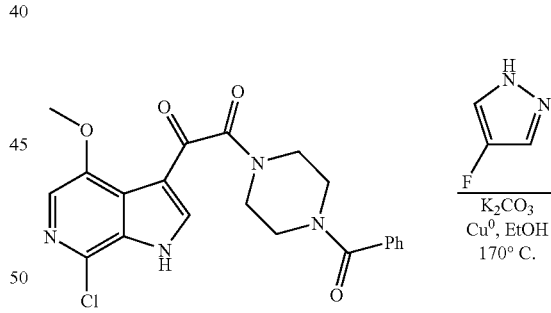

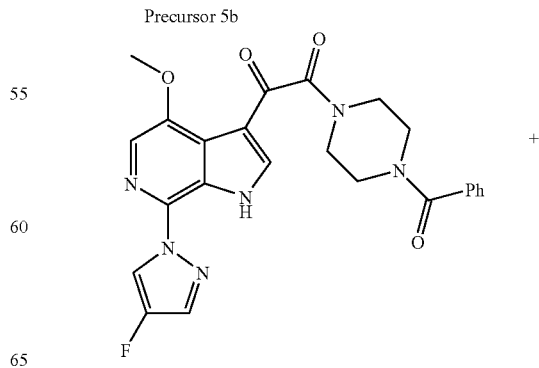

Example 343

-continued

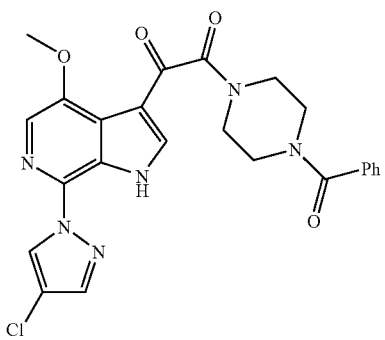

Example 344

Precursor 5b (60 mg, 0.14 mmol), 4-fluoropyrazole (0.30 mL) (prepared as described in Molines, H.; Wakselman, C. *J. Org. Chem.* 1989, 54, 5618-5620), copper(0) (8.0 mg, 0.13 mmol), $K_2CO_3$ (15 mg, 0.11 mmol) and EtOH (0.30 mL) were combined in a sealed tube flushed with nitrogen and heated at 170° C. with microwave irradiation for 1.5 h. The reaction was cooled, filtered and concentrated. The residue was purified by preparative HPLC under the standard conditions described above to provide (6.6 mg, 0.014 mmol) of Example 343 as a yellow solid and Example 344 (3.1 mg. 0.006 mmol) as a greenish solid.

EXAMPLE 343

$^1$H NMR (500 MHz, $CD_3OD$) δ 8.56 (d, J=4.3 Hz, 1H), 8.27 (s, 1H), 7.82-7.79 (m, 2H), 7.47 (br s, 5H), 4.03 (s, 3H), 3.97-3.45 (m, 8H). MS m/z: $(M+H)^+$ calcd for $C_{24}H_{21}FN_6O_2$: 477.16; found 477.16. HPLC retention time: 1.45 minutes (column G).

EXAMPLE 344

$^1$H NMR (500 MHz, $CDCl_3$) δ 11.16 (br s, 1H), 8.59 (s, 1H), 8.19 (s, 1H), 7.78-7.62 (m, 2H), 7.43 (br s, 5H), 4.04 (s, 3H), 3.987-3.40 (m, 8H). MS m/z: $(M+H)^+$ calcd for $C_{24}H_{21}ClN_6O_2$: 493.13; found 493.12. HPLC retention time: 1.59 minutes (column G).

EXAMPLE 353

Precursor 5mn

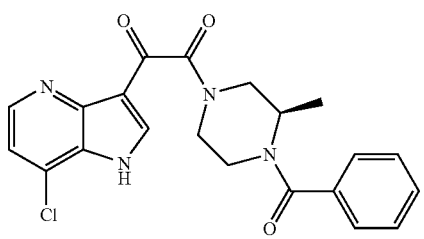

-continued

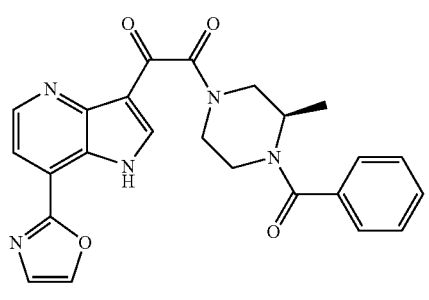

Example 353

Example 353 was prepared from the corresponding 7-chloro precursor 5 nm and 2-tributyl stannyl oxazole via the standard Stille coupling conditions described above. The 7-chloro precursor was prepared similarly to precursor 5d except that 2-(R) methyl piperazine benzamide (precursor 17b) was utilized. Example 353, 4-azaindole-7-(2'-oxazole): $^1$H NMR (500 MHz, $CD_3OD$) δ 8.68 (s, 0.5H), 8.67 (s, 0.5H), 8.45 (s, 0.5H), 8.43 (s, 0.5H), 8.18 (s, 1H), 7.86 (d, J=4.9 Hz, 0.5H), 7.85 (d, J=4.9 Hz, 0.5H), 7.55 (s, 1H), 7.50-7.40 (m, 5H), 4.45-3.06 (m, 7H), 1.48 (d, J=6.7 Hz, 1.5H) 1.24 (d, J=6.7 Hz, 1.5H). MS m/z: $(M+H)^+$ calcd for $C_{24}H_{22}N_5O_4$: 444.16; found 444.23. HPLC retention time: 0.90 minutes (column G).

EXAMPLE 354

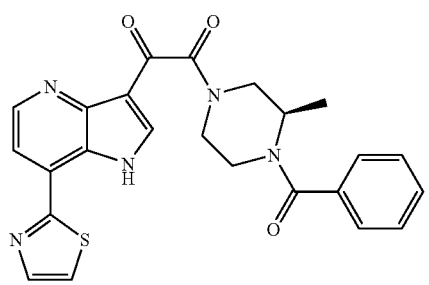

Example 354

Example 354 was prepared from the corresponding 7-chloro precursor 5 nm and 2-tributyl stannyl thiazole via the standard Stille coupling conditions described above. The 7-chloro precursor was prepared similarly to precursor 5d except that 2-(R) methyl piperazine benzamide (precursor 17b) was utilized. Example 354: 4-azaindole-7-(2'-thiazole): $^1$H NMR (500 MHz, $CD_3OD$) δ 8.80 (s, 0.5H), 8.74-8.71 (m, 1.5H), 8.35 (d, J=3.5 Hz, 0.5H), 8.35 (d, J=3.5 Hz, 0.5H), 8.26 (d, J=3.5 Hz, 0.5H), 8.25 (d, J=3.5 Hz, 0.5H), 8.14 (d, J=3.1 Hz, 0.5H), 8.14 (d, J=3.1 Hz, 0.5H), 7.50-7.42 (m, 5H), 4.48-3.08 (m, 7H), 1.36 (d, J=6.7 Hz, 1.5H) 1.32 (d, J=6.7 Hz, 1.5H). MS m/z: $(M+H)^+$ calcd for $C_{24}H_{22}N_5O_3S$: 460.14; found 460.20. HPLC retention time: 0.94 minutes (column G).

EXAMPLE 355

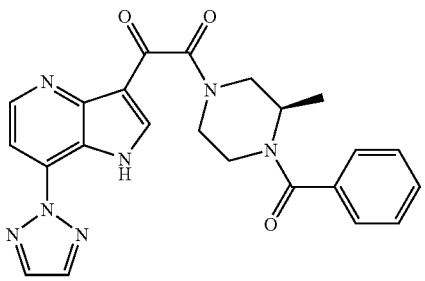

Example 355

Example 355 was prepared via the procedure used for Example 205 from the corresponding 7-chloro precursor 5 nm and 1,2,3, triazole. The 7-chloro precursor was prepared similarly to precursor 5d except that 2-(R) methyl piperazine benzamide (precursor 17b) was utilized. Example 355, 4-aza-indole-7-(2'-triazole): $^1$H NMR (500 MHz, CD$_3$OD) δ 8.79-8.76 (m, 1H), 8.78 (s, 0.5H), 8.70 (s, 0.5H), 8.44 (d, J=5.9 Hz, 0.5H), 8.43 (d, J=5.9 Hz, 0.5H), 8.38 (s, 1H), 8.38 (s, 1H), 7.51-7.42 (m, 5H), 4.50-3.21 (m, 7H), 1.37 (d, J=6.7 Hz, 1.5H) 1.32 (d, J=6.7 Hz, 1.5H). MS m/z: (M+H)$^+$ calcd for C$_{23}$H$_{22}$N$_7$O$_3$: 444.17; found 444.26. HPLC retention time: 0.90 minutes (column G).

EXAMPLE 356

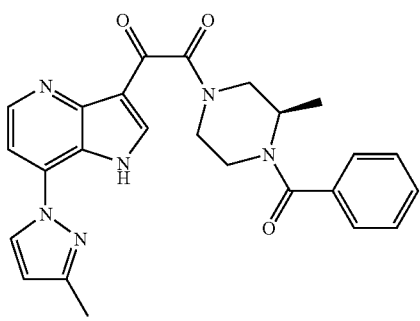

Example 356

Example 356 was prepared via the procedure used for Example 205 from the corresponding 7-chloro precursor 5 nm and 3-methylpyrazole. The 7-chloro precursor was prepared similarly to precursor 5d except that 2-(R) methyl piperazine benzamide (precursor 17b) was utilized. Example 356, 4-azaindole-7-(3'-methyl-2'-pyrazole): $^1$H NMR (500 MHz, CD$_3$OD) δ 8.73-8.71 (m, 1H), 8.70 (s, 0.5H), 8.63 (s, 0.5H), 8.64-8.60 (m, 1H), 8.06 (s, 0.5H), 8.04 (s, 0.5H), 7.52-7.42 (m, 5H), 6.68 (s, 0.5H), 6.67 (s, 0.5H), 4.61-3.21 (m, 7H), 2.51 (s, 3H), 1.35 (d, J=6.5 Hz, 1.5H) 1.32 (d, J=6.5 Hz, 1.5H). MS m/z: (M+H)$^+$ calcd for C$_{25}$H$_{25}$N$_6$O$_3$: 457.19; found 457.33. HPLC retention time: 1.04 minutes (column G).

Biology
"μM" means micromolar;
"mL" means milliliter;
"μl" means microliter;
"mg" means milligram;

The materials and experimental procedures used to obtain the results reported in Tables 1-5 are described below.

Cells:
Virus production—Human embryonic Kidney cell line, 293, propagated in Dulbecco's Modified Eagle Medium (Life Technologies, Gaithersburg, Md.) containing 10% fetal Bovine serum (FBS, Sigma, St. Louis, Mo.).

Virus infection—Human epithelial cell line, HeLa, expressing the HIV-1 receptors CD4 and CCR5 was propagated in Dulbecco's Modified Eagle Medium (Life Technologies, Gaithersburg, Md.) containing 10% fetal Bovine serum (FBS, Sigma, St. Louis, Mo.) and supplemented with 0.2 mg/mL Geneticin (Life Technologies, Gaithersburg, Md.) and 0.4 mg/mL Zeocin (Invitrogen, Carlsbad, Calif.).

Virus—Single-round infectious reporter virus was produced by co-transfecting human embryonic Kidney 293 cells with an HIV-1 envelope DNA expression vector and a proviral cDNA containing an envelope deletion mutation and the luciferase reporter gene inserted in place of HIV-1 nef sequences (Chen et al, Ref. 41). Transfections were performed using lipofectAMINE PLUS reagent as described by the manufacturer (Life Technologies, Gaithersburg, Md.).

Experiment
1. Compound was added to HeLa CD4 CCR5 cells plated in 96 well plates at a cell density of 5×10$^4$ cells per well in 100 μl Dulbecco's Modified Eagle Medium containing 10% fetal Bovine serum at a concentration of <20 μM.
2. 100 μl of single-round infectious reporter virus in Dulbecco's Modified Eagle Medium was then added to the plated cells and compound at an approximate multiplicity of infection (MOI) of 0.01, resulting in a final volume of 200 μl per well and a final compound concentration of <10 μM.
3. Samples were harvested 72 h after infection.
4. Viral infection was monitored by measuring luciferase expression from viral DNA in the infected cells using a luciferase reporter gene assay kit (Roche Molecular Biochemicals, Indianapolis, Ind.). Infected cell supernatants were removed and 50 μl of Dulbecco's Modified Eagle Medium (without phenol red) and 50 μl of luciferase assay reagent reconstituted as described by the manufacturer (Roche Molecular Biochemicals, Indianapolis, Ind.) was added per well. Luciferase activity was then quantified by measuring luminescence using a Wallac microbeta scintillation counter.
5. The percent inhibition for each compound was calculated by quantifying the level of luciferase expression in cells infected in the presence of each compound as a percentage of that observed for cells infected in the absence of compound and subtracting such a determined value from 100.
6. An EC$_{50}$ provides a method for comparing the antiviral potency of the compounds of this invention. The effective concentration for fifty percent inhibition (EC$_{50}$) was calculated with the Microsoft Excel Xlfit curve fitting software. For each compound, curves were generated from percent inhibition calculated at 10 different concentrations by using a four parameter logistic model (model 205). The EC$_{50}$ data for the compounds is shown in Tables 2-4. Table 1 is the key for the data in Tables 2-4.

Cytoxicity assays were conducted with the same HeLa using methodology well known in the art. This method has been described in the literature (S Weislow, R Kiser, D L Fine, J Bader, R H Shoemaker and M R Boyd: New soluble-formazan assay for HIV-1 cytopathic effects: application to high-flux screening of synthetic and natural products for AIDS-antiviral activity. Journal of the National Cancer Institute. 81(8):577-586, 1989.

Cells were incubated in the presence of drug for six days, after which cell viability was measured using a dye reduction assay (MTT) and determined as a CC50. This assay measures the intracellular reducing activity present in actively respiring cells.

Results

TABLE 1

Biological Data Key for $EC_{50}s$

| Compounds* with $EC_{50}s$ > 5 μM | Compounds with $EC_{50}s$ > 1 μM but <5 μM | Compounds with EC50 > 50 nM but not yet tested at higher concentrations | Compounds with EC50 < 1 μM |
|---|---|---|---|
| Group C | Group B | Group A' | Group A |

*Some of these compounds may have been tested at a concentration lower than their $EC_{50}$ but showed some ability to cause inhibition and thus should be evaluated at a higher concentration to determine the exact $EC_{50}$.

TABLE 2

In Tables 2-5, $X_2$, $X_4$ etc. indicates the point of attachment.

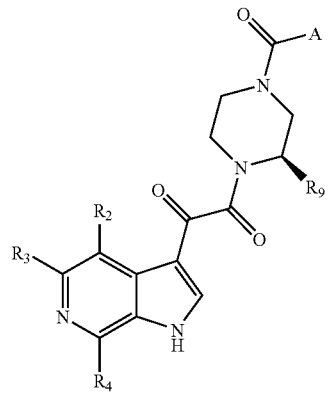

Examples

| Table Entry (Example Number.) | R2 | R3 | R4 | R9 | A | $EC_{50}$ Group from Table 1 |
|---|---|---|---|---|---|---|
| 1 (Example 1) | H | H | $X_2$—⟨phenyl⟩—F | $CH_3$ | $X_4$—⟨phenyl⟩ | A |
| 2 (Example 2) | H | H | $X_2$—⟨phenyl⟩—Cl | $CH_3$ | $X_4$—⟨phenyl⟩ | A |
| 4 (Example 4) | H | H | $X_2$—⟨phenyl⟩—$CO_2H$ | H | $X_4$—⟨phenyl⟩ | A |
| 5 (Example 5) | H | H | $X_2$—⟨benzodioxole⟩ | $CH_3$ | $X_4$—⟨phenyl⟩ | A |
| 6 (Example 6) | H | H | $X_2$—⟨furyl⟩ | $CH_3$ | $X_4$—⟨phenyl⟩ | A |

TABLE 2-continued

In Tables 2-5, X₂, X₄ etc. indicates the point of attachment.

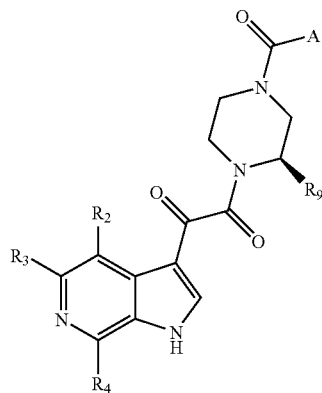

Examples

| Table Entry (Example Number.) | R2 | R3 | R4 | R9 | A | EC$_{50}$ Group from Table 1 |
|---|---|---|---|---|---|---|
| 7 (Example 7) | H | H | X₂—furan-2-yl | H | X₄—phenyl | A |
| 8 (Example 8) | H | H | X₂—benzofuran-2-yl | H | X₄—phenyl | A |
| 9 (Example 9) | H | H | X₂—thiophen-2-yl | CH₃ | X₄—phenyl | A |
| 10 (Example 16) | H | H | X₂—pyrimidin-5-yl | CH₃ | X₄—phenyl | A |
| 11 (Example 17) | H | H | X₂—pyrimidin-5-yl | H | X₄—phenyl | A |
| 12 (Example 18) | H | H | X₂—pyridin-3-yl | CH₃ | X₄—phenyl | A |
| 13 (Example 10) | H | H | X₂—pyridin-4-yl | H | X₄—phenyl | A |

TABLE 2-continued

In Tables 2-5, X₂, X₄ etc. indicates the point of attachment.

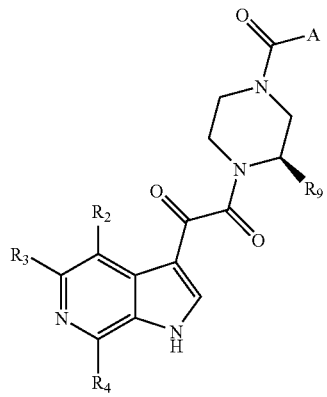

Examples

| Table Entry (Example Number.) | R2 | R3 | R4 | R9 | A | EC₅₀ Group from Table 1 |
|---|---|---|---|---|---|---|
| 14 (Example 19) | H | H | (X₂-pyridin-2-yl) | H | (X₄-phenyl) | A |
| 15 (Example 11) | H | H | (X₂-quinolin-8-yl) | H | (X₄-phenyl) | A' |
| 16 (Example 20) | H | H | (X₂-thiazol-2-yl) | CH₃ | (X₄-phenyl) | A |
| 17 (Example 21) | H | H | (X₂-thiazol-2-yl) | H | (X₄-phenyl) | A |
| 18 (Example 22) | OMe | H | (X₂-1-methylpyrazol-3-yl) | H | (X₄-phenyl) | A |
| 19 (Example 23) | OMe | H | (X₂-pyridazin-4-yl) | H | (X₄-phenyl) | A |

TABLE 2-continued

In Tables 2-5, $X_2$, $X_4$ etc. indicates the point of attachment.

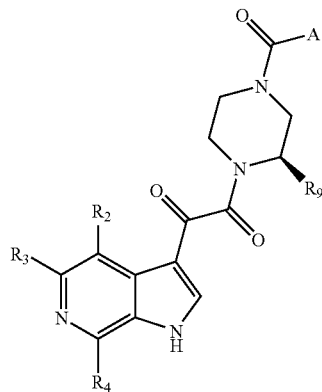

Examples

| Table Entry (Example Number.) | R2 | R3 | R4 | R9 | A | EC$_{50}$ Group from Table 1 |
|---|---|---|---|---|---|---|
| 20 (Example 24) | OMe | H | ![2-aminopyrimidin-5-yl with X2] | H | ![phenyl with X4] | A |
| 21 (Example 25) | OMe | H | ![pyridin-3-yl with X2] | H | ![phenyl with X4] | A |
| 22 (Example 26) | OMe | H | ![5-aminopyrazin-2-yl with X2] | H | ![phenyl with X4] | A |
| 23 (Example 27) | OMe | H | ![1-methylimidazol-2-yl with X2] | H | ![phenyl with X4] | A |
| 24 (Example 28) | OMe | H | ![1-methylpyrrol-2-yl with X2] | H | ![phenyl with X4] | A |

TABLE 2-continued
In Tables 2-5, X$_2$, X$_4$ etc. indicates the point of attachment.
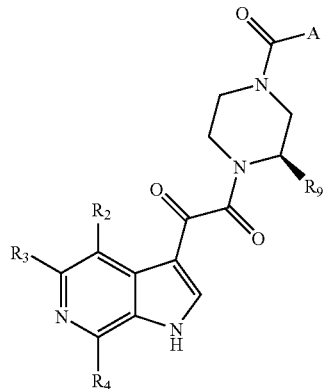
Examples
| Table Entry (Example Number.) | R2 | R3 | R4 | R9 | A | EC$_{50}$ Group from Table 1 |
|---|---|---|---|---|---|---|
| 25 (Example 29) | F | H | ![X$_2$-pyrazole-N-Me] | H | ![X$_4$-phenyl] | A |
| 26 (Example 30) | F | H | ![X$_2$-pyridazine] | H | ![X$_4$-phenyl] | A |
| 27 (Example 15) | OMe | H | ![X$_2$-pyrazine-C(O)NH-C(Me)$_3$] | H | ![X$_4$-phenyl] | A |
| 28 (Example 32) | OMe | H | ![X$_2$-pyrazine] | H | ![X$_4$-phenyl] | A |
| 29 (Example 33) | H | H | ![X$_2$-pyrazine] | Me | ![X$_4$-phenyl] | A |

TABLE 2-continued

In Tables 2-5, $X_2$, $X_4$ etc. indicates the point of attachment.

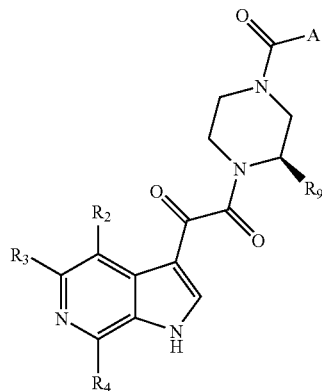

Examples

| Table Entry (Example Number.) | R2 | R3 | R4 | R9 | A | EC$_{50}$ Group from Table 1 |
|---|---|---|---|---|---|---|
| 30 (Example 34) | H | H | ![pyrazine X$_2$] | H | ![X$_4$-phenyl] | A |
| 31 (Example 35) | OMe | H | ![thiazole X$_2$] | H | ![X$_4$-phenyl] | A |
| 32 (Example 36) | OMe | H | ![pyridine X$_2$] | H | ![X$_4$-phenyl] | A |
| 33 (Example 37) | F | H | ![thiazole X$_2$] | Me | ![X$_4$-phenyl] | A |
| 34 (Example 38) | F | H | ![pyrazole X$_2$] | H | ![X$_4$-phenyl] | A |
| 35 (Example 39) | OMe | H | ![pyrazole X$_2$] | H | ![X$_4$-phenyl] | A |

TABLE 2-continued
In Tables 2-5, X₂, X₄ etc. indicates the point of attachment.
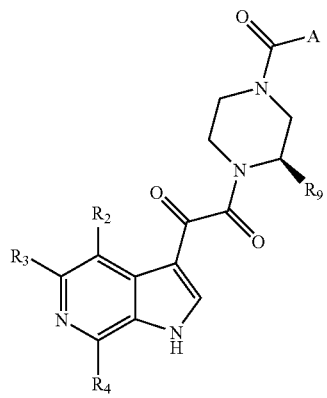
Examples
| Table Entry (Example Number.) | R2 | R3 | R4 | R9 | A | EC₅₀ Group from Table 1 |
|---|---|---|---|---|---|---|
| 36 (Example 40) | OMe | H | X₂-pyrimidin-5-yl | H | X₄-phenyl | A |
| 37 (Example 41) | F | H | X₂-pyrimidin-5-yl | Me | X₄-phenyl | A |
| 38 (Example 42) | F | H | X₂-pyrimidin-5-yl | H | X₄-phenyl | A |
| 41 (Example 45) | OMe | H | X₂-(2-ethoxy-thiazol-5-yl) | H | X₄-phenyl | A |
| 42 (Example 46) | OMe | H | X₂-(6-amino-pyrazin-2-yl) | H | X₄-phenyl | A |

TABLE 2-continued

In Tables 2-5, X$_2$, X$_4$ etc. indicates the point of attachment.

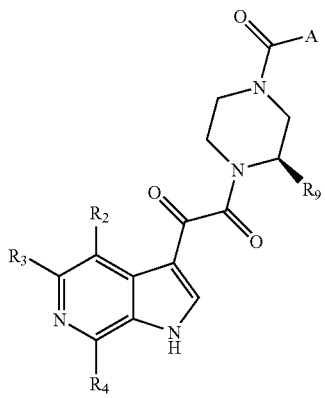

Examples

| Table Entry (Example Number.) | R2 | R3 | R4 | R9 | A | EC$_{50}$ Group from Table 1 |
|---|---|---|---|---|---|---|
| 43 (Example 47) | OMe | H | X$_2$-pyrazine-NHSO$_2$Me | H | X$_4$-phenyl | A |
| 45 (Example 49) | OMe | H | X$_2$-pyrimidine | H | X$_4$-phenyl | A |
| 46 (Example 13) | OMe | H | X$_2$-(2,4-dimethoxy)pyrimidine | H | X$_4$-phenyl | A |
| 47 (Example 55) | OMe | H | X$_2$-pyrazine-C(O)NH$_2$ | H | X$_4$-phenyl | A |
| 48 (Example 50) | OMe | H | X$_2$-thiazole | H | X$_4$-pyridine | A |

TABLE 2-continued

In Tables 2-5, $X_2$, $X_4$ etc. indicates the point of attachment.

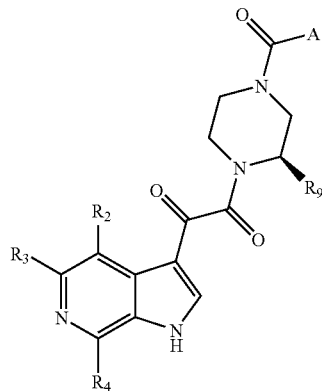

Examples

| Table Entry (Example Number.) | R2 | R3 | R4 | R9 | A | EC$_{50}$ Group from Table 1 |
|---|---|---|---|---|---|---|
| 49 (Example 14) | OMe | H | X$_2$-pyridin-4-yl | H | X$_4$-phenyl | A |
| 50 (Example 68) | OMe | H | X$_2$-(4,6-dimethoxy)pyrimidin-2-yl (MeO, OMe) | H | X$_4$-phenyl | A |
| 51 (Example 69) | OMe | H | X$_2$-(6-methoxy)pyridin-3-yl (OMe) | H | X$_4$-phenyl | A |
| 52 (Example 70) | OMe | H | X$_2$-(2-diethylamino)thiazol-4-yl | H | X$_4$-phenyl | A |
| 53 (Example 71) | OMe | H | X$_2$-thiazol-5-yl | H | X$_4$-phenyl | A |

TABLE 2-continued

In Tables 2-5, $X_2$, $X_4$ etc. indicates the point of attachment.

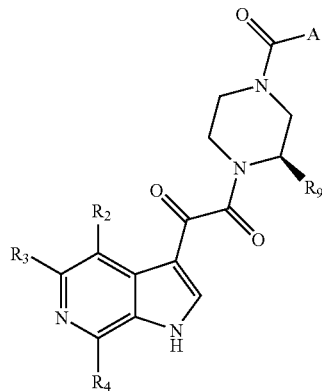

Examples

| Table Entry (Example Number.) | R2 | R3 | R4 | R9 | A | EC$_{50}$ Group from Table 1 |
|---|---|---|---|---|---|---|
| 54 (Example 72) | OMe | H | $X_2$–pyrazine–NMe$_2$ | H | $X_4$–phenyl | A |
| 55 (Example 82) | OMe | H | $X_2$–thiophene | H | $X_4$–phenyl | A |
| 56 (Example 73) | OMe | H | $X_2$–furan | H | $X_4$–phenyl | A |
| 57 (Example 83) | OMe | H | $X_2$–thiophene (3-yl) | H | $X_4$–phenyl | A |
| 58 (Example 84) | OMe | H | $X_2$–thiophene–CHO | H | $X_4$–phenyl | A |
| 59 (Example 85) | OMe | H | $X_2$–furan–CHO | H | $X_4$–phenyl | A |

TABLE 2-continued

In Tables 2-5, X₂, X₄ etc. indicates the point of attachment.

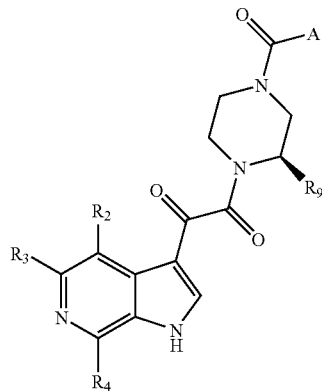

Examples

| Table Entry (Example Number.) | R2 | R3 | R4 | R9 | A | EC₅₀ Group from Table 1 |
|---|---|---|---|---|---|---|
| 60 (Example 74) | OMe | H | ![oxazole with X₂] | H | ![X₄-phenyl] | A |
| 61 (Example 75) | OMe | H | ![pyridine with X₂ and NH₂] | H | ![X₄-phenyl] | A |
| 62 (Example 76) | OMe | H | ![pyridine with X₂ and Me] | H | ![X₄-phenyl] | A |
| 63 (Example 77) | OMe | H | ![pyridine with X₂ and OMe] | H | ![X₄-phenyl] | A |
| 64 (Example 78) | OMe | H | ![thiazole with X₂ and NHAc] | H | ![X₄-phenyl] | A |
| 65 (Example 80) | OMe | H | ![thiazole with X₂ and NH₂] | H | ![X₄-phenyl] | A |

TABLE 2-continued
In Tables 2-5, X₂, X₄ etc. indicates the point of attachment.
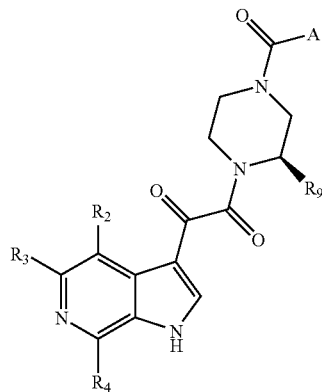
Examples
| Table Entry (Example Number.) | R2 | R3 | R4 | R9 | A | EC₅₀ Group from Table 1 |
|---|---|---|---|---|---|---|
| 66 (Example 79) | OMe | H | $X_2$—pyrazine—NH-ethyl | H | $X_4$—phenyl | A |
| 67 (Example 87) | OMe | H | $X_2$—furan—COOH | H | $X_4$—phenyl | A |
| 68 (Example 81) | OMe | H | $X_2$—furan | H | $X_4$—phenyl | A |
| 69 (Example 88) | OMe | H | $X_2$—thiazole—ethyl | H | $X_4$—phenyl | A |

TABLE 2-continued
In Tables 2-5, X$_2$, X$_4$ etc. indicates the point of attachment.
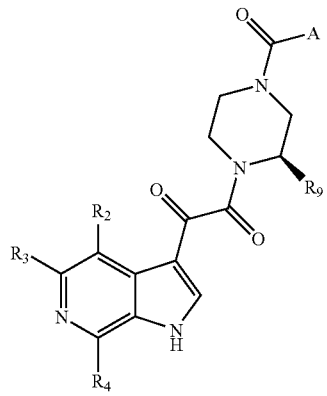
Examples
| Table Entry (Example Number.) | R2 | R3 | R4 | R9 | A | EC$_{50}$ Group from Table 1 |
|---|---|---|---|---|---|---|
| 70 (Example 89) | H | H | X$_2$-thiazole-isobutyl | H | X$_4$-phenyl | A |
| 71 (Example 90) | OMe | H | X$_2$-thiazole-isobutyl | H | X$_4$-phenyl | A |
| 72 (Example 91) | OMe | H | X$_2$-thiazole-sec-butyl | H | X$_4$-phenyl | A |
| 72 (Example 92) | OMe | H | X$_2$-thiazole-thiazole | H | X$_4$-phenyl | A |

TABLE 2-continued

In Tables 2-5, X₂, X₄ etc. indicates the point of attachment.

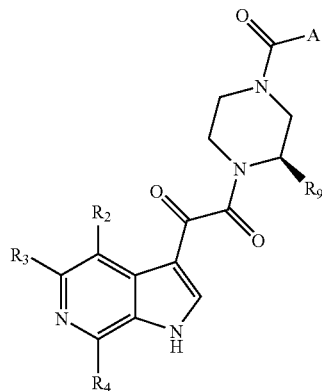

Examples

| Table Entry (Example Number.) | R2 | R3 | R4 | R9 | A | EC₅₀ Group from Table 1 |
|---|---|---|---|---|---|---|
| 73 (Example 93) | OMe | H | ![thiazole with SMe at X₂] | H | X₄-phenyl | A |
| 74 (Example 94) | OMe | H | ![furan-2-carboxamide N-methyl at X₂] | H | X₄-phenyl | A |
| 75 (Example 95) | F | H | ![pyrazine at X₂] | H | X₄-phenyl | A |
| 76 (Example 96) | Cl | H | ![tetrazole at X₂] | H | X₄-phenyl | A |
| 77 (Example 97) | OMe | H | ![hydroxypyrazine at X₂] | H | X₄-phenyl | A |

TABLE 2-continued
In Tables 2-5, $X_2$, $X_4$ etc. indicates the point of attachment.
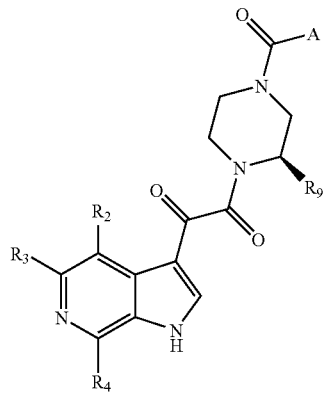
Examples
| Table Entry (Example Number.) | R2 | R3 | R4 | R9 | A | EC$_{50}$ Group from Table 1 |
|---|---|---|---|---|---|---|
| 78 (Example 98) | OMe | H | $X_2$-benzofuran-2-yl | H | $X_4$-phenyl | A |
| 79 (Example 99) | OMe | H | $X_2$-(5-acetamido)pyrazin-2-yl | H | $X_4$-phenyl | A |
| 80 (Example 100) | OMe | H | $X_2$-(3-amino-2-methoxy)pyrazin-5-yl | H | $X_4$-phenyl | A |
| 81 (Example 101) | OMe | H | $X_2$-(3-methylamino-2-methoxy)pyrazin-5-yl | H | $X_4$-phenyl | A |

TABLE 2-continued

In Tables 2-5, X$_2$, X$_4$ etc. indicates the point of attachment.

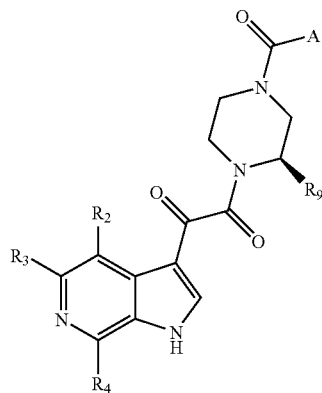

Examples

| Table Entry (Example Number.) | R2 | R3 | R4 | R9 | A | EC$_{50}$ Group from Table 1 |
|---|---|---|---|---|---|---|
| 82 (Example 102) | OMe | H | X$_2$-pyrazinyl | H | X$_4$-pyridyl | A |
| 83 (Example 103) | OMe | H | X$_2$-(5-dimethylamino)pyrazinyl | H | X$_4$-pyridyl | A |
| 84 (Example 104) | OMe | H | X$_2$-furo[3,2-c]pyridyl | H | X$_4$-phenyl | A |
| 85 (Example 105) | H | H | X$_2$-(5-dimethylamino)pyrazinyl | (R)-Me | X$_4$-pyridyl | A |
| 86 (Example 106) | H | H | X$_2$-(5-dimethylamino)pyrazinyl | (S)-Me | X$_4$-pyridyl | A |

TABLE 2-continued
In Tables 2-5, $X_2$, $X_4$ etc. indicates the point of attachment.
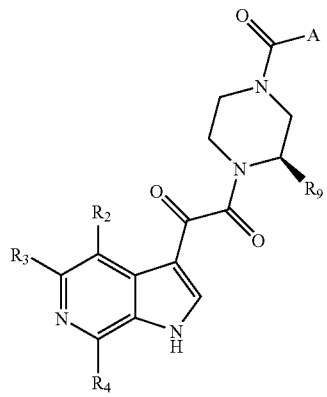
Examples
| Table Entry (Example Number.) | R2 | R3 | R4 | R9 | A | EC$_{50}$ Group from Table 1 |
|---|---|---|---|---|---|---|
| 87 (Example 107) | H | H | 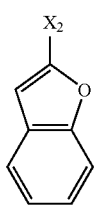 | (R)-Me | 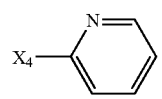 | A |
| 88 (Example 108) | H | H | 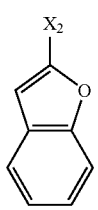 | (S)-Me | 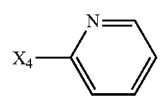 | A |
| 89 (Example 109) | H | H | 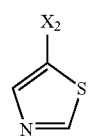 | (R)-Me | 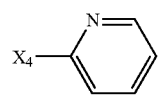 | A |
| 90 (Example 110) | H | H | 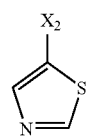 | (S)-Me | 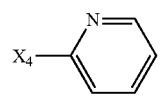 | A |
| 91 (Example 111) | H | H | 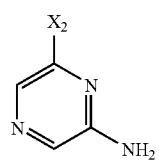 | (R)-Me | 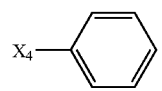 | A |

TABLE 2-continued
In Tables 2-5, X$_2$, X$_4$ etc. indicates the point of attachment.
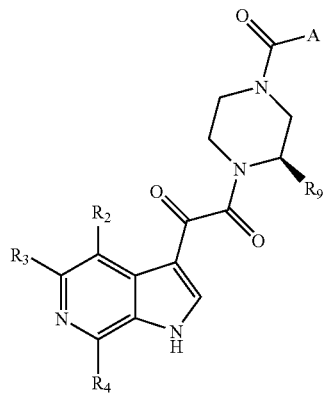
Examples
| Table Entry (Example Number.) | R2 | R3 | R4 | R9 | A | EC$_{50}$ Group from Table 1 |
|---|---|---|---|---|---|---|
| 92 (Example 112) | H | H | X$_2$—pyridine-NH$_2$ (2-amino) | (R)-Me | X$_4$—phenyl | A |
| 93 (Example 113) | H | H | X$_2$—pyridine-NH$_2$ | (R)-Me | X$_4$—phenyl | A |
| 94 (Example 114) | H | H | X$_2$—pyridine-NH$_2$ | (R)-Me | X$_4$—phenyl | A |
| 95 (Example 115) | OMe | H | X$_2$—pyrazine-NHMe | H | X$_4$—phenyl | A |

TABLE 2-continued

In Tables 2-5, $X_2$, $X_4$ etc. indicates the point of attachment.

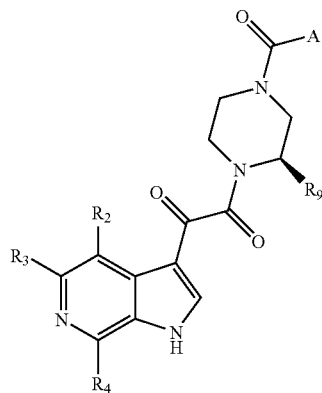

Examples

| Table Entry (Example Number.) | R2 | R3 | R4 | R9 | A | EC$_{50}$ Group from Table 1 |
|---|---|---|---|---|---|---|
| 96 (Example 116) | OMe | H | ![thiazole-pyrrolidinone]($X_2$-thiazol-2-yl-pyrrolidin-2-one) | H | $X_4$—phenyl | A |
| 97 (Example 117) | OMe | H | $X_2$-(2-methoxypyrimidin-5-yl) | H | $X_4$—phenyl | A |
| 98 (Example 118) | OMe | H | $X_2$-(2-(1H-pyrrol-1-yl)pyrimidin-5-yl) | H | $X_4$—phenyl | A |
| 99 (Example 119) | OMe | H | $X_2$-pyrimidin-4-yl | H | $X_4$—phenyl | A |
| 100 (Example 120) | OMe | H | $X_2$-pyridazin-3-yl | H | $X_4$—phenyl | A |

TABLE 2-continued
In Tables 2-5, $X_2$, $X_4$ etc. indicates the point of attachment.
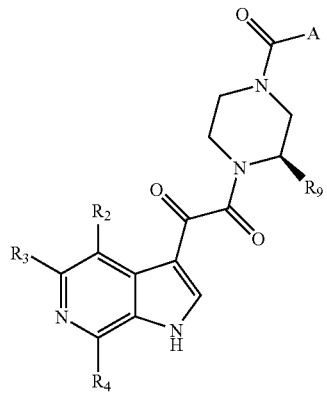
Examples
| Table Entry (Example Number.) | R2 | R3 | R4 | R9 | A | EC$_{50}$ Group from Table 1 |
|---|---|---|---|---|---|---|
| 101 (Example 121) | H | H | ![X2-pyrazine-OH] | (R)-Me | ![X4-phenyl] | A |
| 102 (Example 121-2) | H | H | ![X2-pyrazine N-oxide-OH] | (R)-Me | ![X4-phenyl] | A |
| 103 (Example 122) | H | H | ![X2-pyridine-OH] | (R)-Me | ![X4-phenyl] | A |
| 104 (Example 123) | H | H | ![X2-pyridone] | (R)-Me | ![X4-phenyl] | A |
| 105 (Example 124) | H | H | ![X2-pyridine-OH] | (R)-Me | ![X4-phenyl] | A |

TABLE 2-continued

In Tables 2-5, $X_2$, $X_4$ etc. indicates the point of attachment.

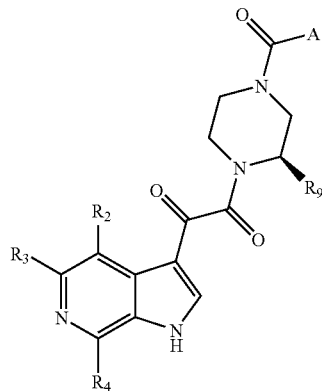

Examples

| Table Entry (Example Number.) | R2 | R3 | R4 | R9 | A | EC$_{50}$ Group from Table 1 |
|---|---|---|---|---|---|---|
| 106 (Example 125) | F | H | X$_2$-pyrimidin-4-yl | H | X$_4$-phenyl | A |
| 107 (Example 138) | OMe | H | X$_2$-(1-methyl-6-oxo-1,6-dihydropyrazin-3-yl) | H | X$_4$-phenyl | A |
| 108 (Example 139) | Br | H | X$_2$-pyrazol-1-yl | (R)-Me | X$_4$-phenyl | A |
| 109 (Example 140) | F | H | X$_2$-oxazol-2-yl | H | X$_4$-phenyl | A |
| 110 (Example 141) | F | H | X$_2$-pyrazin-2-yl | (R)-Me | X$_4$-pyridin-2-yl | A |

TABLE 2-continued

In Tables 2-5, $X_2$, $X_4$ etc. indicates the point of attachment.

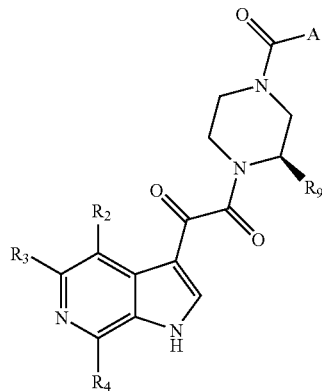

Examples

| Table Entry (Example Number.) | R2 | R3 | R4 | R9 | A | EC$_{50}$ Group from Table 1 |
|---|---|---|---|---|---|---|
| 112 (Example 143) | Cl | H | ![pyrazine-NH2 via X2] | H | ![phenyl via X4] | A |
| 113 (Example 144) | Cl | H | ![pyrimidine via X2] | H | ![phenyl via X4] | A |
| 114 (Example 145) | F | H | ![oxazole via X2] | H | ![phenyl via X4] | A |
| 115 (Example 146) | F | H | ![1,2,4-oxadiazole via X2] | H | ![phenyl via X4] | A |
| 116 (Example 147) | F | H | ![pyridine-NHC(O) via X2] | H | ![phenyl via X4] | A |
| 117 (Example 148) | F | H | ![imidazole via X2] | H | ![phenyl via X4] | A |

TABLE 2-continued
In Tables 2-5, $X_2$, $X_4$ etc. indicates the point of attachment.
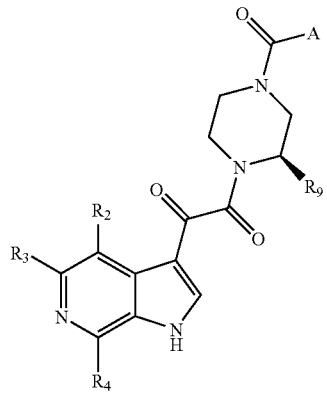
Examples
| Table Entry (Example Number.) | R2 | R3 | R4 | R9 | A | EC$_{50}$ Group from Table 1 |
|---|---|---|---|---|---|---|
| 118 (Example 149) | Cl | H | $X_2$—pyrazine-OH | H | $X_4$—phenyl | A |
| 119 (Example 150) | H | H | $X_2$—pyrazine-NH$_2$ | (R)-Me | $X_4$—phenyl | A |
| 120 (Example 151) | OMe | H | $X_2$—thiazole | H | $X_4$—pyridyl | A |
| 121 (Example 152) | Cl | H | $X_2$—C(O)NH-pyridyl | H | $X_4$—phenyl | A |
| 122 (Example 153) | H | H | $X_2$—pyrimidine-NH$_2$ | (R)-Me | $X_4$—phenyl | A |

TABLE 2-continued

In Tables 2-5, $X_2$, $X_4$ etc. indicates the point of attachment.

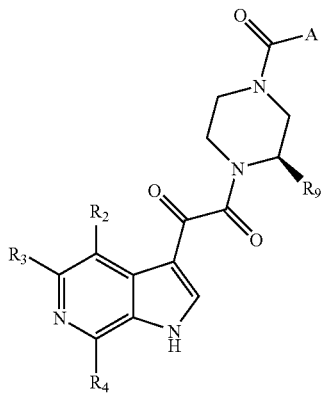

Examples

| Table Entry (Example Number.) | R2 | R3 | R4 | R9 | A | EC$_{50}$ Group from Table 1 |
|---|---|---|---|---|---|---|
| 123 (Example 154) | F | H | $X_2$-pyridazin-3-yl | H | $X_4$-phenyl | A |
| 124 (Example 155) | OMe | H | $X_2$-(6-hydroxypyrazin-2-yl) | H | $X_4$-phenyl | A |
| 125 (Example 156) | OMe | H | $X_2$-(4,4-dimethyl-4,5-dihydrooxazol-2-yl) | H | $X_4$-phenyl | A |
| 126 (Example 157) | H | H | $X_2$-(5-hydroxypyrazin-2-yl) | (R)-Me | $X_4$-phenyl | A |
| 127 (Example 165) | Cl | H | $X_2$-pyrazin-2-yl | H | $X_4$-C(O)OtBu | A |

TABLE 2-continued

In Tables 2-5, $X_2$, $X_4$ etc. indicates the point of attachment.

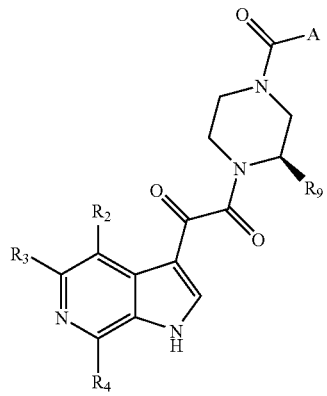

Examples

| Table Entry (Example Number.) | R2 | R3 | R4 | R9 | A | EC$_{50}$ Group from Table 1 |
|---|---|---|---|---|---|---|
| 128 (Example 166) | F | H | $X_2$-NHC(O)-(3-pyridyl) | H | 5-bromo-2-furyl ($X_4$) | |
| 129 (Example 167) | F | H | $X_2$-(1,2,4-oxadiazol-3-yl) | H | 5-bromo-2-furyl ($X_4$) | |
| 130 (Example 162) | H | H | $X_2$-(2-hydroxypyrimidin-5-yl) | (R)-Me | phenyl ($X_4$) | A |
| 131 (Example 163) | Cl | H | $X_2$-(1H-tetrazol-5-yl) | H | phenyl ($X_4$) | A |
| 132 (Example 164) | H | H | $X_2$-(4-carboxyphenyl) | (R)Me | phenyl ($X_4$) | A |

TABLE 2-continued
In Tables 2-5, $X_2$, $X_4$ etc. indicates the point of attachment.
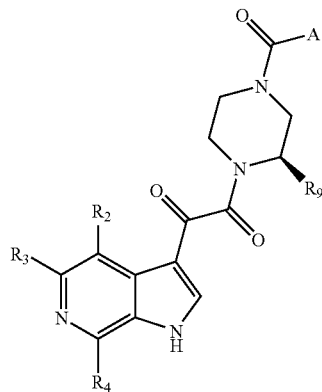
Examples
| Table Entry (Example Number.) | R2 | R3 | R4 | R9 | A | EC$_{50}$ Group from Table 1 |
|---|---|---|---|---|---|---|
| 133 (Example 169) | OMe | H | ![thiazole-NH-C(O)-pyridine with X$_2$] | H | ![X$_4$-phenyl] | |
| 134 (Precursor 5t) | OMe | H | ![pyrazine with X$_2$] | H | ![X$_4$-O-tBu] | A |
| 135 (Example 170) | H | H | ![phenyl-COOH with X$_2$] | (R)-Me | ![X$_4$-phenyl] | A |
| 136 (Example 171) | OMe | H | ![2-methylpyrimidine with X$_2$] | H | ![X$_4$-phenyl] | A |

TABLE 2-continued
In Tables 2-5, $X_2$, $X_4$ etc. indicates the point of attachment.
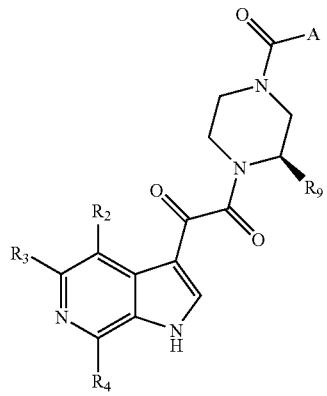
Examples
| Table Entry (Example Number.) | R2 | R3 | R4 | R9 | A | EC$_{50}$ Group from Table 1 |
|---|---|---|---|---|---|---|
| 137 (Example 172) | OMe | H | ![indole with X2] | H | ![2-pyridyl with X4] | A |
| 138 (Example 173) | OMe | H | ![thiazole with X2] | H | ![2-pyridyl with X4] | A |
| 139 (Example 174) | OMe | H | ![thiazole with X2] | H | ![phenyl with X4] | A |
| 140 (Example 175) | OMe | H | ![pyrazine with N(Me)CH2CH2NEt2] | H | ![phenyl with X4] | A |

TABLE 2-continued
In Tables 2-5, $X_2$, $X_4$ etc. indicates the point of attachment.
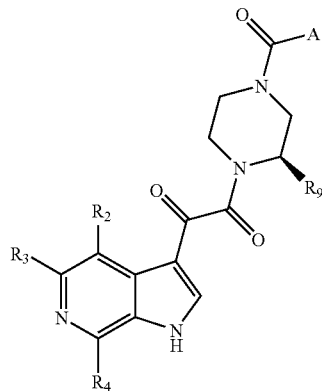
Examples
| Table Entry (Example Number.) | R2 | R3 | R4 | R9 | A | EC$_{50}$ Group from Table 1 |
|---|---|---|---|---|---|---|
| 141 (Example 176) | OMe | H | ![pyrazine with N(Me)CH2CH2NMe2] | H | ![phenyl] | A |
| 142 (Example 177) | OMe | H | ![pyrazine with piperazine] | H | ![phenyl] | A |
| 143 (Example 178) | OMe | H | ![pyrazine with morpholine] | H | ![phenyl] | A |

TABLE 2-continued
In Tables 2-5, $X_2$, $X_4$ etc. indicates the point of attachment.
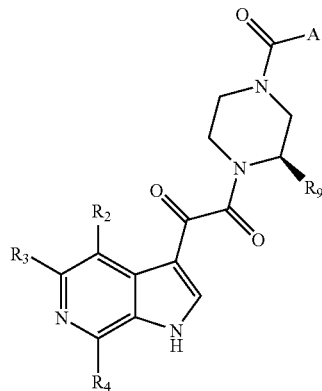
Examples
| Table Entry (Example Number.) | R2 | R3 | R4 | R9 | A | EC$_{50}$ Group from Table 1 |
|---|---|---|---|---|---|---|
| 144 (Example 179) | OMe | H | pyrazine with X$_2$ and NHEt | H | 2-pyridyl (X$_4$) | A |
| 145 (Example 180) | OMe | H | pyrazine with X$_2$ and Me | H | 2-pyridyl (X$_4$) | A |
| 146 (Example 181) | OMe | H | pyrazine with X$_2$ and cyclopropyl | H | 2-pyridyl (X$_4$) | A |
| 147 (Example 182) | OMe | H | pyrazine with X$_2$ and OMe | H | 2-pyridyl (X$_4$) | A |

TABLE 2-continued
In Tables 2-5, X₂, X₄ etc. indicates the point of attachment.
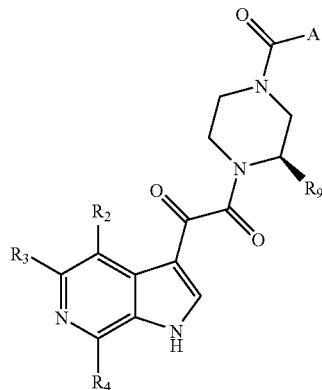
Examples
| Table Entry (Example Number.) | R2 | R3 | R4 | R9 | A | EC₅₀ Group from Table 1 |
|---|---|---|---|---|---|---|
| 148 (Example 183) | OMe | H | X₂-benzofuran-2-yl | H | X₄-pyridin-2-yl | A |
| 149 (Example 184) | OMe | H | X₂-(5-(N,N-diethylcarbamoyl)pyrazin-2-yl) | H | X₄-pyridin-2-yl | A |
| 150 (Example 185) | OMe | H | X₂-(5-(pyrrolidin-1-yl)pyrazin-2-yl) | H | X₄-pyridin-2-yl | A |
| 151 (Example 186) | OMe | H | X₂-quinoxalin-2-yl | H | X₄-pyridin-2-yl | A |

TABLE 2-continued

In Tables 2-5, X₂, X₄ etc. indicates the point of attachment.

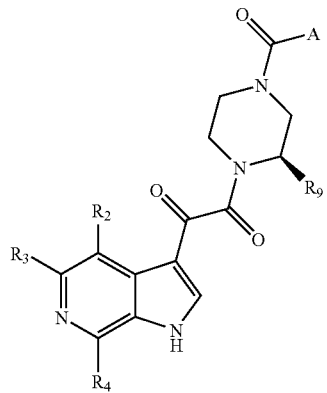

Examples

| Table Entry (Example Number.) | R2 | R3 | R4 | R9 | A | EC₅₀ Group from Table 1 |
|---|---|---|---|---|---|---|
| 152 (Example 187) | OMe | H | (1,2,4-triazol-1-yl, X₂) | H | X₄—phenyl | A |
| 153 (Example 188) | OMe | H | (1,2,3-triazol-1-yl, X₂) | H | X₄—phenyl | A |
| 154 (Example 189) | OMe | H | (pyrazol-1-yl, X₂) | H | X₄—phenyl | A |
| 155 (Example 190) | OMe | H | (3-methylpyrazol-1-yl, X₂) | H | X₄—phenyl | A |
| 156 (Example 191) | OMe | H | (4-methylpyrazol-1-yl, X₂) | H | X₄—phenyl | A |
| 157 (Example 192) | OMe | H | (4-trifluoromethylpyrazol-1-yl, X₂) | H | X₄—phenyl | A |
| 158 (Example 193) | OMe | H | (imidazol-1-yl, X₂) | H | X₄—phenyl | A |

TABLE 2-continued

In Tables 2-5, X₂, X₄ etc. indicates the point of attachment.

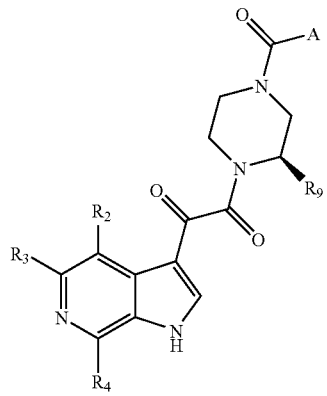

Examples

| Table Entry (Example Number.) | R2 | R3 | R4 | R9 | A | EC₅₀ Group from Table 1 |
|---|---|---|---|---|---|---|
| 159 (Example 195) | OMe | H | X₂-pyrazine | H | X₄-pyrazine | A |
| 160 (Example 196) | OMe | H | X₂-pyrazine | H | X₄-isoxazole | A |
| 161 (Example 197) | OMe | H | X₂-pyrazine | H | X₄-thiadiazole | A |
| 162 (Example 198) | OMe | H | X₂-pyrazine | H | X₄-triazole-NH₂ | A |
| 163 (Example 199) | OMe | H | X₂-pyrazine | H | X₄—O—propyl | A |
| 164 (Example 200) | OMe | H | X₂-pyrazine | H | X₄-(3-methylpyridine) | A |

TABLE 2-continued

In Tables 2-5, $X_2$, $X_4$ etc. indicates the point of attachment.

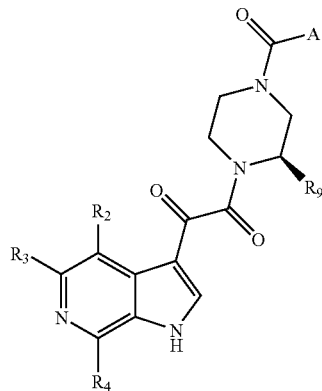

Examples

| Table Entry (Example Number.) | R2 | R3 | R4 | R9 | A | EC$_{50}$ Group from Table 1 |
|---|---|---|---|---|---|---|
| 165 (Example 201) | OMe | H | $X_2$-pyrazinyl | H | $X_4$-(2-methylpyridinyl) | A |
| 166 (Example 209) | F | H | $X_2$-pyrazole-CO-OEt | H | $X_4$-phenyl | A |
| 167 (Example 210) | F | H | $X_2$-pyrazole-CO-NH$_2$ | H | $X_4$-phenyl | A |
| 168 (Example 211) | F | H | $X_2$-pyrazole-CO-NHMe | H | $X_4$-phenyl | A |
| 169 (Example 212) | F | H | $X_2$-pyrazole-CO-NMe$_2$ | H | $X_4$-phenyl | A |

TABLE 2-continued
In Tables 2-5, X₂, X₄ etc. indicates the point of attachment.
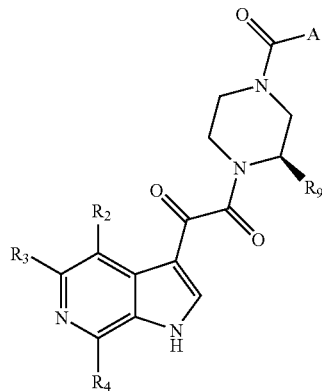
Examples
| Table Entry (Example Number.) | R2 | R3 | R4 | R9 | A | EC₅₀ Group from Table 1 |
|---|---|---|---|---|---|---|
| 170 (Example 213) | F | H | 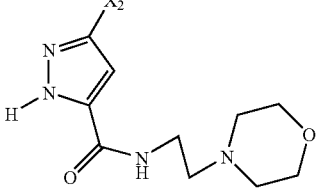 | H | 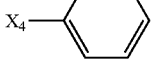 | A |
| 171 (Example 214) | F | H | 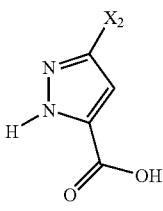 | H | 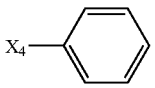 | A |
| 172 (Example 215) | F | H | 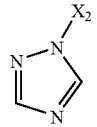 | H | 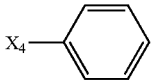 | A |
| 173 (Example 216) | F | H | 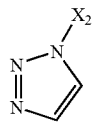 | H | 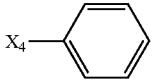 | A |
| 174 (Example 217) | F | H | 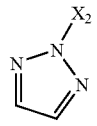 | H | 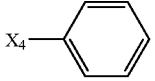 | A |
| 175 (Example 218) | F | H | 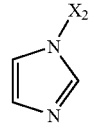 | H | 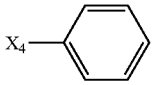 | A |

TABLE 2-continued

In Tables 2-5, $X_2$, $X_4$ etc. indicates the point of attachment.

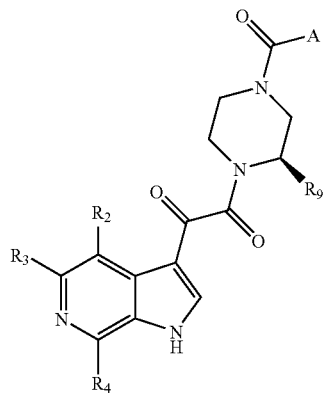

Examples

| Table Entry (Example Number.) | R2 | R3 | R4 | R9 | A | EC$_{50}$ Group from Table 1 |
|---|---|---|---|---|---|---|
| 176 (Example 219) | F | H | $X_2$-pyrazol-1-yl | H | $X_4$-phenyl | A |
| 177 (Example 220) | F | H | $X_2$-pyrrol-1-yl | H | $X_4$-phenyl | A |
| 178 (Example 221) | F | H | $X_2$-pyrrolidin-1-yl | H | $X_4$-phenyl | A |
| 179 (Example 222) | F | H | $X_2$-morpholin-4-yl | H | $X_4$-phenyl | A |
| 180 (Example 223) | OMe | H | $X_2$-tetrazol-5-yl | H | $X_4$-phenyl | A |
| 181 (Example 224) | OMe | H | $X_2$-(1-methyltetrazol-5-yl) | H | $X_4$-phenyl | A |

TABLE 2-continued

In Tables 2-5, X$_2$, X$_4$ etc. indicates the point of attachment.

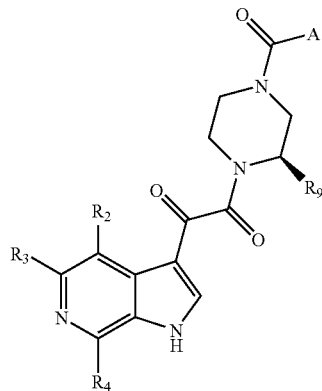

Examples

| Table Entry (Example Number.) | R2 | R3 | R4 | R9 | A | EC$_{50}$ Group from Table 1 |
|---|---|---|---|---|---|---|
| 182 (Example 225) | OMe | H | X$_2$—(2-methyltetrazol-5-yl) | H | X$_4$—phenyl | A |
| 183 (Example 226) | OMe | H | X$_2$—(1,2,4-oxadiazol-3-yl) | H | X$_4$—phenyl | A |
| 185 (Example 240) | OMe | H | X$_2$—(3,5-dimethylpyrazol-1-yl) | H | X$_4$—phenyl | A |
| 186 (Example 247) | OMe | H | X$_2$—(3-(2-hydroxyprop-2-yl)pyrazol-1-yl) | H | X$_4$—phenyl | A |
| 187 (Example 248) | OMe | H | X$_2$—(3-(2-hydroxyethyl)pyrazol-1-yl) | H | X$_4$—phenyl | A |

TABLE 2-continued

In Tables 2-5, X₂, X₄ etc. indicates the point of attachment.

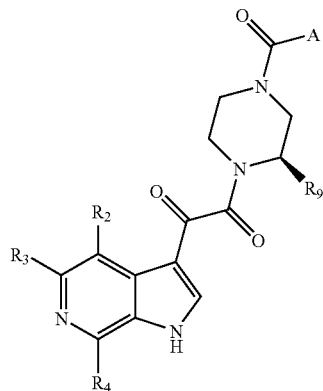

Examples

| Table Entry (Example Number.) | R2 | R3 | R4 | R9 | A | EC₅₀ Group from Table 1 |
|---|---|---|---|---|---|---|
| 188 (Example 249) | OMe | H | ![pyrazole with isopropyl] | H | ![phenyl] | A |
| 189 (Example 250) | OMe | H | ![pyrazole with (CH₂)₄CH₃] | H | ![phenyl] | A |
| 190 (Example 251) | OMe | H | ![pyrazole with NH₂] | H | ![phenyl] | A |
| 191 (Example 252) | OMe | H | ![pyrazole with H₂N] | H | ![phenyl] | A |
| 192 (Example 264) | OMe | H | ![pyrazole with methylpyridine] | H | ![phenyl] | A |

TABLE 2-continued

In Tables 2-5, $X_2$, $X_4$ etc. indicates the point of attachment.

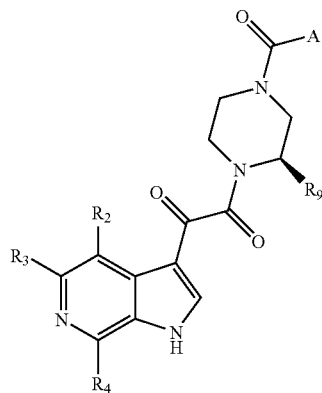

Examples

| Table Entry (Example Number.) | R2 | R3 | R4 | R9 | A | EC$_{50}$ Group from Table 1 |
|---|---|---|---|---|---|---|
| 193 (Example 273) | OMe | H | ![triazole-C(O)NHEt with X$_2$] | H | ![phenyl-X$_4$] | A |
| 194 (Example 274) | OMe | H | ![triazole-C(O)NHMe with X$_2$] | H | ![phenyl-X$_4$] | A |
| 195 (Example 275) | OMe | H | ![triazole-C(O)N(CH$_3$)$_2$ with X$_2$] | H | ![phenyl-X$_4$] | A |
| 196 (Example 276) | OMe | H | ![pyrazole-C(O)NHMe with X$_2$] | H | ![phenyl-X$_4$] | A |
| 197 (Example 277) | OMe | H | ![pyrazole-CH$_2$CH(OH)CH$_3$ with X$_2$] | H | ![phenyl-X$_4$] | A |

TABLE 2-continued

In Tables 2-5, $X_2$, $X_4$ etc. indicates the point of attachment.

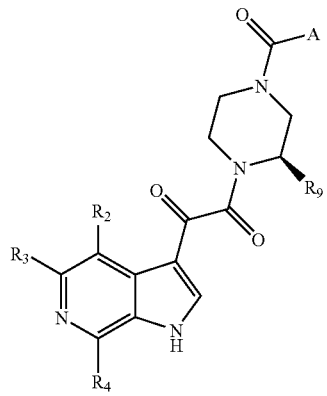

Examples

| Table Entry (Example Number.) | R2 | R3 | R4 | R9 | A | EC$_{50}$ Group from Table 1 |
|---|---|---|---|---|---|---|
| 198 (Example 278) | OMe | H | X$_2$–pyrazole–cyclohexenyl | H | X$_4$–phenyl | A |
| 199 (Example 279) | OMe | H | X$_2$–pyrazole–(CH$_2$)$_3$CN | H | X$_4$–phenyl | A |
| 200 (Example 280) | OMe | H | X$_2$–pyrazole–CH$_2$–thiomorpholine-SO$_2$ | H | X$_4$–phenyl | A |
| 201 (Example 281) | OMe | H | X$_2$–pyrazole–isobutyl | H | X$_4$–phenyl | A |
| 202 (Example 282) | OMe | H | X$_2$–pyrazole–1-hydroxycyclopentyl | H | X$_4$–phenyl | A |

TABLE 2-continued
In Tables 2-5, X₂, X₄ etc. indicates the point of attachment.
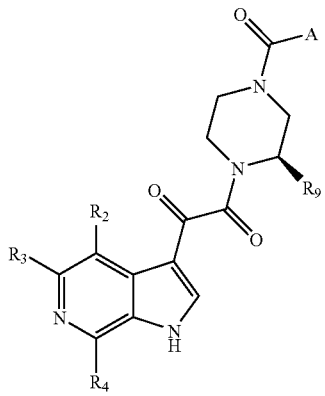
Examples
| Table Entry (Example Number.) | R2 | R3 | R4 | R9 | A | EC₅₀ Group from Table 1 |
|---|---|---|---|---|---|---|
| 203 (Example 283) | OMe | H | ![pyrazole-CH2NHCH3] | H | X₄—Ph | A |
| 204 (Example 284) | OMe | H | ![pyrazole-CH(OH)iPr] | H | X₄—Ph | A |
| 205 (Example 285) | OMe | H | ![pyrazole-CH2O-C6H4-COOEt] | H | X₄—Ph | A |
| 206 (Example 286) | OMe | H | ![pyrazole-SO2-tolyl] | H | X₄—Ph | A |
| 207 (Example 287) | OMe | H | ![pyrazole-C6H4-CF3] | H | X₄—Ph | A |

TABLE 2-continued

In Tables 2-5, X₂, X₄ etc. indicates the point of attachment.

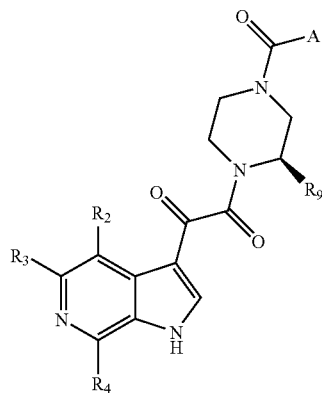

Examples

| Table Entry (Example Number.) | R2 | R3 | R4 | R9 | A | EC₅₀ Group from Table 1 |
|---|---|---|---|---|---|---|
| 208 (Example 288) | OMe | H | ![pyrazole-C6H4-CF3 with X₂] | H | ![X₄-phenyl] | A |
| 209 (Example 289) | OMe | H | ![triazole-S(CH2)2CH3 with X₂] | H | ![X₄-phenyl] | A |
| 210 (Example 290) | OMe | H | ![triazole-SO2(CH2)2CH3 with X₂] | H | ![X₄-phenyl] | A |
| 211 (Example 291) | OMe | H | ![triazole-OCH3 with X₂] | H | ![X₄-phenyl] | A |
| 212 (Example 292) | OMe | H | ![pyrazole-C6H4-COOH with X₂] | H | ![X₄-phenyl] | A |

TABLE 2-continued
In Tables 2-5, X₂, X₄ etc. indicates the point of attachment.
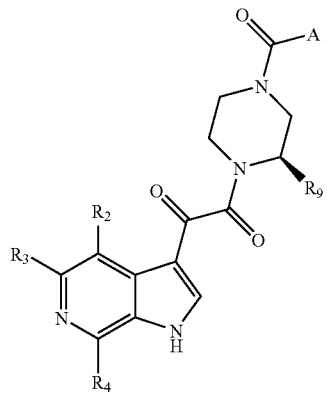
Examples
| Table Entry (Example Number.) | R2 | R3 | R4 | R9 | A | EC₅₀ Group from Table 1 |
|---|---|---|---|---|---|---|
| 213 (Example 293) | OMe | H | 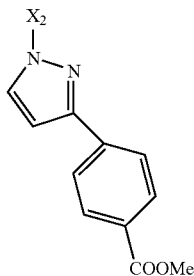 | H | 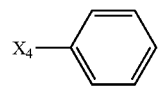 | A |
| 214 (Example 294) | OMe | H | 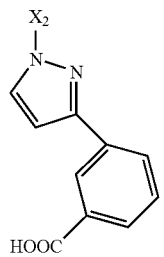 | H | 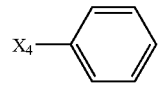 | A |
| 215 (Example 295) | OMe | H | 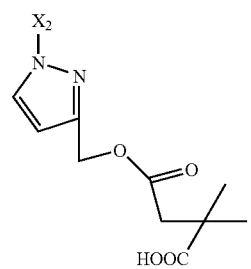 | H | 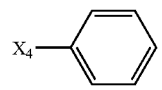 | A |

TABLE 2-continued
In Tables 2-5, $X_2$, $X_4$ etc. indicates the point of attachment.
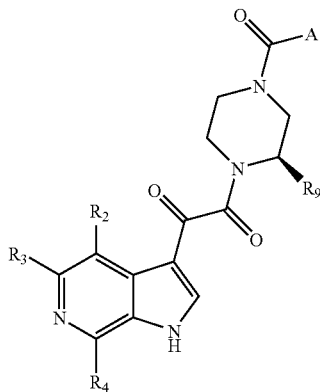
Examples
| Table Entry (Example Number.) | R2 | R3 | R4 | R9 | A | $EC_{50}$ Group from Table 1 |
|---|---|---|---|---|---|---|
| 216 (Example 296) | OMe | H | ![X2-pyrazole-NH-C(O)-epoxide-COOH] | H | ![X4-phenyl] | A |
| 217 (Example 297) | OMe | H | ![X2-pyridine-NH-C(O)-epoxide-COOH] | (R)-Me | ![X4-phenyl] | A |
| 218 (Example 298) | F | H | ![X2-oxadiazole-NHMe] | H | ![X4-phenyl] | A |
| 219 (Example 299) | F | H | ![X2-triazole] | H | ![X4-phenyl] | A |

TABLE 2-continued

In Tables 2-5, X$_2$, X$_4$ etc. indicates the point of attachment.

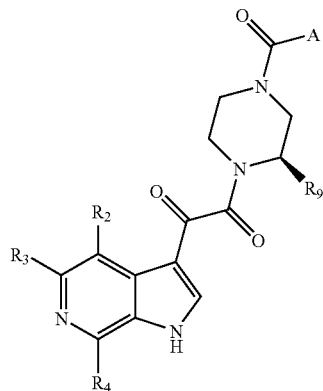

Examples

| Table Entry (Example Number.) | R2 | R3 | R4 | R9 | A | EC$_{50}$ Group from Table 1 |
|---|---|---|---|---|---|---|
| 220 (Example 300) | F | H | X$_2$ on 5-methyl-1,3,4-oxadiazol-2-yl | H | X$_4$—phenyl | A |
| 221 (Example 301) | F | H | X$_2$ on 1-methyl-1H-1,2,4-triazol-5-yl | H | X$_4$—phenyl | A |
| 222 (Example 303) | F | H | X$_2$ on 1H-1,2,4-triazol-1-yl | H | X$_4$—phenyl | A |
| 223 (Example 304) | F | H | X$_2$ on imidazol-1-yl | H | X$_4$—phenyl | A |
| 223 (Example 305) | F | H | X$_2$ on pyrazol-1-yl | H | X$_4$—phenyl | A |
| 224 (Example 306) | F | H | X$_2$ on 3-methyl-1H-1,2,4-triazol-1-yl | H | X$_4$—phenyl | A |

TABLE 2-continued

In Tables 2-5, X$_2$, X$_4$ etc. indicates the point of attachment.

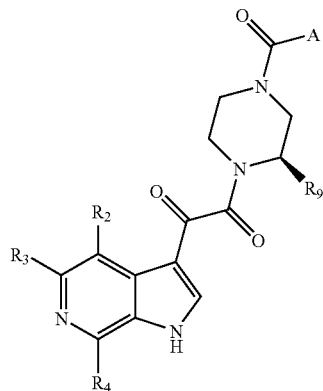

Examples

| Table Entry (Example Number.) | R2 | R3 | R4 | R9 | A | EC$_{50}$ Group from Table 1 |
|---|---|---|---|---|---|---|
| 225 (Example 307) | F | H | ![X$_2$-1-methyl-1,2,4-triazole] | H | ![X$_4$-phenyl] | A |
| 226 (Example 308) | F | H | ![X$_2$-pyrrole] | H | ![X$_4$-phenyl] | A |
| 227 (Example 309) | F | H | ![X$_2$-3-amino-pyrazole] | H | ![X$_4$-phenyl] | A |
| 228 (Example 310) | F | H | ![X$_2$-3-methyl-pyrazole] | H | ![X$_4$-phenyl] | A |
| 229 (Example 311) | F | H | ![X$_2$-3-methyl-5-COOEt-pyrazole] | H | ![X$_4$-phenyl] | A |
| 230 (Example 312) | F | H | ![X$_2$-5-Me-pyrazole] | H | ![X$_4$-phenyl] | A |

TABLE 2-continued

In Tables 2-5, X₂, X₄ etc. indicates the point of attachment.

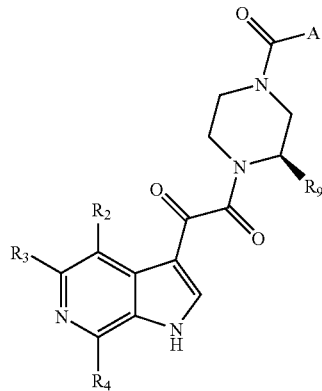

Examples

| Table Entry (Example Number.) | R2 | R3 | R4 | R9 | A | EC₅₀ Group from Table 1 |
|---|---|---|---|---|---|---|
| 231 (Example 313) | F | H | [1-(3-amino-1,2,4-triazolyl)], X₂ | H | phenyl, X₄ | A |
| 232 (Example 316) | MeO | H | [1-(5-methyl-1,2,4-triazolyl)], X₂ | H | phenyl, X₄ | A |
| 233 (Example 318) | MeO | H | [1-(4-methylimidazolyl)], X₂ | H | phenyl, X₄ | A |
| 234 (Example 319) | MeO | H | [1-(5-methyl-1,2,4-triazolyl)], X₂ | H | phenyl, X₄ | A |
| 234 (Example 321) | MeO | H | [1-(3-ethyl-1,2,4-triazolyl)], X₂ | H | phenyl, X₄ | A |
| 235 (Example 323) | MeO | H | [1-(3-methoxymethyl-1,2,4-triazolyl)], X₂ | H | phenyl, X₄ | A |

TABLE 2-continued

In Tables 2-5, $X_2$, $X_4$ etc. indicates the point of attachment.

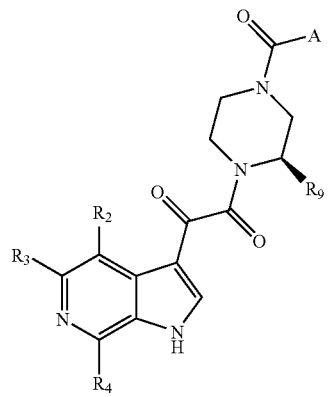

Examples

| Table Entry (Example Number.) | R2 | R3 | R4 | R9 | A | EC$_{50}$ Group from Table 1 |
|---|---|---|---|---|---|---|
| 236 (Example 325) | MeO | H | ![2-methyl-triazol-1-yl with X$_2$] | H | $X_4$—Ph | A |
| 237 (Example 327) | MeO | H | ![4-methyl-triazol-2-yl with X$_2$] | H | $X_4$—Ph | A |
| 238 (Example 329) | MeO | H | ![imidazol-1-yl-propanoic acid with X$_2$] | H | $X_4$—Ph | A |
| 239 (Example 330) | MeO | H | ![2-pyridylamino with X$_2$] | H | $X_4$—Ph | A |
| 240 (Example 331) | MeO | H | ![N-(2-pyridyl)-methanesulfonamide with X$_2$] | H | $X_4$—Ph | B |

TABLE 2-continued
In Tables 2-5, X₂, X₄ etc. indicates the point of attachment.
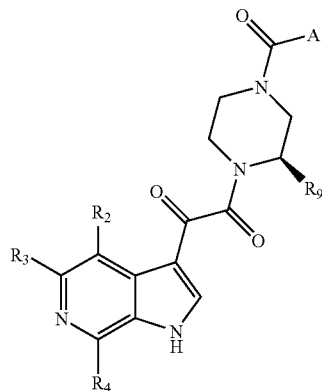
Examples
| Table Entry (Example Number.) | R2 | R3 | R4 | R9 | A | EC₅₀ Group from Table 1 |
|---|---|---|---|---|---|---|
| 241 (Example 342) | MeO | H | 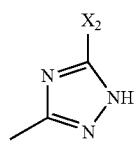 | H | 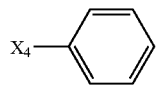 | A |
| 242 (Example 341) | MeO | H | 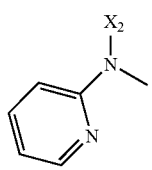 | H | 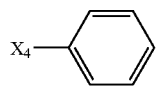 | C |
| 243 (Example 343) | OMe | H | 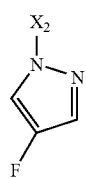 | H | 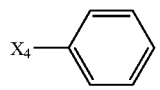 | A |
| 244 (Example 344) | OMe | H | 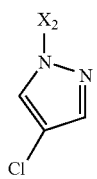 | H | 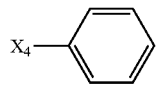 | A |

TABLE 2-continued
In Tables 2-5, $X_2$, $X_4$ etc. indicates the point of attachment.
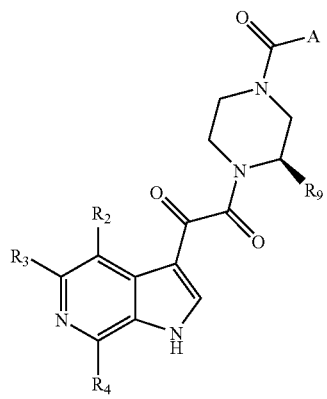
Examples
| Table Entry (Example Number.) | R2 | R3 | R4 | R9 | A | EC$_{50}$ Group from Table 1 |
|---|---|---|---|---|---|---|
| 245 (Example 346) | OMe | H | ![R4 structure: 1,2,4-oxadiazole with X2 and CH3] | H | ![A: phenyl with X4] | A |
| 246 (Example 349) | OMe | H | ![R4 structure: 1,3,4-oxadiazole with X2 and CH3] | H | ![A: phenyl with X4] | A |
| 247 (Example 351) | OMe | H | ![R4 structure: triazole with X2] | H | ![A: phenyl with X4] | A |

TABLE 2-1
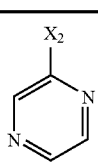
| Table Entry (Example Number.) | R2 | R3 | R4 | R | A | EC50 Group from Table 1 |
|---|---|---|---|---|---|---|
| 1 (Example 194) | OMe | H | X2—pyrazine | Me | X4—pyridin-2-yl | A |
| 2 (Example 227) | OMe | H | X2—pyrazine | (R)-Me | X4—pyridin-2-yl | A |
| 3 (Example 228) | OMe | H | X2—pyrazine | (S)-Me | X4—pyridin-2-yl | A |
| 4 (Example 229) | OMe | H | X2—pyrazine | Et | X4—pyridin-2-yl | A |
| 5 (Example 230) | OMe | H | X2—(3-ethyl-pyrazol-1-yl) | (R)-Me | X4—phenyl | A |
| 6 (Example 231) | OMe | H | X2—(3-propyl-pyrazol-1-yl) | (R)-Me | X4—phenyl | A |

TABLE 2-1-continued

| Table Entry (Example Number.) | R2 | R3 | R4 | R | A | EC$_{50}$ Group from Table 1 |
|---|---|---|---|---|---|---|
| 7 (Example 232) | OMe | H | X$_2$-pyrazol-1-yl-3-cyclobutyl | (R)-Me | X$_4$-phenyl | A |
| 7 (Example 233) | OMe | H | X$_2$-pyrazol-1-yl-3-OEt | (R)-Me | X$_4$-phenyl | A |
| 8 (Example 234) | OMe | H | X$_2$-pyrazol-1-yl-3-(CH$_2$)$_2$COOH | (R)-Me | X$_4$-phenyl | A |
| 8 (Example 235) | OMe | H | X$_2$-pyrazol-1-yl-3-CH(OH)CH$_3$ | (R)-Me | X$_4$-phenyl | A |
| 9 (Example 236) | OMe | H | X$_2$-pyrazol-1-yl-3-CH$_2$OH | (R)-Me | X$_4$-phenyl | A |

TABLE 2-1-continued

| Table Entry (Example Number.) | R2 | R3 | R4 | R | A | EC$_{50}$ Group from Table 1 |
|---|---|---|---|---|---|---|
| 10 (Example 237) | OMe | H | X$_2$-N(N)-CH$_2$OH (1H-pyrazol-5-yl-methanol) | (R)-Me | X$_4$-phenyl | A |
| 11 (Example 238) | OMe | H | X$_2$-N(N)- with CH$_2$OCH$_3$ | (R)-Me | X$_4$-phenyl | A |
| 12 (Example 239) | OMe | H | X$_2$-N(N)- with CH$_2$NMe$_2$ | (R)-Me | X$_4$-phenyl | A |
| 13 (Example 241) | OMe | H | X$_2$-N(N)- with CH$_3$ | (R)-Me | X$_4$-phenyl | A |
| 14 (Example 242) | OMe | H | X$_2$-N(N)- with H$_3$C | (R)-Me | X$_4$-phenyl | A |
| 15 (Example 243) | OMe | H | X$_2$-N(N)- with tBu | (R)-Me | X$_4$-phenyl | A |

TABLE 2-1-continued
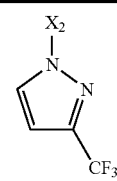
| Table Entry (Example Number.) | R2 | R3 | R4 | R | A | EC$_{50}$ Group from Table 1 |
|---|---|---|---|---|---|---|
| 16 (Example 244) | OMe | H | 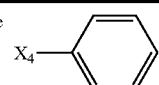 | (R)-Me | 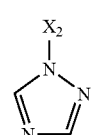 | A |
| 17 (Example 245) | OMe | H | 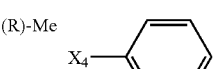 | (R)-Me | 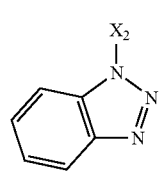 | A |
| 18 (Example 246) | OMe | H | 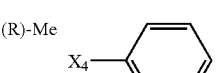 | (R)-Me | 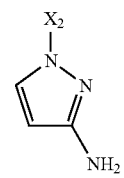 | A |
| 19 (Example 253) | OMe | H | 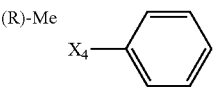 | (R)-Me | 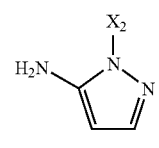 | A |
| 20 (Example 254) | OMe | H | 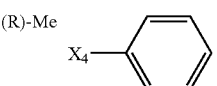 | (R)-Me | 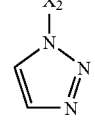 | A |
| 21 (Example 255) | OMe | H | 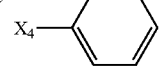 | (R)-Me | 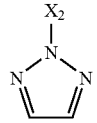 | A |
| 22 (Example 256) | OMe | H | 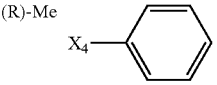 | (R)-Me |  | A |

TABLE 2-1-continued

| Table Entry (Example Number.) | R2 | R3 | R4 | R | A | EC$_{50}$ Group from Table 1 |
|---|---|---|---|---|---|---|
| 23 (Example 257) | OMe | H | X$_2$-pyrazol-1-yl-3-OH | (R)-Me | X$_4$-phenyl | A |
| 24 (Example 258) | OMe | H | X$_2$-1,2,4-triazol-1-yl-3-NH$_2$ | (R)-Me | X$_4$-phenyl | A |
| 25 (Example 259) | OMe | H | X$_2$-pyrazol-1-yl-3-COOCH$_3$ | (R)-Me | X$_4$-phenyl | A |
| 26 (Example 260) | OMe | H | X$_2$-pyrazol-1-yl-3-Ph | (R)-Me | X$_4$-phenyl | A |
| 27 (Example 261) | OMe | H | X$_2$-1,2,4-triazol-1-yl-3-NH-CH$_2$-(2-pyridyl) | (R)-Me | X$_4$-phenyl | A |

TABLE 2-1-continued
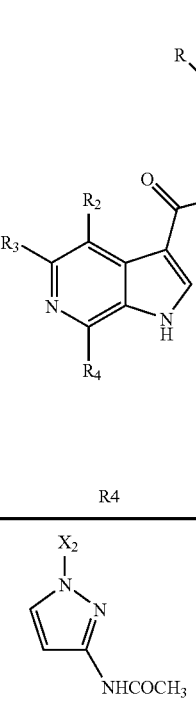
| Table Entry (Example Number.) | R2 | R3 | R4 | R | A | EC$_{50}$ Group from Table 1 |
|---|---|---|---|---|---|---|
| 28 (Example 262) | OMe | H | 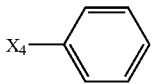 | (R)-Me | 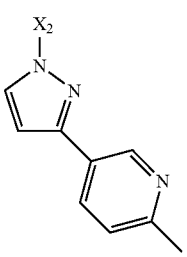 | A |
| 29 (Example 263) | OMe | H | 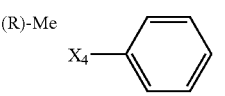 | (R)-Me | 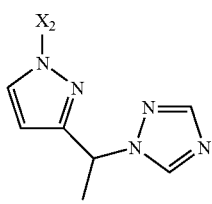 | A |
| 30 (Example 265) | OMe | H | 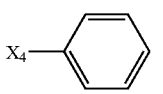 | (R)-Me | 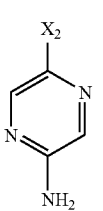 | A |
| 31 (Example 266) | OMe | H | 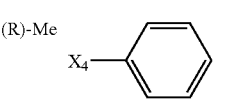 | (R)-Me | 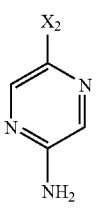 | A |
| 32 (Example 267) | OMe | H | 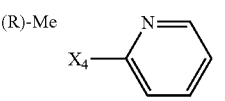 | (R)-Me |  | A |

TABLE 2-1-continued
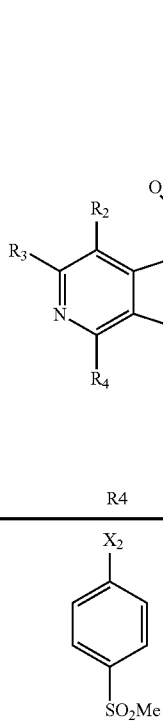
| Table Entry (Example Number.) | R2 | R3 | R4 | R | A | $EC_{50}$ Group from Table 1 |
|---|---|---|---|---|---|---|
| 33 (Example 268) | OMe | H |  | (R)-Me | 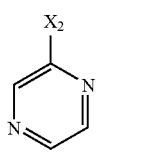 | A |
| 34 (Example 269) | OMe | H | 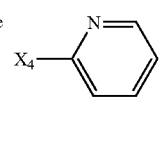 | (R)-Me | 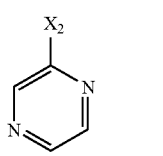 | A |
| 35 (Example 270) | OMe | H | 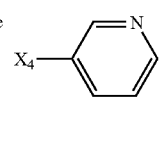 | (R)-Me | 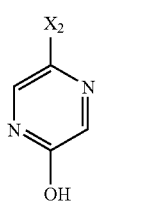 | A |
| 36 (Example 271) | OMe | H | 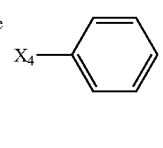 | (R)-Me | 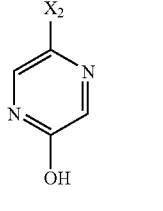 | A |
| 37 (Example 272) | OMe | H | 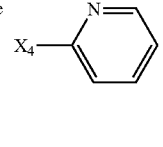 | (R)-Me | 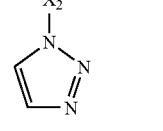 | A |
| 38 (Example 314) | F | H | 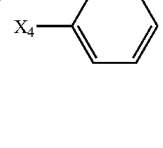 | (R)-Me |  | A |

TABLE 2-1-continued

| Table Entry (Example Number.) | R2 | R3 | R4 | R | A | EC$_{50}$ Group from Table 1 |
|---|---|---|---|---|---|---|
| 39 (Example 315) | F | H | X$_2$-(1H-3-methyl-1,2,4-triazol-1-yl) | (R)-Me | X$_4$-phenyl | A |
| 40 (Example 317) | OMe | H | X$_2$-(1H-3-methyl-1,2,4-triazol-1-yl) | (R)-Me | X$_4$-phenyl | A |
| 41 (Example 322) | MeO | H | X$_2$-(1H-3-ethyl-1,2,4-triazol-1-yl) | (R)-Me | X$_4$-phenyl | A |
| 42 (Example 324) | MeO | H | X$_2$-(1H-3-methoxymethyl-1,2,4-triazol-1-yl) | (R)-Me | X$_4$-phenyl | A |
| 43 (Example 326) | MeO | H | X$_2$-(1H-4-methyl-1,2,3-triazol-1-yl) | (R)-Me | X$_4$-phenyl | A |
| 44 (Example 328) | MeO | H | X$_2$-(2H-4-methyl-1,2,3-triazol-2-yl) | (R)-Me | X$_4$-phenyl | A |

TABLE 2-1-continued

| Table Entry (Example Number.) | R2 | R3 | R4 | R | A | EC$_{50}$ Group from Table 1 |
|---|---|---|---|---|---|---|
| 45 (Example 334) | MeO | H | 3-methyl-1H-1,2,4-triazol-5-yl (X$_2$) | (R)-Me | phenyl (X$_4$) | A |
| 46 (Example 335) | MeO | H | 3-phenyl-1H-1,2,4-triazol-5-yl (X$_2$) | (R)-Me | phenyl (X$_4$) | A |
| 47 (Example 336) | MeO | H | 3-ethyl-1H-1,2,4-triazol-5-yl (X$_2$) | (R)-Me | phenyl (X$_4$) | A |
| 48 (Example 337) | MeO | H | 3-(4-methylphenyl)-1H-1,2,4-triazol-5-yl (X$_2$) | (R)-Me | phenyl (X$_4$) | A |
| 49 (Example 338) | MeO | H | 3-(pyridin-3-yl)-1H-1,2,4-triazol-5-yl (X$_2$) | (R)-Me | phenyl (X$_4$) | A |

TABLE 2-1-continued
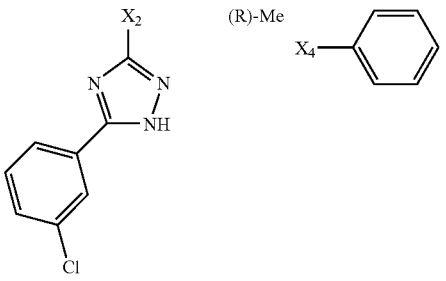
| Table Entry (Example Number.) | R2 | R3 | R4 | R | A | EC50 Group from Table 1 |
|---|---|---|---|---|---|---|
| 50 (Example 339) | MeO | H |  | (R)-Me | 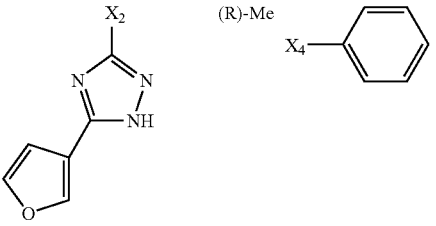 | A |
| 51 (Example 340) | MeO | H |  | (R)-Me | 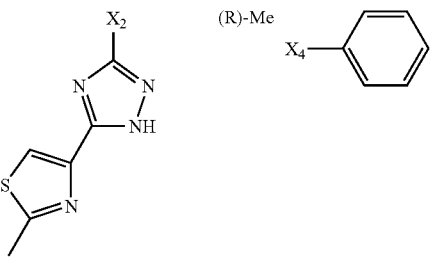 | A |
| 52 (Example 341) | MeO | H |  | (R)-Me | 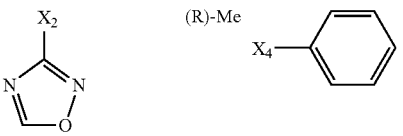 | A |
| 53 (Example 345) | MeO | H |  | (R)-Me | | A |

TABLE 2-1-continued

| Table Entry (Example Number.) | R2 | R3 | R4 | R | A | EC$_{50}$ Group from Table 1 |
|---|---|---|---|---|---|---|
| 54 (Example 347) | MeO | H | 3-methyl-1,2,4-oxadiazol-5-yl (X$_2$) | (R)-Me | phenyl (X$_4$) | A |
| 55 (Example 348) | MeO | H | 5-methyl-1,3,4-oxadiazol-2-yl (X$_2$) | (R)-Me | phenyl (X$_4$) | A |
| 56 (Example 350) | MeO | H | 5-methyl-1,2,4-triazol-1-yl (X$_2$) | (R)-Me | phenyl (X$_4$) | A |
| 57 (Example 352) | MeO | H | 3-methyl-1,2,4-triazol-1-yl (X$_2$) | (S)-Me | phenyl (X$_4$) | A |

TABLE 3
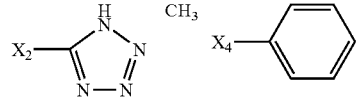
Example 56
| Table Entry (Example number) | R2 | R3 | R4 | R9 | A | EC$_{50}$ Group from Table 1 |
|---|---|---|---|---|---|---|
| 1 (Example 56) | H | H | 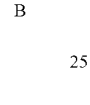 | CH$_3$ | 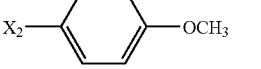 | B |
TABLE 4
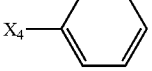
| Table Entry (Example No.) | R2 | R3 | R4 | R9 | A | EC$_{50}$ Group from Table 1 |
|---|---|---|---|---|---|---|
| 1 (Example 65) | H | H | 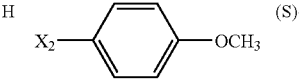 | H | 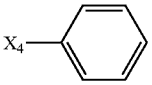 | A |
| 2 (Example 66) | H | H | 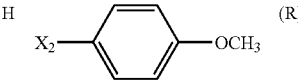 | (S)-CH$_3$ | 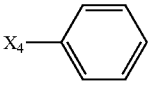 | A |
| 3 (Example 67) | H | H |  | (R)-Me |  | A |

TABLE 4-continued

| Table Entry (Example No.) | R2 | R3 | R4 | R9 | A | EC$_{50}$ Group from Table 1 |
|---|---|---|---|---|---|---|
| 4 Example (57) | H | H | X$_2$-C(O)-N(OMe)(Me) | (R)-Me | X$_4$-phenyl | A |
| 6 (Example 64) | Cl | H | X$_2$-(5-methyl-1H-pyrazol-3-yl) | (R)-Me | X$_4$-phenyl | A |
| 7 (Example 58) | Cl | H | X$_2$-C(O)-N(OMe)(Me) | (R)-Me | X$_4$-phenyl | A |
| 8 (Example 60) | Cl | H | X$_2$-(1H-imidazol-2-yl) | (R)-Me | X$_4$-phenyl | A |
| 9 (Example 61) | Cl | H | X$_2$-(4-methyl-1H-imidazol-2-yl) | (R)-Me | X$_4$-phenyl | A |
| 10 (Example 62) | Cl | H | X$_2$-(4,5-dimethyl-1H-imidazol-2-yl) | (R)-Me | X$_4$-phenyl | A |
| 11 (Example 63) | Cl | H | X$_2$-(oxazol-5-yl) | (R)-Me | X$_4$-phenyl | A |

TABLE 4-continued
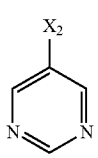
| Table Entry (Example No.) | R2 | R3 | R4 | R9 | A | EC$_{50}$ Group from Table 1 |
|---|---|---|---|---|---|---|
| 13 (Example 51) | H | H | 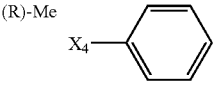 | (R)-Me | 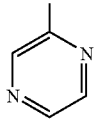 | A |
| 14 (Example 52) | H | H | 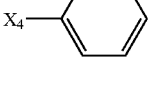 | (R)-Me | 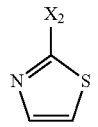 | A |
| 15 (Example 53) | H | H | 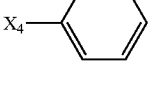 | (R)-Me | 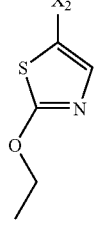 | A |
| 16 (Example 54) | H | H | 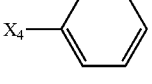 | (R)-Me | 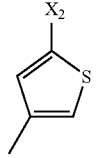 | A |
| 17 (Example 86) | H | H | 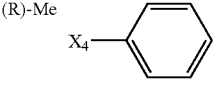 | (R)-Me | 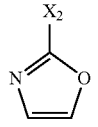 | A |
| 18 (Example 126) | H | H | 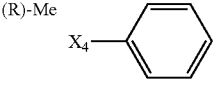 | (R)-Me | 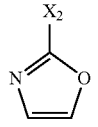 | A |

TABLE 4-continued
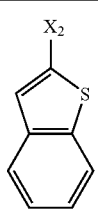
| Table Entry (Example No.) | R2 | R3 | R4 | R9 | A | EC$_{50}$ Group from Table 1 |
|---|---|---|---|---|---|---|
| 19 (Example 127) | H | H | 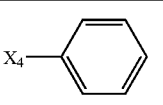 | (R)-Me | 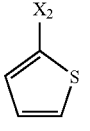 | A |
| 20 (Example 128) | H | H | 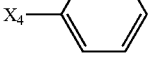 | (R)-Me | 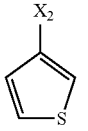 | A |
| 21 (Example 129) | H | H | 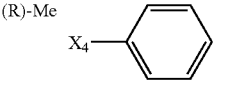 | (R)-Me | 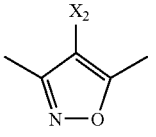 | A |
| 22 (Example 130) | H | H | 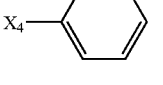 | (R)-Me | 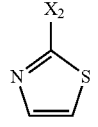 | A |
| 23 (Example 131) | H | H | 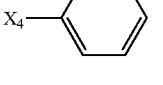 | H | 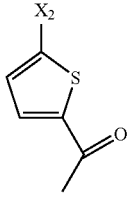 | A |
| 24 (Example 132) | H | H | 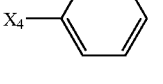 | H | | A |

TABLE 4-continued
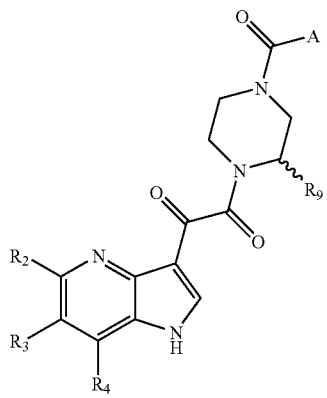
| Table Entry (Example No.) | R2 | R3 | R4 | R9 | A | EC₅₀ Group from Table 1 |
|---|---|---|---|---|---|---|
| 25 (Example 133) | H | H | X₂-thiophene-CHO (5-CHO-thien-2-yl) | H | X₄-phenyl | A |
| 26 (Example 134) | H | H | X₂-(4-methylthien-2-yl) | H | X₄-phenyl | A |
| 27 (Example 135) | H | H | X₂-C(O)NH-CH₂-(4-CF₃-phenyl) | (R)-Me | X₄-phenyl | A |
| 28 (Example 136) | H | H | X₂-C(O)NH-(4-methylthiazol-2-yl) | (R)-Me | X₄-phenyl | A |
| 29 (Example 137) | H | H | X₂-C(O)NH-(thiazol-2-yl) | (R)-Me | X₄-phenyl | A |

TABLE 4-continued
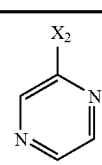
| Table Entry (Example No.) | R2 | R3 | R4 | R9 | A | EC50 Group from Table 1 |
|---|---|---|---|---|---|---|
| 30 (Example 158) | H | H | 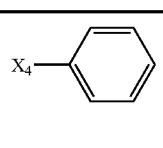 | H | 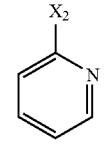 | A |
| 31 (Example 159) | H | H | 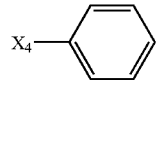 | H | 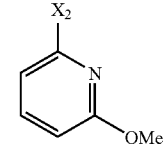 | A |
| 32 (Example 160) | H | H | 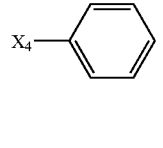 | H | 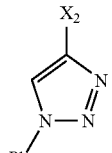 | A |
| 33 (Example 161) | H | H | 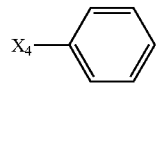 | H | 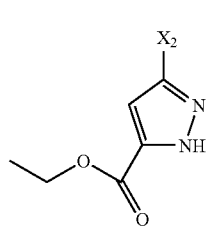 | A |
| 34 (Example 202) | H | H | 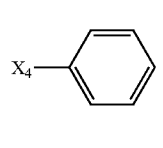 | H | 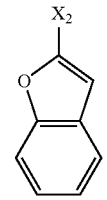 | A |
| 35 (Example 203) | H | H | 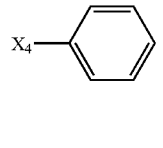 | H | 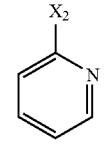 | A |

TABLE 4-continued
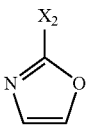
| Table Entry (Example No.) | R2 | R3 | R4 | R9 | A | EC$_{50}$ Group from Table 1 |
|---|---|---|---|---|---|---|
| 36 (Example 204) | H | H | 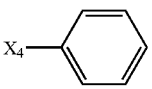 | H | 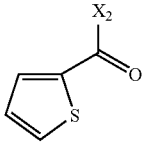 | A |
| 37 (Example 168) | H | H | 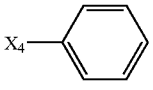 | H | 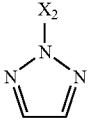 | A |
| 38 (Example 205) | H | H | 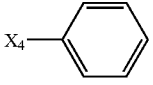 | H | 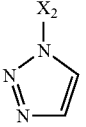 | A |
| 39 (Example 206) | H | H | 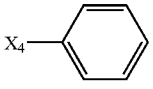 | H | 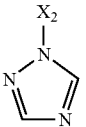 | A |
| 40 (Example 207) | H | H | 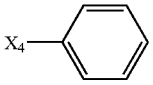 | H | 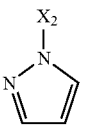 | A |
| 41 (Example 208) | H | H | 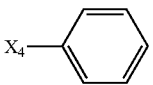 | H | | A |

TABLE 4-1

| Table Entry (Example No.) | R2 | R3 | R4 | R9 | A | EC50 Group from Table 1 |
|---|---|---|---|---|---|---|
| 1 (Example 353) | H | H | X₂—oxazol-2-yl | H | X₄—phenyl | A |
| 2 (Example 354) | H | H | X₂—thiazol-2-yl | (S)-CH₃ | X₄—phenyl | A |
| 3 (Example 355) | H | H | X₂—1,2,3-triazol-2-yl | (R)-Me | X₄—phenyl | A |
| 4 (Example 356) | H | H | X₂—3-methylpyrazol-1-yl | (R)-Me | X₄—phenyl | A |
| 6 (Example 357) | Cl | H | X₂—benzotriazol-2-yl | (R)-Me | X₄—phenyl | A |
| 7 (Example 358) | Cl | H | X₂—benzotriazol-1-yl | (R)-Me | X₄—phenyl | A |

TABLE 4-1-continued

| Table Entry (Example No.) | R2 | R3 | R4 | R9 | A | EC$_{50}$ Group from Table 1 |
|---|---|---|---|---|---|---|
| 8 (Example 359) | Cl | H | (pyrazole with CH$_3$, X$_2$ attachment) | (R)-Me | phenyl (X$_4$) | A |
| 9 (Example 360) | Cl | H | (triazole with H$_3$C, X$_2$ attachment) | (R)-Me | phenyl (X$_4$) | A |
| 10 (Example 361) | Cl | H | (methyl-triazole, X$_2$ attachment) | (R)-Me | phenyl (X$_4$) | A |

Method for Extrapolating % Inhibition at 10 μm

The compounds of Table 5 below were all found to be very potent in the assay described above using % inhibition as a criteria. In Table 5, X$_2$, X$_4$ etc. indicates the point of attachment. The vast majority of the compounds exhibited greater than 98% inhibition at a concentration of 10 uM. The data at 10 μM was calculated in the following manner:

Method for Extrapolating % Inhibition at 10 μm

The data in Table 5 was obtained using the general procedures above and by the following methods. Data is not reported for all compounds since data for all the compounds is reported by the alternate method in the previous Tables 1-4. The percent inhibition for each compound was calculated by quantifying the level of luciferase expression in cells infected in the presence of compound as a percentage of that observed for cells infected in the absence of compound and subtracting such a determined value from 100. For compounds tested at concentrations less than 10 μM, the percent inhibition at 10 μM was determined by extrapolation using the XLfit curve fitting feature of the Microsoft Excel spreadsheet software. Curves were obtained from 10 data points (% inhibition determined at 10 concentrations of compound) by using a four parameter logistic model (XLfit model 205: $y=A+((B-A)/(1+((C/x)^D)))$, where, A=minimum y, B=maximum y, C=logEC$_{50}$, D=slope factor, and x and y are known data values. Extrapolations were performed with the A and B parameters unlocked.

Thus the compounds of this invention are all potent antiviral inhibitors based on this assay.

TABLE 5

Precursor 8

(structure: 4,6-di(H or Ph)-7-azaindole with 3-methyl-piperazine-benzoyl group via oxoacetyl linker)

Example 1

(structure: 7-(4-fluorophenyl)-6-azaindole with 3-methyl-piperazine-benzoyl group via oxoacetyl linker)

| Compound # | Average % inhibition at 10 µM |
|---|---|
| Precursor 8 | 85% |
| Example 1 | 56% |

Other Compounds of the Invention:

The 5-aza inhibitors shown in Table 6 should also be active antiviral agents. They are also part of the invention and could be prepared from precursors 1a or 2s or the corresponding 7-desbromo-7-chloro precursors which are prepared analogously and the methods herein or by using other methods described herein.

TABLE 6

5-aza inhibitors

| Table Entry (Example Number.) | R2 | R3 | R4 | R9 | A |
|---|---|---|---|---|---|
| 1 | MeO | H | $X_2$-(1,2,4-oxadiazol-3-yl) | H | $X_4$-phenyl |
| 2 | MeO | H | $X_2$-(pyrazin-2-yl) | H | $X_4$-phenyl |
| 3 | MeO | H | $X_2$-(thiazol-2-yl) | H | $X_4$-phenyl |
| 4 | MeO | H | $X_2$-(furan-2-yl) | H | $X_4$-phenyl |

The compounds in the following Tables exemplify without restriction some of the many additional inhibitors which could be prepared by using methodology contained herein or exemplified in the preparation of the compounds of the invention.

TABLE 2a
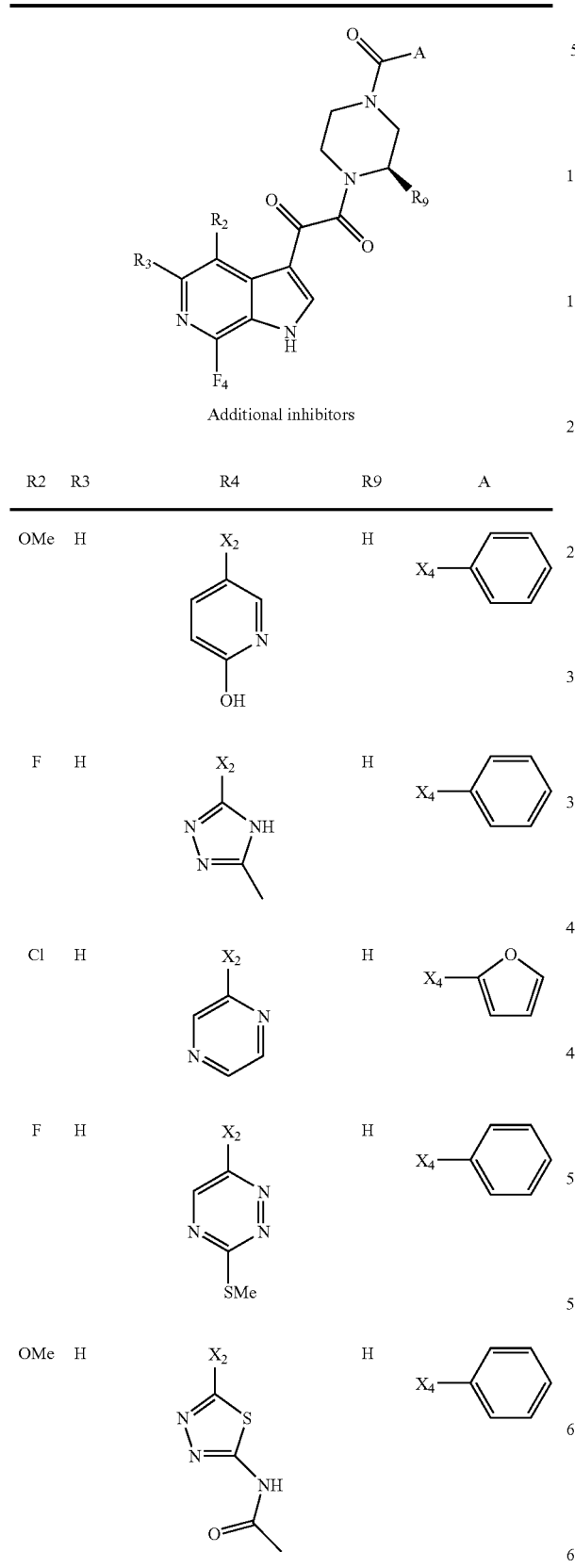
Additional inhibitors
TABLE 2a-continued
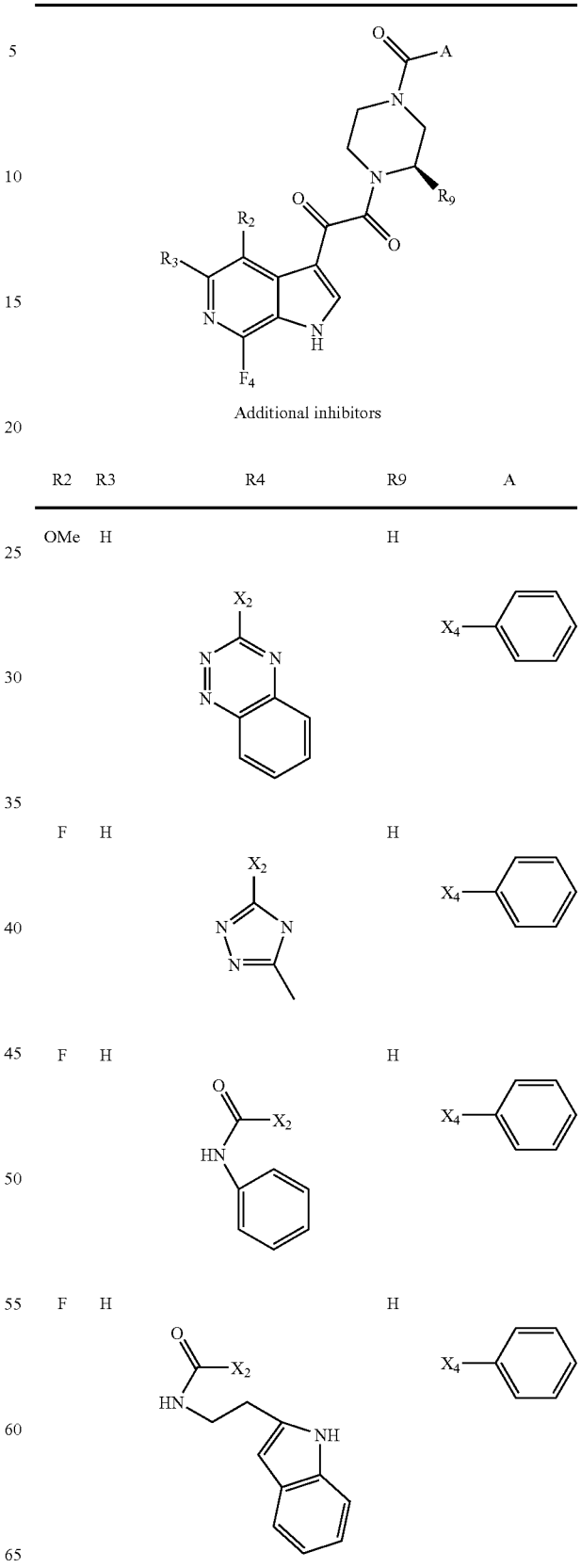
Additional inhibitors TABLE 2a-continued
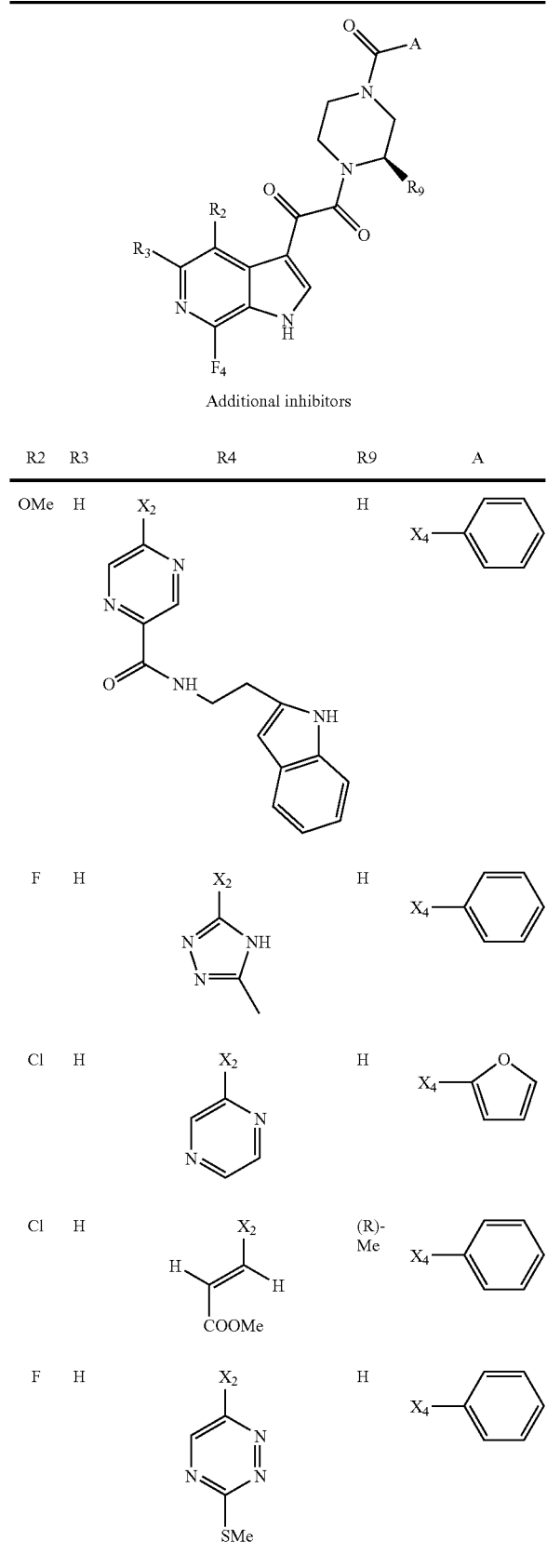
Additional inhibitors
TABLE 2a-continued
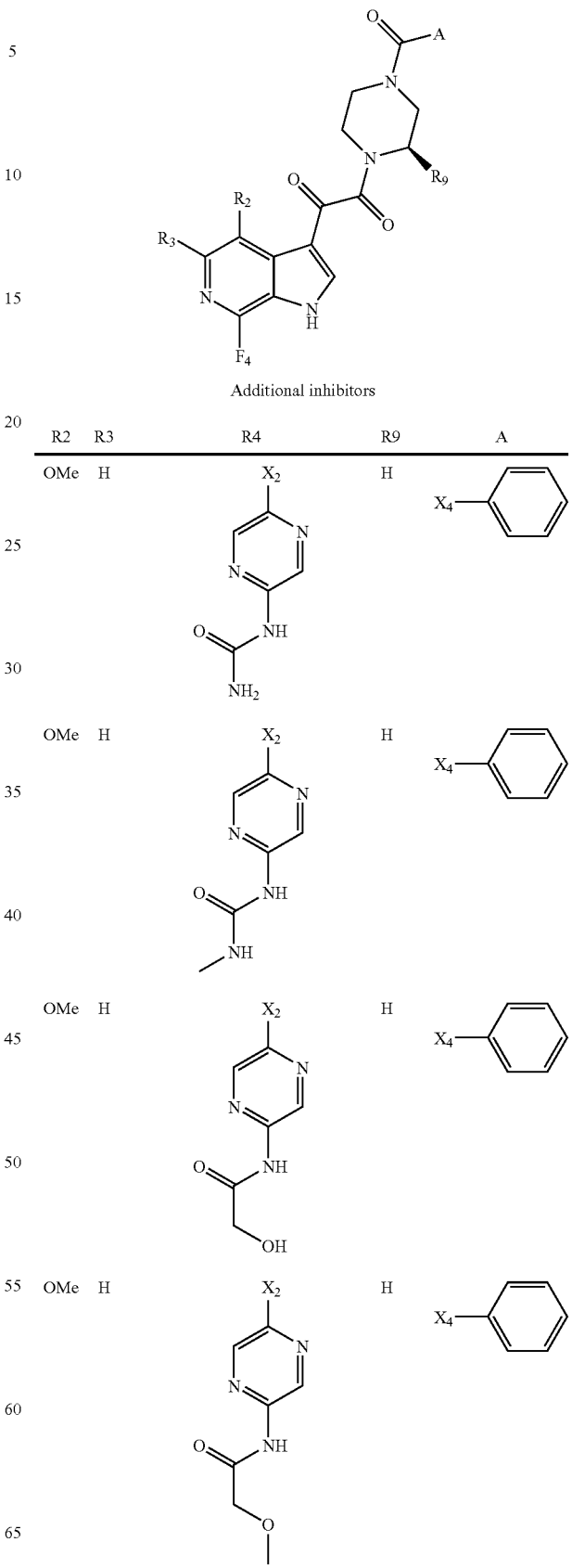
Additional inhibitors TABLE 2a-continued
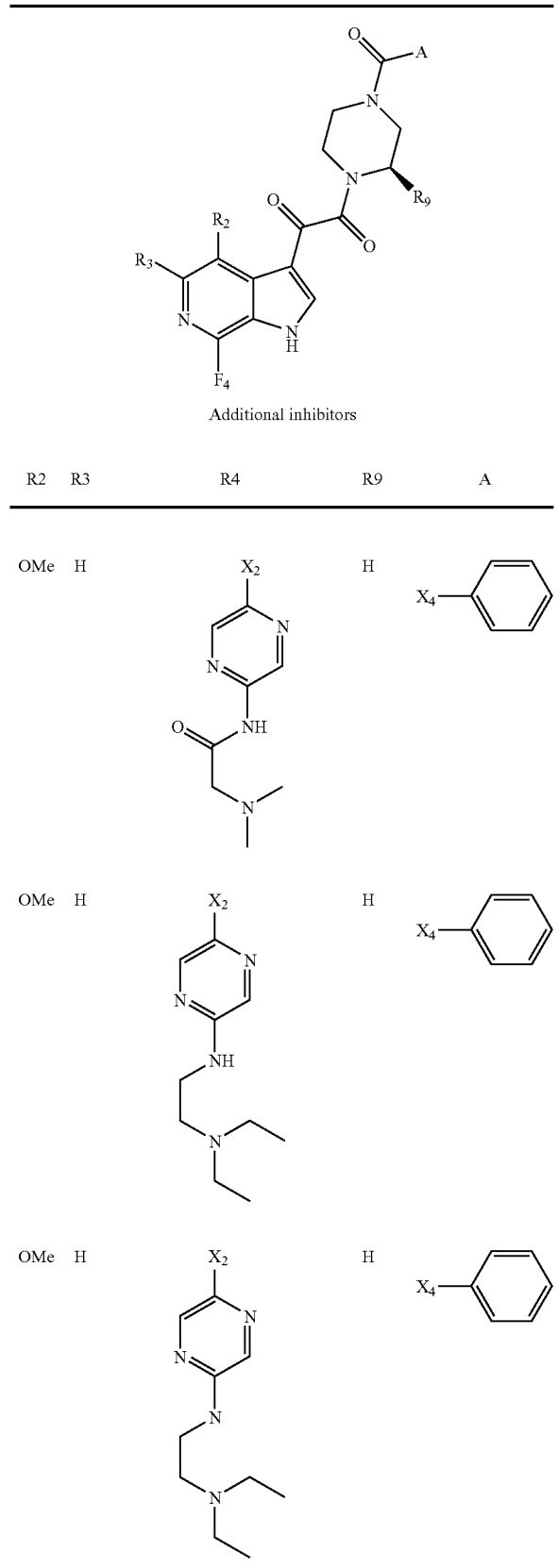
Additional inhibitors
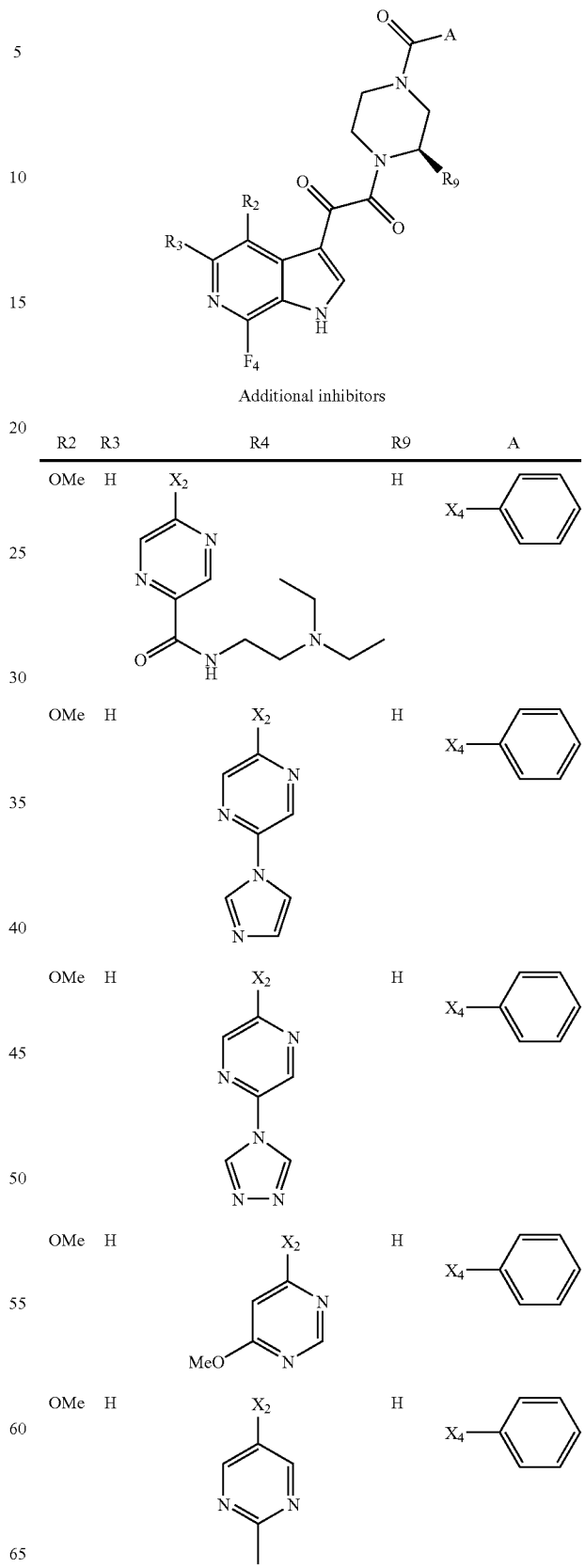
Additional inhibitors TABLE 2a-continued
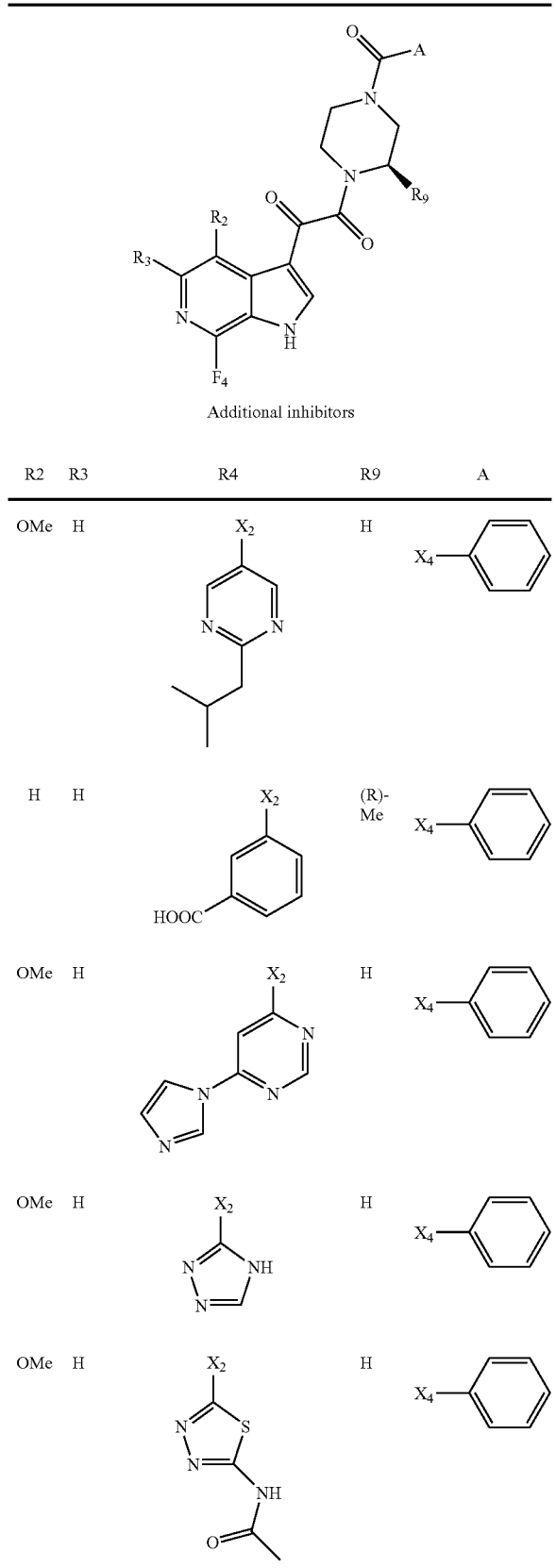
Additional inhibitors
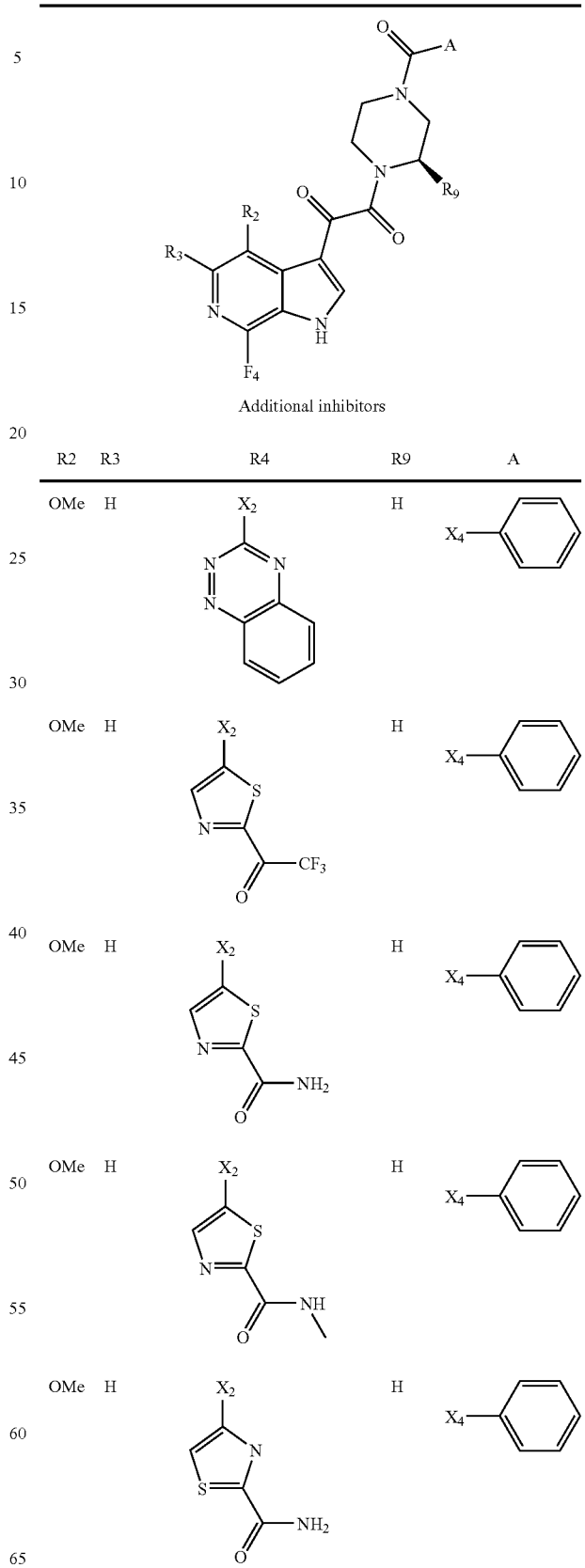
Additional inhibitors TABLE 2a-continued
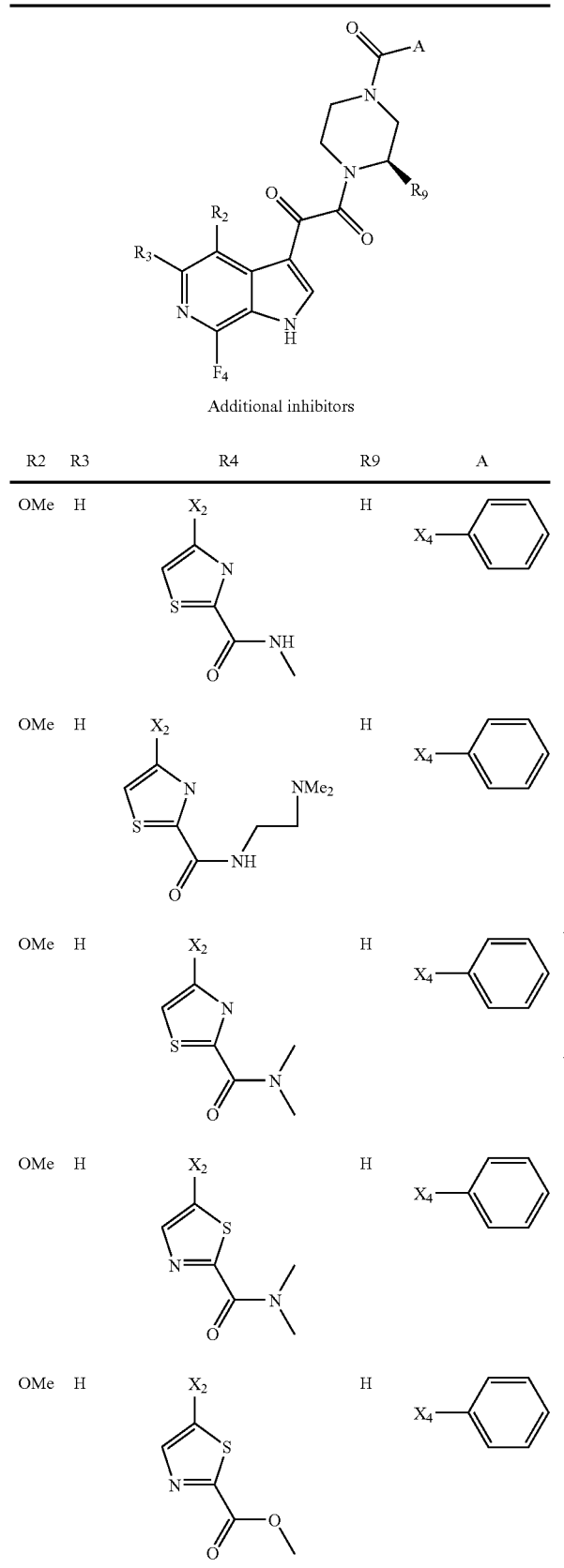
Additional inhibitors
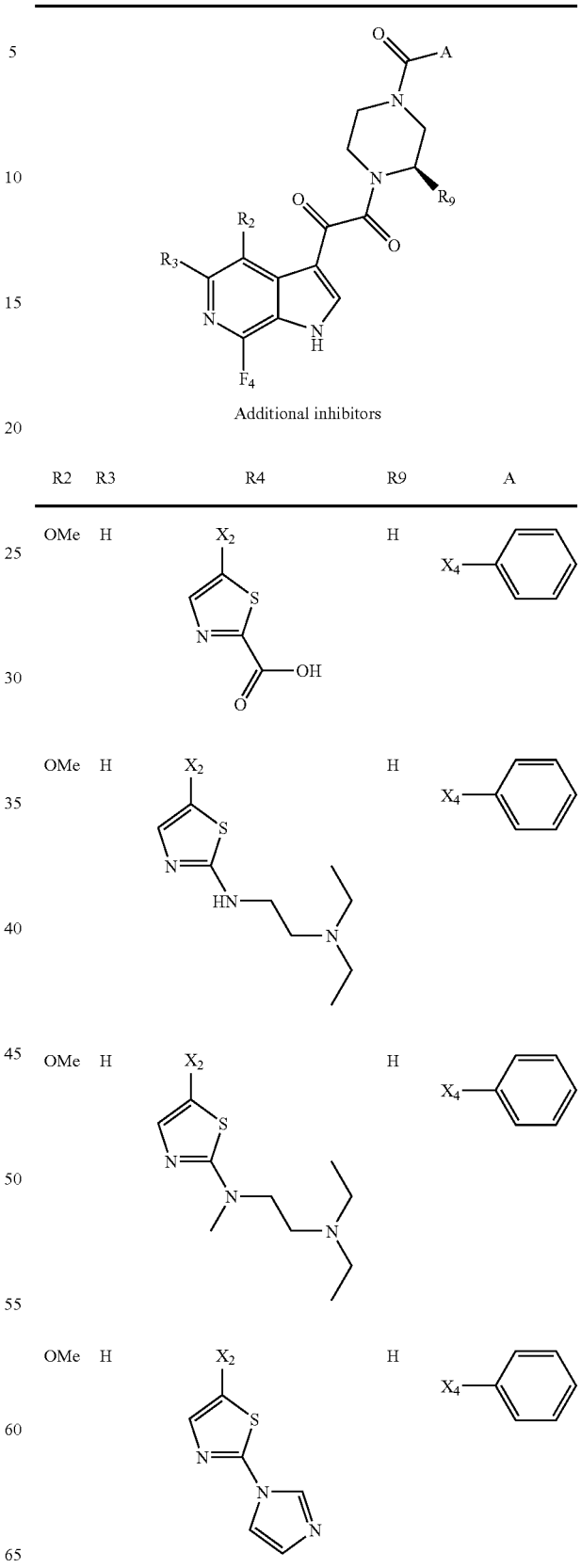
Additional inhibitors TABLE 2a-continued
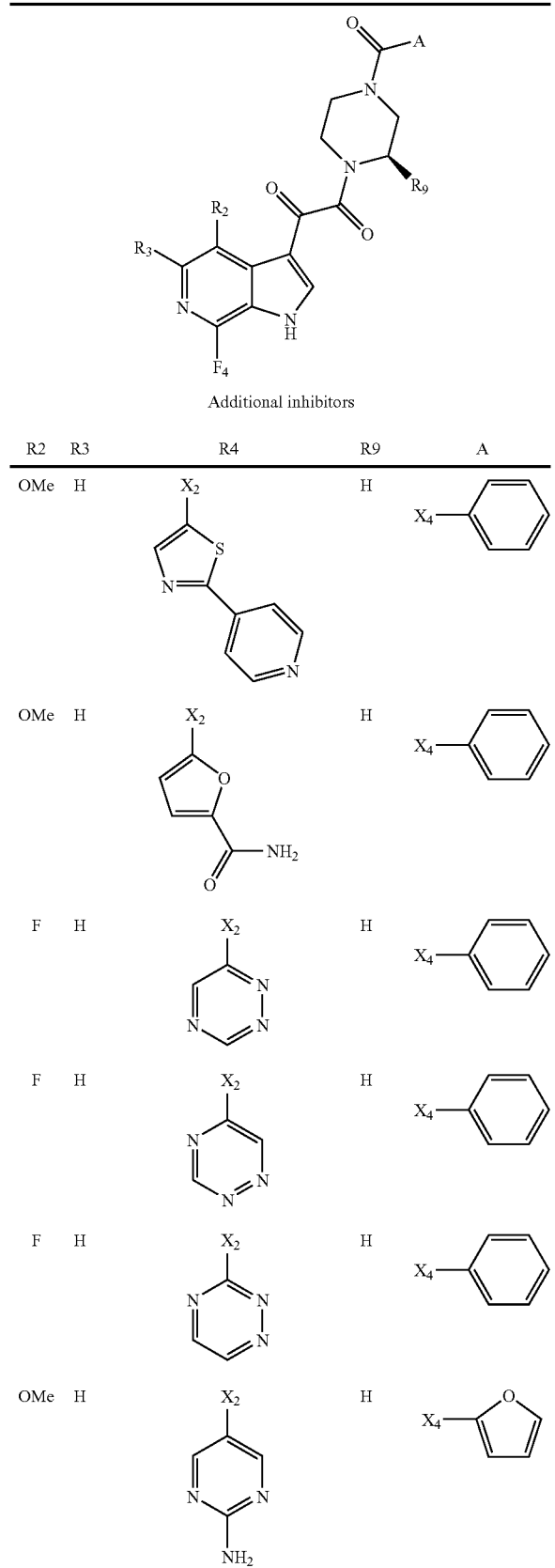
Additional inhibitors
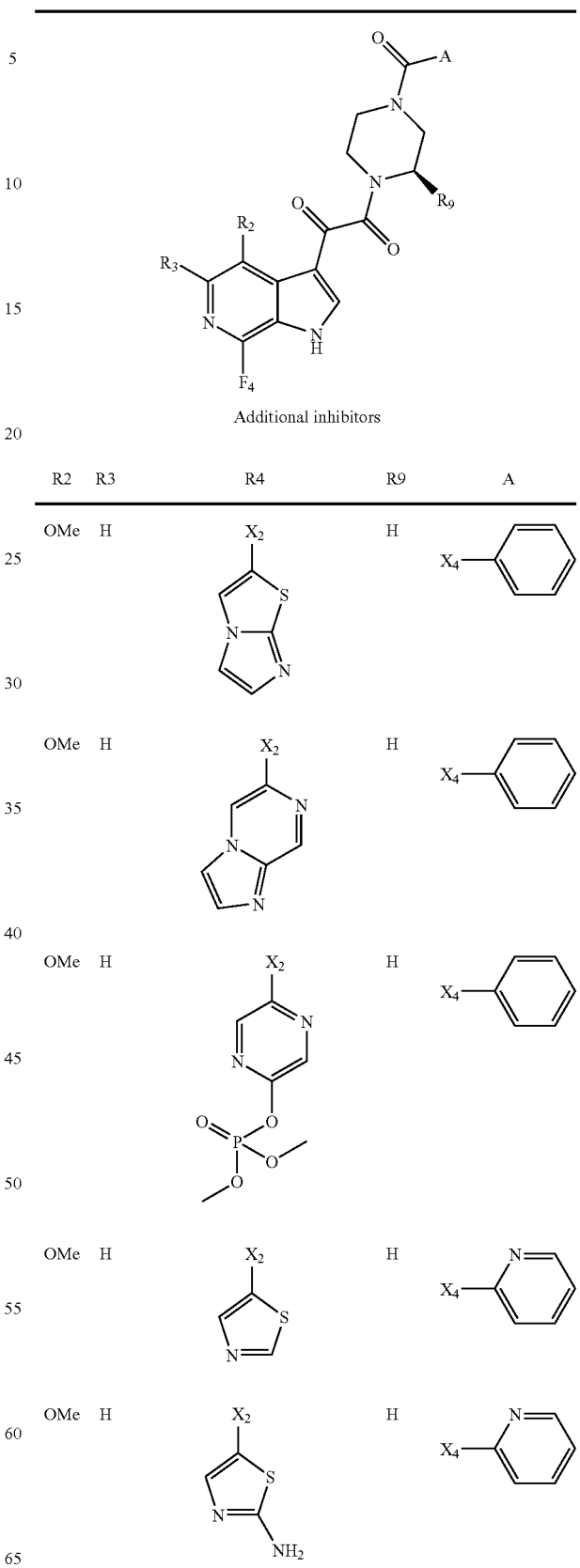
Additional inhibitors TABLE 2a-continued
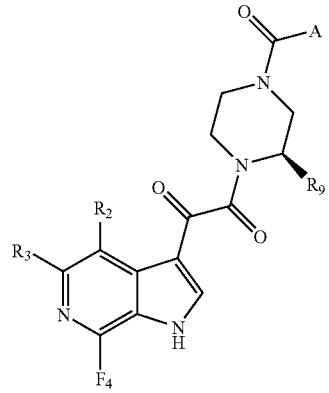
Additional inhibitors
| R2 | R3 | R4 | R9 | A |
|---|---|---|---|---|
| OMe | H | 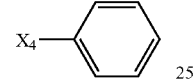 | H | 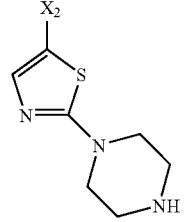 |
| OMe | H | 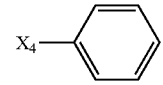 | H | 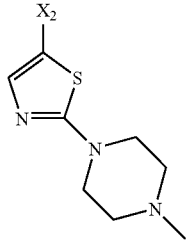 |
| OMe | H | 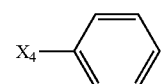 | H | 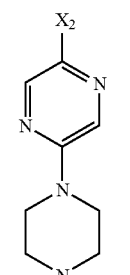 |
| OMe | H |  | H | 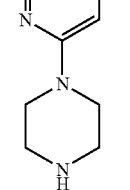 |
TABLE 2a-continued
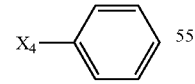
Additional inhibitors
| R2 | R3 | R4 | R9 | A |
|---|---|---|---|---|
| OMe | H | 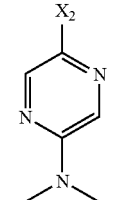 | H |  |
| OMe | H | 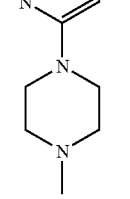 | H | 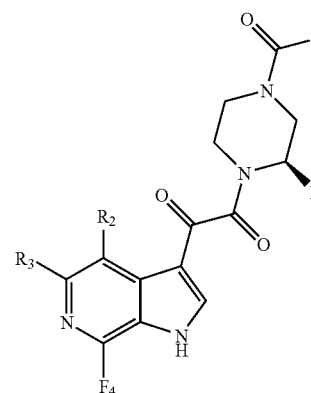 |
| OMe | H | 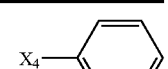 | H | 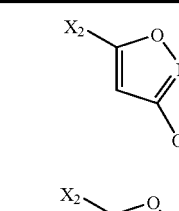 |
| OMe | H | 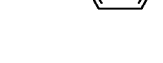 | H | 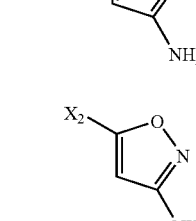 |
| OMe | H | 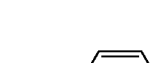 | H | 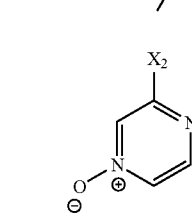 |
| OMe | H | 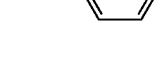 | H | 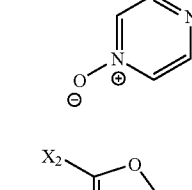 |

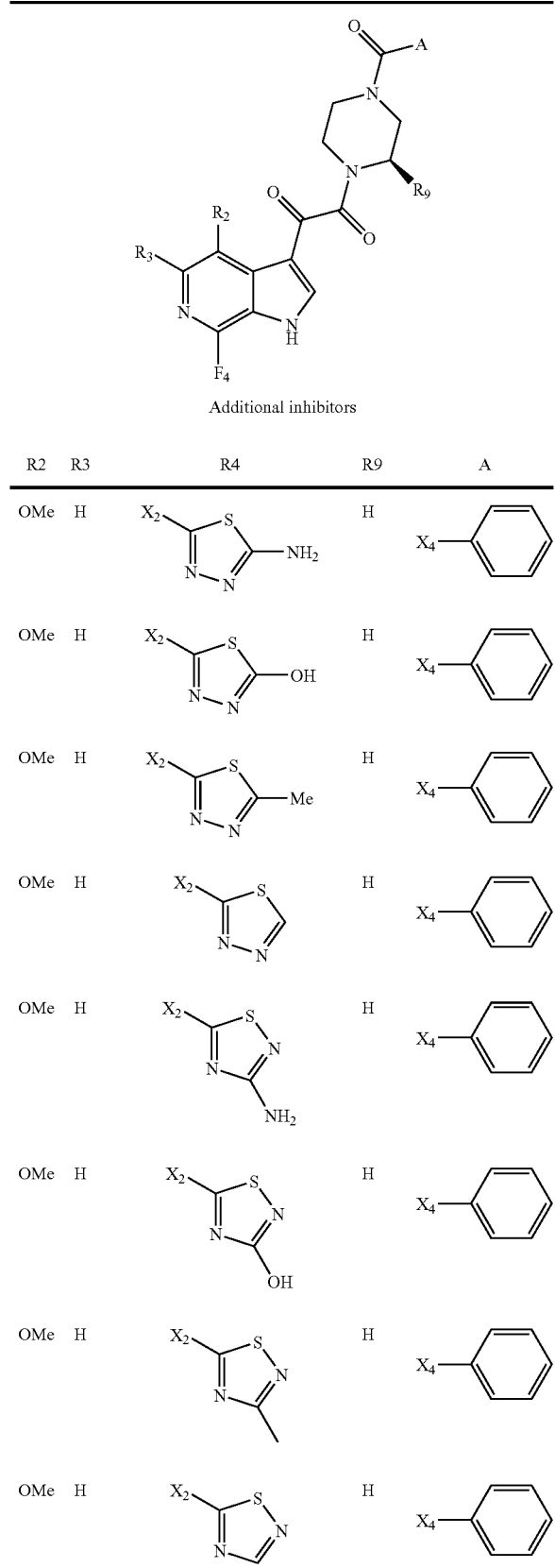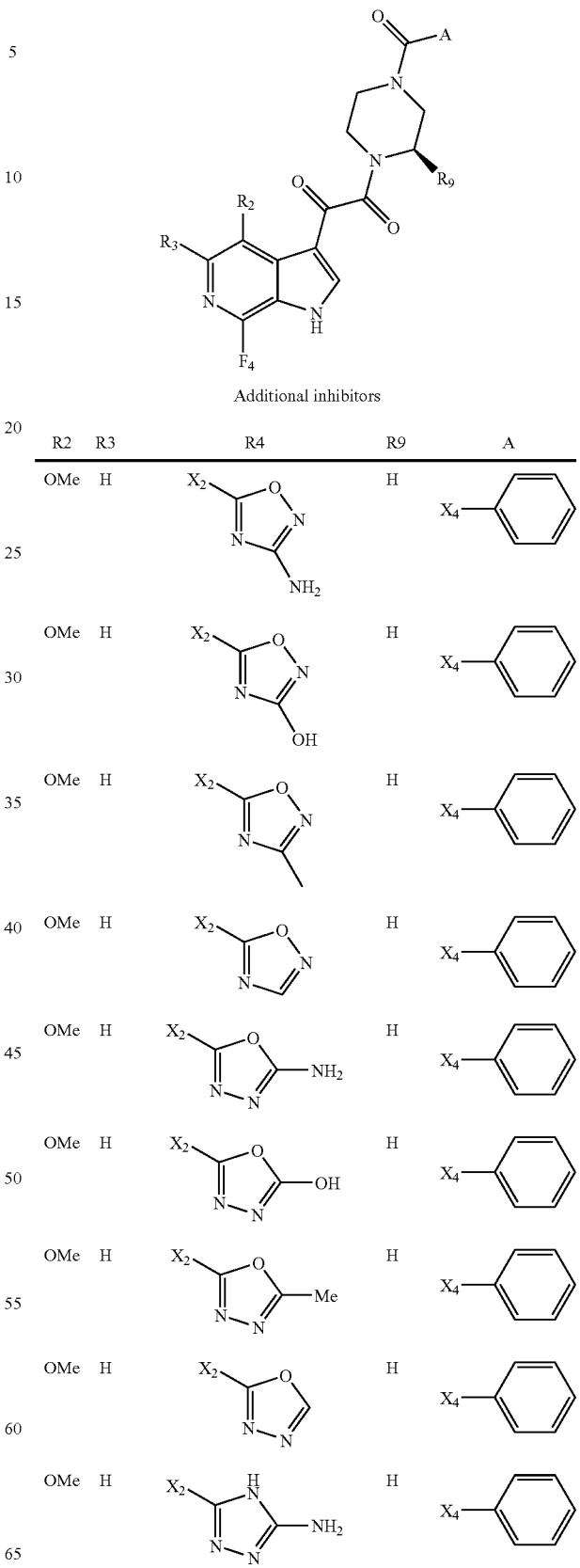

TABLE 2a-continued

Additional inhibitors

| R2 | R3 | R4 | R9 | A |
|---|---|---|---|---|
| OMe | H | (X₂-triazol-OH) | H | X₄-Ph |
| OMe | H | (X₂-triazol-Me) | H | X₄-Ph |
| OMe | H | (X₂-triazole) | H | X₄-Ph |
| OMe | H | (X₂-isothiazol-NH₂) | H | X₄-Ph |
| OMe | H | (X₂-isothiazol-OH) | H | X₄-Ph |
| OMe | H | (X₂-isothiazol-Me) | H | X₄-Ph |
| OMe | H | (X₂-isothiazole) | H | X₄-Ph |
| OMe | H | (X₂-pyrazol-Me) | H | X₄-Ph |
| OMe | H | (X₂-pyrazol-OH) | H | X₄-Ph |
| OMe | H | (X₂-pyrazol-NH₂) | H | X₄-Ph |
| OMe | H | (X₂-oxadiazol-NH₂) | H | X₄-Ph |
| OMe | H | (X₂-oxadiazol-OH) | H | X₄-Ph |
| OMe | H | (X₂-oxadiazol-Me) | H | X₄-Ph |
| OMe | H | (X₂-oxadiazole) | H | X₄-Ph |
| OMe | H | (X₂-thiadiazol-NH₂) | H | X₄-Ph |
| OMe | H | (X₂-thiadiazol-OH) | H | X₄-Ph |
| OMe | H | (X₂-thiadiazol-Me) | H | X₄-Ph |

TABLE 2a-continued
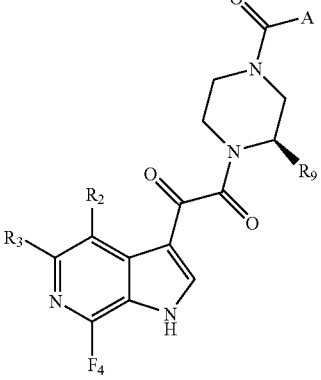
Additional inhibitors
| R2 | R3 | R4 | R9 | A |
|---|---|---|---|---|
| OMe | H | 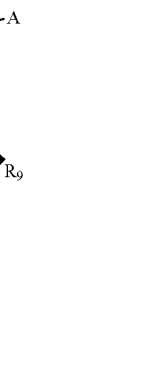 | H | 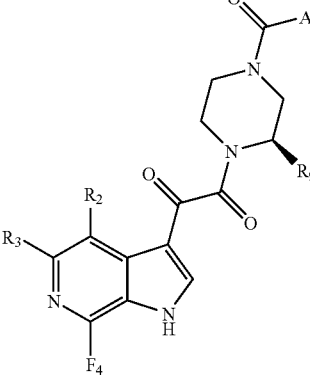 |
| OMe | H | 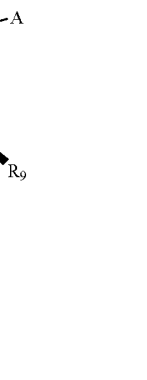 | H | 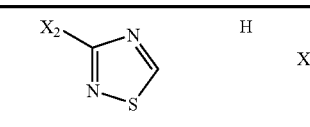 |
| OMe | H | 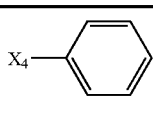 | H | 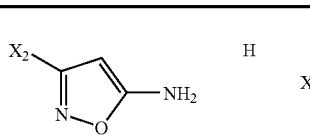 |
| OMe | H | 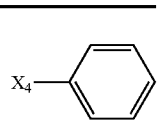 | H | 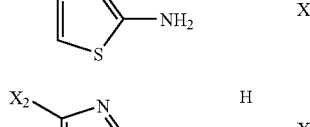 |
| OMe | H | 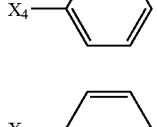 | H | 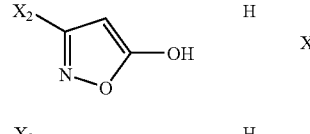 |
| OMe | H | 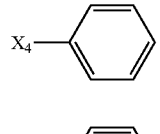 | H | 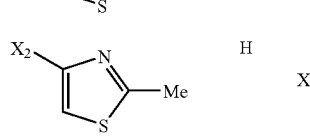 |
| OMe | H | 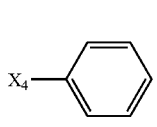 | H | 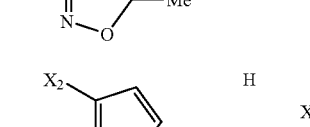 |
| OMe | H | 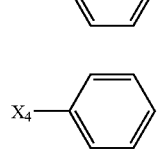 | H | 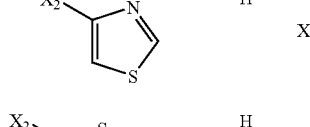 |
| OMe | H | 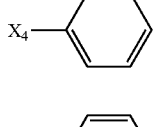 | H | 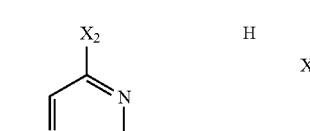 |
| OMe | H | 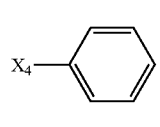 | H | 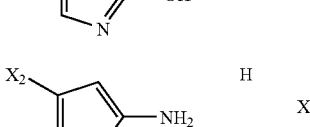 |
TABLE 2a-continued
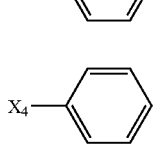
Additional inhibitors
| R2 | R3 | R4 | R9 | A |
|---|---|---|---|---|
| OMe | H | 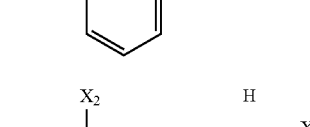 | H | 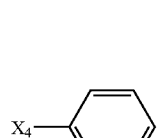 |
| OMe | H | 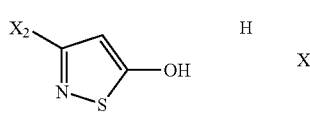 | H | 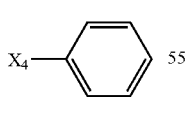 |
| OMe | H | 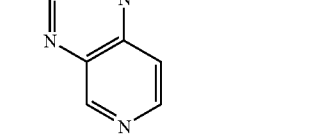 | H |  |
| OMe | H | 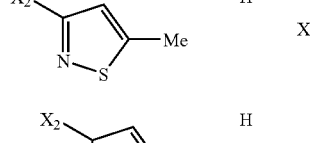 | H | 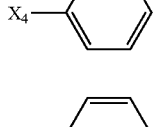 |
| OMe | H | 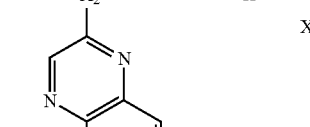 | H | 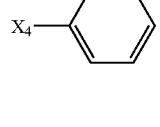 |
| OMe | H |  | H | 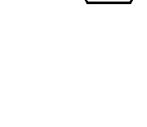 |
| OMe | H | 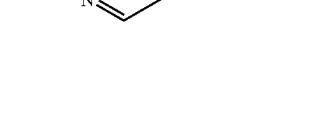 | H |  |

TABLE 2a-continued

Additional inhibitors

| R2 | R3 | R4 | R9 | A |
|---|---|---|---|---|
| OMe | H | X₂-pyrido[3,4-b]pyrazine | H | X₄-phenyl |
| OMe | H | X₂-pyrido[2,3-b]pyrazine | H | X₄-phenyl |
| OMe | H | X₂-pyrazino[2,3-b]pyrazine | H | X₄-phenyl |
| OMe | H | X₂-pteridine | H | X₄-phenyl |
| OMe | H | X₂-pteridine (isomer) | H | X₄-phenyl |

TABLE 2a-continued

Additional inhibitors

| R2 | R3 | R4 | R9 | A |
|---|---|---|---|---|
| OMe | H | X₂-quinoxaline-6-OH | H | X₄-phenyl |
| OMe | H | X₂-quinoxaline-5-OH | H | X₄-phenyl |
| OMe | H | X₂-quinoxaline-6-OH | H | X₄-phenyl |
| OMe | H | X₂-quinoxaline-5-OH | H | X₄-phenyl |
| OMe | H | X₂-quinoxaline-5-COOH | H | X₄-phenyl |

TABLE 2a-continued

Additional inhibitors

| R2 | R3 | R4 | R9 | A |
|---|---|---|---|---|
| OMe | H | 3-X$_2$-quinoxalin-6-yl, 7-COOH | H | X$_4$-phenyl |
| OMe | H | 3-X$_2$-quinoxalin-7-yl, COOH | H | X$_4$-phenyl |
| OMe | H | 3-X$_2$-quinoxalin-5-yl, 8-COOH | H | X$_4$-phenyl |
| OMe | H | 5-X$_2$-3-amino-1,2,4-triazin-6-yl | H | X$_4$-phenyl |
| OMe | H | 5-X$_2$-3-hydroxy-1,2,4-triazin-6-yl | H | X$_4$-phenyl |

TABLE 2a-continued

Additional inhibitors

| R2 | R3 | R4 | R9 | A |
|---|---|---|---|---|
| OMe | H | 5-X$_2$-3-hydroxy-1,2,4-triazin-6-yl | H | X$_4$-phenyl |
| OMe | H | 5-X$_2$-3-phenyl-1,2,4-triazin-6-yl | H | X$_4$-phenyl |
| OMe | H | 5-X$_2$-3-amino-1,2,4-triazin-6-yl | H | X$_4$-phenyl |
| OMe | H | 5-X$_2$-3-hydroxy-1,2,4-triazin-6-yl | H | X$_4$-phenyl |
| OMe | H | 5-X$_2$-3-phenyl-1,2,4-triazin-6-yl | H | X$_4$-phenyl |

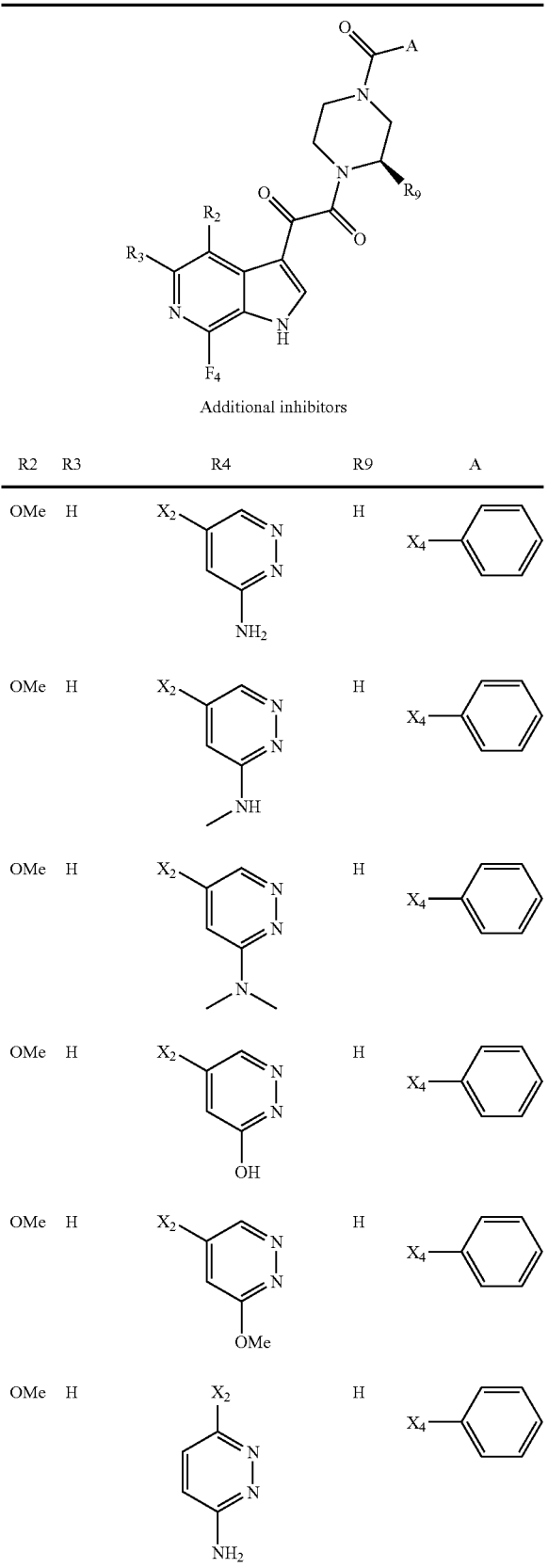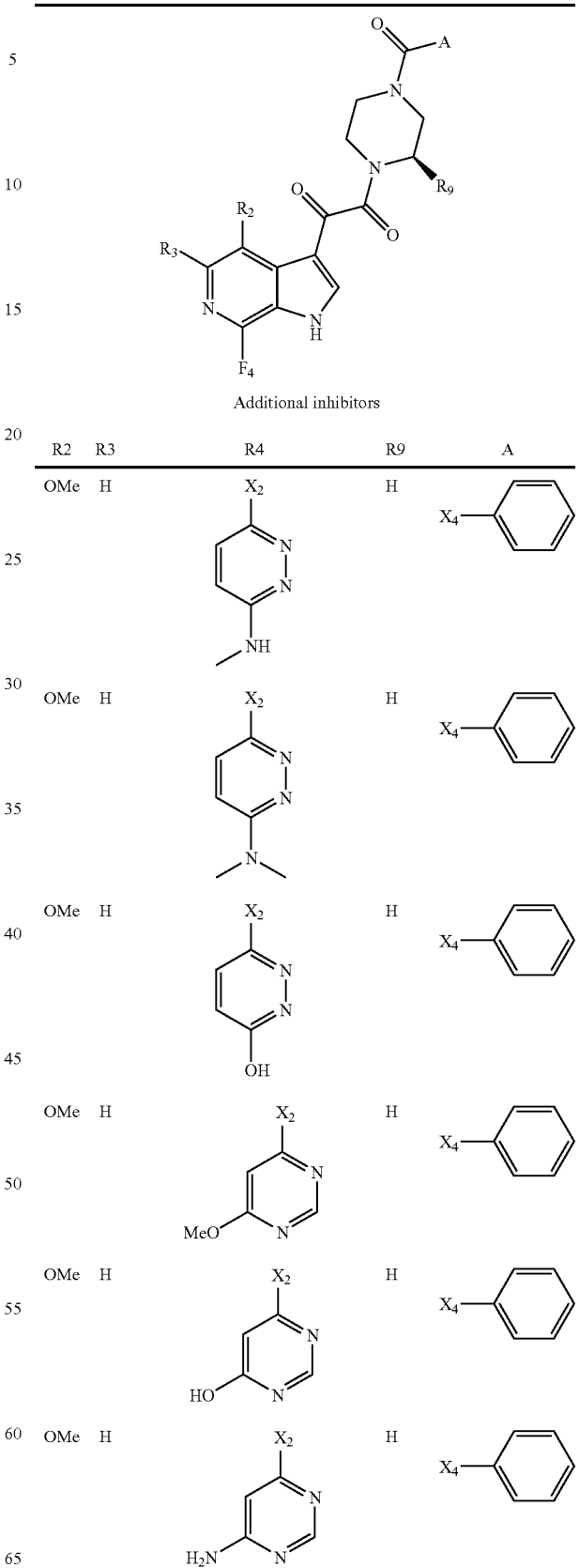

TABLE 2a-continued
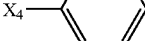
Additional inhibitors
| R2 | R3 | R4 | R9 | A |
|---|---|---|---|---|
| OMe | H | 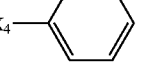 | H | 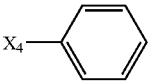 |
| OMe | H | 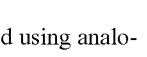 | H | 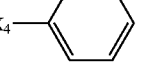 |
TABLE 2a-continued
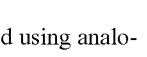
Additional inhibitors
| R2 | R3 | R4 | R9 | A |
|---|---|---|---|---|
| OMe | H | 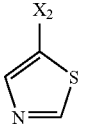 | H | 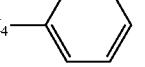 |
The inhibitors in Table 4a could be prepared using analogous procedures which were demonstrated to prepare the examples in Table 4.
TABLE 4a
Other inhibitors
| Table Entry | R2 | R3 | R4 | R9 | A |
|---|---|---|---|---|---|
| 1 | H | H | (thiazole) | $H_3$ | (phenyl with $X_4$) |

TABLE 4a-continued
| 2 | H | H |  | H |  |
| 3 | H | H | 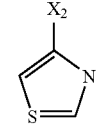 | H | 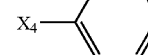 |
| 4 | H | H | 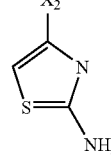 | H | 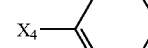 |
| 5 | H | H | 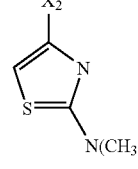 | H | 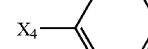 |
| 6 | H | H | 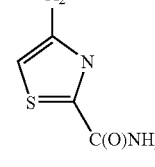 | H | 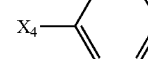 |
| 7 | H | H | 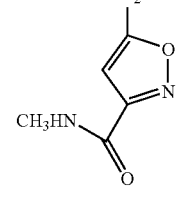 | H | 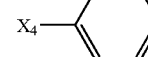 |
| 8 | H | H | 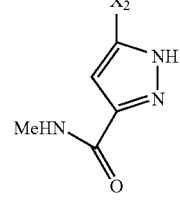 | H | 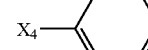 |
| 9 | H | H | 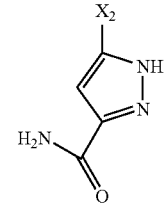 | H | 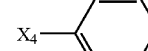 |

TABLE 4a-continued
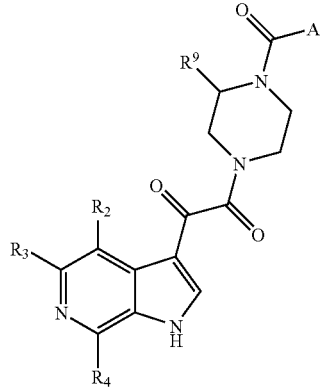
| R2 | R3 | R4 | R9 | A |
|---|---|---|---|---|
| OMe | H | 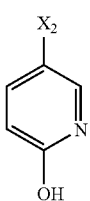 | (R) or (S) Me | 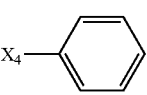 |
| F | H | 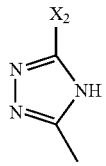 | (R) or (S) Me | 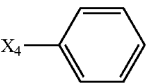 |
| Cl | H | 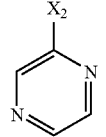 | (R) or (S) Me | 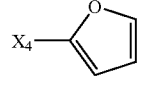 |
| F | H | 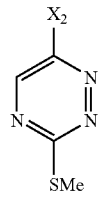 | (R) or (S) Me | 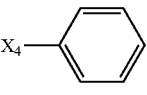 |
| OMe | H | 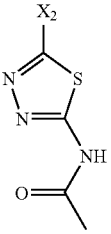 | (R) or (S) Me | 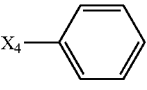 |

TABLE 4a-continued
| | | | | |
|---|---|---|---|---|
| OMe | H | 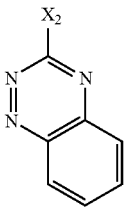 | (R) or (S) Me | 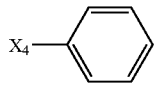 |
| F | H | 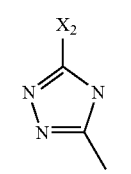 | (R) or (S) Me | 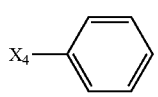 |
| F | H | 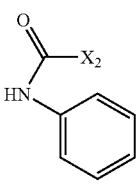 | (R) or (S) Me | 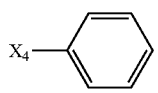 |
| F | H | 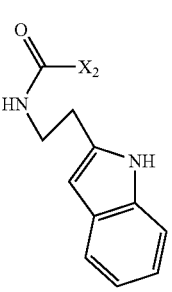 | (R) or (S) Me | 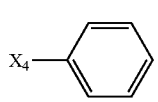 |
| OMe | H | 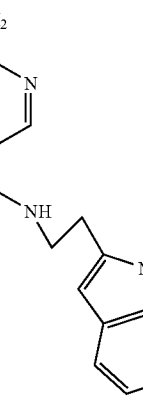 | (R) or (S) Me | 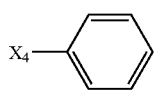 |
| F | H | 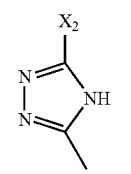 | (R) or (S) Me | 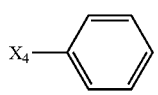 |
| Cl | H | 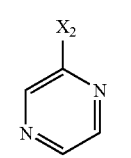 | (R) or (S) Me | 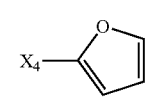 |

TABLE 4a-continued
| | | | | |
|---|---|---|---|---|
| Cl | H | 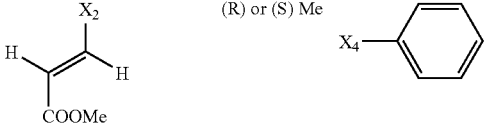 | (R) or (S) Me | 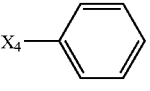 |
| F | H | 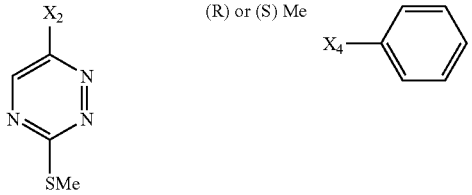 | (R) or (S) Me | 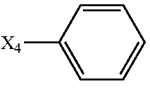 |
| OMe | H | 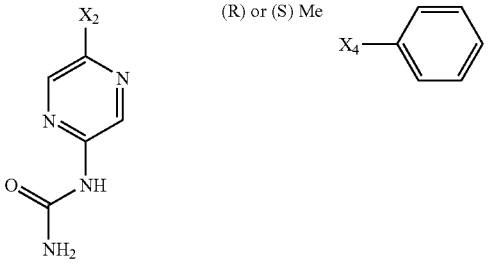 | (R) or (S) Me | 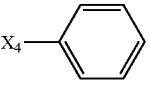 |
| OMe | H | 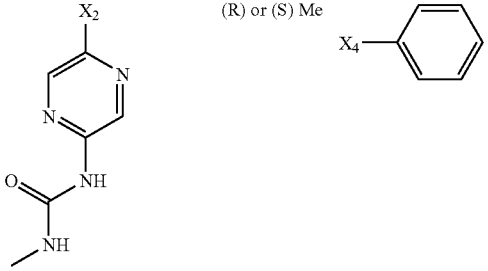 | (R) or (S) Me | 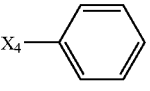 |
| OMe | H | 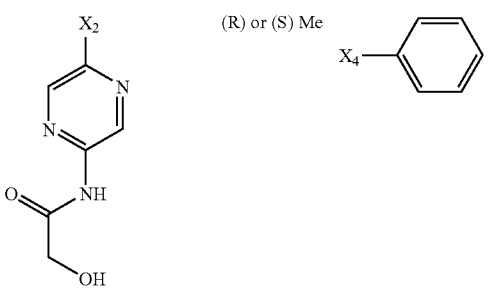 | (R) or (S) Me | 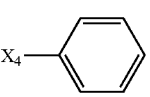 |
| OMe | H | 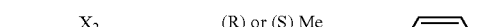 | (R) or (S) Me | 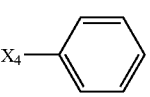 |

TABLE 4a-continued
| OMe | H | 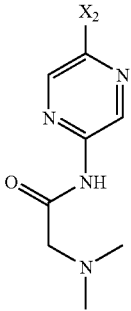 | (R) or (S) Me | 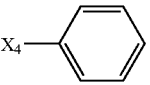 |
| OMe | H | 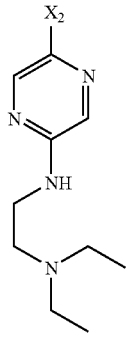 | (R) or (S) Me | 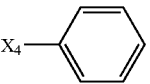 |
| OMe | H | 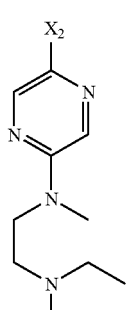 | (R) or (S) Me | 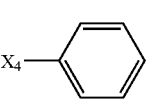 |
| OMe | H | 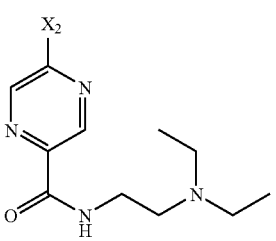 | (R) or (S) Me | 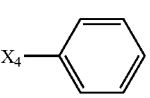 |
| OMe | H | 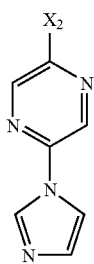 | (R) or (S) Me | 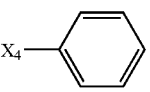 |

TABLE 4a-continued
| | | | | |
|---|---|---|---|---|
| OMe | H | 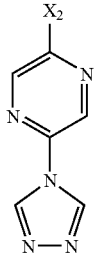 | (R) or (S) Me | 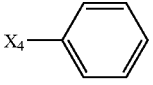 |
| OMe | H | 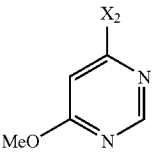 | (R) or (S) Me | 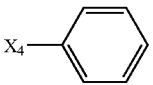 |
| OMe | H | 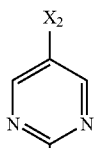 | (R) or (S) Me | 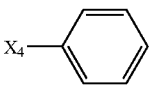 |
| OMe | H | 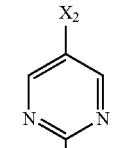 | (R) or (S) Me | 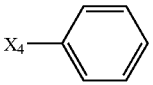 |
| H | H | 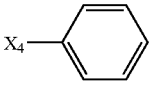 | (R) or (S) Me | 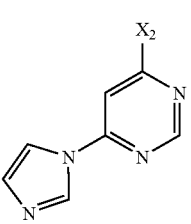 |
| OMe | H | 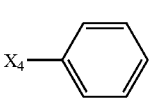 | (R) or (S) Me | 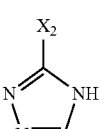 |
| OMe | H | 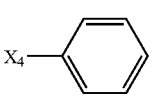 | (R) or (S) Me | |

TABLE 4a-continued
| OMe | H | 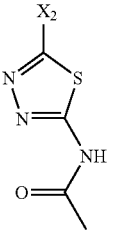 | (R) or (S) Me | 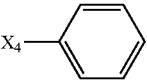 |
| OMe | H | 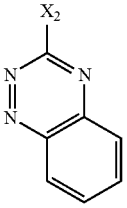 | (R) or (S) Me | 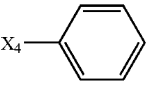 |
| OMe | H | 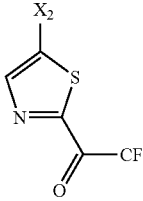 | (R) or (S) Me | 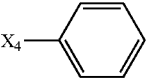 |
| OMe | H | 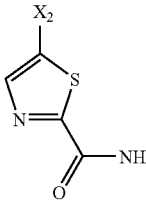 | (R) or (S) Me | 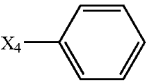 |
| OMe | H | 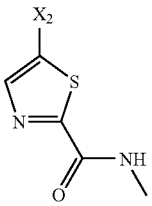 | (R) or (S) Me | 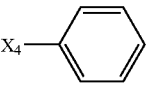 |
| OMe | H | 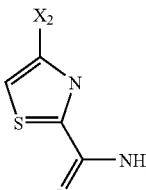 | (R) or (S) Me | 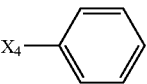 |
| OMe | H | 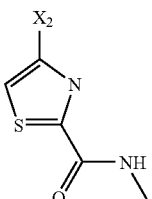 | (R) or (S) Me | 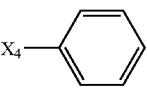 |

TABLE 4a-continued

| | | | | |
|---|---|---|---|---|
| OMe | H | thiazole-2-C(O)NH-CH2CH2-NMe2 (X2 at 4-position) | (R) or (S) Me | X4-phenyl |
| OMe | H | thiazole-2-C(O)N(Me)2 (X2 at 4-position) | (R) or (S) Me | X4-phenyl |
| OMe | H | thiazole-2-C(O)N(Me)2 (X2 at 5-position) | (R) or (S) Me | X4-phenyl |
| OMe | H | thiazole-2-C(O)OMe (X2 at 5-position) | (R) or (S) Me | X4-phenyl |
| OMe | H | thiazole-2-C(O)OH (X2 at 5-position) | (R) or (S) Me | X4-phenyl |
| OMe | H | thiazole-2-NH-CH2CH2-NEt2 (X2 at 5-position) | (R) or (S) Me | X4-phenyl |

TABLE 4a-continued
| | | | | |
|---|---|---|---|---|
| OMe | H | 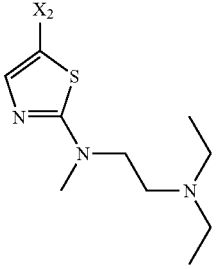 | (R) or (S) Me | 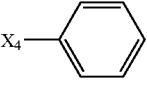 |
| OMe | H | 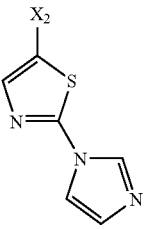 | (R) or (S) Me | 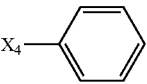 |
| OMe | H | 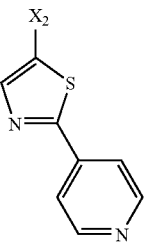 | (R) or (S) Me | 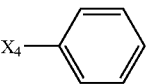 |
| OMe | H | 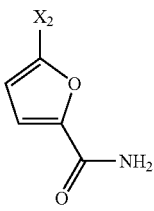 | (R) or (S) Me | 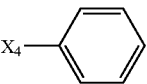 |
| F | H | 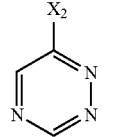 | (R) or (S) Me | 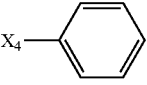 |
| F | H | 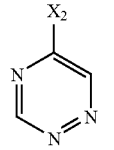 | (R) or (S) Me | 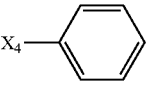 |
| F | H | 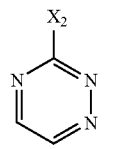 | (R) or (S) Me | 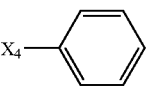 |

TABLE 4a-continued
| OMe | H | 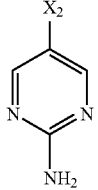 | (R) or (S) Me | 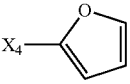 |
| OMe | H | 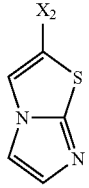 | (R) or (S) Me | 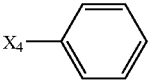 |
| OMe | H | 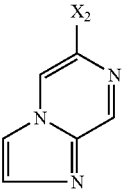 | (R) or (S) Me | 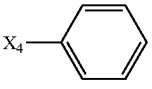 |
| OMe | H | 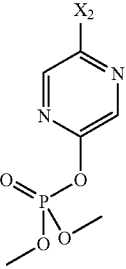 | (R) or (S) Me | 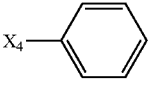 |
| OMe | H | 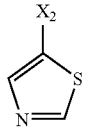 | (R) or (S) Me | 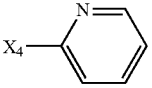 |
| OMe | H | 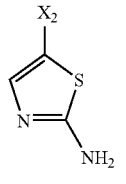 | (R) or (S) Me | 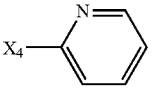 |
| OMe | H | 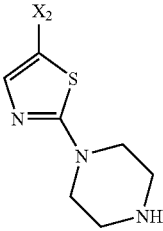 | (R) or (S) Me | 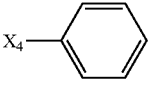 |

TABLE 4a-continued
| OMe | H | 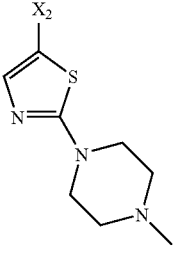 | (R) or (S) Me | 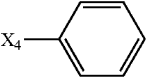 |
| OMe | H | 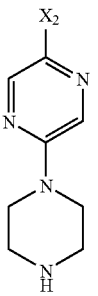 | (R) or (S) Me | 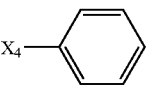 |
| OMe | H | 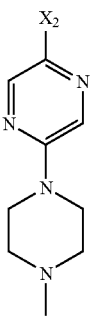 | (R) or (S) Me | 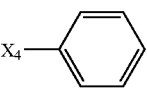 |
| OMe | H | 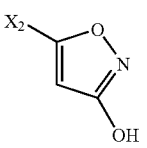 | (R) or (S) Me | 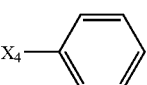 |
| OMe | H | 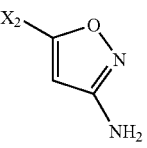 | (R) or (S) Me | 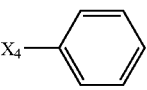 |
| OMe | H | 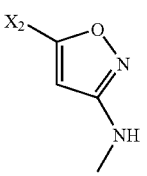 | (R) or (S) Me | 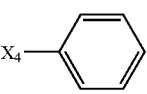 |
| OMe | H | 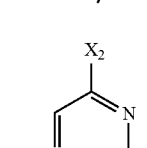 | (R) or (S) Me | 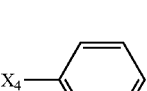 |

TABLE 4a-continued
| | | | | |
|---|---|---|---|---|
| OMe | H | 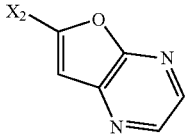 | (R) or (S) Me | 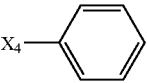 |
| OMe | H | 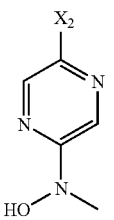 | (R) or (S) Me | 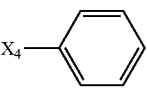 |
| OMe | H | 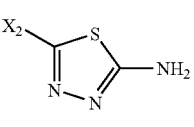 | (R) or (S) Me | 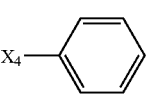 |
| OMe | H | 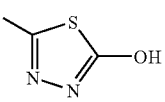 | (R) or (S) Me | 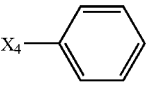 |
| OMe | H | 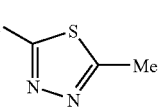 | (R) or (S) Me | 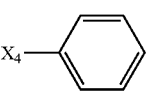 |
| OMe | H | 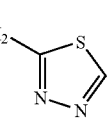 | (R) or (S) Me | 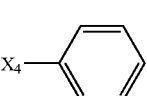 |
| OMe | H | 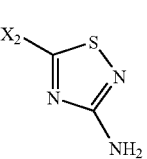 | (R) or (S) Me | 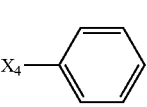 |
| OMe | H | 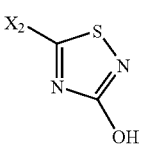 | (R) or (S) Me | 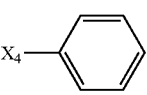 |
| OMe | H | 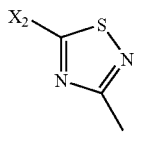 | (R) or (S) Me | 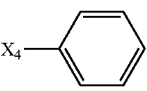 |
| OMe | H | 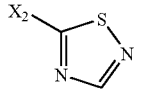 | (R) or (S) Me | 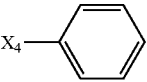 |
| OMe | H | 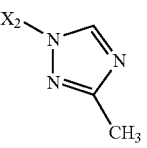 | (R) or (S) Me | 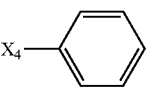 |

TABLE 4a-continued
| OMe | H | 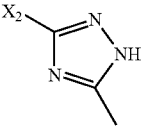 | (R) or (S) Me | 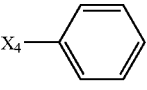 |
| OMe | H | 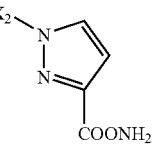 | (R) or (S) Me | 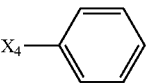 |
| OMe | H | 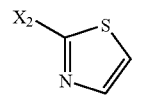 | (R) or (S) Me | 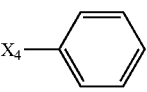 |
| F | H | 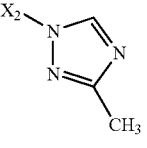 | (R) or (S) Me | 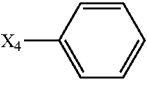 |
| F | H | 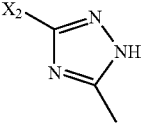 | (R) or (S) Me | 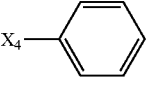 |
| F | H | 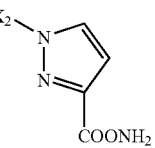 | (R) or (S) Me | 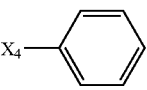 |
| F | H | 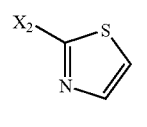 | (R) or (S) Me | 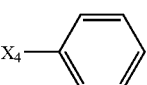 |
| OMe | H | 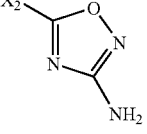 | (R) or (S) Me | 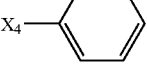 |
| OMe | H | 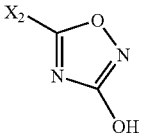 | (R) or (S) Me | 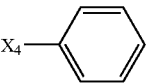 |
| OMe | H | 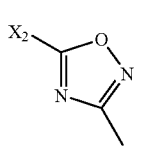 | (R) or (S) Me | 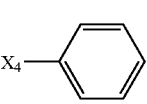 |
| OMe | H | 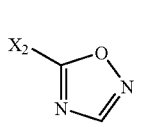 | (R) or (S) Me | 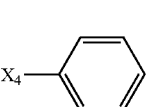 |

TABLE 4a-continued
| OMe | H | 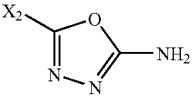 | (R) or (S) Me | 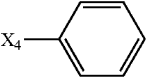 |
| --- | --- | --- | --- | --- |
| OMe | H | 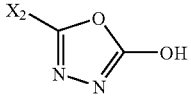 | (R) or (S) Me | 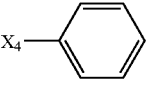 |
| OMe | H | 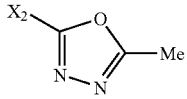 | (R) or (S) Me | 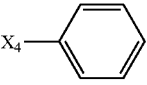 |
| OMe | H | 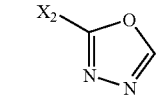 | (R) or (S) Me | 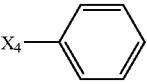 |
| OMe | H | 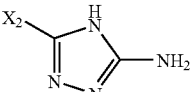 | (R) or (S) Me | 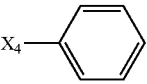 |
| OMe | H | 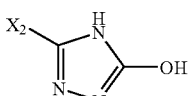 | (R) or (S) Me | 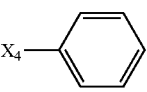 |
| OMe | H | 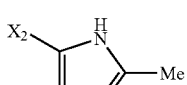 | (R) or (S) Me | 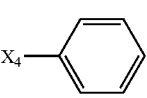 |
| OMe | H | 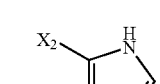 | (R) or (S) Me | 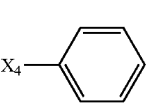 |
| OMe | H | 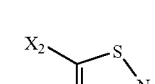 | (R) or (S) Me | 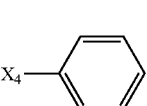 |
| OMe | H | 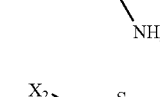 | (R) or (S) Me |  |
| OMe | H | 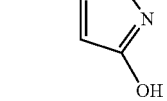 | (R) or (S) Me | 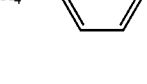 |
| OMe | H | 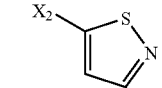 | (R) or (S) Me | 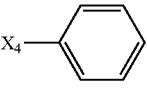 |

TABLE 4a-continued

| | | | | |
|---|---|---|---|---|
| OMe | H | X₂—[5-methyl-1H-pyrazol-3-yl] | (R) or (S) Me | X₄—Ph |
| OMe | H | X₂—[5-hydroxy-1H-pyrazol-3-yl] | (R) or (S) Me | X₄—Ph |
| OMe | H | X₂—[5-amino-1H-pyrazol-3-yl] | (R) or (S) Me | X₄—Ph |
| OMe | H | X₂—[5-amino-1,2,4-oxadiazol-3-yl] | (R) or (S) Me | X₄—Ph |
| OMe | H | X₂—[5-hydroxy-1,2,4-oxadiazol-3-yl] | (R) or (S) Me | X₄—Ph |
| OMe | H | X₂—[5-methyl-1,2,4-oxadiazol-3-yl] | (R) or (S) Me | X₄—Ph |
| OMe | H | X₂—[1,2,4-oxadiazol-3-yl] | (R) or (S) Me | X₄—Ph |
| OMe | H | X₂—[5-amino-1,2,4-thiadiazol-3-yl] | (R) or (S) Me | X₄—Ph |
| OMe | H | X₂—[5-hydroxy-1,2,4-thiadiazol-3-yl] | (R) or (S) Me | X₄—Ph |
| OMe | H | X₂—[5-methyl-1,2,4-thiadiazol-3-yl] | (R) or (S) Me | X₄—Ph |
| OMe | H | X₂—[1,2,4-thiadiazol-3-yl] | (R) or (S) Me | X₄—Ph |
| OMe | H | X₂—[2-amino-thiazol-4-yl] | (R) or (S) Me | X₄—Ph |
| OMe | H | X₂—[2-hydroxy-thiazol-4-yl] | (R) or (S) Me | X₄—Ph |

TABLE 4a-continued
| | | | | |
|---|---|---|---|---|
| OMe | H | 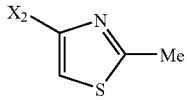 | (R) or (S) Me | 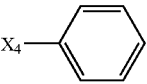 |
| OMe | H | 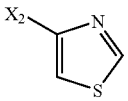 | (R) or (S) Me | 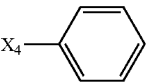 |
| OMe | H | 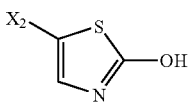 | (R) or (S) Me | 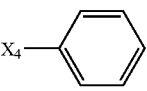 |
| OMe | H | 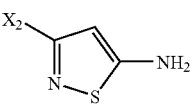 | (R) or (S) Me | 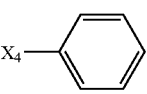 |
| OMe | H | 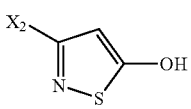 | (R) or (S) Me | 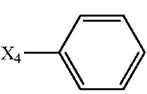 |
| OMe | H | 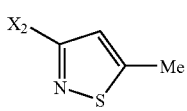 | (R) or (S) Me | 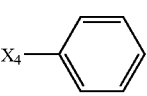 |
| OMe | H | 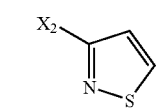 | (R) or (S) Me | 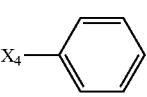 |
| OMe | H | 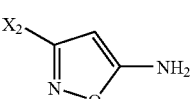 | (R) or (S) Me | 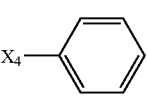 |
| OMe | H | 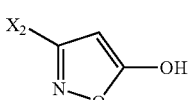 | (R) or (S) Me | 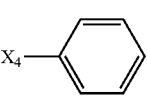 |
| OMe | H | 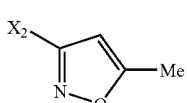 | (R) or (S) Me | 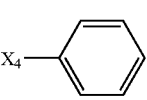 |
| OMe | H | 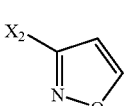 | (R) or (S) Me | 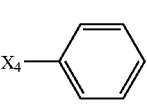 |
| OMe | H | 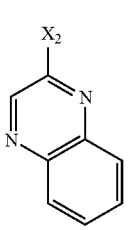 | (R) or (S) Me | 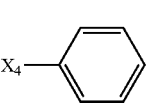 |

TABLE 4a-continued
| OMe | H | 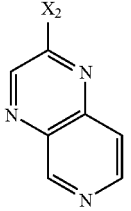 X₂ | (R) or (S) Me | 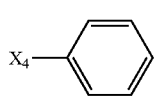 X₄ |
| --- | --- | --- | --- | --- |
| OMe | H | 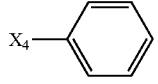 X₂ | (R) or (S) Me | 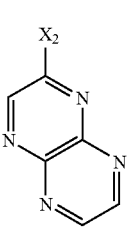 X₄ |
| OMe | H | 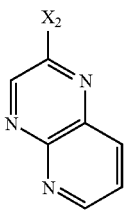 X₂ | (R) or (S) Me | 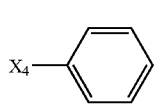 X₄ |
| OMe | H | 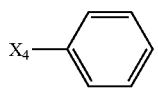 X₂ | (R) or (S) Me | 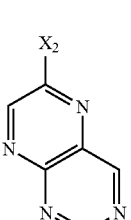 X₄ |
| OMe | H | 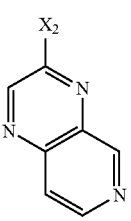 X₂ | (R) or (S) Me | 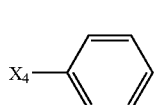 X₄ |
| OMe | H | 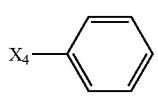 X₂ | (R) or (S) Me | 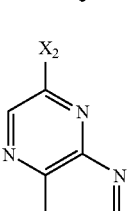 X₄ |
| OMe | H | 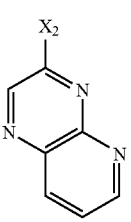 X₂ | (R) or (S) Me | 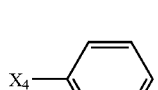 X₄ |

TABLE 4a-continued
| | | | | |
|---|---|---|---|---|
| OMe | H | 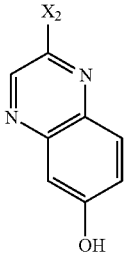 | (R) or (S) Me | 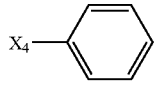 |
| OMe | H | 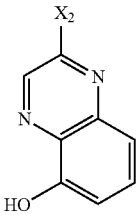 | (R) or (S) Me | 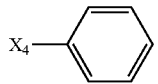 |
| OMe | H | 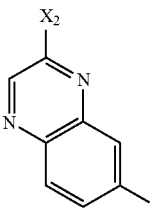 | (R) or (S) Me | 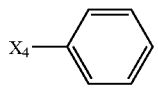 |
| OMe | H | 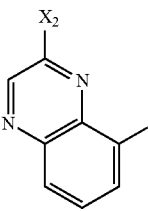 | (R) or (S) Me | 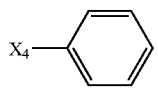 |
| OMe | H | 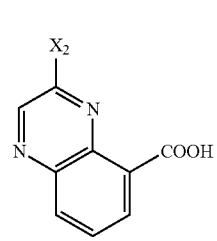 | (R) or (S) Me | 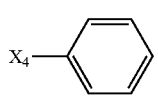 |
| OMe | H | 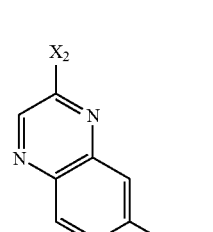 | (R) or (S) Me | 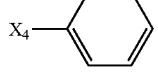 |

TABLE 4a-continued
| | | | | |
|---|---|---|---|---|
| OMe | H | 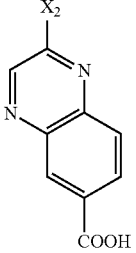 | (R) or (S) Me | 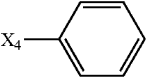 |
| OMe | H | 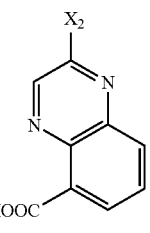 | (R) or (S) Me | 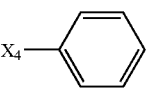 |
| OMe | H | 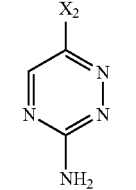 | (R) or (S) Me | 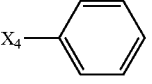 |
| OMe | H | 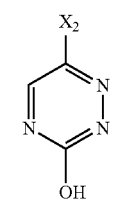 | (R) or (S) Me | 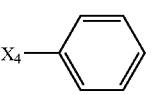 |
| OMe | H | 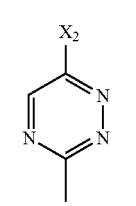 | (R) or (S) Me | 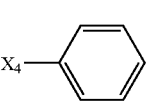 |
| OMe | H | 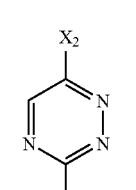 | (R) or (S) Me | 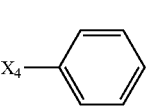 |
| OMe | H | 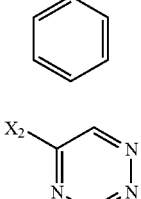 | (R) or (S) Me |  |

TABLE 4a-continued
| OMe | H | 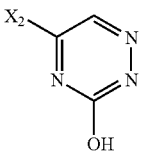 | (R) or (S) Me | 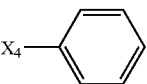 |
| OMe | H | 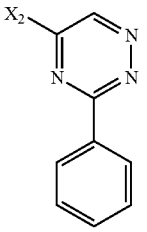 | (R) or (S) Me | 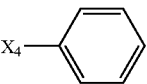 |
| OMe | H | 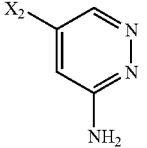 | (R) or (S) Me | 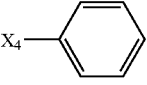 |
| OMe | H | 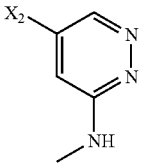 | (R) or (S) Me | 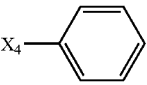 |
| OMe | H | 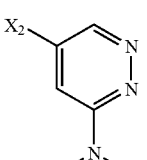 | (R) or (S) Me | 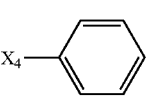 |
| OMe | H | 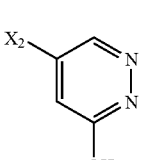 | (R) or (S) Me | 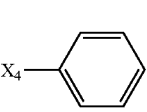 |
| OMe | H | 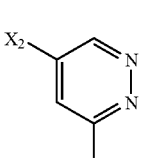 | (R) or (S) Me | 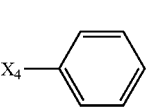 |
| OMe | H | 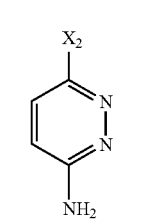 | (R) or (S) Me | 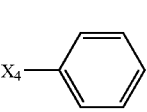 |

TABLE 4a-continued
| | | | | |
|---|---|---|---|---|
| OMe | H | 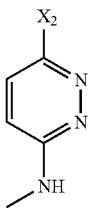 | (R) or (S) Me | 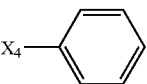 |
| OMe | H | 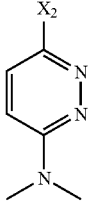 | (R) or (S) Me | 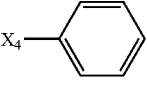 |
| OMe | H | 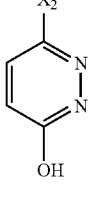 | (R) or (S) Me | 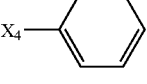 |
| OMe | H | 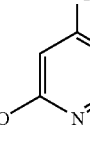 | (R) or (S) Me | 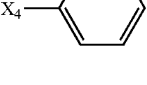 |
| OMe | H | 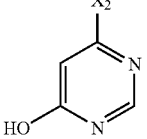 | (R) or (S) Me | 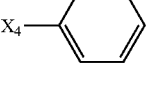 |
| OMe | H | 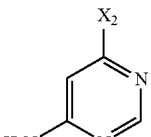 | (R) or (S) Me | 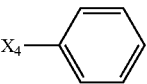 |
| OMe | H | 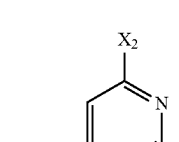 | (R) or (S) Me | 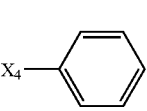 |
| OMe | H | 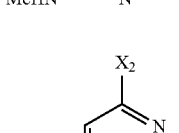 | (R) or (S) Me | 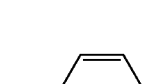 |

TABLE 4a-continued
| | | | | |
|---|---|---|---|---|
| OMe | H | 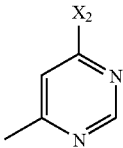 | (R) or (S) Me | 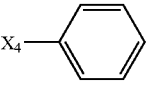 |
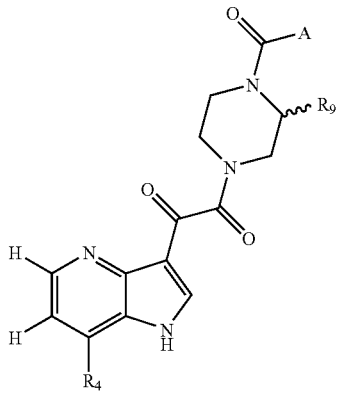
Other Inhibitors
| R4 | R9 | A |
|---|---|---|
| 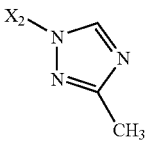 | (R) or (S) Me | 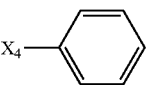 |
| 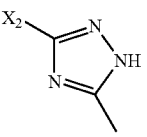 | (R) or (S) Me | 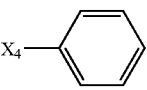 |
| 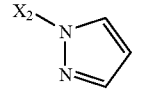 | (R) or (S) Me | 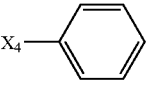 |
| 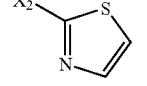 | (R) or (S) Me | 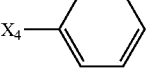 |
| 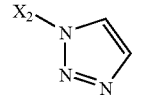 | (R) or (S) Me | 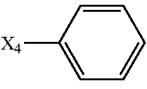 |
| 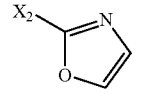 | (R) or (S) Me | 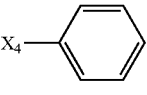 |
| 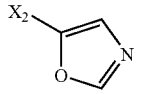 | (R) or (S) Me | 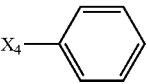 |
| 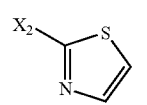 | (R) or (S) Me | 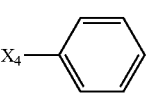 |

Metabolic Stability Studies of compounds in Liver Microsomes. The metabolic stability of compounds were investigated in pooled liver microsomes from humans. The human liver microsomes were obtained from BD Gentest (Lot #16, Woburn, Mass.) with a protein concentration of 20 mg/ml and a total cytochrome P450 (CYP) concentration of 0.55 nmol/mg protein.

A stock solution of drug was prepared in acetonitrile at 1 mM. An aliquot of the stock solution was added to the incubation media to give a final concentration of 3 µM of drug, and the acetonitrile concentration not exceeding 1% in the incubation. The incubation media consisted of potassium phosphate buffer (0.1 M, pH 7.4), liver microsomes (final concentration 0.9 mg/ml), magnesium chloride (0.033 mM), and a NADPH-regenerating system. The cofactors of the NADPH-regenerating system consisted of NADPH (final concentration 0.425 mg/ml), glucose-6-phosphate (final concentration 0.512 mg/ml), and glucose-6-phosphate dehydrogenase (final concentration 0.6 unit/ml). The test compound was pre-incubated in the media for 2 min. The reaction was initiated by the addition of the cofactors. The incubation was carried out at 37° C. for 10 min. The reaction was terminated by drawing an aliquot of 100 µL from the incubation and adding into 200 µL of acetonitrile containing a reference compound as an external analytical standard. Following vortex-mixing and centrifugation, an aliquot of 10 µL of the supernatant was analyzed by LC/MS.

GUIDELINES can be used to categorized test substances as low, intermediate or highly cleared compounds.

| Rate (nmol/min/mg) | Clearance Estimate |
| --- | --- |
| 0-0.100 | Low |
| 0.101-0.200 | Intermediate |
| 0.201-0.300 | High |

Rat Pharmacokinetic Studies:

For the IV and PO pharmacokinetic studies of compounds in rats, the compound was dissolved in PEG-400/ethanol (90/10) as a solution.

Rat. Male Sprague-Dawley rats (300-350 g, Hilltop Lab Animals, Inc., Scottdale, Pa.) with cannulas implanted in the jugular vein were used. The rats were fasted overnight in the PO pharmacokinetic studies. Blood samples of 0.3 ml were collected from the jugular vein in EDTA-containing microtainer tubes (Becton Dickinson, Franklin Lakes, N.J.), and centrifuged to separate plasma.

In the IV study, the test compound was delivered at 1 mg/kg as a bolus over 0.5 min (n=3). Serial blood samples were collected before dosing and 2, 10, 15, 30, 45, 60, 120, 240, 360, 480, and 1440 min after dosing.

In the PO study of the test compound, the rats (n=3) received an oral dose of 5 mg/kg of BMS-585248. Serial blood samples were collected before dosing and 15, 30, 45, 60, 120, 240, 360, 480, and 1440 min after dosing.

Quantitation of Compounds in Plasma. Aliquots of plasma samples from rat, studies were prepared for analysis by precipitating plasma proteins with two volumes of acetonitrile containing an internal standard of a similar compound. The resulting supernates were separated from the precipitated proteins by centrifugation for 10 minutes and transferred to autosampler vials. Samples were either prepared manually, or with the use of the Tomtec automated liquid handler. An aliquot of 5 µL was injected for analysis.

The HPLC system consisted of two Shimadzu LC10AD pumps (Columbia, Md.), a Shimadzu SIL-HTC autosampler (Columbia, Md.), and a Hewlett Packard Series 1100 column compartment (Palo Alto, Calif.). The column was a YMC Pro C18 (2.0×50 mm, 3 µm particles, Waters Co., Milford, Mass.), maintained at 60° C. and a flow rate of 0.3 ml/min. The mobile phase consisted of 10 mM ammonium formate and 0.1% formic acid in water (A) and 100% 10 mM ammonium formate and 0.1% formic acid in methanol (B). The initial mobile phase composition was 95% A. After sample injection, the mobile phase was changed to 15% A/85% B over 2 minutes and held at that composition for an additional 1 minute. The mobile phase was then returned to initial conditions and the column re-equilibrated for 1 minute. Total analysis time was 4 minutes.

The HPLC was interfaced to a Micromass Quattro LC. Ultra high purity nitrogen was used as the nebulizing and desolvation gas at flow rates of 100 L/hr for nebulization and 1100 L/hr for desolvation. The desolvation temperature was 300° C. and the source temperature was 150° C. Data acquisition utilized selected reaction monitoring (SRM). Ions representing the $(M+H)^+$ species for the compound and the internal standard were selected in MS1 and collisionally dissociated with argon at a pressure of $2 \times 10^{-3}$ torr to form specific product ions which were subsequently monitored by MS2.

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Scheme 41a depicts methodology for converting a carboxylic acid to an alkynyl ketone. The alkynyl ketone precursors can then be converted to pyrazoles or isoxazoles upon reaction with hydrazines or hydroxylamines, respectively.

The invention is intended to cover isomers, diastereoisomers, stereoisomers, and enantiomers of the depicted formulas when one or more asymmetric carbons are present in the molecules. An asymmetric carbon is one in which the carbon is attached to four different substitutions. In particular, the invention is intended to cover isomers or a single enantiomer especially when one enantiomer displays superior properties. Enantiomers differ from one another in that the spatial arrangement of the substituents around the chiral centers of the asymmetric carbons result in each molecule being a non-superimposable mirror image of the other. In this application, the configuration of the substituents around an asymmetric carbon are defined unambiguously as either (R) which is a standard representation which stands for Latin rectus, right or (S) which is the standard representation for Latin sinister, left in the Cahn-Ingold-Prelog nomenclature system which has been in use since the 1960s. Standard rules for defining the configuration of these centers are found in any basic organic chemistry textbook. In particular, for this application and based on initial examples, when W contains a single methyl group as depicted below, when the carbon bearing the methyl group is in the (R) configuration it may show a potency advantage over the (S) enantiomer. Occasionally the (R)-methyl piperazine may show a potency advantage over the unsubstituted piperazine. These observations are compound specific effect and are not always present. The unsubstituted piperazine and (S) enantiomers are still potent antiviral compounds despite occasionally being less potent than the (R) enantiomer.

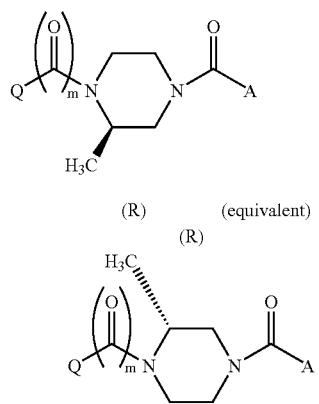

(R)  (equivalent)
(R)

When the configuration of a methyl piperazine shown as below is (R) the methyl group may improve the metabolic stability of the adjacent amide as compared to the (S) methyl piperazine or the unsubstituted piperazine. However, the metabolic stability of the amide bond is compound specific and a methyl substituent is not necessarily required for optimal properties.

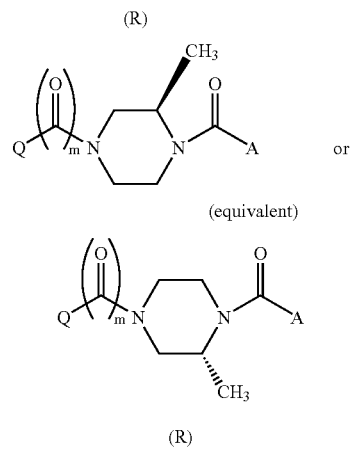

(R)  or
(equivalent)
(R)

It has now also been surprisingly found that compounds of Formula Ia, in which specifically $R_4$ is an N-linked triazolyl group, attached at the 1-nitrogen position, are particularly effective for inhibiting HIV. This is discussed more fully below.

The effective treatment of HIV and other viruses requires compounds that are potent inhibitors of the virus, are selective for the virus, and have the properties which allow them to safely achieve and maintain plasma level concentrations which are a maximum number multiples above the concentration required to minimally inhibit the virus. Higher exposures suppress viral replication and reduced rates of replication mean that strains of virus with resistance to the drug treatment will develop at a slower rate. Potent drugs exhibit equivalent activity from a lower concentration or lower dose than that needed to achieve the same effect from a less potent drug. Drugs which intrinsically produce higher exposures from an equivalent dose in animal models or patients (as determined by pharmacokinetic measurements such as AUC (the sum of the concentration of drug over a particular time), Cmax, or Cmin will also provide greater benefit to the patient. Drugs which have higher stability in the presence of metabolizing pathways and enzymes will maintain their concentrations longer and thus require less frequent dosing or dosing of smaller quantities. In animals or people the rate of clearance is a frequently measured parameter to assess this property but mean retention time is also used. For accuracy, the determined measure of viral inhibition is an EC50; but the minimum plasma concentrations which should be maintained in a patient is generally believed to be at least four or five fold higher. Thus the antiviral or anti HIV drug candidates which will be most likely to provide maximum benefits in patients and those that preclinical research programs strive to identify will exhibit 1) maximum potency 2) no general cytotoxicity vs the cell line used for the assay 3) low predicted rates of metabolism in human based on in vitro models 4) high exposure after oral dosing. Many other properties of potential drug candidates are evaluated in order to determine which compounds will have the best chance of showing optimal utility in human patients but the compounds of this invention were evaluated initially in part by determining:

1) Potency vs HIV as determined by an EC50 in an initial pseudotype assay as described in the biology section.
2) Lack of general cytotoxicity vs a Hela cell line. >100 uM was used as an arbitrary cut off for safety.
3) Measurement of the rate of metabolism vs human liver microsomal preparations and from this data projecting human rate of clearance. Lower is better.
4) Estimating potential exposure in man by measuring parameters such as AUC and rate of clearance by oral and iv dosing in rats. High exposure and low clearance was desired.

Aazaindole oxoacetic piperazine amides have been disclosed in two series of patent applications. The first series discloses azaindole derivatives which have promising potential as antiviral agents (hereinafter called, reference 94) Wang, Tao et al, U.S. Pat. No. 6,476,034 and WO 0162255 A1, filed Jan. 19, 2001, published Aug. 30, 2001. The second series (hereinafter called, reference 106) Wang, Tao, et al discloses HIV Antiviral Activity of Substituted Azaindoleoxoacetic piperazine Derivatives in U.S. patent application Ser. No. 10/214,982 filed Aug. 7, 2002, which is a continuation-in-part application of U.S. Ser. No. 10/038,306 filed Jan. 2, 2002 (corresponding to PCT Int. Appl. (PCT/US02/00455), WO 02/062423 A1, filed Jan. 2, 2002, published Aug. 15, 2002. All of the references for these two series are incorporated by reference herein. Reference 106 describes in part C-7 heteroaryl, aryl or substituted 4, 5, 6, or 7-azaindoles as antiviral agents and is the most relevant prior art.

We have evaluated the properties of many compounds covered within the scope of references 94 and 106 and have found that the compounds having C-7, N-linked triazole groups are surprisingly and unexpectedly superior.

We initially evaluated compounds to determine which showed maximum potency or the lowest EC50 using the pseudotype assay described in the biology section of this application. In our case compounds with EC50s less than 0.20 nM were considered of most interest since this covered the most potent compounds and accounted for assay variability of our initial screen. The stability of compounds were also evaluated to determine metabolic stability when incubated in in vitro preparations of human liver microsomes (HLM). This is one commonly used predictive system for evaluating the potential for human metabolism and projecting clearance rates in man. Compounds with low clearance rates were most desirable. Intermediate and high clearance compounds would be more likely to have difficulty achieving feasible dosing regimen's in man vs low clearance compounds. Compounds for which accurate determinations could not be made were also not advanced.

Surprisingly, when the most promising compounds from the potency and metabolic stability criterias were evaluated in rats to measure their pharmacokinetic properties, one class of C-7 substituents, N linked triazoles of Formula Ia showed very low clearance and very high AUCs (exposure) when compared to the compounds of references 94 and 106.

The compounds I having Formula Ia are described below:

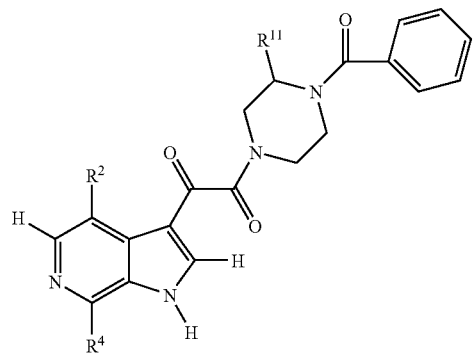

wherein:
$R^2$ is methoxy, fluoro or chloro;

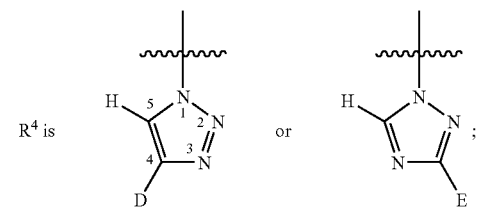

D is hydrogen or $C_1$-$C_3$ alkyl;
E is selected from the group consisting of hydrogen, ($C_1$-$C_3$) alkyl, O($C_1$-$C_3$)alkyl or $CH_2OCH_3$.
$R^{11}$ is either hydrogen or methyl in which the configuration to which the methyl is attached is (R) with the proviso that when $R^4$ is 1,2,3-triazole, then $R^{11}$ is hydrogen.

The C-7 N-linked triazoles thus showed surprising properties as they were essentially equivalent in potency to the most potent compounds covered by references 94 and 106 that we have evaluated to date. They showed metabolic stability in human liver microsomes that was equivalent to the best compounds from the application. Unexpectedly, they showed clearance rates in rats that were much lower, usually 10 fold lower than the best compounds from those described in the applications of reference 94 and were the best of any compounds evaluated in reference 106. Even more surprisingly, they were the only class of compounds to show significantly increased exposure in rats as shown by their AUCs.

In summation, these N-linked triazoles exhibited a surprising combination of properties that would not be obvious to one skilled in the art relying on the disclosure of references 94 and 106. Only a single triazole is disclosed in WO 02/06423. This compound has an $R^4$ substituent which is a C-linked triazole, and not an N-linked triazole, and exhibited potency which was not comparable to the N-linked triazoles. No N-linked triazoles were described in the examples of the published PCT application from reference 106.

The following data tables summarize the potency, predicted human clearance based on human liver microsomes, and the AUC and clearance determined by pharmacokinetic studies in rats for these N-linked triazoles of the invention herein compared with representative compounds and close analogs contained in PCT application WO 02/062423 A1, filed Jan. 2, 2002, published Aug. 15, 2002 and the published applications and patents contained in reference 94. As seen in the following tables the N linked triazoles herein identified as most preferred groups exhibit surprising superiority especially in terms of displaying maximum potency, metabolic stability equivalent to best in class and uniquely a high AUC (exposure) and low clearance in rats which is determined by oral and iv dosing at 5 mg/kg and 1 mg/kg respectively. The rat model is an initial model used to assess potential for exposure in man.

The utility of compounds in the triazole class is surprisingly very dependent on the substitution patterns as depicted. For example the 1,2,3 triazoles attached at the 2-position nitrogen atom have to date shown significantly reduced AUC (exposure) in rats compared to the compounds depicted. In addition, moving the E group when E is methyl, in the 1,2,4-N-linked triazole from position 3 to 5 provides compounds with significantly reduced potency. As can be seen in Table A2, the N-linked triazoles specified showed high potency in an initial antiviral assay.

As evidenced by Tables A3-A8 of Comparator compounds, the metabolic stability of the N-linked triazole compounds Ia of the invention is surprisingly equivalent to or better than any of the compounds covered in either series of published aza-indole applications (i.e. references 94 and 106).

As dramatically shown in the tables, the low clearance and high exposure seen in rats for the compounds in table A2 was surprising and unexpected since the prior art taught compounds did not exhibit these properties as one would have expected.

In the tables that follow these terms have the following in meanings:

"NT" meant not tested.

"Difficulties" means results could not be interpreted (i.e. in HLM test).

Results

TABLE A1

Biological Data Key for $EC_{50}$s in Tables A2-A7

| Compounds* with $EC_{50}$s >1 μM | Compounds with $EC_{50}$s >0.2 nM but <1 μM | Compounds with EC50 ≤0.20 nM |
|---|---|---|
| Group 3 | Group 2 | Group 1 |

TABLE A2

N linked Triazoles as R4 with Surprising Superior Properties

| Example Number | EC50 category | CC50 >100 uM | HLM predicted human clearance class | AUC 24 h (ug · hr/mL) | CL, iv (mL/min/kg) |
|---|---|---|---|---|---|
| 216 | 1 | Yes | Low | 32 ± 12 | 1.6 ± 0.2 |
| 188 | 1 | Yes | Low | 20 ± 4.6 | 2.4 ± 0.08 |
| 187 | 1 | Yes | Low | 22.4 ± 7.2 | 2.4 ± 0.5 |
| 215, 303 | 1 | Yes | Low | 83.7 ± 9.8 | 0.7 ± 0.12 |
| 245 | 1 | Yes | Low | 12.1 ± 1.3 | 5.6 ± 1.8 |
| 313 | 1 | Yes | Low | | |
| 316 | 1 | Yes | Low | 52 ± 12 | 1.3 ± 0.19 |
| 317 | 1 | Yes | Low | 43 ± 12 | 1.9 ± 0.26 |
| 306 | 1 | Yes | Low | 160 ± 11 | 0.39 ± 0.07 |
| 321 | 1 | Yes | Low | | |
| 322 | 1 | Yes | Low | 82 ± 23 | 1.8 ± 0.4 |
| 314 | 1 | Yes | Low | | |
| 315 | 1 | Yes | Low | | |
| 352 | 1 | Yes | Low | | |
| 325 | 1 | Yes | Low | | |
| 326 | 1 | Yes | Low | 9.8 ± 2.9 | 8.3 |
| 274 | 1 | Yes | Low | | |
| 273 | 1 | Yes | Low | | |
| 324 | 1 | Yes | Low | | |
| 275 | 1 | Yes | Low | | |

TABLE A3

Some Other Alternatively Substituted N linked Triazoles at R4 as Comparators

| Example Number | EC50 category | CC50 >100 uM | HLM predicted human clearance class | AUC 24 h (ug · hr/mL) | CL, iv (mL/min/kg) |
|---|---|---|---|---|---|
| 217 | 2 | Yes | NT | NT | NT |
| 307 | 2 | Yes | NT | NT | NT |
| 256 | 2 | Yes | NT | NT | NT |
| 350 | 2 | Yes | Low | NT | NT |
| 327 | 2 | Yes | Low | NT | NT |
| 328 | 1 | Yes | Low | NT | NT |
| 351 | NT | NT | Low | 1.5 ± 0.14 | 16.6 ± 1.4 |

TABLE A4

Some Other Relevant N linked Heteroaryls at R4 as Comparators

| Example Number | EC50 category | CC50 >100 uM | HLM predicted human clearance class | AUC 24 h (ug · hr/mL) | CL, iv (mL/min/kg) |
|---|---|---|---|---|---|
| 139 | 2 | Yes | High | | |
| 219, 305 | 1 | Yes | High | | |
| 193 | 1 | No | Low | 14 ± 8 | 4.5 ± 0.4 |
| 189 | 2 | Yes | Low | | |
| 222 | 2 | Yes | Low | | |
| 221 | 2 | Yes | Low | | |
| 220 | 2 | Yes | NT | | |
| 218, 304 | 2 | Yes | Low | | |
| 190 | 1 | Yes | Low | 7.4 ± 3.4* | 3.7 ± 1.0 |
| 191 | 2 | Yes | NT | | |
| 309 | 1 | Yes | Low | 0.09 ± 0.05 | 34.3 ± 2.6 |

TABLE A4-continued

Some Other Relevant N linked Heteroaryls at R4 as Comparators

| Example Number | EC50 category | CC50 >100 uM | HLM predicted human clearance class | AUC 24 h (ug · hr/mL) | CL, iv (mL/min/kg) |
|---|---|---|---|---|---|
| 318 | 2 | Yes | Low | | |
| 310 | 1 | Yes | Low | 2.1 ± 0.4* | 16.5 ± 3.3 |
| 241 | 1 | Yes | Low | 6.4 ± 4.2* | 11.2 ± 0.9 |
| 312 | 2 | Yes | Low | | |
| 241 | 1 | Yes | Low | 0.0086 ± 0.005** | 131 ± 4.3 |
| 236 | 1 | Yes | Low | 0.56 ± 0.25 | 29 ± 6.7 |
| 251 | 1 | Yes | Low | | |
| 230 | 1 | Yes | Intermediate | | |
| 343 | 1 | Yes | Low | | |
| 344 | 2 | No | Low | | |
| 276 | 1 | Yes | NT | | |
| 255 | 1 | Yes | Intermediate | | |
| 258 | 1 | Yes | Low | | |
| 314 | 1 | Yes | Low | | |
| 315 | 1 | Yes | Low | | |
| 352 | 1 | Yes | Low | | |
| 326 | 1 | Yes | Low | 9.8 ± 2.9 | 8.3 |
| 274 | 1 | Yes | | | |
| 273 | 1 | Yes | | | |
| 275 | 1 | Yes | | | |

TABLE A5

Some Relevant C linked Heteroaryl Comparators

| Example Number | EC50 category | CC50 >100 uM | HLM predicted human clearance class | AUC 24 h (ug · hr/mL) | CL, iv (mL/min/kg) |
|---|---|---|---|---|---|
| 40 | 2 | No | Low | | |
| 42 | 2 | Yes | Low | | |
| 22 | 1 | No | Intermediate | | |
| 35 | 1 | Yes | Intermediate | | |
| 37 | 1 | No | NT | | |
| 38 | 1 | No | Low | | |
| 39 | 2 | No | Intermediate | | |
| 28 | 3 | No | NT | | |
| 29 | 2 | No | High | | |
| 22 | 2 | No | High | | |
| 74 | 2 | No | Intermediate | | |
| 71 | 1 | Yes | Intermediate | | |
| 73 | 1 | Yes | Intermediate | | |
| 78 | 2 | Yes | Intermediate | | |
| 94 | 1 | Yes | NT | | |
| 102 | 2 | Yes | Low | 6.9 ± 1.3 | 12 ± 5.5 |
| 163 | 2 | Yes | Difficulties | | |
| 95 | 1 | Yes | Intermediate | | |
| 140 | 2 | Yes | Intermediate | | |
| 146 | 2 | Yes | Intermediate | | |
| 145 | 1 | Yes | Difficulties | 12 ± 3.8 | 1.4 ± 0.29 |
| 148 | 2 | Yes | NT | | |
| 210 | 1 | Yes | Intermediate | | |
| 211 | 1 | No | Intermediate | | |
| 212 | 1 | Yes | Low | | |
| 223 | 2 | Yes | Low | | |
| 224 | 2 | Yes | Low | | |
| 225 | 2 | Yes | NT | | |
| 227 | 2 | Yes | Low | 3.8 ± 0.83 | 8.8 ± 3.7 |
| 226 | 1 | Yes | Low | 0.5 ± 0.13* | 24.5 ± 3 |
| 299 | 1 | No | Low | | |
| 300 | 2 | Yes | Low | | |
| 266 | 1 | Yes | Low | 0.16 ± 0.04* | 37.4 ± 3.2 |
| 345 | 2 | Yes | Low | | |
| 301 | 2 | Yes | NT | | |

TABLE A5-continued

Some Relevant C linked Heteroaryl Comparators

| Example Number | EC50 category | CC50 >100 uM | HLM predicted human clearance class | AUC 24 h (ug · hr/mL) | CL, iv (mL/min/kg) |
|---|---|---|---|---|---|
| 346 | 2 | Yes | NT | | |
| 347 | 2 | Yes | Low | | |
| 334 | 2 | Yes | NT | | |
| 348 | 2 | Yes | Low | | |
| 349 | 2 | Yes | NT | | |
| 342 | 1 | Yes | Low | | |

TABLE A6

Some Relevant 4-azaindole Comparators and data

| Example Number | EC50 category | CC50 >100 uM | HLM predicted human clearance class | AUC 24 h (ug · hr/mL) | CL, iv (mL/min/kg) |
|---|---|---|---|---|---|
| 204 | 2 | Yes | Low | 1.2 ± 1.4 | 10 ± 1.3 |
| 161 | 1 | Yes | High | | |
| 205 | 2 | Yes | Low | 9.6 ± 1.2 | 5.4 ± 0.4 |
| 207 | 2 | Yes | Low | | |
| 206 | 2 | Yes | NT | | |
| 208 | 2 | Yes | NT | | |
| 353 | 2 | Yes | Low | 1363 ± 307 | 5.6 ± 1.1* |
| 354 | 2 | Yes | Low | 1.26 ± 0.18* | 11.2 ± 0.8 |
| 355 | 2 | Yes | Low | 3.3 ± 0.77* | 13.9 ± 5.3 |
| 356 | 2 | Yes | Low | | |
| 357 | 2 | Yes | Intermediate | | |
| 358 | 2 | Yes | High | | |
| 359 | 2 | Yes | NT | | |
| 360 | 2 | Yes | Low | | |
| 361 | 2 | Yes | NT | | |

TABLE A7

Some Relevant Comparators and data from U.S. patent 6476034 (Reference 94)

| Reference Compound Number | EC50 category | CC50 >100 uM? | HLM predicted human clearance class | AUC 24 h (ug · hr/mL) | CL, iv (mL/min/kg) |
|---|---|---|---|---|---|
| 1 | 2 | Yes | Low | 0.5 | 32 ± 1.8 |
| 2 | 2 | Yes | Intermediate | | |
| 3 | 2 | Yes | Low | 6.3 ± 2.7 | 1.3 ± 4.0 |
| 4 | 2 | Yes | Low | | |
| 5 | 1 | Yes | Intermediate | | |
| 6 | 2 | Yes | Low | 1.7 ± 0.58 | 31 ± 5.9 |
| 7 | 1 | Yes | Low | 2.6 ± 0.12* | 19.3 ± 0.65 |
| 8 | 1 | Yes | Low | 1.03 ± 0.07* | 47.2 ± 11.5 |
| 9 | 2 | Yes | Low | 5.9 ± 2.2 | 5.9 ± 2.2 |
| 10 | 2 | Yes | Low | 2.9 ± 0.3 | 11.7 ± 1.0 |
| 11 | 1 | Yes | | 1.4 ± 0.2* | 24.8 ± 0.41 |
| 12 | 1 | Yes | Low | 4.7 ± 1.1 | 11.9 ± 1.8 |
| 13 | 2 | Yes | NT | | |

Structures of Reference Compounds as a Key for Table A7

REFERENCE COMPOUND 1

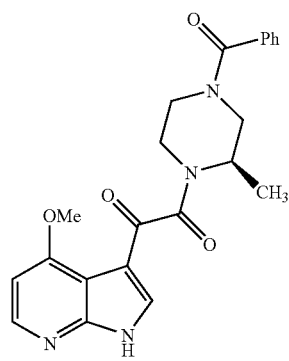

TABLE A8

(Reference compounds structures 2-9)

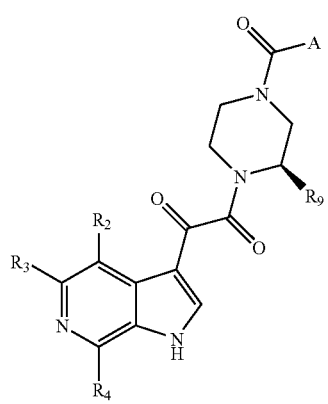

| Reference Compound Number | R2 | R3 | R4 | R9 | A |
|---|---|---|---|---|---|
| 2 | OMe | H | $X_2$-OMe | (R)-Me | 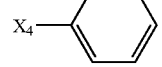 |
| 3 | OMe | H | $X_2$-OMe | H | 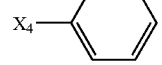 |
| 4 | OMe | H | $X_2$—OH | H | 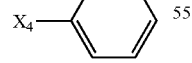 |
| 5 | Cl | H | $X_2$—C(=O)NH_2 | H | 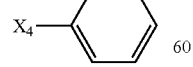 |
| 6 | F | H | $X_2$—C(=O)NHMe | H | 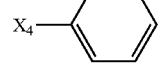 |

TABLE A8-continued (Reference compounds structures 2-9)

| Reference Compound Number | R2 | R3 | R4 | R9 | A |
|---|---|---|---|---|---|
| 7 | F | H | $X_2$—C(=O)NH$_2$ | H | $X_4$-Ph |
| 8 | MeO | H | $X_2$—C(=O)NH$_2$ | H | $X_4$-Ph |
| 9 | MeO | H | $X_2$—C(=O)NHCH$_3$ | H | $X_4$-Ph |

TABLE A9

(Reference compounds 10-12)

| Reference Compound Number | R2 | R3 | R4 | R11 | A |
|---|---|---|---|---|---|
| 10 | MeO | H | $X_2$-OMe | (R)-Me | $X_4$-Ph |

TABLE A9-continued (Reference compounds 10-12)

| Reference Compound Number | R2 | R3 | R4 | R11 | A |
|---|---|---|---|---|---|
| 11 | MeO | H | X₂–C(O)NH₂ | (R)-Me | X₄–phenyl |
| 12 | MeO | H | X₂–C(O)NHCH₃ | (R)-Me | X₄–phenyl |

In Tables A8 and A9, $X_2$ and $X_4$ refer to point of attachment.

What is claimed is:

1. A pharmaceutical formulation which comprises an antiviral effective amount of a compound selected from the group of including pharmaceutically acceptable salts thereof, and a pharmaceutically acceptable carrier, wherein said formulation is administered to humans in a dosage range of 1 to 100 mg/kg body weight.

2. The formulation of claim 1, which is administered to humans in a dosage range of 1 to 20 mg/kg body weight.

3. The formulation of claim 2, which is administered to humans in a dosage range of 1 to 10 mg/kg body weight.

4. The formulation of claim 1, wherein said formulation is orally administered.

5. The formulation of claim 1, wherein said formulation is administered in divided doses.

6. The formulation of claim 4, wherein said formulation is in the form of a suspension or tablet.

7. A method of treating HIV infection, which comprises administering to a human in need thereof the compound in an oral or parenteral formulation.

8. A method of treating HIV infection, which comprises administering to a human in need thereof the compound and in an oral or parenteral formulation.

9. A method of treating HIV infection, which comprises administering to a human in need thereof the compound

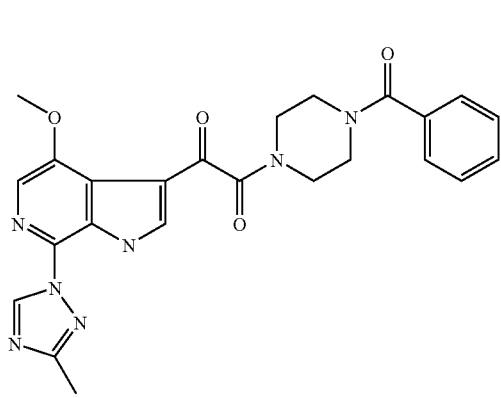

in an oral or parenteral formulation, in combination with an antiviral effective amount of another HIV treatment agent.

10. A method of treating HIV infection, which comprises administering to a human in need thereof the compound

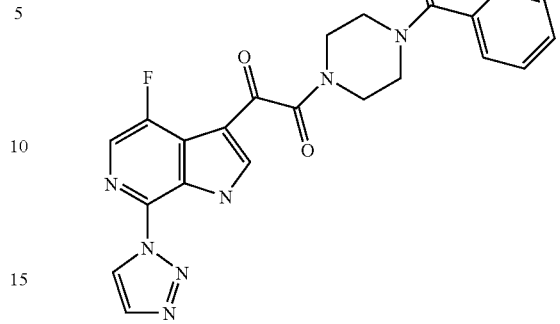

in an oral or parenteral formulation, in combination with an antiviral effective amount of another HIV treatment agent.

* * * * *

UNITED STATES PATENT AND TRADEMARK OFFICE
CERTIFICATE OF CORRECTION

| | |
|---|---|
| PATENT NO. | : 7,501,420 B2 |
| APPLICATION NO. | : 12/015776 |
| DATED | : March 10, 2009 |
| INVENTOR(S) | : Tao Wang et al. |

It is certified that error appears in the above-identified patent and that said Letters Patent is hereby corrected as shown below:

On the Title Page:

Item (54), after "ANTIVIRAL", insert -- ACTIVITY --.

Item (56) References Cited, under OTHER PUBLICATIONS,

A. Fredenhagen, et al. reference, change "Semicochiliodinol" to -- Semicochliodinol --.

The reference should read:

-- A. Fredenhagen, et al., "Semicochliodinol A and B: Inhibitors of HIV-1 Protease and EGF-R Protein Tyrosine Kinase Related to Asterriquinones Produced by the Fungus *Chrysosporium merdarium*," Journal of Antibiotics, 50(5), pp. 395-401, 1997. --.

M. Kato, et al. reference, change "Redlationships" to -- Relationships --.

The reference should read:

-- M. Kato, et al., "New 5HT$_3$ (Serotonin-3) Receptor Antagonists. IV. Synthesis and Structure-Activity Relationships of Azabicycloalkaneacetamide Derivatives." Chem. Pharm. Bull., 43(8), pp. 1351-1357, 1995. --.

Column 1, line 1, after "ANTIVIRAL", insert -- ACTIVITY --.

Signed and Sealed this
Twenty-sixth Day of April, 2011

David J. Kappos
*Director of the United States Patent and Trademark Office*